(12) United States Patent
Das et al.

(10) Patent No.: US 12,385,041 B2
(45) Date of Patent: Aug. 12, 2025

(54) CONDITIONAL-SIRNAS AND USES THEREOF IN TREATING CARDIAC HYPERTROPHY

(71) Applicants: CITY OF HOPE, Duarte, CA (US); CALIFORNIA INSTITUTE OF TECHNOLOGY, Pasadena, CA (US); THE GENERAL HOSPITAL CORPORATION, Boston, MA (US)

(72) Inventors: Saumya Das, Boston, MA (US); Ane Miren Salvador Garicano, Boston, MA (US); Si-ping Han, Duarte, CA (US); Lisa Scherer, Duarte, CA (US); Julia Derogatis, Duarte, CA (US); Robin Hu, Duarte, CA (US); Sahil Sagar, Duarte, CA (US); William A. Goddard, III, Pasadena, CA (US); John Rossi, Duarte, CA (US)

(73) Assignees: City of Hope, Duarte, CA (US); California Institute of Technology, Pasadena, CA (US); The General Hospital Corporation, Boston, MA (US)

( * ) Notice: Subject to any disclaimer, the term of this patent is extended or adjusted under 35 U.S.C. 154(b) by 781 days.

(21) Appl. No.: 16/638,107

(22) PCT Filed: Aug. 10, 2018

(86) PCT No.: PCT/US2018/046379
§ 371 (c)(1),
(2) Date: Feb. 10, 2020

(87) PCT Pub. No.: WO2019/033079
PCT Pub. Date: Feb. 14, 2019

(65) Prior Publication Data
US 2023/0107117 A1 Apr. 6, 2023

Related U.S. Application Data

(60) Provisional application No. 62/543,882, filed on Aug. 10, 2017.

(51) Int. Cl.
C12N 15/11 (2006.01)
C12N 15/113 (2010.01)

(52) U.S. Cl.
CPC ........ *C12N 15/111* (2013.01); *C12N 15/1137* (2013.01); *C12N 2310/315* (2013.01); *C12N 2310/3515* (2013.01)

(58) Field of Classification Search
CPC .............. C12N 15/111; C12N 2310/14; C12N 2310/3519; C12Q 1/6883; C12Q 2600/158; C12Q 2600/178
See application file for complete search history.

(56) References Cited

U.S. PATENT DOCUMENTS

| | | |
|---|---|---|
| 6,255,469 B1 | 7/2001 | Seeman et al. |
| 6,506,559 B1 | 1/2003 | Fire et al. |
| 6,566,058 B1 | 5/2003 | Cardy |
| 6,696,285 B1 | 2/2004 | Mills et al. |
| 7,745,594 B2 | 6/2010 | Seelig et al. |
| 8,241,854 B2 | 8/2012 | Yin et al. |
| 8,318,921 B2 | 11/2012 | Pierce et al. |
| 8,404,831 B2 | 3/2013 | Natt et al. |
| 8,710,199 B2 | 4/2014 | Han et al. |
| 8,962,582 B2 | 2/2015 | Dirks |
| 9,029,524 B2 | 5/2015 | Han et al. |
| 9,115,355 B2 | 8/2015 | Han et al. |
| 9,206,419 B2 | 12/2015 | Han et al. |
| 9,297,010 B2 | 3/2016 | Eimen et al. |
| 9,518,263 B2 | 12/2016 | Han et al. |
| 9,725,715 B2 | 8/2017 | Han et al. |
| 11,643,659 B2 | 5/2023 | Marcucci et al. |
| 11,999,954 B2 | 6/2024 | Han et al. |
| 2005/0079504 A1 | 4/2005 | Amitai et al. |
| 2009/0234109 A1 | 9/2009 | Han et al. |
| 2010/0063134 A1 | 3/2010 | Kaemmerer |
| 2010/0112556 A1 | 5/2010 | Sampson et al. |
| 2011/0195848 A1 | 8/2011 | Roopra et al. |
| 2011/0288826 A1 | 11/2011 | Breaker et al. |
| 2012/0088815 A1 | 4/2012 | Liang |
| 2012/0101147 A1* | 4/2012 | Tsai ....................... A61P 25/28 514/357 |
| 2013/0244327 A1 | 9/2013 | Puri et al. |
| 2013/0330725 A1 | 12/2013 | Saito et al. |

(Continued)

FOREIGN PATENT DOCUMENTS

| | | |
|---|---|---|
| EP | 2101275 A1 | 9/2009 |
| EP | 2213292 B2 | 6/2016 |

(Continued)

OTHER PUBLICATIONS

Huang, Yong, et al. "Biological functions of microRNAs: a review." Journal of physiology and biochemistry 67 (2011): 129-139.*
Wang, Dong, et al. "Atrial natriuretic peptide affects cardiac remodeling, function, heart failure, and survival in a mouse model of dilated cardiomyopathy." Hypertension 63.3 (2014): 514-519.*
De Windt, Leon J., et al. "Targeted inhibition of calcineurin attenuates cardiac hypertrophy in vivo." Proceedings of the National Academy of Sciences 98.6 (2001): 3322-3327.*
U.S. Appl. No. 63/172,030, filed Apr. 7, 2021, Han et al.
U.S. Appl. No. 63/218,862, filed Jul. 6, 2021, Si-ping Han.
U.S. Appl. No. 63/218,833, filed Jul. 6, 2021, Han et al.
U.S. Appl. No. 63/218,850, filed Jul. 6, 2021, Han et al.
U.S. Appl. No. 63/218,865, filed Jul. 6, 2021, Si-ping Han.

(Continued)

*Primary Examiner* — Kimberly Chong
(74) *Attorney, Agent, or Firm* — Dickinson Wright PLLC

(57) ABSTRACT

Disclosed herein are conditional siRNAs activatable by pro-hypertrophic RNA sequences and use thereof for treating conditions such as cardiac hypertrophy. The conditional siRNAs target calcineurin or HDAC2.

21 Claims, 230 Drawing Sheets
(80 of 230 Drawing Sheet(s) Filed in Color)
Specification includes a Sequence Listing.

(56) References Cited

U.S. PATENT DOCUMENTS

| | | |
|---|---|---|
| 2015/0004615 A1 | 1/2015 | Pierce et al. |
| 2015/0065555 A1 | 3/2015 | Brown et al. |
| 2015/0284717 A1 | 10/2015 | Templin et al. |
| 2015/0315581 A1 | 11/2015 | Han et al. |
| 2016/0046934 A1 | 2/2016 | Han et al. |
| 2016/0130581 A1 | 5/2016 | Han et al. |
| 2016/0153036 A1 | 6/2016 | Chen et al. |
| 2017/0183652 A1 | 6/2017 | Thum et al. |
| 2018/0092997 A1 | 4/2018 | Guo et al. |
| 2018/0223344 A1 | 8/2018 | Chandrasekaran et al. |
| 2019/0153437 A1 | 5/2019 | Emerick et al. |
| 2019/0233806 A1 | 8/2019 | Garreau De Loubresse |
| 2020/0291396 A1 | 9/2020 | Zamore et al. |
| 2021/0019973 A1 | 1/2021 | Yin et al. |
| 2021/0032707 A1 | 2/2021 | Talasaz |
| 2021/0095286 A1 | 4/2021 | Weiss et al. |
| 2021/0123060 A1 | 4/2021 | Marcucci et al. |
| 2021/0230593 A1 | 7/2021 | Han et al. |
| 2023/0107117 A1 | 4/2023 | Das et al. |

FOREIGN PATENT DOCUMENTS

| | | |
|---|---|---|
| EP | 2193140 B1 | 11/2016 |
| JP | 2018-007663 A | 1/2018 |
| WO | WO2008076324 | 6/2008 |
| WO | WO2011163526 | 12/2011 |
| WO | WO2013075132 | 5/2013 |
| WO | WO2013142735 | 9/2013 |
| WO | WO2019/014656 | 1/2019 |
| WO | WO2019/033083 | 2/2019 |
| WO | WO2019033079 | 2/2019 |
| WO | WO2020/033938 | 2/2020 |
| WO | WO2023/283546 | 1/2023 |
| WO | WO2023/283548 | 1/2023 |
| WO | WO2023/283550 | 1/2023 |
| WO | WO2023/283551 | 1/2023 |
| WO | WO2023/283552 | 1/2023 |
| WO | WO2023/283553 | 1/2023 |
| WO | WO2023/070057 | 4/2023 |

OTHER PUBLICATIONS

Adams et al., "Patisiran, an RNAi Therapeutic, for Hereditary Transthyretin Amyloidosis," The New England Journal of Medicine 2018, 379(1), 11-21.
Aduri et al., "Amber Force Field Parameters for the Naturally Occurring Modified Nucleosides in RNA," Journal of Chemical Theory and Computation 2007, 3, 1464-1475.
Afonin et al., "Design and self-assembly of siRNA-functionalized RNA nanoparticles for use in automated nanomedicine," Nature Protocols 2011, 6, 2022-2034.
American Cancer Society, "Key Statistics for Acute Myeloid Leukemia (AML)," cancer.org 2023, in 10 pages. https://www.cancer.org/cancer/types/acute-myeloid-leukemia/about/key-statistics.html.
Avino et al., "Oligonucleotide-peptide conjugates: solid-phase synthesis under acidic conditions and use in Elisa assays," Molecules 2012, 17, 13825-13843.
Benenson et al., "An Autonomous Molecular Computer for Logical Control of Gene Expression," Nature 2004, 429, 423-429.
Benenson, "Biomolecular Computing Systems: Principles, Progress and Potential," Nature Reviews Genetics 2012, 13, 455-468.
Beta Lab, "RNAsoft—Software for RNA/DNA secondary structure prediction and design," University of British Columbia 2023, in 1 page. http://www.rnasoft.ca/.
Bhatia et al., "A synthetic icosahedral DNA-based host-cargo complex for functional in vivo imaging," Nature Communications 2011, 2, in 8 pages.
Bindewald et al., "Multistrand Structure Prediction of Nucleic Acid Assemblies and Design of RNA Switches," Nano Letters 2016, 16(3), 1726-1735.
Bobbin & Rossi, "RNA Interference (RNAi)-Based Therapeutics: Delivering on the Promise?" Annual Review of Pharmacology and Toxicology 2016, 56, 103-122.
Boudreau et al., "Rational Design of Therapeutic siRNAs: Minimizing Off-targeting Potential to Improve the Safety of RNAi Therapy for Huntington's Disease," Molecular Therapy 2011, 19(12), 2169-2177.
Bramsen et al., "A Large-Scale Chemical Modification Screen Identifies Design Rules to Generate siRNAs with High Activity, High Stability and Low Toxicity," Nucleic Acids Research 2009, 37(9), 2867-2881.
Bujold et al., "Optimized DNA "Nanosuitcases" for Encapsulation and Conditional Release of siRNA," Journal of the American Chemical Society 2016, 138, 14030-14038.
Camacho et al., "Blast+: Architecture and Applications," BMC Bioinformatics 2009, 10, in 9 pages.
Cao et al., "Histone deacetylase (HDAC) inhibitors attenuate cardiac hypertrophy by suppressing autophagy," Proceedings of the National Academy of Sciences 2011, 108, 4123-4128.
Chatterjee et al., "Nucleic Acid Strand Displacement with Synthetic mRNA Inputs in Living Mammalian Cells," ACS Synthetic Biology 2018, 7(12), 2737-2741.
Chen et al., "DNA Nanotechnology from the Test Tube to the Cell," Nature Nanotechnology 2015, 10, 748-760.
Chojnowski et al., "RNA Bricks—a database of RNA 3D motifs and their interactions," Nucleic Acids Research 2014, 42, D123-D121.
Colasanti et al., "Analyzing and Building Nucleic Acid Structures with 3DNA," Journal of Visualized Experiments 2013, 74, in 10 pages.
Collingwood et al., "Chemical Modification Patterns Compatible with High Potency Dicer-Substrate Small Interfering RNAs," Oligonucleotides 2008, 18, 187-200.
Condon et al., "Optimization of an Amber Force Field for the Artificial Nucleic Acid, LNA, and Benchmarking with NMR of L(CAAU)," The Journal of Physical Chemistry B 2014, 118, 1216-1228.
Dirks et al., "A partition function algorithm for nucleic acid secondary structure including pseudoknots," Journal of Computational Chemistry 2003, 24, 1664-1677.
Dirks et al., "An algorithm for computing nucleic acid base-pairing probabilities including pseudoknots," Journal of Computational Chemistry 2004, 25, 1295-1304.
Dirks et al., "Paradigms for computational nucleic acid design," Nucleic Acids Research 2004, 32, 1392-1403.
Dirks et al., "Thermodynamic analysis of interacting nucleic acid strands," SIAM Review 2007, 49, 65-88.
Dowdy, "Overcoming cellular barriers for RNA therapeutics," Nature Biotechnology 2017, 35(3), 222-229.
Dresselhaus & Meffert, "Cellular specificity of NF-κB function in the nervous system," Frontiers in Immunology 2019, 10, in 14 pages.
Duan et al., "A Point-Charge Force Field for Molecular Mechanics Simulations of Proteins Based on Condensed-Phase Quantum Mechanical Calculations," Journal of Computational Chemistry 2003, 24, 1999-2012.
Duda et al., "Targeting GSK3 signaling as a potential therapy of neurodegenerative diseases and aging," Expert Opinion on Therapeutic Targets 2018, 22(10), 833-848.
Efthymiou et al., "Evaluation of siRNAs that Contain Internal Variable-Length Spacer Linkages," Bioorganic & Medicinal Chemistry Letters 2012, 22, 5590-5594.
Engelen et al., "DNA-Based Control of Protein Activity," Chemical Communications 2016, 52(18), 3598-3610.
Estey, "Acute Myeloid Leukemia: 2012 Update on Diagnosis, Risk Stratification, and Management," American Journal of Hematology 2012, 87(1), 89-99.
Exiqon, "LNA™ Oligo Tools and Design Guidelines," exiqon.com 2020, in 1 page. www.exiqon.com/oligo-tools.
Extended European Search Report and Opinion dated Apr. 14, 2022 in European Patent Application No. 19846651.8.
Filipi et al., "Glial cells—The strategic targets in amyotrophic lateral sclerosis treatment," Journal of Clinical Medicine 2020, 9(1), in 47 pages.

(56) References Cited

OTHER PUBLICATIONS

Final Office Action dated Jul. 21, 2023 in U.S. Appl. No. 17/172,461.
Fleige et al., "Stimuli-responsive polymeric nanocarriers for the controlled transport of active compounds: Concepts and applications," Advanced Drug Delivery Reviews 2012, 64(9), 866-884.
Gawande et al., "Selection of DNA aptamers with two modified bases," Proceedings of the National Academy of Sciences 2017, 114, 2898-2903.
Glaser et al., "Anti-apoptotic Mcl-1 is Essential for the Development and Sustained Growth of Acute Myeloid Leukemia," Genes & Development 2012, 26, 120-125.
Glen Research, "Locked Analog Phosphoramidites and Supports," Glenresearch.com 2023, in 4 pages. https://www.glenresearch.com/products/labels-and-modifiers/backbone-modification/locked-analog-phosphoramidites.html.
Glen Research, "Nucleoside Analog Phosphoramidites," Glenresearch.com 2023, in 3 pages. https://www.glenresearch.com/browse/nucleoside-analog-phosphoramidites.
Glen Research, "Modification and Labeling," glenresearch.com 2023, in 6 pages. www.glenresearch.com/browse/labels-and-modifiers.
Graham et al., "Isolation, Culture, and Functional Characterization of Adult Mouse Cardiomyoctyes," JOVE 2013, 79, in 13 pages.
Green et al., "Complex Cellular Logic Computation Using Ribocomputing Devices," Nature 2017, 548(7665), 117-121.
Green et al., "To kill a microglia: a case for CSF1R inhibitors," Trends in Immunology 2020, 41(9), 771-784.
Groves et al., "Computing in Mammalian Cells with Nucleic Acid Strand Exchange," Nature Nanotechnology 2016, 11(3), 287-294.
GSRS, "Casimersen," nih.gov 2023, in 1 page. https://gsrs.ncats.nih.gov/ginas/app/beta/substances/905e0f05-b9c5-412c-a0e1-5bb898111944.
GSRS, "Eteplirsen," nih.gov 2023, in 1 page. https://gsrs.ncats.nih.gov/ginas/app/beta/substances/4d0cddf7-f088-45af-af78-27659898e442.
GSRS, "Golodirsen," nih.gov 2023, in 1 page. https://gsrs.ncats.nih.gov/ginas/app/beta/substances/e54505d8-4af5-43f6-95b4-f70effe0b457.
Guo, "The Emerging Field of RNA Nanotechnology," Nature Nanotechnology 2010, 5(12), 833-842.
Guttenplan et al., "Knockout of reactive astrocyte activating factors slows disease progression in an ALS mouse model," Nature Communications 2020, 11(1), in 9 pages.
Ha & Kim, "Regulation of MicroRNA Biogenesis," Nature Reviews Molecular Cell Biology 2014, 15, 509-524.
Hammond et al., "Delivery of oligonucleotide-based therapeutics: challenges and opportunities," EMBO Molecular Medicine 2021, 13(4), e13243.
Han et al., "Programmable siRNA Pro-Drugs that Activate RNAi Activity in Response to Specific Cellular RNA Biomarkers," Molecular Therapy—Nucleic Acids 2022, 27, 797-809.
Hartmann et al., "Effects of phenylephrine on calcium current and contractility of feline ventricular myocytes," American Journal of Physiology—Heart and Circulatory Physiology 1988, 255, H1173-H1180.
Heissig et al., "DNA as Tunable Adaptor for siRNA Polyplex Stabilization and Functionalization," Molecular Therapy—Nucleic Acids 2016, 5, in 10 pages.
Hill et al., "Sonic hedgehog signaling in astrocytes," Cellular and Molecular Life Sciences 2021, 78, 1393-1403.
Hochrein et al., "Conditional Dicer Substrate Formation via Shape and Sequence Transduction with Small Conditional RNAs," Journal of the American Chemical Society 2013, 135, 17322-17330.
Hochrein et al., "Signal Transduction in Human Cell Lysate via Dynamic RNA Nanotechnology," ACS Synthetic Biology 2018, 7, 2796-2802.
Hope & Trono, "Structure, Expression, and Regulation of the HIV Genome," HIV in Site 2020, in 11 pages. http://hivinsite.ucsf.edu/InSite?page=kb-OO&doc=kb-02-01-02.
Horizon, "Dharmacon reagents," horizondiscovery.com 2023, in 8 pages. http://dharmacon.horizondiscovery.com/design-center/.
Hu et al., "Therapeutic siRNA: state of the art," Signal Transduction and Targeted Therapy 2020, 5(1), in 25 pages.
Huang et al., "Activation of Wnt/β-catenin signalling via GSK3 inhibitors direct differentiation of human adipose stem cells into functional hepatocytes," Scientific Reports 2017, 7(1), in 12 pages.
Integrated DNA Technologies, "Oligo Modifications," idtdna.com 2023, in 2 pages. https://www.idtdna.com/pages/products/custom-dna-rna/oligo-modifications.
International Search Report and Written Opinion dated Jan. 4, 2019 in PCT Patent Application No. PCT/US2018/046383.
International Search Report and Written Opinion dated Jan. 25, 2023 in PCT Patent Application No. PCT/US2022/078466.
International Search Report and Written Opinion dated Nov. 25, 2019 in PCT Patent Application No. PCT/US2019/046075.
International Search Report and Written Opinion dated Nov. 26, 2018 in PCT Patent Application No. PCT/US2018/046379.
International Search Report and Written Opinion dated Oct. 4, 2022 in PCT Patent Application No. PCT/US2022/073426.
International Search Report and Written Opinion dated Oct. 27, 2022 in PCT Patent Application No. PCT/US2022/073432.
International Search Report and Written Opinion dated Sep. 14, 2022 in PCT Patent Application No. PCT/US2022/073430.
International Search Report and Written Opinion dated Sep. 23, 2022 in PCT Patent Application No. PCT/US2022/073428.
International Search Report and Written Opinion dated Sep. 28, 2022 in PCT Patent Application No. PCT/US2022/073431.
International Search Report and Written Opinion dated Sep. 20, 2018 in PCT Patent Application No. PCT/US2018/042195.
International Search Report and Written Opinion dated Sep. 28, 2022 in PCT Patent Application No. PCT/US2022/073433.
Iwamoto et al., "Control of Phosphorothioate Stereochemistry Substantially Increases the Efficacy of Antisense Oligonucleotides," Nature Biotechnology 2017, 35(9), 845-851.
Jafar-Nejad et al., "The atlas of RNase H antisense oligonucleotide distribution and activity in the CNS of rodents and non-human primates following central administration," Nucleic Acids Research 2021, 49(2), 657-673.
Japanese Office Action dated Jul. 4, 2023 in Japanese Patent Application No. 2021531622.
Japanese Search Report dated Jun. 23, 2023 in Japanese Patent Application No. 2021531622.
Jaramillo-Botero et al., "First-principles-based multiscale, multiparadigm molecular mechanics and dynamics methods for describing complex chemical processes," Multiscale Molecular Methods in Applied Chemistry 2012, 1-42.
Jessup & Brozena, "Heart Failure," New England Journal of Medicine 2003, 348, 2007-2018.
Joe et al., "Astrocytes, microglia, and Parkinson's disease," Experimental Neurobiology 2018, 27(2), 77-87.
Kadkol et al., "Comprehensive Analysis of CBFbeta-MYH11 Fusion Transcripts in Acute Myeloid Leukemia by RT-PCR Analysis," The Journal of Molecular Diagnostics 2004, 6(1), 22-27.
Katanosaka et al., "Calcineurin Inhibits Na+/Ca2+ Exchange in Phenylephrine-treated Hypertrophic Cardiomyocytes," Journal of Biological Chemistry 2005, 280, 5764-5772.
Keum et al., "Design, assembly, and activity of antisense DNA nanostructures," Small 2011, 7(24), 3529-3535.
Khvorova & Watts, "The chemical evolution of oligonucleotide therapies of clinical utility," Nature Biotechnology 2017, 35, 238-248.
Kim et al., "Synthetic dsRNA Dicer Substrates Enhance RNAi Potency and Efficacy," Nature Biotechnology 2005, 23(2), 222-226.
Knerr et al. "Glucagon like peptide 1 receptor agonists for targeted delivery of antisense oligonucleotides to pancreatic beta cell," Journal of the American Chemical Society 2021, 143(9), 3416-3429.
Konstam et al., "Left ventricular remodeling in heart failure: current concepts in clinical significance and assessment," JACC Cardiovasc Imaging 2011, 4(1), 98-108.
Kumar et al., "Combinatorially Inducible RNA Interference Triggered by Chemically Modified Oligonucleotides," Journal of the American Chemical Society 2011, 133, 2783-2788.

(56) References Cited

OTHER PUBLICATIONS

Kundu & Liu, "Function of the inv(16) Fusion Gene CBFB-MYH11," Hematology 2001, 8, 201-205.
Landry et al., "Progress in RNAi-Mediated Molecular Therapy of Acute and Chronic Myeloid Leukemia," Molecular Therapy—Nucleic Acids 2015, 4, in 23 pages.
Lee et al., "Differential Roles of Human Dicer-Binding Proteins TRBP and PACT in Small RNA Processing," Nucleic Acids Research 2013, 41(13), 6568-6576.
Lee et al., "Molecularly self-assembled nucleic acid nanoparticles for targeted in vivo siRNA delivery," Nature Nanotechnology 2012, 7, 389-393.
Lennox et al., "Improved Performance of Anti-miRNA Oligonucleotides Using a Novel Non-Nucleotide Modifier," Molecular Therapy—Nucleic Acids 2013, 2, in 19 pages.
Li et al., "Antiparallel DNA Double Crossover Molecules as Components for Nanoconstruction," Journal of the American Chemical Society 1996, 118, 6131-6140.
Lind et al., "Parameterization and Simulation of the Physical Properties of Phosphorothioate Nucleic Acids," Journal of the American Chemical Society 1998, 3, 41-54.
Liu et al., "miR-222 Is Necessary for Exercise-Induced Cardiac Growth and Protects against Pathological Cardiac Remodeling," Cell Metabolism 2015, 21, 584-595.
Loakes, "Survey and summary: The applications of universal DNA base analogues," Nucleic Acids Research 2001, 29(12), 2437-2447.
Look, "Oncogenic Transcription Factors in the Human Acute Leukemias," Science 1997, 278, 1059-1064.
Lu et al., "Linkers having a crucial role in antibody-drug conjugates," International Journal of Molecular Sciences 2016, 17, 561.
Lutgen et al., "β-Catenin signaling positively regulates glutamate uptake and metabolism in astrocytes," Journal of Neuroinflammation 2016, 13, 1-13.
Macke & Case, "Modeling Unusual Nucleic Acid Structures," ACS Symposium Series, American Chemical Society 1998, 24, 379-393.
Macrae et al., "Structural Basis for Double-Stranded RNA Processing by Dicer," Science 2006, 311, 195-198.
Mark & Nilsson, "Structure and Dynamics of the TIP3P, SPC, and SPC/E Water Models at298 K.," The Journal of Physical Chemistry A 2001, 105, 9954-9960.
Marks et al., "Histone deacetylases and cancer: causes and therapies," Nature Reviews Cancer 2001, 1(3), 194.
Mathews et al., "Expanded Sequence Dependence of Thermodynamic Parameters Improves Prediction of RNA Secondary Structure," Journal of Molecular Biology 1999, 288, 911-940.
Mathews Lab, "RNAstructure, Version 6.4," rochester.edu 2023, in 1 page. http://rna.urmc.rochester.edu/RNAstructure.html.
Mathy et al., "5'-to-3' Exoribonuclease Activity in Bacteria: Role of Rnase J1 in rRNA Maturation and 5' Stability of mRNA," Cell 2007, 129, 681-692.
Matsukura et al., "Phosphorothioate Analogs of Oligodeoxynucleotides: Inhibitors of Replication and Cytopathic Effects of Human Immunodeficiency Virus," Proceedings of the National Academy of Sciences 1987, 84, 7706-7710.
Meggers et al., "Synthesis and Properties of the Simplified Nucleic Acid Glycol Nucleic Acid," Accounts of Chemical Research 2010, 43(8), 1092-1102.
Millipore Sigma, "Locked Nucleic Acid," sigmaaldrich.com 2023, in 5 pages. www.sigmaaldrich.com/technical-documents/articles/biology/locked-nucleic-acids-faq.html.
Mirbase, "Stem-loop sequence hsa-mir-23a," mirbase.org 2023, in 3 pages. https://www.mirbase.org/cgi-bin/mirna_entry.pl?acc=MI0000079.
Molkentin et al., "Calcineurin-Dependent Transcriptional Pathway for Cardiac Hypertrophy," Cell 1998, 93, 215-228.
Morel et al., "Neuronal exosomal miRNA-dependent translational regulation of astroglial glutamate transporter GLT1," Journal of Biological Chemistry 2013, 288(10), 7105-7116.
Mukherjee et al., "Design of a DNA-Programmed Plasminogen Activator," Journal of the American Chemical Society 2018, 140(45), 15516-15524.
Naito & Kumiko, "Designing functional siRNA with reduced off-target effects," siRNA Design: Methods and Protocols 2013, 57-68.
Nearest Neighbor Database, "Introduction and Definitions," rochester.edu 2023, in 4 pages. https://rna.urmc.rochester.edu/NNDB/help.html.
Nearest Neighbor Database, "Version 1.02, Released Apr. 4, 2011," rochester.edu 2023, in 3 pages. https://rna.urmc.rochester.edu/NNDB/index.html.
Nolan et al., "Quantification of mRNA using real-time RT-PCR," Nature Protocols 2006, 1(3), 1559-1582.
Non-Final Office Action dated Dec. 24, 2021 in U.S. Appl. No. 16/786,793.
Non-Final Office Action dated Jun. 23, 2022 in U.S. Appl. No. 16/786,793.
Notice of Allowance dated Jan. 12, 2023 in U.S. Appl. No. 16/786,793.
Office Action dated Feb. 27, 2023 in Chinese Patent Application No. 201880066486.5.
Office Action dated Sep. 20, 2023 in Chinese Patent Application No. 201880066486.5.
Opferman et al., "Obligate Role of Anti-Apoptotic MCL-1 in the Survival of Hematopoietic Stem Cells," Science 2005, 307(5712), 1101-1104.
Orban & Izaurralde, "Decay of mRNAs Targeted by RISC Requires XRN1, the Ski Complex, and the Exosome," RNA 2005, 11, 459-469.
Owczarzy et al., "IDT SciTools: a suite for analysis and design of nucleic acid oligomers," Nucleic Acids Research 2008, 36(suppl_2), W163-W169.
Pajarillo et al., "Astrocyte-specific deletion of the transcription factor Yin Yang 1 in murine substantia nigra mitigates manganese-induced dopaminergic neurotoxicity," Journal of Biological Chemistry 2020, 295(46), 15662-15676.
Paradis et al., "Newborn Hypoxia/Anoxia Inhibits Cardiomyocyte Proliferation and Decreases Cardiomyocyte Endowment in the Developing Heart: Role of Endothelin-1," PLOS ONE 2015, 10, in 21 pages.
Pettersen et al., "UCSF Chimera—A Visualization System for Exploratory Research and Analysis," Journal of Computational Chemistry 2004, 25, 1605-1612.
Pi et al., "RNA nanoparticles harboring annexin A2 aptamer can target ovarian cancer for tumor-specific doxorubicin delivery," Nanomedicine 2017, 13(3), 1183-1193.
Picco & Garnett, "A Road Map for Precision Cancer Medicine Using Personalized Models," Cancer Discovery 2017, 7(5), 456-458.
Plimpton, "Fast Parallel Algorithms for Short-Range Molecular Dynamics," Journal of Computational Physics 1995, 117, 1-19.
Qi et al., "HDAC8 Inhibition Specifically Targets Inv(16) Acute Myeloid Leukemic Stem Cells by Restoring p53 Acetylation," Cell Stem Cell 2015, 17(5), 597-610.
Qiagen, "Design Guidelines," qiagen.com 2020, in 1 page. https://www.qiagen.com/us/service-and-support/learning-hub/technologies-and-research-topics/lna/custom-lna-design-and-applications/lna-design-tools-calculators/lna-oligo-tm-prediction/.
Qiagen, "LNA Oligo Optimizer," qiagen.com 2020, in 1 page. https://www.qiagen.com/us/service-and-support/learning-hub/technologies-and-research-topics/lna/custom-lna-design-and-applications/lna-design-tools-calculators/lna-oligo-optimizer/.
Red Server, "RESP ESP charge Derive server," q4md-forcefieldtools.org 2023, in 2 pages. q4md-forcefieldtools.org/REDServer/.
Restriction Requirement dated Aug. 3, 2023 in U.S. Appl. No. 16/631,134.
Restriction Requirement dated Aug. 19, 2022 in U.S. Appl. No. 17/172,461.
Rij, "Virus meets RNAi. Symposium on Antiviral Applications of RNA Interference," EMBO Reports 2008, 9(8), 725-729.
Robinson et al., "Integrative clinical genomics of metastatic cancer," Nature 2017, 548(7667), 297-303.

(56) References Cited

OTHER PUBLICATIONS

Rojo et al., "GSK-3β down-regulates the transcription factor Nrf2 after oxidant damage: relevance to exposure of neuronal cells to oxidative stress," Journal of Neurochemistry 2008, 105(1), 192-202.
Rothemund, "Folding DNA to create nanoscale shapes and patterns," Nature 2006, 440 (7082), 297-302.
Sabir et al., "Branchpoint expansion in a fully complementary three-way DNA junction," Journal of the American Chemical Society 2012, 134(14), 6280-6285.
Sano et al., "Effect of asymmetric terminal structures of short RNA duplexes on the RNA interference activity and strand selection," Nucleic Acids Research 2008, 36, 5812-5821.
Scherer et al., "Optimization and Characterization of tRNA-shRNA Expression Constructs," Nucleic Acids Research 2007, 35(8), 2620-2628.
Schlegel et al., "Chirality Dependent Potency Enhancement and Structural Impact of Glycol Nucleic Acid Modification on siRNA," Journal of the American Chemical Society 2017, 139, 8537-8546.
Seeman, "DNA in a Material World," Nature 2003, 421, 427-431.
Setten et al., "The Current State and Future Directions of RNAi-Based Therapeutics," Nature Reviews Drug Discovery 2019, 18, 421-446.
Shu et al., "Programmable folding of fusion RNA in vivo and in vitro driven by pRNA 3WJ motif of phi29 DNA packaging motor," Nucleic Acids Research 2014, 42(2), in 9 pages.
Shu et al., "Thermodynamically stable RNA three-way junction for constructing multifunctional nanoparticles for delivery of therapeutics," Nature Nanotechnology 2011, 6, 658-667.
Shukla et al., "Exploring Chemical Modifications for siRNA Therapeutics: A Structural and Functional Outlook," ChemMedChem 2010, 5, 328-349.
Silverman, "Control of Macromolecular Structure and Function Using Covalently Attached Double-Stranded DNA Constraints," Molecular BioSystems 2007, 3, 24-29.
Srinivas et al., "On the Biophysics and Kinetics of Toehold-Mediated DNA Strand Displacement," Nucleic Acids Research 2013, 41(22), 10641-10658.
Srinivasan et al., "Alzheimer's patient microglia exhibit enhanced aging and unique transcriptional activation," Cell Reports 2020, 31(13), in 20 pages.
Supplementary European Search Report and European Search Opinion dated Apr. 8, 2021 in European Patent Application No. 18844244.6.
Sussman et al., "Prevention of Cardiac Hypertrophy in Mice by Calcineurin Inhibition," Science 1998, 281, 1690-1693.
Tham et al., "Pathophysiology of cardiac hypertrophy and heart failure: signaling pathways and novel therapeutic targets," Archives of Toxicology 2015, 89, 1401-1438.
The NUPACK Team, "NUPACK Cloud Alpha," nupack.org 2023, in 1 page. http://nupack.org.
Theoretical Biochemistry Group, "The ViennaRNA Package," Universitat Wien 2023, in 7 pages. https://www.tbi.univie.ac.at/RNA/.
Tolstrup et al., "OligoDesign: Optimal Design of LNA (Locked Nucleic Acid) Oligonucleotide Capture Probes for Gene Expression Profiling," Nucleic Acids Research 2003, 31 (13), 3758-3762.
Trivedi et al., "Hdac2 regulates the cardiac hypertrophic response by modulating Gsk3J3 activity," Nature Medicine 2007, 13, 324-331.
Turner & Mathews, "NNDB: the nearest neighbor parameter database for predicting stability of nucleic acid secondary structure," Nucleic Acids Research 2010, 38(suppl_1), D280-D282.
Vargas & Johnson, "The Nrf2-ARE cytoprotective pathway in astrocytes," Expert Reviews in Molecular Medicine 2009, 11, in 20 pages.
Verma & Eckstein, "Modified oligonucleotides: synthesis and strategy for users," Annual Review of Biochemistry 1998, 67(1), 99-134.
Walsh et al., "DNA cage delivery to mammalian cells," ACS Nano 2011, 5(7), 5427-5432.
Wang et al., "Development and Testing of a General Amber Force Field," Journal of Computational Chemistry 2004, 25, 1157-1174.
Wikipedia, "Locked Nucleic Acid," eikipedia.org 2023, in 4 pages. https://en.wikipedia.org/wiki/Locked_nucleic_acid.
Wolfe et al., "Constrained multistate sequence design for nucleic acid reaction pathway engineering," Journal of the American Chemical Society 2017, 139, 3134-3144.
Wolfe et al., "Sequence design for a test tube of interacting nucleic acid strands," ACS Synthetic Biology 2015, 4, 1086-1100.
X3DNA, "x3DNA-DSSR: The Next Generation of 3DNA with Unmatched Features for RNA Structural Bioinformatics," x3dna.org 2023, in 3 pages. https://x3dna.org/articles/seeing-is-understanding-as-well-as-believing.
Xiao et al., "miR-31a-5p promotes postnatal cardiomyocyte proliferation by targeting RhoBTB1," Experimental & Molecular Medicine 2017, 49, in 10 pages.
Yang et al., "Studies of the 5' Exonuclease and Endonuclease Activities of CPSF-73 in Histone Pre-mRNA Processing," Molecular and Cellular Biology 2009, 29(1), 31-42.
Yurke et al., "A DNA-Fuelled Molecular Machine Made of DNA," Nature 2000, 406, 605-608.
Zadeh et al., "Nucleic acid sequence design via efficient ensemble defect optimization," Journal of Computational Chemistry 2011, 32, 439-452.
Zadeh et al., "NUPACK: analysis and design of nucleic acid systems," Journal of Computational Chemistry 2011, 32, 170-173.
Zhang et al., "Mcl-1 is Critical for Survival in a Subgroup of Non-Small-Cell Lung Cancer Cell Lines," Oncogene 2011, 30, 1963-1968.
Zhang et al., "Structural DNA nanotechnology: state of the art and future perspective," Journal of the American Chemical Society 2014, 136(32), 11198-111211.
Zhou et al., "Selection, Characterization and Application of New RNA HIV gp 120 Aptamers for Facile Delivery of Dicer Substrate siRNAs into HIV Infected Cells," Nucleic Acids Research 2009, 37(9), 3094-3109.
Dai, Yifan et al. "Strand displacement strategies for biosensor applications." Trends in biotechnology 37.12 (2019): 1367-1382.
Fiedler et al., "Quantitative RT-PCR Methods for Mature microRNA Expression Analysis," RT-PCR Protocols: Second Edition 2010, 49-64.
Fornace, Mark E., et al. "NUPACK: analysis and design of nucleic acid structures, devices, and systems." (2022).
GeneCards: The Human Gene Database. Myosin Heavy Chain 7 (MYH7), available at: "www.genecards.org/cgi-bin/carddisp.pl?gene=MYH7", last accessed on Apr. 12, 2024 printed in 34 pages.
Gethers, Matthew Leroy. Therapeutic Opportunities and Approaches to Sequence Control for Nucleic Acids. California Institute of Technology, 2018.
Holohan et al., "Cancer drug resistance: an evolving paradigm," Nat Rev Cancer 2013, 13(10), 714-26.
Naito et al., "Designing Functional siRNA with Reduced Off-Target Effects," siRNA Design: Methods and Protocols 2013, 57-68.
National Library of Medicine. National Center for Biotechnology Information. Reference Sequence: NM_001527.3. *Homo sapiens* histone deacetylase 2 (HDAC2), transcript variant 1, mRNA. Available at: "www.ncbi.nlm.nih.gov/nuccore/NM_001527.3", last accessed on Apr. 12, 2024 printed in 7 pages.
Nearest Neighbor Database, available at: "https://rna.urmc.rochester.edu/NNDB/index.html", last accessed on Jan. 17, 2024 printed in 2 Pages.
Nolan et al., "Quantification of mRNA using real-time RT-PCR," Nature Protocols 2006, 1, 1559-1582.
Non-Final Office Action dated Jan. 24, 2023 in U.S. Appl. No. 17/172,461.
Non-Final Office Action dated Jan. 30, 2024 in U.S. Appl. No. 16/631,134.
Office action dated Jan. 9, 2024 in Japanese Patent Application No. 2021-531622.
Office action dated Jul. 4, 2023 in Japanese Patent Application No. 2021-531622.
Office Action dated Nov. 11, 2023 in Chinese Patent Application No. 201980067384.X.

(56) References Cited

OTHER PUBLICATIONS

Office Action from U.S. Appl. No. 17/172,461 dated Aug. 19, 2022.
RESP ESP charge Derive (RED) Server Development. Avaibale at: "https://upjv.q4md-forcefieldtools.org/REDServer-Development/" last accessed on Apr. 12, 2024, printed in 2 pages.
Restriction Requirement dated Apr. 30, 2021 in U.S. Appl. No. 16/786,793.
Restriction Requirement dated May 23, 2023 in U.S. Appl. No. 16/638,107.
Setten, Ryan L. et al., "The current state and future directions of RNAi-based therapeutics." Nature reviews Drug discovery 18.6 (2019): 421-446.
SFold—Software for Statistical Folding and Studies of Regulatory RNAs, available at "https://sfold.wadsworth.org/cgi-bin/index.pl" last accessed on Jan. 17, 2014, printed in 3 pages.
Simmel, Friedrich C. et al., "Principles and applications of nucleic acid strand displacement reactions." Chemical reviews 119.10 (2019): 6326-6369.
Thermo Fisher Scientific Inc. Ppp3ca (protein phosphatase 3, catalytic subunit, alpha isoform) siRNA ID s72075, available at: "https://www.thermofisher.com/order/genome-database/browse/sirna/keyword/s72075" Last accessed on Apr. 12, 2024 printed in 2 pages.
Thole, Theresa M., et al. "Neuroblastoma cells depend on HDAC11 for mitotic cell cycle progression and survival." Cell death & disease 8.3 (2017): e2635-e2635.
UNAFold, available at: "http://www.unafold.org/", last accessed on Jan. 17, 2024 printed in 1 page.
Zhao et al., "Conditional RNA Interference in gene therapy research progress," Journal of Huazhong University of Science and Technology 2014, 43(4), 478-481.
GeneBank "*Homo sapiens* glycogen synthase kinase 3 beta (GSK3B), transcript variant 1, mRNA" available at: "https://www.ncbi.nlm.nih.gov/nuccore/NM_002093.4" last accessed on Jun. 7, 2024 printed in 5 Pages.
GeneBank "*Homo sapiens* glycogen synthase kinase 3 beta (GSK3B), transcript variant 2, mRNA", available at: "https://www.ncbi.nlm.nih.gov/nuccore/NM_001146156.2" last accessed on Jun. 7, 2024 printed in 6 Pages.
GeneBank "*Homo sapiens* glycogen synthase kinase 3 beta (GSK3B), transcript variant 3, mRNA", available at: "https://www.ncbi.nlm.nih.gov/nuccore/NM_001354596.2" last accessed on Jun. 7, 2024 printed in 5 Pages.
GeneBank "*Homo sapiens* inhibitor of nuclear factor kappa B kinase subunit beta (IKBKB), transcript variant 1, mRNA", available at: "https://www.ncbi.nlm.nih.gov/nuccore/NM_001556.3" last accessed on Jun. 12, 2024 printed in 8 Pages.
GeneBank "*Homo sapiens* inhibitor of nuclear factor kappa B kinase subunit beta (IKBKB), transcript variant 2, mRNA", available at: "https://www.ncbi.nlm.nih.gov/nuccore/1831772119" last accessed on Jun. 12, 2024 printed in 6 Pages.
GeneBank "*Homo sapiens* inhibitor of nuclear factor kappa B kinase subunit beta (IKBKB), transcript variant 7, mRNA", available at: "https://www.ncbi.nlm.nih.gov/nuccore/1677531062" last accessed on Jun. 12, 2024 printed in 6 Pages.
GeneBank "*Homo sapiens* RELA proto-oncogene, NF-kB subunit (RELA), transcript variant 1, mRNA", available at: "https://www.ncbi.nlm.nih.gov/nuccore/NM_021975.4" last accessed on Jun. 12, 2024 printed in 6 Pages.
GeneBank "*Homo sapiens* RELA proto-oncogene, NF-kB subunit (RELA), transcript variant 2, mRNA", available at: "https://www.ncbi.nlm.nih.gov/nuccore/NM_001145138.2" last accessed on Jun. 12, 2024 printed in 6 Pages.
GeneBank "*Homo sapiens* RELA proto-oncogene, NF-kB subunit (RELA), transcript variant 3, mRNA", available at: "https://www.ncbi.nlm.nih.gov/nuccore/NM_001243984.2" last accessed on Jun. 12, 2024 printed in 4 Pages.
GeneBank "*Homo sapiens* RELA proto-oncogene, NF-kB subunit (RELA), transcript variant 4, mRNA", available at: "https://www.ncbi.nlm.nih.gov/nuccore/NM_001243985.2" last accessed on Jun. 12, 2024 printed in 4 Pages.
GeneBank "Mus musculus glycogen synthase kinase 3 beta (Gsk3b), transcript variant 1, mRNA", available at: "https://www.ncbi.nlm.nih.gov/nuccore/1365045870" last accessed on Jun. 12, 2024 printed in 6 Pages.
GeneBank "Mus musculus glycogen synthase kinase 3 beta (Gsk3b), transcript variant 2, mRNA" available at: "https://www.ncbi.nlm.nih.gov/nuccore/NM_001347232.1" last accessed on Jun. 7, 2024 printed in 6 Pages.
GeneBank "Mus musculus inhibitor of kappaB kinase beta (Ikbkb), transcript variant 1, mRNA" available at: "https://www.ncbi.nlm.nih.gov/nuccore/NM_001159774.1" last accessed on Jun. 12, 2024 printed in 7 Pages.
GeneBank "Mus musculus inhibitor of kappaB kinase beta (Ikbkb), transcript variant 2, mRNA" available at: "https://www.ncbi.nlm.nih.gov/nuccore/NM_010546.2" last accessed on Jun. 12, 2024 printed in 7 Pages.
GeneBank "Mus musculus v-rel reticuloendotheliosis viral oncogene homolog A (avian) (Rela), transcript variant 1, mRNA", available at: "https://www.ncbi.nlm.nih.gov/nuccore/NM_009045.5" last accessed on Jun. 12, 2024 printed in 6 Pages.
GeneBank "Mus musculus v-rel reticuloendotheliosis viral oncogene homolog A (avian) (Rela), transcript variant 2, mRNA", available at: "https://www.ncbi.nlm.nih.gov/nuccore/NM_001365067.1" last accessed on Jun. 12, 2024 printed in 6 Pages.
GeneBank "Predicted: Mus musculus glycogen synthase kinase 3 beta (Gsk3b), transcript variant X1, mRNA", available at: "https://www.ncbi.nlm.nih.gov/nuccore/XM_030249221.2" last accessed on Jun. 12, 2024 printed in 3 Pages.
Notice of Allowance from U.S. Appl. No. 17/172,461 dated Feb. 9, 2024.
Notice of Allowance from U.S. Appl. No. 16/631,134 dated Jun. 5, 2024.
Office Action dated Sep. 26, 2024 in Chinese Patent Application No. 201980067384.X.
The Human Protein Atlas available at:"https://www.proteinatlas.org/" last accessed on Jun. 7, 2024 printed in 1 Page.

* cited by examiner

FIG. 4B
FIG. 4C
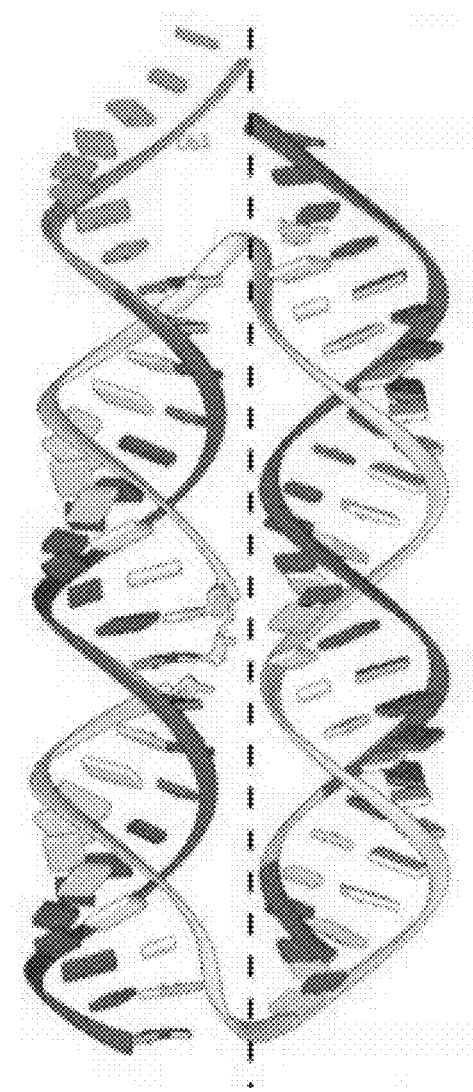
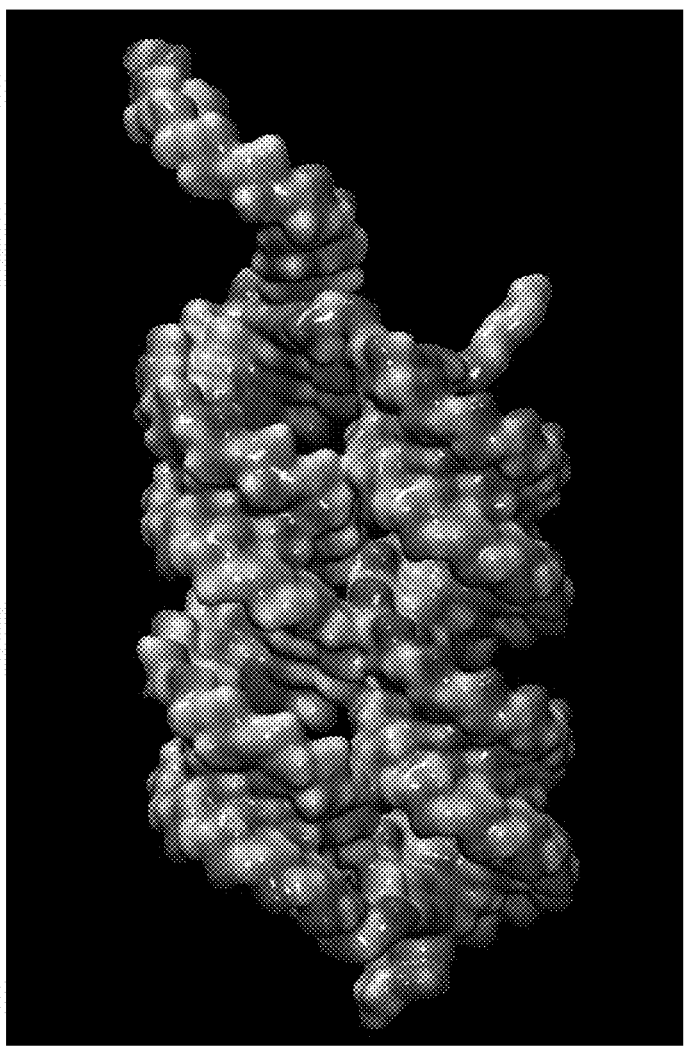

Free energy of secondary structure: -1.40 kcal/mol

FIG. 12A
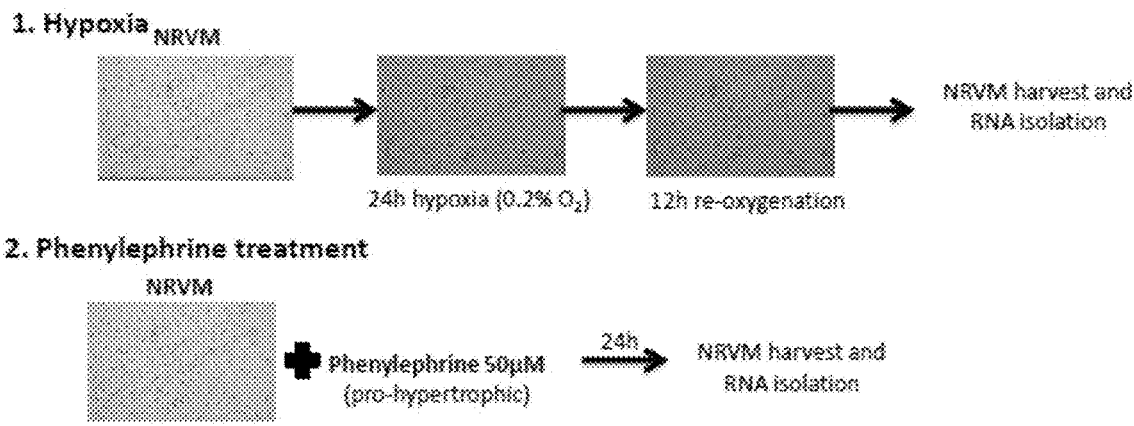
FIG. 12B
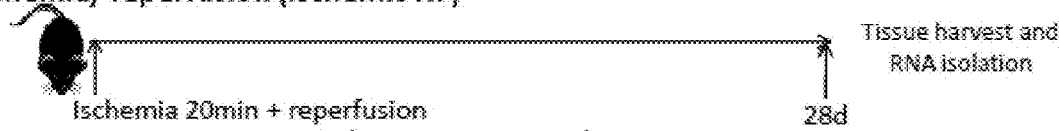
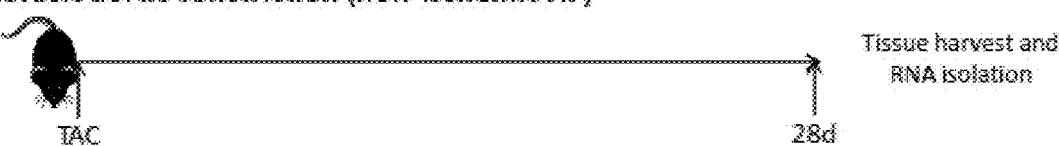

FIG. 13A
FIG. 13B
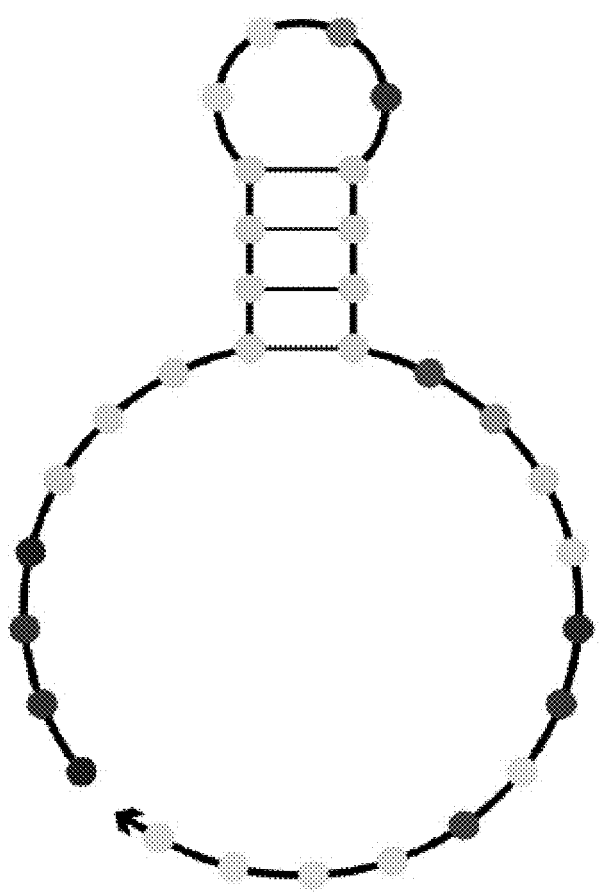
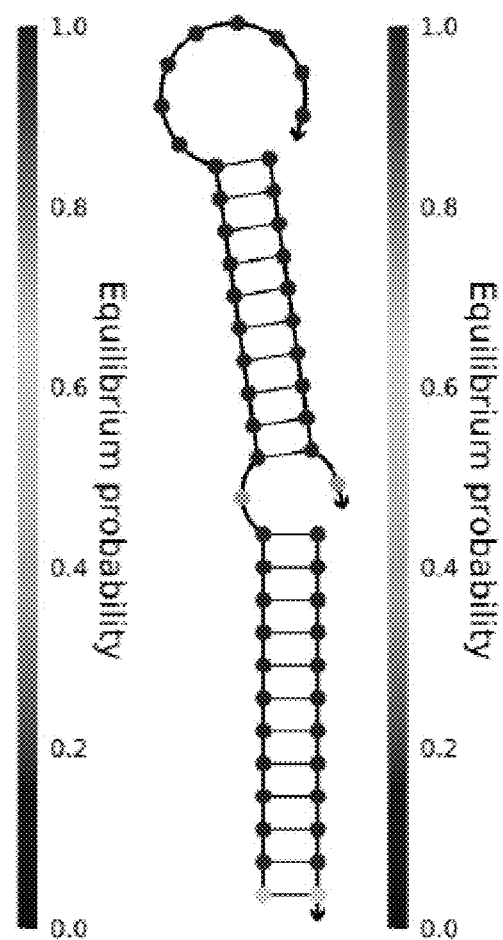

FIG. 14A  FIG. 14B
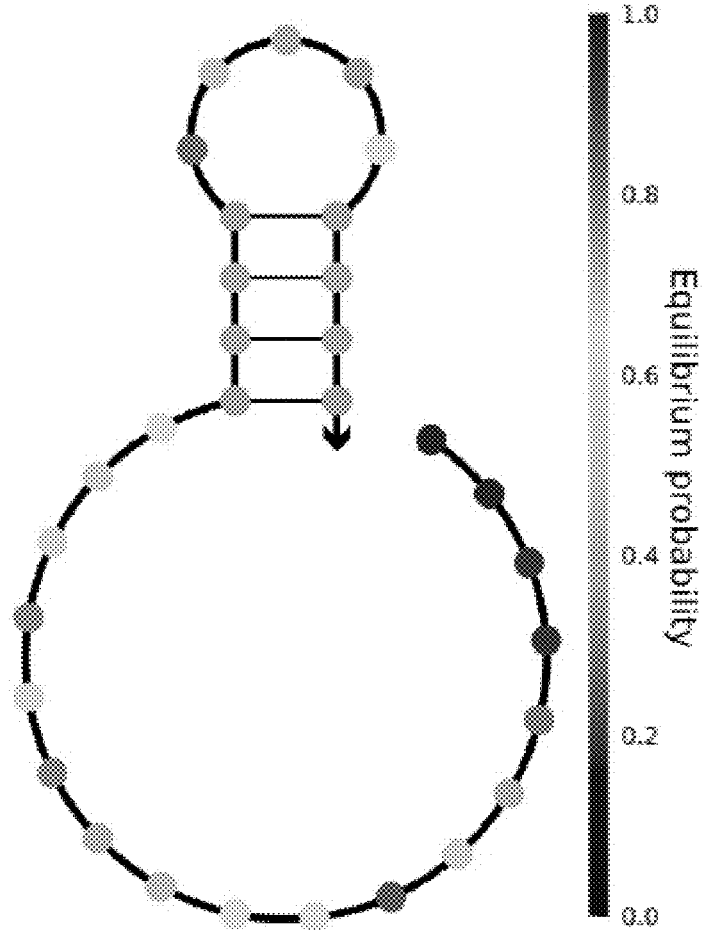
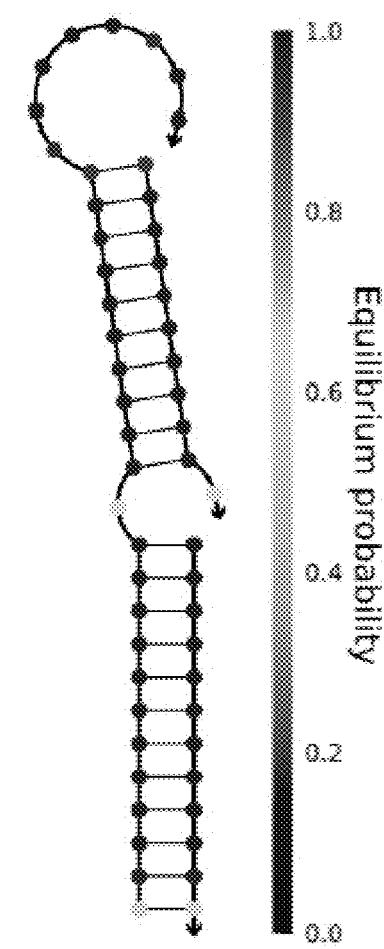

FIG. 15A
FIG. 15B
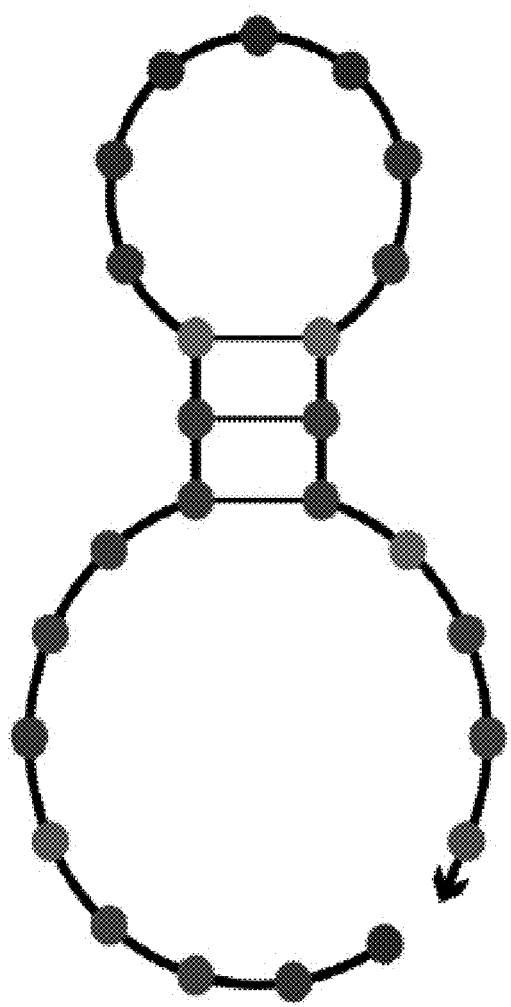
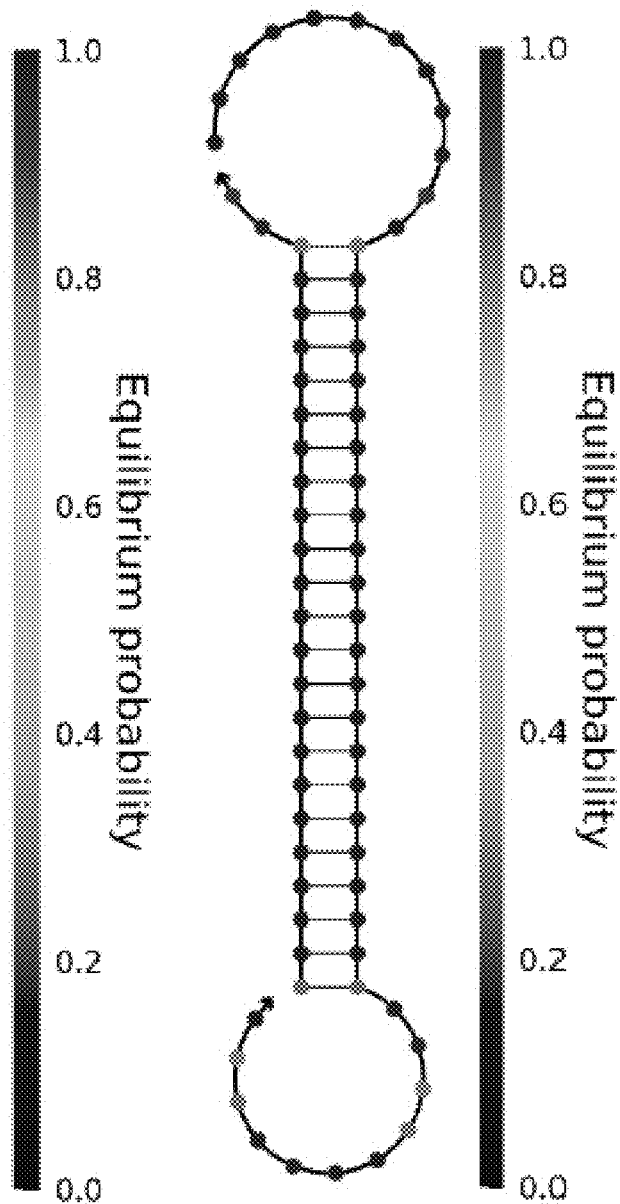

FIG. 16

Original ANP : Calcineurin

SEQ ID NO:10
3'-NH2*A*A*C*C*A*G*C*G*U*A*A*C*G*G*T*G*A*C*U*C*U*C*C*A*C*C*A*C*U*T*C.Sp9-5'
ANP sensor strand
| | | | | | | | | | | | | | | | | | | | | | | |
.A.U.U.G.C.C.A.C.U.G.A.G  A.G.G.U.G.G.U.G.A.A.G.
Core strand C3     ↓          3' 5'                          C3
!G*C.U.C.A.C.A.A.C.A.A.A.C.C.G.A.A.A.A.G.G*A*C! SEQ ID NO:19
Calcineurin guide strand
| | | | | | | | | | | | | | | | | | | | | | | |
5'-NH2.C*G.A.G.U.G.U.U.G.U.U.U.G.G.C.U.U.U.U.C.C.U.G.U.U-3'
         ↑        SEQ ID NO:12

---

New sensor with less PS and one more LNA (middle C) in toehold

SEQ ID NO:10
3'-NH2*A*A*C*C*A*G*C*G*U.A.A.C.G.G.T.G.A.C.U.C.U.C.C.A.C.C.A.C.U.T.C.Sp9-5'
ANP sensor strand
| | | | | | | | | | | | | | | | | | | | | | | |
.A.U.U.G.C.C.A.C.U.G.A.G  A.G.G.U.G.G.U.G.A.A.G.
Core strand C3     ↓          3' 5'                          C3
!G*C.U.C.A.C.A.A.C.A.A.A.C.C.G.A.A.A.A.G.G*A*C! SEQ ID NO:19
Calcineurin guide strand
| | | | | | | | | | | | | | | | | | | | | | | |
5'-NH2.C*G.A.G.U.G.U.U.G.U.U.U.G.G.C.U.U.U.U.C.C.U.G.U.U-3'
         ↑        SEQ ID NO:12

---

New sensor plus modified guide

SEQ ID NO:10
3'-NH2*A*A*C*C*A*G*C*G*U.A.A.C.G.G.T.G.A.C.U.C.U.C.C.A.C.C.A.C.U.T.C.Sp9-5'
ANP sensor strand
| | | | | | | | | | | | | | | | | | | | | | | |
.A.U.U.G.C.C.A.C.U.G.A.G  A.G.G.U.G.G.U.G.A.A.G.
Core strand C3     ↓          3' 5'                          C3
!G*C.U.C.A.C.A.A.C.A.A.A.C.C.G.A.A.A.A.G.G*A*C! SEQ ID NO:19
Calcineurin guide strand
| | | | | | | | | | | | | | | | | | | | | | | |
5'-NH2.C*G.A.G.U.G.U.U.G.U.U.U.G.G.C.U.U.U.U.C.C.U.G.U.U-3'
         ↑ SEQ ID NO:12

---

**New sensor with Cholesterol*TEG, modified guide**

SEQ ID NO:10
3'-Chol*A*A*C*C*A*G*C*G*U.A.A.C.G.G.T.G.A.C.U.C.U.C.C.A.C.C.A.C.U.T.C.Sp9-5'
| | | | | | | | | | | | | | | | | | | | | | | |
.A.U.U.G.C.C.A.C.U.G.A.G  A.G.G.U.G.G.U.G.A.A.G.
C3                             3'  5'                               C3
.G*C.U.C.A.C.A.A.C.A.A.A.C.C.G.A.A.A.A.G.G*A*C. SEQ ID NO:19
| | | | | | | | | | | | | | | | | | | | | | | |
5'-NH2.C*G.A.G.U.G.U.U.G.U.U.U.G.G.C.U.U.U.U.C.C.U.G.U.U-3'
SEQ ID NO:12

---

▓ = LNA; ▓ = 2'-O-methyl; ▓ = RNA; . = phosphodiester; * = phosphorothioate; ↑ = Dicer cleavage site;
▓ = Exonuclease blocking domain; C3 = C3 spacer; Sp9 = triethylene glycol; NH2 = primary amine linker

FIG. 17

Original mir-23a-3p : Calcineurin
SEQ ID NO:1
3'-NH2*T*A*G*T*G*U*A*A*C*G*G*U*C*C*C*U*A*A*A*G*G*C*A*A*G*A*A*G*C.Sp9-5'
mir-23a-3p sensor strand     | | | | | | | | | | | | | | | | | | | | | |
.U.G.C.C.A.G.G.G.A.U.U  U.C.C.G.U.U.C.U.U.C.G.
Core strand C3                                  3' 5'                              C3
!C.U.C.A.C.A.A.C.A.A.A.C.C.G.A.A.A.A.G.! SEQ ID NO:41
Calcineurin guide strand     | | | | | | | | | | | | | | | | | | | | | |
5'-NH2.C*G.A.G.U.G.U.U.G.U.U.U.G.G.C.U.U.U.U.C.C.U.G.U.U-3'
↑    SEQ ID NO:12

Updated with new sensor with no PS and different LNA pattern
SEQ ID NO:2
3'-NH2*U*A*G*T*G*T*A*A.C.G.G.T.C.C.C.U.A.A.A.G.G.C.A.A.G.A.A.G.C.Sp9-5'
mir-23a-3p sensor II         | | | | | | | | | | | | | | | | | | | | | |
.U.G.C.C.A.G.G.G.A.U.U  U.C.C.G.U.U.C.U.U.C.G.
Core strand C3                                  3' 5'                              C3
!C.U.C.A.C.A.A.C.A.A.A.C.C.G.A.A.A.A.G.! SEQ ID NO:41
Calcineurin guide strand     | | | | | | | | | | | | | | | | | | | | | |
5'-NH2.C*G.A.G.U.G.U.U.G.U.U.U.G.G.C.U.U.U.U.C.C.U.G.U.U-3'
↑    SEQ ID NO:12

Updated with new sensor and new guide
SEQ ID NO:2
3'-NH2*U*A*G*T*G*T*A*A.C.G.G.T.C.C.C.U.A.A.A.G.G.C.A.A.G.A.A.G.C.Sp9-5'
mir-23a-3p sensor II         | | | | | | | | | | | | | | | | | | | | | |
.U.G.C.C.A.G.G.G.A.U.U  U.C.C.G.U.U.C.U.U.C.G.
Core strand C3                                  3' 5'                              C3
!C.U.C.A.C.A.A.C.A.A.A.C.C.G.A.A.A.A.G.! SEQ ID NO:41
Calcineurin guide strand     | | | | | | | | | | | | | | | | | | | | | |
5'-NH2.C*G.A.G.U.G.U.U.G.U.U.U.G.G.C.U.U.U.U.C.C.U.G.U.U-3'
↑    SEQ ID NO:12

Updated with new sensor, guide, and cholesterol mod
SEQ ID NO:2
3'-Chol*U*A*G*T*G*T*A*A.C.G.G.T.C.C.C.U.A.A.A.G.G.C.A.A.G.A.A.G.C.Sp9-5'
mir-23a-3p sensor II         | | | | | | | | | | | | | | | | | | | | | |
.U.G.C.C.A.G.G.G.A.U.U  U.C.C.G.U.U.C.U.U.C.G.
Core strand C3                                  3' 5'                              C3
!C.U.C.A.C.A.A.C.A.A.A.C.C.G.A.A.A.A.G.! SEQ ID NO:41
Calcineurin guide strand     | | | | | | | | | | | | | | | | | | | | | |
5'-NH2.C*G.A.G.U.G.U.U.G.U.U.U.G.G.C.U.U.U.U.C.C.U.G.U.U-3'
↑    SEQ ID NO:12

▓ = LNA; ▓ = 2'-O-methyl; ▓ = RNA; . = phosphodiester; * = phosphorothioate; ↑ = Dicer cleavage site;
▓ = Exonuclease blocking domain; C3 = C3 spacer; Sp9 = triethylene glycol; NH2 = primary amine linker

FIG. 21
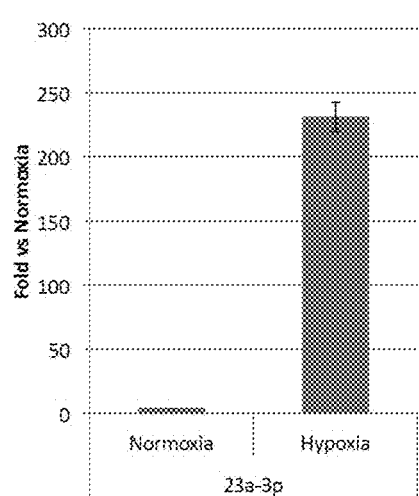
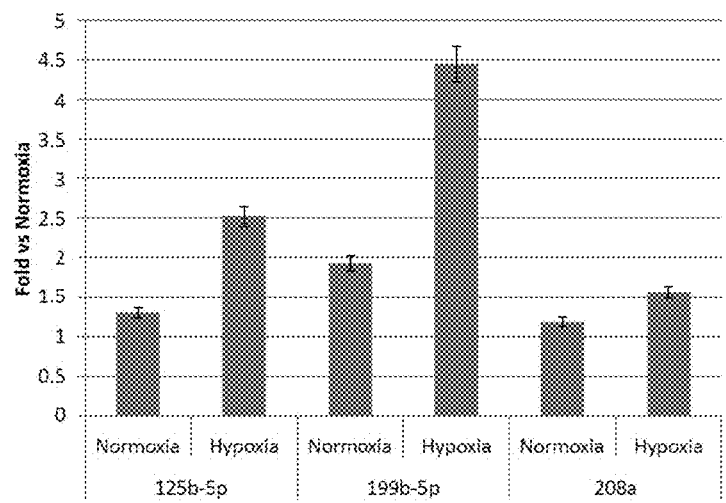

Free energy of secondary structure: -43.68 kcal/mol

FIG. 39

| SEQUENCE | BS | GCNESS | 3LN | NBP | P |
|---|---|---|---|---|---|
| 'CCAAGGAGCUGUUACACAGGCUCCAGCAUGG' (SEQ ID NO:50) | [[], [], []] | 0.580645 | 0.83871 | 0 | 37 |
| 'GGCUCCAGCAUGGGGCUUUGCUGGCACCUCC' (SEQ ID NO:168) | [[], ['GGG'], []] | 0.677419 | 0.903226 | 1 | 55 |
| 'CCAGGGCUGAGCAGAUCAAGAUGUGGCAAAG' (SEQ ID NO:169) | [[], ['GGG'], []] | 0.548387 | 0.870968 | 1 | 84 |
| 'CAGGGCUGAGCAGAUCAAGAUGUGGCAAAGC' (SEQ ID NO:170) | [[], ['GGG'], []] | 0.548387 | 0.870968 | 1 | 85 |
| 'GCUGGCACCUCCAGGGCUGAGCAGAUCAAGA' (SEQ ID NO:171) | [[], ['GGG'], []] | 0.612903 | 0.870968 | 1 | 74 |
| 'CAGGCUCCAGCAUGGGGCUUUGCUGGCACCU' (SEQ ID NO:172) | [[], ['GGG'], []] | 0.645161 | 0.870968 | 1 | 53 |
| 'AGGCUCCAGCAUGGGGCUUUGCUGGCACCUC' (SEQ ID NO:173) | [[], ['GGG'], []] | 0.645161 | 0.870968 | 1 | 54 |
| 'GCUCCAGCAUGGGGCUUUGCUGGCACCUCCA' (SEQ ID NO:174) | [[], ['GGG'], []] | 0.645161 | 0.870968 | 1 | 56 |

| SEQUENCE | BS | GCNESS | 3LN | NBP | P |
|---|---|---|---|---|---|
| 'CUCCAGCAUGGGGCUUUGCUGGCACCUCCAG' (SEQ ID NO:175) | [[], ['GGG'], []] | 0.645161 | 0.870968 | 1 | 57 |
| 'UCCAGCAUGGGGCUUUGCUGGCACCUCCAGG' (SEQ ID NO:176) | [[], ['GGG'], []] | 0.645161 | 0.870968 | 1 | 58 |
| 'AUUCUGCUUCCUCCCAAGGAGCUGUUACACA' (SEQ ID NO:177) | [['CCC'], [], []] | 0.483871 | 0.83871 | 1 | 24 |
| 'UCCAGGGCUGAGCAGAUCAAGAUGUGGCAAA' (SEQ ID NO:178) | [[], ['GGG'], []] | 0.516129 | 0.83871 | 1 | 83 |
| 'UGUUACACAGGCUCCAGCAUGGGGCUUUGCU' (SEQ ID NO:179) | [[], ['GGG'], []] | 0.548387 | 0.83871 | 1 | 46 |
| 'CUCCAGGGCUGAGCAGAUCAAGAUGUGGCAA' (SEQ ID NO:180) | [[], ['GGG'], []] | 0.548387 | 0.83871 | 1 | 82 |
| 'CUCCCAAGGAGCUGUUACACAGGCUCCAGCA' (SEQ ID NO:181) | [['CCC'], [], []] | 0.580645 | 0.83871 | 1 | 34 |
| 'CCCAAGGAGCUGUUACACAGGCUCCAGCAUG' (SEQ ID NO:182) | [['CCC'], [], []] | 0.580645 | 0.83871 | 1 | 36 |

FIG. 39 (Cont'd)

| SEQUENCE | BS | GCNESS | 3LN | NBP | P |
|---|---|---|---|---|---|
| 'CAAGGAGCUGUUACACAGGCUCCAGCAUGGG' (SEQ ID NO:183) | [[], ['GGG'], []] | 0.580645 | 0.83871 | 1 | 38 |
| 'AAGGAGCUGUUACACAGGCUCCAGCAUGGGG' (SEQ ID NO:184) | [[], ['GGG'], []] | 0.580645 | 0.83871 | 1 | 39 |
| 'GCUGUUACACAGGCUCCAGCAUGGGGCUUUG' (SEQ ID NO:185) | [[], ['GGG'], []] | 0.580645 | 0.83871 | 1 | 44 |
| 'CUGUUACACAGGCUCCAGCAUGGGGCUUUGC' (SEQ ID NO:186) | [[], ['GGG'], []] | 0.580645 | 0.83871 | 1 | 45 |
| 'GUUACACAGGCUCCAGCAUGGGGCUUUGCUG' (SEQ ID NO:187) | [[], ['GGG'], []] | 0.580645 | 0.83871 | 1 | 47 |
| 'UUACACAGGCUCCAGCAUGGGGCUUUGCUGG' (SEQ ID NO:188) | [[], ['GGG'], []] | 0.580645 | 0.83871 | 1 | 48 |
| 'CUGGCACCUCCAGGGCUGAGCAGAUCAAGAU' (SEQ ID NO:189) | [[], ['GGG'], []] | 0.580645 | 0.83871 | 1 | 75 |
| 'UGGCACCUCCAGGGCUGAGCAGAUCAAGAUG' (SEQ ID NO:190) | [[], ['GGG'], []] | 0.580645 | 0.83871 | 1 | 76 |

FIG. 39 (Cont'd)

| SEQUENCE | BS | GCNESS | 3LN | NBP | P |
|---|---|---|---|---|---|
| 'GGCACCUCCAGGGCUGAGCAGAUCAAGAUGU' (SEQ ID NO:191) | [[], ['GGG'], []] | 0.580645 | 0.83871 | 1 | 77 |
| 'GCACCUCCAGGGCUGAGCAGAUCAAGAUGUG' (SEQ ID NO:192) | [[], ['GGG'], []] | 0.580645 | 0.83871 | 1 | 78 |
| 'CACCUCCAGGGCUGAGCAGAUCAAGAUGUGG' (SEQ ID NO:193) | [[], ['GGG'], []] | 0.580645 | 0.83871 | 1 | 79 |
| 'ACCUCCAGGGCUGAGCAGAUCAAGAUGUGGC' (SEQ ID NO:194) | [[], ['GGG'], []] | 0.580645 | 0.83871 | 1 | 80 |
| 'CCUCCAGGGCUGAGCAGAUCAAGAUGUGGCA' (SEQ ID NO:195) | [[], ['GGG'], []] | 0.580645 | 0.83871 | 1 | 81 |
| 'CCUCCCAAGGAGCUGUUACACAGGCUCCAGC' (SEQ ID NO:196) | [['CCC'], [], []] | 0.612903 | 0.83871 | 1 | 33 |
| 'AGGAGCUGUUACACAGGCUCCAGCAUGGGGC' (SEQ ID NO:197) | [[], ['GGG'], []] | 0.612903 | 0.83871 | 1 | 40 |
| 'UACACAGGCUCCAGCAUGGGGCUUUGCUGGC' (SEQ ID NO:198) | [[], ['GGG'], []] | 0.612903 | 0.83871 | 1 | 49 |

FIG. 39 (Cont'd)

| SEQUENCE | BS | GCNESS | 3LN | NBP | P |
|---|---|---|---|---|---|
| 'GCUUUGCUGGCACCUCCAGGGCUGAGCAGAU' (SEQ ID NO:199) | [[], ['GGG'], []] | 0.612903 | 0.83871 | 1 | 69 |
| 'CUUUGCUGGCACCUCCAGGGCUGAGCAGAUC' (SEQ ID NO:200) | [[], ['GGG'], []] | 0.612903 | 0.83871 | 1 | 70 |
| 'UGCUGGCACCUCCAGGGCUGAGCAGAUCAAG' (SEQ ID NO:201) | [[], ['GGG'], []] | 0.612903 | 0.83871 | 1 | 73 |
| 'CACAGGCUCCAGCAUGGGGCUUUGCUGGCAC' (SEQ ID NO:202) | [[], ['GGG'], []] | 0.645161 | 0.83871 | 1 | 51 |
| 'ACAGGCUCCAGCAUGGGGCUUUGCUGGCACC' (SEQ ID NO:203) | [[], ['GGG'], []] | 0.645161 | 0.83871 | 1 | 52 |
| 'GGCUUUGCUGGCACCUCCAGGGCUGAGCAGA' (SEQ ID NO:204) | [[], ['GGG'], []] | 0.645161 | 0.83871 | 1 | 68 |
| 'UUCUGCUUCCUCCCAAGGAGCUGUUACACAG' (SEQ ID NO:205) | [['CCC'], [], []] | 0.516129 | 0.806452 | 1 | 25 |
| 'UCUGCUUCCUCCCAAGGAGCUGUUACACAGG' (SEQ ID NO:206) | [['CCC'], [], []] | 0.548387 | 0.806452 | 1 | 26 |

FIG. 39 (Cont'd)

| SEQUENCE | BS | GCNESS | 3LN | NBP | P |
|---|---|---|---|---|---|
| 'UGCUUCCUCCCAAGGAGCUGUUACACAGGCU' (SEQ ID NO:207) | [['CCC'], [], []] | 0.548387 | 0.806452 | 1 | 28 |
| 'UUCCUCCCAAGGAGCUGUUACACAGGCUCCA' (SEQ ID NO:208) | [['CCC'], [], []] | 0.548387 | 0.806452 | 1 | 31 |
| 'UCCCAAGGAGCUGUUACACAGGCUCCAGCAU' (SEQ ID NO:209) | [['CCC'], [], []] | 0.548387 | 0.806452 | 1 | 35 |
| 'AGCUGUUACACAGGCUCCAGCAUGGGGCUUU' (SEQ ID NO:210) | [[], ['GGG'], []] | 0.548387 | 0.806452 | 1 | 43 |
| 'CUGCUUCCUCCCAAGGAGCUGUUACACAGGC' (SEQ ID NO:211) | [['CCC'], [], []] | 0.580645 | 0.806452 | 1 | 27 |
| 'GCUUCCUCCCAAGGAGCUGUUACACAGGCUC' (SEQ ID NO:212) | [['CCC'], [], []] | 0.580645 | 0.806452 | 1 | 29 |
| 'CUUCCUCCCAAGGAGCUGUUACACAGGCUCC' (SEQ ID NO:213) | [['CCC'], [], []] | 0.580645 | 0.806452 | 1 | 30 |
| 'UCCUCCCAAGGAGCUGUUACACAGGCUCCAG' (SEQ ID NO:214) | [['CCC'], [], []] | 0.580645 | 0.806452 | 1 | 32 |

FIG. 39 (Cont'd)

| SEQUENCE | BS | GCNESS | 3LN | NBP | P |
|---|---|---|---|---|---|
| 'GAGCUGUUACACAGGCUCCAGCAUGGGGCUU' (SEQ ID NO:215) | [[], ['GGG'], []] | 0.580645 | 0.806452 | 1 | 42 |
| 'UUUGCUGGCACCUCCAGGGCUGAGCAGAUCA' (SEQ ID NO:216) | [[], ['GGG'], []] | 0.580645 | 0.806452 | 1 | 71 |
| 'UUGCUGGCACCUCCAGGGCUGAGCAGAUCAA' (SEQ ID NO:217) | [[], ['GGG'], []] | 0.580645 | 0.806452 | 1 | 72 |
| 'GGAGCUGUUACACAGGCUCCAGCAUGGGGCU' (SEQ ID NO:218) | [[], ['GGG'], []] | 0.612903 | 0.806452 | 1 | 41 |
| 'ACACAGGCUCCAGCAUGGGCUUUGCUGGCA' (SEQ ID NO:219) | [[], ['GGG'], []] | 0.612903 | 0.806452 | 1 | 50 |
| 'GCAUGGGGCUUUGCUGGCACCUCCAGGGCUG' (SEQ ID NO:220) | [[], ['GGG', 'GGG'], []] | 0.677419 | 0.903226 | 2 | 62 |
| 'UGGGGCUUUGCUGGCACCUCCAGGGCUGAGC' (SEQ ID NO:221) | [[], ['GGG', 'GGG'], []] | 0.677419 | 0.903226 | 2 | 65 |
| 'CUUCAAGGAAAAUUGCUUUAUUCUGCUUCCU' (SEQ ID NO:222) | [[], [], ['AAAA', 'UUUA']] | 0.354839 | 0.870968 | 2 | 5 |

| SEQUENCE | BS | GCNESS | 3LN | NBP | P |
|---|---|---|---|---|---|
| 'UUCAAGGAAAAUUGCUU UAUUCUGCUUCCUC' (SEQ ID NO:223) | [[], [], ['AAAA', 'UUUA']] | 0.354839 | 0.870968 | 2 | 6 |
| 'UCAAGGAAAAUUGCUUU AUUCUGCUUCCUCC' (SEQ ID NO:224) | [[], [], ['AAAA', 'UUUA']] | 0.387097 | 0.870968 | 2 | 7 |
| 'UUGCUUUAUUCUGCUUC CUCCCAAGGAGCUG' (SEQ ID NO:225) | [['CCC'], [], ['UUUA']] | 0.483871 | 0.870968 | 2 | 17 |
| 'UGCUUUAUUCUGCUUCC UCCCAAGGAGCUGU' (SEQ ID NO:226) | [['CCC'], [], ['UUUA']] | 0.483871 | 0.870968 | 2 | 18 |
| 'GCUUUAUUCUGCUUCCU CCCAAGGAGCUGUU' (SEQ ID NO:227) | [['CCC'], [], ['UUUA']] | 0.483871 | 0.870968 | 2 | 19 |
| 'AGCAUGGGGCUUUGCU GGCACCUCCAGGGCU' (SEQ ID NO:228) | [[], ['GGG', 'GGG'], []] | 0.645161 | 0.870968 | 2 | 61 |
| 'CAUGGGGCUUUGCUGG CACCUCCAGGGCUGA' (SEQ ID NO:229) | [[], ['GGG', 'GGG'], []] | 0.645161 | 0.870968 | 2 | 63 |
| 'AUGGGGCUUUGCUGGC ACCUCCAGGGCUGAG' (SEQ ID NO:230) | [[], ['GGG', 'GGG'], []] | 0.645161 | 0.870968 | 2 | 64 |

| SEQUENCE | BS | GCNESS | 3LN | NBP | P |
|---|---|---|---|---|---|
| 'CCAGCAUGGGGCUUUGCUGGCACCUCCAGGG' (SEQ ID NO:231) | [[], ['GGG', 'GGG'], []] | 0.677419 | 0.870968 | 2 | 59 |
| 'CAGCAUGGGGCUUUGCUGGCACCUCCAGGGC' (SEQ ID NO:232) | [[], ['GGG', 'GGG'], []] | 0.677419 | 0.870968 | 2 | 60 |
| 'GGGGCUUUGCUGGCACCUCCAGGGCUGAGCA' (SEQ ID NO:233) | [[], ['GGG', 'GGG'], []] | 0.677419 | 0.870968 | 2 | 66 |
| 'GGGCUUUGCUGGCACCUCCAGGGCUGAGCAG' (SEQ ID NO:234) | [[], ['GGG', 'GGG'], []] | 0.677419 | 0.870968 | 2 | 67 |
| 'GCUUCAAGGAAAAUUGCUUUAUUCUGCUUCC' (SEQ ID NO:235) | [[], [], ['AAAA', 'UUUA']] | 0.387097 | 0.83871 | 2 | 4 |
| 'AUUGCUUUAUUCUGCUUCCUCCCAAGGAGCU' (SEQ ID NO:236) | [['CCC'], [], ['UUUA']] | 0.451613 | 0.83871 | 2 | 16 |
| 'CUUUAUUCUGCUUCCUCCCAAGGAGCUGUUA' (SEQ ID NO:237) | [['CCC'], [], ['UUUA']] | 0.451613 | 0.83871 | 2 | 20 |

FIG. 39 (Cont'd)

| SEQUENCE | BS | GCNESS | 3LN | NBP | P |
|---|---|---|---|---|---|
| 'UUUAUUCUGCUUCCUCCCAAGGAGCUGUUAC' (SEQ ID NO:238) | [['CCC'], [], ['UUUA']] | 0.451613 | 0.83871 | 2 | 21 |
| 'UUAUUCUGCUUCCUCCCAAGGAGCUGUUACA' (SEQ ID NO:239) | [['CCC'], [], ['UUAU']] | 0.451613 | 0.83871 | 2 | 22 |
| 'UAUUCUGCUUCCUCCCAAGGAGCUGUUACAC' (SEQ ID NO:240) | [['CCC'], [], ['UAUU']] | 0.483871 | 0.83871 | 2 | 23 |
| 'UCGGCUUCAAGGAAAAUUGCUUUAUUCUGCU' (SEQ ID NO:241) | [[], [], ['AAAA', 'UUUA']] | 0.387097 | 0.806452 | 2 | 1 |
| 'CGGCUUCAAGGAAAAUUGCUUUAUUCUGCUU' (SEQ ID NO:242) | [[], [], ['AAAA', 'UUUA']] | 0.387097 | 0.806452 | 2 | 2 |
| 'GGCUUCAAGGAAAAUUGCUUUAUUCUGCUUC' (SEQ ID NO:243) | [[], [], ['AAAA', 'UUUA']] | 0.387097 | 0.806452 | 2 | 3 |
| 'CUCGGCUUCAAGGAAAAUUGCUUUAUUCUGC' (SEQ ID NO:244) | [[], [], ['AAAA', 'UUUA']] | 0.419355 | 0.806452 | 2 | 0 |
| 'AAGGAAAAUUGCUUUAUUCUGCUUCCUCCCA' (SEQ ID NO:245) | [['CCC'], [], ['AAAA', 'UUUA']] | 0.387097 | 0.870968 | 3 | 9 |

FIG. 39 (Cont'd)

| SEQUENCE | BS | GCNESS | 3LN | NBP | P |
|---|---|---|---|---|---|
| 'AGGAAAAUUGCUUUAUUCUGCUUCCUCCCAA' (SEQ ID NO:246) | [['CCC'], [], ['AAAA', 'UUUA']] | 0.387097 | 0.870968 | 3 | 10 |
| 'AAAAUUGCUUUAUUCUGCUUCCUCCCAAGGA' (SEQ ID NO:247) | [['CCC'], [], ['AAAA', 'UUUA']] | 0.387097 | 0.870968 | 3 | 13 |
| 'CAAGGAAAAUUGCUUUAUUCUGCUUCCUCCC' (SEQ ID NO:248) | [['CCC'], [], ['AAAA', 'UUUA']] | 0.419355 | 0.870968 | 3 | 8 |
| 'GGAAAAUUGCUUUAUUCUGCUUCCUCCCAAG' (SEQ ID NO:249) | [['CCC'], [], ['AAAA', 'UUUA']] | 0.419355 | 0.83871 | 3 | 11 |
| 'GAAAAUUGCUUUAUUCUGCUUCCUCCCAAGG' (SEQ ID NO:250) | [['CCC'], [], ['AAAA', 'UUUA']] | 0.419355 | 0.83871 | 3 | 12 |
| 'AAAUUGCUUUAUUCUGCUUCCUCCCAAGGAG' (SEQ ID NO:251) | [['CCC'], [], ['AAAU', 'UUUA']] | 0.419355 | 0.83871 | 3 | 14 |

FIG. 39 (Cont'd)

| SEQUENCE | BS | GCNESS | 3LN | NBP | P |
|---|---|---|---|---|---|
| 'AAUUGCUUUAUUCUGCUUCCUCCCAAGGAGC' (SEQ ID NO:252) | [['CCC'], [], ['AAUU', 'UUUA']] | 0.451613 | 0.83871 | 3 | 15 |

| SEQUENCE | BS | GCNESS | 3LN | NBP | P |
|---|---|---|---|---|---|
| 'GUGUUUCUGCCUAAGGUGCUGUUUCAAAGGC' (SEQ ID NO:253) | [[], [], []] | 0.483871 | 0.83871 | 0 | 24 |
| 'GUUUCUGCCUAAGGUGCUGUUUCAAAGGCUC' (SEQ ID NO:254) | [[], [], []] | 0.483871 | 0.83871 | 0 | 26 |
| 'UUUCUGCCUAAGGUGCUGUUUCAAAGGCUCC' (SEQ ID NO:255) | [[], [], []] | 0.483871 | 0.83871 | 0 | 27 |
| 'UGUGUUUCUGCCUAAGGUGCUGUUUCAAAGG' (SEQ ID NO:256) | [[], [], []] | 0.451613 | 0.83871 | 0 | 23 |
| 'UGUUUCUGCCUAAGGUGCUGUUUCAAAGGCU' (SEQ ID NO:257) | [[], [], []] | 0.451613 | 0.83871 | 0 | 25 |
| 'UUGUGUUUCUGCCUAAGGUGCUGUUUCAAAG' (SEQ ID NO:258) | [[], [], []] | 0.419355 | 0.83871 | 0 | 22 |
| 'AUUGUGUUUCUGCCUAAGGUGCUGUUUCAAA' (SEQ ID NO:259) | [[], [], []] | 0.387097 | 0.83871 | 0 | 21 |
| 'CUGCCUAAGGUGCUGUUUCAAAGGCUCCAGG' (SEQ ID NO:260) | [[], [], []] | 0.548387 | 0.806452 | 0 | 30 |

| SEQUENCE | BS | GCNESS | 3LN | NBP | P |
|---|---|---|---|---|---|
| 'GCCUAAGGUGCUGUUUCAAAGGCUCCAGGUC' (SEQ ID NO:261) | [[], [], []] | 0.548387 | 0.806452 | 0 | 32 |
| 'AGGUGCUGUUUCAAAGGCUCCAGGUCUCAGG' (SEQ ID NO:262) | [[], [], []] | 0.548387 | 0.806452 | 0 | 37 |
| 'UCUGCCUAAGGUGCUGUUUCAAAGGCUCCAG' (SEQ ID NO:263) | [[], [], []] | 0.516129 | 0.806452 | 0 | 29 |
| 'UGCCUAAGGUGCUGUUUCAAAGGCUCCAGGU' (SEQ ID NO:264) | [[], [], []] | 0.516129 | 0.806452 | 0 | 31 |
| 'CCUAAGGUGCUGUUUCAAAGGCUCCAGGUCU' (SEQ ID NO:265) | [[], [], []] | 0.516129 | 0.806452 | 0 | 33 |
| 'CUAAGGUGCUGUUUCAAAGGCUCCAGGUCUC' (SEQ ID NO:266) | [[], [], []] | 0.516129 | 0.806452 | 0 | 34 |
| 'UUCUGCCUAAGGUGCUGUUUCAAAGGCUCCA' (SEQ ID NO:267) | [[], [], []] | 0.483871 | 0.806452 | 0 | 28 |
| 'AAGGUGCUGUUUCAAAGGCUCCAGGUCUCAG' (SEQ ID NO:268) | [[], [], []] | 0.516129 | 0.774194 | 0 | 36 |

FIG. 40 (Cont'd)

| SEQUENCE | BS | GCNESS | 3LN | NBP | P |
|---|---|---|---|---|---|
| 'UAAGGUGCUGUUUCAAAGGCUCCAGGUCUCA' (SEQ ID NO:269) | [[], [], []] | 0.483871 | 0.774194 | 0 | 35 |
| 'UUGCUUUAUUGUGUUUCUGCCUAAGGUGCUG' (SEQ ID NO:270) | [[], [], ['UUUA']] | 0.419355 | 0.903226 | 1 | 14 |
| 'UGCUUUAUUGUGUUUCUGCCUAAGGUGCUGU' (SEQ ID NO:271) | [[], [], ['UUUA']] | 0.419355 | 0.903226 | 1 | 15 |
| 'GCUUUAUUGUGUUUCUGCCUAAGGUGCUGUU' (SEQ ID NO:272) | [[], [], ['UUUA']] | 0.419355 | 0.903226 | 1 | 16 |
| 'CUUUAUUGUGUUUCUGCCUAAGGUGCUGUUU' (SEQ ID NO:273) | [[], [], ['UUUA']] | 0.387097 | 0.903226 | 1 | 17 |
| 'UUUAUUGUGUUUCUGCCUAAGGUGCUGUUUC' (SEQ ID NO:274) | [[], [], ['UUUA']] | 0.387097 | 0.903226 | 1 | 18 |
| 'AUUGCUUUAUUGUGUUUCUGCCUAAGGUGCU' (SEQ ID NO:275) | [[], [], ['UUUA']] | 0.387097 | 0.870968 | 1 | 13 |
| 'UUAUUGUGUUUCUGCCUAAGGUGCUGUUUCA' (SEQ ID NO:276) | [[], [], ['UUAU']] | 0.387097 | 0.870968 | 1 | 19 |

FIG. 40 (Cont'd)

| SEQUENCE | BS | GCNESS | 3LN | NBP | P |
|---|---|---|---|---|---|
| 'GGCUCCAGGUCUCAGG GCUUCACAGGCAUCC' (SEQ ID NO:277) | [[], ['GGG'], []] | 0.645161 | 0.83871 | 1 | 52 |
| 'CAAAGGCUCCAGGUCU CAGGGCUUCACAGGC' (SEQ ID NO:278) | [[], ['GGG'], []] | 0.612903 | 0.83871 | 1 | 48 |
| 'GCUCCAGGUCUCAGGG CUUCACAGGCAUCCU' (SEQ ID NO:279) | [[], ['GGG'], []] | 0.612903 | 0.83871 | 1 | 53 |
| 'GGUGCUGUUUCAAAGG CUCCAGGUCUCAGGG' (SEQ ID NO:280) | [[], ['GGG'], []] | 0.580645 | 0.83871 | 1 | 38 |
| 'GUGCUGUUUCAAAGGC UCCAGGUCUCAGGGC' (SEQ ID NO:281) | [[], ['GGG'], []] | 0.580645 | 0.83871 | 1 | 39 |
| 'AAAGGCUCCAGGUCUC AGGGCUUCACAGGCA' (SEQ ID NO:282) | [[], ['GGG'], []] | 0.580645 | 0.83871 | 1 | 49 |
| 'CUCCAGGUCUCAGGGC UUCACAGGCAUCCUU' (SEQ ID NO:283) | [[], ['GGG'], []] | 0.580645 | 0.83871 | 1 | 54 |
| 'UGCUGUUUCAAAGGCU CCAGGUCUCAGGGCU' (SEQ ID NO:284) | [[], ['GGG'], []] | 0.548387 | 0.83871 | 1 | 40 |

FIG. 40 (Cont'd)

| SEQUENCE | BS | GCNESS | 3LN | NBP | P |
|---|---|---|---|---|---|
| 'GCUGUUUCAAAGGCUCCAGGUCUCAGGGCUU' (SEQ ID NO:285) | [[], ['GGG'], []] | 0.548387 | 0.83871 | 1 | 41 |
| 'CUGUUUCAAAGGCUCCAGGUCUCAGGGCUUC' (SEQ ID NO:286) | [[], ['GGG'], []] | 0.548387 | 0.83871 | 1 | 42 |
| 'UAUUGUGUUUCUGCCUAAGGUGCUGUUUCAA' (SEQ ID NO:287) | [[], [], ['UAUU']] | 0.387097 | 0.83871 | 1 | 20 |
| 'AGGCUCCAGGUCUCAGGGCUUCACAGGCAUC' (SEQ ID NO:288) | [[], ['GGG'], []] | 0.612903 | 0.806452 | 1 | 51 |
| 'UCAAAGGCUCCAGGUCUCAGGGCUUCACAGG' (SEQ ID NO:289) | [[], ['GGG'], []] | 0.580645 | 0.806452 | 1 | 47 |
| 'AAGGCUCCAGGUCUCAGGGCUUCACAGGCAU' (SEQ ID NO:290) | [[], ['GGG'], []] | 0.580645 | 0.806452 | 1 | 50 |
| 'CCAGGUCUCAGGGCUUCACAGGCAUCCUUAG' (SEQ ID NO:291) | [[], ['GGG'], []] | 0.580645 | 0.806452 | 1 | 56 |
| 'CAGGUCUCAGGGCUUCACAGGCAUCCUUAGG' (SEQ ID NO:292) | [[], ['GGG'], []] | 0.580645 | 0.806452 | 1 | 57 |

FIG. 40 (Cont'd)

| SEQUENCE | BS | GCNESS | 3LN | NBP | P |
|---|---|---|---|---|---|
| 'GUUCAAAGGCUCCAGGUCUCAGGGCUUCAC' (SEQ ID NO:293) | [[], ['GGG'], []] | 0.548387 | 0.806452 | 1 | 44 |
| 'UCCAGGUCUCAGGGCUUCACAGGCAUCCUUA' (SEQ ID NO:294) | [[], ['GGG'], []] | 0.548387 | 0.806452 | 1 | 55 |
| 'UGUUUCAAAGGCUCCAGGUCUCAGGGCUUCA' (SEQ ID NO:295) | [[], ['GGG'], []] | 0.516129 | 0.806452 | 1 | 43 |
| 'UUCAAAGGCUCCAGGUCUCAGGGCUUCACAG' (SEQ ID NO:296) | [[], ['GGG'], []] | 0.548387 | 0.774194 | 1 | 46 |
| 'UUUCAAAGGCUCCAGGUCUCAGGGCUUCACA' (SEQ ID NO:297) | [[], ['GGG'], []] | 0.516129 | 0.774194 | 1 | 45 |
| 'GGCUUGAAGGAAAAUUGCUUUAUUGUGUUUC' (SEQ ID NO:298) | [[], [], ['AAAA', 'UUUA']] | 0.354839 | 0.903226 | 2 | 0 |
| 'GCUUGAAGGAAAAUUGCUUUAUUGUGUUUCU' (SEQ ID NO:299) | [[], [], ['AAAA', 'UUUA']] | 0.322581 | 0.903226 | 2 | 1 |
| 'CUUGAAGGAAAAUUGCUUUAUUGUGUUUCUG' (SEQ ID NO:300) | [[], [], ['AAAA', 'UUUA']] | 0.322581 | 0.903226 | 2 | 2 |

FIG. 40 (Cont'd)

| SEQUENCE | BS | GCNESS | 3LN | NBP | P |
|---|---|---|---|---|---|
| 'UUGAAGGAAAAUUGCUUUAUUGUGUUUCUGC' (SEQ ID NO:301) | [[], [], ['AAAA', 'UUUA']] | 0.322581 | 0.903226 | 2 | 3 |
| 'UGAAGGAAAAUUGCUUUAUUGUGUUUCUGCC' (SEQ ID NO:302) | [[], [], ['AAAA', 'UUUA']] | 0.354839 | 0.870968 | 2 | 4 |
| 'GAAGGAAAAUUGCUUUAUUGUGUUUCUGCCU' (SEQ ID NO:303) | [[], [], ['AAAA', 'UUUA']] | 0.354839 | 0.870968 | 2 | 5 |
| 'GGAAAAUUGCUUUAUUGUGUUUCUGCCUAAG' (SEQ ID NO:304) | [[], [], ['AAAA', 'UUUA']] | 0.354839 | 0.870968 | 2 | 8 |
| 'GAAAAUUGCUUUAUUGUGUUUCUGCCUAAGG' (SEQ ID NO:305) | [[], [], ['AAAA', 'UUUA']] | 0.354839 | 0.870968 | 2 | 9 |
| 'AAAUUGCUUUAUUGUGUUUCUGCCUAAGGUG' (SEQ ID NO:306) | [[], [], ['AAAU', 'UUUA']] | 0.354839 | 0.870968 | 2 | 11 |
| 'AAGGAAAAUUGCUUUAUUGUGUUUCUGCCUA' (SEQ ID NO:307) | [[], [], ['AAAA', 'UUUA']] | 0.322581 | 0.870968 | 2 | 6 |
| 'AGGAAAAUUGCUUUAUUGUGUUUCUGCCUAA' (SEQ ID NO:308) | [[], [], ['AAAA', 'UUUA']] | 0.322581 | 0.870968 | 2 | 7 |

FIG. 40 (Cont'd)

| SEQUENCE | BS | GCNESS | 3LN | NBP | P |
|---|---|---|---|---|---|
| 'AAAAUUGCUUUAUUGUGUUUCUGCCUAAGGU' (SEQ ID NO:309) | [[], [], ['AAAA', 'UUUA']] | 0.322581 | 0.870968 | 2 | 10 |
| 'GGUCUCAGGGCUUCACAGGCAUCCUUAGGGU' (SEQ ID NO:310) | [[], ['GGG', 'GGG'], []] | 0.580645 | 0.83871 | 2 | 59 |
| 'CUCAGGGCUUCACAGGCAUCCUUAGGGUUGG' (SEQ ID NO:311) | [[], ['GGG', 'GGG'], []] | 0.580645 | 0.83871 | 2 | 62 |
| 'GGCUUCACAGGCAUCCUUAGGGUUGGGUAGC' (SEQ ID NO:312) | [[], ['GGG', 'GGG'], []] | 0.580645 | 0.83871 | 2 | 67 |
| 'GUCUCAGGGCUUCACAGGCAUCCUUAGGGUU' (SEQ ID NO:313) | [[], ['GGG', 'GGG'], []] | 0.548387 | 0.83871 | 2 | 60 |
| 'UCUCAGGGCUUCACAGGCAUCCUUAGGGUUG' (SEQ ID NO:314) | [[], ['GGG', 'GGG'], []] | 0.548387 | 0.83871 | 2 | 61 |
| 'AAUUGCUUUAUUGUGUUUCUGCCUAAGGUGC' (SEQ ID NO:315) | [[], [], ['AAUU', 'UUUA']] | 0.387097 | 0.83871 | 2 | 12 |
| 'AGGUCUCAGGGCUUCACAGGCAUCCUUAGGG' (SEQ ID NO:316) | [[], ['GGG', 'GGG'], []] | 0.580645 | 0.806452 | 2 | 58 |

FIG. 40 (Cont'd)

| SEQUENCE | BS | GCNESS | 3LN | NBP | P |
|---|---|---|---|---|---|
| 'GCUUCACAGGCAUCCU UAGGGUUGGGUAGCA' (SEQ ID NO:317) | [[], ['GGG', 'GGG'], []] | 0.548387 | 0.806452 | 2 | 68 |
| 'CUUCACAGGCAUCCUU AGGGUUGGGUAGCAC' (SEQ ID NO:318) | [[], ['GGG', 'GGG'], []] | 0.548387 | 0.806452 | 2 | 69 |
| 'CACAGGCAUCCUUAGG GUUGGGUAGCACAAG' (SEQ ID NO:319) | [[], ['GGG', 'GGG'], []] | 0.548387 | 0.806452 | 2 | 72 |
| 'ACAGGCAUCCUUAGGG UUGGGUAGCACAAGA' (SEQ ID NO:320) | [[], ['GGG', 'GGG'], []] | 0.516129 | 0.806452 | 2 | 73 |
| 'CAGGCAUCCUUAGGGU UGGGUAGCACAAGAU' (SEQ ID NO:321) | [[], ['GGG', 'GGG'], []] | 0.516129 | 0.806452 | 2 | 74 |
| 'UUCACAGGCAUCCUUA GGGUUGGGUAGCACA' (SEQ ID NO:322) | [[], ['GGG', 'GGG'], []] | 0.516129 | 0.774194 | 2 | 70 |
| 'UCACAGGCAUCCUUAG GGUUGGGUAGCACAA' (SEQ ID NO:323) | [[], ['GGG', 'GGG'], []] | 0.516129 | 0.774194 | 2 | 71 |
| 'UCAGGGCUUCACAGGC AUCCUUAGGGUUGGG' (SEQ ID NO:324) | [[], ['GGG', 'GGG', 'GGG'], []] | 0.580645 | 0.83871 | 3 | 63 |

FIG. 40 (Cont'd)

| SEQUENCE | BS | GCNESS | 3LN | NBP | P |
| --- | --- | --- | --- | --- | --- |
| 'CAGGGCUUCACAGGCAUCCUUAGGGUUGGGU' (SEQ ID NO:325) | [[], ['GGG', 'GGG', 'GGG'], []] | 0.580645 | 0.83871 | 3 | 64 |
| 'GGGCUUCACAGGCAUCCUUAGGGUUGGGUAG' (SEQ ID NO:326) | [[], ['GGG', 'GGG', 'GGG'], []] | 0.580645 | 0.83871 | 3 | 66 |
| 'AGGGCUUCACAGGCAUCCUUAGGGUUGGGUA' (SEQ ID NO:327) | [[], ['GGG', 'GGG', 'GGG'], []] | 0.548387 | 0.806452 | 3 | 65 |

| SEQUENCE | BS | GCNESS | 3LN | NBP | P |
|---|---|---|---|---|---|
| 'GGAGAGGCGAGGAAGUCACCAUCAAACCACU' (SEQ ID NO:328) | [[], [], []] | 0.548387 | 0.903226 | 0 | 90 |
| 'AGAUGUGAGAAGUGUUGACAGGAAGCUGCAG' (SEQ ID NO:329) | [[], [], []] | 0.483871 | 0.903226 | 0 | 139 |
| 'UAAGAUGUGAGAAGUGUUGACAGGAAGCUGC' (SEQ ID NO:330) | [[], [], []] | 0.451613 | 0.903226 | 0 | 137 |
| 'AAGAUGUGAGAAGUGUUGACAGGAAGCUGCA' (SEQ ID NO:331) | [[], [], []] | 0.451613 | 0.903226 | 0 | 138 |
| 'AUUCACUUUCAAACCACUUUCAGUAACAGGU' (SEQ ID NO:332) | [[], [], []] | 0.354839 | 0.903226 | 0 | 26 |
| 'GAGAGGCGAGGAAGUCACCAUCAAACCACUU' (SEQ ID NO:333) | [[], [], []] | 0.516129 | 0.870968 | 0 | 91 |
| 'GAUGUGAGAAGUGUUGACAGGAAGCUGCAGC' (SEQ ID NO:334) | [[], [], []] | 0.516129 | 0.870968 | 0 | 140 |
| 'AUGUGAGAAGUGUUGACAGGAAGCUGCAGCU' (SEQ ID NO:335) | [[], [], []] | 0.483871 | 0.870968 | 0 | 141 |

| SEQUENCE | BS | GCNESS | 3LN | NBP | P |
|---|---|---|---|---|---|
| 'UGUGAGAAGUGUUGACAGGAAGCUGCAGCUU' (SEQ ID NO:336) | [[], [], []] | 0.483871 | 0.870968 | 0 | 142 |
| 'GUGAGAAGUGUUGACAGGAAGCUGCAGCUUA' (SEQ ID NO:337) | [[], [], []] | 0.483871 | 0.870968 | 0 | 143 |
| 'UGAGAAGUGUUGACAGGAAGCUGCAGCUUAG' (SEQ ID NO:338) | [[], [], []] | 0.483871 | 0.870968 | 0 | 144 |
| 'GAGAAGUGUUGACAGGAAGCUGCAGCUUAGA' (SEQ ID NO:339) | [[], [], []] | 0.483871 | 0.870968 | 0 | 145 |
| 'GAAGUGUUGACAGGAAGCUGCAGCUUAGAUG' (SEQ ID NO:340) | [[], [], []] | 0.483871 | 0.870968 | 0 | 147 |
| 'AAGUGUUGACAGGAAGCUGCAGCUUAGAUGG' (SEQ ID NO:341) | [[], [], []] | 0.483871 | 0.870968 | 0 | 148 |
| 'AGAAGUGUUGACAGGAAGCUGCAGCUUAGAU' (SEQ ID NO:342) | [[], [], []] | 0.451613 | 0.870968 | 0 | 146 |
| 'GAUCACAACUCCAUGGCAACAAGAUGACACA' (SEQ ID NO:343) | [[], [], []] | 0.451613 | 0.870968 | 0 | 182 |

FIG. 41 (Cont'd)

| SEQUENCE | BS | GCNESS | 3LN | NBP | P |
|---|---|---|---|---|---|
| 'AUCACAACUCCAUGGCAACAAGAUGACACAA' (SEQ ID NO:344) | [[], [], []] | 0.419355 | 0.870968 | 0 | 183 |
| 'UCACAACUCCAUGGCAACAAGAUGACACAAA' (SEQ ID NO:345) | [[], [], []] | 0.419355 | 0.870968 | 0 | 184 |
| 'UUCACUUUCAAACCACUUUCAGUAACAGGUG' (SEQ ID NO:346) | [[], [], []] | 0.387097 | 0.870968 | 0 | 27 |
| 'UCACUUUCAAACCACUUUCAGUAACAGGUGA' (SEQ ID NO:347) | [[], [], []] | 0.387097 | 0.870968 | 0 | 28 |
| 'AGAGGCGAGGAAGUCACCAUCAAACCACUUU' (SEQ ID NO:348) | [[], [], []] | 0.483871 | 0.83871 | 0 | 92 |
| 'GGAUGAUCACAACUCCAUGGCAACAAGAUGA' (SEQ ID NO:349) | [[], [], []] | 0.451613 | 0.83871 | 0 | 178 |
| 'GAUGAUCACAACUCCAUGGCAACAAGAUGAC' (SEQ ID NO:350) | [[], [], []] | 0.451613 | 0.83871 | 0 | 179 |
| 'UGAUCACAACUCCAUGGCAACAAGAUGACAC' (SEQ ID NO:351) | [[], [], []] | 0.451613 | 0.83871 | 0 | 181 |

FIG. 41 (Cont'd)

| SEQUENCE | BS | GCNESS | 3LN | NBP | P |
|---|---|---|---|---|---|
| 'CACUUUCAAACCACUUUCAGUAACAGGUGAG' (SEQ ID NO:352) | [[], [], []] | 0.419355 | 0.83871 | 0 | 29 |
| 'AUGAUCACAACUCCAUGGCAACAAGAUGACA' (SEQ ID NO:353) | [[], [], []] | 0.419355 | 0.83871 | 0 | 180 |
| 'AACCACUUUCAGUAACAGGUGAGGUUCUACC' (SEQ ID NO:354) | [[], [], []] | 0.451613 | 0.806452 | 0 | 37 |
| 'ACCACUUUCAGUAACAGGUGAGGUUCUACCU' (SEQ ID NO:355) | [[], [], []] | 0.451613 | 0.806452 | 0 | 38 |
| 'CCACUUUCAGUAACAGGUGAGGUUCUACCUU' (SEQ ID NO:356) | [[], [], []] | 0.451613 | 0.806452 | 0 | 39 |
| 'ACUUUCAAACCACUUUCAGUAACAGGUGAGG' (SEQ ID NO:357) | [[], [], []] | 0.419355 | 0.806452 | 0 | 30 |
| 'CUUUCAAACCACUUUCAGUAACAGGUGAGGU' (SEQ ID NO:358) | [[], [], []] | 0.419355 | 0.806452 | 0 | 31 |
| 'UUCAAACCACUUUCAGUAACAGGUGAGGUUC' (SEQ ID NO:359) | [[], [], []] | 0.419355 | 0.806452 | 0 | 33 |

FIG. 41 (Cont'd)

| SEQUENCE | BS | GCNESS | 3LN | NBP | P |
|---|---|---|---|---|---|
| 'UCAAACCACUUUCAGUAACAGGUGAGGUUCU' (SEQ ID NO:360) | [[], [], []] | 0.419355 | 0.806452 | 0 | 34 |
| 'CAAACCACUUUCAGUAACAGGUGAGGUUCUA' (SEQ ID NO:361) | [[], [], []] | 0.419355 | 0.806452 | 0 | 35 |
| 'AAACCACUUUCAGUAACAGGUGAGGUUCUAC' (SEQ ID NO:362) | [[], [], []] | 0.419355 | 0.806452 | 0 | 36 |
| 'CACUUUCAGUAACAGGUGAGGUUCUACCUUA' (SEQ ID NO:363) | [[], [], []] | 0.419355 | 0.806452 | 0 | 40 |
| 'UUUCAAACCACUUUCAGUAACAGGUGAGGUU' (SEQ ID NO:364) | [[], [], []] | 0.387097 | 0.806452 | 0 | 32 |
| 'UUUAUUCACUUUCAAACCACUUUCAGUAACA' (SEQ ID NO:365) | [[], [], ['UUUA']] | 0.290323 | 0.967742 | 1 | 23 |
| 'GGGAGAGGCGAGGAAGUCACCAUCAAACCAC' (SEQ ID NO:366) | [[], ['GGG'], []] | 0.580645 | 0.935484 | 1 | 89 |
| 'GGCAACAAGAUGACACAAAUGCAGCAGAGAC' (SEQ ID NO:367) | [[], [], ['AAAU']] | 0.483871 | 0.935484 | 1 | 196 |

FIG. 41 (Cont'd)

| SEQUENCE | BS | GCNESS | 3LN | NBP | P |
|---|---|---|---|---|---|
| 'GCAACAAGAUGACACAAAUGCAGCAGAGACC' (SEQ ID NO:368) | [[], [], ['AAAU']] | 0.483871 | 0.935484 | 1 | 197 |
| 'GUUAGCAUAAGAUGUGAGAAGUGUUGACAGG' (SEQ ID NO:369) | [[], [], ['AUAA']] | 0.419355 | 0.935484 | 1 | 130 |
| 'AGCAUAAGAUGUGAGAAGUGUUGACAGGAAG' (SEQ ID NO:370) | [[], [], ['AUAA']] | 0.419355 | 0.935484 | 1 | 133 |
| 'AUAAGAUGUGAGAAGUGUUGACAGGAAGCUG' (SEQ ID NO:371) | [[], [], ['AUAA']] | 0.419355 | 0.935484 | 1 | 136 |
| 'UCACCAUCAAACCACUUUAUCUACAGUUAGC' (SEQ ID NO:372) | [[], [], ['UUUA']] | 0.387097 | 0.935484 | 1 | 105 |
| 'CACCAUCAAACCACUUUAUCUACAGUUAGCA' (SEQ ID NO:373) | [[], [], ['UUUA']] | 0.387097 | 0.935484 | 1 | 106 |
| 'AGUUAGCAUAAGAUGUGAGAAGUGUUGACAG' (SEQ ID NO:374) | [[], [], ['AUAA']] | 0.387097 | 0.935484 | 1 | 129 |
| 'UUAGCAUAAGAUGUGAGAAGUGUUGACAGGA' (SEQ ID NO:375) | [[], [], ['AUAA']] | 0.387097 | 0.935484 | 1 | 131 |

FIG. 41 (Cont'd)

| SEQUENCE | BS | GCNESS | 3LN | NBP | P |
|---|---|---|---|---|---|
| 'UAGCAUAAGAUGUGAGA AGUGUUGACAGGAA' (SEQ ID NO:376) | [[], [], ['AUAA']] | 0.387097 | 0.935484 | 1 | 132 |
| 'AAGUCACCAUCAAACCA CUUUAUCUACAGUU' (SEQ ID NO:377) | [[], [], ['UUUA']] | 0.354839 | 0.935484 | 1 | 102 |
| 'AGUCACCAUCAAACCAC UUUAUCUACAGUUA' (SEQ ID NO:378) | [[], [], ['UUUA']] | 0.354839 | 0.935484 | 1 | 103 |
| 'ACCAUCAAACCACUUUA UCUACAGUUAGCAU' (SEQ ID NO:379) | [[], [], ['UUUA']] | 0.354839 | 0.935484 | 1 | 107 |
| 'CCAUCAAACCACUUUAU CUACAGUUAGCAUA' (SEQ ID NO:380) | [[], [], ['UUUA']] | 0.354839 | 0.935484 | 1 | 108 |
| 'UACAGUUAGCAUAAGAU GUGAGAAGUGUUGA' (SEQ ID NO:381) | [[], [], ['AUAA']] | 0.354839 | 0.935484 | 1 | 126 |
| 'CUGAAGUUUAUUCACUU UCAAACCACUUUCA' (SEQ ID NO:382) | [[], [], ['UUUA']] | 0.322581 | 0.935484 | 1 | 17 |
| 'GUUUAUUCACUUUCAAA CCACUUUCAGUAAC' (SEQ ID NO:383) | [[], [], ['UUUA']] | 0.322581 | 0.935484 | 1 | 22 |

FIG. 41 (Cont'd)

| SEQUENCE | BS | GCNESS | 3LN | NBP | P |
|---|---|---|---|---|---|
| 'UUAUUCACUUUCAAACCACUUUCAGUAACAG' (SEQ ID NO:384) | [[], [], ['UUAU']] | 0.322581 | 0.935484 | 1 | 24 |
| 'AAGUUUAUUCACUUUCAACCACUUUCAGUA' (SEQ ID NO:385) | [[], [], ['UUUA']] | 0.290323 | 0.935484 | 1 | 20 |
| 'AGUUUAUUCACUUUCAAACCACUUUCAGUAA' (SEQ ID NO:386) | [[], [], ['UUUA']] | 0.290323 | 0.935484 | 1 | 21 |
| 'GGUGGGAGAGGCGAGGAAGUCACCAUCAAAC' (SEQ ID NO:387) | [[], ['GGG'], []] | 0.580645 | 0.903226 | 1 | 86 |
| 'GUGGGAGAGGCGAGGAAGUCACCAUCAAACC' (SEQ ID NO:388) | [[], ['GGG'], []] | 0.580645 | 0.903226 | 1 | 87 |
| 'UGGGAGAGGCGAGGAAGUCACCAUCAAACCA' (SEQ ID NO:389) | [[], ['GGG'], []] | 0.548387 | 0.903226 | 1 | 88 |
| 'CCAUGGCAACAAGAUGACACAAAUGCAGCAG' (SEQ ID NO:390) | [[], [], ['AAAU']] | 0.483871 | 0.903226 | 1 | 192 |
| 'GCAUAAGAUGUGAGAAGUGUUGACAGGAAGC' (SEQ ID NO:391) | [[], [], ['AUAA']] | 0.451613 | 0.903226 | 1 | 134 |

FIG. 41 (Cont'd)

| SEQUENCE | BS | GCNESS | 3LN | NBP | P |
|---|---|---|---|---|---|
| 'CAUGGCAACAAGAUGACACAAAUGCAGCAGA' (SEQ ID NO:392) | [[], [], ['AAAU']] | 0.451613 | 0.903226 | 1 | 193 |
| 'AUGGCAACAAGAUGACACAAAUGCAGCAGAG' (SEQ ID NO:393) | [[], [], ['AAAU']] | 0.451613 | 0.903226 | 1 | 194 |
| 'UGGCAACAAGAUGACACAAAUGCAGCAGAGA' (SEQ ID NO:394) | [[], [], ['AAAU']] | 0.451613 | 0.903226 | 1 | 195 |
| 'CAUAAGAUGUGAGAAGUGUUGACAGGAAGCU' (SEQ ID NO:395) | [[], [], ['AUAA']] | 0.419355 | 0.903226 | 1 | 135 |
| 'AGGAAGUCACCAUCAAACCACUUUAUCUACA' (SEQ ID NO:396) | [[], [], ['UUUA']] | 0.387097 | 0.903226 | 1 | 99 |
| 'GAAGUCACCAUCAAACCACUUUAUCUACAGU' (SEQ ID NO:397) | [[], [], ['UUUA']] | 0.387097 | 0.903226 | 1 | 101 |
| 'GUCACCAUCAAACCACUUUAUCUACAGUUAG' (SEQ ID NO:398) | [[], [], ['UUUA']] | 0.387097 | 0.903226 | 1 | 104 |
| 'CUACAGUUAGCAUAAGAUGUGAGAAGUGUUG' (SEQ ID NO:399) | [[], [], ['AUAA']] | 0.387097 | 0.903226 | 1 | 125 |

FIG. 41 (Cont'd)

| SEQUENCE | BS | GCNESS | 3LN | NBP | P |
|---|---|---|---|---|---|
| 'ACAGUUAGCAUAAGAUGUGAGAAGUGUUGAC' (SEQ ID NO:400) | [[], [], ['AUAA']] | 0.387097 | 0.903226 | 1 | 127 |
| 'CAGUUAGCAUAAGAUGUGAGAAGUGUUGACA' (SEQ ID NO:401) | [[], [], ['AUAA']] | 0.387097 | 0.903226 | 1 | 128 |
| 'GCUGAAGUUUAUUCACUUUCAAACCACUUUC' (SEQ ID NO:402) | [[], [], ['UUUA']] | 0.354839 | 0.903226 | 1 | 16 |
| 'UAUUCACUUUCAAACCACUUUCAGUAACAGG' (SEQ ID NO:403) | [[], [], ['UAUU']] | 0.354839 | 0.903226 | 1 | 25 |
| 'UAUCUACAGUUAGCAUAAGAUGUGAGAAGUG' (SEQ ID NO:404) | [[], [], ['AUAA']] | 0.354839 | 0.903226 | 1 | 122 |
| 'AUCUACAGUUAGCAUAAGAUGUGAGAAGUGU' (SEQ ID NO:405) | [[], [], ['AUAA']] | 0.354839 | 0.903226 | 1 | 123 |
| 'UCUACAGUUAGCAUAAGAUGUGAGAAGUGUU' (SEQ ID NO:406) | [[], [], ['AUAA']] | 0.354839 | 0.903226 | 1 | 124 |
| 'UGCUGAAGUUUAUUCACUUUCAAACCACUUU' (SEQ ID NO:407) | [[], [], ['UUUA']] | 0.322581 | 0.903226 | 1 | 15 |

FIG. 41 (Cont'd)

| SEQUENCE | BS | GCNESS | 3LN | NBP | P |
|---|---|---|---|---|---|
| 'UGAAGUUUAUUCACUUU CAAACCACUUUCAG' (SEQ ID NO:408) | [[], [], ['UUUA']] | 0.322581 | 0.903226 | 1 | 18 |
| 'GAAGUUUAUUCACUUC AAACCACUUUCAGU' (SEQ ID NO:409) | [[], [], ['UUUA']] | 0.322581 | 0.903226 | 1 | 19 |
| 'AGUGUUGACAGGAAGCU GCAGCUUAGAUGGG' (SEQ ID NO:410) | [[], ['GGG'], []] | 0.516129 | 0.870968 | 1 | 149 |
| 'GUGUUGACAGGAAGCUG CAGCUUAGAUGGGA' (SEQ ID NO:411) | [[], ['GGG'], []] | 0.516129 | 0.870968 | 1 | 150 |
| 'GUUGACAGGAAGCUGCA GCUUAGAUGGGAUG' (SEQ ID NO:412) | [[], ['GGG'], []] | 0.516129 | 0.870968 | 1 | 152 |
| 'UGUUGACAGGAAGCUGC AGCUUAGAUGGGAU' (SEQ ID NO:413) | [[], ['GGG'], []] | 0.483871 | 0.870968 | 1 | 151 |
| 'UUGACAGGAAGCUGCAG CUUAGAUGGGAUGA' (SEQ ID NO:414) | [[], ['GGG'], []] | 0.483871 | 0.870968 | 1 | 153 |
| 'UGACAGGAAGCUGCAGC UUAGAUGGGAUGAU' (SEQ ID NO:415) | [[], ['GGG'], []] | 0.483871 | 0.870968 | 1 | 154 |

FIG. 41 (Cont'd)

| SEQUENCE | BS | GCNESS | 3LN | NBP | P |
| --- | --- | --- | --- | --- | --- |
| 'CUCCAUGGCAACAAGAUGACACAAAUGCAGC' (SEQ ID NO:416) | [[], [], ['AAAU']] | 0.483871 | 0.870968 | 1 | 190 |
| 'CAACUCCAUGGCAACAAGAUGACACAAAUGC' (SEQ ID NO:417) | [[], [], ['AAAU']] | 0.451613 | 0.870968 | 1 | 187 |
| 'ACUCCAUGGCAACAAGAUGACACAAAUGCAG' (SEQ ID NO:418) | [[], [], ['AAAU']] | 0.451613 | 0.870968 | 1 | 189 |
| 'UCCAUGGCAACAAGAUGACACAAAUGCAGCA' (SEQ ID NO:419) | [[], [], ['AAAU']] | 0.451613 | 0.870968 | 1 | 191 |
| 'CGAGGAAGUCACCAUCAACCACUUUAUCUA' (SEQ ID NO:420) | [[], [], ['UUUA']] | 0.419355 | 0.870968 | 1 | 97 |
| 'GAGGAAGUCACCAUCAAACCACUUUAUCUAC' (SEQ ID NO:421) | [[], [], ['UUUA']] | 0.419355 | 0.870968 | 1 | 98 |
| 'GGAAGUCACCAUCAAACCACUUUAUCUACAG' (SEQ ID NO:422) | [[], [], ['UUUA']] | 0.419355 | 0.870968 | 1 | 100 |
| 'CACAACUCCAUGGCAACAAGAUGACACAAAU' (SEQ ID NO:423) | [[], [], ['AAAU']] | 0.419355 | 0.870968 | 1 | 185 |

FIG. 41 (Cont'd)

| SEQUENCE | BS | GCNESS | 3LN | NBP | P |
|---|---|---|---|---|---|
| 'ACAACUCCAUGGCAACAAGAUGACACAAAUG' (SEQ ID NO:424) | [[], [], ['AAAU']] | 0.419355 | 0.870968 | 1 | 186 |
| 'AACUCCAUGGCAACAAGAUGACACAAAUGCA' (SEQ ID NO:425) | [[], [], ['AAAU']] | 0.419355 | 0.870968 | 1 | 188 |
| 'GUGCUGAAGUUUAUUCACUUCAAACCACUU' (SEQ ID NO:426) | [[], [], ['UUUA']] | 0.354839 | 0.870968 | 1 | 14 |
| 'CCAGGGGACAGGAGCCUCUUGCAGUCUGUCC' (SEQ ID NO:427) | [[], ['GGG'], []] | 0.645161 | 0.83871 | 1 | 228 |
| 'GGACAGGAGCCUCUUGCAGUCUGUCCCUAGG' (SEQ ID NO:428) | [['CCC'], [], []] | 0.612903 | 0.83871 | 1 | 233 |
| 'GACAGGAGCCUCUUGCAGUCUGUCCCUAGGC' (SEQ ID NO:429) | [['CCC'], [], []] | 0.612903 | 0.83871 | 1 | 234 |
| 'ACAGGAGCCUCUUGCAGUCUGUCCCUAGGCC' (SEQ ID NO:430) | [['CCC'], [], []] | 0.612903 | 0.83871 | 1 | 235 |
| 'GACAGGAAGCUGCAGCUUAGAUGGGAUGAUC' (SEQ ID NO:431) | [[], ['GGG'], []] | 0.516129 | 0.83871 | 1 | 155 |

FIG. 41 (Cont'd)

| SEQUENCE | BS | GCNESS | 3LN | NBP | P |
|---|---|---|---|---|---|
| 'GAGGCGAGGAAGUCACCAUCAAACCACUUUA' (SEQ ID NO:432) | [[], [], ['UUUA']] | 0.483871 | 0.83871 | 1 | 93 |
| 'ACAGGAAGCUGCAGCUUAGAUGGGAUGAUCA' (SEQ ID NO:433) | [[], ['GGG'], []] | 0.483871 | 0.83871 | 1 | 156 |
| 'AGGAAGCUGCAGCUUAGAUGGGAUGAUCACA' (SEQ ID NO:434) | [[], ['GGG'], []] | 0.483871 | 0.83871 | 1 | 158 |
| 'GGAAGCUGCAGCUUAGAUGGGAUGAUCACAA' (SEQ ID NO:435) | [[], ['GGG'], []] | 0.483871 | 0.83871 | 1 | 159 |
| 'GAUGGGAUGAUCACAACUCCAUGGCAACAAG' (SEQ ID NO:436) | [[], ['GGG'], []] | 0.483871 | 0.83871 | 1 | 174 |
| 'GGGAUGAUCACAACUCCAUGGCAACAAGAUG' (SEQ ID NO:437) | [[], ['GGG'], []] | 0.483871 | 0.83871 | 1 | 177 |
| 'GCGAGGAAGUCACCAUCAAACCACUUUAUCU' (SEQ ID NO:438) | [[], [], ['UUUA']] | 0.451613 | 0.83871 | 1 | 96 |
| 'AGAUGGGAUGAUCACAACUCCAUGGCAACAA' (SEQ ID NO:439) | [[], ['GGG'], []] | 0.451613 | 0.83871 | 1 | 173 |

FIG. 41 (Cont'd)

| SEQUENCE | BS | GCNESS | 3LN | NBP | P |
|---|---|---|---|---|---|
| 'AUGGGAUGAUCACAACUCCAUGGCAACAAGA' (SEQ ID NO:440) | [[], ['GGG'], []] | 0.451613 | 0.83871 | 1 | 175 |
| 'GUCUUCUGUCCAUGGUGCUGAAGUUUAUUCA' (SEQ ID NO:441) | [[], [], ['UUUA']] | 0.419355 | 0.83871 | 1 | 0 |
| 'UCUUCUGUCCAUGGUGCUGAAGUUUAUUCAC' (SEQ ID NO:442) | [[], [], ['UUUA']] | 0.419355 | 0.83871 | 1 | 1 |
| 'CUUCUGUCCAUGGUGCUGAAGUUUAUUCACU' (SEQ ID NO:443) | [[], [], ['UUUA']] | 0.419355 | 0.83871 | 1 | 2 |
| 'CUGUCCAUGGUGCUGAAGUUUAUUCACUUUC' (SEQ ID NO:444) | [[], [], ['UUUA']] | 0.419355 | 0.83871 | 1 | 5 |
| 'UUCUGUCCAUGGUGCUGAAGUUUAUUCACUU' (SEQ ID NO:445) | [[], [], ['UUUA']] | 0.387097 | 0.83871 | 1 | 3 |
| 'UCUGUCCAUGGUGCUGAAGUUUAUUCACUUU' (SEQ ID NO:446) | [[], [], ['UUUA']] | 0.387097 | 0.83871 | 1 | 4 |
| 'CCAUGGUGCUGAAGUUUAUUCACUUUCAAAC' (SEQ ID NO:447) | [[], [], ['UUUA']] | 0.387097 | 0.83871 | 1 | 9 |

FIG. 41 (Cont'd)

| SEQUENCE | BS | GCNESS | 3LN | NBP | P |
|---|---|---|---|---|---|
| 'CAUGGUGCUGAAGUUUAUUCACUUUCAAACC' (SEQ ID NO:448) | [[], [], ['UUUA']] | 0.387097 | 0.83871 | 1 | 10 |
| 'UGGUGCUGAAGUUUAUUCACUUUCAAACCAC' (SEQ ID NO:449) | [[], [], ['UUUA']] | 0.387097 | 0.83871 | 1 | 12 |
| 'GGUGCUGAAGUUUAUUCACUUUCAAACCACU' (SEQ ID NO:450) | [[], [], ['UUUA']] | 0.387097 | 0.83871 | 1 | 13 |
| 'UCCAUGGUGCUGAAGUUUAUUCACUUUCAAA' (SEQ ID NO:451) | [[], [], ['UUUA']] | 0.354839 | 0.83871 | 1 | 8 |
| 'AUGGUGCUGAAGUUUAUUCACUUUCAAACCA' (SEQ ID NO:452) | [[], [], ['UUUA']] | 0.354839 | 0.83871 | 1 | 11 |
| 'UUUCAGUAACAGGUGAGGUUCUACCUUAAAA' (SEQ ID NO:453) | [[], [], ['UUAA']] | 0.354839 | 0.83871 | 1 | 43 |
| 'UUCAGUAACAGGUGAGGUUCUACCUUAAAAU' (SEQ ID NO:454) | [[], [], ['UUAA']] | 0.354839 | 0.83871 | 1 | 44 |
| 'CAGGAAGCUGCAGCUUAGAUGGGAUGAUCAC' (SEQ ID NO:455) | [[], ['GGG'], []] | 0.516129 | 0.806452 | 1 | 157 |

FIG. 41 (Cont'd)

| SEQUENCE | BS | GCNESS | 3LN | NBP | P |
|---|---|---|---|---|---|
| 'GGCGAGGAAGUCACCAUCAAACCACUUUAUC' (SEQ ID NO:456) | [[], [], ['UUUA']] | 0.483871 | 0.806452 | 1 | 95 |
| 'GAAGCUGCAGCUUAGAUGGGAUGAUCACAAC' (SEQ ID NO:457) | [[], ['GGG'], []] | 0.483871 | 0.806452 | 1 | 160 |
| 'AGGCGAGGAAGUCACCAUCAAACCACUUUAU' (SEQ ID NO:458) | [[], [], ['UUUA']] | 0.451613 | 0.806452 | 1 | 94 |
| 'AAGCUGCAGCUUAGAUGGGAUGAUCACAACU' (SEQ ID NO:459) | [[], ['GGG'], []] | 0.451613 | 0.806452 | 1 | 161 |
| 'UAGAUGGGAUGAUCACAACUCCAUGGCAACA' (SEQ ID NO:460) | [[], ['GGG'], []] | 0.451613 | 0.806452 | 1 | 172 |
| 'UGGGAUGAUCACAACUCCAUGGCAACAAGAU' (SEQ ID NO:461) | [[], ['GGG'], []] | 0.451613 | 0.806452 | 1 | 176 |
| 'UGUCCAUGGUGCUGAAGUUUAUUCACUUUCA' (SEQ ID NO:462) | [[], [], ['UUUA']] | 0.387097 | 0.806452 | 1 | 6 |
| 'GUCCAUGGUGCUGAAGUUUAUUCACUUUCAA' (SEQ ID NO:463) | [[], [], ['UUUA']] | 0.387097 | 0.806452 | 1 | 7 |

FIG. 41 (Cont'd)

| SEQUENCE | BS | GCNESS | 3LN | NBP | P |
|---|---|---|---|---|---|
| 'ACUUUCAGUAACAGGUGAGGUUCUACCUUAA' (SEQ ID NO:464) | [[], [], ['UUAA']] | 0.387097 | 0.806452 | 1 | 41 |
| 'CUUUCAGUAACAGGUGAGGUUCUACCUUAAA' (SEQ ID NO:465) | [[], [], ['UUAA']] | 0.387097 | 0.806452 | 1 | 42 |
| 'GCUGCAGCUUAGAUGGGAUGAUCACAACUCC' (SEQ ID NO:466) | [[], ['GGG'], []] | 0.516129 | 0.774194 | 1 | 163 |
| 'AGCUGCAGCUUAGAUGGGAUGAUCACAACUC' (SEQ ID NO:467) | [[], ['GGG'], []] | 0.483871 | 0.774194 | 1 | 162 |
| 'CUGCAGCUUAGAUGGGAUGAUCACAACUCCA' (SEQ ID NO:468) | [[], ['GGG'], []] | 0.483871 | 0.774194 | 1 | 164 |
| 'GCAGCUUAGAUGGGAUGAUCACAACUCCAUG' (SEQ ID NO:469) | [[], ['GGG'], []] | 0.483871 | 0.774194 | 1 | 166 |
| 'CAGCUUAGAUGGGAUGAUCACAACUCCAUGG' (SEQ ID NO:470) | [[], ['GGG'], []] | 0.483871 | 0.774194 | 1 | 167 |
| 'AGCUUAGAUGGGAUGAUCACAACUCCAUGGC' (SEQ ID NO:471) | [[], ['GGG'], []] | 0.483871 | 0.774194 | 1 | 168 |

FIG. 41 (Cont'd)

| SEQUENCE | BS | GCNESS | 3LN | NBP | P |
|---|---|---|---|---|---|
| 'GCUUAGAUGGGAUGAUC ACAACUCCAUGGCA' (SEQ ID NO:472) | [[], ['GGG'], []] | 0.483871 | 0.774194 | 1 | 169 |
| 'UGCAGCUUAGAUGGGAU GAUCACAACUCCAU' (SEQ ID NO:473) | [[], ['GGG'], []] | 0.451613 | 0.774194 | 1 | 165 |
| 'CUUAGAUGGGAUGAUCA CAACUCCAUGGCAA' (SEQ ID NO:474) | [[], ['GGG'], []] | 0.451613 | 0.774194 | 1 | 170 |
| 'UUAGAUGGGAUGAUCAC AACUCCAUGGCAAC' (SEQ ID NO:475) | [[], ['GGG'], []] | 0.451613 | 0.774194 | 1 | 171 |
| 'AAUGCAGCAGAGACCCC AGGGGACAGGAGCC' (SEQ ID NO:476) | [['CCC'], ['GGG'], []] | 0.645161 | 0.967742 | 2 | 213 |
| 'UGCAGCAGAGACCCCAG GGGACAGGAGCCUC' (SEQ ID NO:477) | [['CCC'], ['GGG'], []] | 0.677419 | 0.935484 | 2 | 215 |
| 'GCAGCAGAGACCCCAGG GGACAGGAGCCUCU' (SEQ ID NO:478) | [['CCC'], ['GGG'], []] | 0.677419 | 0.935484 | 2 | 216 |
| 'AUGCAGCAGAGACCCCA GGGGACAGGAGCCU' (SEQ ID NO:479) | [['CCC'], ['GGG'], []] | 0.645161 | 0.935484 | 2 | 214 |

FIG. 41 (Cont'd)

| SEQUENCE | BS | GCNESS | 3LN | NBP | P |
|---|---|---|---|---|---|
| 'CAAGAUGACACAAAUGCAGCAGAGACCCCAG' (SEQ ID NO:480) | [['CCC'], [], ['AAAU']] | 0.516129 | 0.935484 | 2 | 201 |
| 'AAGAUGACACAAAUGCAGCAGAGACCCCAGG' (SEQ ID NO:481) | [['CCC'], [], ['AAAU']] | 0.516129 | 0.935484 | 2 | 202 |
| 'CAACAAGAUGACACAAAUGCAGCAGAGACCC' (SEQ ID NO:482) | [['CCC'], [], ['AAAU']] | 0.483871 | 0.935484 | 2 | 198 |
| 'AACAAGAUGACACAAAUGCAGCAGAGACCCC' (SEQ ID NO:483) | [['CCC'], [], ['AAAU']] | 0.483871 | 0.935484 | 2 | 199 |
| 'ACAAGAUGACACAAAUGCAGCAGAGACCCCA' (SEQ ID NO:484) | [['CCC'], [], ['AAAU']] | 0.483871 | 0.935484 | 2 | 200 |
| 'CAUCAAACCACUUUAUCUACAGUUAGCAUAA' (SEQ ID NO:485) | [[], [], ['UUUA', 'AUAA']] | 0.322581 | 0.935484 | 2 | 109 |
| 'GCAGAGACCCCAGGGGACAGGAGCCUCUUGC' (SEQ ID NO:486) | [['CCC'], ['GGG'], []] | 0.677419 | 0.903226 | 2 | 219 |
| 'GCAUGGGGUGGGAGAGGCGAGGAAGUCACCA' (SEQ ID NO:487) | [[], ['GGG', 'GGG'], []] | 0.645161 | 0.903226 | 2 | 80 |

FIG. 41 (Cont'd)

| SEQUENCE | BS | GCNESS | 3LN | NBP | P |
|---|---|---|---|---|---|
| 'CAGCAGAGACCCCAGGG GACAGGAGCCUCUU' (SEQ ID NO:488) | [['CCC'], ['GGG'], []] | 0.645161 | 0.903226 | 2 | 217 |
| 'AGCAGAGACCCCAGGGG ACAGGAGCCUCUUG' (SEQ ID NO:489) | [['CCC'], ['GGG'], []] | 0.645161 | 0.903226 | 2 | 218 |
| 'CAGAGACCCCAGGGGAC AGGAGCCUCUUGCA' (SEQ ID NO:490) | [['CCC'], ['GGG'], []] | 0.645161 | 0.903226 | 2 | 220 |
| 'AGAGACCCCAGGGGACA GGAGCCUCUUGCAG' (SEQ ID NO:491) | [['CCC'], ['GGG'], []] | 0.645161 | 0.903226 | 2 | 221 |
| 'GGGGUGGGAGAGGCGA GGAAGUCACCAUCAA' (SEQ ID NO:492) | [[], ['GGG', 'GGG'], []] | 0.612903 | 0.903226 | 2 | 84 |
| 'AAUGCAUGGGGUGGGA GAGGCGAGGAAGUCA' (SEQ ID NO:493) | [[], ['GGG', 'GGG'], []] | 0.580645 | 0.903226 | 2 | 77 |
| 'GGGUGGGAGAGGCGAG GAAGUCACCAUCAAA' (SEQ ID NO:494) | [[], ['GGG', 'GGG'], []] | 0.580645 | 0.903226 | 2 | 85 |
| 'AUCAAACCACUUUAUCU ACAGUUAGCAUAAG' (SEQ ID NO:495) | [[], [], ['UUUA', 'AUAA']] | 0.322581 | 0.903226 | 2 | 110 |

FIG. 41 (Cont'd)

| SEQUENCE | BS | GCNESS | 3LN | NBP | P |
|---|---|---|---|---|---|
| 'UCAAACCACUUUAUCUACAGUUAGCAUAAGA' (SEQ ID NO:496) | [[], [], ['UUUA', 'AUAA']] | 0.322581 | 0.903226 | 2 | 111 |
| 'CAAACCACUUUAUCUACAGUUAGCAUAAGAU' (SEQ ID NO:497) | [[], [], ['UUUA', 'AUAA']] | 0.322581 | 0.903226 | 2 | 112 |
| 'UUUAUCUACAGUUAGCAUAAGAUGUGAGAAG' (SEQ ID NO:498) | [[], [], ['UUUA', 'AUAA']] | 0.322581 | 0.903226 | 2 | 120 |
| 'UUAUCUACAGUUAGCAUAAGAUGUGAGAAGU' (SEQ ID NO:499) | [[], [], ['UUAU', 'AUAA']] | 0.322581 | 0.903226 | 2 | 121 |
| 'UGCAUGGGGUGGGAGAGGCGAGGAAGUCACC' (SEQ ID NO:500) | [[], ['GGG', 'GGG'], []] | 0.645161 | 0.870968 | 2 | 79 |
| 'GAGACCCCAGGGGACAGGAGCCUCUUGCAGU' (SEQ ID NO:501) | [['CCC'], ['GGG'], []] | 0.645161 | 0.870968 | 2 | 222 |
| 'AGACCCCAGGGGACAGGAGCCUCUUGCAGUC' (SEQ ID NO:502) | [['CCC'], ['GGG'], []] | 0.645161 | 0.870968 | 2 | 223 |
| 'CAGGAGCCUCUUGCAGUCUGUCCCUAGGCCC' (SEQ ID NO:503) | [['CCC', 'CCC'], [], []] | 0.645161 | 0.870968 | 2 | 236 |

FIG. 41 (Cont'd)

| SEQUENCE | BS | GCNESS | 3LN | NBP | P |
|---|---|---|---|---|---|
| 'GGAGCCUCUUGCAGUCUGUCCCUAGGCCCAG' (SEQ ID NO:504) | [['CCC', 'CCC'], [], []] | 0.645161 | 0.870968 | 2 | 238 |
| 'GAGCCUCUUGCAGUCUGUCCCUAGGCCCAGC' (SEQ ID NO:505) | [['CCC', 'CCC'], [], []] | 0.645161 | 0.870968 | 2 | 239 |
| 'AGCCUCUUGCAGUCUGUCCCUAGGCCCAGCC' (SEQ ID NO:506) | [['CCC', 'CCC'], [], []] | 0.645161 | 0.870968 | 2 | 240 |
| 'AUGCAUGGGGUGGGAGAGGCGAGGAAGUCAC' (SEQ ID NO:507) | [[], ['GGG', 'GGG'], []] | 0.612903 | 0.870968 | 2 | 78 |
| 'CAUGGGGUGGGAGAGGCGAGGAAGUCACCAU' (SEQ ID NO:508) | [[], ['GGG', 'GGG'], []] | 0.612903 | 0.870968 | 2 | 81 |
| 'AUGGGGUGGGAGAGGCGAGGAAGUCACCAUC' (SEQ ID NO:509) | [[], ['GGG', 'GGG'], []] | 0.612903 | 0.870968 | 2 | 82 |
| 'UGGGGUGGGAGAGGCGAGGAAGUCACCAUCA' (SEQ ID NO:510) | [[], ['GGG', 'GGG'], []] | 0.612903 | 0.870968 | 2 | 83 |
| 'AGUAACAGGUGAGGUUCUACCUUAAAAUUUA' (SEQ ID NO:511) | [[], [], ['UUAA', 'AAUU']] | 0.322581 | 0.870968 | 2 | 47 |

FIG. 41 (Cont'd)

| SEQUENCE | BS | GCNESS | 3LN | NBP | P |
|---|---|---|---|---|---|
| 'GUAACAGGUGAGGUUCUACCUUAAAAUUUAA' (SEQ ID NO:512) | [[], [], ['UUAA', 'AAUU']] | 0.322581 | 0.870968 | 2 | 48 |
| 'AAACCACUUUAUCUACAGUUAGCAUAAGAUG' (SEQ ID NO:513) | [[], [], ['UUUA', 'AUAA']] | 0.322581 | 0.870968 | 2 | 113 |
| 'AACCACUUUAUCUACAGUUAGCAUAAGAUGU' (SEQ ID NO:514) | [[], [], ['UUUA', 'AUAA']] | 0.322581 | 0.870968 | 2 | 114 |
| 'ACUUUAUCUACAGUUAGCAUAAGAUGUGAGA' (SEQ ID NO:515) | [[], [], ['UUUA', 'AUAA']] | 0.322581 | 0.870968 | 2 | 118 |
| 'CUUUAUCUACAGUUAGCAUAAGAUGUGAGAA' (SEQ ID NO:516) | [[], [], ['UUUA', 'AUAA']] | 0.322581 | 0.870968 | 2 | 119 |
| 'GACCCCAGGGGACAGGAGCCUCUUGCAGUCU' (SEQ ID NO:517) | [['CCC'], ['GGG'], []] | 0.645161 | 0.83871 | 2 | 224 |
| 'ACCCCAGGGGACAGGAGCCUCUUGCAGUCUG' (SEQ ID NO:518) | [['CCC'], ['GGG'], []] | 0.645161 | 0.83871 | 2 | 225 |
| 'CCCCAGGGGACAGGAGCCUCUUGCAGUCUGU' (SEQ ID NO:519) | [['CCC'], ['GGG'], []] | 0.645161 | 0.83871 | 2 | 226 |

FIG. 41 (Cont'd)

| SEQUENCE | BS | GCNESS | 3LN | NBP | P |
|---|---|---|---|---|---|
| 'CCCAGGGGACAGGAGCCUCUUGCAGUCUGUC' (SEQ ID NO:520) | [['CCC'], ['GGG'], []] | 0.645161 | 0.83871 | 2 | 227 |
| 'CAGGGGACAGGAGCCUCUUGCAGUCUGUCCC' (SEQ ID NO:521) | [['CCC'], ['GGG'], []] | 0.645161 | 0.83871 | 2 | 229 |
| 'AGGGGACAGGAGCCUCUUGCAGUCUGUCCCU' (SEQ ID NO:522) | [['CCC'], ['GGG'], []] | 0.612903 | 0.83871 | 2 | 230 |
| 'GGGGACAGGAGCCUCUUGCAGUCUGUCCCUA' (SEQ ID NO:523) | [['CCC'], ['GGG'], []] | 0.612903 | 0.83871 | 2 | 231 |
| 'GGGACAGGAGCCUCUUGCAGUCUGUCCCUAG' (SEQ ID NO:524) | [['CCC'], ['GGG'], []] | 0.612903 | 0.83871 | 2 | 232 |
| 'AGGAGCCUCUUGCAGUCUGUCCCUAGGCCCA' (SEQ ID NO:525) | [['CCC', 'CCC'], [], []] | 0.612903 | 0.83871 | 2 | 237 |
| 'UCAGUAACAGGUGAGGUUCUACCUUAAAAUU' (SEQ ID NO:526) | [[], [], ['UUAA', 'AAUU']] | 0.354839 | 0.83871 | 2 | 45 |
| 'CAGUAACAGGUGAGGUUCUACCUUAAAAUUU' (SEQ ID NO:527) | [[], [], ['UUAA', 'AAUU']] | 0.354839 | 0.83871 | 2 | 46 |

FIG. 41 (Cont'd)

| SEQUENCE | BS | GCNESS | 3LN | NBP | P |
|---|---|---|---|---|---|
| 'ACCACUUUAUCUACAGUUAGCAUAAGAUGUG' (SEQ ID NO:528) | [[], [], ['UUUA', 'AUAA']] | 0.354839 | 0.83871 | 2 | 115 |
| 'CCACUUUAUCUACAGUUAGCAUAAGAUGUGA' (SEQ ID NO:529) | [[], [], ['UUUA', 'AUAA']] | 0.354839 | 0.83871 | 2 | 116 |
| 'CACUUUAUCUACAGUUAGCAUAAGAUGUGAG' (SEQ ID NO:530) | [[], [], ['UUUA', 'AUAA']] | 0.354839 | 0.83871 | 2 | 117 |
| 'GGCCCAGCCCUGCUUGUCCUCCCUGGCUGUU' (SEQ ID NO:531) | [['CCC', 'CCC', 'CCC'], [], []] | 0.677419 | 0.967742 | 3 | 262 |
| 'CACAAAUGCAGCAGAGACCCCAGGGGACAGG' (SEQ ID NO:532) | [['CCC'], ['GGG'], ['AAAU']] | 0.612903 | 0.967742 | 3 | 209 |
| 'CAAAUGCAGCAGAGACCCCAGGGGACAGGAG' (SEQ ID NO:533) | [['CCC'], ['GGG'], ['AAAU']] | 0.612903 | 0.967742 | 3 | 211 |
| 'AAAUGCAGCAGAGACCCCAGGGGACAGGAGC' (SEQ ID NO:534) | [['CCC'], ['GGG'], ['AAAU']] | 0.612903 | 0.967742 | 3 | 212 |
| 'GACACAAAUGCAGCAGAGACCCCAGGGGACA' (SEQ ID NO:535) | [['CCC'], ['GGG'], ['AAAU']] | 0.580645 | 0.967742 | 3 | 207 |

FIG. 41 (Cont'd)

| SEQUENCE | BS | GCNESS | 3LN | NBP | P |
|---|---|---|---|---|---|
| 'ACACAAAUGCAGCAGAGACCCCAGGGGACAG' (SEQ ID NO:536) | [['CCC'], ['GGG'], ['AAAU']] | 0.580645 | 0.967742 | 3 | 208 |
| 'ACAAAUGCAGCAGAGACCCCAGGGGACAGGA' (SEQ ID NO:537) | [['CCC'], ['GGG'], ['AAAU']] | 0.580645 | 0.967742 | 3 | 210 |
| 'CCUAGGCCCAGCCCUGCUUGUCCUCCCUGGC' (SEQ ID NO:538) | [['CCC', 'CCC', 'CCC'], [], []] | 0.709677 | 0.935484 | 3 | 258 |
| 'CUGUCCUAGGCCCAGCCCUGCUUGUCCUCC' (SEQ ID NO:539) | [['CCC', 'CCC', 'CCC'], [], []] | 0.677419 | 0.935484 | 3 | 253 |
| 'CUAGGCCCAGCCCUGCUUGUCCUCCCUGGCU' (SEQ ID NO:540) | [['CCC', 'CCC', 'CCC'], [], []] | 0.677419 | 0.935484 | 3 | 259 |
| 'UAGGCCCAGCCCUGCUUGUCCUCCCUGGCUG' (SEQ ID NO:541) | [['CCC', 'CCC', 'CCC'], [], []] | 0.677419 | 0.935484 | 3 | 260 |
| 'AGGCCCAGCCCUGCUUGUCCUCCCUGGCUGU' (SEQ ID NO:542) | [['CCC', 'CCC', 'CCC'], [], []] | 0.677419 | 0.935484 | 3 | 261 |

| SEQUENCE | BS | GCNESS | 3LN | NBP | P |
|---|---|---|---|---|---|
| 'GUCUGUCCCUAGGCCCAGCCCUGCUUGUCCU' (SEQ ID NO:543) | [['CCC', 'CCC', 'CCC'], [], []] | 0.645161 | 0.935484 | 3 | 251 |
| 'UCUGUCCCUAGGCCCAGCCCUGCUUGUCCUC' (SEQ ID NO:544) | [['CCC', 'CCC', 'CCC'], [], []] | 0.645161 | 0.935484 | 3 | 252 |
| 'GCCCAGCCCUGCUUGUCCUCCCUGGCUGUUA' (SEQ ID NO:545) | [['CCC', 'CCC', 'CCC'], [], []] | 0.645161 | 0.935484 | 3 | 263 |
| 'CCAGCCCUGCUUGUCCUCCCUGGCUGUUAUC' (SEQ ID NO:546) | [['CCC', 'CCC'], [], ['UUAU']] | 0.612903 | 0.935484 | 3 | 265 |
| 'GAUGACACAAAUGCAGCAGAGACCCCAGGGG' (SEQ ID NO:547) | [['CCC'], ['GGG'], ['AAAU']] | 0.580645 | 0.935484 | 3 | 204 |
| 'UGACACAAAUGCAGCAGAGACCCCAGGGGAC' (SEQ ID NO:548) | [['CCC'], ['GGG'], ['AAAU']] | 0.580645 | 0.935484 | 3 | 206 |
| 'CAGCCCUGCUUGUCCUCCCUGGCUGUUAUCU' (SEQ ID NO:549) | [['CCC', 'CCC'], [], ['UUAU']] | 0.580645 | 0.935484 | 3 | 266 |
| 'UUUAAUGCAUGGGGUGGGAGAGGCGAGGAAG' (SEQ ID NO:550) | [[], ['GGG', 'GGG'], ['UUUA']] | 0.548387 | 0.935484 | 3 | 74 |

| SEQUENCE | BS | GCNESS | 3LN | NBP | P |
|---|---|---|---|---|---|
| 'UUAAUGCAUGGGGUGGGAGAGGCGAGGAAGU' (SEQ ID NO:551) | [[], ['GGG', 'GGG'], ['UUAA']] | 0.548387 | 0.935484 | 3 | 75 |
| 'AGAUGACACAAAUGCAGCAGAGACCCCAGGG' (SEQ ID NO:552) | [['CCC'], ['GGG'], ['AAAU']] | 0.548387 | 0.935484 | 3 | 203 |
| 'AUGACACAAAUGCAGCAGAGACCCCAGGGGA' (SEQ ID NO:553) | [['CCC'], ['GGG'], ['AAAU']] | 0.548387 | 0.935484 | 3 | 205 |
| 'AUUUAAUGCAUGGGGUGGGAGAGGCGAGGAA' (SEQ ID NO:554) | [[], ['GGG', 'GGG'], ['AUUU']] | 0.516129 | 0.935484 | 3 | 73 |
| 'GCCUCUUGCAGUCUGUCCCUAGGCCCAGCCC' (SEQ ID NO:555) | [['CCC', 'CCC', 'CCC'], [], []] | 0.677419 | 0.903226 | 3 | 241 |
| 'CCUCUUGCAGUCUGUCCCUAGGCCCAGCCCU' (SEQ ID NO:556) | [['CCC', 'CCC', 'CCC'], [], []] | 0.645161 | 0.903226 | 3 | 242 |
| 'CUCUUGCAGUCUGUCCCUAGGCCCAGCCCUG' (SEQ ID NO:557) | [['CCC', 'CCC', 'CCC'], [], []] | 0.645161 | 0.903226 | 3 | 243 |

FIG. 41 (Cont'd)

| SEQUENCE | BS | GCNESS | 3LN | NBP | P |
|---|---|---|---|---|---|
| 'UCUUGCAGUCUGUCCCUAGGCCCAGCCCUGC' (SEQ ID NO:558) | [['CCC', 'CCC', 'CCC'], [], []] | 0.645161 | 0.903226 | 3 | 244 |
| 'CUUGCAGUCUGUCCCUAGGCCCAGCCCUGCU' (SEQ ID NO:559) | [['CCC', 'CCC', 'CCC'], [], []] | 0.645161 | 0.903226 | 3 | 245 |
| 'UGCAGUCUGUCCCUAGGCCCAGCCCUGCUUG' (SEQ ID NO:560) | [['CCC', 'CCC', 'CCC'], [], []] | 0.645161 | 0.903226 | 3 | 247 |
| 'GCAGUCUGUCCCUAGGCCCAGCCCUGCUUGU' (SEQ ID NO:561) | [['CCC', 'CCC', 'CCC'], [], []] | 0.645161 | 0.903226 | 3 | 248 |
| 'CAGUCUGUCCCUAGGCCCAGCCCUGCUUGUC' (SEQ ID NO:562) | [['CCC', 'CCC', 'CCC'], [], []] | 0.645161 | 0.903226 | 3 | 249 |
| 'AGUCUGUCCCUAGGCCCAGCCCUGCUUGUCC' (SEQ ID NO:563) | [['CCC', 'CCC', 'CCC'], [], []] | 0.645161 | 0.903226 | 3 | 250 |

| SEQUENCE | BS | GCNESS | 3LN | NBP | P |
|---|---|---|---|---|---|
| 'UUGCAGUCUGUCCCUAG GCCCAGCCCUGCUU' (SEQ ID NO:564) | [['CCC', 'CCC', 'CCC'], [], []] | 0.612903 | 0.903226 | 3 | 246 |
| 'UAAUGCAUGGGGUGGG AGAGGCGAGGAAGUC' (SEQ ID NO:565) | [[], ['GGG', 'GGG'], ['UAAU']] | 0.580645 | 0.903226 | 3 | 76 |
| 'GGUGAGGUUCUACCUUA AAAUUUAAUGCAUG' (SEQ ID NO:566) | [[], [], ['UUAA', 'AAUU', 'UAAU']] | 0.354839 | 0.870968 | 3 | 54 |
| 'GUGAGGUUCUACCUUAA AAUUUAAUGCAUGG' (SEQ ID NO:567) | [[], [], ['UUAA', 'AAUU', 'UAAU']] | 0.354839 | 0.870968 | 3 | 55 |
| 'AACAGGUGAGGUUCUAC CUUAAAAUUUAAUG' (SEQ ID NO:568) | [[], [], ['UUAA', 'AAUU', 'UAAU']] | 0.322581 | 0.870968 | 3 | 50 |
| 'AGGUGAGGUUCUACCUU AAAAUUUAAUGCAU' (SEQ ID NO:569) | [[], [], ['UUAA', 'AAUU', 'UAAU']] | 0.322581 | 0.870968 | 3 | 53 |
| 'UAACAGGUGAGGUUCUA CCUUAAAAUUUAAU' (SEQ ID NO:570) | [[], [], ['UUAA', 'AAUU', 'UAAU']] | 0.290323 | 0.870968 | 3 | 49 |

FIG. 41 (Cont'd)

| SEQUENCE | BS | GCNESS | 3LN | NBP | P |
|---|---|---|---|---|---|
| 'ACAGGUGAGGUUCUACCUUAAAAUUUAAUGC' (SEQ ID NO:571) | [[], [], ['UUAA', 'AAUU', 'UAAU']] | 0.354839 | 0.83871 | 3 | 51 |
| 'CAGGUGAGGUUCUACCUUAAAAUUUAAUGCA' (SEQ ID NO:572) | [[], [], ['UUAA', 'AAUU', 'UAAU']] | 0.354839 | 0.83871 | 3 | 52 |
| 'CCCUAGGCCCAGCCCUGCUUGUCCUCCCUGG' (SEQ ID NO:573) | [['CCC', 'CCC', 'CCC', 'CCC'], [], []] | 0.709677 | 0.935484 | 4 | 257 |
| 'UGUCCCUAGGCCCAGCCCUGCUUGUCCUCCC' (SEQ ID NO:574) | [['CCC', 'CCC', 'CCC', 'CCC'], [], []] | 0.677419 | 0.935484 | 4 | 254 |
| 'GUCCCUAGGCCCAGCCCUGCUUGUCCUCCCU' (SEQ ID NO:575) | [['CCC', 'CCC', 'CCC', 'CCC'], [], []] | 0.677419 | 0.935484 | 4 | 255 |
| 'UCCCUAGGCCCAGCCCUGCUUGUCCUCCCUG' (SEQ ID NO:576) | [['CCC', 'CCC', 'CCC', 'CCC'], [], []] | 0.677419 | 0.935484 | 4 | 256 |

| SEQUENCE | BS | GCNESS | 3LN | NBP | P |
| --- | --- | --- | --- | --- | --- |
| 'CCCAGCCCUGCUUGUCCUCCCUGGCUGUUAU' (SEQ ID NO:577) | [['CCC', 'CCC', 'CCC'], [], ['UUAU']] | 0.612903 | 0.935484 | 4 | 264 |
| 'AAAUUUAAUGCAUGGGGUGGGAGAGGCGAGG' (SEQ ID NO:578) | [[], ['GGG', 'GGG'], ['AAAU', 'UUAA']] | 0.516129 | 0.935484 | 4 | 71 |
| 'AAUUUAAUGCAUGGGGUGGGAGAGGCGAGGA' (SEQ ID NO:579) | [[], ['GGG', 'GGG'], ['AAUU', 'UAAU']] | 0.516129 | 0.935484 | 4 | 72 |
| 'AAAAUUUAAUGCAUGGGGUGGGAGAGGCGAG' (SEQ ID NO:580) | [[], ['GGG', 'GGG'], ['AAAA', 'UUUA']] | 0.483871 | 0.935484 | 4 | 70 |
| 'UAAAAUUUAAUGCAUGGGGUGGGAGAGGCGA' (SEQ ID NO:581) | [[], ['GGG', 'GGG'], ['UAAA', 'AUUU']] | 0.451613 | 0.935484 | 4 | 69 |
| 'GAGGUUCUACCUUAAAAUUUAAUGCAUGGGG' (SEQ ID NO:582) | [[], ['GGG'], ['UUAA', 'AAUU', 'UAAU']] | 0.387097 | 0.870968 | 4 | 57 |

FIG. 41 (Cont'd)

| SEQUENCE | BS | GCNESS | 3LN | NBP | P |
| --- | --- | --- | --- | --- | --- |
| 'GGUUCUACCUUAAAAUUUAAUGCAUGGGGUG' (SEQ ID NO:583) | [[], ['GGG'], ['UUAA', 'AAUU', 'UAAU']] | 0.387097 | 0.870968 | 4 | 59 |
| 'GUUCUACCUUAAAAUUUAAUGCAUGGGGUGG' (SEQ ID NO:584) | [[], ['GGG'], ['UUAA', 'AAUU', 'UAAU']] | 0.387097 | 0.870968 | 4 | 60 |
| 'UGAGGUUCUACCUUAAAAUUUAAUGCAUGGG' (SEQ ID NO:585) | [[], ['GGG'], ['UUAA', 'AAUU', 'UAAU']] | 0.354839 | 0.870968 | 4 | 56 |
| 'AGGUUCUACCUUAAAAUUUAAUGCAUGGGGU' (SEQ ID NO:586) | [[], ['GGG'], ['UUAA', 'AAUU', 'UAAU']] | 0.354839 | 0.870968 | 4 | 58 |
| 'UUAAAAUUUAAUGCAUGGGUGGGAGAGGCG' (SEQ ID NO:587) | [[], ['GGG', 'GGG'], ['UUAA', 'AAUU', 'UAAU']] | 0.451613 | 0.935484 | 5 | 68 |

FIG. 41 (Cont'd)

| SEQUENCE | BS | GCNESS | 3LN | NBP | P |
|---|---|---|---|---|---|
| 'CCUUAAAAUUUAAUGCAUGGGGUGGGAGAGG' (SEQ ID NO:588) | [[], ['GGG', 'GGG'], ['UUAA', 'AAUU', 'UAAU']] | 0.451613 | 0.903226 | 5 | 66 |
| 'CUUAAAAUUUAAUGCAUGGGGUGGGAGAGGC' (SEQ ID NO:589) | [[], ['GGG', 'GGG'], ['UUAA', 'AAUU', 'UAAU']] | 0.451613 | 0.903226 | 5 | 67 |
| 'ACCUUAAAAUUUAAUGCAUGGGGUGGGAGAG' (SEQ ID NO:590) | [[], ['GGG', 'GGG'], ['UUAA', 'AAUU', 'UAAU']] | 0.419355 | 0.903226 | 5 | 65 |
| 'UACCUUAAAAUUUAAUGCAUGGGGUGGGAGA' (SEQ ID NO:591) | [[], ['GGG', 'GGG'], ['UUAA', 'AAUU', 'UAAU']] | 0.387097 | 0.903226 | 5 | 64 |
| 'CUACCUUAAAAUUUAAUGCAUGGGGUGGGAG' (SEQ ID NO:592) | [[], ['GGG', 'GGG'], ['UUAA', 'AAUU', 'UAAU']] | 0.419355 | 0.870968 | 5 | 63 |

FIG. 41 (Cont'd)

| SEQUENCE | BS | GCNESS | 3LN | NBP | P |
|---|---|---|---|---|---|
| 'UUCUACCUUAAAAUUUA AUGCAUGGGGUGGG' (SEQ ID NO:593) | [[], ['GGG', 'GGG'], ['UUAA', 'AAUU', 'UAAU']] | 0.387097 | 0.870968 | 5 | 61 |
| 'UCUACCUUAAAAUUUAA UGCAUGGGGUGGGA' (SEQ ID NO:594) | [[], ['GGG', 'GGG'], ['UUAA', 'AAUU', 'UAAU']] | 0.387097 | 0.870968 | 5 | 62 |

| SEQUENCE | BS | GCNESS | 3LN | NBP | P |
|---|---|---|---|---|---|
| 'GGCCUCAGCGUCUGUCCGUGGUGCUGAAGUU' (SEQ ID NO:595) | [[], [], []] | 0.612903 | 0.903226 | 0 | 2 |
| 'GCCUCAGCGUCUGUCCGUGGUGCUGAAGUUU' (SEQ ID NO:596) | [[], [], []] | 0.580645 | 0.903226 | 0 | 3 |
| 'GAUGAAGACAGGAAGCUGCAGCUCCAGGAGG' (SEQ ID NO:597) | [[], [], []] | 0.580645 | 0.903226 | 0 | 154 |
| 'AGAUGAAGACAGGAAGCUGCAGCUCCAGGAG' (SEQ ID NO:598) | [[], [], []] | 0.548387 | 0.903226 | 0 | 153 |
| 'CAGGCCUCAGCGUCUGUCCGUGGUGCUGAAG' (SEQ ID NO:599) | [[], [], []] | 0.645161 | 0.870968 | 0 | 0 |
| 'AGGCCUCAGCGUCUGUCCGUGGUGCUGAAGU' (SEQ ID NO:600) | [[], [], []] | 0.612903 | 0.870968 | 0 | 1 |
| 'GGCAAUGCGACCAAGCUGUGUGACACACCGC' (SEQ ID NO:601) | [[], [], []] | 0.612903 | 0.870968 | 0 | 204 |
| 'GCAAUGCGACCAAGCUGUGUGACACACCGCA' (SEQ ID NO:602) | [[], [], []] | 0.580645 | 0.870968 | 0 | 205 |

| SEQUENCE | BS | GCNESS | 3LN | NBP | P |
|---|---|---|---|---|---|
| 'AUGCGACCAAGCUGUGUGACACACCGCAAGG' (SEQ ID NO:603) | [[], [], []] | 0.580645 | 0.870968 | 0 | 208 |
| 'CAAUGCGACCAAGCUGUGUGACACACCGCAA' (SEQ ID NO:604) | [[], [], []] | 0.548387 | 0.870968 | 0 | 206 |
| 'AAUGCGACCAAGCUGUGUGACACACCGCAAG' (SEQ ID NO:605) | [[], [], []] | 0.548387 | 0.870968 | 0 | 207 |
| 'GAUAGAUGAAGACAGGAAGCUGCAGCUCCAG' (SEQ ID NO:606) | [[], [], []] | 0.516129 | 0.870968 | 0 | 150 |
| 'AUAGAUGAAGACAGGAAGCUGCAGCUCCAGG' (SEQ ID NO:607) | [[], [], []] | 0.516129 | 0.870968 | 0 | 151 |
| 'UAGAUGAAGACAGGAAGCUGCAGCUCCAGGA' (SEQ ID NO:608) | [[], [], []] | 0.516129 | 0.870968 | 0 | 152 |
| 'GAUCGUGAUAGAUGAAGACAGGAAGCUGCAG' (SEQ ID NO:609) | [[], [], []] | 0.483871 | 0.870968 | 0 | 144 |
| 'AUCGAUCGUGAUAGAUGAAGACAGGAAGCUG' (SEQ ID NO:610) | [[], [], []] | 0.451613 | 0.870968 | 0 | 141 |

FIG. 42 (Cont'd)

| SEQUENCE | BS | GCNESS | 3LN | NBP | P |
|---|---|---|---|---|---|
| 'AACAUCGAUCGUGAUAGAUGAAGACAGGAAG' (SEQ ID NO:611) | [[], [], []] | 0.419355 | 0.870968 | 0 | 138 |
| 'UAACAUCGAUCGUGAUAGAUGAAGACAGGAA' (SEQ ID NO:612) | [[], [], []] | 0.387097 | 0.870968 | 0 | 137 |
| 'UCACCACCUCUCAGUGGCAAUGCGACCAAGC' (SEQ ID NO:613) | [[], [], []] | 0.580645 | 0.83871 | 0 | 189 |
| 'CACCACCUCUCAGUGGCAAUGCGACCAAGCU' (SEQ ID NO:614) | [[], [], []] | 0.580645 | 0.83871 | 0 | 190 |
| 'ACCACCUCUCAGUGGCAAUGCGACCAAGCUG' (SEQ ID NO:615) | [[], [], []] | 0.580645 | 0.83871 | 0 | 191 |
| 'GUGGCAAUGCGACCAAGCUGUGUGACACACC' (SEQ ID NO:616) | [[], [], []] | 0.580645 | 0.83871 | 0 | 202 |
| 'UGGCAAUGCGACCAAGCUGUGUGACACACCG' (SEQ ID NO:617) | [[], [], []] | 0.580645 | 0.83871 | 0 | 203 |
| 'CAGUGGCAAUGCGACCAAGCUGUGUGACACA' (SEQ ID NO:618) | [[], [], []] | 0.548387 | 0.83871 | 0 | 200 |

FIG. 42 (Cont'd)

| SEQUENCE | BS | GCNESS | 3LN | NBP | P |
|---|---|---|---|---|---|
| 'AGUGGCAAUGCGACCAAGCUGUGUGACACAC' (SEQ ID NO:619) | [[], [], []] | 0.548387 | 0.83871 | 0 | 201 |
| 'CGUGAUAGAUGAAGACAGGAAGCUGCAGCUC' (SEQ ID NO:620) | [[], [], []] | 0.516129 | 0.83871 | 0 | 147 |
| 'GUGAUAGAUGAAGACAGGAAGCUGCAGCUCC' (SEQ ID NO:621) | [[], [], []] | 0.516129 | 0.83871 | 0 | 148 |
| 'AUUCACCACCUCUCAGUGGCAAUGCGACCAA' (SEQ ID NO:622) | [[], [], []] | 0.516129 | 0.83871 | 0 | 187 |
| 'UCGAUCGUGAUAGAUGAAGACAGGAAGCUGC' (SEQ ID NO:623) | [[], [], []] | 0.483871 | 0.83871 | 0 | 142 |
| 'CGAUCGUGAUAGAUGAAGACAGGAAGCUGCA' (SEQ ID NO:624) | [[], [], []] | 0.483871 | 0.83871 | 0 | 143 |
| 'AUCGUGAUAGAUGAAGACAGGAAGCUGCAGC' (SEQ ID NO:625) | [[], [], []] | 0.483871 | 0.83871 | 0 | 145 |
| 'UCGUGAUAGAUGAAGACAGGAAGCUGCAGCU' (SEQ ID NO:626) | [[], [], []] | 0.483871 | 0.83871 | 0 | 146 |

FIG. 42 (Cont'd)

| SEQUENCE | BS | GCNESS | 3LN | NBP | P |
|---|---|---|---|---|---|
| 'UGAUAGAUGAAGACAGGAAGCUGCAGCUCCA' (SEQ ID NO:627) | [[], [], []] | 0.483871 | 0.83871 | 0 | 149 |
| 'ACAUCGAUCGUGAUAGAUGAAGACAGGAAGC' (SEQ ID NO:628) | [[], [], []] | 0.451613 | 0.83871 | 0 | 139 |
| 'CAUCGAUCGUGAUAGAUGAAGACAGGAAGCU' (SEQ ID NO:629) | [[], [], []] | 0.451613 | 0.83871 | 0 | 140 |
| 'CCACCUCUCAGUGGCAAUGCGACCAAGCUGU' (SEQ ID NO:630) | [[], [], []] | 0.580645 | 0.806452 | 0 | 192 |
| 'CACCUCUCAGUGGCAAUGCGACCAAGCUGUG' (SEQ ID NO:631) | [[], [], []] | 0.580645 | 0.806452 | 0 | 193 |
| 'CCUCUCAGUGGCAAUGCGACCAAGCUGUGUG' (SEQ ID NO:632) | [[], [], []] | 0.580645 | 0.806452 | 0 | 195 |
| 'UUCACCACCUCUCAGUGGCAAUGCGACCAAG' (SEQ ID NO:633) | [[], [], []] | 0.548387 | 0.806452 | 0 | 188 |
| 'CUCAGUGGCAAUGCGACCAAGCUGUGUGACA' (SEQ ID NO:634) | [[], [], []] | 0.548387 | 0.806452 | 0 | 198 |

FIG. 42 (Cont'd)

| SEQUENCE | BS | GCNESS | 3LN | NBP | P |
|---|---|---|---|---|---|
| 'UCAGUGGCAAUGCGAC CAAGCUGUGUGACAC' (SEQ ID NO:635) | [[], [], []] | 0.548387 | 0.806452 | 0 | 199 |
| 'ACCUCUCAGUGGCAAU GCGACCAAGCUGUGU' (SEQ ID NO:636) | [[], [], []] | 0.548387 | 0.774194 | 0 | 194 |
| 'CUCUCAGUGGCAAUGC GACCAAGCUGUGUGA' (SEQ ID NO:637) | [[], [], []] | 0.548387 | 0.774194 | 0 | 196 |
| 'UCUCAGUGGCAAUGCG ACCAAGCUGUGUGAC' (SEQ ID NO:638) | [[], [], []] | 0.548387 | 0.774194 | 0 | 197 |
| 'UAAGGCCUCACUAAACC ACUCAUCUACACUU' (SEQ ID NO:639) | [[], [], ['UAAA']] | 0.419355 | 0.935484 | 1 | 107 |
| 'AAGGCCUCACUAAACCA CUCAUCUACACUUA' (SEQ ID NO:640) | [[], [], ['UAAA']] | 0.419355 | 0.935484 | 1 | 108 |
| 'AAACCACUCAUCUACAC UUAACAUCGAUCGU' (SEQ ID NO:641) | [[], [], ['UUAA']] | 0.387097 | 0.935484 | 1 | 119 |
| 'GCGACCAAGCUGUGUG ACACACCGCAAGGGC' (SEQ ID NO:642) | [[], ['GGG'], []] | 0.645161 | 0.903226 | 1 | 210 |

FIG. 42 (Cont'd)

| SEQUENCE | BS | GCNESS | 3LN | NBP | P |
|---|---|---|---|---|---|
| 'AUGAAGACAGGAAGCUGCAGCUCCAGGAGGG' (SEQ ID NO:643) | [[], ['GGG'], []] | 0.580645 | 0.903226 | 1 | 155 |
| 'GAAGACAGGAAGCUGCAGCUCCAGGAGGGUA' (SEQ ID NO:644) | [[], ['GGG'], []] | 0.580645 | 0.903226 | 1 | 157 |
| 'GCGUCUGUCCGUGGUGCUGAAGUUUAUUCGG' (SEQ ID NO:645) | [[], [], ['UUUA']] | 0.548387 | 0.903226 | 1 | 9 |
| 'GUAAGGCCUCACUAAACCACUCAUCUACACU' (SEQ ID NO:646) | [[], [], ['UAAA']] | 0.451613 | 0.903226 | 1 | 106 |
| 'AACCACUCAUCUACACUUAACAUCGAUCGUG' (SEQ ID NO:647) | [[], [], ['UUAA']] | 0.419355 | 0.903226 | 1 | 120 |
| 'ACCACUCAUCUACACUUAACAUCGAUCGUGA' (SEQ ID NO:648) | [[], [], ['UUAA']] | 0.419355 | 0.903226 | 1 | 121 |
| 'CCACUCAUCUACACUUAACAUCGAUCGUGAU' (SEQ ID NO:649) | [[], [], ['UUAA']] | 0.419355 | 0.903226 | 1 | 122 |
| 'CACUCAUCUACACUUAACAUCGAUCGUGAUA' (SEQ ID NO:650) | [[], [], ['UUAA']] | 0.387097 | 0.903226 | 1 | 123 |

FIG. 42 (Cont'd)

| SEQUENCE | BS | GCNESS | 3LN | NBP | P |
|---|---|---|---|---|---|
| 'UGCGACCAAGCUGUGUGACACACCGCAAGGG' (SEQ ID NO:651) | [[], ['GGG'], []] | 0.612903 | 0.870968 | 1 | 209 |
| 'CGACCAAGCUGUGUGACACACCGCAAGGGCU' (SEQ ID NO:652) | [[], ['GGG'], []] | 0.612903 | 0.870968 | 1 | 211 |
| 'UGAAGACAGGAAGCUGCAGCUCCAGGAGGGU' (SEQ ID NO:653) | [[], ['GGG'], []] | 0.580645 | 0.870968 | 1 | 156 |
| 'CCUCAGCGUCUGUCCGUGGUGCUGAAGUUUA' (SEQ ID NO:654) | [[], [], ['UUUA']] | 0.548387 | 0.870968 | 1 | 4 |
| 'AAGACAGGAAGCUGCAGCUCCAGGAGGGUAU' (SEQ ID NO:655) | [[], ['GGG'], []] | 0.548387 | 0.870968 | 1 | 158 |
| 'CUCAGCGUCUGUCCGUGGUGCUGAAGUUUAU' (SEQ ID NO:656) | [[], [], ['UUUA']] | 0.516129 | 0.870968 | 1 | 5 |
| 'CAGCGUCUGUCCGUGGUGCUGAAGUUUAUUC' (SEQ ID NO:657) | [[], [], ['UUUA']] | 0.516129 | 0.870968 | 1 | 7 |
| 'AGCGUCUGUCCGUGGUGCUGAAGUUUAUUCG' (SEQ ID NO:658) | [[], [], ['UUUA']] | 0.516129 | 0.870968 | 1 | 8 |

FIG. 42 (Cont'd)

| SEQUENCE | BS | GCNESS | 3LN | NBP | P |
|---|---|---|---|---|---|
| 'CGUCUGUCCGUGGUGCUGAAGUUUAUUCGGA' (SEQ ID NO:659) | [[], [], ['UUUA']] | 0.516129 | 0.870968 | 1 | 10 |
| 'UCAGCGUCUGUCCGUGGUGCUGAAGUUUAUU' (SEQ ID NO:660) | [[], [], ['UUUA']] | 0.483871 | 0.870968 | 1 | 6 |
| 'GUCUGUCCGUGGUGCUGAAGUUUAUUCGGAU' (SEQ ID NO:661) | [[], [], ['UUUA']] | 0.483871 | 0.870968 | 1 | 11 |
| 'GGUAAGGCCUCACUAAACCACUCAUCUACAC' (SEQ ID NO:662) | [[], [], ['UAAA']] | 0.483871 | 0.870968 | 1 | 105 |
| 'UCUGUCCGUGGUGCUGAAGUUUAUUCGGAUU' (SEQ ID NO:663) | [[], [], ['UUUA']] | 0.451613 | 0.870968 | 1 | 12 |
| 'AGGUAAGGCCUCACUAAACCACUCAUCUACA' (SEQ ID NO:664) | [[], [], ['UAAA']] | 0.451613 | 0.870968 | 1 | 104 |
| 'ACUCAUCUACACUUAACAUCGAUCGUGAUAG' (SEQ ID NO:665) | [[], [], ['UUAA']] | 0.387097 | 0.870968 | 1 | 124 |
| 'CUCAUCUACACUUAACAUCGAUCGUGAUAGA' (SEQ ID NO:666) | [[], [], ['UUAA']] | 0.387097 | 0.870968 | 1 | 125 |

FIG. 42 (Cont'd)

| SEQUENCE | BS | GCNESS | 3LN | NBP | P |
|---|---|---|---|---|---|
| 'UUACAUCGAUCGUGA UAGAUGAAGACAGGA' (SEQ ID NO:667) | [[], [], ['UUAA']] | 0.387097 | 0.870968 | 1 | 136 |
| 'UCAUCUACACUUAACAU CGAUCGUGAUAGAU' (SEQ ID NO:668) | [[], [], ['UUAA']] | 0.354839 | 0.870968 | 1 | 126 |
| 'CCAAGCUGUGUGACAC ACCGCAAGGGCUUGG' (SEQ ID NO:669) | [[], ['GGG'], []] | 0.612903 | 0.83871 | 1 | 214 |
| 'GACCAAGCUGUGUGAC ACACCGCAAGGGCUU' (SEQ ID NO:670) | [[], ['GGG'], []] | 0.580645 | 0.83871 | 1 | 212 |
| 'ACCAAGCUGUGUGACA CACCGCAAGGGCUUG' (SEQ ID NO:671) | [[], ['GGG'], []] | 0.580645 | 0.83871 | 1 | 213 |
| 'UAUGCAGAGUGGGAGA GGUAAGGCCUCACUA' (SEQ ID NO:672) | [[], ['GGG'], []] | 0.516129 | 0.83871 | 1 | 89 |
| 'AUGCAGAGUGGGAGAG GUAAGGCCUCACUAA' (SEQ ID NO:673) | [[], ['GGG'], []] | 0.516129 | 0.83871 | 1 | 90 |
| 'GGAGAGGUAAGGCCUC ACUAAACCACUCAUC' (SEQ ID NO:674) | [[], [], ['UAAA']] | 0.516129 | 0.83871 | 1 | 100 |

FIG. 42 (Cont'd)

| SEQUENCE | BS | GCNESS | 3LN | NBP | P |
|---|---|---|---|---|---|
| 'UAUUCACCACCUCUCAGUGGCAAUGCGACCA' (SEQ ID NO:675) | [[], [], ['UAUU']] | 0.516129 | 0.83871 | 1 | 186 |
| 'GAGGUAAGGCCUCACUAAACCACUCAUCUAC' (SEQ ID NO:676) | [[], [], ['UAAA']] | 0.483871 | 0.83871 | 1 | 103 |
| 'UUUCCAACUGCUUUCUGAAAGGGGUGAGGAU' (SEQ ID NO:677) | [[], ['GGG'], []] | 0.451613 | 0.83871 | 1 | 49 |
| 'UGCUUUCUGAAGGGGUGAGGAUCUACCUUA' (SEQ ID NO:678) | [[], ['GGG'], []] | 0.451613 | 0.83871 | 1 | 57 |
| 'AGAGGUAAGGCCUCACUAAACCACUCAUCUA' (SEQ ID NO:679) | [[], [], ['UAAA']] | 0.451613 | 0.83871 | 1 | 102 |
| 'CUUAACAUCGAUCGUGAUAGAUGAAGACAGG' (SEQ ID NO:680) | [[], [], ['UUAA']] | 0.419355 | 0.83871 | 1 | 135 |
| 'CAUCUACACUUAACAUCGAUCGUGAUAGAUG' (SEQ ID NO:681) | [[], [], ['UUAA']] | 0.387097 | 0.83871 | 1 | 127 |
| 'ACUUAACAUCGAUCGUGAUAGAUGAAGACAG' (SEQ ID NO:682) | [[], [], ['UUAA']] | 0.387097 | 0.83871 | 1 | 134 |

FIG. 42 (Cont'd)

| SEQUENCE | BS | GCNESS | 3LN | NBP | P |
|---|---|---|---|---|---|
| 'AUCUACACUUAACAUCGAUCGUGAUAGAUGA' (SEQ ID NO:683) | [[], [], ['UUAA']] | 0.354839 | 0.83871 | 1 | 128 |
| 'UCUACACUUAACAUCGAUCGUGAUAGAUGAA' (SEQ ID NO:684) | [[], [], ['UUAA']] | 0.354839 | 0.83871 | 1 | 129 |
| 'UACACUUAACAUCGAUCGUGAUAGAUGAAGA' (SEQ ID NO:685) | [[], [], ['UUAA']] | 0.354839 | 0.83871 | 1 | 131 |
| 'GUAUUCACCACCUCUCAGUGGCAAUGCGACC' (SEQ ID NO:686) | [[], [], ['UAUU']] | 0.548387 | 0.806452 | 1 | 185 |
| 'UUCCAACUGCUUUCUGAAAGGGGUGAGGAUC' (SEQ ID NO:687) | [[], ['GGG'], []] | 0.483871 | 0.806452 | 1 | 50 |
| 'UCCAACUGCUUUCUGAAAGGGGUGAGGAUCU' (SEQ ID NO:688) | [[], ['GGG'], []] | 0.483871 | 0.806452 | 1 | 51 |
| 'CCAACUGCUUUCUGAAAGGGGUGAGGAUCUA' (SEQ ID NO:689) | [[], ['GGG'], []] | 0.483871 | 0.806452 | 1 | 52 |
| 'CAACUGCUUUCUGAAAGGGGUGAGGAUCUAC' (SEQ ID NO:690) | [[], ['GGG'], []] | 0.483871 | 0.806452 | 1 | 53 |

FIG. 42 (Cont'd)

| SEQUENCE | BS | GCNESS | 3LN | NBP | P |
|---|---|---|---|---|---|
| 'AACUGCUUUCUGAAAGGGGUGAGGAUCUACC' (SEQ ID NO:691) | [[], ['GGG'], []] | 0.483871 | 0.806452 | 1 | 54 |
| 'ACUGCUUUCUGAAAGGGGUGAGGAUCUACCU' (SEQ ID NO:692) | [[], ['GGG'], []] | 0.483871 | 0.806452 | 1 | 55 |
| 'CUGCUUUCUGAAAGGGGUGAGGAUCUACCUU' (SEQ ID NO:693) | [[], ['GGG'], []] | 0.483871 | 0.806452 | 1 | 56 |
| 'GAGAGGUAAGGCCUCACUAAACCACUCAUCU' (SEQ ID NO:694) | [[], [], ['UAAA']] | 0.483871 | 0.806452 | 1 | 101 |
| 'CUACACUUAACAUCGAUCGUGAUAGAUGAAG' (SEQ ID NO:695) | [[], [], ['UUAA']] | 0.387097 | 0.806452 | 1 | 130 |
| 'ACACUUAACAUCGAUCGUGAUAGAUGAAGAC' (SEQ ID NO:696) | [[], [], ['UUAA']] | 0.387097 | 0.806452 | 1 | 132 |
| 'CACUUAACAUCGAUCGUGAUAGAUGAAGACA' (SEQ ID NO:697) | [[], [], ['UUAA']] | 0.387097 | 0.806452 | 1 | 133 |
| 'GGUAUUCACCACCUCUCAGUGGCAAUGCGAC' (SEQ ID NO:698) | [[], [], ['UAUU']] | 0.548387 | 0.774194 | 1 | 184 |

FIG. 42 (Cont'd)

| SEQUENCE | BS | GCNESS | 3LN | NBP | P |
|---|---|---|---|---|---|
| 'CCUCACUAAACCACUCAUCUACACUUAACAU' (SEQ ID NO:699) | [[], [], ['UAAA', 'UUAA']] | 0.387097 | 1 | 2 | 112 |
| 'CUCACUAAACCACUCAUCUACACUUAACAUC' (SEQ ID NO:700) | [[], [], ['UAAA', 'UUAA']] | 0.387097 | 1 | 2 | 113 |
| 'GCCUCACUAAACCACUCAUCUACACUUAACA' (SEQ ID NO:701) | [[], [], ['UAAA', 'UUAA']] | 0.419355 | 0.967742 | 2 | 111 |
| 'UCACUAAACCACUCAUCUACACUUAACAUCG' (SEQ ID NO:702) | [[], [], ['UAAA', 'UUAA']] | 0.387097 | 0.967742 | 2 | 114 |
| 'CACUAAACCACUCAUCUACACUUAACAUCGA' (SEQ ID NO:703) | [[], [], ['UAAA', 'UUAA']] | 0.387097 | 0.967742 | 2 | 115 |
| 'CUAAACCACUCAUCUACACUUAACAUCGAUC' (SEQ ID NO:704) | [[], [], ['UAAA', 'UUAA']] | 0.387097 | 0.967742 | 2 | 117 |
| 'ACUAAACCACUCAUCUACACUUAACAUCGAU' (SEQ ID NO:705) | [[], [], ['UAAA', 'UUAA']] | 0.354839 | 0.967742 | 2 | 116 |
| 'GGCCUCACUAAACCACUCAUCUACACUUAAC' (SEQ ID NO:706) | [[], [], ['UAAA', 'UUAA']] | 0.451613 | 0.935484 | 2 | 110 |

FIG. 42 (Cont'd)

| SEQUENCE | BS | GCNESS | 3LN | NBP | P |
|---|---|---|---|---|---|
| 'AGGCCUCACUAAACCACUCAUCUACACUUAA' (SEQ ID NO:707) | [[], [], ['UAAA', 'UUAA']] | 0.419355 | 0.935484 | 2 | 109 |
| 'UAAACCACUCAUCUACACUUAACAUCGAUCG' (SEQ ID NO:708) | [[], [], ['UAAA', 'UUAA']] | 0.387097 | 0.935484 | 2 | 118 |
| 'UACCUUAAUAUGCAGAGUGGGAGAGGUAAGG' (SEQ ID NO:709) | [[], ['GGG'], ['UUAA']] | 0.451613 | 0.903226 | 2 | 81 |
| 'GCAGAGUGGGAGAGGUAAGGCCUCACUAAAC' (SEQ ID NO:710) | [[], ['GGG'], ['UAAA']] | 0.548387 | 0.870968 | 2 | 92 |
| 'CAGAGUGGGAGAGGUAAGGCCUCACUAAACC' (SEQ ID NO:711) | [[], ['GGG'], ['UAAA']] | 0.548387 | 0.870968 | 2 | 93 |
| 'GAGUGGGAGAGGUAAGGCCUCACUAAACCAC' (SEQ ID NO:712) | [[], ['GGG'], ['UAAA']] | 0.548387 | 0.870968 | 2 | 95 |
| 'GGCUUGGGAUCUUUUGCGAUCUGCUCGAGCA' (SEQ ID NO:713) | [[], ['GGG'], ['UUUU']] | 0.548387 | 0.870968 | 2 | 238 |
| 'GCUUGGGAUCUUUUGCGAUCUGCUCGAGCAG' (SEQ ID NO:714) | [[], ['GGG'], ['UUUU']] | 0.548387 | 0.870968 | 2 | 239 |

FIG. 42 (Cont'd)

| SEQUENCE | BS | GCNESS | 3LN | NBP | P |
|---|---|---|---|---|---|
| 'AGAGUGGGAGAGGUAAGGCCUCACUAAACCA' (SEQ ID NO:715) | [[], ['GGG'], ['UAAA']] | 0.516129 | 0.870968 | 2 | 94 |
| 'CUUUUGCGAUCUGCUCGAGCAGAUUUGGCUG' (SEQ ID NO:716) | [[], [], ['UUUU', 'AUUU']] | 0.516129 | 0.870968 | 2 | 248 |
| 'GGGGUGAGGAUCUACCUUAAUAUGCAGAGUG' (SEQ ID NO:717) | [[], ['GGG'], ['UUAA']] | 0.483871 | 0.870968 | 2 | 69 |
| 'GGGUGAGGAUCUACCUUAAUAUGCAGAGUGG' (SEQ ID NO:718) | [[], ['GGG'], ['UUAA']] | 0.483871 | 0.870968 | 2 | 70 |
| 'GGUGAGGAUCUACCUUAAUAUGCAGAGUGGG' (SEQ ID NO:719) | [[], ['GGG'], ['UUAA']] | 0.483871 | 0.870968 | 2 | 71 |
| 'GGAUCUACCUUAAUAUGCAGAGUGGGAGAGG' (SEQ ID NO:720) | [[], ['GGG'], ['UUAA']] | 0.483871 | 0.870968 | 2 | 76 |
| 'ACCUUAAUAUGCAGAGUGGGAGAGGUAAGGC' (SEQ ID NO:721) | [[], ['GGG'], ['UUAA']] | 0.483871 | 0.870968 | 2 | 82 |
| 'CUUAAUAUGCAGAGUGGGAGAGGUAAGGCCU' (SEQ ID NO:722) | [[], ['GGG'], ['UUAA']] | 0.483871 | 0.870968 | 2 | 84 |

FIG. 42 (Cont'd)

| SEQUENCE | BS | GCNESS | 3LN | NBP | P |
|---|---|---|---|---|---|
| 'UUAAUAUGCAGAGUGG GAGAGGUAAGGCCUC' (SEQ ID NO:723) | [[], ['GGG'], ['UUAA']] | 0.483871 | 0.870968 | 2 | 85 |
| 'UAAUAUGCAGAGUGGG AGAGGUAAGGCCUCA' (SEQ ID NO:724) | [[], ['GGG'], ['UAAU']] | 0.483871 | 0.870968 | 2 | 86 |
| 'UCUUUUGCGAUCUGCU CGAGCAGAUUUGGCU' (SEQ ID NO:725) | [[], [], ['UUUU', 'AUUU']] | 0.483871 | 0.870968 | 2 | 247 |
| 'CUGUCCGUGGUGCUGA AGUUUAUUCGGAUUU' (SEQ ID NO:726) | [[], [], ['UUUA', 'AUUU']] | 0.451613 | 0.870968 | 2 | 13 |
| 'GAAAGGGGUGAGGAUC UACCUUAAUAUGCAG' (SEQ ID NO:727) | [[], ['GGG'], ['UUAA']] | 0.451613 | 0.870968 | 2 | 65 |
| 'AAGGGGUGAGGAUCUA CCUUAAUAUGCAGAG' (SEQ ID NO:728) | [[], ['GGG'], ['UUAA']] | 0.451613 | 0.870968 | 2 | 67 |
| 'AGGGGUGAGGAUCUAC CUUAAUAUGCAGAGU' (SEQ ID NO:729) | [[], ['GGG'], ['UUAA']] | 0.451613 | 0.870968 | 2 | 68 |
| 'GUGAGGAUCUACCUUA AUAUGCAGAGUGGGA' (SEQ ID NO:730) | [[], ['GGG'], ['UUAA']] | 0.451613 | 0.870968 | 2 | 72 |

FIG. 42 (Cont'd)

| SEQUENCE | BS | GCNESS | 3LN | NBP | P |
|---|---|---|---|---|---|
| 'UGAGGAUCUACCUUAAUAUGCAGAGUGGGAG' (SEQ ID NO:731) | [[], ['GGG'], ['UUAA']] | 0.451613 | 0.870968 | 2 | 73 |
| 'GAGGAUCUACCUUAAUAUGCAGAGUGGGAGA' (SEQ ID NO:732) | [[], ['GGG'], ['UUAA']] | 0.451613 | 0.870968 | 2 | 74 |
| 'AGGAUCUACCUUAAUAUGCAGAGUGGGAGAG' (SEQ ID NO:733) | [[], ['GGG'], ['UUAA']] | 0.451613 | 0.870968 | 2 | 75 |
| 'GAUCUACCUUAAUAUGCAGAGUGGGAGAGGU' (SEQ ID NO:734) | [[], ['GGG'], ['UUAA']] | 0.451613 | 0.870968 | 2 | 77 |
| 'CUACCUUAAUAUGCAGAGUGGGAGAGGUAAG' (SEQ ID NO:735) | [[], ['GGG'], ['UUAA']] | 0.451613 | 0.870968 | 2 | 80 |
| 'UGUCCGUGGUGCUGAAGUUUAUUCGGAUUUA' (SEQ ID NO:736) | [[], [], ['UUUA', 'AUUU']] | 0.419355 | 0.870968 | 2 | 14 |
| 'GUCCGUGGUGCUGAAGUUUAUUCGGAUUUAU' (SEQ ID NO:737) | [[], [], ['UUUA', 'AUUU']] | 0.419355 | 0.870968 | 2 | 15 |
| 'UCUGAAAGGGGUGAGGAUCUACCUUAAUAUG' (SEQ ID NO:738) | [[], ['GGG'], ['UUAA']] | 0.419355 | 0.870968 | 2 | 62 |

FIG. 42 (Cont'd)

| SEQUENCE | BS | GCNESS | 3LN | NBP | P |
|---|---|---|---|---|---|
| 'UGAAAGGGGUGAGGAU CUACCUUAAUAUGCA' (SEQ ID NO:739) | [[], ['GGG'], ['UUAA']] | 0.419355 | 0.870968 | 2 | 64 |
| 'AAAGGGGUGAGGAUCU ACCUUAAUAUGCAGA' (SEQ ID NO:740) | [[], ['GGG'], ['UUAA']] | 0.419355 | 0.870968 | 2 | 66 |
| 'AUCUACCUUAAUAUGCA GAGUGGGAGAGGUA' (SEQ ID NO:741) | [[], ['GGG'], ['UUAA']] | 0.419355 | 0.870968 | 2 | 78 |
| 'UCUACCUUAAUAUGCA GAGUGGGAGAGGUAA' (SEQ ID NO:742) | [[], ['GGG'], ['UUAA']] | 0.419355 | 0.870968 | 2 | 79 |
| 'UCCGUGGUGCUGAAGU UUAUUCGGAUUUAUU' (SEQ ID NO:743) | [[], [], ['UUUA', 'AUUU']] | 0.387097 | 0.870968 | 2 | 16 |
| 'UUUCUGAAAGGGGUGA GGAUCUACCUUAAUA' (SEQ ID NO:744) | [[], ['GGG'], ['UUAA']] | 0.387097 | 0.870968 | 2 | 60 |
| 'UUCUGAAAGGGGUGAG GAUCUACCUUAAUAU' (SEQ ID NO:745) | [[], ['GGG'], ['UUAA']] | 0.387097 | 0.870968 | 2 | 61 |
| 'CAAGCUGUGUGACACA CCGCAAGGGCUUGGG' (SEQ ID NO:746) | [[], ['GGG', 'GGG'], []] | 0.612903 | 0.83871 | 2 | 215 |

FIG. 42 (Cont'd)

| SEQUENCE | BS | GCNESS | 3LN | NBP | P |
|---|---|---|---|---|---|
| 'GACAGGAAGCUGCAGCUCCAGGAGGGUAUUC' (SEQ ID NO:747) | [[], ['GGG'], ['UAUU']] | 0.580645 | 0.83871 | 2 | 160 |
| 'CAGGAAGCUGCAGCUCCAGGAGGGUAUUCAC' (SEQ ID NO:748) | [[], ['GGG'], ['UAUU']] | 0.580645 | 0.83871 | 2 | 162 |
| 'AGGAAGCUGCAGCUCCAGGAGGGUAUUCACC' (SEQ ID NO:749) | [[], ['GGG'], ['UAUU']] | 0.580645 | 0.83871 | 2 | 163 |
| 'GGAAGCUGCAGCUCCAGGAGGGUAUUCACCA' (SEQ ID NO:750) | [[], ['GGG'], ['UAUU']] | 0.580645 | 0.83871 | 2 | 164 |
| 'GAAGCUGCAGCUCCAGGAGGGUAUUCACCAC' (SEQ ID NO:751) | [[], ['GGG'], ['UAUU']] | 0.580645 | 0.83871 | 2 | 165 |
| 'AAGCUGCAGCUCCAGGAGGGUAUUCACCACC' (SEQ ID NO:752) | [[], ['GGG'], ['UAUU']] | 0.580645 | 0.83871 | 2 | 166 |
| 'AAGCUGUGUGACACACCGCAAGGGCUUGGGA' (SEQ ID NO:753) | [[], ['GGG', 'GGG'], []] | 0.580645 | 0.83871 | 2 | 216 |
| 'GUGGGAGAGGUAAGGCCUCACUAAACCACUC' (SEQ ID NO:754) | [[], ['GGG'], ['UAAA']] | 0.548387 | 0.83871 | 2 | 97 |

FIG. 42 (Cont'd)

| SEQUENCE | BS | GCNESS | 3LN | NBP | P |
|---|---|---|---|---|---|
| 'AGACAGGAAGCUGCAGCUCCAGGAGGGUAUU' (SEQ ID NO:755) | [[], ['GGG'], ['UAUU']] | 0.548387 | 0.83871 | 2 | 159 |
| 'ACAGGAAGCUGCAGCUCCAGGAGGGUAUUCA' (SEQ ID NO:756) | [[], ['GGG'], ['UAUU']] | 0.548387 | 0.83871 | 2 | 161 |
| 'CCUUAAUAUGCAGAGUGGGAGAGGUAAGGCC' (SEQ ID NO:757) | [[], ['GGG'], ['UUAA']] | 0.516129 | 0.83871 | 2 | 83 |
| 'AAUAUGCAGAGUGGGAGAGGUAAGGCCUCAC' (SEQ ID NO:758) | [[], ['GGG'], ['AAUA']] | 0.516129 | 0.83871 | 2 | 87 |
| 'AUAUGCAGAGUGGGAGAGGUAAGGCCUCACU' (SEQ ID NO:759) | [[], ['GGG'], ['AUAU']] | 0.516129 | 0.83871 | 2 | 88 |
| 'UGCAGAGUGGGAGAGGUAAGGCCUCACUAAA' (SEQ ID NO:760) | [[], ['GGG'], ['UAAA']] | 0.516129 | 0.83871 | 2 | 91 |
| 'AGUGGGAGAGGUAAGGCCUCACUAAACCACU' (SEQ ID NO:761) | [[], ['GGG'], ['UAAA']] | 0.516129 | 0.83871 | 2 | 96 |
| 'UGGGAGAGGUAAGGCCUCACUAAACCACUCA' (SEQ ID NO:762) | [[], ['GGG'], ['UAAA']] | 0.516129 | 0.83871 | 2 | 98 |

FIG. 42 (Cont'd)

| SEQUENCE | BS | GCNESS | 3LN | NBP | P |
|---|---|---|---|---|---|
| 'GGGAGAGGUAAGGCCUCACUAAACCACUCAU' (SEQ ID NO:763) | [[], ['GGG'], ['UAAA']] | 0.516129 | 0.83871 | 2 | 99 |
| 'CUUGGGAUCUUUUGCGAUCUGCUCGAGCAGA' (SEQ ID NO:764) | [[], ['GGG'], ['UUUU']] | 0.516129 | 0.83871 | 2 | 240 |
| 'UUGGGAUCUUUUGCGAUCUGCUCGAGCAGAU' (SEQ ID NO:765) | [[], ['GGG'], ['UUUU']] | 0.483871 | 0.83871 | 2 | 241 |
| 'UGGGAUCUUUUGCGAUCUGCUCGAGCAGAUU' (SEQ ID NO:766) | [[], ['GGG'], ['UUUU']] | 0.483871 | 0.83871 | 2 | 242 |
| 'GGAUCUUUUGCGAUCUGCUCGAGCAGAUUUG' (SEQ ID NO:767) | [[], [], ['UUUU', 'AUUU']] | 0.483871 | 0.83871 | 2 | 244 |
| 'GAUCUUUUGCGAUCUGCUCGAGCAGAUUUGG' (SEQ ID NO:768) | [[], [], ['UUUU', 'AUUU']] | 0.483871 | 0.83871 | 2 | 245 |
| 'AUCUUUUGCGAUCUGCUCGAGCAGAUUUGGC' (SEQ ID NO:769) | [[], [], ['UUUU', 'AUUU']] | 0.483871 | 0.83871 | 2 | 246 |
| 'UUUUUCCAACUGCUUUCUGAAAGGGGUGAGG' (SEQ ID NO:770) | [[], ['GGG'], ['UUUU']] | 0.451613 | 0.83871 | 2 | 47 |

FIG. 42 (Cont'd)

| SEQUENCE | BS | GCNESS | 3LN | NBP | P |
|---|---|---|---|---|---|
| 'UUUUCCAACUGCUUUC UGAAAGGGGUGAGGA' (SEQ ID NO:771) | [[], ['GGG'], ['UUUU']] | 0.451613 | 0.83871 | 2 | 48 |
| 'GCUUUCUGAAAGGGGU GAGGAUCUACCUUAA' (SEQ ID NO:772) | [[], ['GGG'], ['UUAA']] | 0.451613 | 0.83871 | 2 | 58 |
| 'CUGAAAGGGGUGAGGA UCUACCUUAAUAUGC' (SEQ ID NO:773) | [[], ['GGG'], ['UUAA']] | 0.451613 | 0.83871 | 2 | 63 |
| 'UUUUUUCCAACUGCUU UCGAAAGGGGUGAG' (SEQ ID NO:774) | [[], ['GGG'], ['UUUU']] | 0.419355 | 0.83871 | 2 | 46 |
| 'CUUUCUGAAAGGGGUG AGGAUCUACCUUAAU' (SEQ ID NO:775) | [[], ['GGG'], ['UUAA']] | 0.419355 | 0.83871 | 2 | 59 |
| 'UUUUUUUCCAACUGCU UCUGAAAGGGGUGA' (SEQ ID NO:776) | [[], ['GGG'], ['UUUU']] | 0.387097 | 0.83871 | 2 | 45 |
| 'GCUGCAGCUCCAGGAG GGUAUUCACCACCUC' (SEQ ID NO:777) | [[], ['GGG'], ['UAUU']] | 0.612903 | 0.806452 | 2 | 168 |
| 'GCUGUGUGACACACCG CAAGGGCUUGGGAUC' (SEQ ID NO:778) | [[], ['GGG', 'GGG'], []] | 0.612903 | 0.806452 | 2 | 218 |

FIG. 42 (Cont'd)

| SEQUENCE | BS | GCNESS | 3LN | NBP | P |
|---|---|---|---|---|---|
| 'AGCUGCAGCUCCAGGAGGGUAUUCACCACCU' (SEQ ID NO:779) | [[], ['GGG'], ['UAUU']] | 0.580645 | 0.806452 | 2 | 167 |
| 'CUGCAGCUCCAGGAGGGUAUUCACCACCUCU' (SEQ ID NO:780) | [[], ['GGG'], ['UAUU']] | 0.580645 | 0.806452 | 2 | 169 |
| 'UGCAGCUCCAGGAGGGUAUUCACCACCUCUC' (SEQ ID NO:781) | [[], ['GGG'], ['UAUU']] | 0.580645 | 0.806452 | 2 | 170 |
| 'GCAGCUCCAGGAGGGUAUUCACCACCUCUCA' (SEQ ID NO:782) | [[], ['GGG'], ['UAUU']] | 0.580645 | 0.806452 | 2 | 171 |
| 'CAGCUCCAGGAGGGUAUUCACCACCUCUCAG' (SEQ ID NO:783) | [[], ['GGG'], ['UAUU']] | 0.580645 | 0.806452 | 2 | 172 |
| 'GCUCCAGGAGGGUAUUCACCACCUCUCAGUG' (SEQ ID NO:784) | [[], ['GGG'], ['UAUU']] | 0.580645 | 0.806452 | 2 | 174 |
| 'CUCCAGGAGGGUAUUCACCACCUCUCAGUGG' (SEQ ID NO:785) | [[], ['GGG'], ['UAUU']] | 0.580645 | 0.806452 | 2 | 175 |
| 'UCCAGGAGGGUAUUCACCACCUCUCAGUGGC' (SEQ ID NO:786) | [[], ['GGG'], ['UAUU']] | 0.580645 | 0.806452 | 2 | 176 |

FIG. 42 (Cont'd)

| SEQUENCE | BS | GCNESS | 3LN | NBP | P |
|---|---|---|---|---|---|
| 'CCAGGAGGGUAUUCACCACCUCUCAGUGGCA' (SEQ ID NO:787) | [[], ['GGG'], ['UAUU']] | 0.580645 | 0.806452 | 2 | 177 |
| 'AGCUGUGUGACACACCGCAAGGGCUUGGGAU' (SEQ ID NO:788) | [[], ['GGG', 'GGG'], []] | 0.580645 | 0.806452 | 2 | 217 |
| 'CUGUGUGACACACCGCAAGGGCUUGGGAUCU' (SEQ ID NO:789) | [[], ['GGG', 'GGG'], []] | 0.580645 | 0.806452 | 2 | 219 |
| 'CAGGAGGGUAUUCACCACCUCUCAGUGGCAA' (SEQ ID NO:790) | [[], ['GGG'], ['UAUU']] | 0.548387 | 0.806452 | 2 | 178 |
| 'UGUGUGACACACCGCAAGGGCUUGGGAUCUU' (SEQ ID NO:791) | [[], ['GGG', 'GGG'], []] | 0.548387 | 0.806452 | 2 | 220 |
| 'GUGUGACACACCGCAAGGGCUUGGGAUCUUU' (SEQ ID NO:792) | [[], ['GGG', 'GGG'], []] | 0.548387 | 0.806452 | 2 | 221 |
| 'AGCUCCAGGAGGGUAUUCACCACCUCUCAGU' (SEQ ID NO:793) | [[], ['GGG'], ['UAUU']] | 0.548387 | 0.774194 | 2 | 173 |

| SEQUENCE | BS | GCNESS | 3LN | NBP | P |
|---|---|---|---|---|---|
| 'GGAGGGUAUUCACCACCUCUCAGUGGCAAUG' (SEQ ID NO:794) | [[], ['GGG'], ['UAUU']] | 0.548387 | 0.774194 | 2 | 180 |
| 'GAGGGUAUUCACCACCUCUCAGUGGCAAUGC' (SEQ ID NO:795) | [[], ['GGG'], ['UAUU']] | 0.548387 | 0.774194 | 2 | 181 |
| 'AGGGUAUUCACCACCUCUCAGUGGCAAUGCG' (SEQ ID NO:796) | [[], ['GGG'], ['UAUU']] | 0.548387 | 0.774194 | 2 | 182 |
| 'GGGUAUUCACCACCUCUCAGUGGCAAUGCGA' (SEQ ID NO:797) | [[], ['GGG'], ['UAUU']] | 0.548387 | 0.774194 | 2 | 183 |
| 'AGGAGGGUAUUCACCACCUCUCAGUGGCAAU' (SEQ ID NO:798) | [[], ['GGG'], ['UAUU']] | 0.516129 | 0.774194 | 2 | 179 |
| 'GUGGUGCUGAAGUUUAUUCGGAUUUAUUUUU' (SEQ ID NO:799) | [[], [], ['UUUA', 'AUUU', 'AUUU']] | 0.322581 | 0.935484 | 3 | 19 |
| 'UGGUGCUGAAGUUUAUUCGGAUUUAUUUUUU' (SEQ ID NO:800) | [[], [], ['UUUA', 'AUUU', 'AUUU']] | 0.290323 | 0.935484 | 3 | 20 |
| 'GGGCUUGGGAUCUUUUGCGAUCUGCUCGAGC' (SEQ ID NO:801) | [[], ['GGG', 'GGG'], ['UUUU']] | 0.580645 | 0.903226 | 3 | 237 |

| SEQUENCE | BS | GCNESS | 3LN | NBP | P |
|---|---|---|---|---|---|
| 'CGUGGUGCUGAAGUUU AUUCGGAUUUAUUUU' (SEQ ID NO:802) | [[], [], ['UUUA', 'AUUU', 'AUUU']] | 0.354839 | 0.903226 | 3 | 18 |
| 'AUUCGGAUUUAUUUUU UUCCAACUGCUUUCU' (SEQ ID NO:803) | [[], [], ['AUUU', 'AUUU', 'UUUU']] | 0.290323 | 0.903226 | 3 | 34 |
| 'CCGCAAGGGCUUGGGA UCUUUGCGAUCUGC' (SEQ ID NO:804) | [[], ['GGG', 'GGG'], ['UUUU']] | 0.580645 | 0.870968 | 3 | 231 |
| 'CGCAAGGGCUUGGGAU CUUUGCGAUCUGCU' (SEQ ID NO:805) | [[], ['GGG', 'GGG'], ['UUUU']] | 0.548387 | 0.870968 | 3 | 232 |
| 'GCAAGGGCUUGGGAUC UUUGCGAUCUGCUC' (SEQ ID NO:806) | [[], ['GGG', 'GGG'], ['UUUU']] | 0.548387 | 0.870968 | 3 | 233 |
| 'CAAGGGCUUGGGAUCU UUGCGAUCUGCUCG' (SEQ ID NO:807) | [[], ['GGG', 'GGG'], ['UUUU']] | 0.548387 | 0.870968 | 3 | 234 |

FIG. 42 (Cont'd)

| SEQUENCE | BS | GCNESS | 3LN | NBP | P |
|---|---|---|---|---|---|
| 'AGGGCUUGGGAUCUUUUGCGAUCUGCUCGAG' (SEQ ID NO:808) | [[], ['GGG', 'GGG'], ['UUUU']] | 0.548387 | 0.870968 | 3 | 236 |
| 'CCGUGGUGCUGAAGUUUAUUCGGAUUUAUUU' (SEQ ID NO:809) | [[], [], ['UUUA', 'AUUU', 'AUUU']] | 0.387097 | 0.870968 | 3 | 17 |
| 'UUCGGAUUUAUUUUUUUCCAACUGCUUUCUG' (SEQ ID NO:810) | [[], [], ['AUUU', 'AUUU', 'UUUU']] | 0.322581 | 0.870968 | 3 | 35 |
| 'UCGGAUUUAUUUUUUUCCAACUGCUUUCUGA' (SEQ ID NO:811) | [[], [], ['AUUU', 'AUUU', 'UUUU']] | 0.322581 | 0.870968 | 3 | 36 |
| 'CGGAUUUAUUUUUUUCCAACUGCUUUCUGAA' (SEQ ID NO:812) | [[], [], ['AUUU', 'AUUU', 'UUUU']] | 0.322581 | 0.870968 | 3 | 37 |
| 'GGAUUUAUUUUUUUCCAACUGCUUUCUGAAA' (SEQ ID NO:813) | [[], [], ['AUUU', 'AUUU', 'UUUU']] | 0.290323 | 0.870968 | 3 | 38 |

FIG. 42 (Cont'd)

| SEQUENCE | BS | GCNESS | 3LN | NBP | P |
|---|---|---|---|---|---|
| 'GAUUUAUUUUUUUCCA ACUGCUUUCUGAAAG' (SEQ ID NO:814) | [[], [], ['AUUU', 'AUUU', 'UUUU']] | 0.290323 | 0.870968 | 3 | 39 |
| 'AUUUAUUUUUUUCCAAC UGCUUUCUGAAAGG' (SEQ ID NO:815) | [[], [], ['AUUU', 'AUUU', 'UUUU']] | 0.290323 | 0.870968 | 3 | 40 |
| 'CACCGCAAGGGCUUGG GAUCUUUUGCGAUCU' (SEQ ID NO:816) | [[], ['GGG', 'GGG'], ['UUUU']] | 0.548387 | 0.83871 | 3 | 229 |
| 'ACCGCAAGGGCUUGGG AUCUUUUGCGAUCUG' (SEQ ID NO:817) | [[], ['GGG', 'GGG'], ['UUUU']] | 0.548387 | 0.83871 | 3 | 230 |
| 'AAGGGCUUGGGAUCUU UUGCGAUCUGCUCGA' (SEQ ID NO:818) | [[], ['GGG', 'GGG'], ['UUUU']] | 0.516129 | 0.83871 | 3 | 235 |
| 'GGGAUCUUUUGCGAUC UGCUCGAGCAGAUUU' (SEQ ID NO:819) | [[], ['GGG'], ['UUUU', 'AUUU']] | 0.483871 | 0.83871 | 3 | 243 |

FIG. 42 (Cont'd)

| SEQUENCE | BS | GCNESS | 3LN | NBP | P |
|---|---|---|---|---|---|
| 'AUUUUUUUCCAACUGC UUUCUGAAAGGGGUG' (SEQ ID NO:820) | [[], ['GGG'], ['AUUU', 'UUUU']] | 0.387097 | 0.83871 | 3 | 44 |
| 'UUAUUUUUUUCCAACU GCUUUCUGAAAGGGG' (SEQ ID NO:821) | [[], ['GGG'], ['UUAU', 'UUUU']] | 0.354839 | 0.83871 | 3 | 42 |
| 'UAUUUUUUUCCAACUG CUUUCUGAAAGGGGU' (SEQ ID NO:822) | [[], ['GGG'], ['UAUU', 'UUUU']] | 0.354839 | 0.83871 | 3 | 43 |
| 'UUUAUUUUUUUCCAAC UGCUUUCUGAAAGGG' (SEQ ID NO:823) | [[], ['GGG'], ['UUUA', 'UUUU']] | 0.322581 | 0.83871 | 3 | 41 |
| 'GACACACCGCAAGGGC UUGGGAUCUUUUGCG' (SEQ ID NO:824) | [[], ['GGG', 'GGG'], ['UUUU']] | 0.580645 | 0.806452 | 3 | 225 |
| 'GUGACACACCGCAAGG GCUUGGGAUCUUUUG' (SEQ ID NO:825) | [[], ['GGG', 'GGG'], ['UUUU']] | 0.548387 | 0.806452 | 3 | 223 |

FIG. 42 (Cont'd)

| SEQUENCE | BS | GCNESS | 3LN | NBP | P |
|---|---|---|---|---|---|
| 'UGACACACCGCAAGGGCUUGGGAUCUUUUGC' (SEQ ID NO:826) | [[], ['GGG', 'GGG'], ['UUUU']] | 0.548387 | 0.806452 | 3 | 224 |
| 'CACACCGCAAGGGCUUGGGAUCUUUUGCGAU' (SEQ ID NO:827) | [[], ['GGG', 'GGG'], ['UUUU']] | 0.548387 | 0.806452 | 3 | 227 |
| 'ACACCGCAAGGGCUUGGGAUCUUUUGCGAUC' (SEQ ID NO:828) | [[], ['GGG', 'GGG'], ['UUUU']] | 0.548387 | 0.806452 | 3 | 228 |
| 'UGUGACACACCGCAAGGGCUUGGGAUCUUUU' (SEQ ID NO:829) | [[], ['GGG', 'GGG'], ['UUUU']] | 0.516129 | 0.806452 | 3 | 222 |
| 'ACACACCGCAAGGGCUUGGGAUCUUUUGCGA' (SEQ ID NO:830) | [[], ['GGG', 'GGG'], ['UUUU']] | 0.548387 | 0.774194 | 3 | 226 |
| 'GGUGCUGAAGUUUAUUCGGAUUUAUUUUUUU' (SEQ ID NO:831) | [[], [], ['UUUA', 'AUUU', 'AUUU', 'UUUU']] | 0.290323 | 0.935484 | 4 | 21 |

FIG. 42 (Cont'd)

| SEQUENCE | BS | GCNESS | 3LN | NBP | P |
|---|---|---|---|---|---|
| 'GUGCUGAAGUUUAUUC GGAUUUAUUUUUUC' (SEQ ID NO:832) | [[], [], ['UUUA', 'AUUU', 'AUUU', 'UUUU']] | 0.290323 | 0.903226 | 4 | 22 |
| 'UAUUCGGAUUUAUUUU UUCCAACUGCUUUC' (SEQ ID NO:833) | [[], [], ['UAUU', 'AUUU', 'AUUU', 'UUUU']] | 0.290323 | 0.903226 | 4 | 33 |
| 'UUUAUUCGGAUUUAUU UUUUCCAACUGCUU' (SEQ ID NO:834) | [[], [], ['UUUA', 'AUUU', 'AUUU', 'UUUU']] | 0.258065 | 0.903226 | 4 | 31 |
| 'UUAUUCGGAUUUAUUU UUUCCAACUGCUUU' (SEQ ID NO:835) | [[], [], ['UUAU', 'AUUU', 'AUUU', 'UUUU']] | 0.258065 | 0.903226 | 4 | 32 |
| 'UGCUGAAGUUUAUUCG GAUUUAUUUUUUCC' (SEQ ID NO:836) | [[], [], ['UUUA', 'AUUU', 'AUUU', 'UUUU']] | 0.290323 | 0.870968 | 4 | 23 |

FIG. 42 (Cont'd)

| SEQUENCE | BS | GCNESS | 3LN | NBP | P |
| --- | --- | --- | --- | --- | --- |
| 'GCUGAAGUUUAUUCGG AUUUAUUUUUUUCCA' (SEQ ID NO:837) | [[], [], ['UUUA', 'AUUU', 'AUUU', 'UUUU']] | 0.290323 | 0.870968 | 4 | 24 |
| 'AGUUUAUUCGGAUUUA UUUUUUUCCAACUGC' (SEQ ID NO:838) | [[], [], ['UUUA', 'AUUU', 'AUUU', 'UUUU']] | 0.290323 | 0.870968 | 4 | 29 |
| 'GUUUAUUCGGAUUUAU UUUUUUCCAACUGCU' (SEQ ID NO:839) | [[], [], ['UUUA', 'AUUU', 'AUUU', 'UUUU']] | 0.290323 | 0.870968 | 4 | 30 |
| 'CUGAAGUUUAUUCGGA UUUAUUUUUUUCCAA' (SEQ ID NO:840) | [[], [], ['UUUA', 'AUUU', 'AUUU', 'UUUU']] | 0.258065 | 0.870968 | 4 | 25 |
| 'UGAAGUUUAUUCGGAU UUAUUUUUUUCCAAC' (SEQ ID NO:841) | [[], [], ['UUUA', 'AUUU', 'AUUU', 'UUUU']] | 0.258065 | 0.870968 | 4 | 26 |

FIG. 42 (Cont'd)

| SEQUENCE | BS | GCNESS | 3LN | NBP | P |
|---|---|---|---|---|---|
| 'GAAGUUUAUUCGGAUUUAUUUUUUUCCAACU' (SEQ ID NO:842) | [[], [], ['UUUA', 'AUUU', 'AUUU', 'UUUU']] | 0.258065 | 0.870968 | 4 | 27 |
| 'AAGUUUAUUCGGAUUUAUUUUUUCCAACUG' (SEQ ID NO:843) | [[], [], ['UUUA', 'AUUU', 'AUUU', 'UUUU']] | 0.258065 | 0.870968 | 4 | 28 |

| SEQUENCE | BS | GCNESS | 3LN | NBP | P |
|---|---|---|---|---|---|
| 'GGAAUCAGAAGCAGGUGUCUGCAGCCAGGAC' (SEQ ID NO:844) | [[], [], []] | 0.580645 | 0.870968 | 0 | 153 |
| 'GUGGAAUCAGAAGCAGGUGUCUGCAGCCAGG' (SEQ ID NO:845) | [[], [], []] | 0.580645 | 0.83871 | 0 | 151 |
| 'UGGAAUCAGAAGCAGGUGUCUGCAGCCAGGA' (SEQ ID NO:846) | [[], [], []] | 0.548387 | 0.83871 | 0 | 152 |
| 'GAAUCAGAAGCAGGUGUCUGCAGCCAGGACU' (SEQ ID NO:847) | [[], [], []] | 0.548387 | 0.83871 | 0 | 154 |
| 'UCAGAAGCAGGUGUCUGCAGCCAGGACUUCC' (SEQ ID NO:848) | [[], [], []] | 0.580645 | 0.806452 | 0 | 157 |
| 'CAGAAGCAGGUGUCUGCAGCCAGGACUUCCU' (SEQ ID NO:849) | [[], [], []] | 0.580645 | 0.806452 | 0 | 158 |
| 'AGAAGCAGGUGUCUGCAGCCAGGACUUCCUC' (SEQ ID NO:850) | [[], [], []] | 0.580645 | 0.806452 | 0 | 159 |
| 'UGUGGAAUCAGAAGCAGGUGUCUGCAGCCAG' (SEQ ID NO:851) | [[], [], []] | 0.548387 | 0.806452 | 0 | 150 |

| SEQUENCE | BS | GCNESS | 3LN | NBP | P |
|---|---|---|---|---|---|
| 'AUCAGAAGCAGGUGUCUGCAGCCAGGACUUC' (SEQ ID NO:852) | [[], [], []] | 0.548387 | 0.806452 | 0 | 156 |
| 'UUGUGGAAUCAGAAGCAGGUGUCUGCAGCCA' (SEQ ID NO:853) | [[], [], []] | 0.516129 | 0.806452 | 0 | 149 |
| 'AAUCAGAAGCAGGUGUCUGCAGCCAGGACUU' (SEQ ID NO:854) | [[], [], []] | 0.516129 | 0.806452 | 0 | 155 |
| 'CCUUGUGGAAUCAGAAGCAGGUGUCUGCAGC' (SEQ ID NO:855) | [[], [], []] | 0.548387 | 0.774194 | 0 | 147 |
| 'CUUGUGGAAUCAGAAGCAGGUGUCUGCAGCC' (SEQ ID NO:856) | [[], [], []] | 0.548387 | 0.774194 | 0 | 148 |
| 'CACUUCAAAGGCGGCCACAGGGUUGAGGAAA' (SEQ ID NO:857) | [[], ['GGG'], []] | 0.548387 | 0.870968 | 1 | 111 |
| 'AAAAAUGAGUCACUUCAAAGGCGGCCACAGG' (SEQ ID NO:858) | [[], [], ['AAAA']] | 0.483871 | 0.870968 | 1 | 101 |
| 'AAAAAAUGAGUCACUUCAAAGGCGGCCACAG' (SEQ ID NO:859) | [[], [], ['AAAA']] | 0.451613 | 0.870968 | 1 | 100 |

FIG. 43 (Cont'd)

| SEQUENCE | BS | GCNESS | 3LN | NBP | P |
|---|---|---|---|---|---|
| 'ACCGUGGAAAUUUUGUGCUCAAAGGUAAGAA' (SEQ ID NO:860) | [[], [], ['AAAU']] | 0.387097 | 0.870968 | 1 | 26 |
| 'CCGUGGAAAUUUUGUGCUCAAAGGUAAGAAA' (SEQ ID NO:861) | [[], [], ['AAAU']] | 0.387097 | 0.870968 | 1 | 27 |
| 'CGUGGAAAUUUUGUGCUCAAAGGUAAGAAAC' (SEQ ID NO:862) | [[], [], ['AAAU']] | 0.387097 | 0.870968 | 1 | 28 |
| 'GUGGAAAUUUUGUGCUCAAAGGUAAGAAACC' (SEQ ID NO:863) | [[], [], ['AAAU']] | 0.387097 | 0.870968 | 1 | 29 |
| 'UGGAAAUUUUGUGCUCAAAGGUAAGAAACCA' (SEQ ID NO:864) | [[], [], ['AAAU']] | 0.354839 | 0.870968 | 1 | 30 |
| 'GGAAAUUUUGUGCUCAAAGGUAAGAAACCAU' (SEQ ID NO:865) | [[], [], ['AAAU']] | 0.354839 | 0.870968 | 1 | 31 |
| 'GAGUCACUUCAAAGGCGGCCACAGGGUUGAG' (SEQ ID NO:866) | [[], ['GGG'], []] | 0.580645 | 0.83871 | 1 | 107 |
| 'AGUCACUUCAAAGGCGGCCACAGGGUUGAGG' (SEQ ID NO:867) | [[], ['GGG'], []] | 0.580645 | 0.83871 | 1 | 108 |

FIG. 43 (Cont'd)

| SEQUENCE | BS | GCNESS | 3LN | NBP | P |
| --- | --- | --- | --- | --- | --- |
| 'GUCACUUCAAAGGCGG CCACAGGGUUGAGGA' (SEQ ID NO:868) | [[], ['GGG'], []] | 0.580645 | 0.83871 | 1 | 109 |
| 'UCACUUCAAAGGCGGC CACAGGGUUGAGGAA' (SEQ ID NO:869) | [[], ['GGG'], []] | 0.548387 | 0.83871 | 1 | 110 |
| 'UCACCGUGGAAAUUUU GUGCUCAAAGGUAAG' (SEQ ID NO:870) | [[], [], ['AAAU']] | 0.419355 | 0.83871 | 1 | 24 |
| 'CACCGUGGAAAUUUUG UGCUCAAAGGUAAGA' (SEQ ID NO:871) | [[], [], ['AAAU']] | 0.419355 | 0.83871 | 1 | 25 |
| 'UUUCACCGUGGAAAUU UUGUGCUCAAAGGUA' (SEQ ID NO:872) | [[], [], ['AAAU']] | 0.387097 | 0.83871 | 1 | 22 |
| 'UUCACCGUGGAAAUUU UGUGCUCAAAGGUAA' (SEQ ID NO:873) | [[], [], ['AAAU']] | 0.387097 | 0.83871 | 1 | 23 |
| 'GAAAUUUUGUGCUCAA AGGUAAGAAACCAUC' (SEQ ID NO:874) | [[], [], ['AAAU']] | 0.354839 | 0.83871 | 1 | 32 |
| 'AAAUUUUGUGCUCAAA GGUAAGAAACCAUCU' (SEQ ID NO:875) | [[], [], ['AAAU']] | 0.322581 | 0.83871 | 1 | 33 |

FIG. 43 (Cont'd)

| SEQUENCE | BS | GCNESS | 3LN | NBP | P |
|---|---|---|---|---|---|
| 'AAUUUGUGCUCAAAGGUAAGAAACCAUCUU' (SEQ ID NO:876) | [[], [], ['AAUU']] | 0.322581 | 0.83871 | 1 | 34 |
| 'AUUUGUGCUCAAAGGUAAGAAACCAUCUUA' (SEQ ID NO:877) | [[], [], ['AUUU']] | 0.322581 | 0.83871 | 1 | 35 |
| 'UUUGUGCUCAAAGGUAAGAAACCAUCUUAUA' (SEQ ID NO:878) | [[], [], ['UUAU']] | 0.322581 | 0.83871 | 1 | 37 |
| 'UUGUGCUCAAAGGUAAGAAACCAUCUUAUAU' (SEQ ID NO:879) | [[], [], ['UUAU']] | 0.322581 | 0.83871 | 1 | 38 |
| 'UGUGCUCAAAGGUAAGAAACCAUCUUAUAUA' (SEQ ID NO:880) | [[], [], ['UUAU']] | 0.322581 | 0.83871 | 1 | 39 |
| 'GCCCCUUGUGGAAUCAGAAGCAGGUGUCUGC' (SEQ ID NO:881) | [['CCC'], [], []] | 0.580645 | 0.806452 | 1 | 144 |
| 'AUGAGUCACUUCAAAGGCGGCCACAGGGUUG' (SEQ ID NO:882) | [[], ['GGG'], []] | 0.548387 | 0.806452 | 1 | 105 |
| 'UGAGUCACUUCAAAGGCGGCCACAGGGUUGA' (SEQ ID NO:883) | [[], ['GGG'], []] | 0.548387 | 0.806452 | 1 | 106 |

FIG. 43 (Cont'd)

| SEQUENCE | BS | GCNESS | 3LN | NBP | P |
|---|---|---|---|---|---|
| 'AAUGAGUCACUUCAAAGGCGGCCACAGGGUU' (SEQ ID NO:884) | [[], ['GGG'], []] | 0.516129 | 0.806452 | 1 | 104 |
| 'AAAGCCCCUUGUGGAAUCAGAAGCAGGUGUC' (SEQ ID NO:885) | [['CCC'], [], []] | 0.516129 | 0.806452 | 1 | 141 |
| 'AGCCCUUGUGGAAUCAGAAGCAGGUGUCUG' (SEQ ID NO:886) | [['CCC'], [], []] | 0.548387 | 0.774194 | 1 | 143 |
| 'CCCCUUGUGGAAUCAGAAGCAGGUGUCUGCA' (SEQ ID NO:887) | [['CCC'], [], []] | 0.548387 | 0.774194 | 1 | 145 |
| 'CCCUUGUGGAAUCAGAAGCAGGUGUCUGCAG' (SEQ ID NO:888) | [['CCC'], [], []] | 0.548387 | 0.774194 | 1 | 146 |
| 'AAGCCCCUUGUGGAAUCAGAAGCAGGUGUCU' (SEQ ID NO:889) | [['CCC'], [], []] | 0.516129 | 0.774194 | 1 | 142 |
| 'CAAAGGCGGCCACAGGGUUGAGGAAAAAGCC' (SEQ ID NO:890) | [[], ['GGG'], ['AAAA']] | 0.580645 | 0.935484 | 2 | 116 |
| 'GUAAGAAACCAUCUUAUAUAAAACAAUCAAA' (SEQ ID NO:891) | [[], [], ['UUAU', 'AUAA']] | 0.225806 | 0.935484 | 2 | 50 |

FIG. 43 (Cont'd)

| SEQUENCE | BS | GCNESS | 3LN | NBP | P |
|---|---|---|---|---|---|
| 'UCAAAGGCGGCCACAGGGUUGAGGAAAAAGC' (SEQ ID NO:892) | [[], ['GGG'], ['AAAA']] | 0.548387 | 0.903226 | 2 | 115 |
| 'CUCAAAGGUAAGAAACCAUCUUAUAUAAAAC' (SEQ ID NO:893) | [[], [], ['UUAU', 'AUAA']] | 0.290323 | 0.903226 | 2 | 43 |
| 'UCAAAGGUAAGAAACCAUCUUAUAUAAAACA' (SEQ ID NO:894) | [[], [], ['UUAU', 'AUAA']] | 0.258065 | 0.903226 | 2 | 44 |
| 'CAAAGGUAAGAAACCAUCUUAUAUAAAACAA' (SEQ ID NO:895) | [[], [], ['UUAU', 'AUAA']] | 0.258065 | 0.903226 | 2 | 45 |
| 'AAGGUAAGAAACCAUCUUAUAUAAAACAAUC' (SEQ ID NO:896) | [[], [], ['UUAU', 'AUAA']] | 0.258065 | 0.903226 | 2 | 47 |
| 'AGGUAAGAAACCAUCUUAUAUAAAACAAUCA' (SEQ ID NO:897) | [[], [], ['UUAU', 'AUAA']] | 0.258065 | 0.903226 | 2 | 48 |
| 'GGUAAGAAACCAUCUUAUAUAAAACAAUCAA' (SEQ ID NO:898) | [[], [], ['UUAU', 'AUAA']] | 0.258065 | 0.903226 | 2 | 49 |
| 'AAAGGUAAGAAACCAUCUUAUAUAAAACAAU' (SEQ ID NO:899) | [[], [], ['UUAU', 'AUAA']] | 0.225806 | 0.903226 | 2 | 46 |

FIG. 43 (Cont'd)

| SEQUENCE | BS | GCNESS | 3LN | NBP | P |
|---|---|---|---|---|---|
| 'AAAAUGAGUCACUUCAAGGCGGCCACAGGG' (SEQ ID NO:900) | [[], ['GGG'], ['AAAA']] | 0.516129 | 0.870968 | 2 | 102 |
| 'ACUUCAAAGGCGGCCACAGGGUUGAGGAAAA' (SEQ ID NO:901) | [[], ['GGG'], ['AAAA']] | 0.516129 | 0.870968 | 2 | 112 |
| 'CUUCAAAGGCGGCCACAGGGUUGAGGAAAAA' (SEQ ID NO:902) | [[], ['GGG'], ['AAAA']] | 0.516129 | 0.870968 | 2 | 113 |
| 'UUCAAAGGCGGCCACAGGGUUGAGGAAAAAG' (SEQ ID NO:903) | [[], ['GGG'], ['AAAA']] | 0.516129 | 0.870968 | 2 | 114 |
| 'GGAAAAAGCCCCUUGUGGAAUCAGAAGCAGG' (SEQ ID NO:904) | [['CCC'], [], ['AAAA']] | 0.516129 | 0.870968 | 2 | 137 |
| 'GAGGAAAAAGCCCCUUGUGGAAUCAGAAGCA' (SEQ ID NO:905) | [['CCC'], [], ['AAAA']] | 0.483871 | 0.870968 | 2 | 135 |
| 'AGGAAAAAGCCCCUUGUGGAAUCAGAAGCAG' (SEQ ID NO:906) | [['CCC'], [], ['AAAA']] | 0.483871 | 0.870968 | 2 | 136 |
| 'AAAAAAAUGAGUCACUUCAAAGGCGGCCACA' (SEQ ID NO:907) | [[], [], ['AAAA', 'AAAU']] | 0.419355 | 0.870968 | 2 | 99 |

FIG. 43 (Cont'd)

| SEQUENCE | BS | GCNESS | 3LN | NBP | P |
|---|---|---|---|---|---|
| 'GUUGACUUUAUUUCAC CGUGGAAAUUUUGUG' (SEQ ID NO:908) | [[], [], ['UUUA', 'AAAU']] | 0.354839 | 0.870968 | 2 | 12 |
| 'AUGUUGACUUUAUUUC ACCGUGGAAAUUUUG' (SEQ ID NO:909) | [[], [], ['UUUA', 'AAAU']] | 0.322581 | 0.870968 | 2 | 10 |
| 'UGUUGACUUUAUUUCA CCGUGGAAAUUUUGU' (SEQ ID NO:910) | [[], [], ['UUUA', 'AAAU']] | 0.322581 | 0.870968 | 2 | 11 |
| 'AAAGCUUAUAAUGUUG ACUUUAUUUCACCGU' (SEQ ID NO:911) | [[], [], ['UUAU', 'UUUA']] | 0.290323 | 0.870968 | 2 | 0 |
| 'UUAUAAUGUUGACUUU AUUUCACCGUGGAAA' (SEQ ID NO:912) | [[], [], ['UUAU', 'UUUA']] | 0.290323 | 0.870968 | 2 | 5 |
| 'AAUGUUGACUUUAUUU CACCGUGGAAAUUUU' (SEQ ID NO:913) | [[], [], ['UUUA', 'AAAU']] | 0.290323 | 0.870968 | 2 | 9 |
| 'UGCUCAAAGGUAAGAA ACCAUCUUAUAUAAA' (SEQ ID NO:914) | [[], [], ['UUAU', 'AUAA']] | 0.290323 | 0.870968 | 2 | 41 |
| 'GCUCAAAGGUAAGAAA CCAUCUUAUAUAAAA' (SEQ ID NO:915) | [[], [], ['UUAU', 'AUAA']] | 0.290323 | 0.870968 | 2 | 42 |

FIG. 43 (Cont'd)

| SEQUENCE | BS | GCNESS | 3LN | NBP | P |
|---|---|---|---|---|---|
| 'AUACAUUAAAAAAAUGAGUCACUUCAAAGGC' (SEQ ID NO:916) | [[], [], ['AUUA', 'AAAA']] | 0.290323 | 0.870968 | 2 | 92 |
| 'AAAUGAGUCACUUCAAAGGCGGCCACAGGGU' (SEQ ID NO:917) | [[], ['GGG'], ['AAAU']] | 0.516129 | 0.83871 | 2 | 103 |
| 'GGUUGAGGAAAAGCCCCUUGUGGAAUCAGA' (SEQ ID NO:918) | [['CCC'], [], ['AAAA']] | 0.483871 | 0.83871 | 2 | 131 |
| 'UGAGGAAAAGCCCCUUGUGGAAUCAGAAGC' (SEQ ID NO:919) | [['CCC'], [], ['AAAA']] | 0.483871 | 0.83871 | 2 | 134 |
| 'GAAAAGCCCCUUGUGGAAUCAGAAGCAGGU' (SEQ ID NO:920) | [['CCC'], [], ['AAAA']] | 0.483871 | 0.83871 | 2 | 138 |
| 'AAAAGCCCCUUGUGGAAUCAGAAGCAGGUG' (SEQ ID NO:921) | [['CCC'], [], ['AAAA']] | 0.483871 | 0.83871 | 2 | 139 |
| 'GUUGAGGAAAAGCCCCUUGUGGAAUCAGAA' (SEQ ID NO:922) | [['CCC'], [], ['AAAA']] | 0.451613 | 0.83871 | 2 | 132 |
| 'UUGAGGAAAAGCCCCUUGUGGAAUCAGAAG' (SEQ ID NO:923) | [['CCC'], [], ['AAAA']] | 0.451613 | 0.83871 | 2 | 133 |

FIG. 43 (Cont'd)

| SEQUENCE | BS | GCNESS | 3LN | NBP | P |
|---|---|---|---|---|---|
| 'UAAAAAAAUGAGUCACUUCAAAGGCGGCCAC' (SEQ ID NO:924) | [[], [], ['UAAA', 'AAAA']] | 0.419355 | 0.83871 | 2 | 98 |
| 'UAUUCACCGUGGAAAUUUUGUGCUCAAAGG' (SEQ ID NO:925) | [[], [], ['UAUU', 'AAAU']] | 0.387097 | 0.83871 | 2 | 20 |
| 'AUUUCACCGUGGAAAUUUUGUGCUCAAAGGU' (SEQ ID NO:926) | [[], [], ['AUUU', 'AAAU']] | 0.387097 | 0.83871 | 2 | 21 |
| 'AGCUUAUAAUGUUGACUUUAUUUCACCGUGG' (SEQ ID NO:927) | [[], [], ['UUAU', 'UUUA']] | 0.354839 | 0.83871 | 2 | 2 |
| 'GCUUAUAAUGUUGACUUUAUUUCACCGUGGA' (SEQ ID NO:928) | [[], [], ['UUAU', 'UUUA']] | 0.354839 | 0.83871 | 2 | 3 |
| 'UUGACUUUAUUUCACCGUGGAAAUUUUGUGC' (SEQ ID NO:929) | [[], [], ['UUUA', 'AAAU']] | 0.354839 | 0.83871 | 2 | 13 |
| 'UGACUUUAUUUCACCGUGGAAAUUUUGUGCU' (SEQ ID NO:930) | [[], [], ['UUUA', 'AAAU']] | 0.354839 | 0.83871 | 2 | 14 |
| 'ACUUUAUUUCACCGUGGAAAUUUUGUGCUCA' (SEQ ID NO:931) | [[], [], ['UUUA', 'AAAU']] | 0.354839 | 0.83871 | 2 | 16 |

FIG. 43 (Cont'd)

| SEQUENCE | BS | GCNESS | 3LN | NBP | P |
|---|---|---|---|---|---|
| 'CUUUAUUUCACCGUGG AAAUUUUGUGCUCAA' (SEQ ID NO:932) | [[], [], ['UUUA', 'AAAU']] | 0.354839 | 0.83871 | 2 | 17 |
| 'UUAUUUCACCGUGGAA AUUUUGUGCUCAAAG' (SEQ ID NO:933) | [[], [], ['UUAU', 'AAAU']] | 0.354839 | 0.83871 | 2 | 19 |
| 'ACAUUAAAAAAUGAG UCACUUCAAAGGCGG' (SEQ ID NO:934) | [[], [], ['AUUA', 'AAAA']] | 0.354839 | 0.83871 | 2 | 94 |
| 'AAGCUUAUAAUGUUGA CUUUAUUUCACCGUG' (SEQ ID NO:935) | [[], [], ['UUAU', 'UUUA']] | 0.322581 | 0.83871 | 2 | 1 |
| 'CUUAUAAUGUUGACUU UAUUUCACCGUGGAA' (SEQ ID NO:936) | [[], [], ['UUAU', 'UUUA']] | 0.322581 | 0.83871 | 2 | 4 |
| 'UUUAUUUCACCGUGGA AAUUUUGUGCUCAAA' (SEQ ID NO:937) | [[], [], ['UUUA', 'AAAU']] | 0.322581 | 0.83871 | 2 | 18 |
| 'UUUUGUGCUCAAAGGU AAGAAACCAUCUUAU' (SEQ ID NO:938) | [[], [], ['UUUU', 'UUAU']] | 0.322581 | 0.83871 | 2 | 36 |
| 'GUGCUCAAAGGUAAGA AACCAUCUUAUAUAA' (SEQ ID NO:939) | [[], [], ['UUAU', 'AUAA']] | 0.322581 | 0.83871 | 2 | 40 |

FIG. 43 (Cont'd)

| SEQUENCE | BS | GCNESS | 3LN | NBP | P |
|---|---|---|---|---|---|
| 'UACAUUAAAAAAUGAGUCACUUCAAAGGCG' (SEQ ID NO:940) | [[], [], ['AUUA', 'AAAA']] | 0.322581 | 0.83871 | 2 | 93 |
| 'AAAAGCCCCUUGUGGAAUCAGAAGCAGGUGU' (SEQ ID NO:941) | [['CCC'], [], ['AAAA']] | 0.483871 | 0.806452 | 2 | 140 |
| 'GACUUUAUUUCACCGUGGAAAUUUUGUGCUC' (SEQ ID NO:942) | [[], [], ['UUUA', 'AAAU']] | 0.387097 | 0.806452 | 2 | 15 |
| 'CAUUAAAAAAUGAGUCACUUCAAAGGCGGC' (SEQ ID NO:943) | [[], [], ['AUUA', 'AAAA']] | 0.387097 | 0.806452 | 2 | 95 |
| 'AUUAAAAAAUGAGUCACUUCAAAGGCGGCC' (SEQ ID NO:944) | [[], [], ['AUUA', 'AAAA']] | 0.387097 | 0.806452 | 2 | 96 |
| 'UUAAAAAAUGAGUCACUUCAAAGGCGGCCA' (SEQ ID NO:945) | [[], [], ['UUAA', 'AAAA']] | 0.387097 | 0.806452 | 2 | 97 |
| 'UAAGAAACCAUCUUAUAUAAAACAAUCAAAU' (SEQ ID NO:946) | [[], [], ['UUAU', 'AUAA', 'AAAU']] | 0.193548 | 0.967742 | 3 | 51 |
| 'AAGAAACCAUCUUAUAUAAAACAAUCAAAUA' (SEQ ID NO:947) | [[], [], ['UUAU', 'AUAA', 'AAAU']] | 0.193548 | 0.967742 | 3 | 52 |

FIG. 43 (Cont'd)

| SEQUENCE | BS | GCNESS | 3LN | NBP | P |
|---|---|---|---|---|---|
| 'AGAAACCAUCUUAUAUAAAACAAUCAAAUAA' (SEQ ID NO:948) | [[], [], ['UUAU', 'AUAA', 'AAAU']] | 0.193548 | 0.967742 | 3 | 53 |
| 'GAAACCAUCUUAUAUAAAACAAUCAAAUAAA' (SEQ ID NO:949) | [[], [], ['UUAU', 'AUAA', 'AAAU']] | 0.193548 | 0.967742 | 3 | 54 |
| 'AAGGCGGCCACAGGGUUGAGGAAAAGCCCC' (SEQ ID NO:950) | [['CCC'], ['GGG'], ['AAAA']] | 0.612903 | 0.935484 | 3 | 118 |
| 'AAAGGCGGCCACAGGGUUGAGGAAAAGCCC' (SEQ ID NO:951) | [['CCC'], ['GGG'], ['AAAA']] | 0.580645 | 0.935484 | 3 | 117 |
| 'ACAUAAAUACAUUAAAAAAAUGAGUCACUUC' (SEQ ID NO:952) | [[], [], ['AUAA', 'AUUA', 'AAAA']] | 0.225806 | 0.935484 | 3 | 86 |
| 'CAUAAAUACAUUAAAAAAUGAGUCACUUCA' (SEQ ID NO:953) | [[], [], ['AUAA', 'AUUA', 'AAAA']] | 0.225806 | 0.935484 | 3 | 87 |
| 'AUACAUAAAUACAUUAAAAAAAUGAGUCACU' (SEQ ID NO:954) | [[], [], ['AUAA', 'AUUA', 'AAAA']] | 0.193548 | 0.935484 | 3 | 84 |
| 'UACAUAAAUACAUUAAAAAAAUGAGUCACUU' (SEQ ID NO:955) | [[], [], ['AUAA', 'AUUA', 'AAAA']] | 0.193548 | 0.935484 | 3 | 85 |

FIG. 43 (Cont'd)

| SEQUENCE | BS | GCNESS | 3LN | NBP | P |
|---|---|---|---|---|---|
| 'AUAAAUACAUUAAAAAAAUGAGUCACUUCAA' (SEQ ID NO:956) | [[], [], ['AUAA', 'AUUA', 'AAAA']] | 0.193548 | 0.935484 | 3 | 88 |
| 'UAAAUACAUUAAAAAAAUGAGUCACUUCAAA' (SEQ ID NO:957) | [[], [], ['UAAA', 'AUUA', 'AAAA']] | 0.193548 | 0.935484 | 3 | 89 |
| 'AGGCGGCCACAGGGUUGAGGAAAAGCCCCU' (SEQ ID NO:958) | [['CCC'], ['GGG'], ['AAAA']] | 0.612903 | 0.903226 | 3 | 119 |
| 'AAAUACAUUAAAAAAAUGAGUCACUUCAAAG' (SEQ ID NO:959) | [[], [], ['AAAU', 'AUUA', 'AAAA']] | 0.225806 | 0.903226 | 3 | 90 |
| 'GGCGGCCACAGGGUUGAGGAAAAGCCCCUU' (SEQ ID NO:960) | [['CCC'], ['GGG'], ['AAAA']] | 0.612903 | 0.870968 | 3 | 120 |
| 'GCGGCCACAGGGUUGAGGAAAAGCCCCUUG' (SEQ ID NO:961) | [['CCC'], ['GGG'], ['AAAA']] | 0.612903 | 0.870968 | 3 | 121 |
| 'UAUAAUGUUGACUUUAUUUCACCGUGGAAAU' (SEQ ID NO:962) | [[], [], ['UAUA', 'UUUA', 'AAAU']] | 0.290323 | 0.870968 | 3 | 6 |
| 'AUAAUGUUGACUUUAUUUCACCGUGGAAAUU' (SEQ ID NO:963) | [[], [], ['AUAA', 'UUUA', 'AAAU']] | 0.290323 | 0.870968 | 3 | 7 |

FIG. 43 (Cont'd)

| SEQUENCE | BS | GCNESS | 3LN | NBP | P |
|---|---|---|---|---|---|
| 'UAAUGUUGACUUUAUU UCACCGUGGAAAUUU' (SEQ ID NO:964) | [[], [], ['UAAU', 'UUUA', 'AAAU']] | 0.290323 | 0.870968 | 3 | 8 |
| 'AAUACAUUAAAAAAAUG AGUCACUUCAAAGG' (SEQ ID NO:965) | [[], [], ['AAUA', 'AUUA', 'AAAA']] | 0.258065 | 0.870968 | 3 | 91 |
| 'CGGCCACAGGGUUGA GGAAAAAGCCCCUUGU' (SEQ ID NO:966) | [['CCC'], ['GGG'], ['AAAA']] | 0.580645 | 0.83871 | 3 | 122 |
| 'GGCCACAGGGUUGAG GAAAAAGCCCCUUGUG' (SEQ ID NO:967) | [['CCC'], ['GGG'], ['AAAA']] | 0.580645 | 0.83871 | 3 | 123 |
| 'GCCACAGGGUUGAGGA AAAAGCCCCUUGUGG' (SEQ ID NO:968) | [['CCC'], ['GGG'], ['AAAA']] | 0.580645 | 0.83871 | 3 | 124 |
| 'CCACAGGGUUGAGGAA AAAGCCCCUUGUGGA' (SEQ ID NO:969) | [['CCC'], ['GGG'], ['AAAA']] | 0.548387 | 0.83871 | 3 | 125 |
| 'CACAGGGUUGAGGAAA AAGCCCCUUGUGGAA' (SEQ ID NO:970) | [['CCC'], ['GGG'], ['AAAA']] | 0.516129 | 0.83871 | 3 | 126 |
| 'GGGUUGAGGAAAAAGC CCCUUGUGGAAUCAG' (SEQ ID NO:971) | [['CCC'], ['GGG'], ['AAAA']] | 0.516129 | 0.83871 | 3 | 130 |

FIG. 43 (Cont'd)

| SEQUENCE | BS | GCNESS | 3LN | NBP | P |
|---|---|---|---|---|---|
| 'ACAGGGUUGAGGAAAA AGCCCCUUGUGGAAU' (SEQ ID NO:972) | [['CCC'], ['GGG'], ['AAAA']] | 0.483871 | 0.83871 | 3 | 127 |
| 'AGGGUUGAGGAAAAAG CCCCUUGUGGAAUCA' (SEQ ID NO:973) | [['CCC'], ['GGG'], ['AAAA']] | 0.483871 | 0.83871 | 3 | 129 |
| 'CAGGGUUGAGGAAAAA GCCCCUUGUGGAAUC' (SEQ ID NO:974) | [['CCC'], ['GGG'], ['AAAA']] | 0.516129 | 0.806452 | 3 | 128 |
| 'ACCAUCUUAUAUAAAA CAAUCAAAUAAAUAC' (SEQ ID NO:975) | [[], [], ['UUAU', 'AUAA', 'AAAU', 'AAAU']] | 0.193548 | 1 | 4 | 57 |
| 'CCAUCUUAUAUAAAAC AAUCAAAUAAAUACA' (SEQ ID NO:976) | [[], [], ['UUAU', 'AUAA', 'AAAU', 'AAAU']] | 0.193548 | 1 | 4 | 58 |
| 'AAACCAUCUUAUAUAA AACAAUCAAAUAAAU' (SEQ ID NO:977) | [[], [], ['UUAU', 'AUAA', 'AAAU', 'AAAU']] | 0.16129 | 1 | 4 | 55 |
| 'AACCAUCUUAUAUAAA ACAAUCAAAUAAAUA' (SEQ ID NO:978) | [[], [], ['UUAU', 'AUAA', 'AAAU', 'AAAU']] | 0.16129 | 1 | 4 | 56 |
| 'CAUCUUAUAUAAAACA AUCAAAUAAAUACAU' (SEQ ID NO:979) | [[], [], ['UUAU', 'AUAA', 'AAAU', 'AAAU']] | 0.16129 | 1 | 4 | 59 |

FIG. 43 (Cont'd)

| SEQUENCE | BS | GCNESS | 3LN | NBP | P |
|---|---|---|---|---|---|
| 'AUCUUAUAUAAAACAAUCAAAUAAAUACAUA' (SEQ ID NO:980) | [[], [], ['UUAU', 'AUAA', 'AAAU', 'AAAU']] | 0.129032 | 1 | 4 | 60 |
| 'UAUAAACAAUCAAAUAAAUACAUAAAUACA' (SEQ ID NO:981) | [[], [], ['UAUA', 'AAAU', 'AAAU', 'AUAA']] | 0.129032 | 1 | 4 | 66 |
| 'AUAAACAAUCAAAUAAAUACAUAAAUACAU' (SEQ ID NO:982) | [[], [], ['AUAA', 'AAAU', 'AAAU', 'AUAA']] | 0.129032 | 1 | 4 | 67 |
| 'UAAACAAUCAAAUAAAUACAUAAAUACAUU' (SEQ ID NO:983) | [[], [], ['UAAA', 'AAAU', 'AAAU', 'AUAA']] | 0.129032 | 1 | 4 | 68 |
| 'AAACAAUCAAAUAAAUACAUAAAUACAUUAA' (SEQ ID NO:984) | [[], [], ['AAAU', 'AAAU', 'AUAA', 'AUUA']] | 0.129032 | 1 | 4 | 70 |
| 'AACAAUCAAAUAAAUACAUAAAUACAUUAAA' (SEQ ID NO:985) | [[], [], ['AAAU', 'AAAU', 'AUAA', 'AUUA']] | 0.129032 | 1 | 4 | 71 |
| 'ACAAUCAAAUAAAUACAUAAAUACAUUAAAA' (SEQ ID NO:986) | [[], [], ['AAAU', 'AAAU', 'AUAA', 'AUUA']] | 0.129032 | 1 | 4 | 72 |
| 'AAUACAUAAAUACAUUAAAAAAUGAGUCAC' (SEQ ID NO:987) | [[], [], ['AAUA', 'AUAA', 'AUUA', 'AAAA']] | 0.193548 | 0.935484 | 4 | 83 |

FIG. 43 (Cont'd)

| SEQUENCE | BS | GCNESS | 3LN | NBP | P |
|---|---|---|---|---|---|
| 'UAAAUACAUAAAUACAUUAAAAAAAUGAGUC' (SEQ ID NO:988) | [[], [], ['UAAA', 'AUAA', 'AUUA', 'AAAA']] | 0.16129 | 0.935484 | 4 | 81 |
| 'AAAUACAUAAAUACAUUAAAAAAAUGAGUCA' (SEQ ID NO:989) | [[], [], ['AAAU', 'AUAA', 'AUUA', 'AAAA']] | 0.16129 | 0.935484 | 4 | 82 |
| 'AUAAAUACAUAAAUACAUUAAAAAAAUGAGU' (SEQ ID NO:990) | [[], [], ['AUAA', 'AUAA', 'AUUA', 'AAAA']] | 0.129032 | 0.935484 | 4 | 80 |
| 'UCUUAUAUAAAACAAUCAAAUAAAUACAUAA' (SEQ ID NO:991) | [[], [], ['UUAU', 'AUAA', 'AAAU', 'AAAU', 'AUAA']] | 0.129032 | 1 | 5 | 61 |
| 'CUUAUAUAAAACAAUCAAAUAAAUACAUAAA' (SEQ ID NO:992) | [[], [], ['UUAU', 'AUAA', 'AAAU', 'AAAU', 'AUAA']] | 0.129032 | 1 | 5 | 62 |
| 'AUAUAAAACAAUCAAAUAAAUACAUAAAUAC' (SEQ ID NO:993) | [[], [], ['AUAU', 'AAAA', 'AAAU', 'AAAU', 'AUAA']] | 0.129032 | 1 | 5 | 65 |
| 'AAAACAAUCAAAUAAAUACAUAAAUACAUUA' (SEQ ID NO:994) | [[], [], ['AAAA', 'AAAU', 'AAAU', 'AUAA', 'AUUA']] | 0.129032 | 1 | 5 | 69 |
| 'CAAUCAAAUAAAUACAUAAAUACAUUAAAAA' (SEQ ID NO:995) | [[], [], ['AAAU', 'AAAU', 'AUAA', 'AUUA', 'AAAA']] | 0.129032 | 1 | 5 | 73 |

FIG. 43 (Cont'd)

| SEQUENCE | BS | GCNESS | 3LN | NBP | P |
|---|---|---|---|---|---|
| 'UUAUAUAAACAAUCAA AUAAAUACAUAAAU' (SEQ ID NO:996) | [[], [], ['UUAU', 'AUAA', 'AAAU', 'AAAU', 'AUAA']] | 0.096774 | 1 | 5 | 63 |
| 'UAUAUAAACAAUCAAA UAAAUACAUAAAUA' (SEQ ID NO:997) | [[], [], ['UAUA', 'UAAA', 'AAAU', 'AAAU', 'AUAA']] | 0.096774 | 1 | 5 | 64 |
| 'AAUCAAAUAAAUACAUA AAUACAUUAAAAAA' (SEQ ID NO:998) | [[], [], ['AAAU', 'AAAU', 'AUAA', 'AUUA', 'AAAA']] | 0.096774 | 1 | 5 | 74 |
| 'AUCAAAUAAAUACAUAA AUACAUUAAAAAAA' (SEQ ID NO:999) | [[], [], ['AAAU', 'AAAU', 'AUAA', 'AUUA', 'AAAA']] | 0.096774 | 1 | 5 | 75 |
| 'UCAAAUAAAUACAUAAA UACAUUAAAAAAAU' (SEQ ID NO:1000) | [[], [], ['AAAU', 'AAAU', 'AUAA', 'AUUA', 'AAAA']] | 0.096774 | 1 | 5 | 76 |
| 'CAAAUAAAUACAUAAAU ACAUUAAAAAAAUG' (SEQ ID NO:1001) | [[], [], ['AAAU', 'AAAU', 'AUAA', 'AUUA', 'AAAA']] | 0.129032 | 0.967742 | 5 | 77 |
| 'AAAUAAAUACAUAAAUA CAUUAAAAAAAUGA' (SEQ ID NO:1002) | [[], [], ['AAAU', 'AAAU', 'AUAA', 'AUUA', 'AAAA']] | 0.096774 | 0.967742 | 5 | 78 |
| 'AAUAAAUACAUAAAUAC AUUAAAAAAAUGAG' (SEQ ID NO:1003) | [[], [], ['AAUA', 'AAUA', 'AUAA', 'AUUA', 'AAAA']] | 0.129032 | 0.935484 | 5 | 79 |

| SEQUENCE | BS | GCNESS | 3LN | NBP | P |
|---|---|---|---|---|---|
| 'GGCCUCAGCGUCUGUCCGUGGUGCUGAAGUU' (SEQ ID NO:1004) | [[], [], []] | 0.612903226 | 0.903225806 | 0 | 2 |
| 'GCCUCAGCGUCUGUCCGUGGUGCUGAAGUUU' (SEQ ID NO:1005) | [[], [], []] | 0.580645161 | 0.903225806 | 0 | 3 |
| 'GAUGAAGACAGGAAGCUGCAGCUCCAGGAGG' (SEQ ID NO:1006) | [[], [], []] | 0.580645161 | 0.903225806 | 0 | 154 |
| 'AGAUGAAGACAGGAAGCUGCAGCUCCAGGAG' (SEQ ID NO:1007) | [[], [], []] | 0.548387097 | 0.903225806 | 0 | 153 |
| 'CAGGCCUCAGCGUCUGUCCGUGGUGCUGAAG' (SEQ ID NO:1008) | [[], [], []] | 0.64516129 | 0.870967742 | 0 | 0 |
| 'AGGCCUCAGCGUCUGUCCGUGGUGCUGAAGU' (SEQ ID NO:1009) | [[], [], []] | 0.612903226 | 0.870967742 | 0 | 1 |

FIG. 44 (Cont'd)

| SEQUENCE | BS | GCNESS | 3LN | NBP | P |
|---|---|---|---|---|---|
| 'GGCAAUGCGACCAAGCUGUGUGACACACCGC' (SEQ ID NO:1010) | [[], [], []] | 0.612903226 | 0.870967742 | 0 | 204 |
| 'GCAAUGCGACCAAGCUGUGUGACACACCGCA' (SEQ ID NO:1011) | [[], [], []] | 0.580645161 | 0.870967742 | 0 | 205 |
| 'AUGCGACCAAGCUGUGUGACACACCGCAAGG' (SEQ ID NO:1012) | [[], [], []] | 0.580645161 | 0.870967742 | 0 | 208 |
| 'CAAUGCGACCAAGCUGUGUGACACACCGCAA' (SEQ ID NO:1013) | [[], [], []] | 0.548387097 | 0.870967742 | 0 | 206 |
| 'AAUGCGACCAAGCUGUGUGACACACCGCAAG' (SEQ ID NO:1014) | [[], [], []] | 0.548387097 | 0.870967742 | 0 | 207 |
| 'GAUAGAUGAAGACAGGAAGCUGCAGCUCCAG' (SEQ ID NO:1015) | [[], [], []] | 0.516129032 | 0.870967742 | 0 | 150 |
| 'AUAGAUGAAGACAGGAAGCUGCAGCUCCAGG' (SEQ ID NO:1016) | [[], [], []] | 0.516129032 | 0.870967742 | 0 | 151 |

FIG. 44 (Cont'd)

| SEQUENCE | BS | GCNESS | 3LN | NBP | P |
|---|---|---|---|---|---|
| 'UAGAUGAAGACAGGAAGCUGCAGCUCCAGGA' (SEQ ID NO:1017) | [[], [], []] | 0.516129032 | 0.870967742 | 0 | 152 |
| 'GAUCGUGAUAGAUGAAGACAGGAAGCUGCAG' (SEQ ID NO:1018) | [[], [], []] | 0.483870968 | 0.870967742 | 0 | 144 |
| 'AUCGAUCGUGAUAGAUGAAGACAGGAAGCUG' (SEQ ID NO:1019) | [[], [], []] | 0.451612903 | 0.870967742 | 0 | 141 |
| 'AACAUCGAUCGUGAUAGAUGAAGACAGGAAG' (SEQ ID NO:1020) | [[], [], []] | 0.419354839 | 0.870967742 | 0 | 138 |
| 'UAACAUCGAUCGUGAUAGAUGAAGACAGGAA' (SEQ ID NO:1021) | [[], [], []] | 0.387096774 | 0.870967742 | 0 | 137 |
| 'UCACCACCUCUCAGUGGCAAUGCGACCAAGC' (SEQ ID NO:1022) | [[], [], []] | 0.580645161 | 0.838709677 | 0 | 189 |
| 'CACCACCUCUCAGUGGCAAUGCGACCAAGCU' (SEQ ID NO:1023) | [[], [], []] | 0.580645161 | 0.838709677 | 0 | 190 |
| 'ACCACCUCUCAGUGGCAAUGCGACCAAGCUG' (SEQ ID NO:1024) | [[], [], []] | 0.580645161 | 0.838709677 | 0 | 191 |

FIG. 44 (Cont'd)

| SEQUENCE | BS | GCNESS | 3LN | NBP | P |
|---|---|---|---|---|---|
| 'GUGGCAAUGCGACCAAGCUGUGUGACACACC' (SEQ ID NO:1025) | [[], [], []] | 0.580645161 | 0.838709677 | 0 | 202 |
| 'UGGCAAUGCGACCAAGCUGUGUGACACACCG' (SEQ ID NO:1026) | [[], [], []] | 0.580645161 | 0.838709677 | 0 | 203 |
| 'CAGUGGCAAUGCGACCAAGCUGUGUGACACA' (SEQ ID NO:1027) | [[], [], []] | 0.548387097 | 0.838709677 | 0 | 200 |
| 'AGUGGCAAUGCGACCAAGCUGUGUGACACAC' (SEQ ID NO:1028) | [[], [], []] | 0.548387097 | 0.838709677 | 0 | 201 |
| 'CGUGAUAGAUGAAGACAGGAAGCUGCAGCUC' (SEQ ID NO:1029) | [[], [], []] | 0.516129032 | 0.838709677 | 0 | 147 |
| 'GUGAUAGAUGAAGACAGGAAGCUGCAGCUCC' (SEQ ID NO:1030) | [[], [], []] | 0.516129032 | 0.838709677 | 0 | 148 |
| 'AUUCACCACCUCUCAGUGGCAAUGCGACCAA' (SEQ ID NO:1031) | [[], [], []] | 0.516129032 | 0.838709677 | 0 | 187 |

FIG. 44 (Cont'd)

| SEQUENCE | BS | GCNESS | 3LN | NBP | P |
|---|---|---|---|---|---|
| 'UCGAUCGUGAUAGAUGAAGACAGGAAGCUGC' (SEQ ID NO:1032) | [[], [], []] | 0.483870968 | 0.838709677 | 0 | 142 |
| 'CGAUCGUGAUAGAUGAAGACAGGAAGCUGCA' (SEQ ID NO:1033) | [[], [], []] | 0.483870968 | 0.838709677 | 0 | 143 |
| 'AUCGUGAUAGAUGAAGACAGGAAGCUGCAGC' (SEQ ID NO:1034) | [[], [], []] | 0.483870968 | 0.838709677 | 0 | 145 |
| 'UCGUGAUAGAUGAAGACAGGAAGCUGCAGCU' (SEQ ID NO:1035) | [[], [], []] | 0.483870968 | 0.838709677 | 0 | 146 |
| 'UGAUAGAUGAAGACAGGAAGCUGCAGCUCCA' (SEQ ID NO:1036) | [[], [], []] | 0.483870968 | 0.838709677 | 0 | 149 |
| 'ACAUCGAUCGUGAUAGAUGAAGACAGGAAGC' (SEQ ID NO:1037) | [[], [], []] | 0.451612903 | 0.838709677 | 0 | 139 |
| 'CAUCGAUCGUGAUAGAUGAAGACAGGAAGCU' (SEQ ID NO:1038) | [[], [], []] | 0.451612903 | 0.838709677 | 0 | 140 |
| 'CCACCUCUCAGUGGCAAUGCGACCAAGCUGU' (SEQ ID NO:1039) | [[], [], []] | 0.580645161 | 0.806451613 | 0 | 192 |

FIG. 44 (Cont'd)

| SEQUENCE | BS | GCNESS | 3LN | NBP | P |
|---|---|---|---|---|---|
| 'CACCUCUCAGUGGCAAUGCGACCAAGCUGUG' (SEQ ID NO:1040) | [[], [], []] | 0.580645161 | 0.806451613 | 0 | 193 |
| 'CCUCUCAGUGGCAAUGCGACCAAGCUGUGUG' (SEQ ID NO:1041) | [[], [], []] | 0.580645161 | 0.806451613 | 0 | 195 |
| 'UUCACCACCUCUCAGUGGCAAUGCGACCAAG' (SEQ ID NO:1042) | [[], [], []] | 0.548387097 | 0.806451613 | 0 | 188 |
| 'CUCAGUGGCAAUGCGACCAAGCUGUGUGACA' (SEQ ID NO:1043) | [[], [], []] | 0.548387097 | 0.806451613 | 0 | 198 |
| 'UCAGUGGCAAUGCGACCAAGCUGUGUGACAC' (SEQ ID NO:1044) | [[], [], []] | 0.548387097 | 0.806451613 | 0 | 199 |
| 'ACCUCUCAGUGGCAAUGCGACCAAGCUGUGU' (SEQ ID NO:1045) | [[], [], []] | 0.548387097 | 0.774193548 | 0 | 194 |
| 'CUCUCAGUGGCAAUGCGACCAAGCUGUGUGA' (SEQ ID NO:1046) | [[], [], []] | 0.548387097 | 0.774193548 | 0 | 196 |

FIG. 44 (Cont'd)

| SEQUENCE | BS | GCNESS | 3LN | NBP | P |
|---|---|---|---|---|---|
| 'UCUCAGUGGCAAUGCGACCAAGCUGUGUGAC' (SEQ ID NO:1047) | [[], [], []] | 0.548387097 | 0.774193548 | 0 | 197 |
| 'UAAGGCCUCACUAAACCACUCAUCUACACUU' (SEQ ID NO:1048) | [[], [], ['UAAA']] | 0.419354839 | 0.935483871 | 1 | 107 |
| 'AAGGCCUCACUAAACCACUCAUCUACACUA' (SEQ ID NO:1049) | [[], [], ['UAAA']] | 0.419354839 | 0.935483871 | 1 | 108 |
| 'AAACCACUCAUCUACACUUAACAUCGAUCGU' (SEQ ID NO:1050) | [[], [], ['UUAA']] | 0.387096774 | 0.935483871 | 1 | 119 |
| 'GCGACCAAGCUGUGUGACACACCGCAAGGGC' (SEQ ID NO:1051) | [[], ['GGG'], []] | 0.64516129 | 0.903225806 | 1 | 210 |
| 'AUGAAGACAGGAAGCUGCAGCUCCAGGAGGG' (SEQ ID NO:1052) | [[], ['GGG'], []] | 0.580645161 | 0.903225806 | 1 | 155 |
| 'GAAGACAGGAAGCUGCAGCUCCAGGAGGGUA' (SEQ ID NO:1053) | [[], ['GGG'], []] | 0.580645161 | 0.903225806 | 1 | 157 |

FIG. 44 (Cont'd)

| SEQUENCE | BS | GCNESS | 3LN | NBP | P |
|---|---|---|---|---|---|
| 'GCGUCUGUCCGUGGUGCUGAAGUUUAUUCGG' (SEQ ID NO:1054) | [[], [], ['UUUA']] | 0.548387097 | 0.903225806 | 1 | 9 |
| 'GUAAGGCCUCACUAAACCACUCAUCUACACU' (SEQ ID NO:1055) | [[], [], ['UAAA']] | 0.451612903 | 0.903225806 | 1 | 106 |
| 'AACCACUCAUCUACACUUAACAUCGAUCGUG' (SEQ ID NO:1056) | [[], [], ['UUAA']] | 0.419354839 | 0.903225806 | 1 | 120 |
| 'ACCACUCAUCUACACUUAACAUCGAUCGUGA' (SEQ ID NO:1057) | [[], [], ['UUAA']] | 0.419354839 | 0.903225806 | 1 | 121 |
| 'CCACUCAUCUACACUUAACAUCGAUCGUGAU' (SEQ ID NO:1058) | [[], [], ['UUAA']] | 0.419354839 | 0.903225806 | 1 | 122 |
| 'CACUCAUCUACACUUAACAUCGAUCGUGAUA' (SEQ ID NO:1059) | [[], [], ['UUAA']] | 0.387096774 | 0.903225806 | 1 | 123 |
| 'UGCGACCAAGCUGUGUGACACACCGCAAGGG' (SEQ ID NO:1060) | [[], ['GGG'], []] | 0.612903226 | 0.870967742 | 1 | 209 |
| 'CGACCAAGCUGUGUGACACACCGCAAGGGCU' (SEQ ID NO:1061) | [[], ['GGG'], []] | 0.612903226 | 0.870967742 | 1 | 211 |

| SEQUENCE | BS | GCNESS | 3LN | NBP | P |
|---|---|---|---|---|---|
| 'UGAAGACAGGAAGCUGCAGCUCCAGGAGGGU' (SEQ ID NO:1062) | [[], ['GGG'], []] | 0.580645161 | 0.870967742 | 1 | 156 |
| 'CCUCAGCGUCUGUCCGUGGUGCUGAAGUUUA' (SEQ ID NO:1063) | [[], [], ['UUUA']] | 0.548387097 | 0.870967742 | 1 | 4 |
| 'AAGACAGGAAGCUGCAGCUCCAGGAGGGUAU' (SEQ ID NO:1064) | [[], ['GGG'], []] | 0.548387097 | 0.870967742 | 1 | 158 |
| 'CUCAGCGUCUGUCCGUGGUGCUGAAGUUUAU' (SEQ ID NO:1065) | [[], [], ['UUUA']] | 0.516129032 | 0.870967742 | 1 | 5 |
| 'CAGCGUCUGUCCGUGGUGCUGAAGUUUAUUC' (SEQ ID NO:1066) | [[], [], ['UUUA']] | 0.516129032 | 0.870967742 | 1 | 7 |
| 'AGCGUCUGUCCGUGGUGCUGAAGUUUAUUCG' (SEQ ID NO:1067) | [[], [], ['UUUA']] | 0.516129032 | 0.870967742 | 1 | 8 |

FIG. 44 (Cont'd)

| SEQUENCE | BS | GCNESS | 3LN | NBP | P |
|---|---|---|---|---|---|
| 'CGUCUGUCCGUGGUGCUGAAGUUUAUUCGGA' (SEQ ID NO:1068) | [[], [], ['UUUA']] | 0.516129032 | 0.870967742 | 1 | 10 |
| 'UCAGCGUCUGUCCGUGGUGCUGAAGUUUAUU' (SEQ ID NO:1069) | [[], [], ['UUUA']] | 0.483870968 | 0.870967742 | 1 | 6 |
| 'GUCUGUCCGUGGUGCUGAAGUUUAUUCGGAU' (SEQ ID NO:1070) | [[], [], ['UUUA']] | 0.483870968 | 0.870967742 | 1 | 11 |
| 'GGUAAGGCCUCACUAAACCACUCAUCUACAC' (SEQ ID NO:1071) | [[], [], ['UAAA']] | 0.483870968 | 0.870967742 | 1 | 105 |
| 'UCUGUCCGUGGUGCUGAAGUUUAUUCGGAUU' (SEQ ID NO:1072) | [[], [], ['UUUA']] | 0.451612903 | 0.870967742 | 1 | 12 |
| 'AGGUAAGGCCUCACUAAACCACUCAUCUACA' (SEQ ID NO:1073) | [[], [], ['UAAA']] | 0.451612903 | 0.870967742 | 1 | 104 |
| 'ACUCAUCUACACUUAACAUCGAUCGUGAUAG' (SEQ ID NO:1074) | [[], [], ['UUAA']] | 0.387096774 | 0.870967742 | 1 | 124 |

FIG. 44 (Cont'd)

| SEQUENCE | BS | GCNESS | 3LN | NBP | P |
|---|---|---|---|---|---|
| 'CUCAUCUACACUUAACAUCGAUCGUGAUAGA' (SEQ ID NO:1075) | [[], [], ['UUAA']] | 0.387096774 | 0.870967742 | 1 | 125 |
| 'UUAACAUCGAUCGUGAUAGAUGAAGACAGGA' (SEQ ID NO:1076) | [[], [], ['UUAA']] | 0.387096774 | 0.870967742 | 1 | 136 |
| 'UCAUCUACACUUAACAUCGAUCGUGAUAGAU' (SEQ ID NO:1077) | [[], [], ['UUAA']] | 0.35483871 | 0.870967742 | 1 | 126 |
| 'CCAAGCUGUGUGACACACCGCAAGGGCUGG' (SEQ ID NO:1078) | [[], ['GGG'], []] | 0.612903226 | 0.838709677 | 1 | 214 |
| 'GACCAAGCUGUGUGACACACCGCAAGGGCUU' (SEQ ID NO:1079) | [[], ['GGG'], []] | 0.580645161 | 0.838709677 | 1 | 212 |
| 'ACCAAGCUGUGUGACACACCGCAAGGGCUUG' (SEQ ID NO:1080) | [[], ['GGG'], []] | 0.580645161 | 0.838709677 | 1 | 213 |
| 'UAUGCAGAGUGGGAGAGGUAAGGCCUCACUA' (SEQ ID NO:1081) | [[], ['GGG'], []] | 0.516129032 | 0.838709677 | 1 | 89 |

FIG. 44 (Cont'd)

| SEQUENCE | BS | GCNESS | 3LN | NBP | P |
|---|---|---|---|---|---|
| 'AUGCAGAGUGGGAGAGGUAAGGCCUCACUAA' (SEQ ID NO:1082) | [[], ['GGG'], []] | 0.516129032 | 0.838709677 | 1 | 90 |
| 'GGAGAGGUAAGGCCUCACUAAACCACUCAUC' (SEQ ID NO:1083) | [[], [], ['UAAA']] | 0.516129032 | 0.838709677 | 1 | 100 |
| 'UAUUCACCACCUCUCAGUGGCAAUGCGACCA' (SEQ ID NO:1084) | [[], [], ['UAUU']] | 0.516129032 | 0.838709677 | 1 | 186 |
| 'GAGGUAAGGCCUCACUAAACCACUCAUCUAC' (SEQ ID NO:1085) | [[], [], ['UAAA']] | 0.483870968 | 0.838709677 | 1 | 103 |
| 'UUUCCAACUGCUUUCUGAAAGGGGUGAGGAU' (SEQ ID NO:1086) | [[], ['GGG'], []] | 0.451612903 | 0.838709677 | 1 | 49 |
| 'UGCUUUCUGAAAGGGGUGAGGAUCUACCUUA' (SEQ ID NO:1087) | [[], ['GGG'], []] | 0.451612903 | 0.838709677 | 1 | 57 |
| 'AGAGGUAAGGCCUCACUAAACCACUCAUCUA' (SEQ ID NO:1088) | [[], [], ['UAAA']] | 0.451612903 | 0.838709677 | 1 | 102 |

| SEQUENCE | BS | GCNESS | 3LN | NBP | P |
|---|---|---|---|---|---|
| 'CUUAACAUCGAUCGUGAUAGAUGAAGACAGG' (SEQ ID NO:1089) | [[], [], ['UUAA']] | 0.419354839 | 0.838709677 | 1 | 135 |
| 'CAUCUACACUUAACAUCGAUCGUGAUAGAUG' (SEQ ID NO:1090) | [[], [], ['UUAA']] | 0.387096774 | 0.838709677 | 1 | 127 |
| 'ACUUAACAUCGAUCGUGAUAGAUGAAGACAG' (SEQ ID NO:1091) | [[], [], ['UUAA']] | 0.387096774 | 0.838709677 | 1 | 134 |
| 'AUCUACACUUAACAUCGAUCGUGAUAGAUGA' (SEQ ID NO:1092) | [[], [], ['UUAA']] | 0.35483871 | 0.838709677 | 1 | 128 |
| 'UCUACACUUAACAUCGAUCGUGAUAGAUGAA' (SEQ ID NO:1093) | [[], [], ['UUAA']] | 0.35483871 | 0.838709677 | 1 | 129 |
| 'UACACUUAACAUCGAUCGUGAUAGAUGAAGA' (SEQ ID NO:1094) | [[], [], ['UUAA']] | 0.35483871 | 0.838709677 | 1 | 131 |
| 'GUAUUCACCACCUCUCAGUGGCAAUGCGACC' (SEQ ID NO:1095) | [[], [], ['UAUU']] | 0.548387097 | 0.806451613 | 1 | 185 |
| 'UUCCAACUGCUUUCUGAAAGGGGUGAGGAUC' (SEQ ID NO:1096) | [[], ['GGG'], []] | 0.483870968 | 0.806451613 | 1 | 50 |

FIG. 44 (Cont'd)

| SEQUENCE | BS | GCNESS | 3LN | NBP | P |
|---|---|---|---|---|---|
| 'UCCAACUGCUUUCUGAAAGGGGUGAGGAUCU' (SEQ ID NO:1097) | [[], ['GGG'], []] | 0.483870968 | 0.806451613 | 1 | 51 |
| 'CCAACUGCUUUCUGAAAGGGGUGAGGAUCUA' (SEQ ID NO:1098) | [[], ['GGG'], []] | 0.483870968 | 0.806451613 | 1 | 52 |
| 'CAACUGCUUUCUGAAAGGGGUGAGGAUCUAC' (SEQ ID NO:1099) | [[], ['GGG'], []] | 0.483870968 | 0.806451613 | 1 | 53 |
| 'AACUGCUUUCUGAAAGGGGUGAGGAUCUACC' (SEQ ID NO:1100) | [[], ['GGG'], []] | 0.483870968 | 0.806451613 | 1 | 54 |
| 'ACUGCUUUCUGAAAGGGGUGAGGAUCUACCU' (SEQ ID NO:1101) | [[], ['GGG'], []] | 0.483870968 | 0.806451613 | 1 | 55 |
| 'CUGCUUUCUGAAAGGGGUGAGGAUCUACCUU' (SEQ ID NO:1102) | [[], ['GGG'], []] | 0.483870968 | 0.806451613 | 1 | 56 |
| 'GAGAGGUAAGGCCUCACUAAACCACUCAUCU' (SEQ ID NO:1103) | [[], [], ['UAAA']] | 0.483870968 | 0.806451613 | 1 | 101 |

FIG. 44 (Cont'd)

| SEQUENCE | BS | GCNESS | 3LN | NBP | P |
|---|---|---|---|---|---|
| 'CUACACUUAACAUCGAUCGUGAUAGAUGAAG' (SEQ ID NO:1104) | [[], [], ['UUAA']] | 0.387096774 | 0.806451613 | 1 | 130 |
| 'ACACUUAACAUCGAUCGUGAUAGAUGAAGAC' (SEQ ID NO:1105) | [[], [], ['UUAA']] | 0.387096774 | 0.806451613 | 1 | 132 |
| 'CACUUAACAUCGAUCGUGAUAGAUGAAGACA' (SEQ ID NO:1106) | [[], [], ['UUAA']] | 0.387096774 | 0.806451613 | 1 | 133 |
| 'GGUAUUCACCACCUCUCAGUGGCAAUGCGAC' (SEQ ID NO:1107) | [[], [], ['UAUU']] | 0.548387097 | 0.774193548 | 1 | 184 |
| 'CCUCACUAAACCACUCAUCUACACUUAACAU' (SEQ ID NO:1108) | [[], [], ['UAAA', 'UUAA']] | 0.387096774 | 1 | 2 | 112 |
| 'CUCACUAAACCACUCAUCUACACUUAACAUC' (SEQ ID NO:1109) | [[], [], ['UAAA', 'UUAA']] | 0.387096774 | 1 | 2 | 113 |
| 'GCCUCACUAAACCACUCAUCUACACUUAACA' (SEQ ID NO:1110) | [[], [], ['UAAA', 'UUAA']] | 0.419354839 | 0.967741935 | 2 | 111 |
| 'UCACUAAACCACUCAUCUACACUUAACAUCG' (SEQ ID NO:1111) | [[], [], ['UAAA', 'UUAA']] | 0.387096774 | 0.967741935 | 2 | 114 |

| SEQUENCE | BS | GCNESS | 3LN | NBP | P |
|---|---|---|---|---|---|
| 'CACUAAACCACUCAUCUACACUUAACAUCGA' (SEQ ID NO:1112) | [[], [], ['UAAA', 'UUAA']] | 0.387096774 | 0.967741935 | 2 | 115 |
| 'CUAAACCACUCAUCUACACUUAACAUCGAUC' (SEQ ID NO:1113) | [[], [], ['UAAA', 'UUAA']] | 0.387096774 | 0.967741935 | 2 | 117 |
| 'ACUAAACCACUCAUCUACACUUAACAUCGAU' (SEQ ID NO:1114) | [[], [], ['UAAA', 'UUAA']] | 0.35483871 | 0.967741935 | 2 | 116 |
| 'GGCCUCACUAAACCACUCAUCUACACUUAAC' (SEQ ID NO:1115) | [[], [], ['UAAA', 'UUAA']] | 0.451612903 | 0.935483871 | 2 | 110 |
| 'AGGCCUCACUAAACCACUCAUCUACACUUAA' (SEQ ID NO:1116) | [[], [], ['UAAA', 'UUAA']] | 0.419354839 | 0.935483871 | 2 | 109 |
| 'UAAACCACUCAUCUACACUUAACAUCGAUCG' (SEQ ID NO:1117) | [[], [], ['UAAA', 'UUAA']] | 0.387096774 | 0.935483871 | 2 | 118 |
| 'UACCUUAAUAUGCAGAGUGGGAGAGGUAAGG' (SEQ ID NO:1118) | [[], ['GGG'], ['UUAA']] | 0.451612903 | 0.903225806 | 2 | 81 |
| 'GCAGAGUGGGAGAGGUAAGGCCUCACUAAAC' (SEQ ID NO:1119) | [[], ['GGG'], ['UAAA']] | 0.548387097 | 0.870967742 | 2 | 92 |

| SEQUENCE | BS | GCNESS | 3LN | NBP | P |
|---|---|---|---|---|---|
| 'CAGAGUGGGAGAGGUAAGGCCUCACUAAACC' (SEQ ID NO:1120) | [[], ['GGG'], ['UAAA']] | 0.548387097 | 0.870967742 | 2 | 93 |
| 'GAGUGGGAGAGGUAAGGCCUCACUAAACCAC' (SEQ ID NO:1121) | [[], ['GGG'], ['UAAA']] | 0.548387097 | 0.870967742 | 2 | 95 |
| 'GGCUUGGGAUCUUUUGCGAUCUGCUCGAGCA' (SEQ ID NO:1122) | [[], ['GGG'], ['UUUU']] | 0.548387097 | 0.870967742 | 2 | 238 |
| 'GCUUGGGAUCUUUUGCGAUCUGCUCGAGCAG' (SEQ ID NO:1123) | [[], ['GGG'], ['UUUU']] | 0.548387097 | 0.870967742 | 2 | 239 |
| 'AGAGUGGGAGAGGUAAGGCCUCACUAAACCA' (SEQ ID NO:1124) | [[], ['GGG'], ['UAAA']] | 0.516129032 | 0.870967742 | 2 | 94 |
| 'CUUUUGCGAUCUGCUCGAGCAGAUUUGGCUG' (SEQ ID NO:1125) | [[], [], ['UUUU', 'AUUU']] | 0.516129032 | 0.870967742 | 2 | 248 |
| 'GGGGUGAGGAUCUACCUUAAUAUGCAGAGUG' (SEQ ID NO:1126) | [[], ['GGG'], ['UUAA']] | 0.483870968 | 0.870967742 | 2 | 69 |
| 'GGGUGAGGAUCUACCUUAAUAUGCAGAGUGG' (SEQ ID NO:1127) | [[], ['GGG'], ['UUAA']] | 0.483870968 | 0.870967742 | 2 | 70 |

FIG. 44 (Cont'd)

| SEQUENCE | BS | GCNESS | 3LN | NBP | P |
|---|---|---|---|---|---|
| 'GGUGAGGAUCUACCUUAAUAUGCAGAGUGGG' (SEQ ID NO:1128) | [[], ['GGG'], ['UUAA']] | 0.483870968 | 0.870967742 | 2 | 71 |
| 'GGAUCUACCUUAAUAUGCAGAGUGGGAGAGG' (SEQ ID NO:1129) | [[], ['GGG'], ['UUAA']] | 0.483870968 | 0.870967742 | 2 | 76 |
| 'ACCUUAAUAUGCAGAGUGGGAGAGGUAAGGC' (SEQ ID NO:1130) | [[], ['GGG'], ['UUAA']] | 0.483870968 | 0.870967742 | 2 | 82 |
| 'CUUAAUAUGCAGAGUGGGAGAGGUAAGGCCU' (SEQ ID NO:1131) | [[], ['GGG'], ['UUAA']] | 0.483870968 | 0.870967742 | 2 | 84 |
| 'UUAAUAUGCAGAGUGGGAGAGGUAAGGCCUC' (SEQ ID NO:1132) | [[], ['GGG'], ['UUAA']] | 0.483870968 | 0.870967742 | 2 | 85 |
| 'UAAUAUGCAGAGUGGGAGAGGUAAGGCCUCA' (SEQ ID NO:1133) | [[], ['GGG'], ['UAAU']] | 0.483870968 | 0.870967742 | 2 | 86 |
| 'UCUUUUGCGAUCUGCUCGAGCAGAUUUGGCU' (SEQ ID NO:1134) | [[], [], ['UUUU', 'AUUU']] | 0.483870968 | 0.870967742 | 2 | 247 |

| SEQUENCE | BS | GCNESS | 3LN | NBP | P |
| --- | --- | --- | --- | --- | --- |
| 'CUGUCCGUGGUGCUGAAGUUUAUUCGGAUUU' (SEQ ID NO:1135) | [[], [], ['UUUA', 'AUUU']] | 0.451612903 | 0.870967742 | 2 | 13 |
| 'GAAAGGGGUGAGGAUCUACCUUAAUAUGCAG' (SEQ ID NO:1136) | [[], ['GGG'], ['UUAA']] | 0.451612903 | 0.870967742 | 2 | 65 |
| 'AAGGGGUGAGGAUCUACCUUAAUAUGCAGAG' (SEQ ID NO:1137) | [[], ['GGG'], ['UUAA']] | 0.451612903 | 0.870967742 | 2 | 67 |
| 'AGGGGUGAGGAUCUACCUUAAUAUGCAGAGU' (SEQ ID NO:1138) | [[], ['GGG'], ['UUAA']] | 0.451612903 | 0.870967742 | 2 | 68 |
| 'GUGAGGAUCUACCUUAAUAUGCAGAGUGGGA' (SEQ ID NO:1139) | [[], ['GGG'], ['UUAA']] | 0.451612903 | 0.870967742 | 2 | 72 |
| 'UGAGGAUCUACCUUAAUAUGCAGAGUGGGAG' (SEQ ID NO:1140) | [[], ['GGG'], ['UUAA']] | 0.451612903 | 0.870967742 | 2 | 73 |
| 'GAGGAUCUACCUUAAUAUGCAGAGUGGGAGA' (SEQ ID NO:1141) | [[], ['GGG'], ['UUAA']] | 0.451612903 | 0.870967742 | 2 | 74 |

FIG. 44 (Cont'd)

| SEQUENCE | BS | GCNESS | 3LN | NBP | P |
|---|---|---|---|---|---|
| 'AGGAUCUACCUUAAUAUGCAGAGUGGGAGAG' (SEQ ID NO:1142) | [[], ['GGG'], ['UUAA']] | 0.451612903 | 0.870967742 | 2 | 75 |
| 'GAUCUACCUUAAUAUGCAGAGUGGGAGAGGU' (SEQ ID NO:1143) | [[], ['GGG'], ['UUAA']] | 0.451612903 | 0.870967742 | 2 | 77 |
| 'CUACCUUAAUAUGCAGAGUGGGAGAGGUAAG' (SEQ ID NO:1144) | [[], ['GGG'], ['UUAA']] | 0.451612903 | 0.870967742 | 2 | 80 |
| 'UGUCCGUGGUGCUGAAGUUUAUUCGGAUUUA' (SEQ ID NO:1145) | [[], [], ['UUUA', 'AUUU']] | 0.419354839 | 0.870967742 | 2 | 14 |
| 'GUCCGUGGUGCUGAAGUUUAUUCGGAUUUAU' (SEQ ID NO:1146) | [[], [], ['UUUA', 'AUUU']] | 0.419354839 | 0.870967742 | 2 | 15 |
| 'UCUGAAGGGGUGAGGAUCUACCUUAAUAUG' (SEQ ID NO:1147) | [[], ['GGG'], ['UUAA']] | 0.419354839 | 0.870967742 | 2 | 62 |
| 'UGAAGGGGUGAGGAUCUACCUUAAUAUGCA' (SEQ ID NO:1148) | [[], ['GGG'], ['UUAA']] | 0.419354839 | 0.870967742 | 2 | 64 |

FIG. 44 (Cont'd)

| SEQUENCE | BS | GCNESS | 3LN | NBP | P |
| --- | --- | --- | --- | --- | --- |
| 'AAAGGGGUGAGGAUCUACCUUAAUAUGCAGA' (SEQ ID NO:1149) | [[], ['GGG'], ['UUAA']] | 0.419354839 | 0.870967742 | 2 | 66 |
| 'AUCUACCUUAAUAUGCAGAGUGGGAGAGGUA' (SEQ ID NO:1150) | [[], ['GGG'], ['UUAA']] | 0.419354839 | 0.870967742 | 2 | 78 |
| 'UCUACCUUAAUAUGCAGAGUGGGAGAGGUAA' (SEQ ID NO:1151) | [[], ['GGG'], ['UUAA']] | 0.419354839 | 0.870967742 | 2 | 79 |
| 'UCCGUGGUGCUGAAGUUUAUUCGGAUUUAUU' (SEQ ID NO:1152) | [[], [], ['UUUA', 'AUUU']] | 0.387096774 | 0.870967742 | 2 | 16 |
| 'UUUCUGAAAGGGGUGAGGAUCUACCUUAAUA' (SEQ ID NO:1153) | [[], ['GGG'], ['UUAA']] | 0.387096774 | 0.870967742 | 2 | 60 |
| 'UUCUGAAAGGGGUGAGGAUCUACCUUAAUAU' (SEQ ID NO:1154) | [[], ['GGG'], ['UUAA']] | 0.387096774 | 0.870967742 | 2 | 61 |
| 'CAAGCUGUGUGACACACCGCAAGGGCUUGGG' (SEQ ID NO:1155) | [[], ['GGG', 'GGG'], []] | 0.612903226 | 0.838709677 | 2 | 215 |

FIG. 44 (Cont'd)

| SEQUENCE | BS | GCNESS | 3LN | NBP | P |
|---|---|---|---|---|---|
| 'GACAGGAAGCUGCAGCUCCAGGAGGGUAUUC' (SEQ ID NO:1156) | [[], ['GGG'], ['UAUU']] | 0.580645161 | 0.838709677 | 2 | 160 |
| 'CAGGAAGCUGCAGCUCCAGGAGGGUAUUCAC' (SEQ ID NO:1157) | [[], ['GGG'], ['UAUU']] | 0.580645161 | 0.838709677 | 2 | 162 |
| 'AGGAAGCUGCAGCUCCAGGAGGGUAUUCACC' (SEQ ID NO:1158) | [[], ['GGG'], ['UAUU']] | 0.580645161 | 0.838709677 | 2 | 163 |
| 'GGAAGCUGCAGCUCCAGGAGGGUAUUCACCA' (SEQ ID NO:1159) | [[], ['GGG'], ['UAUU']] | 0.580645161 | 0.838709677 | 2 | 164 |
| 'GAAGCUGCAGCUCCAGGAGGGUAUUCACCAC' (SEQ ID NO:1160) | [[], ['GGG'], ['UAUU']] | 0.580645161 | 0.838709677 | 2 | 165 |
| 'AAGCUGCAGCUCCAGGAGGGUAUUCACCACC' (SEQ ID NO:1161) | [[], ['GGG'], ['UAUU']] | 0.580645161 | 0.838709677 | 2 | 166 |

| SEQUENCE | BS | GCNESS | 3LN | NBP | P |
|---|---|---|---|---|---|
| 'AAGCUGUGUGACACACCGCAAGGGCUUGGGA' (SEQ ID NO:1162) | [[], ['GGG', 'GGG'], []] | 0.580645161 | 0.838709677 | 2 | 216 |
| 'GUGGGAGAGGUAAGGCCUCACUAAACCACUC' (SEQ ID NO:1163) | [[], ['GGG'], ['UAAA']] | 0.548387097 | 0.838709677 | 2 | 97 |
| 'AGACAGGAAGCUGCAGCUCCAGGAGGGUAUU' (SEQ ID NO:1164) | [[], ['GGG'], ['UAUU']] | 0.548387097 | 0.838709677 | 2 | 159 |
| 'ACAGGAAGCUGCAGCUCCAGGAGGGUAUUCA' (SEQ ID NO:1165) | [[], ['GGG'], ['UAUU']] | 0.548387097 | 0.838709677 | 2 | 161 |
| 'CCUUAAUAUGCAGAGUGGGAGAGGUAAGGCC' (SEQ ID NO:1166) | [[], ['GGG'], ['UUAA']] | 0.516129032 | 0.838709677 | 2 | 83 |
| 'AAUAUGCAGAGUGGGAGAGGUAAGGCCUCAC' (SEQ ID NO:1167) | [[], ['GGG'], ['AAUA']] | 0.516129032 | 0.838709677 | 2 | 87 |
| 'AUAUGCAGAGUGGGAGAGGUAAGGCCUCACU' (SEQ ID NO:1168) | [[], ['GGG'], ['AUAU']] | 0.516129032 | 0.838709677 | 2 | 88 |

| SEQUENCE | BS | GCNESS | 3LN | NBP | P |
|---|---|---|---|---|---|
| 'UGCAGAGUGGGAGAGGUAAGGCCUCACUAAA' (SEQ ID NO:1169) | [[], ['GGG'], ['UAAA']] | 0.516129032 | 0.838709677 | 2 | 91 |
| 'AGUGGGAGAGGUAAGGCCUCACUAAACCACU' (SEQ ID NO:1170) | [[], ['GGG'], ['UAAA']] | 0.516129032 | 0.838709677 | 2 | 96 |
| 'UGGGAGAGGUAAGGCCUCACUAAACCACUCA' (SEQ ID NO:1171) | [[], ['GGG'], ['UAAA']] | 0.516129032 | 0.838709677 | 2 | 98 |
| 'GGGAGAGGUAAGGCCUCACUAAACCACUCAU' (SEQ ID NO:1172) | [[], ['GGG'], ['UAAA']] | 0.516129032 | 0.838709677 | 2 | 99 |
| 'CUUGGGAUCUUUUGCGAUCUGCUCGAGCAGA' (SEQ ID NO:1173) | [[], ['GGG'], ['UUUU']] | 0.516129032 | 0.838709677 | 2 | 240 |
| 'UUGGGAUCUUUUGCGAUCUGCUCGAGCAGAU' (SEQ ID NO:1174) | [[], ['GGG'], ['UUUU']] | 0.483870968 | 0.838709677 | 2 | 241 |
| 'UGGGAUCUUUUGCGAUCUGCUCGAGCAGAAUU' (SEQ ID NO:1175) | [[], ['GGG'], ['UUUU']] | 0.483870968 | 0.838709677 | 2 | 242 |

| SEQUENCE | BS | GCNESS | 3LN | NBP | P |
|---|---|---|---|---|---|
| 'GGAUCUUUUGCGAUCUGCUCGAGCAGAUUUG' (SEQ ID NO:1176) | [[], [], ['UUUU', 'AUUU']] | 0.483870968 | 0.838709677 | 2 | 244 |
| 'GAUCUUUUGCGAUCUGCUCGAGCAGAUUUGG' (SEQ ID NO:1177) | [[], [], ['UUUU', 'AUUU']] | 0.483870968 | 0.838709677 | 2 | 245 |
| 'AUCUUUUGCGAUCUGCUCGAGCAGAUUUGGC' (SEQ ID NO:1178) | [[], [], ['UUUU', 'AUUU']] | 0.483870968 | 0.838709677 | 2 | 246 |
| 'UUUUUCCAACUGCUUUCUGAAAGGGGUGAGG' (SEQ ID NO:1179) | [[], ['GGG'], ['UUUU']] | 0.451612903 | 0.838709677 | 2 | 47 |
| 'UUUUCCAACUGCUUUCUGAAAGGGGUGAGGA' (SEQ ID NO:1180) | [[], ['GGG'], ['UUUU']] | 0.451612903 | 0.838709677 | 2 | 48 |
| 'GCUUUCUGAAAGGGGUGAGGAUCUACCUUAA' (SEQ ID NO:1181) | [[], ['GGG'], ['UUAA']] | 0.451612903 | 0.838709677 | 2 | 58 |
| 'CUGAAAGGGGUGAGGAUCUACCUUAAUAUGC' (SEQ ID NO:1182) | [[], ['GGG'], ['UUAA']] | 0.451612903 | 0.838709677 | 2 | 63 |

| SEQUENCE | BS | GCNESS | 3LN | NBP | P |
| --- | --- | --- | --- | --- | --- |
| 'UUUUUUCCAACUGCUUUCUGAAAGGGGUGAG' (SEQ ID NO:1183) | [[], ['GGG'], ['UUUU']] | 0.419354839 | 0.838709677 | 2 | 46 |
| 'CUUUCUGAAAGGGGUGAGGAUCUACCUUAAU' (SEQ ID NO:1184) | [[], ['GGG'], ['UUAA']] | 0.419354839 | 0.838709677 | 2 | 59 |
| 'UUUUUUCCAACUGCUUUCUGAAAGGGUGA' (SEQ ID NO:1185) | [[], ['GGG'], ['UUUU']] | 0.387096774 | 0.838709677 | 2 | 45 |
| 'GCUGCAGCUCCAGGAGGGUAUUCACCACCUC' (SEQ ID NO:1186) | [[], ['GGG'], ['UAUU']] | 0.612903226 | 0.806451613 | 2 | 168 |
| 'GCUGUGUGACACACCGCAAGGGCUUGGGAUC' (SEQ ID NO:1187) | [[], ['GGG', 'GGG'], []] | 0.612903226 | 0.806451613 | 2 | 218 |
| 'AGCUGCAGCUCCAGGAGGGUAUUCACCACCU' (SEQ ID NO:1188) | [[], ['GGG'], ['UAUU']] | 0.580645161 | 0.806451613 | 2 | 167 |
| 'CUGCAGCUCCAGGAGGGUAUUCACCACCUCU' (SEQ ID NO:1189) | [[], ['GGG'], ['UAUU']] | 0.580645161 | 0.806451613 | 2 | 169 |

| SEQUENCE | BS | GCNESS | 3LN | NBP | P |
|---|---|---|---|---|---|
| 'UGCAGCUCCAGGAGGGUAUUCACCACCUCUC' (SEQ ID NO:1190) | [[], ['GGG'], ['UAUU']] | 0.580645161 | 0.806451613 | 2 | 170 |
| 'GCAGCUCCAGGAGGGUAUUCACCACCUCUCA' (SEQ ID NO:1191) | [[], ['GGG'], ['UAUU']] | 0.580645161 | 0.806451613 | 2 | 171 |
| 'CAGCUCCAGGAGGGUAUUCACCACCUCUCAG' (SEQ ID NO:1192) | [[], ['GGG'], ['UAUU']] | 0.580645161 | 0.806451613 | 2 | 172 |
| 'GCUCCAGGAGGGUAUUCACCACCUCUCAGUG' (SEQ ID NO:1193) | [[], ['GGG'], ['UAUU']] | 0.580645161 | 0.806451613 | 2 | 174 |
| 'CUCCAGGAGGGUAUUCACCACCUCUCAGUGG' (SEQ ID NO:1194) | [[], ['GGG'], ['UAUU']] | 0.580645161 | 0.806451613 | 2 | 175 |
| 'UCCAGGAGGGUAUUCACCACCUCUCAGUGGC' (SEQ ID NO:1195) | [[], ['GGG'], ['UAUU']] | 0.580645161 | 0.806451613 | 2 | 176 |
| 'CCAGGAGGGUAUUCACCACCUCUCAGUGGCA' (SEQ ID NO:1196) | [[], ['GGG'], ['UAUU']] | 0.580645161 | 0.806451613 | 2 | 177 |
| 'AGCUGUGUGACACACCGCAAGGGCUUGGGAU' (SEQ ID NO:1197) | [[], ['GGG', 'GGG'], []] | 0.580645161 | 0.806451613 | 2 | 217 |

| SEQUENCE | BS | GCNESS | 3LN | NBP | P |
|---|---|---|---|---|---|
| 'CUGUGUGACACACCGCAAGGGCUUGGGAUCU' (SEQ ID NO:1198) | [[], ['GGG', 'GGG'], []] | 0.580645161 | 0.806451613 | 2 | 219 |
| 'CAGGAGGGUAUUCACCACCUCUCAGUGGCAA' (SEQ ID NO:1199) | [[], ['GGG'], ['UAUU']] | 0.548387097 | 0.806451613 | 2 | 178 |
| 'UGUGUGACACACCGCAAGGGCUUGGGAUCUU' (SEQ ID NO:1200) | [[], ['GGG', 'GGG'], []] | 0.548387097 | 0.806451613 | 2 | 220 |
| 'GUGUGACACACCGCAAGGGCUUGGGAUCUUU' (SEQ ID NO:1201) | [[], ['GGG', 'GGG'], []] | 0.548387097 | 0.806451613 | 2 | 221 |
| 'AGCUCCAGGAGGGUAUUCACCACCUCUCAGU' (SEQ ID NO:1202) | [[], ['GGG'], ['UAUU']] | 0.548387097 | 0.774193548 | 2 | 173 |
| 'GGAGGGUAUUCACCACCUCUCAGUGGCAAUG' (SEQ ID NO:1203) | [[], ['GGG'], ['UAUU']] | 0.548387097 | 0.774193548 | 2 | 180 |
| 'GAGGGUAUUCACCACCUCUCAGUGGCAAUGC' (SEQ ID NO:1204) | [[], ['GGG'], ['UAUU']] | 0.548387097 | 0.774193548 | 2 | 181 |

FIG. 44 (Cont'd)

| SEQUENCE | BS | GCNESS | 3LN | NBP | P |
|---|---|---|---|---|---|
| 'AGGGUAUUCACCAC CUCUCAGUGGCAAU GCG' (SEQ ID NO:1205) | [[], ['GGG'], ['UAUU']] | 0.548387097 | 0.774193548 | 2 | 182 |
| 'GGGUAUUCACCACC UCUCAGUGGCAAUG CGA' (SEQ ID NO:1206) | [[], ['GGG'], ['UAUU']] | 0.548387097 | 0.774193548 | 2 | 183 |
| 'AGGAGGGUAUUCAC CACCUCUCAGUGGC AAU' (SEQ ID NO:1207) | [[], ['GGG'], ['UAUU']] | 0.516129032 | 0.774193548 | 2 | 179 |
| 'GUGGUGCUGAAGUU UAUUCGGAUUUAUUU UU' (SEQ ID NO:1208) | [[], [], ['UUUA', 'AUUU', 'AUUU']] | 0.322580645 | 0.935483871 | 3 | 19 |
| 'UGGUGCUGAAGUUU AUUCGGAUUUAUUUU UU' (SEQ ID NO:1209) | [[], [], ['UUUA', 'AUUU', 'AUUU']] | 0.290322581 | 0.935483871 | 3 | 20 |
| 'GGGCUUGGGAUCUU UUGCGAUCUGCUCG AGC' (SEQ ID NO:1210) | [[], ['GGG', 'GGG'], ['UUUU']] | 0.580645161 | 0.903225806 | 3 | 237 |

FIG. 44 (Cont'd)

| SEQUENCE | BS | GCNESS | 3LN | NBP | P |
|---|---|---|---|---|---|
| 'CGUGGUGCUGAAGU UUAUUCGGAUUUAUU UU' (SEQ ID NO:1211) | [[], [], ['UUUA', 'AUUU', 'AUUU']] | 0.35483871 | 0.903225806 | 3 | 18 |
| 'AUUCGGAUUUAUUU UUUUCCAACUGCUUU CU' (SEQ ID NO:1212) | [[], [], ['AUUU', 'AUUU', 'UUUU']] | 0.290322581 | 0.903225806 | 3 | 34 |
| 'CCGCAAGGGCUUGG GAUCUUUUGCGAUC UGC' (SEQ ID NO:1213) | [[], ['GGG', 'GGG'], ['UUUU']] | 0.580645161 | 0.870967742 | 3 | 231 |
| 'CGCAAGGGCUUGGG AUCUUUUGCGAUCU GCU' (SEQ ID NO:1214) | [[], ['GGG', 'GGG'], ['UUUU']] | 0.548387097 | 0.870967742 | 3 | 232 |
| 'GCAAGGGCUUGGGA UCUUUUGCGAUCUG CUC' (SEQ ID NO:1215) | [[], ['GGG', 'GGG'], ['UUUU']] | 0.548387097 | 0.870967742 | 3 | 233 |
| 'CAAGGGCUUGGGAU CUUUUGCGAUCUGC UCG' (SEQ ID NO:1216) | [[], ['GGG', 'GGG'], ['UUUU']] | 0.548387097 | 0.870967742 | 3 | 234 |

FIG. 44 (Cont'd)

| SEQUENCE | BS | GCNESS | 3LN | NBP | P |
|---|---|---|---|---|---|
| 'AGGGCUUGGGAUCUUUUGCGAUCUGCUCGAG' (SEQ ID NO:1217) | [[], ['GGG', 'GGG'], ['UUUU']] | 0.548387097 | 0.870967742 | 3 | 236 |
| 'CCGUGGUGCUGAAGUUUAUUCGGAUUUAUUU' (SEQ ID NO:1218) | [[], [], ['UUUA', 'AUUU', 'AUUU']] | 0.387096774 | 0.870967742 | 3 | 17 |
| 'UUCGGAUUUAUUUUUUUCCAACUGCUUUCUG' (SEQ ID NO:1219) | [[], [], ['AUUU', 'AUUU', 'UUUU']] | 0.322580645 | 0.870967742 | 3 | 35 |
| 'UCGGAUUUAUUUUUUUCCAACUGCUUUCUGA' (SEQ ID NO:1220) | [[], [], ['AUUU', 'AUUU', 'UUUU']] | 0.322580645 | 0.870967742 | 3 | 36 |
| 'CGGAUUUAUUUUUUUCCAACUGCUUUCUGAA' (SEQ ID NO:1221) | [[], [], ['AUUU', 'AUUU', 'UUUU']] | 0.322580645 | 0.870967742 | 3 | 37 |
| 'GGAUUUAUUUUUUUCCAACUGCUUUCUGAAA' (SEQ ID NO:1222) | [[], [], ['AUUU', 'AUUU', 'UUUU']] | 0.290322581 | 0.870967742 | 3 | 38 |

FIG. 44 (Cont'd)

| SEQUENCE | BS | GCNESS | 3LN | NBP | P |
|---|---|---|---|---|---|
| 'GAUUUAUUUUUUC CAACUGCUUUCUGAA AG' (SEQ ID NO:1223) | [[], [], ['AUUU', 'AUUU', 'UUUU']] | 0.290322581 | 0.870967742 | 3 | 39 |
| 'AUUUAUUUUUUUCC AACUGCUUUCUGAAA GG' (SEQ ID NO:1224) | [[], [], ['AUUU', 'AUUU', 'UUUU']] | 0.290322581 | 0.870967742 | 3 | 40 |
| 'CACCGCAAGGGCUU GGGAUCUUUUGCGA UCU' (SEQ ID NO:1225) | [[], ['GGG', 'GGG'], ['UUUU']] | 0.548387097 | 0.838709677 | 3 | 229 |
| 'ACCGCAAGGGCUUG GGAUCUUUUGCGAU CUG' (SEQ ID NO:1226) | [[], ['GGG', 'GGG'], ['UUUU']] | 0.548387097 | 0.838709677 | 3 | 230 |
| 'AAGGGCUUGGGAUC UUUUGCGAUCUGCU CGA' (SEQ ID NO:1227) | [[], ['GGG', 'GGG'], ['UUUU']] | 0.516129032 | 0.838709677 | 3 | 235 |
| 'GGGAUCUUUUGCGA UCUGCUCGAGCAGA UUU' (SEQ ID NO:1228) | [[], ['GGG'], ['UUUU', 'AUUU']] | 0.483870968 | 0.838709677 | 3 | 243 |

FIG. 44 (Cont'd)

| SEQUENCE | BS | GCNESS | 3LN | NBP | P |
|---|---|---|---|---|---|
| 'AUUUUUUCCAACU GCUUUCUGAAAGGG GUG' (SEQ ID NO:1229) | [[], ['GGG'], ['AUUU', 'UUUU']] | 0.387096774 | 0.838709677 | 3 | 44 |
| 'UUAUUUUUUCCAA CUGCUUUCUGAAAG GGG' (SEQ ID NO:1230) | [[], ['GGG'], ['UUAU', 'UUUU']] | 0.35483871 | 0.838709677 | 3 | 42 |
| 'UAUUUUUUCCAAC UGCUUUCUGAAAGG GGU' (SEQ ID NO:1231) | [[], ['GGG'], ['UAUU', 'UUUU']] | 0.35483871 | 0.838709677 | 3 | 43 |
| 'UUUAUUUUUUUCCA ACUGCUUUCUGAAAG GG' (SEQ ID NO:1232) | [[], ['GGG'], ['UUUA', 'UUUU']] | 0.322580645 | 0.838709677 | 3 | 41 |
| 'GACACACCGCAAGG GCUUGGGAUCUUUU GCG' (SEQ ID NO:1233) | [[], ['GGG', 'GGG'], ['UUUU']] | 0.580645161 | 0.806451613 | 3 | 225 |
| 'GUGACACACCGCAA GGGCUUGGGAUCUU UUG' (SEQ ID NO:1234) | [[], ['GGG', 'GGG'], ['UUUU']] | 0.548387097 | 0.806451613 | 3 | 223 |

FIG. 44 (Cont'd)

| SEQUENCE | BS | GCNESS | 3LN | NBP | P |
|---|---|---|---|---|---|
| 'UGACACACCGCAAGGGCUUGGGAUCUUUUGC' (SEQ ID NO:1235) | [[], ['GGG', 'GGG'], ['UUUU']] | 0.548387097 | 0.806451613 | 3 | 224 |
| 'CACACCGCAAGGGCUUGGGAUCUUUUGCGAU' (SEQ ID NO:1236) | [[], ['GGG', 'GGG'], ['UUUU']] | 0.548387097 | 0.806451613 | 3 | 227 |
| 'ACACCGCAAGGGCUUGGGAUCUUUUGCGAUC' (SEQ ID NO:1237) | [[], ['GGG', 'GGG'], ['UUUU']] | 0.548387097 | 0.806451613 | 3 | 228 |
| 'UGUGACACACCGCAAGGGCUUGGGAUCUUU' (SEQ ID NO:1238) | [[], ['GGG', 'GGG'], ['UUUU']] | 0.516129032 | 0.806451613 | 3 | 222 |
| 'ACACACCGCAAGGGCUUGGGAUCUUUUGCGA' (SEQ ID NO:1239) | [[], ['GGG', 'GGG'], ['UUUU']] | 0.548387097 | 0.774193548 | 3 | 226 |
| 'GGUGCUGAAGUUUAUUCGGAUUUAUUUUUUU' (SEQ ID NO:1240) | [[], [], ['UUUA', 'AUUU', 'AUUU', 'UUUU']] | 0.290322581 | 0.935483871 | 4 | 21 |

FIG. 44 (Cont'd)

| SEQUENCE | BS | GCNESS | 3LN | NBP | P |
|---|---|---|---|---|---|
| 'GUGCUGAAGUUUAUUCGGAUUUAUUUUUUUC' (SEQ ID NO:1241) | [[], [], ['UUUA', 'AUUU', 'AUUU', 'UUUU']] | 0.290322581 | 0.903225806 | 4 | 22 |
| 'UAUUCGGAUUUAUUUUUUCCAACUGCUUUC' (SEQ ID NO:1242) | [[], [], ['UAUU', 'AUUU', 'AUUU', 'UUUU']] | 0.290322581 | 0.903225806 | 4 | 33 |
| 'UUUAUUCGGAUUUAUUUUUUUCCAACUGCUU' (SEQ ID NO:1243) | [[], [], ['UUUA', 'AUUU', 'AUUU', 'UUUU']] | 0.258064516 | 0.903225806 | 4 | 31 |
| 'UUAUUCGGAUUUAUUUUUUCCAACUGCUU' (SEQ ID NO:1244) | [[], [], ['UUAU', 'AUUU', 'AUUU', 'UUUU']] | 0.258064516 | 0.903225806 | 4 | 32 |
| 'UGCUGAAGUUUAUUCGGAUUUAUUUUUUUCC' (SEQ ID NO:1245) | [[], [], ['UUUA', 'AUUU', 'AUUU', 'UUUU']] | 0.290322581 | 0.870967742 | 4 | 23 |

FIG. 44 (Cont'd)

| SEQUENCE | BS | GCNESS | 3LN | NBP | P |
| --- | --- | --- | --- | --- | --- |
| 'GCUGAAGUUUAUUCGGAUUUAUUUUUUCCA' (SEQ ID NO:1246) | [[], [], ['UUUA', 'AUUU', 'AUUU', 'UUUU']] | 0.290322581 | 0.870967742 | 4 | 24 |
| 'AGUUUAUUCGGAUUUAUUUUUUCCAACUGC' (SEQ ID NO:1247) | [[], [], ['UUUA', 'AUUU', 'AUUU', 'UUUU']] | 0.290322581 | 0.870967742 | 4 | 29 |
| 'GUUUAUUCGGAUUUAUUUUUUCCAACUGCU' (SEQ ID NO:1248) | [[], [], ['UUUA', 'AUUU', 'AUUU', 'UUUU']] | 0.290322581 | 0.870967742 | 4 | 30 |
| 'CUGAAGUUUAUUCGGAUUUAUUUUUUCCAA' (SEQ ID NO:1249) | [[], [], ['UUUA', 'AUUU', 'AUUU', 'UUUU']] | 0.258064516 | 0.870967742 | 4 | 25 |
| 'UGAAGUUUAUUCGGAUUUAUUUUUUCCAAC' (SEQ ID NO:1250) | [[], [], ['UUUA', 'AUUU', 'AUUU', 'UUUU']] | 0.258064516 | 0.870967742 | 4 | 26 |

FIG. 44 (Cont'd)

| SEQUENCE | BS | GCNESS | 3LN | NBP | P |
|---|---|---|---|---|---|
| 'GAAGUUUAUUCGGAUUUAUUUUUUCCAACU' (SEQ ID NO:1251) | [[], [], ['UUUA', 'AUUU', 'AUUU', 'UUUU']] | 0.258064516 | 0.870967742 | 4 | 27 |
| 'AAGUUUAUUCGGAUUUAUUUUUUCCAACUG' (SEQ ID NO:1252) | [[], [], ['UUUA', 'AUUU', 'AUUU', 'UUUU']] | 0.258064516 | 0.870967742 | 4 | 28 |

FIG. 44 (Cont'd)

■ Guide strand
■ Core strand
■ Sensor strand
■ Sensor toehold
■ Dicer cleavage site

FIG. 48

- Calcineurin (PPP3CA) guide check: 5' CGAG UGUUG UUUGG CUUUU CCUG UU 3' (SEQ ID NO:11)

https://blast.ncbi.nlm.nih.gov/Blast.cgi
  Homo sapiens protein phosphatase 3 catalytic subunit alpha (PPP3CA), transcript variant 3, mRNA
  Sequence ID: NM_001130692.1  Length: 4520  Number of Matches: 1

Range 1: 1547 to 1566  Graphics

| Score | Expect | Identities | Gaps | Strand |
  |---|---|---|---|---|
  | 40.1 bits(20) | 0.040 | 20/20(100%) | 0/20(0%) | Plus/Minus |

Query  5     TTTTGTTTTGCCTTTTCCTGT   24   (SEQ ID NO:107)
  Sbjct  1566  TGATGTTTTGCCTTTTCCTGT  1547

- HDAC2 check guide: 5' GC ACUUA GAUUG AAACA ACCCA GUU 3' (25 bp) (SEQ ID NO: 13)

https://blast.ncbi.nlm.nih.gov/Blast.cgi
  PREDICTED: Homo sapiens histone deacetylase 2 (HDAC2), transcript variant X2, mRNA
  Sequence ID: XM_017010785.1  Length: 2072  Number of Matches: 1

Range 1: 1074 to 1093  Graphics

| Score | Expect | Identities | Gaps | Strand |
  |---|---|---|---|---|
  | 40.1 bits(20) | 0.040 | 20/20(100%) | 0/20(0%) | Plus/Minus |

Query  5     TTAAATTGAACAACCAGT   24   (SEQ ID NO: 108)
  Sbjct  1093  TTACATTGAACAACCCAGT  1074

FIG. 50A
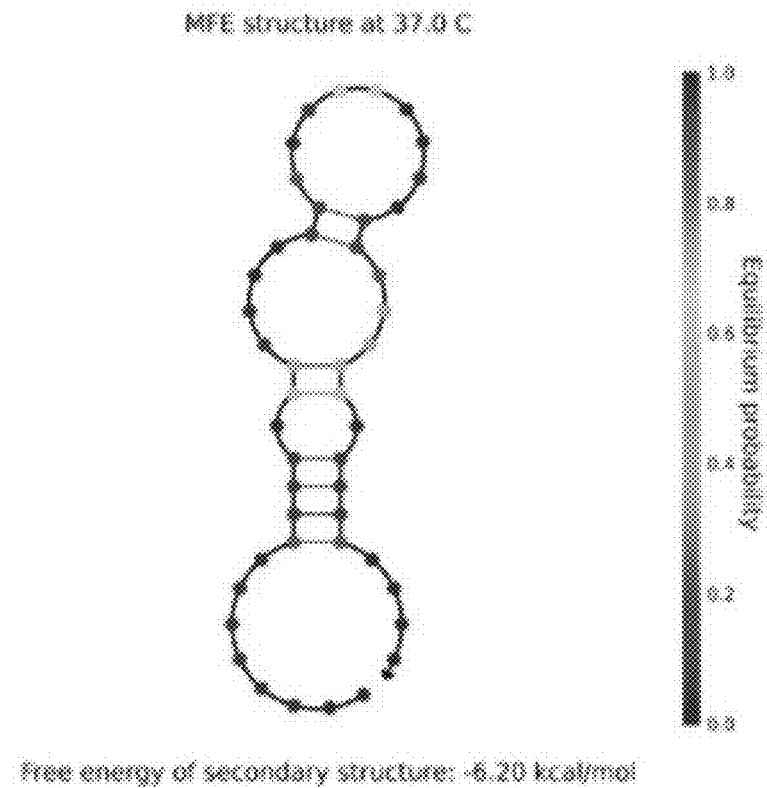
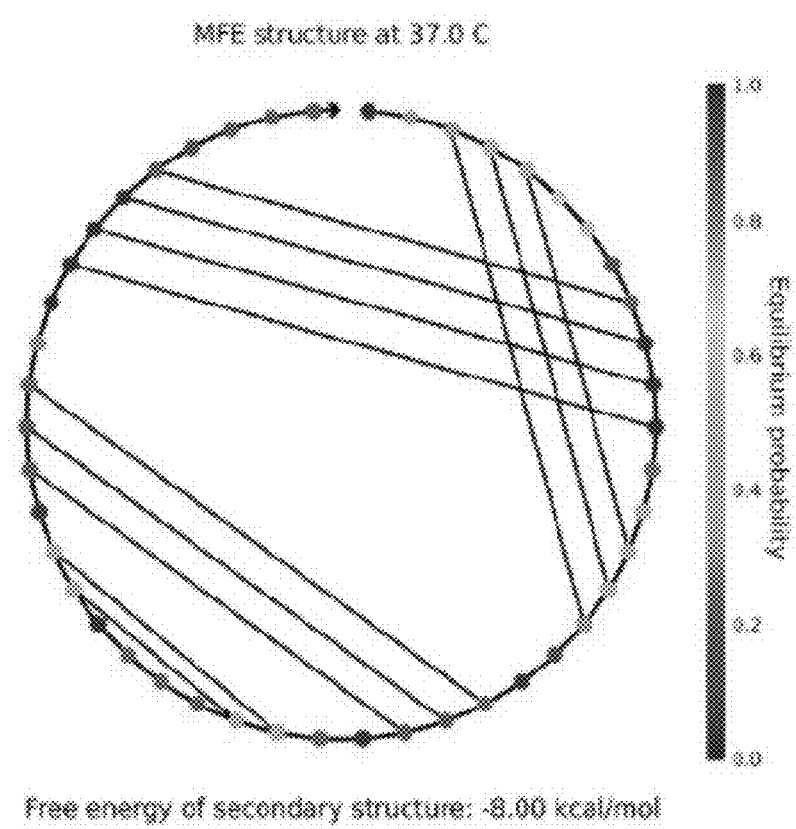

Free energy of secondary structure: -44.76 kcal/mol

```
5' AUCAGAAGCAGGUGUCUGCAGCCAGGACUUC 3'  (SENSOR) (SEQ ID NO: 4)
    UAGUCUUCGUCC 5')  (3' ACAGACGUCGG  (CORE NICK)

ACGGUCAAUAACACCAGAUCUCG          (CORE GUIDE) (SEQ ID NO: 122)
3'  UUUGCCAGUUAUUGUGGUCUAGAGC  5'    (GUIDE +2 U) (SEQ ID NO: 133)
```

FIG. 57A
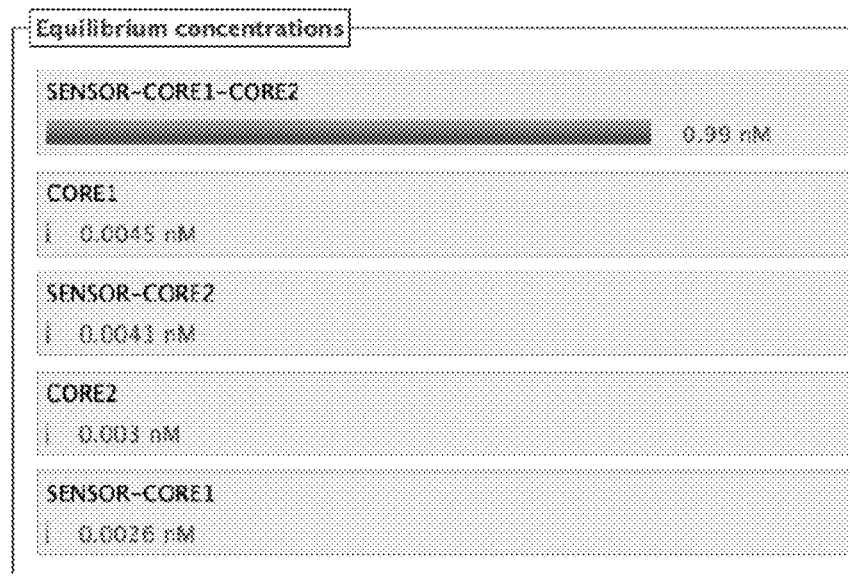
SENSOR WITH CORE OVERHANGS
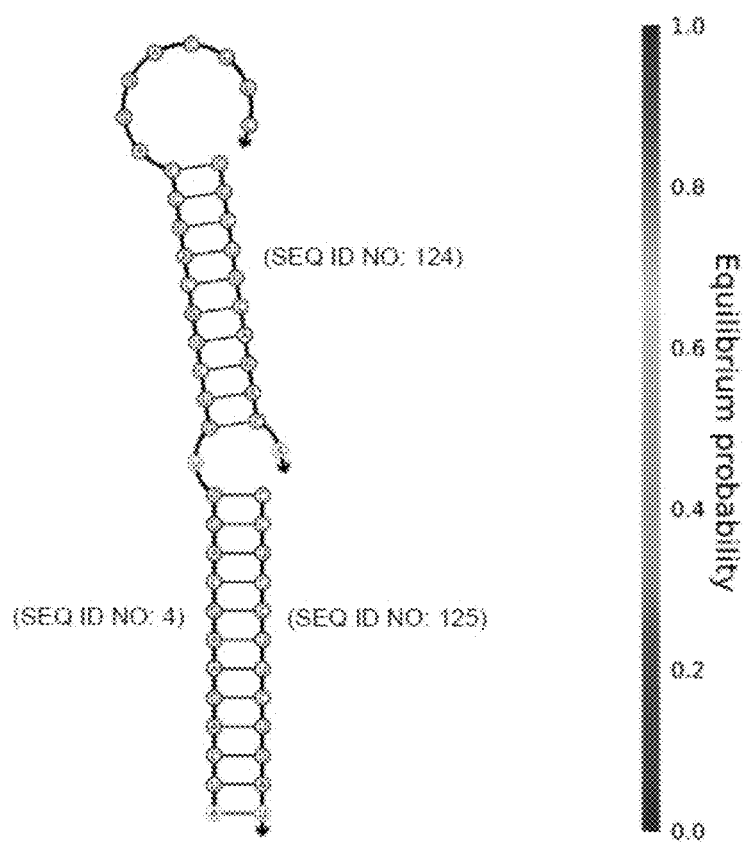
Free energy of secondary structure: -47.36 kcal/mol

FIG. 57B
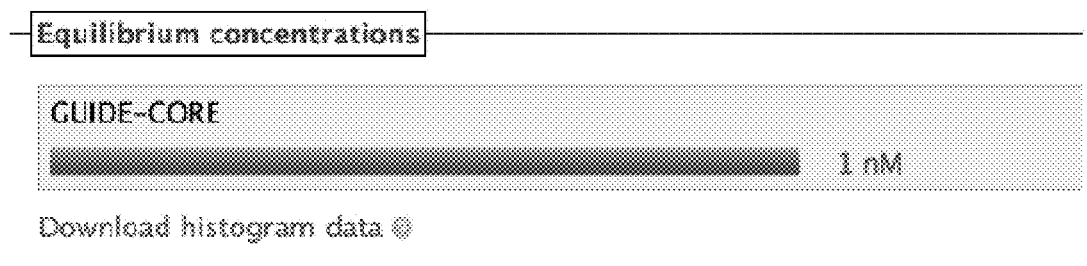
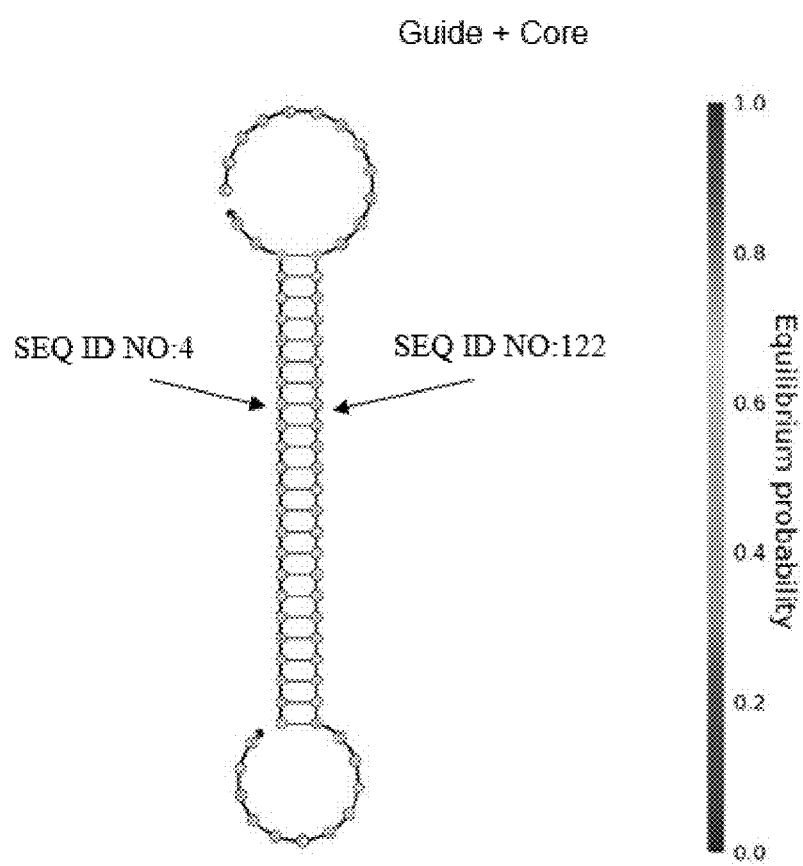
Free energy of secondary structure: -45.08 kcal/mol Free energy of secondary structure: -5.10 kcal/mol

FIG. 60

```
5'  CUUGUGGAAUCAGAAGCAGGUGUCUGCAGCC  3'   (SENSOR) (SEQ ID NO: 5)

GAACACCUUAG 5' )   ( 3' UCUUCGUCCACA    (CORE W/NICK 12 BP FROM
                                              TOP)

ACGGUCAAUAACACCAGAUCUCG           (CORE GUIDE) (SEQ ID NO: 22)
3'   UUUGCCAGUUAUUGUGGUCUAGAGC   5'  (GUIDE +2 U) (SEQ ID NO: 132)
```

FIG. 61A
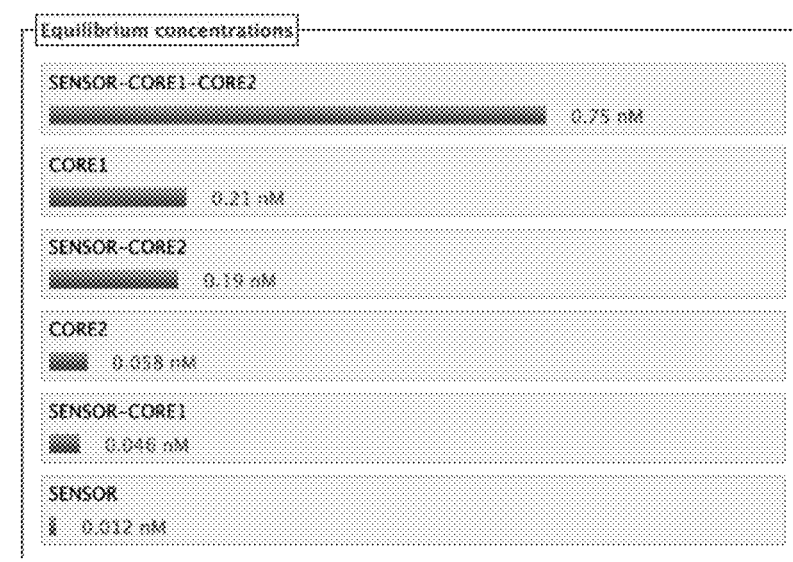
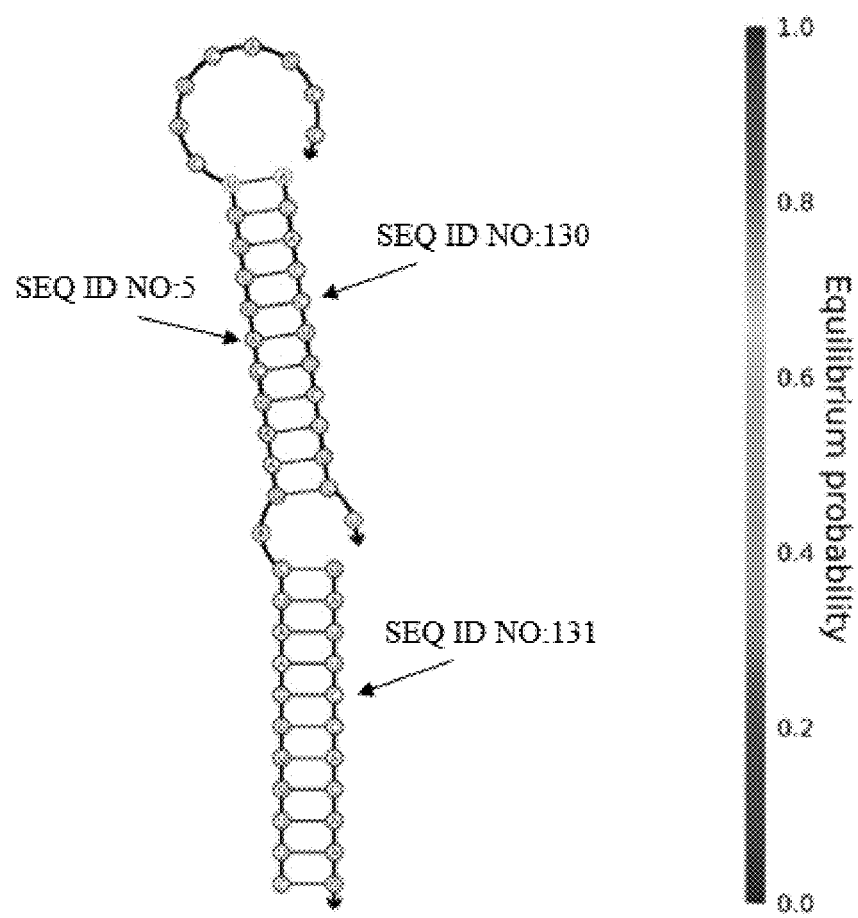
Free energy of secondary structure: -41.56 kcal/mol

FIG. 62 (Cont'd)

Sensor vs NCBI human transcripts

PREDICTED: Homo sapiens tissue factor pathway inhibitor (TFPI), transcript variant X1, mRNA
Sequence ID: XM_011510707.2 Length: 4075 Number of Matches: 1

Range 1: 18806 to 18820 GenBank Graphics

| Score | Expect | Identities | Gaps | Strand |
|---|---|---|---|---|
| 30.2 bits(15) | 71 | 15/15(100%) | 0/15(0%) | Plus/Minus |

Query  9   ATTAAAACCATTTTT   23      SEQ ID NO:137
Sbjct  1820 ATTAAAACCATTTTT  1806

PREDICTED: Homo sapiens zinc finger CCHC-type containing 2 (ZCCHC2), transcript variant X1, misc_RNA
Sequence ID: XR_001753205.1 Length: 4636 Number of Matches: 1

Range 1: 4310 to 4328 GenBank Graphics

| Score | Expect | Identities | Gaps | Strand |
|---|---|---|---|---|
| 30.2 bits(15) | 71 | 18/19(95%) | 0/19(0%) | Plus/Minus |

Query  13  GAACCAATTTTCAAATTTT  31    SEQ ID NO:138
Sbjct  4328 GAACCAAACCTTCAAATTTT  4310   SEQ ID NO:139

PREDICTED: Homo sapiens LLGL2, scribble cell polarity complex component (LLGL2), transcript variant X12, mRNA
Sequence ID: XM_017023832.1 Length: 2903 Number of Matches: 1

Range 1: 477 to 491 GenBank Graphics

| Score | Expect | Identities | Gaps | Strand |
|---|---|---|---|---|
| 30.2 bits(15) | 71 | 15/15(100%) | 0/15(0%) | Plus/Minus |

Query  3   TTTTTTTCCCTTTTT  17    SEQ ID NO:140
Sbjct  491 TTTTTTTCCCTTTTT  477

Free energy of secondary structure: -4.80 kcal/mol

FIG. 64

```
5'  CAAAGGCGGCCACAGGGUUGAGGAAAAAGCC  3'   (SENSOR) (SEQ ID NO: 6)
     GUUCCGCCGG 5')  (3' UGUCCCAACUCC   (CORE NICK)

ACGGUCAAUAACACCAGAUCUCG           (CORE GUIDE) (SEQ ID NO: 23)
3'  UUGCCAGUUAUUGUGGUCUAGAGC  5'  (GUIDE +2 U) (SEQ ID NO: 132)
```

FIG. 66 (Cont'd)

Sensor vs NCBI human transcripts

PREDICTED: Homo sapiens tissue factor pathway inhibitor (TFPI), transcript variant X1, mRNA Sequence ID: XM_011511707.2  Length: 4075  Number of Matches: 1

Range 1: 18898 to 18920

| Score | Expect | Identities | Gaps | Strand |
|---|---|---|---|---|
| 30.2 bits(15) | 71 | 15/15(100%) | 0/15(0%) | Plus/Minus |

Query  9   ATCACAAACAGTTT   23      SEQ ID NO:137
Sbjct  1820  ATCACAAACAGCHGT  1806

PREDICTED: Homo sapiens zinc finger CCHC-type containing 2 (ZCCHC2), transcript variant X1, misc_RNA Sequence ID: XR_001752205.1  Length: 4636  Number of Matches: 1

Range 1: 4310 to 4328

| Score | Expect | Identities | Gaps | Strand |
|---|---|---|---|---|
| 30.2 bits(15) | 71 | 18/19(95%) | 0/19(0%) | Plus/Minus |

Query  13   GAGCAGATCTTCCAGCC   31      SEQ ID NO:138
Sbjct  4328  GAGCCAGAATCCCAGACC  4310

PREDICTED: Homo sapiens LLGL2, scribble cell polarity complex component (LLGL2), transcript variant X12, mRNA Sequence ID: XM_017028832.1  Length: 2900  Number of Matches: 1

Range 1: 477 to 491

| Score | Expect | Identities | Gaps | Strand |
|---|---|---|---|---|
| 30.2 bits(15) | 71 | 15/15(100%) | 0/15(0%) | Plus/Minus |

Query  3    TGGAATATACAAC    17     SEQ ID NO:140
Sbjct  491                        477

Free energy of secondary structure: -3.50 kcal/mol

FIG. 68

```
5'  AUCUUGAUCUGCUCAGCCUGGAGGUGCCAG  3'   (SENSOR) (SEQ ID NO: 7)
      UAGAACUAGACG 5' ) (3' AGUCGGGACCU    (CORE NICK)

ACGGUCAAUAACACCAGAUCUCG              (CORE GUIDE) (SEQ ID NO: 24)
3'  UUUGCCAGUUAUUGUGGUCUAGAGC  5' (GUIDE +2 U) (SEQ ID NO: 132)
```

FIG. 69B
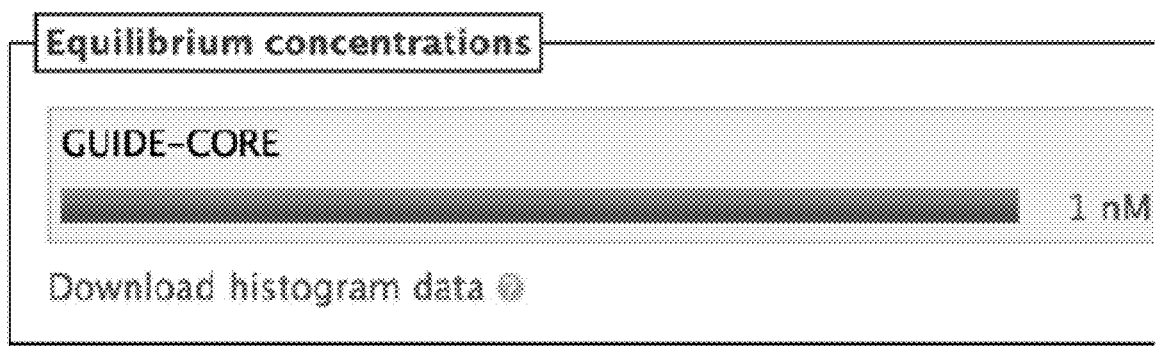
MFE structure
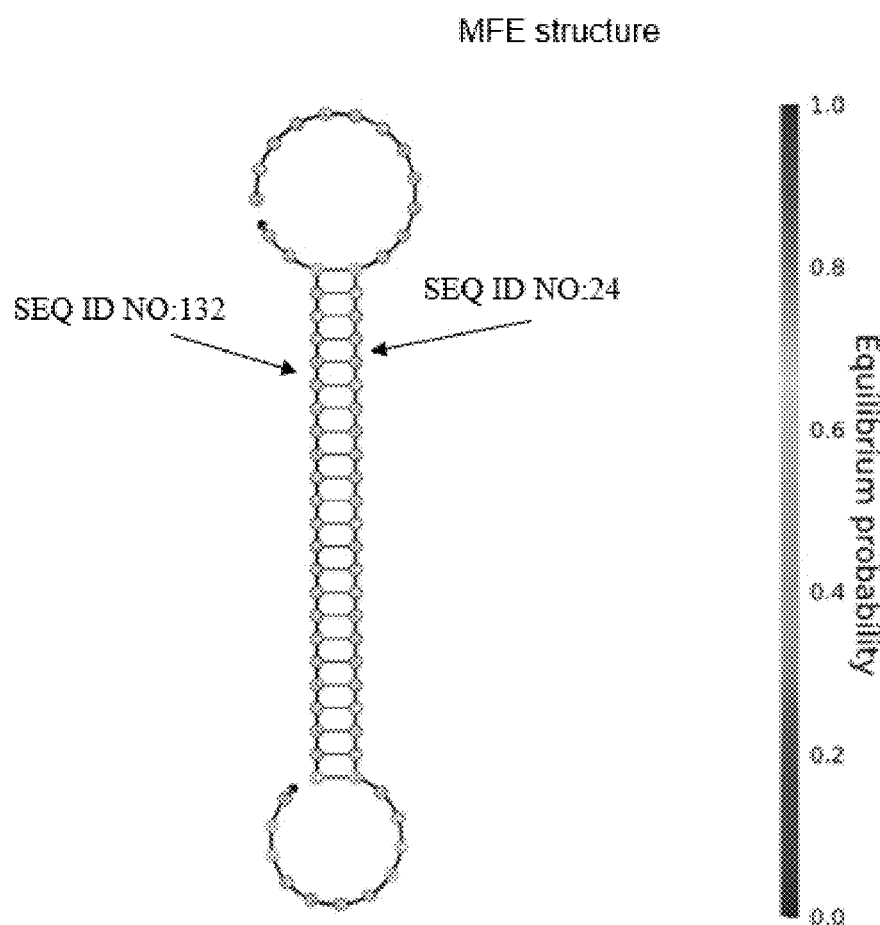
Free energy of secondary structure: -44.38 kcal/mol

FIG. 71
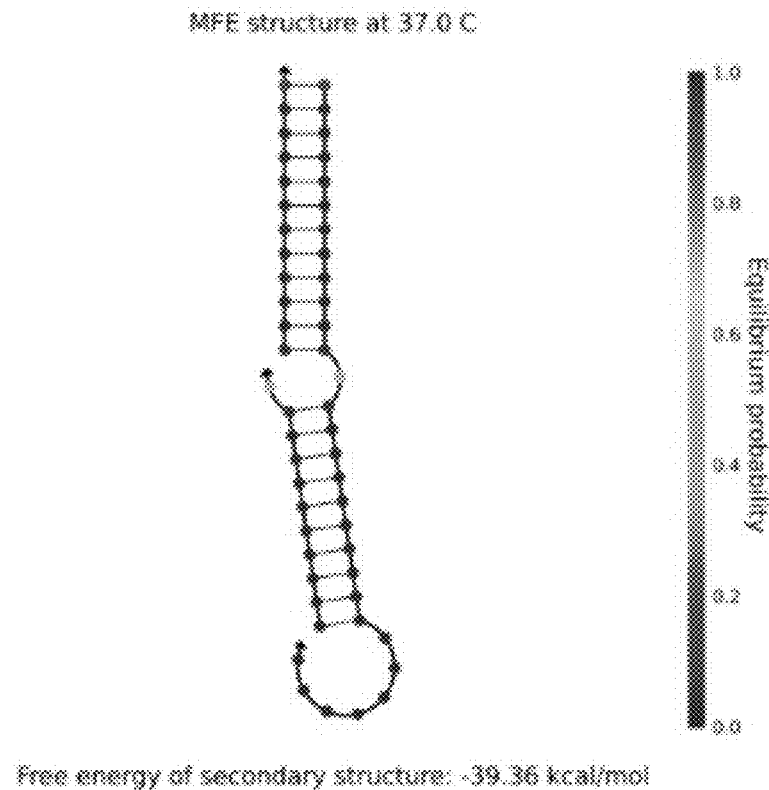
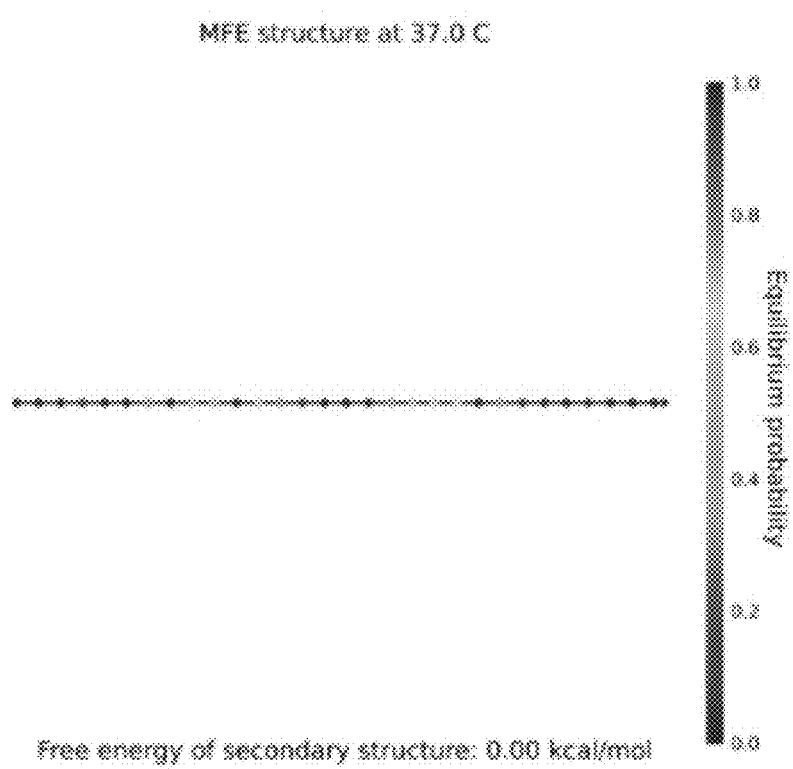

FIG. 72
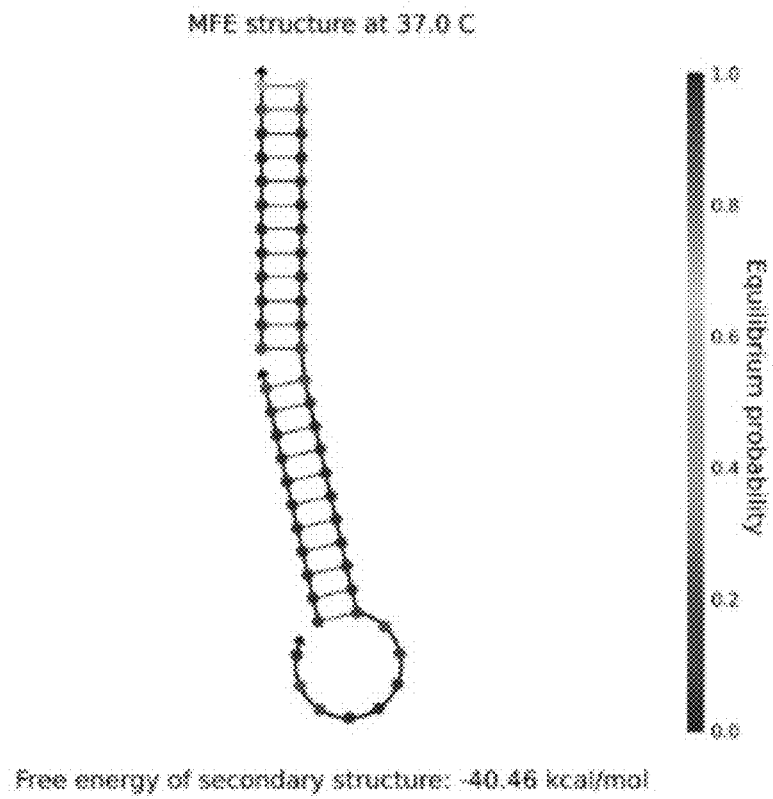
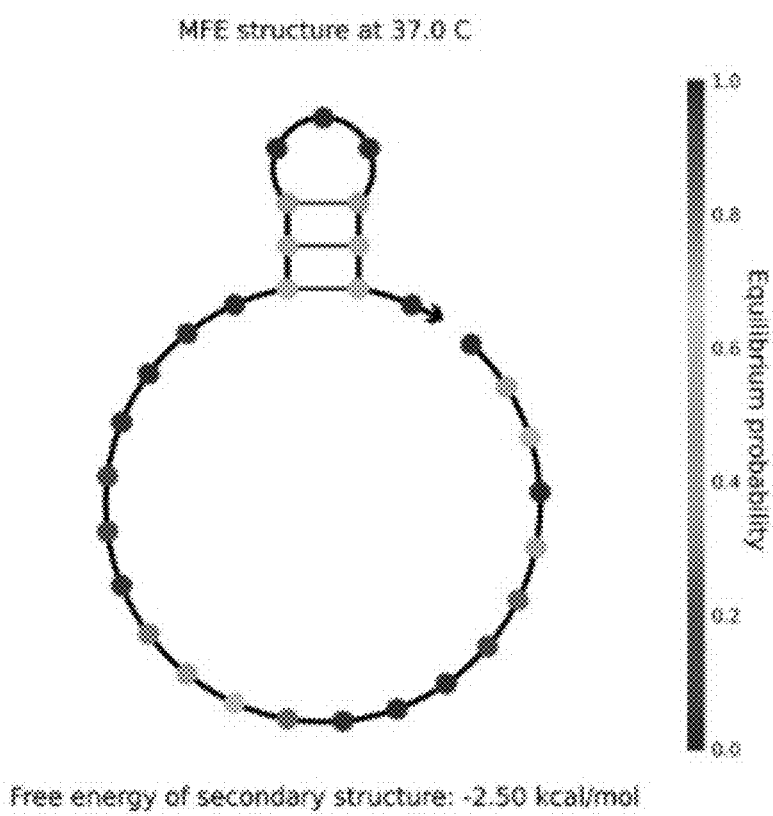

SEQUENCE LISTING

<160> NUMBER OF SEQ ID NOS: 1252

<210> SEQ ID NO 1
<211> LENGTH: 29
<212> TYPE: DNA
<213> ORGANISM: Artificial Sequence
<220> FEATURE:
<223> OTHER INFORMATION: MIR-23A-3P sensor

<400> SEQUENCE: 1
cgaagaacgg aaaucccugg caaugtgat                                            29

<210> SEQ ID NO 2
<211> LENGTH: 29
<212> TYPE: DNA
<213> ORGANISM: Artificial Sequence
<220> FEATURE:
<223> OTHER INFORMATION: MIR-23A-3P Sensor

<400> SEQUENCE: 2
cgaagaacgg aaauccctgg caatgtgau                                            29

<210> SEQ ID NO 3
<211> LENGTH: 31
<212> TYPE: RNA
<213> ORGANISM: Artificial Sequence
<220> FEATURE:
<223> OTHER INFORMATION: MIR-23A-3P Sensor

<400> SEQUENCE: 3
ggagaagaac ggaaaucccu ggcaauguga u                                         31

<210> SEQ ID NO 4
<211> LENGTH: 31
<212> TYPE: RNA
<213> ORGANISM: Artificial Sequence
<220> FEATURE:
<223> OTHER INFORMATION: BNP sensor

<400> SEQUENCE: 4
aucagaagca ggugucugca gccaggacuu c                                         31

<210> SEQ ID NO 5
<211> LENGTH: 31
<212> TYPE: RNA
<213> ORGANISM: Artificial Sequence
<220> FEATURE:
<223> OTHER INFORMATION: BNP sensor

<400> SEQUENCE: 5 cuugugggaau cagaagcagg ugucugcagc c                                        31

-continued

```
<210> SEQ ID NO 6
<211> LENGTH: 31
<212> TYPE: RNA
<213> ORGANISM: Artificial Sequence
<220> FEATURE:
<223> OTHER INFORMATION: BNP sensor

<400> SEQUENCE: 6
caaaggcggc cacagdgguug aggaaaaagc c                                    31

<210> SEQ ID NO 7
<211> LENGTH: 31
<212> TYPE: RNA
<213> ORGANISM: Artificial Sequence
<220> FEATURE:
<223> OTHER INFORMATION: MHCbeta/myh7 Sensor

<400> SEQUENCE: 7
aucuugaucu gcucagcccu ggaggugcca g                                     31

<210> SEQ ID NO 8
<211> LENGTH: 31
<212> TYPE: RNA
<213> ORGANISM: Artificial Sequence
<220> FEATURE:
<223> OTHER INFORMATION: ANP sensor

<400> SEQUENCE: 8
caacaagaug acacaaaugc agcagagacc c                                     31

<210> SEQ ID NO 9
<211> LENGTH: 31
<212> TYPE: RNA
<213> ORGANISM: Artificial Sequence
<220> FEATURE:
<223> OTHER INFORMATION: ANP sensor

<400> SEQUENCE: 9
augacacaaa ugcagcagag accccagggg a                                     31

<210> SEQ ID NO 10
<211> LENGTH: 31
<212> TYPE: DNA
<213> ORGANISM: Artificial Sequence
<220> FEATURE:
<223> OTHER INFORMATION: ANP sensor

<400> SEQUENCE: 10
ctucaccacc ucucagtggc aaugcgacca a                                     31

<210> SEQ ID NO 11
<211> LENGTH: 25
<212> TYPE: RNA
<213> ORGANISM: Artificial Sequence
<220> FEATURE:
<223> OTHER INFORMATION: calcineurin guide strand

<400> SEQUENCE: 11
cgaguguugu uuggcuuuuc cuguu                                            25

<210> SEQ ID NO 12
<211> LENGTH: 25
<212> TYPE: RNA
<213> ORGANISM: Artificial Sequence
<220> FEATURE:
```

```
<223> OTHER INFORMATION: calcineurin guide strand

<400> SEQUENCE: 12
cgaguguugu uggcuuuuc cuguu                                          25

<210> SEQ ID NO 13
<211> LENGTH: 25
<212> TYPE: RNA
<213> ORGANISM: Artificial Sequence
<220> FEATURE:
<223> OTHER INFORMATION: HDAC2 guide

<400> SEQUENCE: 13
gcacuuagau ugaaacaacc caguu                                         25

<210> SEQ ID NO 14
<211> LENGTH: 23
<212> TYPE: RNA
<213> ORGANISM: Artificial Sequence
<220> FEATURE:
<223> OTHER INFORMATION: HDAC2 guide

<400> SEQUENCE: 14
uguuaucugg uguuauugac cgu                                           23

<210> SEQ ID NO 15
<211> LENGTH: 23
<212> TYPE: RNA
<213> ORGANISM: Artificial Sequence
<220> FEATURE:
<223> OTHER INFORMATION: HDAC2 guide

<400> SEQUENCE: 15
cgagaucugg uguuauugac cgu                                           23

<210> SEQ ID NO 16
<211> LENGTH: 25
<212> TYPE: RNA
<213> ORGANISM: Artificial Sequence
<220> FEATURE:
<223> OTHER INFORMATION: HDAC2 guide

<400> SEQUENCE: 16
gcucuuagau ugaaacaacc caguu                                         25

<210> SEQ ID NO 17
<211> LENGTH: 46
<212> TYPE: RNA
<213> ORGANISM: Artificial Sequence
<220> FEATURE:
<223> OTHER INFORMATION: Calcineurin core strand

<400> SEQUENCE: 17
cguucuucuc ccaggaaaag ccaaacaaca cucggccagg gauuuc                  46

<210> SEQ ID NO 18
<211> LENGTH: 46
<212> TYPE: RNA
<213> ORGANISM: Artificial Sequence
<220> FEATURE:
<223> OTHER INFORMATION: Calcineurin core strand

<400> SEQUENCE: 18
gucaucuugu ugcaggaaaa gccaaacaac acucggcugc auuugu                  46
```

```
<210> SEQ ID NO 19
<211> LENGTH: 46
<212> TYPE: RNA
<213> ORGANISM: Artificial Sequence
<220> FEATURE:
<223> OTHER INFORMATION: Calcineurin core strand

<400> SEQUENCE: 19
agguggugaa gcaggaaaag ccaaacaaca cucgauugcc acugag        46

<210> SEQ ID NO 20
<211> LENGTH: 46
<212> TYPE: RNA
<213> ORGANISM: Artificial Sequence
<220> FEATURE:
<223> OTHER INFORMATION: HDAC2 core strand

<400> SEQUENCE: 20
cguucuucuc ccuggguugu uucaaucuaa gugcgccagg gauuuc        46

<210> SEQ ID NO 21
<211> LENGTH: 46
<212> TYPE: RNA
<213> ORGANISM: Artificial Sequence
<220> FEATURE:
<223> OTHER INFORMATION: HDAC2 core strand

<400> SEQUENCE: 21
ccugcuucug auacggucaa uaacaccaga ucucgggcug cagaca        46

<210> SEQ ID NO 22
<211> LENGTH: 46
<212> TYPE: RNA
<213> ORGANISM: Artificial Sequence
<220> FEATURE:
<223> OTHER INFORMATION: HDAC2 core strand

<400> SEQUENCE: 22
gauuccacaa gacggucaau aacaccagau cucgacaccu gcuucu        46

<210> SEQ ID NO 23
<211> LENGTH: 46
<212> TYPE: RNA
<213> ORGANISM: Artificial Sequence
<220> FEATURE:
<223> OTHER INFORMATION: HDAC2 core strand

<400> SEQUENCE: 23
ggccgccuuu gacggucaau aacaccagau cucgccucaa cccugu        46

<210> SEQ ID NO 24
<211> LENGTH: 46
<212> TYPE: RNA
<213> ORGANISM: Artificial Sequence
<220> FEATURE:
<223> OTHER INFORMATION: HDAC2 core strand

<400> SEQUENCE: 24
gcagaucaag auacggucaa uaacaccaga ucucguccag ggcuga        46

<210> SEQ ID NO 25
<211> LENGTH: 46
<212> TYPE: RNA
<213> ORGANISM: Artificial Sequence
<220> FEATURE:
<223> OTHER INFORMATION: HDAC2 core strand
```

<400> SEQUENCE: 25
gucaucuugu ugcugggüug uuucaaucua agagcgcugc auuugu            46

<210> SEQ ID NO 26
<211> LENGTH: 44
<212> TYPE: RNA
<213> ORGANISM: Artificial Sequence
<220> FEATURE:
<223> OTHER INFORMATION: HDAC2 core strand

<400> SEQUENCE: 26 cauugugüc auuguuagau ugaaacaacc cagggucucu gcug              44

<210> SEQ ID NO 27
<211> LENGTH: 253
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (8)..(16)
<223> OTHER INFORMATION: n is a, c, t, or g
<220> FEATURE:
<221> NAME/KEY: misc_feature
<222> LOCATION: (8)..(16)
<223> OTHER INFORMATION: n is a, c, g, or t
<220> FEATURE:
<221> NAME/KEY: modified_base
<222> LOCATION: (211)..(214)
<223> OTHER INFORMATION: n is a, c, t, or g
<220> FEATURE:
<221> NAME/KEY: misc_feature
<222> LOCATION: (211)..(214)
<223> OTHER INFORMATION: n is a, c, g, or t
<220> FEATURE:
<221> NAME/KEY: modified_base
<222> LOCATION: (216)..(217)
<223> OTHER INFORMATION: n is a, c, t, or g
<220> FEATURE:
<221> NAME/KEY: misc_feature
<222> LOCATION: (216)..(217)
<223> OTHER INFORMATION: n is a, c, g, or t
<220> FEATURE:
<221> NAME/KEY: modified_base
<222> LOCATION: (219)..(222)
<223> OTHER INFORMATION: n is a, c, t, or g
<220> FEATURE:
<221> NAME/KEY: misc_feature
<222> LOCATION: (219)..(222)
<223> OTHER INFORMATION: n is a, c, g, or t
<220> FEATURE:
<221> NAME/KEY: modified_base
<222> LOCATION: (224)..(253)
<223> OTHER INFORMATION: n is a, c, t, or g
<220> FEATURE:
<221> NAME/KEY: misc_feature
<222> LOCATION: (224)..(253)
<223> OTHER INFORMATION: n is a, c, g, or t

<400> SEQUENCE: 27
tcagccannn nnnnnngagc agatcgcaaa agatcccaag gccttgcggt gtgtcacaca      60
gcttggtcgc attgccactg agaggtggtg aatacccctcc tggagctgca gcttcctgtc    120
ttcatctatc acgatcgatg ttaagtgtag atgagtggtt tagtgaggcc ttacctctcc     180
cactctgcat attaaggtag atcctcaccc nnnnannann nncnnnnnnn nnnnnnnnn      240 nnnnnnnnnn nnn                                                       253

<210> SEQ ID NO 28
<211> LENGTH: 194

<212> TYPE: DNA
<213> ORGANISM: Artificial Sequence
<220> FEATURE:
<223> OTHER INFORMATION: central sequence

<400> SEQUENCE: 28
gagcagatcg caaaagatcc caaggccttg cggtgtgtca cacagcttgg tcgcattgcc    60
actgagaggt ggtgaatacc ctcctggagc tgcagcttcc tgtcttcatc tatcacgatc   120
gatgttaagt gtagatgagt ggtttagtga ggccttacct ctcccactct gcatattaag   180
gtagatcctc accc                                                     194

<210> SEQ ID NO 29
<211> LENGTH: 253
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(30)
<223> OTHER INFORMATION: n is a, c, t, or g
<220> FEATURE:
<221> NAME/KEY: misc_feature
<222> LOCATION: (1)..(30)
<223> OTHER INFORMATION: n is a, c, g, or t
<220> FEATURE:
<221> NAME/KEY: modified_base
<222> LOCATION: (32)..(35)
<223> OTHER INFORMATION: n is a, c, t, or g
<220> FEATURE:
<221> NAME/KEY: misc_feature
<222> LOCATION: (32)..(35)
<223> OTHER INFORMATION: n is a, c, g, or t
<220> FEATURE:
<221> NAME/KEY: modified_base
<222> LOCATION: (37)..(38)
<223> OTHER INFORMATION: n is a, c, t, or g
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (40)..(43)
<223> OTHER INFORMATION: n is a, c, t, or g
<220> FEATURE:
<221> NAME/KEY: misc_feature
<222> LOCATION: (40)..(43)
<223> OTHER INFORMATION: n is a, c, g, or t
<220> FEATURE:
<221> NAME/KEY: modified_base
<222> LOCATION: (238)..(246)
<223> OTHER INFORMATION: n is a, c, t, or g
<220> FEATURE:
<221> NAME/KEY: misc_feature
<222> LOCATION: (238)..(246)
<223> OTHER INFORMATION: n is a, c, g, or t

<400> SEQUENCE: 29
nnnnnnnnnn nnnnnnnnnn nnnnnnnnnn gnnnntnntn nnngggtgag gatctacctt    60
aatatgcaga gtgggagagg taaggcctca ctaaaccact catctacact taacatcgat   120
cgtgatagat gaagacagga agctgcagct ccaggagggt attcaccacc tctcagtggc   180
aatgcgacca agctgtgtga cacaccgcaa ggccttggga tcttttgcga tctgctcnnn   240
nnnnnntggc tga                                                      253

<210> SEQ ID NO 30
<211> LENGTH: 31
<212> TYPE: DNA

```
<213> ORGANISM: Artificial Sequence
<220> FEATURE:
<223> OTHER INFORMATION: sensor strand

<400> SEQUENCE: 30
attcaccacc tctcagtggc aatgcgacca a                              31

<210> SEQ ID NO 31
<211> LENGTH: 31
<212> TYPE: RNA
<213> ORGANISM: Artificial Sequence
<220> FEATURE:
<223> OTHER INFORMATION: sensor strand
<220> FEATURE:
<221> NAME/KEY: modified_base
<222> LOCATION: (1)..(1)
<223> OTHER INFORMATION: a or c

<400> SEQUENCE: 31
cuucaccacc ucucaguggc aaugcgacca a                              31

<210> SEQ ID NO 32
<211> LENGTH: 21
<212> TYPE: RNA
<213> ORGANISM: Artificial Sequence
<220> FEATURE:
<223> OTHER INFORMATION: guide sequence

<400> SEQUENCE: 32
uguuguuugg cuuuuccugu u                                         21

<210> SEQ ID NO 33
<211> LENGTH: 31
<212> TYPE: RNA
<213> ORGANISM: Artificial Sequence
<220> FEATURE:
<223> OTHER INFORMATION: sensor sequence

<400> SEQUENCE: 33
cuucaccacc ucucaguggc aaugcgacca a                              31

<210> SEQ ID NO 34
<211> LENGTH: 31
<212> TYPE: DNA
<213> ORGANISM: Artificial Sequence
<220> FEATURE:
<223> OTHER INFORMATION: sensor strand

<400> SEQUENCE: 34
ctucaccacc ucucagtggc aaugcgacca a                              31

<210> SEQ ID NO 35
<211> LENGTH: 26
<212> TYPE: RNA
<213> ORGANISM: Artificial Sequence
<220> FEATURE:
<223> OTHER INFORMATION: guide strand
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (3)..(3)
<223> OTHER INFORMATION: phosphorothioate backbone connection
<220> FEATURE:
<221> NAME/KEY: misc_feature
<222> LOCATION: (4)..(4)
<223> OTHER INFORMATION: LNA
```

```
<400> SEQUENCE: 35
cngaguguug uuuggcuuuu ccuguu                                      26

<210> SEQ ID NO 36
<211> LENGTH: 49
<212> TYPE: RNA
<213> ORGANISM: Artificial Sequence
<220> FEATURE:
<223> OTHER INFORMATION: core strand sequence
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (14)..(14)
<223> OTHER INFORMATION: phosphorothioate backbone connection
<220> FEATURE:
<221> NAME/KEY: misc_feature
<222> LOCATION: (15)..(15)
<223> OTHER INFORMATION: LNA
<220> FEATURE:
<221> NAME/KEY: misc_feature
<222> LOCATION: (16)..(16)
<223> OTHER INFORMATION: phosphorothioate backbone connection
<220> FEATURE:
<221> NAME/KEY: misc_feature
<222> LOCATION: (36)..(36)
<223> OTHER INFORMATION: n is a, c, g, or u
<220> FEATURE:
<221> NAME/KEY: misc_feature
<222> LOCATION: (37)..(37)
<223> OTHER INFORMATION: phosphorothioate backbone connection

<400> SEQUENCE: 36
agguggugaa gcnanggaaa agccaaacaa cacucngauu gccacugag             49

<210> SEQ ID NO 37
<211> LENGTH: 21
<212> TYPE: RNA
<213> ORGANISM: Artificial Sequence
<220> FEATURE:
<223> OTHER INFORMATION: mir-23a-3P

<400> SEQUENCE: 37
aucacauugc cagggauuuc c                                          21

<210> SEQ ID NO 38
<211> LENGTH: 21
<212> TYPE: RNA
<213> ORGANISM: Artificial Sequence
<220> FEATURE:
<223> OTHER INFORMATION: mir-23a-3p

<400> SEQUENCE: 38 ggaaucccu ggcaauguga u                                           21

<210> SEQ ID NO 39
<211> LENGTH: 29
<212> TYPE: RNA
<213> ORGANISM: Artificial Sequence
<220> FEATURE:
<223> OTHER INFORMATION: Calcineurin sensor

<400> SEQUENCE: 39
cgaagaacgg aaaucccugg caaugugau                                  29

<210> SEQ ID NO 40
```

```
<211> LENGTH: 8
<212> TYPE: RNA
<213> ORGANISM: Artificial Sequence
<220> FEATURE:
<223> OTHER INFORMATION: synthetic

<400> SEQUENCE: 40 cgaagaac                                                                    8

<210> SEQ ID NO 41
<211> LENGTH: 45
<212> TYPE: RNA
<213> ORGANISM: Artificial Sequence
<220> FEATURE:
<223> OTHER INFORMATION: Calcineurin PPP3CA siRNA guide

<400> SEQUENCE: 41
uccguucuuc gcaggaaaag ccaaacaaca cucgugccag ggauu            45

<210> SEQ ID NO 42
<211> LENGTH: 27
<212> TYPE: RNA
<213> ORGANISM: Artificial Sequence
<220> FEATURE:
<223> OTHER INFORMATION: Calcineurin guide
<220> FEATURE:
<221> NAME/KEY: misc_feature
<222> LOCATION: (1)..(1)
<223> OTHER INFORMATION: C6 Amine
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (3)..(3)
<223> OTHER INFORMATION: phosphorothioate backbone connection
<220> FEATURE:
<221> NAME/KEY: misc_feature
<222> LOCATION: (4)..(4)
<223> OTHER INFORMATION: LNA

<400> SEQUENCE: 42
ccngaguguu guuuggcuuu uccuguu                                              27

<210> SEQ ID NO 43
<211> LENGTH: 30
<212> TYPE: DNA
<213> ORGANISM: Artificial Sequence
<220> FEATURE:
<223> OTHER INFORMATION: Mir-23a-3p sensor
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (31)..(31)
<223> OTHER INFORMATION: primary amine modification

<400> SEQUENCE: 43
cgaagaacgg aaaucccugg caaugtgatn                                           30

<210> SEQ ID NO 44
<211> LENGTH: 48
<212> TYPE: RNA
<213> ORGANISM: Artificial Sequence
<220> FEATURE:
<223> OTHER INFORMATION: core strand
<220> FEATURE:
<221> NAME/KEY: misc_feature
```

```
<222> LOCATION: (1)..(1)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: phosphorothioate backbone connection
<220> FEATURE:
<221> NAME/KEY: misc_feature
<222> LOCATION: (15)..(15)
<223> OTHER INFORMATION: LNA
<220> FEATURE:
<221> NAME/KEY: misc_feature
<222> LOCATION: (16)..(16)
<223> OTHER INFORMATION: phosphorothioate backbone connection
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (36)..(36)
<223> OTHER INFORMATION: n is a, c, g, or u
<220> FEATURE:
<221> NAME/KEY: misc_feature
<222> LOCATION: (37)..(37)
<223> OTHER INFORMATION: phosphorothioate backbone connection
<220> FEATURE:
<221> NAME/KEY: misc_feature
<222> LOCATION: (38)..(38)
<223> OTHER INFORMATION: 2'-O-methyl
<220> FEATURE:
<221> NAME/KEY: misc_feature
<222> LOCATION: (48)..(48)
<223> OTHER INFORMATION: 2'-O-methyl
<220> FEATURE:
<221> NAME/KEY: misc_feature
<222> LOCATION: (50)..(50)
<223> OTHER INFORMATION: 2'-O-methyl

<400> SEQUENCE: 44
uccguucuuc gcnanggaaa agccaaacaa cacucngugc cagggauu          48

<210> SEQ ID NO 45
<211> LENGTH: 25
<212> TYPE: RNA
<213> ORGANISM: Artificial Sequence
<220> FEATURE:
<223> OTHER INFORMATION: cond-siRNA guide

<400> SEQUENCE: 45
ccacuuuacc agcaucucag ucauu                                   25

<210> SEQ ID NO 46
<211> LENGTH: 31
<212> TYPE: RNA
<213> ORGANISM: Artificial Sequence
<220> FEATURE:
<223> OTHER INFORMATION: Cond-siRNA Sensor

<400> SEQUENCE: 46
ggagaggcga ggaagucacc aucaaaccac u                            31

<210> SEQ ID NO 47
<211> LENGTH: 46
<212> TYPE: RNA
<213> ORGANISM: Artificial Sequence
<220> FEATURE:
<223> OTHER INFORMATION: core strand
```

```
<400> SEQUENCE: 47
cucgccucuc cugacugaga ugcugguaaa gugggauggu gacuuc        46

<210> SEQ ID NO 48
<211> LENGTH: 31
<212> TYPE: RNA
<213> ORGANISM: Artificial Sequence
<220> FEATURE:
<223> OTHER INFORMATION: cond-siRNA sensor

<400> SEQUENCE: 48
ggaaucagaa gcaggugucu gcagccagga c                        31

<210> SEQ ID NO 49
<211> LENGTH: 46
<212> TYPE: RNA
<213> ORGANISM: Artificial Sequence
<220> FEATURE:
<223> OTHER INFORMATION: core strand

<400> SEQUENCE: 49
cuucugauuc cugacugaga ugcugguaaa guggugcaga caccug        46

<210> SEQ ID NO 50
<211> LENGTH: 31
<212> TYPE: RNA
<213> ORGANISM: Artificial Sequence
<220> FEATURE:
<223> OTHER INFORMATION: cond-siRNA sensor

<400> SEQUENCE: 50
ccaaggagcu guuacacagg cuccagcaug g                        31

<210> SEQ ID NO 51
<211> LENGTH: 46
<212> TYPE: RNA
<213> ORGANISM: Artificial Sequence
<220> FEATURE:
<223> OTHER INFORMATION: core strand

<400> SEQUENCE: 51
cagcuccuug gugacugaga ugcugguaaa gugggagccu guguaa        46

<210> SEQ ID NO 52
<211> LENGTH: 25
<212> TYPE: RNA
<213> ORGANISM: Artificial Sequence
<220> FEATURE:
<223> OTHER INFORMATION: cond-siRNA guide

<400> SEQUENCE: 52
ccacuucauc acaagcuauc cgcuu                               25

<210> SEQ ID NO 53
<211> LENGTH: 46
<212> TYPE: RNA
<213> ORGANISM: Artificial Sequence
<220> FEATURE:
<223> OTHER INFORMATION: core strand

<400> SEQUENCE: 53
cucgccucuc cgcggauagc uugugaugaa gugggauggu gacuuc        46

<210> SEQ ID NO 54
<211> LENGTH: 46
```

```
<212> TYPE: RNA
<213> ORGANISM: Artificial Sequence
<220> FEATURE:
<223> OTHER INFORMATION: core strand

<400> SEQUENCE: 54
cuucugauuc cgcggauagc uugugaugaa guggugcaga caccug                    46

<210> SEQ ID NO 55
<211> LENGTH: 46
<212> TYPE: RNA
<213> ORGANISM: Artificial Sequence
<220> FEATURE:
<223> OTHER INFORMATION: core strand

<400> SEQUENCE: 55
cagcuccuug ggcggauagc uugugaugaa gugggagccu guguaa                    46

<210> SEQ ID NO 56
<211> LENGTH: 45
<212> TYPE: RNA
<213> ORGANISM: Artificial Sequence
<220> FEATURE:
<223> OTHER INFORMATION: core strand

<400> SEQUENCE: 56
uccguucuuc gugacugaga ugcugguaaa guggugccag ggauu                     45

<210> SEQ ID NO 57
<211> LENGTH: 29
<212> TYPE: RNA
<213> ORGANISM: Artificial Sequence
<220> FEATURE:
<223> OTHER INFORMATION: Cond-siRNA sensor

<400> SEQUENCE: 57
cgacaguuca caaguuaggg ucucaggga                                       29

<210> SEQ ID NO 58
<211> LENGTH: 45
<212> TYPE: RNA
<213> ORGANISM: Artificial Sequence
<220> FEATURE:
<223> OTHER INFORMATION: core strand

<400> SEQUENCE: 58
gugaacuguc gugacugaga ugcugguaaa gugggacccu aacuu                     45

<210> SEQ ID NO 59
<211> LENGTH: 29
<212> TYPE: RNA
<213> ORGANISM: Artificial Sequence
<220> FEATURE:
<223> OTHER INFORMATION: Cond-siRNA sensor

<400> SEQUENCE: 59
ccugaagaac agauagucua aacacuggg                                       29

<210> SEQ ID NO 60
<211> LENGTH: 45
<212> TYPE: RNA
<213> ORGANISM: Artificial Sequence
<220> FEATURE:
<223> OTHER INFORMATION: core strand

<400> SEQUENCE: 60
```
uguucuucag gugacugaga ugcugguaaa gugguuuaga cuauc    45

<210> SEQ ID NO 61
<211> LENGTH: 47
<212> TYPE: RNA
<213> ORGANISM: Artificial Sequence
<220> FEATURE:
<223> OTHER INFORMATION: core strand

<400> SEQUENCE: 61
aacagcuccu ugggcggaua gcuugugaug aaguggggag ccugugu    47

<210> SEQ ID NO 62
<211> LENGTH: 45
<212> TYPE: RNA
<213> ORGANISM: Artificial Sequence
<220> FEATURE:
<223> OTHER INFORMATION: core strand

<400> SEQUENCE: 62
uccguucuuc ggcggauagc uugugaugaa guggugccag ggauu    45

<210> SEQ ID NO 63
<211> LENGTH: 45
<212> TYPE: RNA
<213> ORGANISM: Artificial Sequence
<220> FEATURE:
<223> OTHER INFORMATION: core strand

<400> SEQUENCE: 63
uguucuucag ggcggauagc uugugaugaa gugguuuaga cuauc    45

<210> SEQ ID NO 64
<211> LENGTH: 21
<212> TYPE: RNA
<213> ORGANISM: Artificial Sequence
<220> FEATURE:
<223> OTHER INFORMATION: siRNA target site

<400> SEQUENCE: 64
gaacaagauc cgagcaauau u    21

<210> SEQ ID NO 65
<211> LENGTH: 21
<212> TYPE: RNA
<213> ORGANISM: Artificial Sequence
<220> FEATURE:
<223> OTHER INFORMATION: siRNA guide strand

<400> SEQUENCE: 65
uauugcucgg aucuuguucu u    21

<210> SEQ ID NO 66
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 66
cgacuauugc ucggaucuug uucuu    25

<210> SEQ ID NO 67
<211> LENGTH: 21
<212> TYPE: RNA
<213> ORGANISM: Artificial Sequence

```
<220> FEATURE:
<223> OTHER INFORMATION: siRNA target site

<400> SEQUENCE: 67
ugacugagau gcugguaaau u                                              21

<210> SEQ ID NO 68
<211> LENGTH: 21
<212> TYPE: RNA
<213> ORGANISM: Artificial Sequence
<220> FEATURE:
<223> OTHER INFORMATION: siRNA guide strand

<400> SEQUENCE: 68
uuuaccagca ucucagucau u                                              21

<210> SEQ ID NO 69
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 69
cgacuuuacc agcaucucag ucauu                                          25

<210> SEQ ID NO 70
<211> LENGTH: 21
<212> TYPE: RNA
<213> ORGANISM: Artificial Sequence
<220> FEATURE:
<223> OTHER INFORMATION: siRNA target site

<400> SEQUENCE: 70
ggucagaaga agauggauuu u                                              21

<210> SEQ ID NO 71
<211> LENGTH: 21
<212> TYPE: RNA
<213> ORGANISM: Artificial Sequence
<220> FEATURE:
<223> OTHER INFORMATION: siRNA guide strand

<400> SEQUENCE: 71
aauccaucuu cuucugaccu u                                              21

<210> SEQ ID NO 72
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 72
ccacaaucca ucuucuucug accuu                                          25

<210> SEQ ID NO 73
<211> LENGTH: 21
<212> TYPE: RNA
<213> ORGANISM: Artificial Sequence
<220> FEATURE:
<223> OTHER INFORMATION: siRNA target site

<400> SEQUENCE: 73
gcuauagaau guacagaaau u                                              21
```

```
<210> SEQ ID NO 74
<211> LENGTH: 21
<212> TYPE: RNA
<213> ORGANISM: Artificial Sequence
<220> FEATURE:
<223> OTHER INFORMATION: siRNA guide strand

<400> SEQUENCE: 74
uuucuguaca uucuauagcu u                                              21

<210> SEQ ID NO 75
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 75
cgacuuucug uacauucuau agcuu                                          25

<210> SEQ ID NO 76
<211> LENGTH: 21
<212> TYPE: RNA
<213> ORGANISM: Artificial Sequence
<220> FEATURE:
<223> OTHER INFORMATION: siRNA target site

<400> SEQUENCE: 76
ccuuuaagca ggaauguaau u                                              21

<210> SEQ ID NO 77
<211> LENGTH: 21
<212> TYPE: RNA
<213> ORGANISM: Artificial Sequence
<220> FEATURE:
<223> OTHER INFORMATION: siRNA guide strand

<400> SEQUENCE: 77
uuacauuccu gcuuaaaggu u                                              21

<210> SEQ ID NO 78
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 78
ggacuuacau uccugcuuaa agguu                                          25

<210> SEQ ID NO 79
<211> LENGTH: 21
<212> TYPE: RNA
<213> ORGANISM: Artificial Sequence
<220> FEATURE:
<223> OTHER INFORMATION: siRNA target site

<400> SEQUENCE: 79
gcaauuggca agauggcaau u                                              21

<210> SEQ ID NO 80
<211> LENGTH: 21
<212> TYPE: RNA
<213> ORGANISM: Artificial Sequence
<220> FEATURE:
<223> OTHER INFORMATION: siRNA guide strand
```

```
<400> SEQUENCE: 80
uugccaucuu gccaauugcu u                                              21

<210> SEQ ID NO 81
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 81
ccacuugcca ucuugccaau ugcuu                                          25

<210> SEQ ID NO 82
<211> LENGTH: 21
<212> TYPE: RNA
<213> ORGANISM: Artificial Sequence
<220> FEATURE:
<223> OTHER INFORMATION: siRNA target site

<400> SEQUENCE: 82
guauagagug ugugcuguau u                                              21

<210> SEQ ID NO 83
<211> LENGTH: 21
<212> TYPE: RNA
<213> ORGANISM: Artificial Sequence
<220> FEATURE:
<223> OTHER INFORMATION: siRNA guide strand

<400> SEQUENCE: 83
uacagcacac acucuauacu u                                              21

<210> SEQ ID NO 84
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 84
ccacuacagc acacacucua uacuu                                          25

<210> SEQ ID NO 85
<211> LENGTH: 21
<212> TYPE: RNA
<213> ORGANISM: Artificial Sequence
<220> FEATURE:
<223> OTHER INFORMATION: siRNA target site

<400> SEQUENCE: 85
aguauuugag aaugggaaau u                                              21

<210> SEQ ID NO 86
<211> LENGTH: 21
<212> TYPE: RNA
<213> ORGANISM: Artificial Sequence
<220> FEATURE:
<223> OTHER INFORMATION: siRNA guide strand

<400> SEQUENCE: 86
uuucccauuc ucaaauacuu u                                              21

<210> SEQ ID NO 87
```

```
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 87
ccacuuuccc auucucaaau acuuu                                              25

<210> SEQ ID NO 88
<211> LENGTH: 21
<212> TYPE: RNA
<213> ORGANISM: Artificial Sequence
<220> FEATURE:
<223> OTHER INFORMATION: siRNA target site

<400> SEQUENCE: 88
cuauguggac agaggcuauu u                                                  21

<210> SEQ ID NO 89
<211> LENGTH: 21
<212> TYPE: RNA
<213> ORGANISM: Artificial Sequence
<220> FEATURE:
<223> OTHER INFORMATION: siRNA guide strand

<400> SEQUENCE: 89
auagccucug uccacauagu u                                                  21

<210> SEQ ID NO 90
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 90
ccacauagcc ucuguccaca uaguu                                              25

<210> SEQ ID NO 91
<211> LENGTH: 21
<212> TYPE: RNA
<213> ORGANISM: Artificial Sequence
<220> FEATURE:
<223> OTHER INFORMATION: siRNA target site

<400> SEQUENCE: 91
gcggauagcu ugugaugaau u                                                  21

<210> SEQ ID NO 92
<211> LENGTH: 21
<212> TYPE: RNA
<213> ORGANISM: Artificial Sequence
<220> FEATURE:
<223> OTHER INFORMATION: siRNA guide strand

<400> SEQUENCE: 92
uucaucacaa gcuauccgcu u                                                  21

<210> SEQ ID NO 93
<211> LENGTH: 21
<212> TYPE: RNA
<213> ORGANISM: Artificial Sequence
<220> FEATURE:
<223> OTHER INFORMATION: siRNA target site

<400> SEQUENCE: 93
```
ggauauuggu gcuggaaaau u          21

<210> SEQ ID NO 94
<211> LENGTH: 21
<212> TYPE: RNA
<213> ORGANISM: Artificial Sequence
<220> FEATURE:
<223> OTHER INFORMATION: siRNA guide strand

<400> SEQUENCE: 94
uuuuccagca ccaauauccu u          21

<210> SEQ ID NO 95
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 95
ccacuuuucc agcaccaaua uccuu          25

<210> SEQ ID NO 96
<211> LENGTH: 21
<212> TYPE: RNA
<213> ORGANISM: Artificial Sequence
<220> FEATURE:
<223> OTHER INFORMATION: siRNA target site

<400> SEQUENCE: 96
aagcagaugc agagauuuau u          21

<210> SEQ ID NO 97
<211> LENGTH: 21
<212> TYPE: RNA
<213> ORGANISM: Artificial Sequence
<220> FEATURE:
<223> OTHER INFORMATION: siRNA guide strand

<400> SEQUENCE: 97
uaaaucucug caucugcuuu u          21

<210> SEQ ID NO 98
<211> LENGTH: 25
<212> TYPE: RNA
<213> ORGANISM: Artificial Sequence
<220> FEATURE:
<223> OTHER INFORMATION: Cond-siRNA guide

<400> SEQUENCE: 98
ccacuaaauc ucugcaucug cuuuu          25

<210> SEQ ID NO 99
<211> LENGTH: 22
<212> TYPE: RNA
<213> ORGANISM: Artificial Sequence
<220> FEATURE:
<223> OTHER INFORMATION: hsa-miR-125b-5p MIMAT0000423

<400> SEQUENCE: 99
ucccugagac ccuaacuugu ga          22

<210> SEQ ID NO 100
<211> LENGTH: 22
<212> TYPE: RNA

```
<213> ORGANISM: Artificial Sequence
<220> FEATURE:
<223> OTHER INFORMATION: reverse complement hsa-miR-125b-5p MIMAT0000423

<400> SEQUENCE: 100
ucacaaguua gggucucagg ga                                              22

<210> SEQ ID NO 101
<211> LENGTH: 23
<212> TYPE: RNA
<213> ORGANISM: Artificial Sequence
<220> FEATURE:
<223> OTHER INFORMATION: hsa-miR-199b-5p MIMAT0000263

<400> SEQUENCE: 101
cccaguguuu agacuaucug uuc                                             23

<210> SEQ ID NO 102
<211> LENGTH: 23
<212> TYPE: RNA
<213> ORGANISM: Artificial Sequence
<220> FEATURE:
<223> OTHER INFORMATION: reverse complement hsa-miR-199b-5p MIMAT0000263

<400> SEQUENCE: 102
gaacagauag ucuaaacacu ggg                                             23

<210> SEQ ID NO 103
<211> LENGTH: 23
<212> TYPE: RNA
<213> ORGANISM: Artificial Sequence
<220> FEATURE:
<223> OTHER INFORMATION: mmu-miR-199b-5p MIMAT0000672

<400> SEQUENCE: 103
cccaguguuu agacuaccug uuc                                             23

<210> SEQ ID NO 104
<211> LENGTH: 73
<212> TYPE: RNA
<213> ORGANISM: Homo sapiens

<400> SEQUENCE: 104
ggccggcugg gguuccuggg gaugggauuu gcuuccuguc acaaaucaca uugccaggga     60
uuuccaaccg acc                                                        73

<210> SEQ ID NO 105
<211> LENGTH: 21
<212> TYPE: DNA
<213> ORGANISM: Homo sapiens

<400> SEQUENCE: 105
ggaaatccct ggcaatgtga t                                               21

<210> SEQ ID NO 106
<211> LENGTH: 21
<212> TYPE: DNA
<213> ORGANISM: Homo sapiens

<400> SEQUENCE: 106
ggtaatccct ggcaatgtga t                                               21

<210> SEQ ID NO 107
<211> LENGTH: 20
```

```
<212> TYPE: DNA
<213> ORGANISM: Homo sapiens

<400> SEQUENCE: 107
tgttgtttgg cttttcctgt                                              20

<210> SEQ ID NO 108
<211> LENGTH: 20
<212> TYPE: DNA
<213> ORGANISM: Homo sapiens

<400> SEQUENCE: 108
ttagattgaa acaacccagt                                              20

<210> SEQ ID NO 109
<211> LENGTH: 31
<212> TYPE: DNA
<213> ORGANISM: Artificial Sequence
<220> FEATURE:
<223> OTHER INFORMATION: miR-23a-3p sensor strand with LNA modifications

<400> SEQUENCE: 109
ggagaagaac ggaaatccct ggcaatgtga t                                 31

<210> SEQ ID NO 110
<211> LENGTH: 18
<212> TYPE: DNA
<213> ORGANISM: Artificial Sequence
<220> FEATURE:
<223> OTHER INFORMATION: synthetic

<400> SEQUENCE: 110
tccctggcat ccctggca                                                18

<210> SEQ ID NO 111
<211> LENGTH: 23
<212> TYPE: DNA
<213> ORGANISM: Artificial Sequence
<220> FEATURE:
<223> OTHER INFORMATION: HDAC2 target guide

<400> SEQUENCE: 111
acggtcaata agaccagata aca                                          23

<210> SEQ ID NO 112
<211> LENGTH: 23
<212> TYPE: RNA
<213> ORGANISM: Artificial Sequence
<220> FEATURE:
<223> OTHER INFORMATION: HDAC2 target guide

<400> SEQUENCE: 112 acgucaaua acaccagaua aca                                           23

<210> SEQ ID NO 113
<211> LENGTH: 17
<212> TYPE: DNA
<213> ORGANISM: Homo sapiens

<400> SEQUENCE: 113
atctggtgtt attgacc                                                 17

<210> SEQ ID NO 114
<211> LENGTH: 17
<212> TYPE: DNA
```

```
<213> ORGANISM: Homo sapiens

<400> SEQUENCE: 114
atctggtgta attgacc                                                    17

<210> SEQ ID NO 115
<211> LENGTH: 13
<212> TYPE: DNA
<213> ORGANISM: Homo sapiens

<400> SEQUENCE: 115
atctggtgtt att                                                        13

<210> SEQ ID NO 116
<211> LENGTH: 17
<212> TYPE: DNA
<213> ORGANISM: Homo sapiens

<400> SEQUENCE: 116
gagatctggt gttattg                                                    17

<210> SEQ ID NO 117
<211> LENGTH: 17
<212> TYPE: DNA
<213> ORGANISM: Homo sapiens

<400> SEQUENCE: 117
gagatctggt cttattg                                                    17

<210> SEQ ID NO 118
<211> LENGTH: 14
<212> TYPE: DNA
<213> ORGANISM: Homo sapiens

<400> SEQUENCE: 118
gagatctggt gtta                                                       14

<210> SEQ ID NO 119
<211> LENGTH: 13
<212> TYPE: DNA
<213> ORGANISM: Homo sapiens

<400> SEQUENCE: 119
ctggtgttat tga                                                        13

<210> SEQ ID NO 120
<211> LENGTH: 14
<212> TYPE: DNA
<213> ORGANISM: Homo sapiens

<400> SEQUENCE: 120
gatctggtgt tatt                                                       14

<210> SEQ ID NO 121
<211> LENGTH: 201
<212> TYPE: RNA
<213> ORGANISM: Artificial Sequence
<220> FEATURE:
<223> OTHER INFORMATION: BNP mRNA

<400> SEQUENCE: 121
aaaaaaaaaa auuucgaaua uuacaacuga aauaaagugg caccuuuaaa acacgaguuu     60
ccauucuuug guagaauaua uuuguuagu uauuuaugu auuauguaa uuuuuuacu        120
```
cagugaaguu uccgccggug ucccaacucc uuuuucgggg aacaccuuag ucuucgucca      180
cagacgucgg uccugaagga g                                                201

<210> SEQ ID NO 122
<211> LENGTH: 46
<212> TYPE: RNA
<213> ORGANISM: Artificial Sequence
<220> FEATURE:
<223> OTHER INFORMATION: core guide strand

<400> SEQUENCE: 122
ccugcuucug auacggucaa uaacaccaga ucucgggcug cagaca                     46

<210> SEQ ID NO 123
<211> LENGTH: 16
<212> TYPE: DNA
<213> ORGANISM: Homo sapiens

<400> SEQUENCE: 123
cttgatctgc tcagcc                                                      16

<210> SEQ ID NO 124
<211> LENGTH: 11
<212> TYPE: RNA
<213> ORGANISM: Artificial Sequence
<220> FEATURE:
<223> OTHER INFORMATION: sensor strand

<400> SEQUENCE: 124
ggcugcagac a                                                           11

<210> SEQ ID NO 125
<211> LENGTH: 12
<212> TYPE: RNA
<213> ORGANISM: Artificial Sequence
<220> FEATURE:
<223> OTHER INFORMATION: sensor strand

<400> SEQUENCE: 125
ccugcuucug au                                                          12

<210> SEQ ID NO 126
<211> LENGTH: 20
<212> TYPE: DNA
<213> ORGANISM: Homo sapiens

<400> SEQUENCE: 126
aggtgtctgc agccaggact                                                  20

<210> SEQ ID NO 127
<211> LENGTH: 20
<212> TYPE: DNA
<213> ORGANISM: Homo sapiens

<400> SEQUENCE: 127
aggtgtctgc aggcaggact                                                  20

<210> SEQ ID NO 128
<211> LENGTH: 20
<212> TYPE: DNA
<213> ORGANISM: Homo sapiens

<400> SEQUENCE: 128
agcaggtgtc tgcagccagg                                          20

<210> SEQ ID NO 129
<211> LENGTH: 20
<212> TYPE: DNA
<213> ORGANISM: Homo sapiens

<400> SEQUENCE: 129
agcaggtctc tgcagccagg                                          20

<210> SEQ ID NO 130
<211> LENGTH: 12
<212> TYPE: RNA
<213> ORGANISM: Artificial Sequence
<220> FEATURE:
<223> OTHER INFORMATION: BNP sensor

<400> SEQUENCE: 130
acaccugcuu cu                                                  12

<210> SEQ ID NO 131
<211> LENGTH: 11
<212> TYPE: RNA
<213> ORGANISM: Artificial Sequence
<220> FEATURE:
<223> OTHER INFORMATION: BNP sensor

<400> SEQUENCE: 131
gauuccacaa g                                                   11

<210> SEQ ID NO 132
<211> LENGTH: 25
<212> TYPE: RNA
<213> ORGANISM: Artificial Sequence
<220> FEATURE:
<223> OTHER INFORMATION: MFE structure

<400> SEQUENCE: 132
cgagaucugg uguuauugac cguuu                                    25

<210> SEQ ID NO 133
<211> LENGTH: 46
<212> TYPE: RNA
<213> ORGANISM: Artificial Sequence
<220> FEATURE:
<223> OTHER INFORMATION: MFE structure

<400> SEQUENCE: 133
gauuccacaa gacggucaau aacaccagau cucgacaccu gcuucu             46

<210> SEQ ID NO 134
<211> LENGTH: 16
<212> TYPE: DNA
<213> ORGANISM: Homo sapiens

<400> SEQUENCE: 134
agaagcaggt gtctgc                                              16

<210> SEQ ID NO 135
<211> LENGTH: 16
<212> TYPE: DNA
<213> ORGANISM: Homo sapiens

<400> SEQUENCE: 135
gaatcagaag caggtg                                              16

<210> SEQ ID NO 136
<211> LENGTH: 16
<212> TYPE: DNA
<213> ORGANISM: Homo sapiens

<400> SEQUENCE: 136
aagcaggtgt ctgcag                                                     16

<210> SEQ ID NO 137
<211> LENGTH: 15
<212> TYPE: DNA
<213> ORGANISM: Homo sapiens

<400> SEQUENCE: 137
atcagaagca ggtgt                                                      15

<210> SEQ ID NO 138
<211> LENGTH: 19
<212> TYPE: DNA
<213> ORGANISM: Homo sapiens

<400> SEQUENCE: 138
gaagcaggtg tctgcagcc                                                  19

<210> SEQ ID NO 139
<211> LENGTH: 19
<212> TYPE: DNA
<213> ORGANISM: Homo sapiens

<400> SEQUENCE: 139
gaagcaggtg cctgcagcc                                                  19

<210> SEQ ID NO 140
<211> LENGTH: 15
<212> TYPE: DNA
<213> ORGANISM: Homo sapiens

<400> SEQUENCE: 140
tgtggaatca gaagc                                                      15

<210> SEQ ID NO 141
<211> LENGTH: 16
<212> TYPE: DNA
<213> ORGANISM: Homo sapiens

<400> SEQUENCE: 141
ggccacaggg ttgagg                                                     16

<210> SEQ ID NO 142
<211> LENGTH: 15
<212> TYPE: DNA
<213> ORGANISM: Homo sapiens

<400> SEQUENCE: 142
agggttgagg aaaaa                                                      15

<210> SEQ ID NO 143
<211> LENGTH: 130
<212> TYPE: RNA
<213> ORGANISM: Artificial Sequence
<220> FEATURE:
<223> OTHER INFORMATION: UTR of MYH7 mRNA

```
<400> SEQUENCE: 143
gaaacggugu agaacuagac gagucgggac cuccacgguc guuucggggu acgaccucgg        60
acacauuguc gaggaacccu ccuucgucuu auuucguuaa aaggaacuuc ggcucuuuuu       120
uuuuuuuuuu                                                              130

<210> SEQ ID NO 144
<211> LENGTH: 11
<212> TYPE: RNA
<213> ORGANISM: Artificial Sequence
<220> FEATURE:
<223> OTHER INFORMATION: MFE structure

<400> SEQUENCE: 144
uccagggcug a                                                             11

<210> SEQ ID NO 145
<211> LENGTH: 12
<212> TYPE: RNA
<213> ORGANISM: Artificial Sequence
<220> FEATURE:
<223> OTHER INFORMATION: MFE structure

<400> SEQUENCE: 145
gcagaucaag au                                                            12

<210> SEQ ID NO 146
<211> LENGTH: 16
<212> TYPE: DNA
<213> ORGANISM: Homo sapiens

<400> SEQUENCE: 146
atcttgatct gctcag                                                        16

<210> SEQ ID NO 147
<211> LENGTH: 31
<212> TYPE: DNA
<213> ORGANISM: Artificial Sequence
<220> FEATURE:
<223> OTHER INFORMATION: sensor strand

<400> SEQUENCE: 147
caacaagatg acacaaatgc agcagagacc c                                       31

<210> SEQ ID NO 148
<211> LENGTH: 31
<212> TYPE: DNA
<213> ORGANISM: Artificial Sequence
<220> FEATURE:
<223> OTHER INFORMATION: sensor strand

<400> SEQUENCE: 148
atgacacaaa tgcagcagag accccagggg a                                       31

<210> SEQ ID NO 149
<211> LENGTH: 46
<212> TYPE: RNA
<213> ORGANISM: Artificial Sequence
<220> FEATURE:
<223> OTHER INFORMATION: core strand

<400> SEQUENCE: 149
gucaucuugu ugcaggaaaa gccaaacaac acucggcugc auuugu                       46
```

```
<210> SEQ ID NO 150
<211> LENGTH: 116
<212> TYPE: DNA
<213> ORGANISM: Homo sapiens

<400> SEQUENCE: 150
gctttgccac atcttgatct gctcagccct ggaggtgcca gcaaagcccc atgctggagc    60
ctgtgtaaca gctccttggg aggaagcaga ataaagcaat tttccttgaa gccgag       116

<210> SEQ ID NO 151
<211> LENGTH: 297
<212> TYPE: DNA
<213> ORGANISM: Homo sapiens

<400> SEQUENCE: 151
agataacagc cagggaggac aagcagggct gggcctaggg acagactgca agaggctcct    60
gtcccctggg gtctctgctg catttgtgtc atcttgttgc catggagttg tgatcatccc   120
atctaagctg cagcttcctg tcaacacttc tcacatctta tgctaactgt agataaagtg   180
gtttgatggt gacttcctcg cctctcccac cccatgcatt aaattttaag gtagaacctc   240
acctgttact gaaagtggtt tgaaagtgaa taaacttcag caccatggac agaagac      297

<210> SEQ ID NO 152
<211> LENGTH: 190
<212> TYPE: DNA
<213> ORGANISM: Homo sapiens

<400> SEQUENCE: 152
gaggaagtcc tggctgcaga cacctgcttc tgattccaca aggggctttt tcctcaaccc    60
tgtggccgcc tttgaagtga ctcattttt taatgtattt atgtatttat ttgattgttt    120
tatataagat ggtttcttac ctttgagcac aaaatttcca cggtgaaata aagtcaacat   180
tataagcttt                                                          190

<210> SEQ ID NO 153
<211> LENGTH: 105
<212> TYPE: DNA
<213> ORGANISM: Rattus norvegicus

<400> SEQUENCE: 153
atcttgtgct acccaacccct aaggatgcct gtgaagccct gagacctgga gcctttgaaa   60 cagcaccttta ggcagaaaca caataaagca attttccttc aagcc                  105

<210> SEQ ID NO 154
<211> LENGTH: 279
<212> TYPE: DNA
<213> ORGANISM: Rattus norvegicus

<400> SEQUENCE: 154
cagccaaatc tgctcgagca gatcgcaaaa gatcccaagc ccttgcggtg tgtcacacag    60
cttggtcgca ttgccactga gaggtggtga ataccctcct ggagctgcag cttcctgtct   120
tcatctatca cgatcgatgt taagtgtaga tgagtggttt agtgaggcct tacctctccc   180
actctgcata ttaaggtaga tcctcacccc tttcagaaag cagttggaaa aaataaaatc   240
cgaataaact tcagcaccac ggacagacgc tgaggcctg                          279

<210> SEQ ID NO 155
<211> LENGTH: 205
<212> TYPE: DNA
```

<213> ORGANISM: Rattus norvegicus

<400> SEQUENCE: 155

```
gaagacctcc tggctgcaga ctccggcttc tgactctgcc tgcggctctt ctttccccag    60
ctctgggacc acctctcaag tgatcctgtt tatttatttg tttatttatt tattttatg   120
ttgctgattt tctacaagac tgtttcttat cttccagcac aaacttgcca cagtgtaata   180
aacatagcct atttcttgct tttgg                                         205
```

<210> SEQ ID NO 156
<211> LENGTH: 1935
<212> TYPE: PRT
<213> ORGANISM: Homo sapiens

<400> SEQUENCE: 156

| | | | | | | | | | | | | | | |
|---|---|---|---|---|---|---|---|---|---|---|---|---|---|---|
| Met | Gly | Asp | Ser | Glu | Met | Ala | Val | Phe | Gly | Ala | Ala | Pro | Tyr | Leu |
| 1 | | | | 5 | | | | | 10 | | | | | 15 |
| Arg | Lys | Ser | Glu | Lys | Glu | Arg | Leu | Glu | Ala | Gln | Thr | Arg | Pro | Phe | Asp |
| | | | 20 | | | | | 25 | | | | | 30 | | |
| Leu | Lys | Lys | Asp | Val | Phe | Val | Pro | Asp | Asp | Lys | Gln | Glu | Phe | Val | Lys |
| | | | 35 | | | | | 40 | | | | | 45 | | |
| Ala | Lys | Ile | Val | Ser | Arg | Glu | Gly | Gly | Lys | Val | Thr | Ala | Glu | Thr | Glu |
| | 50 | | | | | 55 | | | | | 60 | | | | |
| Tyr | Gly | Lys | Thr | Val | Thr | Val | Lys | Glu | Asp | Gln | Val | Met | Gln | Gln | Asn |
| 65 | | | | | 70 | | | | | 75 | | | | | 80 |
| Pro | Pro | Lys | Phe | Asp | Lys | Ile | Glu | Asp | Met | Ala | Met | Leu | Thr | Phe | Leu |
| | | | | 85 | | | | | 90 | | | | | 95 | |
| His | Glu | Pro | Ala | Val | Leu | Tyr | Asn | Leu | Lys | Asp | Arg | Tyr | Gly | Ser | Trp |
| | | | 100 | | | | | 105 | | | | | 110 | | |
| Met | Ile | Tyr | Thr | Tyr | Ser | Gly | Leu | Phe | Cys | Val | Thr | Val | Asn | Pro | Tyr |
| | | | 115 | | | | | 120 | | | | | 125 | | |
| Lys | Trp | Leu | Pro | Val | Tyr | Thr | Pro | Glu | Val | Val | Ala | Ala | Tyr | Arg | Gly |
| | 130 | | | | | 135 | | | | | 140 | | | | |
| Lys | Lys | Arg | Ser | Glu | Ala | Pro | Pro | His | Ile | Phe | Ser | Ile | Ser | Asp | Asn |
| 145 | | | | | 150 | | | | | 155 | | | | | 160 |
| Ala | Tyr | Gln | Tyr | Met | Leu | Thr | Asp | Arg | Glu | Asn | Gln | Ser | Ile | Leu | Ile |
| | | | | 165 | | | | | 170 | | | | | 175 | |
| Thr | Gly | Glu | Ser | Gly | Ala | Gly | Lys | Thr | Val | Asn | Thr | Lys | Arg | Val | Ile |
| | | | 180 | | | | | 185 | | | | | 190 | | |
| Gln | Tyr | Phe | Ala | Val | Ile | Ala | Ala | Ile | Gly | Asp | Arg | Ser | Lys | Lys | Asp |
| | | | 195 | | | | | 200 | | | | | 205 | | |
| Gln | Ser | Pro | Gly | Lys | Gly | Thr | Leu | Glu | Asp | Gln | Ile | Ile | Gln | Ala | Asn |
| | 210 | | | | | 215 | | | | | 220 | | | | |
| Pro | Ala | Leu | Glu | Ala | Phe | Gly | Asn | Ala | Lys | Thr | Val | Arg | Asn | Asp | Asn |
| 225 | | | | | 230 | | | | | 235 | | | | | 240 |
| Ser | Ser | Arg | Phe | Gly | Lys | Phe | Ile | Arg | Ile | His | Phe | Gly | Ala | Thr | Gly |
| | | | | 245 | | | | | 250 | | | | | 255 | |
| Lys | Leu | Ala | Ser | Ala | Asp | Ile | Glu | Thr | Tyr | Leu | Leu | Glu | Lys | Ser | Arg |
| | | | 260 | | | | | 265 | | | | | 270 | | |
| Val | Ile | Phe | Gln | Leu | Lys | Ala | Glu | Arg | Asp | Tyr | His | Ile | Phe | Tyr | Gln |
| | | | 275 | | | | | 280 | | | | | 285 | | |
| Ile | Leu | Ser | Asn | Lys | Lys | Pro | Glu | Leu | Leu | Asp | Met | Leu | Leu | Ile | Thr |
| | 290 | | | | | 295 | | | | | 300 | | | | |
| Asn | Asn | Pro | Tyr | Asp | Tyr | Ala | Phe | Ile | Ser | Gln | Gly | Glu | Thr | Thr | Val |
| 305 | | | | | 310 | | | | | 315 | | | | | 320 |

-continued

```
Ala Ser Ile Asp Asp Ala Glu Glu Leu Met Ala Thr Asp Asn Ala Phe
            325                 330                 335

Asp Val Leu Gly Phe Thr Ser Glu Glu Lys Asn Ser Met Tyr Lys Leu
            340                 345                 350

Thr Gly Ala Ile Met His Phe Gly Asn Met Lys Phe Lys Leu Lys Gln
            355                 360                 365

Arg Glu Glu Gln Ala Glu Pro Asp Gly Thr Glu Glu Ala Asp Lys Ser
        370                 375                 380

Ala Tyr Leu Met Gly Leu Asn Ser Ala Asp Leu Leu Lys Gly Leu Cys
385                 390                 395                 400

His Pro Arg Val Lys Val Gly Asn Glu Tyr Val Thr Lys Gly Gln Asn
                405                 410                 415

Val Gln Gln Val Ile Tyr Ala Thr Gly Ala Leu Ala Lys Ala Val Tyr
                420                 425                 430

Glu Arg Met Phe Asn Trp Met Val Thr Arg Ile Asn Ala Thr Leu Glu
            435                 440                 445

Thr Lys Gln Pro Arg Gln Tyr Phe Ile Gly Val Leu Asp Ile Ala Gly
            450                 455                 460

Phe Glu Ile Phe Asp Phe Asn Ser Phe Glu Gln Leu Cys Ile Asn Phe
465                 470                 475                 480

Thr Asn Glu Lys Leu Gln Gln Phe Phe Asn His His Met Phe Val Leu
                485                 490                 495

Glu Gln Glu Glu Tyr Lys Lys Glu Gly Ile Glu Trp Thr Phe Ile Asp
                500                 505                 510

Phe Gly Met Asp Leu Gln Ala Cys Ile Asp Leu Ile Glu Lys Pro Met
            515                 520                 525

Gly Ile Met Ser Ile Leu Glu Glu Glu Cys Met Phe Pro Lys Ala Thr
            530                 535                 540

Asp Met Thr Phe Lys Ala Lys Leu Phe Asp Asn His Leu Gly Lys Ser
545                 550                 555                 560

Ala Asn Phe Gln Lys Pro Arg Asn Ile Lys Gly Lys Pro Glu Ala His
                565                 570                 575

Phe Ser Leu Ile His Tyr Ala Gly Ile Val Asp Tyr Asn Ile Ile Gly
            580                 585                 590

Trp Leu Gln Lys Asn Lys Asp Pro Leu Asn Glu Thr Val Val Gly Leu
            595                 600                 605

Tyr Gln Lys Ser Ser Leu Lys Leu Leu Ser Thr Leu Phe Ala Asn Tyr
        610                 615                 620

Ala Gly Ala Asp Ala Pro Ile Glu Lys Gly Lys Gly Lys Ala Lys Lys
625                 630                 635                 640

Gly Ser Ser Phe Gln Thr Val Ser Ala Leu His Arg Glu Asn Leu Asn
                645                 650                 655

Lys Leu Met Thr Asn Leu Arg Ser Thr His Pro His Phe Val Arg Cys
            660                 665                 670

Ile Ile Pro Asn Glu Thr Lys Ser Pro Gly Val Met Asp Asn Pro Leu
            675                 680                 685

Val Met His Gln Leu Arg Cys Asn Gly Val Leu Glu Gly Ile Arg Ile
        690                 695                 700

Cys Arg Lys Gly Phe Pro Asn Arg Ile Leu Tyr Gly Asp Phe Arg Gln
705                 710                 715                 720

Arg Tyr Arg Ile Leu Asn Pro Ala Ala Ile Pro Glu Gly Gln Phe Ile
                725                 730                 735
```

Asp Ser Arg Lys Gly Ala Glu Lys Leu Leu Ser Ser Leu Asp Ile Asp
                740                 745                 750

His Asn Gln Tyr Lys Phe Gly His Thr Lys Val Phe Phe Lys Ala Gly
            755                 760                 765

Leu Leu Gly Leu Leu Glu Glu Met Arg Asp Glu Arg Leu Ser Arg Ile
        770                 775                 780

Ile Thr Arg Ile Gln Ala Gln Ser Arg Gly Val Leu Ala Arg Met Glu
785                 790                 795                 800

Tyr Lys Lys Leu Leu Glu Arg Arg Asp Ser Leu Leu Val Ile Gln Trp
                805                 810                 815

Asn Ile Arg Ala Phe Met Gly Val Lys Asn Trp Pro Trp Met Lys Leu
            820                 825                 830

Tyr Phe Lys Ile Lys Pro Leu Leu Lys Ser Ala Glu Arg Glu Lys Glu
        835                 840                 845

Met Ala Ser Met Lys Glu Glu Phe Thr Arg Leu Lys Glu Ala Leu Glu
850                 855                 860

Lys Ser Glu Ala Arg Arg Lys Glu Leu Glu Glu Lys Met Val Ser Leu
865                 870                 875                 880

Leu Gln Glu Lys Asn Asp Leu Gln Leu Gln Val Gln Ala Glu Gln Asp
                885                 890                 895

Asn Leu Ala Asp Ala Glu Glu Arg Cys Asp Gln Leu Ile Lys Asn Lys
            900                 905                 910

Ile Gln Leu Glu Ala Lys Val Lys Glu Met Asn Glu Arg Leu Glu Asp
        915                 920                 925

Glu Glu Glu Met Asn Ala Glu Leu Thr Ala Lys Lys Arg Lys Leu Glu
930                 935                 940

Asp Glu Cys Ser Glu Leu Lys Arg Asp Ile Asp Asp Leu Glu Leu Thr
945                 950                 955                 960

Leu Ala Lys Val Glu Lys Glu Lys His Ala Thr Glu Asn Lys Val Lys
                965                 970                 975

Asn Leu Thr Glu Glu Met Ala Gly Leu Asp Glu Ile Ile Ala Lys Leu
            980                 985                 990

Thr Lys Glu Lys Lys Ala Leu Gln Glu Ala His Gln Gln Ala Leu Asp
        995                 1000                1005

Asp Leu Gln Ala Glu Glu Asp Lys Val Asn Thr Leu Thr Lys Ala
1010                    1015                1020

Lys Val Lys Leu Glu Gln Gln Val Asp Asp Leu Glu Gly Ser Leu
1025                    1030                1035

Glu Gln Glu Lys Lys Val Arg Met Asp Leu Glu Arg Ala Lys Arg
1040                    1045                1050

Lys Leu Glu Gly Asp Leu Lys Leu Thr Gln Glu Ser Ile Met Asp
1055                    1060                1065

Leu Glu Asn Asp Lys Gln Gln Leu Asp Glu Arg Leu Lys Lys Lys
1070                    1075                1080

Asp Phe Glu Leu Asn Ala Leu Asn Ala Arg Ile Glu Asp Glu Gln
1085                    1090                1095

Ala Leu Gly Ser Gln Leu Gln Lys Lys Leu Lys Glu Leu Gln Ala
1100                    1105                1110

Arg Ile Glu Glu Leu Glu Glu Glu Leu Glu Ala Glu Arg Thr Ala
1115                    1120                1125

Arg Ala Lys Val Glu Lys Leu Arg Ser Asp Leu Ser Arg Glu Leu
1130                    1135                1140

Glu Glu Ile Ser Glu Arg Leu Glu Glu Ala Gly Gly Ala Thr Ser

-continued

|  | 1145 |  |  | 1150 |  |  | 1155 |  |  |
| --- | --- | --- | --- | --- | --- | --- | --- | --- | --- |
| Val | Gln | Ile | Glu | Met | Asn | Lys | Lys | Arg | Glu | Ala | Glu | Phe | Gln | Lys |
|  | 1160 |  |  | 1165 |  |  | 1170 |  |  |
| Met | Arg | Arg | Asp | Leu | Glu | Glu | Ala | Thr | Leu | Gln | His | Glu | Ala | Thr |
|  | 1175 |  |  | 1180 |  |  | 1185 |  |  |
| Ala | Ala | Ala | Leu | Arg | Lys | Lys | His | Ala | Asp | Ser | Val | Ala | Glu | Leu |
|  | 1190 |  |  | 1195 |  |  | 1200 |  |  |
| Gly | Glu | Gln | Ile | Asp | Asn | Leu | Gln | Arg | Val | Lys | Gln | Lys | Leu | Glu |
|  | 1205 |  |  | 1210 |  |  | 1215 |  |  |
| Lys | Glu | Lys | Ser | Glu | Phe | Lys | Leu | Glu | Leu | Asp | Asp | Val | Thr | Ser |
|  | 1220 |  |  | 1225 |  |  | 1230 |  |  |
| Asn | Met | Glu | Gln | Ile | Ile | Lys | Ala | Lys | Ala | Asn | Leu | Glu | Lys | Met |
|  | 1235 |  |  | 1240 |  |  | 1245 |  |  |
| Cys | Arg | Thr | Leu | Glu | Asp | Gln | Met | Asn | Glu | His | Arg | Ser | Lys | Ala |
|  | 1250 |  |  | 1255 |  |  | 1260 |  |  |
| Glu | Glu | Thr | Gln | Arg | Ser | Val | Asn | Asp | Leu | Thr | Ser | Gln | Arg | Ala |
|  | 1265 |  |  | 1270 |  |  | 1275 |  |  |
| Lys | Leu | Gln | Thr | Glu | Asn | Gly | Glu | Leu | Ser | Arg | Gln | Leu | Asp | Glu |
|  | 1280 |  |  | 1285 |  |  | 1290 |  |  |
| Lys | Glu | Ala | Leu | Ile | Ser | Gln | Leu | Thr | Arg | Gly | Lys | Leu | Thr | Tyr |
|  | 1295 |  |  | 1300 |  |  | 1305 |  |  |
| Thr | Gln | Gln | Leu | Glu | Asp | Leu | Lys | Arg | Gln | Leu | Glu | Glu | Glu | Val |
|  | 1310 |  |  | 1315 |  |  | 1320 |  |  |
| Lys | Ala | Lys | Asn | Ala | Leu | Ala | His | Ala | Leu | Gln | Ser | Ala | Arg | His |
|  | 1325 |  |  | 1330 |  |  | 1335 |  |  |
| Asp | Cys | Asp | Leu | Leu | Arg | Glu | Gln | Tyr | Glu | Glu | Glu | Thr | Glu | Ala |
|  | 1340 |  |  | 1345 |  |  | 1350 |  |  |
| Lys | Ala | Glu | Leu | Gln | Arg | Val | Leu | Ser | Lys | Ala | Asn | Ser | Glu | Val |
|  | 1355 |  |  | 1360 |  |  | 1365 |  |  |
| Ala | Gln | Trp | Arg | Thr | Lys | Tyr | Glu | Thr | Asp | Ala | Ile | Gln | Arg | Thr |
|  | 1370 |  |  | 1375 |  |  | 1380 |  |  |
| Glu | Glu | Leu | Glu | Glu | Ala | Lys | Lys | Lys | Leu | Ala | Gln | Arg | Leu | Gln |
|  | 1385 |  |  | 1390 |  |  | 1395 |  |  |
| Glu | Ala | Glu | Glu | Ala | Val | Glu | Ala | Val | Asn | Ala | Lys | Cys | Ser | Ser |
|  | 1400 |  |  | 1405 |  |  | 1410 |  |  |
| Leu | Glu | Lys | Thr | Lys | His | Arg | Leu | Gln | Asn | Glu | Ile | Glu | Asp | Leu |
|  | 1415 |  |  | 1420 |  |  | 1425 |  |  |
| Met | Val | Asp | Val | Glu | Arg | Ser | Asn | Ala | Ala | Ala | Ala | Leu | Asp |
|  | 1430 |  |  | 1435 |  |  | 1440 |  |  |
| Lys | Lys | Gln | Arg | Asn | Phe | Asp | Lys | Ile | Leu | Ala | Glu | Trp | Lys | Gln |
|  | 1445 |  |  | 1450 |  |  | 1455 |  |  |
| Lys | Tyr | Glu | Glu | Ser | Gln | Ser | Glu | Leu | Glu | Ser | Ser | Gln | Lys | Glu |
|  | 1460 |  |  | 1465 |  |  | 1470 |  |  |
| Ala | Arg | Ser | Leu | Ser | Thr | Glu | Leu | Phe | Lys | Leu | Lys | Asn | Ala | Tyr |
|  | 1475 |  |  | 1480 |  |  | 1485 |  |  |
| Glu | Glu | Ser | Leu | Glu | His | Leu | Glu | Thr | Phe | Lys | Arg | Glu | Asn | Lys |
|  | 1490 |  |  | 1495 |  |  | 1500 |  |  |
| Asn | Leu | Gln | Glu | Glu | Ile | Ser | Asp | Leu | Thr | Glu | Gln | Leu | Gly | Ser |
|  | 1505 |  |  | 1510 |  |  | 1515 |  |  |
| Ser | Gly | Lys | Thr | Ile | His | Glu | Leu | Glu | Lys | Val | Arg | Lys | Gln | Leu |
|  | 1520 |  |  | 1525 |  |  | 1530 |  |  |
| Glu | Ala | Glu | Lys | Met | Glu | Leu | Gln | Ser | Ala | Leu | Glu | Glu | Ala | Glu |
|  | 1535 |  |  | 1540 |  |  | 1545 |  |  |

```
Ala Ser Leu Glu His Glu Glu Gly Lys Ile Leu Arg Ala Gln Leu
1550                1555                1560

Glu Phe Asn Gln Ile Lys Ala Glu Ile Glu Arg Lys Leu Ala Glu
1565                1570                1575

Lys Asp Glu Glu Met Glu Gln Ala Lys Arg Asn His Leu Arg Val
1580                1585                1590

Val Asp Ser Leu Gln Thr Ser Leu Asp Ala Glu Thr Arg Ser Arg
1595                1600                1605

Asn Glu Ala Leu Arg Val Lys Lys Lys Met Glu Gly Asp Leu Asn
1610                1615                1620

Glu Met Glu Ile Gln Leu Ser His Ala Asn Arg Met Ala Ala Glu
1625                1630                1635

Ala Gln Lys Gln Val Lys Ser Leu Gln Ser Leu Leu Lys Asp Thr
1640                1645                1650

Gln Ile Gln Leu Asp Asp Ala Val Arg Ala Asn Asp Asp Leu Lys
1655                1660                1665

Glu Asn Ile Ala Ile Val Glu Arg Arg Asn Asn Leu Leu Gln Ala
1670                1675                1680

Glu Leu Glu Glu Leu Arg Ala Val Val Glu Gln Thr Glu Arg Ser
1685                1690                1695

Arg Lys Leu Ala Glu Gln Glu Leu Ile Glu Thr Ser Glu Arg Val
1700                1705                1710

Gln Leu Leu His Ser Gln Asn Thr Ser Leu Ile Asn Gln Lys Lys
1715                1720                1725

Lys Met Asp Ala Asp Leu Ser Gln Leu Gln Thr Glu Val Glu Glu
1730                1735                1740

Ala Val Gln Glu Cys Arg Asn Ala Glu Glu Lys Ala Lys Lys Ala
1745                1750                1755

Ile Thr Asp Ala Ala Met Met Ala Glu Glu Leu Lys Lys Glu Gln
1760                1765                1770

Asp Thr Ser Ala His Leu Glu Arg Met Lys Lys Asn Met Glu Gln
1775                1780                1785

Thr Ile Lys Asp Leu Gln His Arg Leu Asp Glu Ala Glu Gln Ile
1790                1795                1800

Ala Leu Lys Gly Gly Lys Lys Gln Leu Gln Lys Leu Glu Ala Arg
1805                1810                1815

Val Arg Glu Leu Glu Asn Glu Leu Glu Ala Glu Gln Lys Arg Asn
1820                1825                1830

Ala Glu Ser Val Lys Gly Met Arg Lys Ser Glu Arg Arg Ile Lys
1835                1840                1845

Glu Leu Thr Tyr Gln Thr Glu Glu Asp Arg Lys Asn Leu Leu Arg
1850                1855                1860

Leu Gln Asp Leu Val Asp Lys Leu Gln Leu Lys Val Lys Ala Tyr
1865                1870                1875

Lys Arg Gln Ala Glu Glu Ala Glu Glu Gln Ala Asn Thr Asn Leu
1880                1885                1890

Ser Lys Phe Arg Lys Val Gln His Glu Leu Asp Glu Ala Glu Glu
1895                1900                1905

Arg Ala Asp Ile Ala Glu Ser Gln Val Asn Lys Leu Arg Ala Lys
1910                1915                1920

Ser Arg Asp Ile Gly Thr Lys Gly Leu Asn Glu Glu
1925                1930                1935
```

<210> SEQ ID NO 157
<211> LENGTH: 6069
<212> TYPE: DNA
<213> ORGANISM: Homo sapiens

<400> SEQUENCE: 157

| | | | | | |
|---|---|---|---|---|---|
| cagcccctga | gaccaggtct | ggctccacag | ctctgtcctg | ctctgtgtct | ttccctgctg | 60 |
| ctctcaggtc | ccctgcaggc | cttggcccct | ttcctcatct | gtagacacac | ttgagtagcc | 120 |
| caggcacagc | catgggagat | tcggagatgg | cagtctttgg | ggctgccgcc | ccctacctgc | 180 |
| gcaagtcaga | gaaggagcgg | ctagaagcgc | agaccaggcc | ttttgacctc | aagaaggatg | 240 |
| tcttcgtgcc | tgatgacaaa | caggagtttg | tcaaggccaa | gatcgtgtct | cgagagggtg | 300 |
| gcaaagtcac | tgccgagacc | gagtatggca | agacagtgac | cgtgaaggag | gaccaggtga | 360 |
| tgcagcagaa | cccacccaag | ttcgacaaaa | tcgaggacat | ggccatgctg | accttcctgc | 420 |
| atgagcccgc | ggtgctctac | aacctcaagg | atcgctacgg | ctcctggatg | atctacacct | 480 |
| actcgggcct | cttctgtgtc | accgtcaacc | cttacaagtg | gctgccggtg | tacactcctg | 540 |
| aggtggtggc | tgcctaccgg | ggcaagaaga | ggagcgaggc | cccgccccac | atcttctcca | 600 |
| tctccgacaa | cgcctatcag | tacatgctga | cagacagaga | aaaccagtcc | atcctgatca | 660 |
| ccggagaatc | cggagcaggg | aagacagtca | acaccaagag | ggtcatccag | tactttgctg | 720 |
| ttattgcagc | cattggggac | cgcagcaaga | aggaccagag | cccgggcaag | ggcaccctgg | 780 |
| aggaccagat | catccaggcc | aaccctgctc | tggaggcctt | tggcaatgcc | aagaccgtcc | 840 |
| ggaacgacaa | ctcctcccgc | ttcgggaaat | tcattcgaat | tcattttggg | gcaacaggaa | 900 |
| agttggcatc | tgcagacata | gagacctatc | ttctggaaaa | atccagagtt | attttccagc | 960 |
| tgaaagcaga | gagagattat | cacattttct | accaaatcct | gtctaacaaa | aagcctgagc | 1020 |
| tgctggacat | gctgctgatc | accaacaacc | cctacgatta | tgcattcatc | tcccaaggag | 1080 |
| agaccaccgt | ggcctccatt | gatgacgctg | aggagctcat | ggccactgat | aacgcttttg | 1140 |
| atgtgctggg | cttcacttca | gaggagaaaa | actccatgta | taagctgaca | ggcgccatca | 1200 |
| tgcactttgg | aaacatgaag | ttcaagctga | agcagcggga | ggagcaggcg | gagccagacg | 1260 |
| gcactgaaga | ggctgacaag | tctgcctacc | tcatggggct | gaactcagcc | gacctgctca | 1320 |
| aggggctgtg | ccaccctcgg | gtgaaagtgg | gcaatgagta | cgtcaccaag | gggcagaatg | 1380 |
| tccagcaggt | gatatatgcc | actggggcac | tggccaaggc | agtgtatgag | aggatgttca | 1440 |
| actggatggt | gacgcgcatc | aatgccaccc | tggagaccaa | gcagccacgc | cagtacttca | 1500 |
| taggagtcct | ggacatcgct | ggcttcgaga | tcttcgattt | caacagcttt | gagcagctct | 1560 |
| gcatcaactt | caccaacgag | aagctgcagc | agttcttcaa | ccaccacatg | tttgtgctgg | 1620 |
| agcaggagga | gtacaagaag | gagggcatcg | agtggacatt | cattgacttt | ggcatggacc | 1680 |
| tgcaggcctg | cattgacctc | atcgagaagc | ccatgggcat | catgtccatc | ctggaagagg | 1740 |
| agtgcatgtt | ccccaaggcc | accgacatga | ccttcaaggc | caagctgttt | gacaaccacc | 1800 |
| tgggcaaatc | cgccaacttc | agaagccac | gcaatatcaa | ggggaagcct | gaagcccact | 1860 |
| tctccctgat | ccactatgcc | ggcatcgtgg | actacaacat | cattggctgg | ctgcagaaga | 1920 |
| acaaggatcc | tctcaatgag | actgtcgtgg | gcttgtatca | gaagtcttcc | ctcaagctgc | 1980 |
| tcagcaccct | gtttgccaac | tatgctgggg | ctgatgcgcc | tattgagaag | gcaaaggca | 2040 |
| aggccaagaa | aggctcgtcc | tttcagactg | tgtcagctct | gcacagggaa | aatctgaaca | 2100 |
| agctgatgac | caacttgcgc | tccacccat | cccacttttgt | acgttgtatc | atccctaatg | 2160 |

```
agacaaagtc tccaggggtg atggacaacc ccctggtcat gcaccagctg cgctgcaatg    2220
gtgtgctgga gggcatccgc atctgcagga aaggcttccc caaccgcatc ctctacgggg    2280
acttccggca gaggtatcgc atcctgaacc cagcggccat ccctgaggga cagttcattg    2340
atagcaggaa gggggcagag aagctgctca gctccctgga cattgatcac aaccagtaca    2400
agtttggcca caccaaggtg ttcttcaagg ccgggctgct ggggctgctg gaggaaatga    2460
gggacgagag gctgagccgc atcatcacgc gtatccaggc ccagtcccga ggtgtgctcg    2520
ccagaatgga gtacaaaaag ctgctggaac gtagagactc cctgctggta atccagtgga    2580
acattcgggc cttcatgggg gtcaagaatt ggccctggat gaagctctac ttcaagatca    2640
agccgctgct gaagagtgca gaaagagaga aggagatggc ctccatgaag gaggagttca    2700
cacgcctcaa agaggcgcta gagaagtccg aggctcgccg caaggagctg aggagaagaa    2760
tggtgtccct gctgcaggag aagaatgacc tgcagctcca agtgcaggcg aacaagaca    2820 acctggcaga tgctgaggag cgctgtgatc agctgatcaa aaacaagatt cagctggagg    2880
ccaaggtgaa ggagatgaac gagaggctgg aggatgagga ggagatgaat gctgagctca    2940
ctgccaagaa gcgcaagctg gaagatgagt gctcagagct caaaagggac atcgatgatc    3000
tggagctgac actggccaaa gtggagaagg agaaacacgc aacagagaac aaggtgaaaa    3060
acctgacaga ggagatggct gggctggatg agatcattgc caagctgacc aaggagaaga    3120
aagctctgca agaggcccac caacaggctc tggatgacct tcaggccgag gaggacaagg    3180
tcaacaccct gactaaggcc aaagtcaagc tggagcagca agtggatgat ctggaaggat    3240
ccctggagca agagaagaag gtgcgcatgg acctggagcg agcgaagcgg aagctggagg    3300
gcgacctgaa gctgacccag gagagcatca tggacctgga gaatgacaag cagcagctgg    3360
atgagcggct gaaaaaaaaa gactttgagc tgaatgctct caacgcaagg attgaggatg    3420
aacaggccct cggcagccag ctgcagaaga agctcaagga gcttcaggca cgcatcgagg    3480
agctggagga ggagctggag gccgagcgca ccgccagggc taaggtggag aagctgcgct    3540
cagacctgtc tcgggagctg gaggagatca gcgagcggct ggaagaggcc ggcgggccga    3600
cgtccgtgca gatcgagatg aacaagaagc gcgaggccga gttccagaag atgcggcggg    3660
acctggagga ggccacgctg cagcacgagg ccactgccgc ggccctgcgc aagaagcacg    3720
ccgacagcgt ggccgagctg ggcgagcaga tcgacaacct gcagcgggtg aagcagaagc    3780
tggagaagga gaagagcgag ttcaagctgg agctggatga cgtcacctcc aacatggagc    3840
agatcatcaa ggccaaggct aacctggaga agatgtgccg gaccttggaa gaccagatga    3900
atgagcaccg gagcaaggcg gaggagaccc agcgttctgt caacgacctc accagccagc    3960
gggccaagtt gcaaaccgag aatggtgagc tgtcccggca gctggatgag aaggaggcac    4020
tgatctccca gctgacccga ggcaagctca cctacaccca gcagctggag gacctcaaga    4080
ggcagctgga ggaggaggtt aaggcgaaga acgccctggc ccacgcactg cagtcggccc    4140
ggcatgactg cgacctgctg cgggagcagt acgaggagga gacggaggcc aaggccgagc    4200
tgcagcgcgt cctttccaag gccaactcgg aggtggccca gtggaggacc aagtatgaga    4260
cggacgccat tcagcggact gaggagctcg aggaggccaa gaagaagctg gcccagcggc    4320
tgcaggaagc tgaggaggcc gtggaggctg ttaatgccaa gtgctcctcg ctggagaaga    4380
ccaagcaccg gctacagaat gagatcgagg acttgatggt ggacgtagag cgctccaatg    4440
ctgctgctgc agccctggac aagaagcaga ggaacttcga caagatcctg gccgagtgga    4500
```

-continued

```
agcagaagta tgaggagtcg cagtcggagc tggagtcctc gcagaaggag gctcgctccc    4560
tcagcacaga gctcttcaaa ctcaagaacg cctatgagga gtccctggaa catctggaga    4620
ccttcaagcg ggagaacaaa aacctgcagg aggagatctc cgacttgact gagcagttgg    4680
gttccagcgg aaagactatc catgagctgg agaaggtccg aaagcagctg gaggccgaga    4740
agatggagct gcagtcagcc ctggaggagg ccgaggcctc cctggagcac gaggagggca    4800
agatcctccg ggcccagctg gagttcaacc agatcaaggc agagatcgag cggaagctgg    4860
cagagaagga cgaggagatg aacaggcca agcgcaacca cctgcgggtg gtggactcgc    4920
tgcagaccct cctggacgca gagacacgca gccgcaacga ggccctgagg gtgaagaaga    4980
agatggaagg agacctcaat gagatggaga tccagctcag ccacgccaac cgcatggccg    5040
ccgaggccca gaagcaagtc aagagcctcc agagcttgtt gaaggacacc agattcagc    5100 tggacgatgc agtccgtgcc aacgacgacc tgaaggagaa catcgccatc gtggagcggc    5160
gcaacaacct gctgcaggct gagctggagg agttgcgtgc cgtggtggag cagacagagc    5220
ggtcccggaa gctggcggag caggagctga ttgagactag tgagcgggtg cagctgctgc    5280
attcccagaa caccagcctc atcaaccaga agaagaagat ggatgctgac ctgtcccagc    5340
tccagactga agtggaggag gcagtgcagg agtgcaggaa tgctgaggag aaggccaaga    5400
aggccatcac ggatgccgcc atgatggcag aggagctgaa aaggagcag gacaccagcg    5460 cccacctgga gcgcatgaag aagaacatgg aacagaccat taaggacctg cagcaccggc    5520
tggacgaagc cgagcagatc gccctcaagg gcggcaagaa gcagctgcag aagctggaag    5580
cgcgggtgcg ggagctggag aatgagctgg aggccgagca gaagcgcaac gcagagtcgg    5640
tgaagggcat gaggaagagc gagcggcgca tcaaggagct cacctaccag acggaggagg    5700
acaggaaaaa cctgctgcgg ctgcaggacc tggtagacaa gctgcagcta aaggtcaagg    5760
cctacaagcg ccaggccgag gaggcggagg agcaagccaa caccaacctg tccaagttcc    5820
gcaaggtgca gcacgagctg gatgaggcag aggagcgggc ggacatcgcc gagtcccagg    5880
tcaacaagct gcgggccaag agccgtgaca ttggcacgaa gggcttgaat gaggagtagc    5940
tttgccacat cttgatctgc tcagccctgg aggtgccagc aaagccccat gctggagcct    6000
gtgtaacagc tccttgggag gaagcagaat aaagcaattt tccttgaagc cgagaaaaaa    6060
aaaaaaaaa                                                           6069
```

<210> SEQ ID NO 158
<211> LENGTH: 151
<212> TYPE: PRT
<213> ORGANISM: Homo sapiens

<400> SEQUENCE: 158

```
Met Ser Ser Phe Ser Thr Thr Thr Val Ser Phe Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95
```

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150

<210> SEQ ID NO 159
<211> LENGTH: 858
<212> TYPE: DNA
<213> ORGANISM: Homo sapiens

<400> SEQUENCE: 159
gagacaggga cagacgtagg ccaagagagg ggaaccagag aggaaccaga ggggagagac    60
agagcagcaa gcagtggatt gctccttgac gacgccagca tgagctcctt ctccaccacc   120
accgtgagct tcctcctttt actggcattc agctcctag gtcagaccag agctaatccc   180
atgtacaatg ccgtgtccaa cgcagacctg atggatttca gaatttgct ggaccatttg   240 gaagaaaaga tgcctttaga agatgaggtc gtgcccccac aagtgctcag tgagccgaat   300
gaagaagcgg gggctgctct cagcccccctc cctgaggtgc ctccctggac cggggaagtc   360
agcccagccc agagagatgg aggtgccctc gggcggggcc cctgggactc tctgatcga   420 tctgccctcc taaaaagcaa gctgagggcg ctgctcactg cccctcggag cctgcggaga   480
tccagctgct tcgggggcag gatggacagg attggagccc agagcggact gggctgtaac   540
agcttccggt actgaagata acagccaggg aggacaagca gggctgggcc tagggacaga   600
ctgcaagagg ctcctgtccc ctggggtctc tgctgcattt gtgtcatctt gttgccatgg   660
agttgtgatc atcccatcta agctgcagct tcctgtcaac acttctcaca tcttatgcta   720
actgtagata aagtggtttg atggtgactt cctcgcctct cccaccccat gcattaaatt   780
ttaaggtaga acctcacctg ttactgaaag tggtttgaaa gtgaataaac ttcagcacca   840
tggacagaag acaaaaaa                                                 858

<210> SEQ ID NO 160
<211> LENGTH: 134
<212> TYPE: PRT
<213> ORGANISM: Homo sapiens

<400> SEQUENCE: 160

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

```
Phe Gly Arg Lys Met Asp Arg Ile Ser Ser Ser Gly Leu Gly Cys
        115                 120                 125

Lys Val Leu Arg Arg His
    130
```

<210> SEQ ID NO 161
<211> LENGTH: 708
<212> TYPE: DNA
<213> ORGANISM: Homo sapiens

<400> SEQUENCE: 161

```
ccccgcaggc tgagggcagg tgggaagcaa acccggacgc atcgcagcag cagcagcagc      60
agcagaagca gcagcagcag cctccgcagt ccctccagag acatggatcc ccagacagca     120
ccttcccggg cgctcctgct cctgctcttc ttgcatctgg ctttcctggg aggtcgttcc     180
cacccgctgg gcagccccgg ttcagcctcg gacttggaaa cgtccgggtt acaggagcag     240
cgcaaccatt tgcagggcaa actgtcggag ctgcaggtgg agcagacatc cctggagccc     300
ctccaggaga gcccccgtcc cacaggtgtc tggaagtccc gggaggtagc caccgagggc     360
atccgtgggc accgcaaaat ggtcctctac accctgcggg caccacgaag ccccaagatg     420
gtgcaagggt ctggctgctt tgggaggaag atggaccgga tcagctcctc cagtggcctg     480
ggctgcaaag tgctgaggcg gcattaagag gaagtcctgg ctgcagacac ctgcttctga     540
ttccacaagg ggcttttttcc tcaaccctgt ggccgccttt gaagtgactc attttttaa      600
tgtatttatg tatttatttg attgttttat ataagatggt ttcttacctt tgagcacaaa     660
atttccacgg tgaaataaag tcaacattat aagctttaaa aaaaaaaa                  708
```

<210> SEQ ID NO 162
<211> LENGTH: 1935
<212> TYPE: PRT
<213> ORGANISM: Rattus norvegicus

<400> SEQUENCE: 162

```
Met Ala Asp Arg Glu Met Ala Ala Phe Gly Ala Gly Ala Pro Phe Leu
1               5                   10                  15

Arg Lys Ser Glu Lys Glu Arg Leu Glu Ala Gln Thr Arg Pro Phe Asp
            20                  25                  30

Leu Lys Lys Asp Val Phe Val Pro Asp Lys Glu Glu Phe Val Lys
        35                  40                  45

Ala Lys Ile Val Ser Arg Glu Gly Gly Lys Val Thr Ala Glu Thr Glu
    50                  55                  60

Asn Gly Lys Thr Val Thr Val Lys Glu Asp Gln Val Met Gln Gln Asn
65                  70                  75                  80

Pro Pro Lys Phe Asp Lys Ile Glu Asp Met Ala Met Leu Thr Phe Leu
                85                  90                  95

His Glu Pro Ala Val Leu Tyr Asn Leu Lys Glu Arg Tyr Ala Ser Trp
            100                 105                 110

Met Ile Tyr Thr Tyr Ser Gly Leu Phe Cys Val Thr Val Asn Pro Tyr
        115                 120                 125

Lys Trp Leu Pro Val Tyr Asn Ala Gln Val Val Ala Ala Tyr Arg Gly
    130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175
```

```
Thr Gly Glu Ser Gly Ala Gly Lys Thr Val Asn Thr Lys Arg Val Ile
            180                 185                 190

Gln Tyr Phe Ala Val Ile Ala Ala Ile Gly Asp Arg Ser Lys Lys Asp
        195                 200                 205

Gln Thr Pro Gly Lys Gly Thr Leu Glu Asp Gln Ile Ile Gln Ala Asn
    210                 215                 220

Pro Ala Leu Glu Ala Phe Gly Asn Ala Lys Thr Val Arg Asn Asp Asn
225                 230                 235                 240

Ser Ser Arg Phe Gly Lys Phe Ile Arg Ile His Phe Gly Ala Thr Gly
                245                 250                 255

Lys Leu Ala Ser Ala Asp Ile Glu Thr Tyr Leu Leu Glu Lys Ser Arg
            260                 265                 270

Val Ile Phe Gln Leu Lys Ala Glu Arg Asp Tyr His Ile Phe Tyr Gln
        275                 280                 285

Ile Leu Ser Asn Lys Lys Pro Glu Leu Leu Asp Met Leu Leu Ile Thr
    290                 295                 300

Asn Asn Pro Tyr Asp Tyr Ala Phe Phe Ser Gln Gly Glu Thr Thr Val
305                 310                 315                 320

Ala Ser Ile Asp Asp Ser Glu Glu His Met Ala Thr Asp Ser Ala Phe
                325                 330                 335

Asp Val Leu Gly Phe Thr Pro Glu Glu Lys Asn Ser Ile Tyr Lys Leu
            340                 345                 350

Thr Gly Ala Ile Met His Phe Gly Asn Met Lys Phe Lys Gln Lys Gln
        355                 360                 365

Arg Glu Glu Gln Ala Glu Pro Asp Gly Thr Glu Glu Ala Asp Lys Ser
    370                 375                 380

Ala Tyr Leu Met Gly Leu Asn Ser Ala Asp Leu Leu Lys Gly Leu Cys
385                 390                 395                 400

His Pro Arg Val Lys Val Gly Asn Glu Tyr Val Thr Lys Gly Gln Asn
                405                 410                 415

Val Gln Gln Val Ala Tyr Ala Ile Gly Ala Leu Ala Lys Ser Val Tyr
            420                 425                 430

Glu Lys Met Phe Asn Trp Met Val Thr Arg Ile Asn Ala Thr Leu Glu
        435                 440                 445

Thr Lys Gln Pro Arg Gln Tyr Phe Ile Gly Val Leu Asp Ile Ala Gly
    450                 455                 460

Phe Glu Ile Phe Asp Phe Asn Ser Phe Glu Gln Leu Cys Ile Asn Phe
465                 470                 475                 480

Thr Asn Glu Lys Leu Gln Gln Phe Phe Asn His His Met Phe Val Leu
                485                 490                 495

Glu Gln Glu Glu Tyr Lys Lys Glu Gly Ile Glu Trp Thr Phe Ile Asp
            500                 505                 510

Phe Gly Met Asp Leu Gln Ala Cys Ile Asp Leu Ile Glu Lys Pro Met
        515                 520                 525

Gly Ile Met Ser Ile Leu Glu Glu Cys Met Phe Pro Lys Ala Thr
    530                 535                 540

Asp Met Thr Phe Lys Ala Lys Leu Tyr Asp Asn His Leu Gly Lys Ser
545                 550                 555                 560

Asn Asn Phe Gln Lys Pro Arg Asn Ile Lys Gly Lys Gln Glu Ala His
                565                 570                 575

Phe Ser Leu Ile His Tyr Ala Gly Thr Val Asp Tyr Asn Ile Leu Gly
            580                 585                 590
```

-continued

```
Trp Leu Gln Lys Asn Lys Asp Pro Leu Asn Glu Thr Val Val Gly Leu
            595                 600                 605

Tyr Gln Lys Ser Ser Leu Lys Leu Leu Ser Asn Leu Phe Ala Asn Tyr
610                 615                 620

Ala Gly Ala Asp Ala Pro Val Asp Lys Gly Lys Gly Lys Ala Lys Lys
625                 630                 635                 640

Gly Ser Ser Phe Gln Thr Val Ser Ala Leu His Arg Glu Asn Leu Asn
            645                 650                 655

Lys Leu Met Thr Asn Leu Arg Ser Thr His Pro His Phe Val Arg Cys
                660                 665                 670

Ile Ile Pro Asn Glu Thr Lys Ser Pro Gly Val Met Asp Asn Pro Leu
                675                 680                 685

Val Met His Gln Leu Arg Cys Asn Gly Val Leu Glu Gly Ile Arg Ile
            690                 695                 700

Cys Arg Lys Gly Phe Pro Asn Arg Ile Leu Tyr Gly Asp Phe Arg Gln
705                 710                 715                 720

Arg Tyr Arg Ile Leu Asn Pro Ala Ala Ile Pro Glu Gly Gln Phe Ile
                725                 730                 735

Asp Ser Arg Lys Gly Ala Glu Lys Leu Leu Gly Ser Leu Asp Ile Asp
            740                 745                 750

His Asn Gln Tyr Lys Phe Gly His Thr Lys Val Phe Phe Lys Ala Gly
            755                 760                 765

Leu Leu Gly Leu Leu Glu Glu Met Arg Asp Glu Arg Leu Ser Arg Ile
            770                 775                 780

Ile Thr Arg Ile Gln Ala Gln Ser Arg Gly Val Leu Ser Arg Met Glu
785                 790                 795                 800

Phe Lys Lys Leu Leu Glu Arg Arg Asp Ser Leu Leu Ile Ile Gln Trp
                805                 810                 815

Asn Ile Arg Ala Phe Met Gly Val Lys Asn Trp Pro Trp Met Lys Leu
                820                 825                 830

Tyr Phe Lys Ile Lys Pro Leu Leu Lys Ser Ala Glu Thr Glu Lys Glu
            835                 840                 845

Met Ala Asn Met Lys Glu Glu Phe Gly Arg Val Lys Asp Ala Leu Glu
850                 855                 860

Lys Ser Glu Ala Arg Arg Lys Glu Leu Glu Glu Lys Met Val Ser Leu
865                 870                 875                 880

Leu Gln Glu Lys Asn Asp Leu Gln Leu Gln Val Gln Ala Glu Gln Asp
                885                 890                 895

Asn Leu Ala Asp Ala Glu Glu Arg Cys Asp Gln Leu Ile Lys Asn Lys
            900                 905                 910

Ile Gln Leu Glu Ala Lys Val Lys Glu Met Thr Glu Arg Leu Glu Asp
            915                 920                 925

Glu Glu Glu Met Asn Ala Glu Leu Thr Ala Lys Lys Arg Lys Leu Glu
930                 935                 940

Asp Glu Cys Ser Glu Leu Lys Arg Asp Ile Asp Asp Leu Glu Leu Thr
945                 950                 955                 960

Leu Ala Lys Val Glu Lys Glu Lys His Ala Thr Glu Asn Lys Val Lys
                965                 970                 975

Asn Leu Thr Glu Glu Met Ala Gly Leu Asp Glu Ile Ile Val Lys Leu
            980                 985                 990

Thr Lys Glu Lys Lys Ala Leu Gln  Glu Ala His Gln Gln  Ala Leu Asp
            995                 1000                1005

Asp Leu  Gln Ala Glu Glu Asp  Lys Val Asn Thr Leu  Thr Lys Ala
```

```
                1010               1015                1020
Lys Val Lys Leu Glu Gln Gln Val Asp Asp Leu Glu Gly Ser Leu
    1025               1030                1035
Asp Gln Asp Lys Lys Val Arg Met Asp Leu Glu Arg Ala Lys Arg
    1040               1045                1050
Lys Leu Glu Gly Asp Leu Lys Leu Thr Gln Glu Ser Ile Met Asp
    1055               1060                1065
Leu Glu Asn Asp Lys Gln Gln Leu Asp Glu Arg Leu Lys Lys Lys
    1070               1075                1080
Asp Phe Glu Leu Asn Ala Leu Asn Ala Arg Ile Glu Asp Glu Gln
    1085               1090                1095
Ala Leu Gly Ser Gln Leu Gln Lys Lys Leu Lys Glu Leu Gln Ala
    1100               1105                1110
Arg Ile Glu Glu Leu Glu Glu Glu Leu Glu Ala Glu Arg Thr Ala
    1115               1120                1125
Arg Ala Lys Val Glu Lys Leu Arg Ser Asp Leu Ser Arg Glu Leu
    1130               1135                1140
Glu Glu Ile Ser Glu Arg Leu Glu Glu Ala Gly Gly Ala Thr Ser
    1145               1150                1155
Val Gln Ile Glu Met Asn Lys Lys Arg Glu Ala Glu Phe Gln Lys
    1160               1165                1170
Met Arg Arg Asp Leu Glu Glu Ala Thr Leu Gln His Glu Ala Thr
    1175               1180                1185
Ala Ala Ala Leu Arg Lys Lys His Ala Asp Ser Val Ala Glu Leu
    1190               1195                1200
Gly Glu Gln Ile Asp Asn Leu Gln Arg Val Lys Gln Lys Leu Glu
    1205               1210                1215
Lys Glu Lys Ser Glu Phe Lys Leu Glu Leu Asp Asp Val Thr Ser
    1220               1225                1230
Asn Met Glu Gln Ile Ile Lys Ala Lys Ala Asn Leu Glu Lys Met
    1235               1240                1245
Cys Arg Thr Leu Glu Asp Gln Met Asn Glu His Arg Ser Lys Ala
    1250               1255                1260
Glu Glu Thr Gln Arg Ser Val Asn Asp Leu Thr Arg Gln Arg Ala
    1265               1270                1275
Lys Leu Gln Thr Glu Asn Gly Glu Leu Ser Arg Gln Leu Asp Glu
    1280               1285                1290
Lys Glu Ala Leu Ile Ser Gln Leu Thr Arg Gly Lys Leu Thr Tyr
    1295               1300                1305
Thr Gln Gln Leu Glu Asp Leu Lys Arg Gln Leu Glu Glu Glu Val
    1310               1315                1320
Lys Ala Lys Asn Ala Leu Ala His Ala Leu Gln Ser Ala Arg His
    1325               1330                1335
Asp Cys Asp Leu Leu Arg Glu Gln Tyr Glu Glu Glu Thr Glu Ala
    1340               1345                1350
Lys Ala Glu Leu Gln Arg Val Leu Ser Lys Ala Asn Ser Glu Val
    1355               1360                1365
Ala Gln Trp Arg Thr Lys Tyr Glu Thr Asp Ala Ile Gln Arg Thr
    1370               1375                1380
Glu Glu Leu Glu Glu Ala Lys Lys Lys Leu Ala Gln Arg Leu Gln
    1385               1390                1395
Asp Ala Glu Glu Ala Val Glu Ala Val Asn Ala Lys Cys Ser Ser
    1400               1405                1410
```

```
Leu Glu Lys Thr Lys His Arg Leu Gln Asn Glu Ile Glu Asp Leu
    1415            1420                1425

Met Val Asp Val Glu Arg Ser Asn Ala Ala Ala Ala Leu Asp
    1430            1435                1440

Lys Lys Gln Arg Asn Phe Asp Lys Ile Leu Val Glu Trp Lys Gln
    1445            1450                1455

Lys Tyr Glu Glu Ser Gln Ser Glu Leu Glu Ser Ser Gln Lys Glu
    1460            1465                1470

Ala Arg Ser Leu Ser Thr Glu Leu Phe Lys Leu Lys Asn Ala Tyr
    1475            1480                1485

Glu Glu Ser Leu Glu His Leu Glu Thr Phe Lys Arg Glu Asn Lys
    1490            1495                1500

Asn Leu Gln Glu Glu Ile Ser Asp Leu Thr Glu Gln Leu Gly Ser
    1505            1510                1515

Thr Gly Lys Ser Ile His Glu Leu Glu Lys Ile Arg Lys Gln Leu
    1520            1525                1530

Glu Ala Glu Lys Leu Glu Leu Gln Ser Ala Leu Glu Glu Ala Glu
    1535            1540                1545

Ala Ser Leu Glu His Glu Glu Gly Lys Ile Leu Arg Ala Gln Leu
    1550            1555                1560

Glu Phe Asn Gln Ile Lys Ala Glu Ile Glu Arg Lys Leu Ala Glu
    1565            1570                1575

Lys Asp Glu Glu Met Glu Gln Ala Lys Arg Asn His Leu Arg Val
    1580            1585                1590

Val Asp Ser Leu Gln Thr Ser Leu Asp Ala Glu Thr Arg Ser Arg
    1595            1600                1605

Asn Glu Ala Leu Arg Val Lys Lys Lys Met Glu Gly Asp Leu Asn
    1610            1615                1620

Glu Met Glu Ile Gln Leu Ser His Ala Asn Arg Met Ala Ala Glu
    1625            1630                1635

Ala Gln Lys Gln Val Lys Ser Leu Gln Ser Leu Leu Lys Asp Thr
    1640            1645                1650

Gln Ile Gln Leu Asp Asp Ala Val Arg Ala Asn Asp Asp Leu Lys
    1655            1660                1665

Glu Asn Ile Ala Ile Val Glu Arg Arg Asn Asn Leu Leu Gln Ala
    1670            1675                1680

Glu Leu Glu Glu Leu Arg Ala Val Val Glu Gln Thr Glu Arg Ser
    1685            1690                1695

Arg Lys Leu Ala Glu Gln Glu Leu Ile Glu Thr Ser Glu Arg Val
    1700            1705                1710

Gln Leu Leu His Ser Gln Asn Thr Ser Leu Ile Asn Gln Lys Lys
    1715            1720                1725

Lys Met Asp Ala Asp Leu Ser Gln Leu Gln Thr Glu Val Glu Glu
    1730            1735                1740

Ala Val Gln Glu Cys Arg Asn Ala Glu Glu Lys Ala Lys Lys Ala
    1745            1750                1755

Ile Thr Asp Ala Ala Met Met Ala Glu Glu Leu Lys Lys Glu Gln
    1760            1765                1770

Asp Thr Ser Ala His Leu Glu Arg Met Lys Asn Asn Met Glu Gln
    1775            1780                1785

Thr Ile Lys Asp Leu Gln His Arg Leu Asp Glu Ala Glu Gln Ile
    1790            1795                1800
```

```
Ala Leu Lys Gly Gly Lys Lys Gln Leu Gln Lys Leu Glu Ala Arg
    1805            1810                1815

Val Arg Glu Leu Glu Asn Glu Leu Glu Ala Glu Gln Lys Arg Asn
    1820            1825                1830

Ala Glu Ser Val Lys Gly Met Arg Lys Ser Glu Arg Arg Ile Lys
    1835            1840                1845

Glu Leu Thr Tyr Gln Thr Glu Glu Asp Arg Lys Asn Leu Leu Arg
    1850            1855                1860

Leu Gln Asp Leu Val Asp Lys Leu Gln Leu Lys Val Lys Ala Tyr
    1865            1870                1875

Lys Arg Gln Ala Glu Glu Ala Glu Glu Gln Ala Asn Thr Asn Leu
    1880            1885                1890

Ser Lys Phe Arg Lys Val Gln His Glu Leu Asp Glu Ala Glu Glu
    1895            1900                1905

Arg Ala Asp Ile Ala Glu Ser Gln Val Asn Lys Leu Arg Ala Lys
    1910            1915                1920

Ser Arg Asp Ile Gly Ala Lys Gly Leu Asn Glu Glu
    1925            1930                1935

<210> SEQ ID NO 163
<211> LENGTH: 5923
<212> TYPE: DNA
<213> ORGANISM: Rattus norvegicus

<400> SEQUENCE: 163
gctcagtcat ggcggatcga gagatggctg catttggggc cggagccccc ttcctgcgaa      60
aatctgagaa ggagcggctg gaggcgcaga ccaggcccct tgacctcaag aaagatgttt     120
ttgtgcctga tgacaaagaa gagtttgtca aggccaagat cgtgtctcga gagggtggca     180
aagtcaccgc tgagacagag aatggcaaga cggtgactgt gaaggaggac caggtgatgc     240
agcagaaccc tcccaagttc gacaagatcg aggacatggc catgctgacc ttcctgcacg     300
agccggctgt gctctacaat ctcaaggaga ggtacgcttc ctggatgatc tacacctact     360
caggcctctt ctgtgtcacc gtcaacccct ataagtggct gccagtgtac aatgcgcaag     420
tggtagctgc ctaccggggc aagaagagga gcgaggctcc accccacatc ttctccatct     480
ctgacaacgc ctatcagtac atgctgacag atcgggagaa ccagtccatc ctcatcaccg     540
gagaatccgg agctggtaag accgtcaaca ccaagagggt catccaatat tttgctgtta     600
ttgctgccat tggggaccgc agcaagaagg accagacccc aggcaagggc accttggaag     660
atcaaatcat ccaagccaac cccgctctgg aggcctttgg caatgccaag acagttcgga     720
atgataactc ctcccgattt gggaaattca ttcgaatcca ttttgggca acaggaaagt     780
tggcatctgc agatatagag acctaccttc tggaaaaatc cagagttatt ttccagctga     840
aagcagaaag agattatcac attttctacc aaatcctgtc taataaaaag cctgagcttc     900
tagacatgct gctgatcacc aacaacccct acgattatgc gttcttctcc caggagagaa     960
cgactgtggc ctcaatagat gactctgaag agcacatggc caccgatagc gcctttgatg    1020
tgctgggctt cactccagaa gagaagaact ccatttacaa gctgacaggc gccatcatgc    1080
actttggaaa catgaagttc aaacagaagc agagggagga gcaggcagag ccagacggca    1140
cggaagaagc tgacaagtca gcctacctca tgggactgaa ctcggctgac ctgctcaagg    1200
ggttgtgcca ccctcgagtc aaagtgggca cgagtatgt caccaaaggg cagaatgtcc    1260
agcaggtggc atatgccatc ggggcactgg ccaagtcagt gtacgagaag atgttcaact    1320
```

```
ggatggtgac acgcatcaac gcaaccctgg agaccaagca gccacgccag tacttcatag    1380
gtgtcctgga catcgccggc tttgagatct ttgatttcaa cagctttgag cagctgtgca    1440
tcaacttcac caatgagaag ctgcagcagt tcttcaacca ccacatgttc gtgctggagc    1500
aggaggagta caagaaggaa ggcatcgagt ggacgtttat tgacttcggc atggacctgc    1560
aggcctgcat cgacctcatc gagaagccca tgggcatcat gtccatcctg gaggaggagt    1620
gcatgttccc caaggccacg gacatgacct tcaaggccaa gctgtacgac aaccacctgg    1680
gcaagtccaa caacttccag aagcctcgca atatcaaggg aaagcaggaa gcccacttct    1740
ctctgatcca ctatgctggc accgtggact acaatatcct gggctggcta cagaagaaca    1800
aggaccctct caatgagacg gtggtggggc tgtaccagaa gtcctccctc aagctcctaa    1860
gtaatctgtt tgccaactat gctggagctg atgcacctgt agacaagggc aaaggcaaag    1920
caaagaaagg ctcatccttt cagaccgtgt ccgcactgca cagggaaaat ctgaacaaac    1980
ttatgacaaa cctgcgctcc acgcaccctc actttgtacg ctgcatcatc cccaatgaga    2040
cgaagtctcc aggggtgatg acaaccccc tggtcatgca ccagctgcga tgcaacggag    2100
tgctggaggg tatccgcatc tgtaggaagg gcttccccaa ccgcattctt tatgggact    2160 tccggcagag gtatcgaatc ctgaacccag cagccatccc tgagggccaa ttcattgata    2220
gccggaaagg ggctgagaag ctgctgggct ccctggacat tgaccacaac cagtacaagt    2280
ttggccacac caaggtgttc ttcaaggcgg ggctgctggg gctgctggag gagatgcgag    2340
atgagaggct gagccgcatc atcaccagaa tccaggccca gtcccgaggt gtactttcca    2400
gaatggagtt taagaagctg ctggagcgca gagactccct gctgattatc cagtggaaca    2460
tccgcgcctt catgggggtc aagaattggc cgtggatgaa gctctacttc aagatcaagc    2520
cgctgctgaa gagcgcagag acagagaagg agatggccaa catgaaggag gagttcgggc    2580
gagtcaaaga tgcactagag aagtctgagg ctcgccgcaa ggagctggag agaagatgg    2640 tgtccctgct gcaggagaag aatgacctgc agctccaagt gcaggcggaa caagacaacc    2700
tggcagatgc cgaggagcgc tgcgaccagc tgatcaagaa caagatccag ctggaggcca    2760
aggtgaagga gatgaccgag aggctggagg acgaggagga tgaacgcc gagctcacgg    2820 ccaagaagcg caaactggaa gacgagtgct cagagctcaa gagagatatc gatgacctgg    2880
agctgaccct ggccaaggtg gagaaggaaa agcacgcaac agagaacaag gtgaaaaacc    2940
tgacagagga gatggctggg ctggacgaga tcattgtcaa gctgaccaag gagaagaaag    3000
ctctacaaga ggcccaccag caagccctag atgaccttca ggctgaggag gacaaggtca    3060
acactctgac caaggccaag gtcaagctgg agcagcaagt ggatgatctg gagggatccc    3120
tggatcagga caagaaggtg cgcatggacc tggagcgagc aaagcggaag ctggaggtg    3180 acctgaagct gacccaggag agcatcatgg acctggaaa cgacaagcag cagttggatg    3240
agcgactcaa aaagaaggac tttgagttaa atgcactcaa cgccaggatt gaggatgagc    3300
aggccctggg cagccagctg cagaagaagc tcaaagagct tcaggcacgc atcgaggagc    3360
tggaggagga gctggaggct gagcgcacag cccgggccaa ggtggagaag ctgcgctcag    3420
acctgtcccg ggagctggag gagatcagtg agaggctaga ggaagccggt ggggccacat    3480
ctgtgcagat agagatgaac aagaagcgcg aggccgagtt ccagaagatg cggcgggacc    3540
tagaggaggc cacgctgcag catgaggcca cagctgcggc cctgcgcaag aaacacgcgg    3600
acagcgtggc cgagctgggc gagcagatag acaatctaca gcgggtgaag cagaagctgg    3660
agaaagagaa gagcgagttc aagctggagc tggatgacgt tacctccaac atggagcaga    3720
```

```
tcatcaaggc caaggctaac ctggagaaga tgtgccggac cctggaggac cagatgaatg   3780
aacaccggag caaggctgag gagacacagc gttctgtcaa tgacctcacc cgccagcggg   3840
ccaagctgca gacagagaat ggggagctgt ccagacagct ggatgagaag gaggctctta   3900
tctctcagct gacccgaggc aagctcacgt atacccagca gctggaggac ctcaagaggc   3960
agctggagga ggaggtcaag gccaagaatg ccctggccca cgcactgcag tcagcccggc   4020
atgattgcga cctgctgcgg gaacagtacg aggaggaaac agaagccaag gctgagctgc   4080
agcgtgtcct gtccaaggcc aactcagagg tggcccagtg gaggaccaag tatgagacgg   4140
acgccataca gaggacggag gagctggagg aagccaagaa gaagctggct cagaggcttc   4200
aggatgctga ggaggcagtg gaggccgtca cgccaagtg ctcctcgctg gagaagacca   4260
agcacaggct gcagaacgag atcgaggacc tgatggtgga tgtggagcgc tccaatgcgg   4320
ccgccgcagc cctggacaag aagcagagga acttcgacaa gatcctggtt gagtggaagc   4380
agaagtatga ggagtcccag tcagagctgg agtcttccca gaaggaggcg cgctccctga   4440
gcacagagct cttcaagctg aagaatgcct atgaggagtc tctggagcac ctggagacct   4500
tcaagcggga gaacaagaac ctccaggagg agatctcaga cctgactgaa cagctgggct   4560
caactgggaa gagcatccac gagctggaga agatccgaaa gcaactggag gctgagaagc   4620
tggagctgca gtcagccctg gaagaggctg aggcctccct ggagcatgag gagggcaaga   4680
tcctccgagc ccagctggag ttcaaccaga tcaaggcaga gatcgaaagg aagctggcag   4740
agaaggacga ggagatggag caggccaagc gcaaccacct gcgggtggtg gactccctgc   4800
agacctccct ggatgccgag acgcgcagcc gcaacgaggc cctgcgggtg aagaagaaga   4860
tggagggcga cctcaacgag atggagatcc agctcagtca tgccaaccgc atggctgctg   4920
aggcccagaa acaagtgaag agcctccaga gtttgctgaa ggacactcaa atccagctgg   4980
atgacgcagt ccgtgccaat gacgacctga aggagaacat cgccatcgtg gagcggcgca   5040
acaacctgct gcaggcggag ctggaggagc tgcgggccgt ggtggagcag acggagcggt   5100
ctcggaagct ggcagagcag gagctgatcg agaccagcga gcgggtgcag ctgctgcact   5160
cccagaacac cagcctcatc aaccagaaga agaagatgga tgcagacctc tcccagctcc   5220
agacagaggt ggaggaggcg gtgcaggagt gtaggaacgc agaggagaag gccagaaggg   5280
ccatcacaga tgccgccatg atggccgagg agctgaagaa ggagcaggac accagcgccc   5340
acctggagcg catgaagaat aacatggagc agaccatcaa ggacctgcag caccggctgg   5400
acgaggcaga gcagatcgcc ctcaagggtg gcaagaagca gctgcagaag ctggaggccc   5460
gggtccggga gctggagaat gagctggagg ctgagcagaa gcgcaatgcg gagtcggtga   5520
agggcatgag gaagagcgag cggcgcatca aggagctcac ctaccagaca gaggaagaca   5580
ggaagaacct actgcgactg caggacctgg tggacaagct gcagttaaag gtgaaggcct   5640
acaagcgcca ggctgaggag gcggaggaac aggccaacac caacctgtcc aagttccgca   5700
aggtgcagca cgagctggat gaggcagagg agagggcgga cattgccgag tcccaggtca   5760
acaagctgcg ggccaagagc cgtgacattg gcgccaaggg cctgaatgaa gagtagatct   5820
tgtgctaccc aaccctaagg atgcctgtga agccctgaga cctggagcct ttgaaacagc   5880
accttaggca gaaacacaat aaagcaattt tccttcaagc caa                    5923

<210> SEQ ID NO 164
<211> LENGTH: 152
<212> TYPE: PRT
```

<213> ORGANISM: Rattus norvegicus

<400> SEQUENCE: 164

```
Met Gly Ser Phe Ser Ile Thr Lys Gly Phe Phe Leu Phe Leu Ala Phe
1               5                   10                  15
Trp Leu Pro Gly His Ile Gly Ala Asn Pro Val Tyr Ser Ala Val Ser
            20                  25                  30
Asn Thr Asp Leu Met Asp Phe Lys Asn Leu Leu Asp His Leu Glu Glu
        35                  40                  45
Lys Met Pro Val Glu Asp Glu Val Met Pro Pro Gln Ala Leu Ser Glu
    50                  55                  60
Gln Thr Asp Glu Ala Gly Ala Ala Leu Ser Ser Leu Ser Glu Val Pro
65                  70                  75                  80
Pro Trp Thr Gly Glu Val Asn Pro Ser Gln Arg Asp Gly Gly Ala Leu
                85                  90                  95
Gly Arg Gly Pro Trp Asp Pro Ser Asp Arg Ser Ala Leu Leu Lys Ser
            100                 105                 110
Lys Leu Arg Ala Leu Leu Ala Gly Pro Arg Ser Leu Arg Arg Ser Ser
        115                 120                 125
Cys Phe Gly Gly Arg Ile Asp Arg Ile Gly Ala Gln Ser Gly Leu Gly
    130                 135                 140
Cys Asn Ser Phe Arg Tyr Arg Arg
145                 150
```

<210> SEQ ID NO 165
<211> LENGTH: 831
<212> TYPE: DNA
<213> ORGANISM: Rattus norvegicus

<400> SEQUENCE: 165

```
cggacaaagg ctgagagaga aaccagagag tgagccgaga cagcaaacat cagatcgtgc    60
cccgacccac gccagcatgg gctccttctc catcaccaag ggcttcttcc tcttcctggc   120
cttttggctc ccaggccata ttggagcaaa tcccgtatac agtgcggtgt ccaacacaga   180
tctgatggat ttcaagaacc tgctagacca cctggaggag aagatgccgg tagaagatga   240
ggtcatgcct ccgcaggccc tgagcgagca gaccgatgaa gcgggggcgg cacttagctc   300
cctctctgag gtgcctccct ggactgggga agtcaacccg tctcagagag atggaggtgc   360
tctcgggcgc ggcccctggg acccctccga tagatctgcc ctcttgaaaa gcaaactgag   420
ggctctgctc gctggccctc ggagcctgcg aaggtcaagc tgcttcgggg gtaggattga   480
caggattgga gcccagagcg gactaggctg caacagcttc cggtaccgaa gataacagcc   540
aaatctgctc gagcagatcg caaaagatcc caagcccttg cggtgtgtca cacagcttgg   600
tcgcattgcc actgagaggt ggtgaatacc ctcctggagc tgcagcttcc tgtcttcatc   660
tatcacgatc gatgttaagt gtagatgagt ggtttagtga ggccttacct ctcccactct   720
gcatattaag gtagatcctc accccctttca gaaagcagtt ggaaaaaaat aaatccgaat   780
aaacttcagc accacggaca gacgctgagg cctgaaaaaa aaaaaaaaaa a            831
```

<210> SEQ ID NO 166
<211> LENGTH: 121
<212> TYPE: PRT
<213> ORGANISM: Rattus norvegicus

<400> SEQUENCE: 166

Met Asp Leu Gln Lys Val Leu Pro Gln Met Ile Leu Leu Leu Leu Phe

```
1               5                  10                 15
Leu Asn Leu Ser Pro Leu Gly Gly His Ser His Pro Leu Gly Ser Pro
                20                 25                 30
Ser Gln Ser Pro Glu Gln Ser Thr Met Gln Lys Leu Leu Glu Leu Ile
        35                 40                 45
Arg Glu Lys Ser Glu Glu Met Ala Gln Arg Gln Leu Ser Lys Asp Gln
        50                 55                 60
Gly Pro Thr Lys Glu Leu Leu Lys Arg Val Leu Arg Ser Gln Asp Ser
65                 70                 75                 80
Ala Phe Arg Ile Gln Glu Arg Leu Arg Asn Ser Lys Met Ala His Ser
                85                 90                 95
Ser Ser Cys Phe Gly Gln Lys Ile Asp Arg Ile Gly Ala Val Ser Arg
                100                105                110
Leu Gly Cys Asp Gly Leu Arg Leu Phe
                115                120
```

<210> SEQ ID NO 167
<211> LENGTH: 628
<212> TYPE: DNA
<213> ORGANISM: Rattus norvegicus

<400> SEQUENCE: 167

```
gcgagacaag agagagcagg acaccatcgc agctgcctgg cccatcactt ctgcagcatg    60
gatctccaga aggtgctgcc ccagatgatt ctgctcctgc ttttccttaa tctgtcgccg   120
ctgggaggtc actcccatcc cctgggaagt cctagccagt ctccagaaca atccacgatg   180
cagaagctgc tggagctgat aagagaaaag tcagaggaaa tggctcagag acagctctca   240
aaggaccaag ccctacaaa agaacttcta aaaagagtcc ttaggtctca agacagcgcc   300
ttccggatcc aggagagact cgaaattcc aagatggcac atagttcaag ctgctttggg   360
cagaagatag accggatcgg cgcagtcagt cgcttgggct gtgacgggct gaggttgttt   420
taggaagacc tcctggctgc agactccggc ttctgactct gcctgcggct cttctttccc   480
cagctctggg accacctctc aagtgatcct gtttatttat ttgtttattt atttattttt   540
atgttgctga ttttctacaa gactgtttct tatcttccag cacaaacttg ccacagtgta   600
ataaacatag cctatttctt gcttttgg                                      628
```

<210> SEQ ID NO 168
<211> LENGTH: 31
<212> TYPE: RNA
<213> ORGANISM: Homo sapiens

<400> SEQUENCE: 168

```
ggcuccagca ugggcuuug cuggcaccuc c                                    31
```

<210> SEQ ID NO 169
<211> LENGTH: 31
<212> TYPE: RNA
<213> ORGANISM: Homo sapiens

<400> SEQUENCE: 169

```
ccagggcuga gcagaucaag auguggcaaa g                                   31
```

<210> SEQ ID NO 170
<211> LENGTH: 31
<212> TYPE: RNA
<213> ORGANISM: Homo sapiens

```
<400> SEQUENCE: 170
cagggcugag cagaucaaga uguggcaaag c                               31

<210> SEQ ID NO 171
<211> LENGTH: 31
<212> TYPE: RNA
<213> ORGANISM: Homo sapiens

<400> SEQUENCE: 171
gcuggcaccu ccagggcuga gcagaucaag a                               31

<210> SEQ ID NO 172
<211> LENGTH: 31
<212> TYPE: RNA
<213> ORGANISM: Homo sapiens

<400> SEQUENCE: 172
caggcuccag caugggcuu ugcuggcacc u                                31

<210> SEQ ID NO 173
<211> LENGTH: 31
<212> TYPE: RNA
<213> ORGANISM: Homo sapiens

<400> SEQUENCE: 173
aggcuccagc augggcuuu gcuggcaccu c                                31

<210> SEQ ID NO 174
<211> LENGTH: 31
<212> TYPE: RNA
<213> ORGANISM: Homo sapiens

<400> SEQUENCE: 174
gcuccagcau ggggcuuugc uggcaccucc a                               31

<210> SEQ ID NO 175
<211> LENGTH: 31
<212> TYPE: RNA
<213> ORGANISM: Homo sapiens

<400> SEQUENCE: 175
cuccagcaug gggcuuugcu ggcaccucca g                               31

<210> SEQ ID NO 176
<211> LENGTH: 31
<212> TYPE: RNA
<213> ORGANISM: Homo sapiens

<400> SEQUENCE: 176
uccagcaugg ggcuuugcug gcaccuccag g                               31

<210> SEQ ID NO 177
<211> LENGTH: 31
<212> TYPE: RNA
<213> ORGANISM: Homo sapiens

<400> SEQUENCE: 177
auucugcuuc cucccaagga gcuguuacac a                               31

<210> SEQ ID NO 178
<211> LENGTH: 31
<212> TYPE: RNA
<213> ORGANISM: Homo sapiens
```

```
<400> SEQUENCE: 178
uccagggcug agcagaucaa gauguggcaa a                                    31

<210> SEQ ID NO 179
<211> LENGTH: 31
<212> TYPE: RNA
<213> ORGANISM: Homo sapiens

<400> SEQUENCE: 179
uguuacacag gcuccagcau ggggcuuugc u                                    31

<210> SEQ ID NO 180
<211> LENGTH: 31
<212> TYPE: RNA
<213> ORGANISM: Homo sapiens

<400> SEQUENCE: 180
cuccagggcu gagcagauca agauguggca a                                    31

<210> SEQ ID NO 181
<211> LENGTH: 31
<212> TYPE: RNA
<213> ORGANISM: Homo sapiens

<400> SEQUENCE: 181
cucccaagga gcuguuacac aggcuccagc a                                    31

<210> SEQ ID NO 182
<211> LENGTH: 31
<212> TYPE: RNA
<213> ORGANISM: Homo sapiens

<400> SEQUENCE: 182
cccaaggagc uguuacacag gcuccagcau g                                    31

<210> SEQ ID NO 183
<211> LENGTH: 31
<212> TYPE: RNA
<213> ORGANISM: Homo sapiens

<400> SEQUENCE: 183
caaggagcug uuacacaggc uccagcaugg g                                    31

<210> SEQ ID NO 184
<211> LENGTH: 31
<212> TYPE: RNA
<213> ORGANISM: Homo sapiens

<400> SEQUENCE: 184
aaggagcugu uacacaggcu ccagcauggg g                                    31

<210> SEQ ID NO 185
<211> LENGTH: 31
<212> TYPE: RNA
<213> ORGANISM: Homo sapiens

<400> SEQUENCE: 185
gcuguuacac aggcuccagc auggggcuuu g                                    31

<210> SEQ ID NO 186
<211> LENGTH: 31
<212> TYPE: RNA
```

```
<213> ORGANISM: Homo sapiens

<400> SEQUENCE: 186 cguuacaca ggcuccagca uggggcuuug c                               31

<210> SEQ ID NO 187
<211> LENGTH: 31
<212> TYPE: RNA
<213> ORGANISM: Homo sapiens

<400> SEQUENCE: 187
guuacacagg cuccagcaug gggcuuugcu g                              31

<210> SEQ ID NO 188
<211> LENGTH: 31
<212> TYPE: RNA
<213> ORGANISM: Homo sapiens

<400> SEQUENCE: 188
uuacacaggc uccagcaugg ggcuuugcug g                              31

<210> SEQ ID NO 189
<211> LENGTH: 31
<212> TYPE: RNA
<213> ORGANISM: Homo sapiens

<400> SEQUENCE: 189
cuggcaccuc cagggcugag cagaucaaga u                              31

<210> SEQ ID NO 190
<211> LENGTH: 31
<212> TYPE: RNA
<213> ORGANISM: Homo sapiens

<400> SEQUENCE: 190
uggcaccucc agggcugagc agaucaagau g                              31

<210> SEQ ID NO 191
<211> LENGTH: 31
<212> TYPE: RNA
<213> ORGANISM: Homo sapiens

<400> SEQUENCE: 191
ggcaccucca gggcugagca gaucaagaug u                              31

<210> SEQ ID NO 192
<211> LENGTH: 31
<212> TYPE: RNA
<213> ORGANISM: Homo sapiens

<400> SEQUENCE: 192
gcaccuccag ggcugagcag aucaagaugu g                              31

<210> SEQ ID NO 193
<211> LENGTH: 31
<212> TYPE: RNA
<213> ORGANISM: Homo sapiens

<400> SEQUENCE: 193
caccuccagg gcugagcaga ucaagaugug g                              31

<210> SEQ ID NO 194
<211> LENGTH: 31
```

```
<212> TYPE: RNA
<213> ORGANISM: Homo sapiens

<400> SEQUENCE: 194
accuccaggg cugagcagau caagaugugg c                            31

<210> SEQ ID NO 195
<211> LENGTH: 31
<212> TYPE: RNA
<213> ORGANISM: Homo sapiens

<400> SEQUENCE: 195
ccuccagggc ugagcagauc aagaugggc a                             31

<210> SEQ ID NO 196
<211> LENGTH: 31
<212> TYPE: RNA
<213> ORGANISM: Homo sapiens

<400> SEQUENCE: 196
ccucccaagg agcuguuaca caggcuccag c                            31

<210> SEQ ID NO 197
<211> LENGTH: 31
<212> TYPE: RNA
<213> ORGANISM: Homo sapiens

<400> SEQUENCE: 197
aggagcuguu acacaggcuc cagcaugggg c                            31

<210> SEQ ID NO 198
<211> LENGTH: 31
<212> TYPE: RNA
<213> ORGANISM: Homo sapiens

<400> SEQUENCE: 198
uacacaggcu ccagcauggg gcuuugcugg c                            31

<210> SEQ ID NO 199
<211> LENGTH: 31
<212> TYPE: RNA
<213> ORGANISM: Homo sapiens

<400> SEQUENCE: 199
gcuuugcugg caccuccagg gcugagcaga u                            31

<210> SEQ ID NO 200
<211> LENGTH: 31
<212> TYPE: RNA
<213> ORGANISM: Homo sapiens

<400> SEQUENCE: 200
cuuugcuggc accuccaggg cugagcagau c                            31

<210> SEQ ID NO 201
<211> LENGTH: 31
<212> TYPE: RNA
<213> ORGANISM: Homo sapiens

<400> SEQUENCE: 201
ugcuggcacc uccagggcug agcagaucaa g                            31

<210> SEQ ID NO 202
```

```
<211> LENGTH: 31
<212> TYPE: RNA
<213> ORGANISM: Homo sapiens

<400> SEQUENCE: 202
cacaggcucc agcaugggc uuugcuggca c                            31

<210> SEQ ID NO 203
<211> LENGTH: 31
<212> TYPE: RNA
<213> ORGANISM: Homo sapiens

<400> SEQUENCE: 203
acaggcucca gcaugggcu uugcuggcac c                            31

<210> SEQ ID NO 204
<211> LENGTH: 31
<212> TYPE: RNA
<213> ORGANISM: Homo sapiens

<400> SEQUENCE: 204
ggcuuugcug gcaccuccag ggcugagcag a                           31

<210> SEQ ID NO 205
<211> LENGTH: 31
<212> TYPE: RNA
<213> ORGANISM: Homo sapiens

<400> SEQUENCE: 205
uucugcuucc ucccaaggag cuguuacaca g                           31

<210> SEQ ID NO 206
<211> LENGTH: 31
<212> TYPE: RNA
<213> ORGANISM: Homo sapiens

<400> SEQUENCE: 206
ucugcuuccu cccaaggagc uguuacacag g                           31

<210> SEQ ID NO 207
<211> LENGTH: 31
<212> TYPE: RNA
<213> ORGANISM: Homo sapiens

<400> SEQUENCE: 207
ugcuuccucc caaggagcug uuacacaggc u                           31

<210> SEQ ID NO 208
<211> LENGTH: 31
<212> TYPE: RNA
<213> ORGANISM: Homo sapiens

<400> SEQUENCE: 208
uuccucccaa ggagcuguua cacaggcucc a                           31

<210> SEQ ID NO 209
<211> LENGTH: 31
<212> TYPE: RNA
<213> ORGANISM: Homo sapiens

<400> SEQUENCE: 209
ucccaaggag cuguuacaca ggcuccagca u                           31
```

```
<210> SEQ ID NO 210
<211> LENGTH: 31
<212> TYPE: RNA
<213> ORGANISM: Homo sapiens

<400> SEQUENCE: 210
agcuguuaca caggcuccag caugggggcuu u                                          31

<210> SEQ ID NO 211
<211> LENGTH: 31
<212> TYPE: RNA
<213> ORGANISM: Homo sapiens

<400> SEQUENCE: 211
cugcuuccuc ccaaggagcu guuacacagg c                                           31

<210> SEQ ID NO 212
<211> LENGTH: 31
<212> TYPE: RNA
<213> ORGANISM: Homo sapiens

<400> SEQUENCE: 212
gcuuccuccc aaggagcugu uacacaggcu c                                           31

<210> SEQ ID NO 213
<211> LENGTH: 31
<212> TYPE: RNA
<213> ORGANISM: Homo sapiens

<400> SEQUENCE: 213
cuuccuccca aggagcuguu acacaggcuc c                                           31

<210> SEQ ID NO 214
<211> LENGTH: 31
<212> TYPE: RNA
<213> ORGANISM: Homo sapiens

<400> SEQUENCE: 214
uccucccaag gagcuguuac acaggcucca g                                           31

<210> SEQ ID NO 215
<211> LENGTH: 31
<212> TYPE: RNA
<213> ORGANISM: Homo sapiens

<400> SEQUENCE: 215
gagcuguuac acaggcucca gcauggggcu u                                           31

<210> SEQ ID NO 216
<211> LENGTH: 31
<212> TYPE: RNA
<213> ORGANISM: Homo sapiens

<400> SEQUENCE: 216
uuugcuggca ccuccagggc ugagcagauc a                                           31

<210> SEQ ID NO 217
<211> LENGTH: 31
<212> TYPE: RNA
<213> ORGANISM: Homo sapiens

<400> SEQUENCE: 217
uugcuggcac cuccagggcu gagcagauca a                                           31
```

```
<210> SEQ ID NO 218
<211> LENGTH: 31
<212> TYPE: RNA
<213> ORGANISM: Homo sapiens

<400> SEQUENCE: 218
ggagcuguua cacaggcucc agcauggggc u                           31

<210> SEQ ID NO 219
<211> LENGTH: 31
<212> TYPE: RNA
<213> ORGANISM: Homo sapiens

<400> SEQUENCE: 219
acacaggcuc cagcaugggg cuuugcuggc a                           31

<210> SEQ ID NO 220
<211> LENGTH: 31
<212> TYPE: RNA
<213> ORGANISM: Homo sapiens

<400> SEQUENCE: 220 gcaugggcu uugcuggcac cuccagggcu g                            31

<210> SEQ ID NO 221
<211> LENGTH: 31
<212> TYPE: RNA
<213> ORGANISM: Homo sapiens

<400> SEQUENCE: 221 ugggcuuug cuggcaccuc cagggcugag c                            31

<210> SEQ ID NO 222
<211> LENGTH: 31
<212> TYPE: RNA
<213> ORGANISM: Homo sapiens

<400> SEQUENCE: 222
cuucaaggaa aauugcuuua uucugcuucc u                           31

<210> SEQ ID NO 223
<211> LENGTH: 31
<212> TYPE: RNA
<213> ORGANISM: Homo sapiens

<400> SEQUENCE: 223
uucaaggaaa auugcuuuau ucugcuuccu c                           31

<210> SEQ ID NO 224
<211> LENGTH: 31
<212> TYPE: RNA
<213> ORGANISM: Homo sapiens

<400> SEQUENCE: 224
ucaaggaaaa uugcuuuauu cugcuuccuc c                           31

<210> SEQ ID NO 225
<211> LENGTH: 31
<212> TYPE: RNA
<213> ORGANISM: Homo sapiens

<400> SEQUENCE: 225
uugcuuuauu cugcuuccuc ccaaggagcu g                           31
```

<210> SEQ ID NO 226
<211> LENGTH: 31
<212> TYPE: RNA
<213> ORGANISM: Homo sapiens

<400> SEQUENCE: 226
ugcuuuauuc ugcuuccucc caaggagcug u                                    31

<210> SEQ ID NO 227
<211> LENGTH: 31
<212> TYPE: RNA
<213> ORGANISM: Homo sapiens

<400> SEQUENCE: 227
gcuuuauucu gcuuccuccc aaggagcugu u                                    31

<210> SEQ ID NO 228
<211> LENGTH: 31
<212> TYPE: RNA
<213> ORGANISM: Homo sapiens

<400> SEQUENCE: 228 agcaugggc uuugcuggca ccuccagggc u                                     31

<210> SEQ ID NO 229
<211> LENGTH: 31
<212> TYPE: RNA
<213> ORGANISM: Homo sapiens

<400> SEQUENCE: 229 caugggcuu ugcuggcacc uccagggcug a                                     31

<210> SEQ ID NO 230
<211> LENGTH: 31
<212> TYPE: RNA
<213> ORGANISM: Homo sapiens

<400> SEQUENCE: 230 augggggcuuu gcuggcaccu ccagggcuga g                                   31

<210> SEQ ID NO 231
<211> LENGTH: 31
<212> TYPE: RNA
<213> ORGANISM: Homo sapiens

<400> SEQUENCE: 231
ccagcauggg gcuuugcugg caccuccagg g                                    31

<210> SEQ ID NO 232
<211> LENGTH: 31
<212> TYPE: RNA
<213> ORGANISM: Homo sapiens

<400> SEQUENCE: 232 cagcauggggg cuuugcuggc accuccaggg c                                   31

<210> SEQ ID NO 233
<211> LENGTH: 31
<212> TYPE: RNA
<213> ORGANISM: Homo sapiens

<400> SEQUENCE: 233
ggggcuuugc uggcaccucc agggcugagc a          31

<210> SEQ ID NO 234
<211> LENGTH: 31
<212> TYPE: RNA
<213> ORGANISM: Homo sapiens

<400> SEQUENCE: 234
gggcuuugcu ggcaccucca gggcugagca g          31

<210> SEQ ID NO 235
<211> LENGTH: 31
<212> TYPE: RNA
<213> ORGANISM: Homo sapiens

<400> SEQUENCE: 235
gcuucaagga aaauugcuuu auucugcuuc c          31

<210> SEQ ID NO 236
<211> LENGTH: 31
<212> TYPE: RNA
<213> ORGANISM: Homo sapiens

<400> SEQUENCE: 236
auugcuuuau ucugcuuccu cccaaggagc u          31

<210> SEQ ID NO 237
<211> LENGTH: 31
<212> TYPE: RNA
<213> ORGANISM: Homo sapiens

<400> SEQUENCE: 237
cuuuauucug cuuccuccca aggagcuguu a          31

<210> SEQ ID NO 238
<211> LENGTH: 31
<212> TYPE: RNA
<213> ORGANISM: Homo sapiens

<400> SEQUENCE: 238
uuuauucugc uuccucccaa ggagcuguua c          31

<210> SEQ ID NO 239
<211> LENGTH: 31
<212> TYPE: RNA
<213> ORGANISM: Homo sapiens

<400> SEQUENCE: 239
uuauucugcu uccucccaag gagcuguuac a          31

<210> SEQ ID NO 240
<211> LENGTH: 31
<212> TYPE: RNA
<213> ORGANISM: Homo sapiens

<400> SEQUENCE: 240
uauucugcuu ccucccaagg agcuguuaca c          31

<210> SEQ ID NO 241
<211> LENGTH: 31
<212> TYPE: RNA
<213> ORGANISM: Homo sapiens

<400> SEQUENCE: 241
ucggcuucaa ggaaaauugc uuuauucugc u					31

<210> SEQ ID NO 242
<211> LENGTH: 31
<212> TYPE: RNA
<213> ORGANISM: Homo sapiens

<400> SEQUENCE: 242
cggcuucaag gaaaauugcu uuauucugcu u					31

<210> SEQ ID NO 243
<211> LENGTH: 31
<212> TYPE: RNA
<213> ORGANISM: Homo sapiens

<400> SEQUENCE: 243
ggcuucaagg aaaauugcuu uauucugcuu c					31

<210> SEQ ID NO 244
<211> LENGTH: 31
<212> TYPE: RNA
<213> ORGANISM: Homo sapiens

<400> SEQUENCE: 244
cucggcuuca aggaaaauug cuuuauucug c					31

<210> SEQ ID NO 245
<211> LENGTH: 31
<212> TYPE: RNA
<213> ORGANISM: Homo sapiens

<400> SEQUENCE: 245
aaggaaaauu gcuuuauucu gcuuccuccc a					31

<210> SEQ ID NO 246
<211> LENGTH: 31
<212> TYPE: RNA
<213> ORGANISM: Homo sapiens

<400> SEQUENCE: 246
aggaaaauug cuuuauucug cuuccuccca a					31

<210> SEQ ID NO 247
<211> LENGTH: 31
<212> TYPE: RNA
<213> ORGANISM: Homo sapiens

<400> SEQUENCE: 247
aaaauugcuu uauucugcuu ccucccaagg a					31

<210> SEQ ID NO 248
<211> LENGTH: 31
<212> TYPE: RNA
<213> ORGANISM: Homo sapiens

<400> SEQUENCE: 248
caaggaaaau ugcuuuauuc ugcuuccucc c					31

<210> SEQ ID NO 249
<211> LENGTH: 31
<212> TYPE: RNA
<213> ORGANISM: Homo sapiens

```
<400> SEQUENCE: 249
ggaaaauugc uuuauucugc uuccucccaa g                              31

<210> SEQ ID NO 250
<211> LENGTH: 31
<212> TYPE: RNA
<213> ORGANISM: Homo sapiens

<400> SEQUENCE: 250
gaaaauugcu uuauucugcu uccucccaag g                              31

<210> SEQ ID NO 251
<211> LENGTH: 31
<212> TYPE: RNA
<213> ORGANISM: Homo sapiens

<400> SEQUENCE: 251
aaauugcuuu auucugcuuc cucccaagga g                              31

<210> SEQ ID NO 252
<211> LENGTH: 31
<212> TYPE: RNA
<213> ORGANISM: Homo sapiens

<400> SEQUENCE: 252
aauugcuuua uucugcuucc ucccaaggag c                              31

<210> SEQ ID NO 253
<211> LENGTH: 31
<212> TYPE: RNA
<213> ORGANISM: Mus musculus

<400> SEQUENCE: 253
guguuucugc cuaaggugcu guuucaaagg c                              31

<210> SEQ ID NO 254
<211> LENGTH: 31
<212> TYPE: RNA
<213> ORGANISM: Mus musculus

<400> SEQUENCE: 254
guuucugccu aaggugcugu ucaaaggcu c                               31

<210> SEQ ID NO 255
<211> LENGTH: 31
<212> TYPE: RNA
<213> ORGANISM: Mus musculus

<400> SEQUENCE: 255
uuucugccua aggugcuguu ucaaaggcuc c                              31

<210> SEQ ID NO 256
<211> LENGTH: 31
<212> TYPE: RNA
<213> ORGANISM: Mus musculus

<400> SEQUENCE: 256 uguuuucug ccuaaggugc uguuucaaag g                               31

<210> SEQ ID NO 257
<211> LENGTH: 31
<212> TYPE: RNA
<213> ORGANISM: Mus musculus
```

```
<400> SEQUENCE: 257
uguuucugcc uaaggugcug uuucaaaggc u                              31

<210> SEQ ID NO 258
<211> LENGTH: 31
<212> TYPE: RNA
<213> ORGANISM: Mus musculus

<400> SEQUENCE: 258
uuguguuucu gccuaaggug cuguuucaaa g                              31

<210> SEQ ID NO 259
<211> LENGTH: 31
<212> TYPE: RNA
<213> ORGANISM: Mus musculus

<400> SEQUENCE: 259
auuguguuuc ugccuaaggu gcuguuucaa a                              31

<210> SEQ ID NO 260
<211> LENGTH: 31
<212> TYPE: RNA
<213> ORGANISM: Mus musculus

<400> SEQUENCE: 260
cugccuaagg ugcuguuuca aaggcuccag g                              31

<210> SEQ ID NO 261
<211> LENGTH: 31
<212> TYPE: RNA
<213> ORGANISM: Mus musculus

<400> SEQUENCE: 261
gccuaaggug cuguuucaaa ggcuccaggu c                              31

<210> SEQ ID NO 262
<211> LENGTH: 31
<212> TYPE: RNA
<213> ORGANISM: Mus musculus

<400> SEQUENCE: 262
aggugcuguu ucaaaggcuc caggucucag g                              31

<210> SEQ ID NO 263
<211> LENGTH: 31
<212> TYPE: RNA
<213> ORGANISM: Mus musculus

<400> SEQUENCE: 263
ucugccuaag gugcuguuuc aaaggcucca g                              31

<210> SEQ ID NO 264
<211> LENGTH: 31
<212> TYPE: RNA
<213> ORGANISM: Mus musculus

<400> SEQUENCE: 264
ugccuaaggu gcuguuucaa aggcuccagg u                              31

<210> SEQ ID NO 265
<211> LENGTH: 31
<212> TYPE: RNA
```

```
<213> ORGANISM: Mus musculus

<400> SEQUENCE: 265
ccuaaggugc uguuucaaag gcuccagguc u          31

<210> SEQ ID NO 266
<211> LENGTH: 31
<212> TYPE: RNA
<213> ORGANISM: Mus musculus

<400> SEQUENCE: 266
cuaaggugcu guuucaaagg cuccaggucu c          31

<210> SEQ ID NO 267
<211> LENGTH: 31
<212> TYPE: RNA
<213> ORGANISM: Mus musculus

<400> SEQUENCE: 267
uucugccuaa ggugcuguuu caaaggcucc a          31

<210> SEQ ID NO 268
<211> LENGTH: 31
<212> TYPE: RNA
<213> ORGANISM: Mus musculus

<400> SEQUENCE: 268
aaggugcugu uucaaaggcu ccaggucuca g          31

<210> SEQ ID NO 269
<211> LENGTH: 31
<212> TYPE: RNA
<213> ORGANISM: Mus musculus

<400> SEQUENCE: 269
uaaggugcug uuucaaaggc uccaggucuc a          31

<210> SEQ ID NO 270
<211> LENGTH: 31
<212> TYPE: RNA
<213> ORGANISM: Mus musculus

<400> SEQUENCE: 270
uugcuuuauu uguuucugc cuaaggugcu g           31

<210> SEQ ID NO 271
<211> LENGTH: 31
<212> TYPE: RNA
<213> ORGANISM: Mus musculus

<400> SEQUENCE: 271
ugcuuuauug uguuucugcc uaaggugcug u          31

<210> SEQ ID NO 272
<211> LENGTH: 31
<212> TYPE: RNA
<213> ORGANISM: Mus musculus

<400> SEQUENCE: 272
gcuuuauugu guuucugccu aaggugcugu u          31

<210> SEQ ID NO 273
<211> LENGTH: 31
```

```
<212> TYPE: RNA
<213> ORGANISM: Mus musculus

<400> SEQUENCE: 273
cuuuauugug uuucugccua aggugcuguu u                              31

<210> SEQ ID NO 274
<211> LENGTH: 31
<212> TYPE: RNA
<213> ORGANISM: Mus musculus

<400> SEQUENCE: 274
uuuauugugu uucugccuaa ggugcuguuu c                              31

<210> SEQ ID NO 275
<211> LENGTH: 31
<212> TYPE: RNA
<213> ORGANISM: Mus musculus

<400> SEQUENCE: 275
auugcuuuau uguguuucug ccuaaggugc u                              31

<210> SEQ ID NO 276
<211> LENGTH: 31
<212> TYPE: RNA
<213> ORGANISM: Mus musculus

<400> SEQUENCE: 276
uuauuguguu ucugccuaag gugcuguuuc a                              31

<210> SEQ ID NO 277
<211> LENGTH: 31
<212> TYPE: RNA
<213> ORGANISM: Mus musculus

<400> SEQUENCE: 277
ggcuccaggu cucagggcuu cacaggcauc c                              31

<210> SEQ ID NO 278
<211> LENGTH: 31
<212> TYPE: RNA
<213> ORGANISM: Mus musculus

<400> SEQUENCE: 278
caaaggcucc aggucucagg gcuucacagg c                              31

<210> SEQ ID NO 279
<211> LENGTH: 31
<212> TYPE: RNA
<213> ORGANISM: Mus musculus

<400> SEQUENCE: 279
gcuccagguc ucagggcuuc acaggcaucc u                              31

<210> SEQ ID NO 280
<211> LENGTH: 31
<212> TYPE: RNA
<213> ORGANISM: Mus musculus

<400> SEQUENCE: 280
ggugcuguuu caaaggcucc aggucucagg g                              31

<210> SEQ ID NO 281
```

-continued

```
<211> LENGTH: 31
<212> TYPE: RNA
<213> ORGANISM: Mus musculus

<400> SEQUENCE: 281
gugcuguuuc aaaggcucca ggucucaggg c                                   31

<210> SEQ ID NO 282
<211> LENGTH: 31
<212> TYPE: RNA
<213> ORGANISM: Mus musculus

<400> SEQUENCE: 282
aaaggcucca ggucucaggg cuucacaggc a                                   31

<210> SEQ ID NO 283
<211> LENGTH: 31
<212> TYPE: RNA
<213> ORGANISM: Mus musculus

<400> SEQUENCE: 283
cuccaggucu cagggcuuca caggcauccu u                                   31

<210> SEQ ID NO 284
<211> LENGTH: 31
<212> TYPE: RNA
<213> ORGANISM: Mus musculus

<400> SEQUENCE: 284
ugcuguuuca aaggcuccag gucucagggc u                                   31

<210> SEQ ID NO 285
<211> LENGTH: 31
<212> TYPE: RNA
<213> ORGANISM: Mus musculus

<400> SEQUENCE: 285
gcuguuucaa aggcuccagg ucucagggcu u                                   31

<210> SEQ ID NO 286
<211> LENGTH: 31
<212> TYPE: RNA
<213> ORGANISM: Mus musculus

<400> SEQUENCE: 286
cuguuucaaa ggcuccaggu cucagggcuu c                                   31

<210> SEQ ID NO 287
<211> LENGTH: 31
<212> TYPE: RNA
<213> ORGANISM: Mus musculus

<400> SEQUENCE: 287
uauuguguuu cugccuaagg ugcuguuuca a                                   31

<210> SEQ ID NO 288
<211> LENGTH: 31
<212> TYPE: RNA
<213> ORGANISM: Mus musculus

<400> SEQUENCE: 288
aggcuccagg ucucagggcu ucacaggcau c                                   31
```

-continued

<210> SEQ ID NO 289
<211> LENGTH: 31
<212> TYPE: RNA
<213> ORGANISM: Mus musculus

<400> SEQUENCE: 289
ucaaaggcuc caggucucag ggcuucacag g                          31

<210> SEQ ID NO 290
<211> LENGTH: 31
<212> TYPE: RNA
<213> ORGANISM: Mus musculus

<400> SEQUENCE: 290
aaggcuccag gucucagggc uucacaggca u                          31

<210> SEQ ID NO 291
<211> LENGTH: 31
<212> TYPE: RNA
<213> ORGANISM: Mus musculus

<400> SEQUENCE: 291
ccaggucuca gggcuucaca ggcauccuua g                          31

<210> SEQ ID NO 292
<211> LENGTH: 31
<212> TYPE: RNA
<213> ORGANISM: Mus musculus

<400> SEQUENCE: 292
caggucucag ggcuucacag gcauccuuag g                          31

<210> SEQ ID NO 293
<211> LENGTH: 31
<212> TYPE: RNA
<213> ORGANISM: Mus musculus

<400> SEQUENCE: 293
guuucaaagg cuccaggucu cagggcuuca c                          31

<210> SEQ ID NO 294
<211> LENGTH: 31
<212> TYPE: RNA
<213> ORGANISM: Mus musculus

<400> SEQUENCE: 294
uccaggucuc agggcuucac aggcauccuu a                          31

<210> SEQ ID NO 295
<211> LENGTH: 31
<212> TYPE: RNA
<213> ORGANISM: Mus musculus

<400> SEQUENCE: 295
uguuucaaag gcuccagguc ucagggcuuc a                          31

<210> SEQ ID NO 296
<211> LENGTH: 31
<212> TYPE: RNA
<213> ORGANISM: Mus musculus

<400> SEQUENCE: 296
uucaaaggcu ccaggucuca gggcuucaca g                          31

<210> SEQ ID NO 297
<211> LENGTH: 31
<212> TYPE: RNA
<213> ORGANISM: Mus musculus

<400> SEQUENCE: 297
uuucaaaggc uccaggucuc agggcuucac a                            31

<210> SEQ ID NO 298
<211> LENGTH: 31
<212> TYPE: RNA
<213> ORGANISM: Mus musculus

<400> SEQUENCE: 298
ggcuugaagg aaaauugcuu uauuguguuu c                            31

<210> SEQ ID NO 299
<211> LENGTH: 31
<212> TYPE: RNA
<213> ORGANISM: Mus musculus

<400> SEQUENCE: 299
gcuugaagga aaauugcuuu auuguguuuc u                            31

<210> SEQ ID NO 300
<211> LENGTH: 31
<212> TYPE: RNA
<213> ORGANISM: Mus musculus

<400> SEQUENCE: 300
cuugaaggaa aauugcuuua uuguguuucu g                            31

<210> SEQ ID NO 301
<211> LENGTH: 31
<212> TYPE: RNA
<213> ORGANISM: Mus musculus

<400> SEQUENCE: 301
uugaaggaaa auugcuuuau uguguuucug c                            31

<210> SEQ ID NO 302
<211> LENGTH: 31
<212> TYPE: RNA
<213> ORGANISM: Mus musculus

<400> SEQUENCE: 302
ugaaggaaaa uugcuuuauu guguuucugc c                            31

<210> SEQ ID NO 303
<211> LENGTH: 31
<212> TYPE: RNA
<213> ORGANISM: Mus musculus

<400> SEQUENCE: 303
gaaggaaaau ugcuuuauug uguuucugcc u                            31

<210> SEQ ID NO 304
<211> LENGTH: 31
<212> TYPE: RNA
<213> ORGANISM: Mus musculus

<400> SEQUENCE: 304
ggaaaauugc uuuauugugu uucugccuaa g                            31

<210> SEQ ID NO 305
<211> LENGTH: 31
<212> TYPE: RNA
<213> ORGANISM: Mus musculus

<400> SEQUENCE: 305
gaaaauugcu uuauuguguu ucugccuaag g                                    31

<210> SEQ ID NO 306
<211> LENGTH: 31
<212> TYPE: RNA
<213> ORGANISM: Mus musculus

<400> SEQUENCE: 306
aaauugcuuu auuguguuuc ugccuaaggu g                                    31

<210> SEQ ID NO 307
<211> LENGTH: 31
<212> TYPE: RNA
<213> ORGANISM: Mus musculus

<400> SEQUENCE: 307
aaggaaaauu gcuuuauugu guuucugccu a                                    31

<210> SEQ ID NO 308
<211> LENGTH: 31
<212> TYPE: RNA
<213> ORGANISM: Mus musculus

<400> SEQUENCE: 308
aggaaaauug cuuuauugug uuucugccua a                                    31

<210> SEQ ID NO 309
<211> LENGTH: 31
<212> TYPE: RNA
<213> ORGANISM: Mus musculus

<400> SEQUENCE: 309
aaaauugcuu uauuguguuu cugccuaagg u                                    31

<210> SEQ ID NO 310
<211> LENGTH: 31
<212> TYPE: RNA
<213> ORGANISM: Mus musculus

<400> SEQUENCE: 310
ggucucaggg cuucacaggc auccuuaggg u                                    31

<210> SEQ ID NO 311
<211> LENGTH: 31
<212> TYPE: RNA
<213> ORGANISM: Mus musculus

<400> SEQUENCE: 311
cucagggcuu cacaggcauc cuuaggguug g                                    31

<210> SEQ ID NO 312
<211> LENGTH: 31
<212> TYPE: RNA
<213> ORGANISM: Mus musculus

<400> SEQUENCE: 312
ggcuucacag gcauccuuag gguuggguag c            31

<210> SEQ ID NO 313
<211> LENGTH: 31
<212> TYPE: RNA
<213> ORGANISM: Mus musculus

<400> SEQUENCE: 313
gucucagggc uucacaggca uccuuagggu u            31

<210> SEQ ID NO 314
<211> LENGTH: 31
<212> TYPE: RNA
<213> ORGANISM: Mus musculus

<400> SEQUENCE: 314
ucucagggcu ucacaggcau ccuuaggguu g            31

<210> SEQ ID NO 315
<211> LENGTH: 31
<212> TYPE: RNA
<213> ORGANISM: Mus musculus

<400> SEQUENCE: 315
aauugcuuua uuguguuucu gccuaaggug c            31

<210> SEQ ID NO 316
<211> LENGTH: 31
<212> TYPE: RNA
<213> ORGANISM: Mus musculus

<400> SEQUENCE: 316
aggucucagg gcuucacagg cauccuuagg g            31

<210> SEQ ID NO 317
<211> LENGTH: 31
<212> TYPE: RNA
<213> ORGANISM: Mus musculus

<400> SEQUENCE: 317
gcuucacagg cauccuuagg guugggguagc a           31

<210> SEQ ID NO 318
<211> LENGTH: 31
<212> TYPE: RNA
<213> ORGANISM: Mus musculus

<400> SEQUENCE: 318
cuucacaggc auccuuaggg uugggguagca c           31

<210> SEQ ID NO 319
<211> LENGTH: 31
<212> TYPE: RNA
<213> ORGANISM: Mus musculus

<400> SEQUENCE: 319
cacaggcauc cuuaggguug gguagcacaa g            31

<210> SEQ ID NO 320
<211> LENGTH: 31
<212> TYPE: RNA
<213> ORGANISM: Mus musculus

<400> SEQUENCE: 320
acaggcaucc uuaggguugg guagcacaag a                              31

<210> SEQ ID NO 321
<211> LENGTH: 31
<212> TYPE: RNA
<213> ORGANISM: Mus musculus

<400> SEQUENCE: 321
caggcauccu uaggguuggg uagcacaaga u                              31

<210> SEQ ID NO 322
<211> LENGTH: 31
<212> TYPE: RNA
<213> ORGANISM: Mus musculus

<400> SEQUENCE: 322
uucacaggca uccuuagggu uggguagcac a                              31

<210> SEQ ID NO 323
<211> LENGTH: 31
<212> TYPE: RNA
<213> ORGANISM: Mus musculus

<400> SEQUENCE: 323
ucacaggcau ccuuagggu u ggguagcaca a                             31

<210> SEQ ID NO 324
<211> LENGTH: 31
<212> TYPE: RNA
<213> ORGANISM: Mus musculus

<400> SEQUENCE: 324
ucagggcuuc acaggcaucc uuaggguugg g                              31

<210> SEQ ID NO 325
<211> LENGTH: 31
<212> TYPE: RNA
<213> ORGANISM: Mus musculus

<400> SEQUENCE: 325
cagggcuuca caggcauccu uaggguuggg u                              31

<210> SEQ ID NO 326
<211> LENGTH: 31
<212> TYPE: RNA
<213> ORGANISM: Mus musculus

<400> SEQUENCE: 326
gggcuucaca ggcauccuua ggguugggua g                              31

<210> SEQ ID NO 327
<211> LENGTH: 31
<212> TYPE: RNA
<213> ORGANISM: Mus musculus

<400> SEQUENCE: 327
agggcuucac aggcauccuu aggguuggu a                               31

<210> SEQ ID NO 328
<211> LENGTH: 31
<212> TYPE: RNA
<213> ORGANISM: Homo sapiens

```
<400> SEQUENCE: 328
ggagaggcga ggaagucacc aucaaaccac u                           31

<210> SEQ ID NO 329
<211> LENGTH: 31
<212> TYPE: RNA
<213> ORGANISM: Homo sapiens

<400> SEQUENCE: 329
agaugugaga aguguugaca ggaagcugca g                           31

<210> SEQ ID NO 330
<211> LENGTH: 31
<212> TYPE: RNA
<213> ORGANISM: Homo sapiens

<400> SEQUENCE: 330
uaagauguga gaaguguuga caggaagcug c                           31

<210> SEQ ID NO 331
<211> LENGTH: 31
<212> TYPE: RNA
<213> ORGANISM: Homo sapiens

<400> SEQUENCE: 331
aagaugugag aguguugac aggaagcugc a                            31

<210> SEQ ID NO 332
<211> LENGTH: 31
<212> TYPE: RNA
<213> ORGANISM: Homo sapiens

<400> SEQUENCE: 332
auucacuuuc aaaccacuuu caguaacagg u                           31

<210> SEQ ID NO 333
<211> LENGTH: 31
<212> TYPE: RNA
<213> ORGANISM: Homo sapiens

<400> SEQUENCE: 333
gagaggcgag gaagucacca ucaaaccacu u                           31

<210> SEQ ID NO 334
<211> LENGTH: 31
<212> TYPE: RNA
<213> ORGANISM: Homo sapiens

<400> SEQUENCE: 334
gaugugagaa guguugacag gaagcugcag c                           31

<210> SEQ ID NO 335
<211> LENGTH: 31
<212> TYPE: RNA
<213> ORGANISM: Homo sapiens

<400> SEQUENCE: 335
augugagaag uguugacagg aagcugcagc u                           31

<210> SEQ ID NO 336
<211> LENGTH: 31
<212> TYPE: RNA
<213> ORGANISM: Homo sapiens
```

```
<400> SEQUENCE: 336
ugugagaagu guugacagga agcugcagcu u                              31

<210> SEQ ID NO 337
<211> LENGTH: 31
<212> TYPE: RNA
<213> ORGANISM: Homo sapiens

<400> SEQUENCE: 337
gugagaagug uugacaggaa gcugcagcuu a                              31

<210> SEQ ID NO 338
<211> LENGTH: 31
<212> TYPE: RNA
<213> ORGANISM: Homo sapiens

<400> SEQUENCE: 338
ugagaagugu ugacaggaag cugcagcuua g                              31

<210> SEQ ID NO 339
<211> LENGTH: 31
<212> TYPE: RNA
<213> ORGANISM: Homo sapiens

<400> SEQUENCE: 339
gagaaguguu gacaggaagc ugcagcuuag a                              31

<210> SEQ ID NO 340
<211> LENGTH: 31
<212> TYPE: RNA
<213> ORGANISM: Homo sapiens

<400> SEQUENCE: 340
gaaguguuga caggaagcug cagcuuagau g                              31

<210> SEQ ID NO 341
<211> LENGTH: 31
<212> TYPE: RNA
<213> ORGANISM: Homo sapiens

<400> SEQUENCE: 341
aaguguugac aggaagcugc agcuuagaug g                              31

<210> SEQ ID NO 342
<211> LENGTH: 31
<212> TYPE: RNA
<213> ORGANISM: Homo sapiens

<400> SEQUENCE: 342
agaaguguug acaggaagcu gcagcuuaga u                              31

<210> SEQ ID NO 343
<211> LENGTH: 31
<212> TYPE: RNA
<213> ORGANISM: Homo sapiens

<400> SEQUENCE: 343
gaucacaacu ccauggcaac aagaugacac a                              31

<210> SEQ ID NO 344
<211> LENGTH: 31
<212> TYPE: RNA
```

```
<213> ORGANISM: Homo sapiens

<400> SEQUENCE: 344
aucacaacuc cauggcaaca agaugacaca a                              31

<210> SEQ ID NO 345
<211> LENGTH: 31
<212> TYPE: RNA
<213> ORGANISM: Homo sapiens

<400> SEQUENCE: 345
ucacaacucc auggcaacaa gaugacacaa a                              31

<210> SEQ ID NO 346
<211> LENGTH: 31
<212> TYPE: RNA
<213> ORGANISM: Homo sapiens

<400> SEQUENCE: 346
uucacuuuca aaccacuuuc aguaacaggu g                              31

<210> SEQ ID NO 347
<211> LENGTH: 31
<212> TYPE: RNA
<213> ORGANISM: Homo sapiens

<400> SEQUENCE: 347
ucacuuucaa accacuuuca guaacaggug a                              31

<210> SEQ ID NO 348
<211> LENGTH: 31
<212> TYPE: RNA
<213> ORGANISM: Homo sapiens

<400> SEQUENCE: 348
agaggcgagg aagucaccau caaaccacuu u                              31

<210> SEQ ID NO 349
<211> LENGTH: 31
<212> TYPE: RNA
<213> ORGANISM: Homo sapiens

<400> SEQUENCE: 349
ggaugaucac aacuccaugg caacaagaug a                              31

<210> SEQ ID NO 350
<211> LENGTH: 31
<212> TYPE: RNA
<213> ORGANISM: Homo sapiens

<400> SEQUENCE: 350
gaugaucaca acuccauggc aacaagauga c                              31

<210> SEQ ID NO 351
<211> LENGTH: 31
<212> TYPE: RNA
<213> ORGANISM: Homo sapiens

<400> SEQUENCE: 351
ugaucacaac uccauggcaa caagaugaca c                              31

<210> SEQ ID NO 352
<211> LENGTH: 31
```

```
<212> TYPE: RNA
<213> ORGANISM: Homo sapiens

<400> SEQUENCE: 352
cacuuucaaa ccacuuucag uaacagguga g                              31

<210> SEQ ID NO 353
<211> LENGTH: 31
<212> TYPE: RNA
<213> ORGANISM: Homo sapiens

<400> SEQUENCE: 353
augaucacaa cuccauggca acaagaugac a                              31

<210> SEQ ID NO 354
<211> LENGTH: 31
<212> TYPE: RNA
<213> ORGANISM: Homo sapiens

<400> SEQUENCE: 354
aaccacuuuc aguaacaggu gagguucuac c                              31

<210> SEQ ID NO 355
<211> LENGTH: 31
<212> TYPE: RNA
<213> ORGANISM: Homo sapiens

<400> SEQUENCE: 355
accacuuuca guaacaggug agguucuacc u                              31

<210> SEQ ID NO 356
<211> LENGTH: 31
<212> TYPE: RNA
<213> ORGANISM: Homo sapiens

<400> SEQUENCE: 356
ccacuuucag uaacagguga gguucuaccu u                              31

<210> SEQ ID NO 357
<211> LENGTH: 31
<212> TYPE: RNA
<213> ORGANISM: Homo sapiens

<400> SEQUENCE: 357
acuuucaaac cacuuucagu aacaggugag g                              31

<210> SEQ ID NO 358
<211> LENGTH: 31
<212> TYPE: RNA
<213> ORGANISM: Homo sapiens

<400> SEQUENCE: 358
cuuucaaacc acuuucagua acaggugagg u                              31

<210> SEQ ID NO 359
<211> LENGTH: 31
<212> TYPE: RNA
<213> ORGANISM: Homo sapiens

<400> SEQUENCE: 359
uucaaaccac uuucaguaac aggugagguu c                              31

<210> SEQ ID NO 360
```

```
<211> LENGTH: 31
<212> TYPE: RNA
<213> ORGANISM: Homo sapiens

<400> SEQUENCE: 360
ucaaaccacu uucaguaaca ggugagguuc u                              31

<210> SEQ ID NO 361
<211> LENGTH: 31
<212> TYPE: RNA
<213> ORGANISM: Homo sapiens

<400> SEQUENCE: 361
caaaccacuu ucaguaacag gugagguucu a                              31

<210> SEQ ID NO 362
<211> LENGTH: 31
<212> TYPE: RNA
<213> ORGANISM: Homo sapiens

<400> SEQUENCE: 362
aaaccacuuu caguaacagg ugagguucua c                              31

<210> SEQ ID NO 363
<211> LENGTH: 31
<212> TYPE: RNA
<213> ORGANISM: Homo sapiens

<400> SEQUENCE: 363
cacuuucagu aacaggugag guucuaccuu a                              31

<210> SEQ ID NO 364
<211> LENGTH: 31
<212> TYPE: RNA
<213> ORGANISM: Homo sapiens

<400> SEQUENCE: 364
uuucaaacca cuuucaguaa caggugaggu u                              31

<210> SEQ ID NO 365
<211> LENGTH: 31
<212> TYPE: RNA
<213> ORGANISM: Homo sapiens

<400> SEQUENCE: 365
uuuauucacu uucaaaccac uuucaguaac a                              31

<210> SEQ ID NO 366
<211> LENGTH: 31
<212> TYPE: RNA
<213> ORGANISM: Homo sapiens

<400> SEQUENCE: 366
gggagaggcg aggaagucac caucaaacca c                              31

<210> SEQ ID NO 367
<211> LENGTH: 31
<212> TYPE: RNA
<213> ORGANISM: Homo sapiens

<400> SEQUENCE: 367
ggcaacaaga ugacacaaau gcagcagaga c                              31
```

```
<210> SEQ ID NO 368
<211> LENGTH: 31
<212> TYPE: RNA
<213> ORGANISM: Homo sapiens

<400> SEQUENCE: 368
gcaacaagau gacacaaaug cagcagagac c                              31

<210> SEQ ID NO 369
<211> LENGTH: 31
<212> TYPE: RNA
<213> ORGANISM: Homo sapiens

<400> SEQUENCE: 369
guuagcauaa gaugugagaa guuugacag g                               31

<210> SEQ ID NO 370
<211> LENGTH: 31
<212> TYPE: RNA
<213> ORGANISM: Homo sapiens

<400> SEQUENCE: 370
agcauaagau gugagaagug uugacaggaa g                              31

<210> SEQ ID NO 371
<211> LENGTH: 31
<212> TYPE: RNA
<213> ORGANISM: Homo sapiens

<400> SEQUENCE: 371
auaagaugug agaaguguug acaggaagcu g                              31

<210> SEQ ID NO 372
<211> LENGTH: 31
<212> TYPE: RNA
<213> ORGANISM: Homo sapiens

<400> SEQUENCE: 372
ucaccaucaa accacuuuau cuacaguuag c                              31

<210> SEQ ID NO 373
<211> LENGTH: 31
<212> TYPE: RNA
<213> ORGANISM: Homo sapiens

<400> SEQUENCE: 373
caccaucaaa ccacuuuauc uacaguuagc a                              31

<210> SEQ ID NO 374
<211> LENGTH: 31
<212> TYPE: RNA
<213> ORGANISM: Homo sapiens

<400> SEQUENCE: 374
aguuagcaua agaugugaga aguuugaca g                               31

<210> SEQ ID NO 375
<211> LENGTH: 31
<212> TYPE: RNA
<213> ORGANISM: Homo sapiens

<400> SEQUENCE: 375
uuagcauaag augugagaag uguugacagg a                              31
```

```
<210> SEQ ID NO 376
<211> LENGTH: 31
<212> TYPE: RNA
<213> ORGANISM: Homo sapiens

<400> SEQUENCE: 376
uagcauaaga ugugagaagu guugacagga a                              31

<210> SEQ ID NO 377
<211> LENGTH: 31
<212> TYPE: RNA
<213> ORGANISM: Homo sapiens

<400> SEQUENCE: 377
aagucaccau caaaccacuu uaucuacagu u                              31

<210> SEQ ID NO 378
<211> LENGTH: 31
<212> TYPE: RNA
<213> ORGANISM: Homo sapiens

<400> SEQUENCE: 378
agucaccauc aaaccacuuu aucuacaguu a                              31

<210> SEQ ID NO 379
<211> LENGTH: 31
<212> TYPE: RNA
<213> ORGANISM: Homo sapiens

<400> SEQUENCE: 379
accaucaaac cacuuuaucu acaguuagca u                              31

<210> SEQ ID NO 380
<211> LENGTH: 31
<212> TYPE: RNA
<213> ORGANISM: Homo sapiens

<400> SEQUENCE: 380
ccaucaaacc acuuuaucua caguuagcau a                              31

<210> SEQ ID NO 381
<211> LENGTH: 31
<212> TYPE: RNA
<213> ORGANISM: Homo sapiens

<400> SEQUENCE: 381
uacaguuagc auaagaugug agaaguguug a                              31

<210> SEQ ID NO 382
<211> LENGTH: 31
<212> TYPE: RNA
<213> ORGANISM: Homo sapiens

<400> SEQUENCE: 382
cugaaguuua uucacuuuca aaccacuuuc a                              31

<210> SEQ ID NO 383
<211> LENGTH: 31
<212> TYPE: RNA
<213> ORGANISM: Homo sapiens

<400> SEQUENCE: 383
guuuauucac uuucaaacca cuuucaguaa c                              31
```

<210> SEQ ID NO 384
<211> LENGTH: 31
<212> TYPE: RNA
<213> ORGANISM: Homo sapiens

<400> SEQUENCE: 384
uuauucacuu ucaaaccacu uucaguaaca g                          31

<210> SEQ ID NO 385
<211> LENGTH: 31
<212> TYPE: RNA
<213> ORGANISM: Homo sapiens

<400> SEQUENCE: 385
aaguuuauuc acuucaaac cacuuucagu a                           31

<210> SEQ ID NO 386
<211> LENGTH: 31
<212> TYPE: RNA
<213> ORGANISM: Homo sapiens

<400> SEQUENCE: 386
aguuuauuca cuucaaacc acuuucagua a                           31

<210> SEQ ID NO 387
<211> LENGTH: 31
<212> TYPE: RNA
<213> ORGANISM: Homo sapiens

<400> SEQUENCE: 387
ggugggagag gcgaggaagu caccaucaaa c                          31

<210> SEQ ID NO 388
<211> LENGTH: 31
<212> TYPE: RNA
<213> ORGANISM: Homo sapiens

<400> SEQUENCE: 388
gugggagagg cgaggaaguc accaucaaac c                          31

<210> SEQ ID NO 389
<211> LENGTH: 31
<212> TYPE: RNA
<213> ORGANISM: Homo sapiens

<400> SEQUENCE: 389
ugggagaggc gaggaaguca ccaucaaacc a                          31

<210> SEQ ID NO 390
<211> LENGTH: 31
<212> TYPE: RNA
<213> ORGANISM: Homo sapiens

<400> SEQUENCE: 390
ccauggcaac aagaugacac aaaugcagca g                          31

<210> SEQ ID NO 391
<211> LENGTH: 31
<212> TYPE: RNA
<213> ORGANISM: Homo sapiens

<400> SEQUENCE: 391

-continued gcauaagaug ugagaagugu ugacaggaag c                                  31

<210> SEQ ID NO 392
<211> LENGTH: 31
<212> TYPE: RNA
<213> ORGANISM: Homo sapiens

<400> SEQUENCE: 392
cauggcaaca agaugacaca aaugcagcag a                                  31

<210> SEQ ID NO 393
<211> LENGTH: 31
<212> TYPE: RNA
<213> ORGANISM: Homo sapiens

<400> SEQUENCE: 393
auggcaacaa gaugcacaa augcagcaga g                                   31

<210> SEQ ID NO 394
<211> LENGTH: 31
<212> TYPE: RNA
<213> ORGANISM: Homo sapiens

<400> SEQUENCE: 394
uggcaacaag augcacaaa ugcagcagag a                                   31

<210> SEQ ID NO 395
<211> LENGTH: 31
<212> TYPE: RNA
<213> ORGANISM: Homo sapiens

<400> SEQUENCE: 395
cauaagaugu gagaaguguu gacaggaagc u                                  31

<210> SEQ ID NO 396
<211> LENGTH: 31
<212> TYPE: RNA
<213> ORGANISM: Homo sapiens

<400> SEQUENCE: 396
aggaagucac caucaaacca cuuuaucuac a                                  31

<210> SEQ ID NO 397
<211> LENGTH: 31
<212> TYPE: RNA
<213> ORGANISM: Homo sapiens

<400> SEQUENCE: 397
gaagucacca ucaaaccacu uuaucuacag u                                  31

<210> SEQ ID NO 398
<211> LENGTH: 31
<212> TYPE: RNA
<213> ORGANISM: Homo sapiens

<400> SEQUENCE: 398
gucaccauca aaccacuuua ucuacaguua g                                  31

<210> SEQ ID NO 399
<211> LENGTH: 31
<212> TYPE: RNA
<213> ORGANISM: Homo sapiens

<400> SEQUENCE: 399
cuacaguuag cauaagaugu gagaagguguu g     31

<210> SEQ ID NO 400
<211> LENGTH: 31
<212> TYPE: RNA
<213> ORGANISM: Homo sapiens

<400> SEQUENCE: 400
acaguuagca uaagauguga gaaguguuga c     31

<210> SEQ ID NO 401
<211> LENGTH: 31
<212> TYPE: RNA
<213> ORGANISM: Homo sapiens

<400> SEQUENCE: 401
caguuagcau aagaugugag aaguguugac a     31

<210> SEQ ID NO 402
<211> LENGTH: 31
<212> TYPE: RNA
<213> ORGANISM: Homo sapiens

<400> SEQUENCE: 402
gcugaaguuu auucacuuuc aaaccacuuu c     31

<210> SEQ ID NO 403
<211> LENGTH: 31
<212> TYPE: RNA
<213> ORGANISM: Homo sapiens

<400> SEQUENCE: 403
uauucacuuu caaaccacuu ucaguaacag g     31

<210> SEQ ID NO 404
<211> LENGTH: 31
<212> TYPE: RNA
<213> ORGANISM: Homo sapiens

<400> SEQUENCE: 404
uaucuacagu uagcauaaga ugugagaagu g     31

<210> SEQ ID NO 405
<211> LENGTH: 31
<212> TYPE: RNA
<213> ORGANISM: Homo sapiens

<400> SEQUENCE: 405
aucuacaguu agcauaagau gugagaagug u     31

<210> SEQ ID NO 406
<211> LENGTH: 31
<212> TYPE: RNA
<213> ORGANISM: Homo sapiens

<400> SEQUENCE: 406
ucuacaguua gcauaagaug ugagaagugu u     31

<210> SEQ ID NO 407
<211> LENGTH: 31
<212> TYPE: RNA
<213> ORGANISM: Homo sapiens -continued

```
<400> SEQUENCE: 407
ugcugaaguu uauucacuuu caaaccacuu u                                      31

<210> SEQ ID NO 408
<211> LENGTH: 31
<212> TYPE: RNA
<213> ORGANISM: Homo sapiens

<400> SEQUENCE: 408
ugaaguuuau ucacuuucaa accacuuuca g                                      31

<210> SEQ ID NO 409
<211> LENGTH: 31
<212> TYPE: RNA
<213> ORGANISM: Homo sapiens

<400> SEQUENCE: 409
gaaguuuauu cacuuucaaa ccacuuucag u                                      31

<210> SEQ ID NO 410
<211> LENGTH: 31
<212> TYPE: RNA
<213> ORGANISM: Homo sapiens

<400> SEQUENCE: 410
aguguugaca ggaagcugca gcuuagaugg g                                      31

<210> SEQ ID NO 411
<211> LENGTH: 31
<212> TYPE: RNA
<213> ORGANISM: Homo sapiens

<400> SEQUENCE: 411
guguugacag gaagcugcag cuuagauggg a                                      31

<210> SEQ ID NO 412
<211> LENGTH: 31
<212> TYPE: RNA
<213> ORGANISM: Homo sapiens

<400> SEQUENCE: 412
guugacagga agcugcagcu uagaugggau g                                      31

<210> SEQ ID NO 413
<211> LENGTH: 31
<212> TYPE: RNA
<213> ORGANISM: Homo sapiens

<400> SEQUENCE: 413
uguugacagg aagcugcagc uuagauggga u                                      31

<210> SEQ ID NO 414
<211> LENGTH: 31
<212> TYPE: RNA
<213> ORGANISM: Homo sapiens

<400> SEQUENCE: 414
uugacaggaa gcugcagcuu agaugggaug a                                      31

<210> SEQ ID NO 415
<211> LENGTH: 31
<212> TYPE: RNA
<213> ORGANISM: Homo sapiens
```

<400> SEQUENCE: 415
ugacaggaag cugcagcuua gaugggauga u         31

<210> SEQ ID NO 416
<211> LENGTH: 31
<212> TYPE: RNA
<213> ORGANISM: Homo sapiens

<400> SEQUENCE: 416
cuccauggca acaagaugac acaaaugcag c         31

<210> SEQ ID NO 417
<211> LENGTH: 31
<212> TYPE: RNA
<213> ORGANISM: Homo sapiens

<400> SEQUENCE: 417
caacuccaug gcaacaagau gacacaaaug c         31

<210> SEQ ID NO 418
<211> LENGTH: 31
<212> TYPE: RNA
<213> ORGANISM: Homo sapiens

<400> SEQUENCE: 418
acuccauggc aacaagauga cacaaaugca g         31

<210> SEQ ID NO 419
<211> LENGTH: 31
<212> TYPE: RNA
<213> ORGANISM: Homo sapiens

<400> SEQUENCE: 419
uccauggcaa caagaugaca caaaugcagc a         31

<210> SEQ ID NO 420
<211> LENGTH: 31
<212> TYPE: RNA
<213> ORGANISM: Homo sapiens

<400> SEQUENCE: 420
cgaggaaguc accaucaaac cacuuuaucu a         31

<210> SEQ ID NO 421
<211> LENGTH: 31
<212> TYPE: RNA
<213> ORGANISM: Homo sapiens

<400> SEQUENCE: 421
gaggaaguca ccaucaaacc acuuuaucua c         31

<210> SEQ ID NO 422
<211> LENGTH: 31
<212> TYPE: RNA
<213> ORGANISM: Homo sapiens

<400> SEQUENCE: 422
ggaagucacc aucaaaccac uuuaucuaca g         31

<210> SEQ ID NO 423
<211> LENGTH: 31
<212> TYPE: RNA

<213> ORGANISM: Homo sapiens

<400> SEQUENCE: 423
cacaacucca uggcaacaag augacacaaa u                               31

<210> SEQ ID NO 424
<211> LENGTH: 31
<212> TYPE: RNA
<213> ORGANISM: Homo sapiens

<400> SEQUENCE: 424
acaacuccau ggcaacaaga ugacacaaau g                               31

<210> SEQ ID NO 425
<211> LENGTH: 31
<212> TYPE: RNA
<213> ORGANISM: Homo sapiens

<400> SEQUENCE: 425
aacuccaugg caacaagaug acacaaaugc a                               31

<210> SEQ ID NO 426
<211> LENGTH: 31
<212> TYPE: RNA
<213> ORGANISM: Homo sapiens

<400> SEQUENCE: 426
gugcugaagu uuauucacuu ucaaaccacu u                               31

<210> SEQ ID NO 427
<211> LENGTH: 31
<212> TYPE: RNA
<213> ORGANISM: Homo sapiens

<400> SEQUENCE: 427 ccagggaca ggagccucuu gcagucuguc c                                31

<210> SEQ ID NO 428
<211> LENGTH: 31
<212> TYPE: RNA
<213> ORGANISM: Homo sapiens

<400> SEQUENCE: 428
ggacaggagc cucuugcagu cugcccuag g                                31

<210> SEQ ID NO 429
<211> LENGTH: 31
<212> TYPE: RNA
<213> ORGANISM: Homo sapiens

<400> SEQUENCE: 429
gacaggagcc ucuugcaguc ugcccuagg c                                31

<210> SEQ ID NO 430
<211> LENGTH: 31
<212> TYPE: RNA
<213> ORGANISM: Homo sapiens

<400> SEQUENCE: 430
acaggagccu cuugcagucu gucccuaggc c                               31

<210> SEQ ID NO 431
<211> LENGTH: 31

```
<212> TYPE: RNA
<213> ORGANISM: Homo sapiens

<400> SEQUENCE: 431
gacaggaagc ugcagcuuag augggaugau c                              31

<210> SEQ ID NO 432
<211> LENGTH: 31
<212> TYPE: RNA
<213> ORGANISM: Homo sapiens

<400> SEQUENCE: 432
gaggcgagga agucaccauc aaaccacuuu a                              31

<210> SEQ ID NO 433
<211> LENGTH: 31
<212> TYPE: RNA
<213> ORGANISM: Homo sapiens

<400> SEQUENCE: 433
acaggaagcu gcagcuuaga ugggaugauc a                              31

<210> SEQ ID NO 434
<211> LENGTH: 31
<212> TYPE: RNA
<213> ORGANISM: Homo sapiens

<400> SEQUENCE: 434
aggaagcugc agcuuagaug ggaugaucac a                              31

<210> SEQ ID NO 435
<211> LENGTH: 31
<212> TYPE: RNA
<213> ORGANISM: Homo sapiens

<400> SEQUENCE: 435
ggaagcugca gcuuagaugg gaugaucaca a                              31

<210> SEQ ID NO 436
<211> LENGTH: 31
<212> TYPE: RNA
<213> ORGANISM: Homo sapiens

<400> SEQUENCE: 436
gaugggauga ucacaacucc auggcaacaa g                              31

<210> SEQ ID NO 437
<211> LENGTH: 31
<212> TYPE: RNA
<213> ORGANISM: Homo sapiens

<400> SEQUENCE: 437
gggaugauca caacuccaug gcaacaagau g                              31

<210> SEQ ID NO 438
<211> LENGTH: 31
<212> TYPE: RNA
<213> ORGANISM: Homo sapiens

<400> SEQUENCE: 438
gcgaggaagu caccaucaaa ccacuuuauc u                              31

<210> SEQ ID NO 439
```

```
<211> LENGTH: 31
<212> TYPE: RNA
<213> ORGANISM: Homo sapiens

<400> SEQUENCE: 439
agaugggaug aucacaacuc cauggcaaca a                              31

<210> SEQ ID NO 440
<211> LENGTH: 31
<212> TYPE: RNA
<213> ORGANISM: Homo sapiens

<400> SEQUENCE: 440
augggaugau cacaacucca uggcaacaag a                              31

<210> SEQ ID NO 441
<211> LENGTH: 31
<212> TYPE: RNA
<213> ORGANISM: Homo sapiens

<400> SEQUENCE: 441
gucuucuguc cauggugcug aaguuuauuc a                              31

<210> SEQ ID NO 442
<211> LENGTH: 31
<212> TYPE: RNA
<213> ORGANISM: Homo sapiens

<400> SEQUENCE: 442
ucuucugucc auggugcuga aguuuauuca c                              31

<210> SEQ ID NO 443
<211> LENGTH: 31
<212> TYPE: RNA
<213> ORGANISM: Homo sapiens

<400> SEQUENCE: 443
cuucugucca uggugcugaa guuuauucac u                              31

<210> SEQ ID NO 444
<211> LENGTH: 31
<212> TYPE: RNA
<213> ORGANISM: Homo sapiens

<400> SEQUENCE: 444
cuguccaugg ugcugaaguu uauucacuuu c                              31

<210> SEQ ID NO 445
<211> LENGTH: 31
<212> TYPE: RNA
<213> ORGANISM: Homo sapiens

<400> SEQUENCE: 445
uucuguccau ggugcugaag uuuauucacu u                              31

<210> SEQ ID NO 446
<211> LENGTH: 31
<212> TYPE: RNA
<213> ORGANISM: Homo sapiens

<400> SEQUENCE: 446
ucuguccaug gugcugaagu uuauucacuu u                              31
```

```
<210> SEQ ID NO 447
<211> LENGTH: 31
<212> TYPE: RNA
<213> ORGANISM: Homo sapiens

<400> SEQUENCE: 447
ccauggugcu gaaguuuauu cacuuucaaa c                          31

<210> SEQ ID NO 448
<211> LENGTH: 31
<212> TYPE: RNA
<213> ORGANISM: Homo sapiens

<400> SEQUENCE: 448
cauggugcug aaguuuauuc acuuucaaac c                          31

<210> SEQ ID NO 449
<211> LENGTH: 31
<212> TYPE: RNA
<213> ORGANISM: Homo sapiens

<400> SEQUENCE: 449
uggugcugaa guuuauucac uuucaaacca c                          31

<210> SEQ ID NO 450
<211> LENGTH: 31
<212> TYPE: RNA
<213> ORGANISM: Homo sapiens

<400> SEQUENCE: 450
ggugcugaag uuuauucacu uucaaaccac u                          31

<210> SEQ ID NO 451
<211> LENGTH: 31
<212> TYPE: RNA
<213> ORGANISM: Homo sapiens

<400> SEQUENCE: 451
uccauggugc ugaaguuuau ucacuuucaa a                          31

<210> SEQ ID NO 452
<211> LENGTH: 31
<212> TYPE: RNA
<213> ORGANISM: Homo sapiens

<400> SEQUENCE: 452
auggugcuga aguuuauuca cuuucaaacc a                          31

<210> SEQ ID NO 453
<211> LENGTH: 31
<212> TYPE: RNA
<213> ORGANISM: Homo sapiens

<400> SEQUENCE: 453
uuucaguaac aggugagguu cuaccuuaaa a                          31

<210> SEQ ID NO 454
<211> LENGTH: 31
<212> TYPE: RNA
<213> ORGANISM: Homo sapiens

<400> SEQUENCE: 454
uucaguaaca ggugagguuc uaccuuaaaa u                          31
```

<210> SEQ ID NO 455
<211> LENGTH: 31
<212> TYPE: RNA
<213> ORGANISM: Homo sapiens

<400> SEQUENCE: 455
caggaagcug cagcuuagau gggaugauca c                          31

<210> SEQ ID NO 456
<211> LENGTH: 31
<212> TYPE: RNA
<213> ORGANISM: Homo sapiens

<400> SEQUENCE: 456
ggcgaggaag ucaccaucaa accacuuuau c                          31

<210> SEQ ID NO 457
<211> LENGTH: 31
<212> TYPE: RNA
<213> ORGANISM: Homo sapiens

<400> SEQUENCE: 457
gaagcugcag cuuagauggg augaucacaa c                          31

<210> SEQ ID NO 458
<211> LENGTH: 31
<212> TYPE: RNA
<213> ORGANISM: Homo sapiens

<400> SEQUENCE: 458
aggcgaggaa gucaccauca aaccacuuua u                          31

<210> SEQ ID NO 459
<211> LENGTH: 31
<212> TYPE: RNA
<213> ORGANISM: Homo sapiens

<400> SEQUENCE: 459
aagcugcagc uuagauggga ugaucacaac u                          31

<210> SEQ ID NO 460
<211> LENGTH: 31
<212> TYPE: RNA
<213> ORGANISM: Homo sapiens

<400> SEQUENCE: 460
uagaugggau gaucacaacu ccauggcaac a                          31

<210> SEQ ID NO 461
<211> LENGTH: 31
<212> TYPE: RNA
<213> ORGANISM: Homo sapiens

<400> SEQUENCE: 461
ugggaugauc acaacuccau ggcaacaaga u                          31

<210> SEQ ID NO 462
<211> LENGTH: 31
<212> TYPE: RNA
<213> ORGANISM: Homo sapiens

<400> SEQUENCE: 462
uguccauggu gcugaaguuu auucacuuuc a                          31

```
<210> SEQ ID NO 463
<211> LENGTH: 31
<212> TYPE: RNA
<213> ORGANISM: Homo sapiens

<400> SEQUENCE: 463
guccauggug cugaaguuua uucacuuuca a                                          31

<210> SEQ ID NO 464
<211> LENGTH: 31
<212> TYPE: RNA
<213> ORGANISM: Homo sapiens

<400> SEQUENCE: 464
acuuucagua acaggugagg uucuaccuua a                                          31

<210> SEQ ID NO 465
<211> LENGTH: 31
<212> TYPE: RNA
<213> ORGANISM: Homo sapiens

<400> SEQUENCE: 465
cuuucaguaa caggugaggu ucuaccuuaa a                                          31

<210> SEQ ID NO 466
<211> LENGTH: 31
<212> TYPE: RNA
<213> ORGANISM: Homo sapiens

<400> SEQUENCE: 466
gcugcagcuu agaugggaug aucacaacuc c                                          31

<210> SEQ ID NO 467
<211> LENGTH: 31
<212> TYPE: RNA
<213> ORGANISM: Homo sapiens

<400> SEQUENCE: 467
agcugcagcu uagaugggau gaucacaacu c                                          31

<210> SEQ ID NO 468
<211> LENGTH: 31
<212> TYPE: RNA
<213> ORGANISM: Homo sapiens

<400> SEQUENCE: 468
cugcagcuua gaugggauga ucacaacucc a                                          31

<210> SEQ ID NO 469
<211> LENGTH: 31
<212> TYPE: RNA
<213> ORGANISM: Homo sapiens

<400> SEQUENCE: 469
gcagcuuaga ugggaugauc acaacuccau g                                          31

<210> SEQ ID NO 470
<211> LENGTH: 31
<212> TYPE: RNA
<213> ORGANISM: Homo sapiens

<400> SEQUENCE: 470
```

```
cagcuuagau gggaugauca caacuccaug g                                    31

<210> SEQ ID NO 471
<211> LENGTH: 31
<212> TYPE: RNA
<213> ORGANISM: Homo sapiens

<400> SEQUENCE: 471
agcuuagaug ggaugaucac aacuccaugg c                                    31

<210> SEQ ID NO 472
<211> LENGTH: 31
<212> TYPE: RNA
<213> ORGANISM: Homo sapiens

<400> SEQUENCE: 472
gcuuagaugg gaugaucaca acuccauggc a                                    31

<210> SEQ ID NO 473
<211> LENGTH: 31
<212> TYPE: RNA
<213> ORGANISM: Homo sapiens

<400> SEQUENCE: 473
ugcagcuuag augggaugau cacaacucca u                                    31

<210> SEQ ID NO 474
<211> LENGTH: 31
<212> TYPE: RNA
<213> ORGANISM: Homo sapiens

<400> SEQUENCE: 474
cuuagauggg augaucacaa cuccauggca a                                    31

<210> SEQ ID NO 475
<211> LENGTH: 31
<212> TYPE: RNA
<213> ORGANISM: Homo sapiens

<400> SEQUENCE: 475
uuagauggga ugaucacaac uccauggcaa c                                    31

<210> SEQ ID NO 476
<211> LENGTH: 31
<212> TYPE: RNA
<213> ORGANISM: Homo sapiens

<400> SEQUENCE: 476
aaugcagcag agaccccagg ggacaggagc c                                    31

<210> SEQ ID NO 477
<211> LENGTH: 31
<212> TYPE: RNA
<213> ORGANISM: Homo sapiens

<400> SEQUENCE: 477
ugcagcagag accccagggg acaggagccu c                                    31

<210> SEQ ID NO 478
<211> LENGTH: 31
<212> TYPE: RNA
<213> ORGANISM: Homo sapiens

<400> SEQUENCE: 478
```

```
gcagcagaga ccccagggga caggagccuc u                                31

<210> SEQ ID NO 479
<211> LENGTH: 31
<212> TYPE: RNA
<213> ORGANISM: Homo sapiens

<400> SEQUENCE: 479
augcagcaga gaccccaggg gacaggagcc u                                31

<210> SEQ ID NO 480
<211> LENGTH: 31
<212> TYPE: RNA
<213> ORGANISM: Homo sapiens

<400> SEQUENCE: 480
caagaugaca caaaugcagc agagacccca g                                31

<210> SEQ ID NO 481
<211> LENGTH: 31
<212> TYPE: RNA
<213> ORGANISM: Homo sapiens

<400> SEQUENCE: 481
aagaugacac aaaugcagca gagacccag g                                 31

<210> SEQ ID NO 482
<211> LENGTH: 31
<212> TYPE: RNA
<213> ORGANISM: Homo sapiens

<400> SEQUENCE: 482
caacaagaug acacaaaugc agcagagacc c                                31

<210> SEQ ID NO 483
<211> LENGTH: 31
<212> TYPE: RNA
<213> ORGANISM: Homo sapiens

<400> SEQUENCE: 483
aacaagauga cacaaaugca gcagagaccc c                                31

<210> SEQ ID NO 484
<211> LENGTH: 31
<212> TYPE: RNA
<213> ORGANISM: Homo sapiens

<400> SEQUENCE: 484
acaagaugac acaaaugcag cagagacccc a                                31

<210> SEQ ID NO 485
<211> LENGTH: 31
<212> TYPE: RNA
<213> ORGANISM: Homo sapiens

<400> SEQUENCE: 485
caucaaacca cuuuaucuac aguuagcaua a                                31

<210> SEQ ID NO 486
<211> LENGTH: 31
<212> TYPE: RNA
<213> ORGANISM: Homo sapiens
```

```
<400> SEQUENCE: 486
gcagagaccc caggggacag gagccucuug c                                31

<210> SEQ ID NO 487
<211> LENGTH: 31
<212> TYPE: RNA
<213> ORGANISM: Homo sapiens

<400> SEQUENCE: 487 gcaugggug ggagaggcga ggaagucacc a                                 31

<210> SEQ ID NO 488
<211> LENGTH: 31
<212> TYPE: RNA
<213> ORGANISM: Homo sapiens

<400> SEQUENCE: 488
cagcagagac cccaggggac aggagccucu u                                31

<210> SEQ ID NO 489
<211> LENGTH: 31
<212> TYPE: RNA
<213> ORGANISM: Homo sapiens

<400> SEQUENCE: 489
agcagagacc ccaggggaca ggagccucuu g                                31

<210> SEQ ID NO 490
<211> LENGTH: 31
<212> TYPE: RNA
<213> ORGANISM: Homo sapiens

<400> SEQUENCE: 490
cagagacccc aggggacagg agccucuugc a                                31

<210> SEQ ID NO 491
<211> LENGTH: 31
<212> TYPE: RNA
<213> ORGANISM: Homo sapiens

<400> SEQUENCE: 491
agagacccca ggggacagga gccucuugca g                                31

<210> SEQ ID NO 492
<211> LENGTH: 31
<212> TYPE: RNA
<213> ORGANISM: Homo sapiens

<400> SEQUENCE: 492
ggggugggag aggcgaggaa gucaccauca a                                31

<210> SEQ ID NO 493
<211> LENGTH: 31
<212> TYPE: RNA
<213> ORGANISM: Homo sapiens

<400> SEQUENCE: 493
aaugcauggg gugggagagg cgaggaaguc a                                31

<210> SEQ ID NO 494
<211> LENGTH: 31
<212> TYPE: RNA
<213> ORGANISM: Homo sapiens
```

<400> SEQUENCE: 494 ggguggggaga ggcgaggaag ucaccaucaa a         31

<210> SEQ ID NO 495
<211> LENGTH: 31
<212> TYPE: RNA
<213> ORGANISM: Homo sapiens

<400> SEQUENCE: 495
aucaaaccac uuuaucuaca guuagcauaa g          31

<210> SEQ ID NO 496
<211> LENGTH: 31
<212> TYPE: RNA
<213> ORGANISM: Homo sapiens

<400> SEQUENCE: 496
ucaaaccacu uuaucuacag uuagcauaag a          31

<210> SEQ ID NO 497
<211> LENGTH: 31
<212> TYPE: RNA
<213> ORGANISM: Homo sapiens

<400> SEQUENCE: 497
caaaccacuu uaucuacagu uagcauaaga u          31

<210> SEQ ID NO 498
<211> LENGTH: 31
<212> TYPE: RNA
<213> ORGANISM: Homo sapiens

<400> SEQUENCE: 498
uuuaucuaca guuagcauaa gaugugagaa g          31

<210> SEQ ID NO 499
<211> LENGTH: 31
<212> TYPE: RNA
<213> ORGANISM: Homo sapiens

<400> SEQUENCE: 499
uuaucuacag uuagcauaag augugagaag u          31

<210> SEQ ID NO 500
<211> LENGTH: 31
<212> TYPE: RNA
<213> ORGANISM: Homo sapiens

<400> SEQUENCE: 500
ugcauggggu gggagaggcg aggaagucac c          31

<210> SEQ ID NO 501
<211> LENGTH: 31
<212> TYPE: RNA
<213> ORGANISM: Homo sapiens

<400> SEQUENCE: 501
gagaccccag gggacaggag ccucuugcag u          31

<210> SEQ ID NO 502
<211> LENGTH: 31
<212> TYPE: RNA

```
<213> ORGANISM: Homo sapiens

<400> SEQUENCE: 502 agacccagg ggacaggagc cucuugcagu c                              31

<210> SEQ ID NO 503
<211> LENGTH: 31
<212> TYPE: RNA
<213> ORGANISM: Homo sapiens

<400> SEQUENCE: 503
caggagccuc uugcagucug ucccuaggcc c                             31

<210> SEQ ID NO 504
<211> LENGTH: 31
<212> TYPE: RNA
<213> ORGANISM: Homo sapiens

<400> SEQUENCE: 504
ggagccucuu gcagucuguc ccuaggccca g                             31

<210> SEQ ID NO 505
<211> LENGTH: 31
<212> TYPE: RNA
<213> ORGANISM: Homo sapiens

<400> SEQUENCE: 505
gagccucuug cagucugucc cuaggccag c                              31

<210> SEQ ID NO 506
<211> LENGTH: 31
<212> TYPE: RNA
<213> ORGANISM: Homo sapiens

<400> SEQUENCE: 506
agccucuugc agucugucc uaggcccagc c                              31

<210> SEQ ID NO 507
<211> LENGTH: 31
<212> TYPE: RNA
<213> ORGANISM: Homo sapiens

<400> SEQUENCE: 507
augcaugggg ugggagaggc gaggaaguca c                             31

<210> SEQ ID NO 508
<211> LENGTH: 31
<212> TYPE: RNA
<213> ORGANISM: Homo sapiens

<400> SEQUENCE: 508 caugggugg gagaggcgag gaagucacca u                              31

<210> SEQ ID NO 509
<211> LENGTH: 31
<212> TYPE: RNA
<213> ORGANISM: Homo sapiens

<400> SEQUENCE: 509 auggggugg agaggcgagg aagucaccau c                              31

<210> SEQ ID NO 510
<211> LENGTH: 31
```

```
<212> TYPE: RNA
<213> ORGANISM: Homo sapiens

<400> SEQUENCE: 510 uggggguggga gaggcgagga agucaccauc a                                      31

<210> SEQ ID NO 511
<211> LENGTH: 31
<212> TYPE: RNA
<213> ORGANISM: Homo sapiens

<400> SEQUENCE: 511
aguaacaggu gagguucuac cuuaaaauuu a                                       31

<210> SEQ ID NO 512
<211> LENGTH: 31
<212> TYPE: RNA
<213> ORGANISM: Homo sapiens

<400> SEQUENCE: 512
guaacaggug agguucuacc uuaaaauuua a                                       31

<210> SEQ ID NO 513
<211> LENGTH: 31
<212> TYPE: RNA
<213> ORGANISM: Homo sapiens

<400> SEQUENCE: 513
aaaccacuuu aucuacaguu agcauaagau g                                       31

<210> SEQ ID NO 514
<211> LENGTH: 31
<212> TYPE: RNA
<213> ORGANISM: Homo sapiens

<400> SEQUENCE: 514
aaccacuuua ucuacaguua gcauaagaug u                                       31

<210> SEQ ID NO 515
<211> LENGTH: 31
<212> TYPE: RNA
<213> ORGANISM: Homo sapiens

<400> SEQUENCE: 515
acuuuaucua caguuagcau aagaugugag a                                       31

<210> SEQ ID NO 516
<211> LENGTH: 31
<212> TYPE: RNA
<213> ORGANISM: Homo sapiens

<400> SEQUENCE: 516
cuuuaucuac aguuagcaua agaugugaga a                                       31

<210> SEQ ID NO 517
<211> LENGTH: 31
<212> TYPE: RNA
<213> ORGANISM: Homo sapiens

<400> SEQUENCE: 517
gaccccaggg gacaggagcc ucuugcaguc u                                       31

<210> SEQ ID NO 518
```

```
<211> LENGTH: 31
<212> TYPE: RNA
<213> ORGANISM: Homo sapiens

<400> SEQUENCE: 518
accccagggg acaggagccu cuugcagucu g                              31

<210> SEQ ID NO 519
<211> LENGTH: 31
<212> TYPE: RNA
<213> ORGANISM: Homo sapiens

<400> SEQUENCE: 519
ccccagggga caggagccuc uugcagucug u                              31

<210> SEQ ID NO 520
<211> LENGTH: 31
<212> TYPE: RNA
<213> ORGANISM: Homo sapiens

<400> SEQUENCE: 520 cccagggac aggagccucu ugcagucugu c                               31

<210> SEQ ID NO 521
<211> LENGTH: 31
<212> TYPE: RNA
<213> ORGANISM: Homo sapiens

<400> SEQUENCE: 521
caggggacag gagccucuug cagucugucc c                              31

<210> SEQ ID NO 522
<211> LENGTH: 31
<212> TYPE: RNA
<213> ORGANISM: Homo sapiens

<400> SEQUENCE: 522
aggggacagg agccucuugc agucugu ccc u                             31

<210> SEQ ID NO 523
<211> LENGTH: 31
<212> TYPE: RNA
<213> ORGANISM: Homo sapiens

<400> SEQUENCE: 523
ggggacagga gccucuugca gucugucccu a                              31

<210> SEQ ID NO 524
<211> LENGTH: 31
<212> TYPE: RNA
<213> ORGANISM: Homo sapiens

<400> SEQUENCE: 524
gggacaggag ccucuugcag ucugucccua g                              31

<210> SEQ ID NO 525
<211> LENGTH: 31
<212> TYPE: RNA
<213> ORGANISM: Homo sapiens

<400> SEQUENCE: 525
aggagccucu ugcagucugu cccuaggccc a                              31
```

<210> SEQ ID NO 526
<211> LENGTH: 31
<212> TYPE: RNA
<213> ORGANISM: Homo sapiens

<400> SEQUENCE: 526
ucaguaacag gugagguucu accuuaaaau u            31

<210> SEQ ID NO 527
<211> LENGTH: 31
<212> TYPE: RNA
<213> ORGANISM: Homo sapiens

<400> SEQUENCE: 527
caguaacagg ugagguucua ccuuaaaauu u            31

<210> SEQ ID NO 528
<211> LENGTH: 31
<212> TYPE: RNA
<213> ORGANISM: Homo sapiens

<400> SEQUENCE: 528
accacuuuau cuacaguuag cauaagaugu g            31

<210> SEQ ID NO 529
<211> LENGTH: 31
<212> TYPE: RNA
<213> ORGANISM: Homo sapiens

<400> SEQUENCE: 529
ccacuuuauc uacaguuagc auaagaugug a            31

<210> SEQ ID NO 530
<211> LENGTH: 31
<212> TYPE: RNA
<213> ORGANISM: Homo sapiens

<400> SEQUENCE: 530
cacuuuaucu acaguuagca uaagauguga g            31

<210> SEQ ID NO 531
<211> LENGTH: 31
<212> TYPE: RNA
<213> ORGANISM: Homo sapiens

<400> SEQUENCE: 531
ggcccagccc ugcuuguccu cccuggcugu u            31

<210> SEQ ID NO 532
<211> LENGTH: 31
<212> TYPE: RNA
<213> ORGANISM: Homo sapiens

<400> SEQUENCE: 532
cacaaaugca gcagagaccc caggggacag g            31

<210> SEQ ID NO 533
<211> LENGTH: 31
<212> TYPE: RNA
<213> ORGANISM: Homo sapiens

<400> SEQUENCE: 533
caaaugcagc agagacccca ggggacagga g            31

<210> SEQ ID NO 534
<211> LENGTH: 31
<212> TYPE: RNA
<213> ORGANISM: Homo sapiens

<400> SEQUENCE: 534
aaaugcagca gagacccag gggacaggag c				31

<210> SEQ ID NO 535
<211> LENGTH: 31
<212> TYPE: RNA
<213> ORGANISM: Homo sapiens

<400> SEQUENCE: 535
gacacaaaug cagcagagac cccaggggac a				31

<210> SEQ ID NO 536
<211> LENGTH: 31
<212> TYPE: RNA
<213> ORGANISM: Homo sapiens

<400> SEQUENCE: 536
acacaaaugc agcagagacc ccaggggaca g				31

<210> SEQ ID NO 537
<211> LENGTH: 31
<212> TYPE: RNA
<213> ORGANISM: Homo sapiens

<400> SEQUENCE: 537
acaaaugcag cagagacccc agggacagg a				31

<210> SEQ ID NO 538
<211> LENGTH: 31
<212> TYPE: RNA
<213> ORGANISM: Homo sapiens

<400> SEQUENCE: 538
ccuaggccca gcccugcuug uccucccugg c				31

<210> SEQ ID NO 539
<211> LENGTH: 31
<212> TYPE: RNA
<213> ORGANISM: Homo sapiens

<400> SEQUENCE: 539
cugucccuag gcccagcccu gcuuguccuc c				31

<210> SEQ ID NO 540
<211> LENGTH: 31
<212> TYPE: RNA
<213> ORGANISM: Homo sapiens

<400> SEQUENCE: 540
cuaggcccag cccugcuugu ccucccuggc u				31

<210> SEQ ID NO 541
<211> LENGTH: 31
<212> TYPE: RNA
<213> ORGANISM: Homo sapiens

<400> SEQUENCE: 541
uaggcccagc ccugcuuguc cucccuggcu g				31

```
<210> SEQ ID NO 542
<211> LENGTH: 31
<212> TYPE: RNA
<213> ORGANISM: Homo sapiens

<400> SEQUENCE: 542
aggcccagcc cugcuugucc ucccuggcug u                              31

<210> SEQ ID NO 543
<211> LENGTH: 31
<212> TYPE: RNA
<213> ORGANISM: Homo sapiens

<400> SEQUENCE: 543
gucugucccu aggcccagcc cugcuugucc u                              31

<210> SEQ ID NO 544
<211> LENGTH: 31
<212> TYPE: RNA
<213> ORGANISM: Homo sapiens

<400> SEQUENCE: 544
ucugucccua ggcccagccc ugcuuguccu c                              31

<210> SEQ ID NO 545
<211> LENGTH: 31
<212> TYPE: RNA
<213> ORGANISM: Homo sapiens

<400> SEQUENCE: 545
gcccagcccu gcuuguccuc ccuggcuguu a                              31

<210> SEQ ID NO 546
<211> LENGTH: 31
<212> TYPE: RNA
<213> ORGANISM: Homo sapiens

<400> SEQUENCE: 546
ccagcccugc uuguccuccc uggcuguuau c                              31

<210> SEQ ID NO 547
<211> LENGTH: 31
<212> TYPE: RNA
<213> ORGANISM: Homo sapiens

<400> SEQUENCE: 547
gaugacacaa augcagcaga gaccccaggg g                              31

<210> SEQ ID NO 548
<211> LENGTH: 31
<212> TYPE: RNA
<213> ORGANISM: Homo sapiens

<400> SEQUENCE: 548
ugacacaaau gcagcagaga ccccagggga c                              31

<210> SEQ ID NO 549
<211> LENGTH: 31
<212> TYPE: RNA
<213> ORGANISM: Homo sapiens

<400> SEQUENCE: 549
```

-continued cagcccugcu uguccucccu ggcuguuauc u                                31

<210> SEQ ID NO 550
<211> LENGTH: 31
<212> TYPE: RNA
<213> ORGANISM: Homo sapiens

<400> SEQUENCE: 550
uuuaaugcau gggguggggag aggcgaggaa g                               31

<210> SEQ ID NO 551
<211> LENGTH: 31
<212> TYPE: RNA
<213> ORGANISM: Homo sapiens

<400> SEQUENCE: 551
uuaaugcaug ggugggaga ggcgaggaag u                                 31

<210> SEQ ID NO 552
<211> LENGTH: 31
<212> TYPE: RNA
<213> ORGANISM: Homo sapiens

<400> SEQUENCE: 552
agaugacaca aaugcagcag agaccccagg g                                31

<210> SEQ ID NO 553
<211> LENGTH: 31
<212> TYPE: RNA
<213> ORGANISM: Homo sapiens

<400> SEQUENCE: 553
augacacaaa ugcagcagag accccagggg a                                31

<210> SEQ ID NO 554
<211> LENGTH: 31
<212> TYPE: RNA
<213> ORGANISM: Homo sapiens

<400> SEQUENCE: 554
auuuaaugca uggggguggga gaggcgagga a                               31

<210> SEQ ID NO 555
<211> LENGTH: 31
<212> TYPE: RNA
<213> ORGANISM: Homo sapiens

<400> SEQUENCE: 555 gcccucuugca gucugucccu aggcccagcc c                               31

<210> SEQ ID NO 556
<211> LENGTH: 31
<212> TYPE: RNA
<213> ORGANISM: Homo sapiens

<400> SEQUENCE: 556
ccucuugcag ucugucccua ggcccagccc u                                31

<210> SEQ ID NO 557
<211> LENGTH: 31
<212> TYPE: RNA
<213> ORGANISM: Homo sapiens

<400> SEQUENCE: 557

-continued cucuugcagu cugucccuag gcccagcccu g    31

<210> SEQ ID NO 558
<211> LENGTH: 31
<212> TYPE: RNA
<213> ORGANISM: Homo sapiens

<400> SEQUENCE: 558
ucuugcaguc ugucccuagg cccagcccug c    31

<210> SEQ ID NO 559
<211> LENGTH: 31
<212> TYPE: RNA
<213> ORGANISM: Homo sapiens

<400> SEQUENCE: 559
cuugcagucu gucccuaggc cagcccugc u    31

<210> SEQ ID NO 560
<211> LENGTH: 31
<212> TYPE: RNA
<213> ORGANISM: Homo sapiens

<400> SEQUENCE: 560
ugcagucugu cccuaggccc agcccugcuu g    31

<210> SEQ ID NO 561
<211> LENGTH: 31
<212> TYPE: RNA
<213> ORGANISM: Homo sapiens

<400> SEQUENCE: 561
gcagucuguc ccuaggccca gcccugcuug u    31

<210> SEQ ID NO 562
<211> LENGTH: 31
<212> TYPE: RNA
<213> ORGANISM: Homo sapiens

<400> SEQUENCE: 562
cagucugucc cuaggcccag cccugcuugu c    31

<210> SEQ ID NO 563
<211> LENGTH: 31
<212> TYPE: RNA
<213> ORGANISM: Homo sapiens

<400> SEQUENCE: 563
agucuguccc uaggcccagc ccugcuuguc c    31

<210> SEQ ID NO 564
<211> LENGTH: 31
<212> TYPE: RNA
<213> ORGANISM: Homo sapiens

<400> SEQUENCE: 564
uugcagucug ucccuaggcc cagcccugcu u    31

<210> SEQ ID NO 565
<211> LENGTH: 31
<212> TYPE: RNA
<213> ORGANISM: Homo sapiens

```
<400> SEQUENCE: 565
uaaugcaugg gguggggagag gcgaggaagu c                               31

<210> SEQ ID NO 566
<211> LENGTH: 31
<212> TYPE: RNA
<213> ORGANISM: Homo sapiens

<400> SEQUENCE: 566
ggugagguuc uaccuuaaaa uuuaaugcau g                                31

<210> SEQ ID NO 567
<211> LENGTH: 31
<212> TYPE: RNA
<213> ORGANISM: Homo sapiens

<400> SEQUENCE: 567
gugagguucu accuuaaaau uuaaugcaug g                                31

<210> SEQ ID NO 568
<211> LENGTH: 31
<212> TYPE: RNA
<213> ORGANISM: Homo sapiens

<400> SEQUENCE: 568
aacaggugag guucuaccuu aaaauuuaau g                                31

<210> SEQ ID NO 569
<211> LENGTH: 31
<212> TYPE: RNA
<213> ORGANISM: Homo sapiens

<400> SEQUENCE: 569
aggugagguu cuaccuuaaa auuuaaugca u                                31

<210> SEQ ID NO 570
<211> LENGTH: 31
<212> TYPE: RNA
<213> ORGANISM: Homo sapiens

<400> SEQUENCE: 570
uaacagguga gguucuaccu uaaaauuuaa u                                31

<210> SEQ ID NO 571
<211> LENGTH: 31
<212> TYPE: RNA
<213> ORGANISM: Homo sapiens

<400> SEQUENCE: 571
acaggugagg uucuaccuua aaauuuaaug c                                31

<210> SEQ ID NO 572
<211> LENGTH: 31
<212> TYPE: RNA
<213> ORGANISM: Homo sapiens

<400> SEQUENCE: 572
caggugaggu ucuaccuuaa aauuuaaugc a                                31

<210> SEQ ID NO 573
<211> LENGTH: 31
<212> TYPE: RNA
<213> ORGANISM: Homo sapiens
```

```
<400> SEQUENCE: 573
cccuaggccc agcccugcuu guccucccug g                                          31

<210> SEQ ID NO 574
<211> LENGTH: 31
<212> TYPE: RNA
<213> ORGANISM: Homo sapiens

<400> SEQUENCE: 574
ugucccuagg cccagcccug cuuguccucc c                                          31

<210> SEQ ID NO 575
<211> LENGTH: 31
<212> TYPE: RNA
<213> ORGANISM: Homo sapiens

<400> SEQUENCE: 575
gucccuaggc ccagcccugc uuguccuccc u                                          31

<210> SEQ ID NO 576
<211> LENGTH: 31
<212> TYPE: RNA
<213> ORGANISM: Homo sapiens

<400> SEQUENCE: 576
ucccuaggcc cagcccugcu uguccucccu g                                          31

<210> SEQ ID NO 577
<211> LENGTH: 31
<212> TYPE: RNA
<213> ORGANISM: Homo sapiens

<400> SEQUENCE: 577
cccagcccug cuuguccucc cuggcuguua u                                          31

<210> SEQ ID NO 578
<211> LENGTH: 31
<212> TYPE: RNA
<213> ORGANISM: Homo sapiens

<400> SEQUENCE: 578
aaauuuaaug caugggguggg gagaggcgag g                                         31

<210> SEQ ID NO 579
<211> LENGTH: 31
<212> TYPE: RNA
<213> ORGANISM: Homo sapiens

<400> SEQUENCE: 579
aauuuaaugc auggggugggg agaggcgagg a                                         31

<210> SEQ ID NO 580
<211> LENGTH: 31
<212> TYPE: RNA
<213> ORGANISM: Homo sapiens

<400> SEQUENCE: 580
aaaauuuaau gcaugggguug ggagaggcga g                                         31

<210> SEQ ID NO 581
<211> LENGTH: 31
<212> TYPE: RNA
```

<213> ORGANISM: Homo sapiens

<400> SEQUENCE: 581
uaaaauuuaa ugcauggggu gggagaggcg a                              31

<210> SEQ ID NO 582
<211> LENGTH: 31
<212> TYPE: RNA
<213> ORGANISM: Homo sapiens

<400> SEQUENCE: 582
gagguucuac cuuaaaauuu aaugcauggg g                              31

<210> SEQ ID NO 583
<211> LENGTH: 31
<212> TYPE: RNA
<213> ORGANISM: Homo sapiens

<400> SEQUENCE: 583
gguucuaccu uaaauuuaa ugcauggggu g                               31

<210> SEQ ID NO 584
<211> LENGTH: 31
<212> TYPE: RNA
<213> ORGANISM: Homo sapiens

<400> SEQUENCE: 584
guucuaccuu aaaauuuaau gcauggggug g                              31

<210> SEQ ID NO 585
<211> LENGTH: 31
<212> TYPE: RNA
<213> ORGANISM: Homo sapiens

<400> SEQUENCE: 585
ugagguucua ccuuaaaauu uaaugcaugg g                              31

<210> SEQ ID NO 586
<211> LENGTH: 31
<212> TYPE: RNA
<213> ORGANISM: Homo sapiens

<400> SEQUENCE: 586
agguucuacc uuaaaauuua augcaugggg u                              31

<210> SEQ ID NO 587
<211> LENGTH: 31
<212> TYPE: RNA
<213> ORGANISM: Homo sapiens

<400> SEQUENCE: 587
uuaaaauuua augcaugggg ugggagaggc g                              31

<210> SEQ ID NO 588
<211> LENGTH: 31
<212> TYPE: RNA
<213> ORGANISM: Homo sapiens

<400> SEQUENCE: 588
ccuuaaaauu uaaugcaugg gguggagag g                               31

<210> SEQ ID NO 589
<211> LENGTH: 31

```
<212> TYPE: RNA
<213> ORGANISM: Homo sapiens

<400> SEQUENCE: 589
cuuaaaauuu aaugcauggg gugggagagg c                              31

<210> SEQ ID NO 590
<211> LENGTH: 31
<212> TYPE: RNA
<213> ORGANISM: Homo sapiens

<400> SEQUENCE: 590
accuuaaaau uuaaugcaug ggguggggaga g                             31

<210> SEQ ID NO 591
<211> LENGTH: 31
<212> TYPE: RNA
<213> ORGANISM: Homo sapiens

<400> SEQUENCE: 591
uaccuuaaaa uuuaaugcau gggguggag a                               31

<210> SEQ ID NO 592
<211> LENGTH: 31
<212> TYPE: RNA
<213> ORGANISM: Homo sapiens

<400> SEQUENCE: 592
cuaccuuaaa auuuaaugca uggggugga g                               31

<210> SEQ ID NO 593
<211> LENGTH: 31
<212> TYPE: RNA
<213> ORGANISM: Homo sapiens

<400> SEQUENCE: 593
uucuaccuua aaauuuaaug caugggguggg g                             31

<210> SEQ ID NO 594
<211> LENGTH: 31
<212> TYPE: RNA
<213> ORGANISM: Homo sapiens

<400> SEQUENCE: 594
ucuaccuuaa aauuuaaugc auggggugg a                               31

<210> SEQ ID NO 595
<211> LENGTH: 31
<212> TYPE: RNA
<213> ORGANISM: Mus musculus

<400> SEQUENCE: 595
ggccucagcg ucuguccgug gugcugaagu u                              31

<210> SEQ ID NO 596
<211> LENGTH: 31
<212> TYPE: RNA
<213> ORGANISM: Mus musculus

<400> SEQUENCE: 596 gcccucagcgu cuguccgugg ugcugaaguu u                             31

<210> SEQ ID NO 597
```

```
<211> LENGTH: 31
<212> TYPE: RNA
<213> ORGANISM: Mus musculus

<400> SEQUENCE: 597
gaugaagaca ggaagcugca gcuccaggag g                              31

<210> SEQ ID NO 598
<211> LENGTH: 31
<212> TYPE: RNA
<213> ORGANISM: Mus musculus

<400> SEQUENCE: 598
agaugaagac aggaagcugc agcuccagga g                              31

<210> SEQ ID NO 599
<211> LENGTH: 31
<212> TYPE: RNA
<213> ORGANISM: Mus musculus

<400> SEQUENCE: 599
caggccucag cgucuguccg uggugcugaa g                              31

<210> SEQ ID NO 600
<211> LENGTH: 31
<212> TYPE: RNA
<213> ORGANISM: Mus musculus

<400> SEQUENCE: 600
aggccucagc gucuguccgu ggugcugaag u                              31

<210> SEQ ID NO 601
<211> LENGTH: 31
<212> TYPE: RNA
<213> ORGANISM: Mus musculus

<400> SEQUENCE: 601
ggcaaugcga ccaagcugug ugacacaccg c                              31

<210> SEQ ID NO 602
<211> LENGTH: 31
<212> TYPE: RNA
<213> ORGANISM: Mus musculus

<400> SEQUENCE: 602
gcaaugcgac caagcugugu gacacaccgc a                              31

<210> SEQ ID NO 603
<211> LENGTH: 31
<212> TYPE: RNA
<213> ORGANISM: Mus musculus

<400> SEQUENCE: 603
augcgaccaa gcugugugac acaccgcaag g                              31

<210> SEQ ID NO 604
<211> LENGTH: 31
<212> TYPE: RNA
<213> ORGANISM: Mus musculus

<400> SEQUENCE: 604
caaugcgacc aagcugugug acacaccgca a                              31
```

```
<210> SEQ ID NO 605
<211> LENGTH: 31
<212> TYPE: RNA
<213> ORGANISM: Mus musculus

<400> SEQUENCE: 605
aaugcgacca agcuguguga cacaccgcaa g                              31

<210> SEQ ID NO 606
<211> LENGTH: 31
<212> TYPE: RNA
<213> ORGANISM: Mus musculus

<400> SEQUENCE: 606
gauagaugaa gacaggaagc ugcagcucca g                              31

<210> SEQ ID NO 607
<211> LENGTH: 31
<212> TYPE: RNA
<213> ORGANISM: Mus musculus

<400> SEQUENCE: 607
auagaugaag acaggaagcu gcagcuccag g                              31

<210> SEQ ID NO 608
<211> LENGTH: 31
<212> TYPE: RNA
<213> ORGANISM: Mus musculus

<400> SEQUENCE: 608
uagaugaaga caggaagcug cagcuccagg a                              31

<210> SEQ ID NO 609
<211> LENGTH: 31
<212> TYPE: RNA
<213> ORGANISM: Mus musculus

<400> SEQUENCE: 609
gaucgugaua gaugaagaca ggaagcugca g                              31

<210> SEQ ID NO 610
<211> LENGTH: 31
<212> TYPE: RNA
<213> ORGANISM: Mus musculus

<400> SEQUENCE: 610
aucgaucgug auagaugaag acaggaagcu g                              31

<210> SEQ ID NO 611
<211> LENGTH: 31
<212> TYPE: RNA
<213> ORGANISM: Mus musculus

<400> SEQUENCE: 611
aacaucgauc gugauagaug aagacaggaa g                              31

<210> SEQ ID NO 612
<211> LENGTH: 31
<212> TYPE: RNA
<213> ORGANISM: Mus musculus

<400> SEQUENCE: 612
uaacaucgau cgugauagau gaagacagga a                              31
```

```
<210> SEQ ID NO 613
<211> LENGTH: 31
<212> TYPE: RNA
<213> ORGANISM: Mus musculus

<400> SEQUENCE: 613
ucaccaccuc ucaguggcaa ugcgaccaag c                              31

<210> SEQ ID NO 614
<211> LENGTH: 31
<212> TYPE: RNA
<213> ORGANISM: Mus musculus

<400> SEQUENCE: 614
caccaccucu caguggcaau gcgaccaagc u                              31

<210> SEQ ID NO 615
<211> LENGTH: 31
<212> TYPE: RNA
<213> ORGANISM: Mus musculus

<400> SEQUENCE: 615
accaccucuc aguggcaaug cgaccaagcu g                              31

<210> SEQ ID NO 616
<211> LENGTH: 31
<212> TYPE: RNA
<213> ORGANISM: Mus musculus

<400> SEQUENCE: 616
guggcaaugc gaccaagcug ugugacacac c                              31

<210> SEQ ID NO 617
<211> LENGTH: 31
<212> TYPE: RNA
<213> ORGANISM: Mus musculus

<400> SEQUENCE: 617
uggcaaugcg accaagcugu gugacacacc g                              31

<210> SEQ ID NO 618
<211> LENGTH: 31
<212> TYPE: RNA
<213> ORGANISM: Mus musculus

<400> SEQUENCE: 618
caguggcaau gcgaccaagc ugugugacac a                              31

<210> SEQ ID NO 619
<211> LENGTH: 31
<212> TYPE: RNA
<213> ORGANISM: Mus musculus

<400> SEQUENCE: 619
aguggcaaug cgaccaagcu gugugacaca c                              31

<210> SEQ ID NO 620
<211> LENGTH: 31
<212> TYPE: RNA
<213> ORGANISM: Mus musculus

<400> SEQUENCE: 620
cgugauagau gaagacagga agcugcagcu c                              31
```

```
<210> SEQ ID NO 621
<211> LENGTH: 31
<212> TYPE: RNA
<213> ORGANISM: Mus musculus

<400> SEQUENCE: 621
gugauagaug aagacaggaa gcugcagcuc c                          31

<210> SEQ ID NO 622
<211> LENGTH: 31
<212> TYPE: RNA
<213> ORGANISM: Mus musculus

<400> SEQUENCE: 622
auucaccacc ucucaguggc aaugcgacca a                          31

<210> SEQ ID NO 623
<211> LENGTH: 31
<212> TYPE: RNA
<213> ORGANISM: Mus musculus

<400> SEQUENCE: 623
ucgaucguga uagaugaaga caggaagcug c                          31

<210> SEQ ID NO 624
<211> LENGTH: 31
<212> TYPE: RNA
<213> ORGANISM: Mus musculus

<400> SEQUENCE: 624
cgaucgugau agaugaagac aggaagcugc a                          31

<210> SEQ ID NO 625
<211> LENGTH: 31
<212> TYPE: RNA
<213> ORGANISM: Mus musculus

<400> SEQUENCE: 625
aucgugauag augaagacag gaagcugcag c                          31

<210> SEQ ID NO 626
<211> LENGTH: 31
<212> TYPE: RNA
<213> ORGANISM: Mus musculus

<400> SEQUENCE: 626
ucgugauaga ugaagacagg aagcugcagc u                          31

<210> SEQ ID NO 627
<211> LENGTH: 31
<212> TYPE: RNA
<213> ORGANISM: Mus musculus

<400> SEQUENCE: 627
ugauagauga agacaggaag cugcagcucc a                          31

<210> SEQ ID NO 628
<211> LENGTH: 31
<212> TYPE: RNA
<213> ORGANISM: Mus musculus

<400> SEQUENCE: 628
```
acaucgaucg ugauagauga agacaggaag c                                          31

<210> SEQ ID NO 629
<211> LENGTH: 31
<212> TYPE: RNA
<213> ORGANISM: Mus musculus

<400> SEQUENCE: 629
caucgaucgu gauagaugaa gacaggaagc u                                          31

<210> SEQ ID NO 630
<211> LENGTH: 31
<212> TYPE: RNA
<213> ORGANISM: Mus musculus

<400> SEQUENCE: 630
ccaccucuca guggcaaugc gaccaagcug u                                          31

<210> SEQ ID NO 631
<211> LENGTH: 31
<212> TYPE: RNA
<213> ORGANISM: Mus musculus

<400> SEQUENCE: 631
caccucucag uggcaaugcg accaagcugu g                                          31

<210> SEQ ID NO 632
<211> LENGTH: 31
<212> TYPE: RNA
<213> ORGANISM: Mus musculus

<400> SEQUENCE: 632
ccucucagug gcaaugcgac caagcugugu g                                          31

<210> SEQ ID NO 633
<211> LENGTH: 31
<212> TYPE: RNA
<213> ORGANISM: Mus musculus

<400> SEQUENCE: 633
uucaccaccu cucaguggca augcgaccaa g                                          31

<210> SEQ ID NO 634
<211> LENGTH: 31
<212> TYPE: RNA
<213> ORGANISM: Mus musculus

<400> SEQUENCE: 634
cucaguggca augcgaccaa gcugugugac a                                          31

<210> SEQ ID NO 635
<211> LENGTH: 31
<212> TYPE: RNA
<213> ORGANISM: Mus musculus

<400> SEQUENCE: 635
ucaguggcaa ugcgaccaag cugugugaca c                                          31

<210> SEQ ID NO 636
<211> LENGTH: 31
<212> TYPE: RNA
<213> ORGANISM: Mus musculus

<400> SEQUENCE: 636
accucucagu ggcaaugcga ccaagcugug u    31

<210> SEQ ID NO 637
<211> LENGTH: 31
<212> TYPE: RNA
<213> ORGANISM: Mus musculus

<400> SEQUENCE: 637
cucucagugg caaugcgacc aagcugugug a    31

<210> SEQ ID NO 638
<211> LENGTH: 31
<212> TYPE: RNA
<213> ORGANISM: Mus musculus

<400> SEQUENCE: 638
ucucaguggc aaugcgacca agcuguguga c    31

<210> SEQ ID NO 639
<211> LENGTH: 31
<212> TYPE: RNA
<213> ORGANISM: Mus musculus

<400> SEQUENCE: 639
uaaggccuca cuaaaccacu caucuacacu u    31

<210> SEQ ID NO 640
<211> LENGTH: 31
<212> TYPE: RNA
<213> ORGANISM: Mus musculus

<400> SEQUENCE: 640
aaggccucac uaaaccacuc aucuacacuu a    31

<210> SEQ ID NO 641
<211> LENGTH: 31
<212> TYPE: RNA
<213> ORGANISM: Mus musculus

<400> SEQUENCE: 641
aaaccacuca ucuacacuua acaucgaucg u    31

<210> SEQ ID NO 642
<211> LENGTH: 31
<212> TYPE: RNA
<213> ORGANISM: Mus musculus

<400> SEQUENCE: 642
gcgaccaagc ugugugacac accgcaaggg c    31

<210> SEQ ID NO 643
<211> LENGTH: 31
<212> TYPE: RNA
<213> ORGANISM: Mus musculus

<400> SEQUENCE: 643
augaagacag gaagcugcag cuccaggagg g    31

<210> SEQ ID NO 644
<211> LENGTH: 31
<212> TYPE: RNA
<213> ORGANISM: Mus musculus

```
<400> SEQUENCE: 644
gaagacagga agcugcagcu ccaggagggu a                              31

<210> SEQ ID NO 645
<211> LENGTH: 31
<212> TYPE: RNA
<213> ORGANISM: Mus musculus

<400> SEQUENCE: 645
gcgucugucc guggugcuga aguuuauucg g                              31

<210> SEQ ID NO 646
<211> LENGTH: 31
<212> TYPE: RNA
<213> ORGANISM: Mus musculus

<400> SEQUENCE: 646
guaaggccuc acuaaaccac ucaucuacac u                              31

<210> SEQ ID NO 647
<211> LENGTH: 31
<212> TYPE: RNA
<213> ORGANISM: Mus musculus

<400> SEQUENCE: 647
aaccacucau cuacacuuaa caucgaucgu g                              31

<210> SEQ ID NO 648
<211> LENGTH: 31
<212> TYPE: RNA
<213> ORGANISM: Mus musculus

<400> SEQUENCE: 648
accacucauc uacacuuaac aucgaucgug a                              31

<210> SEQ ID NO 649
<211> LENGTH: 31
<212> TYPE: RNA
<213> ORGANISM: Mus musculus

<400> SEQUENCE: 649
ccacucaucu acacuuaaca ucgaucguga u                              31

<210> SEQ ID NO 650
<211> LENGTH: 31
<212> TYPE: RNA
<213> ORGANISM: Mus musculus

<400> SEQUENCE: 650
cacucaucua cacuuaacau cgaucgugau a                              31

<210> SEQ ID NO 651
<211> LENGTH: 31
<212> TYPE: RNA
<213> ORGANISM: Mus musculus

<400> SEQUENCE: 651
ugcgaccaag cugugugaca caccgcaagg g                              31

<210> SEQ ID NO 652
<211> LENGTH: 31
<212> TYPE: RNA
<213> ORGANISM: Mus musculus
```

```
<400> SEQUENCE: 652
cgaccaagcu gugugacaca ccgcaagggc u                              31

<210> SEQ ID NO 653
<211> LENGTH: 31
<212> TYPE: RNA
<213> ORGANISM: Mus musculus

<400> SEQUENCE: 653
ugaagacagg aagcugcagc uccaggaggg u                              31

<210> SEQ ID NO 654
<211> LENGTH: 31
<212> TYPE: RNA
<213> ORGANISM: Mus musculus

<400> SEQUENCE: 654
ccucagcguc uguccguggu gcugaaguuu a                              31

<210> SEQ ID NO 655
<211> LENGTH: 31
<212> TYPE: RNA
<213> ORGANISM: Mus musculus

<400> SEQUENCE: 655
aagacaggaa gcugcagcuc caggagggua u                              31

<210> SEQ ID NO 656
<211> LENGTH: 31
<212> TYPE: RNA
<213> ORGANISM: Mus musculus

<400> SEQUENCE: 656
cucagcgucu guccgguggug cugaaguuua u                             31

<210> SEQ ID NO 657
<211> LENGTH: 31
<212> TYPE: RNA
<213> ORGANISM: Mus musculus

<400> SEQUENCE: 657
cagcgucugu ccguggugcu gaaguuuauu c                              31

<210> SEQ ID NO 658
<211> LENGTH: 31
<212> TYPE: RNA
<213> ORGANISM: Mus musculus

<400> SEQUENCE: 658
agcgucuguc cguggugcug aaguuuauuc g                              31

<210> SEQ ID NO 659
<211> LENGTH: 31
<212> TYPE: RNA
<213> ORGANISM: Mus musculus

<400> SEQUENCE: 659
cgucuguccg uggugcugaa guuuauucgg a                              31

<210> SEQ ID NO 660
<211> LENGTH: 31
<212> TYPE: RNA
```

```
<213> ORGANISM: Mus musculus

<400> SEQUENCE: 660
ucagcgucug uccguggugc ugaaguuuau u                              31

<210> SEQ ID NO 661
<211> LENGTH: 31
<212> TYPE: RNA
<213> ORGANISM: Mus musculus

<400> SEQUENCE: 661 gucguccgu ggugcugaag uuuauucgga u                               31

<210> SEQ ID NO 662
<211> LENGTH: 31
<212> TYPE: RNA
<213> ORGANISM: Mus musculus

<400> SEQUENCE: 662
gguaaggccu cacuaaacca cucaucuaca c                              31

<210> SEQ ID NO 663
<211> LENGTH: 31
<212> TYPE: RNA
<213> ORGANISM: Mus musculus

<400> SEQUENCE: 663
ucuguccgug gugcugaagu uuauucggau u                              31

<210> SEQ ID NO 664
<211> LENGTH: 31
<212> TYPE: RNA
<213> ORGANISM: Mus musculus

<400> SEQUENCE: 664
agguaaggcc ucacuaaacc acucaucuac a                              31

<210> SEQ ID NO 665
<211> LENGTH: 31
<212> TYPE: RNA
<213> ORGANISM: Mus musculus

<400> SEQUENCE: 665
acucaucuac acuuaacauc gaucgugaua g                              31

<210> SEQ ID NO 666
<211> LENGTH: 31
<212> TYPE: RNA
<213> ORGANISM: Mus musculus

<400> SEQUENCE: 666
cucaucuaca cuuaacaucg aucgugauag a                              31

<210> SEQ ID NO 667
<211> LENGTH: 31
<212> TYPE: RNA
<213> ORGANISM: Mus musculus

<400> SEQUENCE: 667
uuaacaucga ucgugauaga ugaagacagg a                              31

<210> SEQ ID NO 668
<211> LENGTH: 31
```

<212> TYPE: RNA
<213> ORGANISM: Mus musculus

<400> SEQUENCE: 668
ucaucuacac uuaacaucga ucgugauaga u          31

<210> SEQ ID NO 669
<211> LENGTH: 31
<212> TYPE: RNA
<213> ORGANISM: Mus musculus

<400> SEQUENCE: 669
ccaagcugug ugacacaccg caagggcuug g          31

<210> SEQ ID NO 670
<211> LENGTH: 31
<212> TYPE: RNA
<213> ORGANISM: Mus musculus

<400> SEQUENCE: 670
gaccaagcug ugugacacac cgcaagggcu u          31

<210> SEQ ID NO 671
<211> LENGTH: 31
<212> TYPE: RNA
<213> ORGANISM: Mus musculus

<400> SEQUENCE: 671
accaagcugu gugacacacc gcaagggcuu g          31

<210> SEQ ID NO 672
<211> LENGTH: 31
<212> TYPE: RNA
<213> ORGANISM: Mus musculus

<400> SEQUENCE: 672
uaugcagagu gggagaggua aggccucacu a          31

<210> SEQ ID NO 673
<211> LENGTH: 31
<212> TYPE: RNA
<213> ORGANISM: Mus musculus

<400> SEQUENCE: 673
augcagagug ggagagguaa ggccucacua a          31

<210> SEQ ID NO 674
<211> LENGTH: 31
<212> TYPE: RNA
<213> ORGANISM: Mus musculus

<400> SEQUENCE: 674
ggagagguaa ggccucacua aaccacucau c          31

<210> SEQ ID NO 675
<211> LENGTH: 31
<212> TYPE: RNA
<213> ORGANISM: Mus musculus

<400> SEQUENCE: 675
uauucaccac cucucagugg caaugcgacc a          31

<210> SEQ ID NO 676

```
<211> LENGTH: 31
<212> TYPE: RNA
<213> ORGANISM: Mus musculus

<400> SEQUENCE: 676
gagguaaggc cucacuaaac cacucaucua c                               31

<210> SEQ ID NO 677
<211> LENGTH: 31
<212> TYPE: RNA
<213> ORGANISM: Mus musculus

<400> SEQUENCE: 677
uuuccaacug cuuucugaaa ggggugagga u                               31

<210> SEQ ID NO 678
<211> LENGTH: 31
<212> TYPE: RNA
<213> ORGANISM: Mus musculus

<400> SEQUENCE: 678
ugcuuucuga aaggggugag gaucuaccuu a                               31

<210> SEQ ID NO 679
<211> LENGTH: 31
<212> TYPE: RNA
<213> ORGANISM: Mus musculus

<400> SEQUENCE: 679
agagguaagg ccucacuaaa ccacucaucu a                               31

<210> SEQ ID NO 680
<211> LENGTH: 31
<212> TYPE: RNA
<213> ORGANISM: Mus musculus

<400> SEQUENCE: 680
cuuaacaucg aucgugauag augaagacag g                               31

<210> SEQ ID NO 681
<211> LENGTH: 31
<212> TYPE: RNA
<213> ORGANISM: Mus musculus

<400> SEQUENCE: 681
caucuacacu uaacaucgau cgugauagau g                               31

<210> SEQ ID NO 682
<211> LENGTH: 31
<212> TYPE: RNA
<213> ORGANISM: Mus musculus

<400> SEQUENCE: 682
acuuaacauc gaucgugaua gaugaagaca g                               31

<210> SEQ ID NO 683
<211> LENGTH: 31
<212> TYPE: RNA
<213> ORGANISM: Mus musculus

<400> SEQUENCE: 683
aucuacacuu aacaucgauc gugauagaug a                               31
```

```
<210> SEQ ID NO 684
<211> LENGTH: 31
<212> TYPE: RNA
<213> ORGANISM: Mus musculus

<400> SEQUENCE: 684
ucuacacuua acaucgaucg ugauagauga a                          31

<210> SEQ ID NO 685
<211> LENGTH: 31
<212> TYPE: RNA
<213> ORGANISM: Mus musculus

<400> SEQUENCE: 685
uacacuuaac aucgaucgug auagaugaag a                          31

<210> SEQ ID NO 686
<211> LENGTH: 31
<212> TYPE: RNA
<213> ORGANISM: Mus musculus

<400> SEQUENCE: 686
guauucacca ccucucagug gcaaugcgac c                          31

<210> SEQ ID NO 687
<211> LENGTH: 31
<212> TYPE: RNA
<213> ORGANISM: Mus musculus

<400> SEQUENCE: 687
uuccaacugc uuucugaaag gggugaggau c                          31

<210> SEQ ID NO 688
<211> LENGTH: 31
<212> TYPE: RNA
<213> ORGANISM: Mus musculus

<400> SEQUENCE: 688
uccaacugcu uucugaaagg ggugaggauc u                          31

<210> SEQ ID NO 689
<211> LENGTH: 31
<212> TYPE: RNA
<213> ORGANISM: Mus musculus

<400> SEQUENCE: 689
ccaacugcuu ucugaaaggg gugaggaucu a                          31

<210> SEQ ID NO 690
<211> LENGTH: 31
<212> TYPE: RNA
<213> ORGANISM: Mus musculus

<400> SEQUENCE: 690
caacugcuuu cugaaagggg ugaggaucua c                          31

<210> SEQ ID NO 691
<211> LENGTH: 31
<212> TYPE: RNA
<213> ORGANISM: Mus musculus

<400> SEQUENCE: 691
aacugcuuuc ugaaaggggu gaggaucuac c                          31
```

```
<210> SEQ ID NO 692
<211> LENGTH: 31
<212> TYPE: RNA
<213> ORGANISM: Mus musculus

<400> SEQUENCE: 692
acugcuuucu gaaaggggug aggaucuacc u                               31

<210> SEQ ID NO 693
<211> LENGTH: 31
<212> TYPE: RNA
<213> ORGANISM: Mus musculus

<400> SEQUENCE: 693
cugcuuucug aaagggguga ggaucuaccu u                               31

<210> SEQ ID NO 694
<211> LENGTH: 31
<212> TYPE: RNA
<213> ORGANISM: Mus musculus

<400> SEQUENCE: 694
gagagguaag gccucacuaa accacucauc u                               31

<210> SEQ ID NO 695
<211> LENGTH: 31
<212> TYPE: RNA
<213> ORGANISM: Mus musculus

<400> SEQUENCE: 695
cuacacuuaa caucgaucgu gauagaugaa g                               31

<210> SEQ ID NO 696
<211> LENGTH: 31
<212> TYPE: RNA
<213> ORGANISM: Mus musculus

<400> SEQUENCE: 696
acacuuaaca ucgaucguga uagaugaaga c                               31

<210> SEQ ID NO 697
<211> LENGTH: 31
<212> TYPE: RNA
<213> ORGANISM: Mus musculus

<400> SEQUENCE: 697
cacuuaacau cgaucgugau agaugaagac a                               31

<210> SEQ ID NO 698
<211> LENGTH: 31
<212> TYPE: RNA
<213> ORGANISM: Mus musculus

<400> SEQUENCE: 698
gguauucacc accucucagu ggcaaugcga c                               31

<210> SEQ ID NO 699
<211> LENGTH: 31
<212> TYPE: RNA
<213> ORGANISM: Mus musculus

<400> SEQUENCE: 699
ccucacuaaa ccacucaucu acacuuaaca u                               31
```

<210> SEQ ID NO 700
<211> LENGTH: 31
<212> TYPE: RNA
<213> ORGANISM: Mus musculus

<400> SEQUENCE: 700
cucacuaaac cacucaucua cacuuaacau c                          31

<210> SEQ ID NO 701
<211> LENGTH: 31
<212> TYPE: RNA
<213> ORGANISM: Mus musculus

<400> SEQUENCE: 701
gccucacuaa accacucauc uacacuuaac a                          31

<210> SEQ ID NO 702
<211> LENGTH: 31
<212> TYPE: RNA
<213> ORGANISM: Mus musculus

<400> SEQUENCE: 702
ucacuaaacc acucaucuac acuuaacauc g                          31

<210> SEQ ID NO 703
<211> LENGTH: 31
<212> TYPE: RNA
<213> ORGANISM: Mus musculus

<400> SEQUENCE: 703
cacuaaacca cucaucuaca cuuaacaucg a                          31

<210> SEQ ID NO 704
<211> LENGTH: 31
<212> TYPE: RNA
<213> ORGANISM: Mus musculus

<400> SEQUENCE: 704
cuaaaccacu caucuacacu uaacaucgau c                          31

<210> SEQ ID NO 705
<211> LENGTH: 31
<212> TYPE: RNA
<213> ORGANISM: Mus musculus

<400> SEQUENCE: 705
acuaaaccac ucaucuacac uuaacaucga u                          31

<210> SEQ ID NO 706
<211> LENGTH: 31
<212> TYPE: RNA
<213> ORGANISM: Mus musculus

<400> SEQUENCE: 706
ggccucacua aaccacucau cuacacuuaa c                          31

<210> SEQ ID NO 707
<211> LENGTH: 31
<212> TYPE: RNA
<213> ORGANISM: Mus musculus

<400> SEQUENCE: 707
aggccucacu aaaccacuca ucuacacuua a    31

<210> SEQ ID NO 708
<211> LENGTH: 31
<212> TYPE: RNA
<213> ORGANISM: Mus musculus

<400> SEQUENCE: 708
uaaaccacuc aucuacacuu aacaucgauc g    31

<210> SEQ ID NO 709
<211> LENGTH: 31
<212> TYPE: RNA
<213> ORGANISM: Mus musculus

<400> SEQUENCE: 709
uaccuuaaua ugcagagugg gagagguaag g    31

<210> SEQ ID NO 710
<211> LENGTH: 31
<212> TYPE: RNA
<213> ORGANISM: Mus musculus

<400> SEQUENCE: 710 gcagagiggg agagguaagg ccucacuaaa c    31

<210> SEQ ID NO 711
<211> LENGTH: 31
<212> TYPE: RNA
<213> ORGANISM: Mus musculus

<400> SEQUENCE: 711 cagagiggga gagguaaggc cucacuaaac c    31

<210> SEQ ID NO 712
<211> LENGTH: 31
<212> TYPE: RNA
<213> ORGANISM: Mus musculus

<400> SEQUENCE: 712 gagigggaga gguaaggccu cacuaaacca c    31

<210> SEQ ID NO 713
<211> LENGTH: 31
<212> TYPE: RNA
<213> ORGANISM: Mus musculus

<400> SEQUENCE: 713
ggcuugggau cuuuugcgau cugcucgagc a    31

<210> SEQ ID NO 714
<211> LENGTH: 31
<212> TYPE: RNA
<213> ORGANISM: Mus musculus

<400> SEQUENCE: 714
gcuugggauc uuuugcgauc ugcucgagca g    31

<210> SEQ ID NO 715
<211> LENGTH: 31
<212> TYPE: RNA
<213> ORGANISM: Mus musculus

<400> SEQUENCE: 715

```
agagugggag agguaaggcc ucacuaaacc a                               31

<210> SEQ ID NO 716
<211> LENGTH: 31
<212> TYPE: RNA
<213> ORGANISM: Mus musculus

<400> SEQUENCE: 716
cuuuugcgau cugcucgagc agauuuggcu g                               31

<210> SEQ ID NO 717
<211> LENGTH: 31
<212> TYPE: RNA
<213> ORGANISM: Mus musculus

<400> SEQUENCE: 717
ggggugagga ucuaccuuaa uaugcagagu g                               31

<210> SEQ ID NO 718
<211> LENGTH: 31
<212> TYPE: RNA
<213> ORGANISM: Mus musculus

<400> SEQUENCE: 718
gggugaggau cuaccuuaau augcagagug g                               31

<210> SEQ ID NO 719
<211> LENGTH: 31
<212> TYPE: RNA
<213> ORGANISM: Mus musculus

<400> SEQUENCE: 719
ggugaggauc uaccuuaaua ugcagagugg g                               31

<210> SEQ ID NO 720
<211> LENGTH: 31
<212> TYPE: RNA
<213> ORGANISM: Mus musculus

<400> SEQUENCE: 720
ggaucuaccu uaauaugcag agugggagag g                               31

<210> SEQ ID NO 721
<211> LENGTH: 31
<212> TYPE: RNA
<213> ORGANISM: Mus musculus

<400> SEQUENCE: 721
accuuaauau gcagaguggg agagguaagg c                               31

<210> SEQ ID NO 722
<211> LENGTH: 31
<212> TYPE: RNA
<213> ORGANISM: Mus musculus

<400> SEQUENCE: 722
cuuaauaugc agagugggag agguaaggcc u                               31

<210> SEQ ID NO 723
<211> LENGTH: 31
<212> TYPE: RNA
<213> ORGANISM: Mus musculus
```

<400> SEQUENCE: 723
uuaauaugca gagugggaga gguaaggccu c                                31

<210> SEQ ID NO 724
<211> LENGTH: 31
<212> TYPE: RNA
<213> ORGANISM: Mus musculus

<400> SEQUENCE: 724
uaauaugcag agugggagag guaaggccuc a                                31

<210> SEQ ID NO 725
<211> LENGTH: 31
<212> TYPE: RNA
<213> ORGANISM: Mus musculus

<400> SEQUENCE: 725
ucuuuugcga ucugcucgag cagauuuggc u                                31

<210> SEQ ID NO 726
<211> LENGTH: 31
<212> TYPE: RNA
<213> ORGANISM: Mus musculus

<400> SEQUENCE: 726
cuguccgugg ugcugaaguu uauucggauu u                                31

<210> SEQ ID NO 727
<211> LENGTH: 31
<212> TYPE: RNA
<213> ORGANISM: Mus musculus

<400> SEQUENCE: 727
gaaaggggug aggaucuacc uuaauaugca g                                31

<210> SEQ ID NO 728
<211> LENGTH: 31
<212> TYPE: RNA
<213> ORGANISM: Mus musculus

<400> SEQUENCE: 728
aaggggugag gaucuaccuu aauaugcaga g                                31

<210> SEQ ID NO 729
<211> LENGTH: 31
<212> TYPE: RNA
<213> ORGANISM: Mus musculus

<400> SEQUENCE: 729
aggggugagg aucuaccuua auaugcagag u                                31

<210> SEQ ID NO 730
<211> LENGTH: 31
<212> TYPE: RNA
<213> ORGANISM: Mus musculus

<400> SEQUENCE: 730
gugaggaucu accuuaauau gcagaguggg a                                31

<210> SEQ ID NO 731
<211> LENGTH: 31
<212> TYPE: RNA
<213> ORGANISM: Mus musculus -continued

```
<400> SEQUENCE: 731
ugaggaucua ccuuaauaug cagagugggA g                                     31

<210> SEQ ID NO 732
<211> LENGTH: 31
<212> TYPE: RNA
<213> ORGANISM: Mus musculus

<400> SEQUENCE: 732
gaggaucuac cuuaauaugc agaguggag a                                      31

<210> SEQ ID NO 733
<211> LENGTH: 31
<212> TYPE: RNA
<213> ORGANISM: Mus musculus

<400> SEQUENCE: 733
aggaucuacc uuaauaugca gagugggaga g                                     31

<210> SEQ ID NO 734
<211> LENGTH: 31
<212> TYPE: RNA
<213> ORGANISM: Mus musculus

<400> SEQUENCE: 734
gaucuaccuu aauaugcaga gugggagagg u                                     31

<210> SEQ ID NO 735
<211> LENGTH: 31
<212> TYPE: RNA
<213> ORGANISM: Mus musculus

<400> SEQUENCE: 735
cuaccuuaau augcagagug ggagagguaa g                                     31

<210> SEQ ID NO 736
<211> LENGTH: 31
<212> TYPE: RNA
<213> ORGANISM: Mus musculus

<400> SEQUENCE: 736
uguccguggu gcugaaguuu auucggauuu a                                     31

<210> SEQ ID NO 737
<211> LENGTH: 31
<212> TYPE: RNA
<213> ORGANISM: Mus musculus

<400> SEQUENCE: 737
guccguggug cugaaguuua uucggauuua u                                     31

<210> SEQ ID NO 738
<211> LENGTH: 31
<212> TYPE: RNA
<213> ORGANISM: Mus musculus

<400> SEQUENCE: 738 ucugaaggg gugaggaucu accuuaauau g                                      31

<210> SEQ ID NO 739
<211> LENGTH: 31
<212> TYPE: RNA
```

<213> ORGANISM: Mus musculus

<400> SEQUENCE: 739 ugaaagggu gaggaucuac cuuaauaugc a                              31

<210> SEQ ID NO 740
<211> LENGTH: 31
<212> TYPE: RNA
<213> ORGANISM: Mus musculus

<400> SEQUENCE: 740
aaagggguga ggaucuaccu uaauaugcag a                             31

<210> SEQ ID NO 741
<211> LENGTH: 31
<212> TYPE: RNA
<213> ORGANISM: Mus musculus

<400> SEQUENCE: 741
aucuaccuua auaugcagag ugggagaggu a                             31

<210> SEQ ID NO 742
<211> LENGTH: 31
<212> TYPE: RNA
<213> ORGANISM: Mus musculus

<400> SEQUENCE: 742
ucuaccuuaa uaugcagagu gggagaggua a                             31

<210> SEQ ID NO 743
<211> LENGTH: 31
<212> TYPE: RNA
<213> ORGANISM: Mus musculus

<400> SEQUENCE: 743
uccguggugc ugaaguuuau ucggauuuau u                             31

<210> SEQ ID NO 744
<211> LENGTH: 31
<212> TYPE: RNA
<213> ORGANISM: Mus musculus

<400> SEQUENCE: 744
uuucugaaag gggugaggau cuaccuuaau a                             31

<210> SEQ ID NO 745
<211> LENGTH: 31
<212> TYPE: RNA
<213> ORGANISM: Mus musculus

<400> SEQUENCE: 745
uucugaaagg ggugaggauc uaccuuaaua u                             31

<210> SEQ ID NO 746
<211> LENGTH: 31
<212> TYPE: RNA
<213> ORGANISM: Mus musculus

<400> SEQUENCE: 746
caagcugugu gacacaccgc aagggcuugg g                             31

<210> SEQ ID NO 747
<211> LENGTH: 31

<212> TYPE: RNA
<213> ORGANISM: Mus musculus

<400> SEQUENCE: 747
gacaggaagc ugcagcucca ggagggauau c      31

<210> SEQ ID NO 748
<211> LENGTH: 31
<212> TYPE: RNA
<213> ORGANISM: Mus musculus

<400> SEQUENCE: 748
caggaagcug cagcuccagg aggguauuca c      31

<210> SEQ ID NO 749
<211> LENGTH: 31
<212> TYPE: RNA
<213> ORGANISM: Mus musculus

<400> SEQUENCE: 749
aggaagcugc agcuccagga ggguauucac c      31

<210> SEQ ID NO 750
<211> LENGTH: 31
<212> TYPE: RNA
<213> ORGANISM: Mus musculus

<400> SEQUENCE: 750
ggaagcugca gcuccaggag gguauucacc a      31

<210> SEQ ID NO 751
<211> LENGTH: 31
<212> TYPE: RNA
<213> ORGANISM: Mus musculus

<400> SEQUENCE: 751
gaagcugcag cuccaggagg guauucacca c      31

<210> SEQ ID NO 752
<211> LENGTH: 31
<212> TYPE: RNA
<213> ORGANISM: Mus musculus

<400> SEQUENCE: 752
aagcugcagc uccaggaggg uauucaccac c      31

<210> SEQ ID NO 753
<211> LENGTH: 31
<212> TYPE: RNA
<213> ORGANISM: Mus musculus

<400> SEQUENCE: 753
aagcugugug acacaccgca agggcuuggg a      31

<210> SEQ ID NO 754
<211> LENGTH: 31
<212> TYPE: RNA
<213> ORGANISM: Mus musculus

<400> SEQUENCE: 754
gugggagagg uaaggccuca cuaaaccacu c      31

<210> SEQ ID NO 755

<210> SEQ ID NO 755
<211> LENGTH: 31
<212> TYPE: RNA
<213> ORGANISM: Mus musculus

<400> SEQUENCE: 755
agacaggaag cugcagcucc aggagggua u                                     31

<210> SEQ ID NO 756
<211> LENGTH: 31
<212> TYPE: RNA
<213> ORGANISM: Mus musculus

<400> SEQUENCE: 756
acaggaagcu gcagcuccag gagguauuc a                                     31

<210> SEQ ID NO 757
<211> LENGTH: 31
<212> TYPE: RNA
<213> ORGANISM: Mus musculus

<400> SEQUENCE: 757
ccuuaauaug cagaguggga gagguaaggc c                                    31

<210> SEQ ID NO 758
<211> LENGTH: 31
<212> TYPE: RNA
<213> ORGANISM: Mus musculus

<400> SEQUENCE: 758
aauaugcaga gugggagagg uaaggccuca c                                    31

<210> SEQ ID NO 759
<211> LENGTH: 31
<212> TYPE: RNA
<213> ORGANISM: Mus musculus

<400> SEQUENCE: 759
auaugcagag ugggagaggu aaggccucac u                                    31

<210> SEQ ID NO 760
<211> LENGTH: 31
<212> TYPE: RNA
<213> ORGANISM: Mus musculus

<400> SEQUENCE: 760
ugcagagugg gagagguaag gccucacuaa a                                    31

<210> SEQ ID NO 761
<211> LENGTH: 31
<212> TYPE: RNA
<213> ORGANISM: Mus musculus

<400> SEQUENCE: 761
agugggagag guaaggccuc acuaaaccac u                                    31

<210> SEQ ID NO 762
<211> LENGTH: 31
<212> TYPE: RNA
<213> ORGANISM: Mus musculus

<400> SEQUENCE: 762
ugggagaggu aaggccucac uaaaccacuc a                                    31

```
<210> SEQ ID NO 763
<211> LENGTH: 31
<212> TYPE: RNA
<213> ORGANISM: Mus musculus

<400> SEQUENCE: 763
gggagaggua aggccucacu aaaccacuca u                              31

<210> SEQ ID NO 764
<211> LENGTH: 31
<212> TYPE: RNA
<213> ORGANISM: Mus musculus

<400> SEQUENCE: 764
cuugggaucu uuugcgaucu gcucgagcag a                              31

<210> SEQ ID NO 765
<211> LENGTH: 31
<212> TYPE: RNA
<213> ORGANISM: Mus musculus

<400> SEQUENCE: 765
uugggaucuu uugcgaucug cucgagcaga u                              31

<210> SEQ ID NO 766
<211> LENGTH: 31
<212> TYPE: RNA
<213> ORGANISM: Mus musculus

<400> SEQUENCE: 766
ugggaucuuu ugcgaucugc ucgagcagau u                              31

<210> SEQ ID NO 767
<211> LENGTH: 31
<212> TYPE: RNA
<213> ORGANISM: Mus musculus

<400> SEQUENCE: 767
ggaucuuuug cgaucugcuc gagcagauuu g                              31

<210> SEQ ID NO 768
<211> LENGTH: 31
<212> TYPE: RNA
<213> ORGANISM: Mus musculus

<400> SEQUENCE: 768
gaucuuuugc gaucugcucg agcagauuug g                              31

<210> SEQ ID NO 769
<211> LENGTH: 31
<212> TYPE: RNA
<213> ORGANISM: Mus musculus

<400> SEQUENCE: 769
aucuuuugcg aucugcucga gcagauuugg c                              31

<210> SEQ ID NO 770
<211> LENGTH: 31
<212> TYPE: RNA
<213> ORGANISM: Mus musculus

<400> SEQUENCE: 770
uuuuuccaac ugcuuucuga aaggggugag g                              31
```

```
<210> SEQ ID NO 771
<211> LENGTH: 31
<212> TYPE: RNA
<213> ORGANISM: Mus musculus

<400> SEQUENCE: 771
uuuuccaacu gcuuucugaa aggggugagg a                                     31

<210> SEQ ID NO 772
<211> LENGTH: 31
<212> TYPE: RNA
<213> ORGANISM: Mus musculus

<400> SEQUENCE: 772
gcuuucugaa aggggugagg aucuaccuua a                                     31

<210> SEQ ID NO 773
<211> LENGTH: 31
<212> TYPE: RNA
<213> ORGANISM: Mus musculus

<400> SEQUENCE: 773
cugaaagggg ugaggaucua ccuuaauaug c                                     31

<210> SEQ ID NO 774
<211> LENGTH: 31
<212> TYPE: RNA
<213> ORGANISM: Mus musculus

<400> SEQUENCE: 774
uuuuuuccaa cugcuuucug aaagggguga g                                     31

<210> SEQ ID NO 775
<211> LENGTH: 31
<212> TYPE: RNA
<213> ORGANISM: Mus musculus

<400> SEQUENCE: 775
cuuucugaaa ggggugagga ucuaccuuaa u                                     31

<210> SEQ ID NO 776
<211> LENGTH: 31
<212> TYPE: RNA
<213> ORGANISM: Mus musculus

<400> SEQUENCE: 776
uuuuuuucca acugcuuucu gaaaggggug a                                     31

<210> SEQ ID NO 777
<211> LENGTH: 31
<212> TYPE: RNA
<213> ORGANISM: Mus musculus

<400> SEQUENCE: 777
gcugcagcuc caggagggua uucaccaccu c                                     31

<210> SEQ ID NO 778
<211> LENGTH: 31
<212> TYPE: RNA
<213> ORGANISM: Mus musculus

<400> SEQUENCE: 778
gcugugugac acaccgcaag ggcuugggau c                                     31
```

<210> SEQ ID NO 779
<211> LENGTH: 31
<212> TYPE: RNA
<213> ORGANISM: Mus musculus

<400> SEQUENCE: 779
agcugcagcu ccaggagggu auucaccacc u                                    31

<210> SEQ ID NO 780
<211> LENGTH: 31
<212> TYPE: RNA
<213> ORGANISM: Mus musculus

<400> SEQUENCE: 780
cugcagcucc aggaggguau ucaccaccuc u                                    31

<210> SEQ ID NO 781
<211> LENGTH: 31
<212> TYPE: RNA
<213> ORGANISM: Mus musculus

<400> SEQUENCE: 781
ugcagcucca ggaggguauu caccaccucu c                                    31

<210> SEQ ID NO 782
<211> LENGTH: 31
<212> TYPE: RNA
<213> ORGANISM: Mus musculus

<400> SEQUENCE: 782
gcagcuccag gaggguauuc accaccucuc a                                    31

<210> SEQ ID NO 783
<211> LENGTH: 31
<212> TYPE: RNA
<213> ORGANISM: Mus musculus

<400> SEQUENCE: 783
cagcuccagg agggua uuca ccaccucuca g                                   31

<210> SEQ ID NO 784
<211> LENGTH: 31
<212> TYPE: RNA
<213> ORGANISM: Mus musculus

<400> SEQUENCE: 784
gcuccaggag gguauucacc accucucagu g                                    31

<210> SEQ ID NO 785
<211> LENGTH: 31
<212> TYPE: RNA
<213> ORGANISM: Mus musculus

<400> SEQUENCE: 785
cuccaggagg guauucacca ccucucagug g                                    31

<210> SEQ ID NO 786
<211> LENGTH: 31
<212> TYPE: RNA
<213> ORGANISM: Mus musculus

<400> SEQUENCE: 786

-continued uccaggaggg uauucaccac cucucagugg c                                31

<210> SEQ ID NO 787
<211> LENGTH: 31
<212> TYPE: RNA
<213> ORGANISM: Mus musculus

<400> SEQUENCE: 787
ccaggagggu auucaccacc ucucaguggc a                                31

<210> SEQ ID NO 788
<211> LENGTH: 31
<212> TYPE: RNA
<213> ORGANISM: Mus musculus

<400> SEQUENCE: 788
agcuguguga cacaccgcaa gggcuuggga u                                31

<210> SEQ ID NO 789
<211> LENGTH: 31
<212> TYPE: RNA
<213> ORGANISM: Mus musculus

<400> SEQUENCE: 789
cugugugaca caccgcaagg gcuugggauc u                                31

<210> SEQ ID NO 790
<211> LENGTH: 31
<212> TYPE: RNA
<213> ORGANISM: Mus musculus

<400> SEQUENCE: 790
caggagggua uucaccaccu cucaguggca a                                31

<210> SEQ ID NO 791
<211> LENGTH: 31
<212> TYPE: RNA
<213> ORGANISM: Mus musculus

<400> SEQUENCE: 791
ugugugacac accgcaaggg cuugggaucu u                                31

<210> SEQ ID NO 792
<211> LENGTH: 31
<212> TYPE: RNA
<213> ORGANISM: Mus musculus

<400> SEQUENCE: 792
gugugacaca ccgcaagggc uugggaucuu u                                31

<210> SEQ ID NO 793
<211> LENGTH: 31
<212> TYPE: RNA
<213> ORGANISM: Mus musculus

<400> SEQUENCE: 793
agcuccagga ggguauucac caccucucag u                                31

<210> SEQ ID NO 794
<211> LENGTH: 31
<212> TYPE: RNA
<213> ORGANISM: Mus musculus

<400> SEQUENCE: 794 ggagggu auu caccaccucu caguggcaau g       31

<210> SEQ ID NO 795
<211> LENGTH: 31
<212> TYPE: RNA
<213> ORGANISM: Mus musculus

<400> SEQUENCE: 795
gaggguauuc accaccucuc aguggcaaug c       31

<210> SEQ ID NO 796
<211> LENGTH: 31
<212> TYPE: RNA
<213> ORGANISM: Mus musculus

<400> SEQUENCE: 796
aggguauuca ccaccucuca guggcaaugc g       31

<210> SEQ ID NO 797
<211> LENGTH: 31
<212> TYPE: RNA
<213> ORGANISM: Mus musculus

<400> SEQUENCE: 797
ggguauucac caccucucag uggcaaugcg a       31

<210> SEQ ID NO 798
<211> LENGTH: 31
<212> TYPE: RNA
<213> ORGANISM: Mus musculus

<400> SEQUENCE: 798 aggagggu au ucaccaccuc ucaguggcaa u       31

<210> SEQ ID NO 799
<211> LENGTH: 31
<212> TYPE: RNA
<213> ORGANISM: Mus musculus

<400> SEQUENCE: 799
guggugcuga aguuuauucg gauuuauuuu u       31

<210> SEQ ID NO 800
<211> LENGTH: 31
<212> TYPE: RNA
<213> ORGANISM: Mus musculus

<400> SEQUENCE: 800
uggugcugaa guuuauucgg auuuauuuuu u       31

<210> SEQ ID NO 801
<211> LENGTH: 31
<212> TYPE: RNA
<213> ORGANISM: Mus musculus

<400> SEQUENCE: 801
gggcuuggga ucuuuugcga ucugcucgag c       31

<210> SEQ ID NO 802
<211> LENGTH: 31
<212> TYPE: RNA
<213> ORGANISM: Mus musculus
<210> SEQ ID NO 802
<211> LENGTH: 31
<212> TYPE: RNA
<213> ORGANISM: Mus musculus

<400> SEQUENCE: 802
cguggugcug aaguuuauuc ggauuuauuu u                                    31

<210> SEQ ID NO 803
<211> LENGTH: 31
<212> TYPE: RNA
<213> ORGANISM: Mus musculus

<400> SEQUENCE: 803
auucggauuu auuuuuuucc aacugcuuuc u                                    31

<210> SEQ ID NO 804
<211> LENGTH: 31
<212> TYPE: RNA
<213> ORGANISM: Mus musculus

<400> SEQUENCE: 804
ccgcaagggc uugggaucuu uugcgaucug c                                    31

<210> SEQ ID NO 805
<211> LENGTH: 31
<212> TYPE: RNA
<213> ORGANISM: Mus musculus

<400> SEQUENCE: 805
cgcaagggcu ugggaucuuu ugcgaucugc u                                    31

<210> SEQ ID NO 806
<211> LENGTH: 31
<212> TYPE: RNA
<213> ORGANISM: Mus musculus

<400> SEQUENCE: 806
gcaagggcuu gggaucuuuu gcgaucugcu c                                    31

<210> SEQ ID NO 807
<211> LENGTH: 31
<212> TYPE: RNA
<213> ORGANISM: Mus musculus

<400> SEQUENCE: 807
caagggcuug ggaucuuuug cgaucugcuc g                                    31

<210> SEQ ID NO 808
<211> LENGTH: 31
<212> TYPE: RNA
<213> ORGANISM: Mus musculus

<400> SEQUENCE: 808
agggcuuggg aucuuuugcg aucugcucga g                                    31

<210> SEQ ID NO 809
<211> LENGTH: 31
<212> TYPE: RNA
<213> ORGANISM: Mus musculus

<400> SEQUENCE: 809
ccguggugcu gaaguuuauu cggauuuauu u                                    31

<210> SEQ ID NO 810
<211> LENGTH: 31
<212> TYPE: RNA
<213> ORGANISM: Mus musculus

<400> SEQUENCE: 810
uucggauuua uuuuuuucca acugcuuucu g                                              31

<210> SEQ ID NO 811
<211> LENGTH: 31
<212> TYPE: RNA
<213> ORGANISM: Mus musculus

<400> SEQUENCE: 811
ucggauuuau uuuuuuccaa cugcuuucug a                                              31

<210> SEQ ID NO 812
<211> LENGTH: 31
<212> TYPE: RNA
<213> ORGANISM: Mus musculus

<400> SEQUENCE: 812
cggauuuauu uuuuccaac ugcuuucuga a                                               31

<210> SEQ ID NO 813
<211> LENGTH: 31
<212> TYPE: RNA
<213> ORGANISM: Mus musculus

<400> SEQUENCE: 813
ggauuuauuu uuuccaacu gcuuucugaa a                                               31

<210> SEQ ID NO 814
<211> LENGTH: 31
<212> TYPE: RNA
<213> ORGANISM: Mus musculus

<400> SEQUENCE: 814
gauuuauuuu uuccaacug cuuucugaaa g                                               31

<210> SEQ ID NO 815
<211> LENGTH: 31
<212> TYPE: RNA
<213> ORGANISM: Mus musculus

<400> SEQUENCE: 815
auuuauuuuu uccaacugc uuucugaaag g                                               31

<210> SEQ ID NO 816
<211> LENGTH: 31
<212> TYPE: RNA
<213> ORGANISM: Mus musculus

<400> SEQUENCE: 816
caccgcaagg gcuugggauc uuuugcgauc u                                              31

<210> SEQ ID NO 817
<211> LENGTH: 31
<212> TYPE: RNA
<213> ORGANISM: Mus musculus

<400> SEQUENCE: 817
accgcaaggg cuugggaucu uuugcgaucu g                                              31

<210> SEQ ID NO 818
<211> LENGTH: 31
<212> TYPE: RNA

```
<213> ORGANISM: Mus musculus

<400> SEQUENCE: 818
aagggcuugg gaucuuuugc gaucugcucg a                               31

<210> SEQ ID NO 819
<211> LENGTH: 31
<212> TYPE: RNA
<213> ORGANISM: Mus musculus

<400> SEQUENCE: 819
gggaucuuuu gcgaucugcu cgagcagauu u                               31

<210> SEQ ID NO 820
<211> LENGTH: 31
<212> TYPE: RNA
<213> ORGANISM: Mus musculus

<400> SEQUENCE: 820 auuuuuucc aacugcuuuc ugaaaggggu g                                31

<210> SEQ ID NO 821
<211> LENGTH: 31
<212> TYPE: RNA
<213> ORGANISM: Mus musculus

<400> SEQUENCE: 821
uuauuuuuuu ccaacugcuu ucugaaaggg g                               31

<210> SEQ ID NO 822
<211> LENGTH: 31
<212> TYPE: RNA
<213> ORGANISM: Mus musculus

<400> SEQUENCE: 822 uauuuuuuc caacugcuuu cugaaagggg u                                31

<210> SEQ ID NO 823
<211> LENGTH: 31
<212> TYPE: RNA
<213> ORGANISM: Mus musculus

<400> SEQUENCE: 823
uuuauuuuuu uccaacugcu uucugaaagg g                               31

<210> SEQ ID NO 824
<211> LENGTH: 31
<212> TYPE: RNA
<213> ORGANISM: Mus musculus

<400> SEQUENCE: 824
gacacaccgc aagggcuugg gaucuuuugc g                               31

<210> SEQ ID NO 825
<211> LENGTH: 31
<212> TYPE: RNA
<213> ORGANISM: Mus musculus

<400> SEQUENCE: 825
gugacacacc gcaagggcuu gggaucuuuu g                               31

<210> SEQ ID NO 826
<211> LENGTH: 31
```

```
<212> TYPE: RNA
<213> ORGANISM: Mus musculus

<400> SEQUENCE: 826
ugacacaccg caagggcuug ggaucuuuug c                              31

<210> SEQ ID NO 827
<211> LENGTH: 31
<212> TYPE: RNA
<213> ORGANISM: Mus musculus

<400> SEQUENCE: 827
cacaccgcaa gggcuuggga ucuuugcga u                               31

<210> SEQ ID NO 828
<211> LENGTH: 31
<212> TYPE: RNA
<213> ORGANISM: Mus musculus

<400> SEQUENCE: 828
acaccgcaag ggcuugggau cuuugcgau c                               31

<210> SEQ ID NO 829
<211> LENGTH: 31
<212> TYPE: RNA
<213> ORGANISM: Mus musculus

<400> SEQUENCE: 829
ugugacacac cgcaagggcu ugggaucuuu u                              31

<210> SEQ ID NO 830
<211> LENGTH: 31
<212> TYPE: RNA
<213> ORGANISM: Mus musculus

<400> SEQUENCE: 830
acacaccgca agggcuuggg aucuuuugcg a                              31

<210> SEQ ID NO 831
<211> LENGTH: 31
<212> TYPE: RNA
<213> ORGANISM: Mus musculus

<400> SEQUENCE: 831
ggugcugaag uuuauucgga uuuauuuuuu u                              31

<210> SEQ ID NO 832
<211> LENGTH: 31
<212> TYPE: RNA
<213> ORGANISM: Mus musculus

<400> SEQUENCE: 832
gugcugaagu uuauucggau uuauuuuuuu c                              31

<210> SEQ ID NO 833
<211> LENGTH: 31
<212> TYPE: RNA
<213> ORGANISM: Mus musculus

<400> SEQUENCE: 833
uauucggauu uauuuuuuuc caacugcuuu c                              31

<210> SEQ ID NO 834
```

```
<211> LENGTH: 31
<212> TYPE: RNA
<213> ORGANISM: Mus musculus

<400> SEQUENCE: 834
uuuauucgga uuuauuuuuu uccaacugcu u                                  31

<210> SEQ ID NO 835
<211> LENGTH: 31
<212> TYPE: RNA
<213> ORGANISM: Mus musculus

<400> SEQUENCE: 835
uuauucggau uuauuuuuuu ccaacugcuu u                                  31

<210> SEQ ID NO 836
<211> LENGTH: 31
<212> TYPE: RNA
<213> ORGANISM: Mus musculus

<400> SEQUENCE: 836
ugcugaaguu uauucggauu uauuuuuuuc c                                  31

<210> SEQ ID NO 837
<211> LENGTH: 31
<212> TYPE: RNA
<213> ORGANISM: Mus musculus

<400> SEQUENCE: 837
gcugaaguuu auucggauuu auuuuuuucc a                                  31

<210> SEQ ID NO 838
<211> LENGTH: 31
<212> TYPE: RNA
<213> ORGANISM: Mus musculus

<400> SEQUENCE: 838
aguuuauucg gauuuauuuu uuccaacug c                                   31

<210> SEQ ID NO 839
<211> LENGTH: 31
<212> TYPE: RNA
<213> ORGANISM: Mus musculus

<400> SEQUENCE: 839
guuuauucgg auuuauuuuu uuccaacugc u                                  31

<210> SEQ ID NO 840
<211> LENGTH: 31
<212> TYPE: RNA
<213> ORGANISM: Mus musculus

<400> SEQUENCE: 840
cugaaguuua uucggauuua uuuuuuucca a                                  31

<210> SEQ ID NO 841
<211> LENGTH: 31
<212> TYPE: RNA
<213> ORGANISM: Mus musculus

<400> SEQUENCE: 841
ugaaguuuau ucggauuuau uuuuuuccaa c                                  31
```

```
<210> SEQ ID NO 842
<211> LENGTH: 31
<212> TYPE: RNA
<213> ORGANISM: Mus musculus

<400> SEQUENCE: 842
gaaguuuauu cggauuuauu uuuuccaac u                              31

<210> SEQ ID NO 843
<211> LENGTH: 31
<212> TYPE: RNA
<213> ORGANISM: Mus musculus

<400> SEQUENCE: 843
aaguuuauuc ggauuuauuu uuuccaacu g                              31

<210> SEQ ID NO 844
<211> LENGTH: 31
<212> TYPE: RNA
<213> ORGANISM: Homo sapiens

<400> SEQUENCE: 844
ggaaucagaa gcaggugucu gcagccagga c                             31

<210> SEQ ID NO 845
<211> LENGTH: 31
<212> TYPE: RNA
<213> ORGANISM: Homo sapiens

<400> SEQUENCE: 845
guggaaucag aagcaggugu cugcagccag g                             31

<210> SEQ ID NO 846
<211> LENGTH: 31
<212> TYPE: RNA
<213> ORGANISM: Homo sapiens

<400> SEQUENCE: 846
uggaaucaga agcagguguc ugcagccagg a                             31

<210> SEQ ID NO 847
<211> LENGTH: 31
<212> TYPE: RNA
<213> ORGANISM: Homo sapiens

<400> SEQUENCE: 847
gaaucagaag caggugucug cagccaggac u                             31

<210> SEQ ID NO 848
<211> LENGTH: 31
<212> TYPE: RNA
<213> ORGANISM: Homo sapiens

<400> SEQUENCE: 848
ucagaagcag gugucugcag ccaggacuuc c                             31

<210> SEQ ID NO 849
<211> LENGTH: 31
<212> TYPE: RNA
<213> ORGANISM: Homo sapiens

<400> SEQUENCE: 849
cagaagcagg ugucugcagc caggacuucc u                             31
```

<210> SEQ ID NO 850
<211> LENGTH: 31
<212> TYPE: RNA
<213> ORGANISM: Homo sapiens

<400> SEQUENCE: 850
agaagcaggu gucugcagcc aggacuuccu c                                    31

<210> SEQ ID NO 851
<211> LENGTH: 31
<212> TYPE: RNA
<213> ORGANISM: Homo sapiens

<400> SEQUENCE: 851
uguggaauca gaagcaggug ucugcagcca g                                    31

<210> SEQ ID NO 852
<211> LENGTH: 31
<212> TYPE: RNA
<213> ORGANISM: Homo sapiens

<400> SEQUENCE: 852
aucagaagca ggugucugca gccaggacuu c                                    31

<210> SEQ ID NO 853
<211> LENGTH: 31
<212> TYPE: RNA
<213> ORGANISM: Homo sapiens

<400> SEQUENCE: 853
uuguggaauc agaagcaggu gucugcagcc a                                    31

<210> SEQ ID NO 854
<211> LENGTH: 31
<212> TYPE: RNA
<213> ORGANISM: Homo sapiens

<400> SEQUENCE: 854
aaucagaagc aggugucugc agccaggacu u                                    31

<210> SEQ ID NO 855
<211> LENGTH: 31
<212> TYPE: RNA
<213> ORGANISM: Homo sapiens

<400> SEQUENCE: 855
ccuuguggaa ucagaagcag gugucugcag c                                    31

<210> SEQ ID NO 856
<211> LENGTH: 31
<212> TYPE: RNA
<213> ORGANISM: Homo sapiens

<400> SEQUENCE: 856
cuuguggaau cagaagcagg ugucugcagc c                                    31

<210> SEQ ID NO 857
<211> LENGTH: 31
<212> TYPE: RNA
<213> ORGANISM: Homo sapiens

<400> SEQUENCE: 857
cacuucaaag gcggccacag gguugaggaa a                                    31

```
<210> SEQ ID NO 858
<211> LENGTH: 31
<212> TYPE: RNA
<213> ORGANISM: Homo sapiens

<400> SEQUENCE: 858
aaaaaugagu cacuucaaag gcggccacag g                              31

<210> SEQ ID NO 859
<211> LENGTH: 31
<212> TYPE: RNA
<213> ORGANISM: Homo sapiens

<400> SEQUENCE: 859 aaaaaugag ucacuucaaa ggcggccaca g                               31

<210> SEQ ID NO 860
<211> LENGTH: 31
<212> TYPE: RNA
<213> ORGANISM: Homo sapiens

<400> SEQUENCE: 860
accguggaaa uuuugugcuc aaagguaaga a                              31

<210> SEQ ID NO 861
<211> LENGTH: 31
<212> TYPE: RNA
<213> ORGANISM: Homo sapiens

<400> SEQUENCE: 861
ccguggaaau uugugcuca aagguaagaa a                               31

<210> SEQ ID NO 862
<211> LENGTH: 31
<212> TYPE: RNA
<213> ORGANISM: Homo sapiens

<400> SEQUENCE: 862
cguggaaauu uugugcucaa agguaagaaa c                              31

<210> SEQ ID NO 863
<211> LENGTH: 31
<212> TYPE: RNA
<213> ORGANISM: Homo sapiens

<400> SEQUENCE: 863
guggaaauuu ugugcucaaa gguaagaaac c                              31

<210> SEQ ID NO 864
<211> LENGTH: 31
<212> TYPE: RNA
<213> ORGANISM: Homo sapiens

<400> SEQUENCE: 864
uggaaauuuu gugcucaaag guaagaaacc a                              31

<210> SEQ ID NO 865
<211> LENGTH: 31
<212> TYPE: RNA
<213> ORGANISM: Homo sapiens

<400> SEQUENCE: 865
```

```
ggaaauuuug ugcucaaagg uaagaaacca u                                31

<210> SEQ ID NO 866
<211> LENGTH: 31
<212> TYPE: RNA
<213> ORGANISM: Homo sapiens

<400> SEQUENCE: 866
gagucacuuc aaaggcggcc acaggguuga g                                31

<210> SEQ ID NO 867
<211> LENGTH: 31
<212> TYPE: RNA
<213> ORGANISM: Homo sapiens

<400> SEQUENCE: 867
agucacuuca aaggcggcca caggguugag g                                31

<210> SEQ ID NO 868
<211> LENGTH: 31
<212> TYPE: RNA
<213> ORGANISM: Homo sapiens

<400> SEQUENCE: 868
gucacuucaa aggcggccac aggguugagg a                                31

<210> SEQ ID NO 869
<211> LENGTH: 31
<212> TYPE: RNA
<213> ORGANISM: Homo sapiens

<400> SEQUENCE: 869
ucacuucaaa ggcggccaca ggguugagga a                                31

<210> SEQ ID NO 870
<211> LENGTH: 31
<212> TYPE: RNA
<213> ORGANISM: Homo sapiens

<400> SEQUENCE: 870
ucaccgugga aauuuugugc ucaaagguaa g                                31

<210> SEQ ID NO 871
<211> LENGTH: 31
<212> TYPE: RNA
<213> ORGANISM: Homo sapiens

<400> SEQUENCE: 871
caccguggaa auuuugugcu caaagguaag a                                31

<210> SEQ ID NO 872
<211> LENGTH: 31
<212> TYPE: RNA
<213> ORGANISM: Homo sapiens

<400> SEQUENCE: 872
uuucaccgug gaaauuuugu gcucaaaggu a                                31

<210> SEQ ID NO 873
<211> LENGTH: 31
<212> TYPE: RNA
<213> ORGANISM: Homo sapiens

<400> SEQUENCE: 873
```

```
uucaccgugg aaauuugug cucaaaggua a                               31

<210> SEQ ID NO 874
<211> LENGTH: 31
<212> TYPE: RNA
<213> ORGANISM: Homo sapiens

<400> SEQUENCE: 874 gaaauuugu gcucaaaggu aagaaaccau c                               31

<210> SEQ ID NO 875
<211> LENGTH: 31
<212> TYPE: RNA
<213> ORGANISM: Homo sapiens

<400> SEQUENCE: 875 aaauuugug cucaaaggua agaaaccauc u                               31

<210> SEQ ID NO 876
<211> LENGTH: 31
<212> TYPE: RNA
<213> ORGANISM: Homo sapiens

<400> SEQUENCE: 876 aauuugugc ucaaagguaa gaaaccaucu u                               31

<210> SEQ ID NO 877
<211> LENGTH: 31
<212> TYPE: RNA
<213> ORGANISM: Homo sapiens

<400> SEQUENCE: 877 auuugugcu caaagguaag aaaccaucuu a                               31

<210> SEQ ID NO 878
<211> LENGTH: 31
<212> TYPE: RNA
<213> ORGANISM: Homo sapiens

<400> SEQUENCE: 878
uuugugcuca aagguaagaa accaucuuau a                              31

<210> SEQ ID NO 879
<211> LENGTH: 31
<212> TYPE: RNA
<213> ORGANISM: Homo sapiens

<400> SEQUENCE: 879
uugugcucaa agguaagaaa ccaucuuaua u                              31

<210> SEQ ID NO 880
<211> LENGTH: 31
<212> TYPE: RNA
<213> ORGANISM: Homo sapiens

<400> SEQUENCE: 880
ugugcucaaa gguaagaaac caucuuauau a                              31

<210> SEQ ID NO 881
<211> LENGTH: 31
<212> TYPE: RNA
<213> ORGANISM: Homo sapiens
```

```
<400> SEQUENCE: 881
gccccuugug gaaucagaag cagguguucug c                              31

<210> SEQ ID NO 882
<211> LENGTH: 31
<212> TYPE: RNA
<213> ORGANISM: Homo sapiens

<400> SEQUENCE: 882
augagucacu ucaaaggcgg ccacaggguu g                              31

<210> SEQ ID NO 883
<211> LENGTH: 31
<212> TYPE: RNA
<213> ORGANISM: Homo sapiens

<400> SEQUENCE: 883
ugagucacuu caaaggcggc cacaggguug a                              31

<210> SEQ ID NO 884
<211> LENGTH: 31
<212> TYPE: RNA
<213> ORGANISM: Homo sapiens

<400> SEQUENCE: 884
aaugagucac uucaaaggcg gccacagggu u                              31

<210> SEQ ID NO 885
<211> LENGTH: 31
<212> TYPE: RNA
<213> ORGANISM: Homo sapiens

<400> SEQUENCE: 885
aaagccccuu guggaaucag aagcaggugu c                              31

<210> SEQ ID NO 886
<211> LENGTH: 31
<212> TYPE: RNA
<213> ORGANISM: Homo sapiens

<400> SEQUENCE: 886
agccccuugu ggaaucagaa gcaggugucu g                              31

<210> SEQ ID NO 887
<211> LENGTH: 31
<212> TYPE: RNA
<213> ORGANISM: Homo sapiens

<400> SEQUENCE: 887
ccccuugugg aaucagaagc aggugucugc a                              31

<210> SEQ ID NO 888
<211> LENGTH: 31
<212> TYPE: RNA
<213> ORGANISM: Homo sapiens

<400> SEQUENCE: 888
cccuuguuga aucagaagca ggugucugca g                              31

<210> SEQ ID NO 889
<211> LENGTH: 31
<212> TYPE: RNA
<213> ORGANISM: Homo sapiens
```

```
<400> SEQUENCE: 889 aagcccuug uggaaucaga agcaggguguc u                              31

<210> SEQ ID NO 890
<211> LENGTH: 31
<212> TYPE: RNA
<213> ORGANISM: Homo sapiens

<400> SEQUENCE: 890
caaaggcggc cacaggguug aggaaaaagc c                              31

<210> SEQ ID NO 891
<211> LENGTH: 31
<212> TYPE: RNA
<213> ORGANISM: Homo sapiens

<400> SEQUENCE: 891
guaagaaacc aucuuauaua aaacaaucaa a                              31

<210> SEQ ID NO 892
<211> LENGTH: 31
<212> TYPE: RNA
<213> ORGANISM: Homo sapiens

<400> SEQUENCE: 892
ucaaaggcgg ccacagggu gaggaaaaag c                               31

<210> SEQ ID NO 893
<211> LENGTH: 31
<212> TYPE: RNA
<213> ORGANISM: Homo sapiens

<400> SEQUENCE: 893
cucaaaggua agaaaccauc uuauauaaaa c                              31

<210> SEQ ID NO 894
<211> LENGTH: 31
<212> TYPE: RNA
<213> ORGANISM: Homo sapiens

<400> SEQUENCE: 894
ucaaagguaa gaaaccaucu uauauaaaac a                              31

<210> SEQ ID NO 895
<211> LENGTH: 31
<212> TYPE: RNA
<213> ORGANISM: Homo sapiens

<400> SEQUENCE: 895
caaagguaag aaaccaucuu auauaaaaca a                              31

<210> SEQ ID NO 896
<211> LENGTH: 31
<212> TYPE: RNA
<213> ORGANISM: Homo sapiens

<400> SEQUENCE: 896
aagguaagaa accaucuuau auaaaacaau c                              31

<210> SEQ ID NO 897
<211> LENGTH: 31
<212> TYPE: RNA
```

-continued

```
<213> ORGANISM: Homo sapiens

<400> SEQUENCE: 897
agguaagaaa ccaucuuaua uaaaacaauc a                              31

<210> SEQ ID NO 898
<211> LENGTH: 31
<212> TYPE: RNA
<213> ORGANISM: Homo sapiens

<400> SEQUENCE: 898
gguaagaaac caucuuauau aaaacaauca a                              31

<210> SEQ ID NO 899
<211> LENGTH: 31
<212> TYPE: RNA
<213> ORGANISM: Homo sapiens

<400> SEQUENCE: 899
aaagguaaga aaccaucuua uauaaaacaa u                              31

<210> SEQ ID NO 900
<211> LENGTH: 31
<212> TYPE: RNA
<213> ORGANISM: Homo sapiens

<400> SEQUENCE: 900
aaaaugaguc acuucaaagg cggccacagg g                              31

<210> SEQ ID NO 901
<211> LENGTH: 31
<212> TYPE: RNA
<213> ORGANISM: Homo sapiens

<400> SEQUENCE: 901
acuucaaagg cggccacagg guugaggaaa a                              31

<210> SEQ ID NO 902
<211> LENGTH: 31
<212> TYPE: RNA
<213> ORGANISM: Homo sapiens

<400> SEQUENCE: 902
cuucaaaggc ggccacaggg uugaggaaaa a                              31

<210> SEQ ID NO 903
<211> LENGTH: 31
<212> TYPE: RNA
<213> ORGANISM: Homo sapiens

<400> SEQUENCE: 903
uucaaaggcg gccacagggu ugaggaaaaa g                              31

<210> SEQ ID NO 904
<211> LENGTH: 31
<212> TYPE: RNA
<213> ORGANISM: Homo sapiens

<400> SEQUENCE: 904
ggaaaaagcc ccuuguggaa ucagaagcag g                              31

<210> SEQ ID NO 905
<211> LENGTH: 31
```

```
<212> TYPE: RNA
<213> ORGANISM: Homo sapiens

<400> SEQUENCE: 905
gaggaaaaag ccccuugugg aaucagaagc a                              31

<210> SEQ ID NO 906
<211> LENGTH: 31
<212> TYPE: RNA
<213> ORGANISM: Homo sapiens

<400> SEQUENCE: 906
aggaaaaagc ccuugugga aucagaagca g                               31

<210> SEQ ID NO 907
<211> LENGTH: 31
<212> TYPE: RNA
<213> ORGANISM: Homo sapiens

<400> SEQUENCE: 907 aaaaaauga gucacuucaa aggcggccac a                               31

<210> SEQ ID NO 908
<211> LENGTH: 31
<212> TYPE: RNA
<213> ORGANISM: Homo sapiens

<400> SEQUENCE: 908
guugacuuua uuucaccgug gaaauuugu g                               31

<210> SEQ ID NO 909
<211> LENGTH: 31
<212> TYPE: RNA
<213> ORGANISM: Homo sapiens

<400> SEQUENCE: 909
auguugacuu uauuucaccg uggaaauuuu g                              31

<210> SEQ ID NO 910
<211> LENGTH: 31
<212> TYPE: RNA
<213> ORGANISM: Homo sapiens

<400> SEQUENCE: 910
uguugacuuu auuucaccgu ggaaauuuug u                              31

<210> SEQ ID NO 911
<211> LENGTH: 31
<212> TYPE: RNA
<213> ORGANISM: Homo sapiens

<400> SEQUENCE: 911
aaagcuuaua auguugacuu uauuucaccg u                              31

<210> SEQ ID NO 912
<211> LENGTH: 31
<212> TYPE: RNA
<213> ORGANISM: Homo sapiens

<400> SEQUENCE: 912
uuauaauguu gacuuuauuu caccguggaa a                              31

<210> SEQ ID NO 913
```

```
<211> LENGTH: 31
<212> TYPE: RNA
<213> ORGANISM: Homo sapiens

<400> SEQUENCE: 913
aauguugacu uuauuucacc guggaaauuu u                                    31

<210> SEQ ID NO 914
<211> LENGTH: 31
<212> TYPE: RNA
<213> ORGANISM: Homo sapiens

<400> SEQUENCE: 914
ugcucaaagg uaagaaacca ucuuauauaa a                                    31

<210> SEQ ID NO 915
<211> LENGTH: 31
<212> TYPE: RNA
<213> ORGANISM: Homo sapiens

<400> SEQUENCE: 915
gcucaaaggu aagaaaccau cuuauauaaa a                                    31

<210> SEQ ID NO 916
<211> LENGTH: 31
<212> TYPE: RNA
<213> ORGANISM: Homo sapiens

<400> SEQUENCE: 916
auacauuaaa aaaaugaguc acuucaaagg c                                    31

<210> SEQ ID NO 917
<211> LENGTH: 31
<212> TYPE: RNA
<213> ORGANISM: Homo sapiens

<400> SEQUENCE: 917
aaaugaguca cuucaaaggc ggccacaggg u                                    31

<210> SEQ ID NO 918
<211> LENGTH: 31
<212> TYPE: RNA
<213> ORGANISM: Homo sapiens

<400> SEQUENCE: 918
gguugaggaa aaagccccuu guggaaucag a                                    31

<210> SEQ ID NO 919
<211> LENGTH: 31
<212> TYPE: RNA
<213> ORGANISM: Homo sapiens

<400> SEQUENCE: 919
ugaggaaaaa gccccuugug gaaucagaag c                                    31

<210> SEQ ID NO 920
<211> LENGTH: 31
<212> TYPE: RNA
<213> ORGANISM: Homo sapiens

<400> SEQUENCE: 920 gaaaagccc cuugguggaau cagaagcagg u                                    31
```

```
<210> SEQ ID NO 921
<211> LENGTH: 31
<212> TYPE: RNA
<213> ORGANISM: Homo sapiens

<400> SEQUENCE: 921
aaaaagcccc uuguggaauc agaagcaggu g                                    31

<210> SEQ ID NO 922
<211> LENGTH: 31
<212> TYPE: RNA
<213> ORGANISM: Homo sapiens

<400> SEQUENCE: 922
guugaggaaa agcccccuug uggaaucaga a                                    31

<210> SEQ ID NO 923
<211> LENGTH: 31
<212> TYPE: RNA
<213> ORGANISM: Homo sapiens

<400> SEQUENCE: 923
uugaggaaaa agcccuugu ggaaucagaa g                                     31

<210> SEQ ID NO 924
<211> LENGTH: 31
<212> TYPE: RNA
<213> ORGANISM: Homo sapiens

<400> SEQUENCE: 924
uaaaaaaaug agucacuuca aaggcggcca c                                    31

<210> SEQ ID NO 925
<211> LENGTH: 31
<212> TYPE: RNA
<213> ORGANISM: Homo sapiens

<400> SEQUENCE: 925
uauuucaccg uggaaauuuu gugcucaaag g                                    31

<210> SEQ ID NO 926
<211> LENGTH: 31
<212> TYPE: RNA
<213> ORGANISM: Homo sapiens

<400> SEQUENCE: 926
auuucaccgu ggaaauuuug ugcucaaagg u                                    31

<210> SEQ ID NO 927
<211> LENGTH: 31
<212> TYPE: RNA
<213> ORGANISM: Homo sapiens

<400> SEQUENCE: 927
agcuuauaau guugacuuua uuucaccgug g                                    31

<210> SEQ ID NO 928
<211> LENGTH: 31
<212> TYPE: RNA
<213> ORGANISM: Homo sapiens

<400> SEQUENCE: 928
gcuuauaaug uugacuuuau uucaccgugg a                                    31
```

```
<210> SEQ ID NO 929
<211> LENGTH: 31
<212> TYPE: RNA
<213> ORGANISM: Homo sapiens

<400> SEQUENCE: 929
uugacuuuau uucaccgugg aaauuugug c                              31

<210> SEQ ID NO 930
<211> LENGTH: 31
<212> TYPE: RNA
<213> ORGANISM: Homo sapiens

<400> SEQUENCE: 930
ugacuuuauu ucaccgugga aauuugugc u                              31

<210> SEQ ID NO 931
<211> LENGTH: 31
<212> TYPE: RNA
<213> ORGANISM: Homo sapiens

<400> SEQUENCE: 931
acuuuauuuc accgggaaa uuugugcuc a                               31

<210> SEQ ID NO 932
<211> LENGTH: 31
<212> TYPE: RNA
<213> ORGANISM: Homo sapiens

<400> SEQUENCE: 932
cuuuauuuca ccguggaaau uugugcuca a                              31

<210> SEQ ID NO 933
<211> LENGTH: 31
<212> TYPE: RNA
<213> ORGANISM: Homo sapiens

<400> SEQUENCE: 933
uuauuucacc guggaaauuu ugugcucaaa g                             31

<210> SEQ ID NO 934
<211> LENGTH: 31
<212> TYPE: RNA
<213> ORGANISM: Homo sapiens

<400> SEQUENCE: 934
acauuaaaaa aaugagucac uucaaaggcg g                             31

<210> SEQ ID NO 935
<211> LENGTH: 31
<212> TYPE: RNA
<213> ORGANISM: Homo sapiens

<400> SEQUENCE: 935
aagcuuauaa uguugacuuu auuucaccgu g                             31

<210> SEQ ID NO 936
<211> LENGTH: 31
<212> TYPE: RNA
<213> ORGANISM: Homo sapiens

<400> SEQUENCE: 936
cuuauaaugu ugacuuuauu ucaccgugga a                             31
```

<210> SEQ ID NO 937
<211> LENGTH: 31
<212> TYPE: RNA
<213> ORGANISM: Homo sapiens

<400> SEQUENCE: 937
uuuauuucac cguggaaauu uugugcucaa a                                      31

<210> SEQ ID NO 938
<211> LENGTH: 31
<212> TYPE: RNA
<213> ORGANISM: Homo sapiens

<400> SEQUENCE: 938
uuuugugcuc aaagguaaga aaccaucuua u                                      31

<210> SEQ ID NO 939
<211> LENGTH: 31
<212> TYPE: RNA
<213> ORGANISM: Homo sapiens

<400> SEQUENCE: 939
gugcucaaag guaagaaacc aucuuauaua a                                      31

<210> SEQ ID NO 940
<211> LENGTH: 31
<212> TYPE: RNA
<213> ORGANISM: Homo sapiens

<400> SEQUENCE: 940
uacauuaaaa aaaugaguca cuucaaaggc g                                      31

<210> SEQ ID NO 941
<211> LENGTH: 31
<212> TYPE: RNA
<213> ORGANISM: Homo sapiens

<400> SEQUENCE: 941
aaaagccccu uguggaauca gaagcaggug u                                      31

<210> SEQ ID NO 942
<211> LENGTH: 31
<212> TYPE: RNA
<213> ORGANISM: Homo sapiens

<400> SEQUENCE: 942
gacuuuauuu caccguggaa auuuugugcu c                                      31

<210> SEQ ID NO 943
<211> LENGTH: 31
<212> TYPE: RNA
<213> ORGANISM: Homo sapiens

<400> SEQUENCE: 943
cauuaaaaaa augagucacu ucaaaggcgg c                                      31

<210> SEQ ID NO 944
<211> LENGTH: 31
<212> TYPE: RNA
<213> ORGANISM: Homo sapiens

<400> SEQUENCE: 944
auuaaaaaaa ugagucacuu caaaggcggc c				31

<210> SEQ ID NO 945
<211> LENGTH: 31
<212> TYPE: RNA
<213> ORGANISM: Homo sapiens

<400> SEQUENCE: 945
uuaaaaaaau gagucacuuc aaaggcggcc a				31

<210> SEQ ID NO 946
<211> LENGTH: 31
<212> TYPE: RNA
<213> ORGANISM: Homo sapiens

<400> SEQUENCE: 946
uaagaaacca ucuuauauaa aacaaucaaa u				31

<210> SEQ ID NO 947
<211> LENGTH: 31
<212> TYPE: RNA
<213> ORGANISM: Homo sapiens

<400> SEQUENCE: 947
aagaaaccau cuuauauaaa acaaucaaau a				31

<210> SEQ ID NO 948
<211> LENGTH: 31
<212> TYPE: RNA
<213> ORGANISM: Homo sapiens

<400> SEQUENCE: 948
agaaaccauc uuauauaaaa caaucaaaua a				31

<210> SEQ ID NO 949
<211> LENGTH: 31
<212> TYPE: RNA
<213> ORGANISM: Homo sapiens

<400> SEQUENCE: 949
gaaaccaucu uauauaaaac aaucaaauaa a				31

<210> SEQ ID NO 950
<211> LENGTH: 31
<212> TYPE: RNA
<213> ORGANISM: Homo sapiens

<400> SEQUENCE: 950
aaggcggcca caggguugag gaaaaagccc c				31

<210> SEQ ID NO 951
<211> LENGTH: 31
<212> TYPE: RNA
<213> ORGANISM: Homo sapiens

<400> SEQUENCE: 951
aaaggcggcc acaggguuga ggaaaaagcc c				31

<210> SEQ ID NO 952
<211> LENGTH: 31
<212> TYPE: RNA
<213> ORGANISM: Homo sapiens

<400> SEQUENCE: 952
acauaaauac auuaaaaaaa ugagucacuu c                                31

<210> SEQ ID NO 953
<211> LENGTH: 31
<212> TYPE: RNA
<213> ORGANISM: Homo sapiens

<400> SEQUENCE: 953
cauaaauaca uuaaaaaaau gagucacuuc a                                31

<210> SEQ ID NO 954
<211> LENGTH: 31
<212> TYPE: RNA
<213> ORGANISM: Homo sapiens

<400> SEQUENCE: 954
auacauaaau acauuaaaaa aaugagucac u                                31

<210> SEQ ID NO 955
<211> LENGTH: 31
<212> TYPE: RNA
<213> ORGANISM: Homo sapiens

<400> SEQUENCE: 955
uacauaaaua cauuaaaaaa augagucacu u                                31

<210> SEQ ID NO 956
<211> LENGTH: 31
<212> TYPE: RNA
<213> ORGANISM: Homo sapiens

<400> SEQUENCE: 956
auaaauacau uaaaaaaaug agucacuuca a                                31

<210> SEQ ID NO 957
<211> LENGTH: 31
<212> TYPE: RNA
<213> ORGANISM: Homo sapiens

<400> SEQUENCE: 957
uaaauacauu aaaaaaauga gucacuucaa a                                31

<210> SEQ ID NO 958
<211> LENGTH: 31
<212> TYPE: RNA
<213> ORGANISM: Homo sapiens

<400> SEQUENCE: 958
aggcggccac aggguugagg aaaaagcccc u                                31

<210> SEQ ID NO 959
<211> LENGTH: 31
<212> TYPE: RNA
<213> ORGANISM: Homo sapiens

<400> SEQUENCE: 959
aaauacauua aaaaaugag ucacuucaaa g                                 31

<210> SEQ ID NO 960
<211> LENGTH: 31
<212> TYPE: RNA
<213> ORGANISM: Homo sapiens

```
<400> SEQUENCE: 960
ggcggccaca ggguugagga aaaagcccu u                            31

<210> SEQ ID NO 961
<211> LENGTH: 31
<212> TYPE: RNA
<213> ORGANISM: Homo sapiens

<400> SEQUENCE: 961
gcggccacag gguugaggaa aaagcccuu g                            31

<210> SEQ ID NO 962
<211> LENGTH: 31
<212> TYPE: RNA
<213> ORGANISM: Homo sapiens

<400> SEQUENCE: 962
uauaauguug acuuuauuuc accguggaaa u                           31

<210> SEQ ID NO 963
<211> LENGTH: 31
<212> TYPE: RNA
<213> ORGANISM: Homo sapiens

<400> SEQUENCE: 963
auaauguuga cuuuauuuca ccguggaaau u                           31

<210> SEQ ID NO 964
<211> LENGTH: 31
<212> TYPE: RNA
<213> ORGANISM: Homo sapiens

<400> SEQUENCE: 964
uaauguugac uuuauuucac cguggaaauu u                           31

<210> SEQ ID NO 965
<211> LENGTH: 31
<212> TYPE: RNA
<213> ORGANISM: Homo sapiens

<400> SEQUENCE: 965
aauacauuaa aaaaugagu cacuucaaag g                            31

<210> SEQ ID NO 966
<211> LENGTH: 31
<212> TYPE: RNA
<213> ORGANISM: Homo sapiens

<400> SEQUENCE: 966
cggccacagg guugaggaaa aagcccuug u                            31

<210> SEQ ID NO 967
<211> LENGTH: 31
<212> TYPE: RNA
<213> ORGANISM: Homo sapiens

<400> SEQUENCE: 967
ggccacaggg uugaggaaaa agcccuugu g                            31

<210> SEQ ID NO 968
<211> LENGTH: 31
<212> TYPE: RNA
<213> ORGANISM: Homo sapiens
```

```
<400> SEQUENCE: 968
gccacagggu ugaggaaaaa gccccuugug g                                    31

<210> SEQ ID NO 969
<211> LENGTH: 31
<212> TYPE: RNA
<213> ORGANISM: Homo sapiens

<400> SEQUENCE: 969
ccacaggguu gaggaaaaag ccccuugugg a                                    31

<210> SEQ ID NO 970
<211> LENGTH: 31
<212> TYPE: RNA
<213> ORGANISM: Homo sapiens

<400> SEQUENCE: 970
cacaggguug aggaaaaagc cccuuggga a                                     31

<210> SEQ ID NO 971
<211> LENGTH: 31
<212> TYPE: RNA
<213> ORGANISM: Homo sapiens

<400> SEQUENCE: 971
ggguugagga aaagccccu uguggaauca g                                     31

<210> SEQ ID NO 972
<211> LENGTH: 31
<212> TYPE: RNA
<213> ORGANISM: Homo sapiens

<400> SEQUENCE: 972
acaggguuga ggaaaaagcc ccuuguggaa u                                    31

<210> SEQ ID NO 973
<211> LENGTH: 31
<212> TYPE: RNA
<213> ORGANISM: Homo sapiens

<400> SEQUENCE: 973
aggguugagg aaaagcccc uuguggaauc a                                     31

<210> SEQ ID NO 974
<211> LENGTH: 31
<212> TYPE: RNA
<213> ORGANISM: Homo sapiens

<400> SEQUENCE: 974
caggguugag gaaaagccc cuuguggaau c                                     31

<210> SEQ ID NO 975
<211> LENGTH: 31
<212> TYPE: RNA
<213> ORGANISM: Homo sapiens

<400> SEQUENCE: 975
accaucuuau auaaaacaau caaauaaaua c                                    31

<210> SEQ ID NO 976
<211> LENGTH: 31
<212> TYPE: RNA
```

<213> ORGANISM: Homo sapiens

<400> SEQUENCE: 976
ccaucuuaua uaaaacaauc aaauaaauac a         31

<210> SEQ ID NO 977
<211> LENGTH: 31
<212> TYPE: RNA
<213> ORGANISM: Homo sapiens

<400> SEQUENCE: 977
aaaccaucuu auauaaaaca aucaaauaaa u         31

<210> SEQ ID NO 978
<211> LENGTH: 31
<212> TYPE: RNA
<213> ORGANISM: Homo sapiens

<400> SEQUENCE: 978
aaccaucuua uauaaaacaa ucaaauaaau a         31

<210> SEQ ID NO 979
<211> LENGTH: 31
<212> TYPE: RNA
<213> ORGANISM: Homo sapiens

<400> SEQUENCE: 979
caucuuauau aaaacaauca auaaauaca u         31

<210> SEQ ID NO 980
<211> LENGTH: 31
<212> TYPE: RNA
<213> ORGANISM: Homo sapiens

<400> SEQUENCE: 980
aucuuauaua aaacaaucaa auaaauacau a         31

<210> SEQ ID NO 981
<211> LENGTH: 31
<212> TYPE: RNA
<213> ORGANISM: Homo sapiens

<400> SEQUENCE: 981
uauaaaacaa ucaaauaaau acauaaauac a         31

<210> SEQ ID NO 982
<211> LENGTH: 31
<212> TYPE: RNA
<213> ORGANISM: Homo sapiens

<400> SEQUENCE: 982
auaaaacaau caaauaaaua cauaaauaca u         31

<210> SEQ ID NO 983
<211> LENGTH: 31
<212> TYPE: RNA
<213> ORGANISM: Homo sapiens

<400> SEQUENCE: 983
uaaaacaauc aaauaaauac auaaauacau u         31

<210> SEQ ID NO 984
<211> LENGTH: 31

<212> TYPE: RNA
<213> ORGANISM: Homo sapiens

<400> SEQUENCE: 984
aaacaaucaa auaaauacau aaauacauua a        31

<210> SEQ ID NO 985
<211> LENGTH: 31
<212> TYPE: RNA
<213> ORGANISM: Homo sapiens

<400> SEQUENCE: 985
aacaaucaaa uaaauacaua aauacauuaa a        31

<210> SEQ ID NO 986
<211> LENGTH: 31
<212> TYPE: RNA
<213> ORGANISM: Homo sapiens

<400> SEQUENCE: 986
acaaucaaau aaauacauaa auacauuaaa a        31

<210> SEQ ID NO 987
<211> LENGTH: 31
<212> TYPE: RNA
<213> ORGANISM: Homo sapiens

<400> SEQUENCE: 987
aauacauaaa uacauuaaaa aaaugaguca c        31

<210> SEQ ID NO 988
<211> LENGTH: 31
<212> TYPE: RNA
<213> ORGANISM: Homo sapiens

<400> SEQUENCE: 988
uaaauacaua aauacauuaa aaaaaugagu c        31

<210> SEQ ID NO 989
<211> LENGTH: 31
<212> TYPE: RNA
<213> ORGANISM: Homo sapiens

<400> SEQUENCE: 989
aaauacauaa auacauuaaa aaaaugaguc a        31

<210> SEQ ID NO 990
<211> LENGTH: 31
<212> TYPE: RNA
<213> ORGANISM: Homo sapiens

<400> SEQUENCE: 990
auaaauacau aaauacauua aaaaaaugag u        31

<210> SEQ ID NO 991
<211> LENGTH: 31
<212> TYPE: RNA
<213> ORGANISM: Homo sapiens

<400> SEQUENCE: 991
ucuuauauaa aacaaucaaa uaaauacaua a        31

<210> SEQ ID NO 992

-continued

<211> LENGTH: 31
<212> TYPE: RNA
<213> ORGANISM: Homo sapiens

<400> SEQUENCE: 992
cuuauauaaa acaaucaaau aaauacauaa a                                31

<210> SEQ ID NO 993
<211> LENGTH: 31
<212> TYPE: RNA
<213> ORGANISM: Homo sapiens

<400> SEQUENCE: 993
auauaaaaca aucaaauaaa uacauaaaua c                                31

<210> SEQ ID NO 994
<211> LENGTH: 31
<212> TYPE: RNA
<213> ORGANISM: Homo sapiens

<400> SEQUENCE: 994
aaaacaauca aauaaauaca uaaauacauu a                                31

<210> SEQ ID NO 995
<211> LENGTH: 31
<212> TYPE: RNA
<213> ORGANISM: Homo sapiens

<400> SEQUENCE: 995
caaucaaaua aauacauaaa uacauuaaaa a                                31

<210> SEQ ID NO 996
<211> LENGTH: 31
<212> TYPE: RNA
<213> ORGANISM: Homo sapiens

<400> SEQUENCE: 996
uuauauaaaa caaucaaaua aauacauaaa u                                31

<210> SEQ ID NO 997
<211> LENGTH: 31
<212> TYPE: RNA
<213> ORGANISM: Homo sapiens

<400> SEQUENCE: 997
uauauaaaac aaucaaauaa auacauaaau a                                31

<210> SEQ ID NO 998
<211> LENGTH: 31
<212> TYPE: RNA
<213> ORGANISM: Homo sapiens

<400> SEQUENCE: 998
aaucaaauaa auacauaaau acauuaaaaa a                                31

<210> SEQ ID NO 999
<211> LENGTH: 31
<212> TYPE: RNA
<213> ORGANISM: Homo sapiens

<400> SEQUENCE: 999
aucaaauaaa uacauaaaua cauuaaaaaa a                                31

```
<210> SEQ ID NO 1000
<211> LENGTH: 31
<212> TYPE: RNA
<213> ORGANISM: Homo sapiens

<400> SEQUENCE: 1000
ucaaauaaau acauaaauac auuaaaaaaa u            31

<210> SEQ ID NO 1001
<211> LENGTH: 31
<212> TYPE: RNA
<213> ORGANISM: Homo sapiens

<400> SEQUENCE: 1001
caaauaaaua cauaaauaca uuaaaaaaau g            31

<210> SEQ ID NO 1002
<211> LENGTH: 31
<212> TYPE: RNA
<213> ORGANISM: Homo sapiens

<400> SEQUENCE: 1002
aaauaaauac auaaauacau uaaaaaaaug a            31

<210> SEQ ID NO 1003
<211> LENGTH: 31
<212> TYPE: RNA
<213> ORGANISM: Homo sapiens

<400> SEQUENCE: 1003
aauaaauaca uaaauacauu aaaaaaauga g            31

<210> SEQ ID NO 1004
<211> LENGTH: 31
<212> TYPE: RNA
<213> ORGANISM: Mus musculus

<400> SEQUENCE: 1004
ggccucagcg ucuguccgug gugcugaagu u            31

<210> SEQ ID NO 1005
<211> LENGTH: 31
<212> TYPE: RNA
<213> ORGANISM: Mus musculus

<400> SEQUENCE: 1005
gccucagcgu cuguccgugg ugcugaaguu u            31

<210> SEQ ID NO 1006
<211> LENGTH: 31
<212> TYPE: RNA
<213> ORGANISM: Mus musculus

<400> SEQUENCE: 1006
gaugaagaca ggaagcugca gcuccaggag g            31

<210> SEQ ID NO 1007
<211> LENGTH: 31
<212> TYPE: RNA
<213> ORGANISM: Mus musculus

<400> SEQUENCE: 1007
agaugaagac aggaagcugc agcuccagga g            31
```

<210> SEQ ID NO 1008
<211> LENGTH: 31
<212> TYPE: RNA
<213> ORGANISM: Mus musculus

<400> SEQUENCE: 1008
caggccucag cgucuguccg uggugcugaa g                           31

<210> SEQ ID NO 1009
<211> LENGTH: 31
<212> TYPE: RNA
<213> ORGANISM: Mus musculus

<400> SEQUENCE: 1009
aggccucagc gucuguccgu ggugcugaag u                           31

<210> SEQ ID NO 1010
<211> LENGTH: 31
<212> TYPE: RNA
<213> ORGANISM: Mus musculus

<400> SEQUENCE: 1010
ggcaaugcga ccaagcugug ugacacaccg c                           31

<210> SEQ ID NO 1011
<211> LENGTH: 31
<212> TYPE: RNA
<213> ORGANISM: Mus musculus

<400> SEQUENCE: 1011
gcaaugcgac caagcugugu gacacaccgc a                           31

<210> SEQ ID NO 1012
<211> LENGTH: 31
<212> TYPE: RNA
<213> ORGANISM: Mus musculus

<400> SEQUENCE: 1012
augcgaccaa gcugugugac acaccgcaag g                           31

<210> SEQ ID NO 1013
<211> LENGTH: 31
<212> TYPE: RNA
<213> ORGANISM: Mus musculus

<400> SEQUENCE: 1013
caaugcgacc aagcugugug acacaccgca a                           31

<210> SEQ ID NO 1014
<211> LENGTH: 31
<212> TYPE: RNA
<213> ORGANISM: Mus musculus

<400> SEQUENCE: 1014
aaugcgacca agcuguguga cacaccgcaa g                           31

<210> SEQ ID NO 1015
<211> LENGTH: 31
<212> TYPE: RNA
<213> ORGANISM: Mus musculus

<400> SEQUENCE: 1015
gauagaugaa gacaggaagc ugcagcucca g                           31

```
<210> SEQ ID NO 1016
<211> LENGTH: 31
<212> TYPE: RNA
<213> ORGANISM: Mus musculus

<400> SEQUENCE: 1016
auagaugaag acaggaagcu gcagcuccag g                              31

<210> SEQ ID NO 1017
<211> LENGTH: 31
<212> TYPE: RNA
<213> ORGANISM: Mus musculus

<400> SEQUENCE: 1017
uagaugaaga caggaagcug cagcuccagg a                              31

<210> SEQ ID NO 1018
<211> LENGTH: 31
<212> TYPE: RNA
<213> ORGANISM: Mus musculus

<400> SEQUENCE: 1018
gaucgugaua gaugaagaca ggaagcugca g                              31

<210> SEQ ID NO 1019
<211> LENGTH: 31
<212> TYPE: RNA
<213> ORGANISM: Mus musculus

<400> SEQUENCE: 1019
aucgaucgug auagaugaag acaggaagcu g                              31

<210> SEQ ID NO 1020
<211> LENGTH: 31
<212> TYPE: RNA
<213> ORGANISM: Mus musculus

<400> SEQUENCE: 1020
aacaucgauc gugauagaug aagacaggaa g                              31

<210> SEQ ID NO 1021
<211> LENGTH: 31
<212> TYPE: RNA
<213> ORGANISM: Mus musculus

<400> SEQUENCE: 1021
uaacaucgau cgugauagau gaagacagga a                              31

<210> SEQ ID NO 1022
<211> LENGTH: 31
<212> TYPE: RNA
<213> ORGANISM: Mus musculus

<400> SEQUENCE: 1022
ucaccaccuc ucaguggcaa ugcgaccaag c                              31

<210> SEQ ID NO 1023
<211> LENGTH: 31
<212> TYPE: RNA
<213> ORGANISM: Mus musculus

<400> SEQUENCE: 1023
```

-continued caccaccucu caguggcaau gcgaccaagc u                31

<210> SEQ ID NO 1024
<211> LENGTH: 31
<212> TYPE: RNA
<213> ORGANISM: Mus musculus

<400> SEQUENCE: 1024
accaccucuc aguggcaaug cgaccaagcu g                31

<210> SEQ ID NO 1025
<211> LENGTH: 31
<212> TYPE: RNA
<213> ORGANISM: Mus musculus

<400> SEQUENCE: 1025
guggcaaugc gaccaagcug ugugacacac c                31

<210> SEQ ID NO 1026
<211> LENGTH: 31
<212> TYPE: RNA
<213> ORGANISM: Mus musculus

<400> SEQUENCE: 1026
uggcaaugcg accaagcugu gugacacacc g                31

<210> SEQ ID NO 1027
<211> LENGTH: 31
<212> TYPE: RNA
<213> ORGANISM: Mus musculus

<400> SEQUENCE: 1027
caguggcaau gcgaccaagc ugugugacac a                31

<210> SEQ ID NO 1028
<211> LENGTH: 31
<212> TYPE: RNA
<213> ORGANISM: Mus musculus

<400> SEQUENCE: 1028
aguggcaaug cgaccaagcu gugugacaca c                31

<210> SEQ ID NO 1029
<211> LENGTH: 31
<212> TYPE: RNA
<213> ORGANISM: Mus musculus

<400> SEQUENCE: 1029
cgugauagau gaagacagga agcugcagcu c                31

<210> SEQ ID NO 1030
<211> LENGTH: 31
<212> TYPE: RNA
<213> ORGANISM: Mus musculus

<400> SEQUENCE: 1030
gugauagaug aagacaggaa gcugcagcuc c                31

<210> SEQ ID NO 1031
<211> LENGTH: 31
<212> TYPE: RNA
<213> ORGANISM: Mus musculus

<400> SEQUENCE: 1031
auucaccacc ucucaguggc aaugcgacca a    31

<210> SEQ ID NO 1032
<211> LENGTH: 31
<212> TYPE: RNA
<213> ORGANISM: Mus musculus

<400> SEQUENCE: 1032
ucgaucguga uagaugaaga caggaagcug c    31

<210> SEQ ID NO 1033
<211> LENGTH: 31
<212> TYPE: RNA
<213> ORGANISM: Mus musculus

<400> SEQUENCE: 1033
cgaucgugau agaugaagac aggaagcugc a    31

<210> SEQ ID NO 1034
<211> LENGTH: 31
<212> TYPE: RNA
<213> ORGANISM: Mus musculus

<400> SEQUENCE: 1034
aucgugauag augaagacag gaagcugcag c    31

<210> SEQ ID NO 1035
<211> LENGTH: 31
<212> TYPE: RNA
<213> ORGANISM: Mus musculus

<400> SEQUENCE: 1035
ucgugauaga ugaagacagg aagcugcagc u    31

<210> SEQ ID NO 1036
<211> LENGTH: 31
<212> TYPE: RNA
<213> ORGANISM: Mus musculus

<400> SEQUENCE: 1036
ugauagauga agacaggaag cugcagcucc a    31

<210> SEQ ID NO 1037
<211> LENGTH: 31
<212> TYPE: RNA
<213> ORGANISM: Mus musculus

<400> SEQUENCE: 1037
acaucgaucg ugauagauga agacaggaag c    31

<210> SEQ ID NO 1038
<211> LENGTH: 31
<212> TYPE: RNA
<213> ORGANISM: Mus musculus

<400> SEQUENCE: 1038
caucgaucgu gauagaugaa gacaggaagc u    31

<210> SEQ ID NO 1039
<211> LENGTH: 31
<212> TYPE: RNA
<213> ORGANISM: Mus musculus

<400> SEQUENCE: 1039
ccaccucuca guggcaaugc gaccaagcug u     31

<210> SEQ ID NO 1040
<211> LENGTH: 31
<212> TYPE: RNA
<213> ORGANISM: Mus musculus

<400> SEQUENCE: 1040
caccucucag uggcaaugcg accaagcugu g     31

<210> SEQ ID NO 1041
<211> LENGTH: 31
<212> TYPE: RNA
<213> ORGANISM: Mus musculus

<400> SEQUENCE: 1041
ccucucagug gcaaugcgac caagcugugu g     31

<210> SEQ ID NO 1042
<211> LENGTH: 31
<212> TYPE: RNA
<213> ORGANISM: Mus musculus

<400> SEQUENCE: 1042
uucaccaccu cucaguggca augcgaccaa g     31

<210> SEQ ID NO 1043
<211> LENGTH: 31
<212> TYPE: RNA
<213> ORGANISM: Mus musculus

<400> SEQUENCE: 1043
cucaguggca augcgaccaa gcugugugac a     31

<210> SEQ ID NO 1044
<211> LENGTH: 31
<212> TYPE: RNA
<213> ORGANISM: Mus musculus

<400> SEQUENCE: 1044
ucaguggcaa ugcgaccaag cugugugaca c     31

<210> SEQ ID NO 1045
<211> LENGTH: 31
<212> TYPE: RNA
<213> ORGANISM: Mus musculus

<400> SEQUENCE: 1045
accucucagu ggcaaugcga ccaagcugug u     31

<210> SEQ ID NO 1046
<211> LENGTH: 31
<212> TYPE: RNA
<213> ORGANISM: Mus musculus

<400> SEQUENCE: 1046
cucucagugg caaugcgacc aagcugugug a     31

<210> SEQ ID NO 1047
<211> LENGTH: 31
<212> TYPE: RNA
<213> ORGANISM: Mus musculus

```
<400> SEQUENCE: 1047
ucucaguggc aaugcgacca agcuguguga c                              31

<210> SEQ ID NO 1048
<211> LENGTH: 31
<212> TYPE: RNA
<213> ORGANISM: Mus musculus

<400> SEQUENCE: 1048
uaaggccuca cuaaaccacu caucuacacu u                              31

<210> SEQ ID NO 1049
<211> LENGTH: 31
<212> TYPE: RNA
<213> ORGANISM: Mus musculus

<400> SEQUENCE: 1049
aaggccucac uaaaccacuc aucuacacuu a                              31

<210> SEQ ID NO 1050
<211> LENGTH: 31
<212> TYPE: RNA
<213> ORGANISM: Mus musculus

<400> SEQUENCE: 1050
aaaccacuca ucuacacuua acaucgaucg u                              31

<210> SEQ ID NO 1051
<211> LENGTH: 31
<212> TYPE: RNA
<213> ORGANISM: Mus musculus

<400> SEQUENCE: 1051
gcgaccaagc ugugugacac accgcaaggg c                              31

<210> SEQ ID NO 1052
<211> LENGTH: 31
<212> TYPE: RNA
<213> ORGANISM: Mus musculus

<400> SEQUENCE: 1052
augaagacag gaagcugcag cuccaggagg g                              31

<210> SEQ ID NO 1053
<211> LENGTH: 31
<212> TYPE: RNA
<213> ORGANISM: Mus musculus

<400> SEQUENCE: 1053
gaagacagga agcugcagcu ccaggagggu a                              31

<210> SEQ ID NO 1054
<211> LENGTH: 31
<212> TYPE: RNA
<213> ORGANISM: Mus musculus

<400> SEQUENCE: 1054
gcgucugucc guggugcuga aguuuauucg g                              31

<210> SEQ ID NO 1055
<211> LENGTH: 31
<212> TYPE: RNA
```

```
<213> ORGANISM: Mus musculus

<400> SEQUENCE: 1055
guaaggccuc acuaaaccac ucaucuacac u                               31

<210> SEQ ID NO 1056
<211> LENGTH: 31
<212> TYPE: RNA
<213> ORGANISM: Mus musculus

<400> SEQUENCE: 1056
aaccacucau cuacacuuaa caucgaucgu g                               31

<210> SEQ ID NO 1057
<211> LENGTH: 31
<212> TYPE: RNA
<213> ORGANISM: Mus musculus

<400> SEQUENCE: 1057
accacucauc uacacuuaac aucgaucgug a                               31

<210> SEQ ID NO 1058
<211> LENGTH: 31
<212> TYPE: RNA
<213> ORGANISM: Mus musculus

<400> SEQUENCE: 1058
ccacucaucu acacuuaaca ucgaucguga u                               31

<210> SEQ ID NO 1059
<211> LENGTH: 31
<212> TYPE: RNA
<213> ORGANISM: Mus musculus

<400> SEQUENCE: 1059
cacucaucua cacuuaacau cgaucgugau a                               31

<210> SEQ ID NO 1060
<211> LENGTH: 31
<212> TYPE: RNA
<213> ORGANISM: Mus musculus

<400> SEQUENCE: 1060
ugcgaccaag cugugugaca caccgcaagg g                               31

<210> SEQ ID NO 1061
<211> LENGTH: 31
<212> TYPE: RNA
<213> ORGANISM: Mus musculus

<400> SEQUENCE: 1061
cgaccaagcu gugugacaca ccgcaagggc u                               31

<210> SEQ ID NO 1062
<211> LENGTH: 31
<212> TYPE: RNA
<213> ORGANISM: Mus musculus

<400> SEQUENCE: 1062
ugaagacagg aagcugcagc uccaggaggg u                               31

<210> SEQ ID NO 1063
<211> LENGTH: 31
```

<212> TYPE: RNA
<213> ORGANISM: Mus musculus

<400> SEQUENCE: 1063
ccucagcguc uguccguggu gcugaaguuu a                                   31

<210> SEQ ID NO 1064
<211> LENGTH: 31
<212> TYPE: RNA
<213> ORGANISM: Mus musculus

<400> SEQUENCE: 1064
aagacaggaa gcugcagcuc caggagggua u                                   31

<210> SEQ ID NO 1065
<211> LENGTH: 31
<212> TYPE: RNA
<213> ORGANISM: Mus musculus

<400> SEQUENCE: 1065
cucagcgucu guccguggug cugaaguuua u                                   31

<210> SEQ ID NO 1066
<211> LENGTH: 31
<212> TYPE: RNA
<213> ORGANISM: Mus musculus

<400> SEQUENCE: 1066
cagcgucugu ccguggugcu gaaguuuauu c                                   31

<210> SEQ ID NO 1067
<211> LENGTH: 31
<212> TYPE: RNA
<213> ORGANISM: Mus musculus

<400> SEQUENCE: 1067
agcgucuguc cguggugcug aaguuuauuc g                                   31

<210> SEQ ID NO 1068
<211> LENGTH: 31
<212> TYPE: RNA
<213> ORGANISM: Mus musculus

<400> SEQUENCE: 1068
cgucuguccg uggugcugaa guuuauucgg a                                   31

<210> SEQ ID NO 1069
<211> LENGTH: 31
<212> TYPE: RNA
<213> ORGANISM: Mus musculus

<400> SEQUENCE: 1069
ucagcgucug uccguggugc ugaaguuuau u                                   31

<210> SEQ ID NO 1070
<211> LENGTH: 31
<212> TYPE: RNA
<213> ORGANISM: Mus musculus

<400> SEQUENCE: 1070
gucuguccgu ggugcugaag uuuauucgga u                                   31

<210> SEQ ID NO 1071

```
<211> LENGTH: 31
<212> TYPE: RNA
<213> ORGANISM: Mus musculus

<400> SEQUENCE: 1071
gguaaggccu cacuaaacca cucaucuaca c                                31

<210> SEQ ID NO 1072
<211> LENGTH: 31
<212> TYPE: RNA
<213> ORGANISM: Mus musculus

<400> SEQUENCE: 1072
ucuguccgug gugcugaagu uuauucggau u                                31

<210> SEQ ID NO 1073
<211> LENGTH: 31
<212> TYPE: RNA
<213> ORGANISM: Mus musculus

<400> SEQUENCE: 1073
agguaaggcc ucacuaaacc acucaucuac a                                31

<210> SEQ ID NO 1074
<211> LENGTH: 31
<212> TYPE: RNA
<213> ORGANISM: Mus musculus

<400> SEQUENCE: 1074
acucaucuac acuuaacauc gaucgugaua g                                31

<210> SEQ ID NO 1075
<211> LENGTH: 31
<212> TYPE: RNA
<213> ORGANISM: Mus musculus

<400> SEQUENCE: 1075
cucaucuaca cuuaacaucg aucgugauag a                                31

<210> SEQ ID NO 1076
<211> LENGTH: 31
<212> TYPE: RNA
<213> ORGANISM: Mus musculus

<400> SEQUENCE: 1076
uuaacaucga ucgugauaga ugaagacagg a                                31

<210> SEQ ID NO 1077
<211> LENGTH: 31
<212> TYPE: RNA
<213> ORGANISM: Mus musculus

<400> SEQUENCE: 1077
ucaucuacac uuaacaucga ucgugauaga u                                31

<210> SEQ ID NO 1078
<211> LENGTH: 31
<212> TYPE: RNA
<213> ORGANISM: Mus musculus

<400> SEQUENCE: 1078
ccaagcugug ugacacaccg caagggcuug g                                31
```

```
<210> SEQ ID NO 1079
<211> LENGTH: 31
<212> TYPE: RNA
<213> ORGANISM: Mus musculus

<400> SEQUENCE: 1079
gaccaagcug ugugacacac cgcaagggcu u                           31

<210> SEQ ID NO 1080
<211> LENGTH: 31
<212> TYPE: RNA
<213> ORGANISM: Mus musculus

<400> SEQUENCE: 1080
accaagcugu gugacacacc gcaagggcuu g                           31

<210> SEQ ID NO 1081
<211> LENGTH: 31
<212> TYPE: RNA
<213> ORGANISM: Mus musculus

<400> SEQUENCE: 1081
uaugcagagu gggagaggua aggccucacu a                           31

<210> SEQ ID NO 1082
<211> LENGTH: 31
<212> TYPE: RNA
<213> ORGANISM: Mus musculus

<400> SEQUENCE: 1082
augcagagug ggagagguaa ggccucacua a                           31

<210> SEQ ID NO 1083
<211> LENGTH: 31
<212> TYPE: RNA
<213> ORGANISM: Mus musculus

<400> SEQUENCE: 1083
ggagagguaa ggccucacua aaccacucau c                           31

<210> SEQ ID NO 1084
<211> LENGTH: 31
<212> TYPE: RNA
<213> ORGANISM: Mus musculus

<400> SEQUENCE: 1084
uauucaccac cucucagugg caaugcgacc a                           31

<210> SEQ ID NO 1085
<211> LENGTH: 31
<212> TYPE: RNA
<213> ORGANISM: Mus musculus

<400> SEQUENCE: 1085
gagguaaggc cucacuaaac cacucaucua c                           31

<210> SEQ ID NO 1086
<211> LENGTH: 31
<212> TYPE: RNA
<213> ORGANISM: Mus musculus

<400> SEQUENCE: 1086
uuuccaacug cuuucugaaa ggggugagga u                           31
```

```
<210> SEQ ID NO 1087
<211> LENGTH: 31
<212> TYPE: RNA
<213> ORGANISM: Mus musculus

<400> SEQUENCE: 1087
ugcuuucuga aagggguagag gaucuaccuu a                                        31

<210> SEQ ID NO 1088
<211> LENGTH: 31
<212> TYPE: RNA
<213> ORGANISM: Mus musculus

<400> SEQUENCE: 1088
agagguaagg ccucacuaaa ccacucaucu a                                         31

<210> SEQ ID NO 1089
<211> LENGTH: 31
<212> TYPE: RNA
<213> ORGANISM: Mus musculus

<400> SEQUENCE: 1089
cuuaacaucg aucgugauag augaagacag g                                         31

<210> SEQ ID NO 1090
<211> LENGTH: 31
<212> TYPE: RNA
<213> ORGANISM: Mus musculus

<400> SEQUENCE: 1090
caucuacacu uaacaucgau cgugauagau g                                         31

<210> SEQ ID NO 1091
<211> LENGTH: 31
<212> TYPE: RNA
<213> ORGANISM: Mus musculus

<400> SEQUENCE: 1091
acuuaacauc gaucgugaua gaugaagaca g                                         31

<210> SEQ ID NO 1092
<211> LENGTH: 31
<212> TYPE: RNA
<213> ORGANISM: Mus musculus

<400> SEQUENCE: 1092
aucuacacuu aacaucgauc gugauagaug a                                         31

<210> SEQ ID NO 1093
<211> LENGTH: 31
<212> TYPE: RNA
<213> ORGANISM: Mus musculus

<400> SEQUENCE: 1093
ucuacacuua acaucgaucg ugauagauga a                                         31

<210> SEQ ID NO 1094
<211> LENGTH: 31
<212> TYPE: RNA
<213> ORGANISM: Mus musculus

<400> SEQUENCE: 1094
uacacuuaac aucgaucgug auagaugaag a                                         31
```

<210> SEQ ID NO 1095
<211> LENGTH: 31
<212> TYPE: RNA
<213> ORGANISM: Mus musculus

<400> SEQUENCE: 1095
guauucacca ccucucagug gcaaugcgac c                                    31

<210> SEQ ID NO 1096
<211> LENGTH: 31
<212> TYPE: RNA
<213> ORGANISM: Mus musculus

<400> SEQUENCE: 1096
uuccaacugc uuucugaaag gggugaggau c                                    31

<210> SEQ ID NO 1097
<211> LENGTH: 31
<212> TYPE: RNA
<213> ORGANISM: Mus musculus

<400> SEQUENCE: 1097
uccaacugcu uucugaaagg ggugaggauc u                                    31

<210> SEQ ID NO 1098
<211> LENGTH: 31
<212> TYPE: RNA
<213> ORGANISM: Mus musculus

<400> SEQUENCE: 1098
ccaacugcuu ucugaaaggg gugaggaucu a                                    31

<210> SEQ ID NO 1099
<211> LENGTH: 31
<212> TYPE: RNA
<213> ORGANISM: Mus musculus

<400> SEQUENCE: 1099
caacugcuuu cugaaagggg ugaggaucua c                                    31

<210> SEQ ID NO 1100
<211> LENGTH: 31
<212> TYPE: RNA
<213> ORGANISM: Mus musculus

<400> SEQUENCE: 1100
aacugcuuuc ugaaaggggu gaggaucuac c                                    31

<210> SEQ ID NO 1101
<211> LENGTH: 31
<212> TYPE: RNA
<213> ORGANISM: Mus musculus

<400> SEQUENCE: 1101
acugcuuucu gaaaggggug aggaucuacc u                                    31

<210> SEQ ID NO 1102
<211> LENGTH: 31
<212> TYPE: RNA
<213> ORGANISM: Mus musculus

<400> SEQUENCE: 1102
cugcuuucug aaaggggvga ggaucuaccu u                                31

<210> SEQ ID NO 1103
<211> LENGTH: 31
<212> TYPE: RNA
<213> ORGANISM: Mus musculus

<400> SEQUENCE: 1103
gagagguaag gccucacuaa accacucauc u                                31

<210> SEQ ID NO 1104
<211> LENGTH: 31
<212> TYPE: RNA
<213> ORGANISM: Mus musculus

<400> SEQUENCE: 1104
cuacacuuaa caucgaucgu gauagaugaa g                                31

<210> SEQ ID NO 1105
<211> LENGTH: 31
<212> TYPE: RNA
<213> ORGANISM: Mus musculus

<400> SEQUENCE: 1105
acacuuaaca ucgaucguga uagaugaaga c                                31

<210> SEQ ID NO 1106
<211> LENGTH: 31
<212> TYPE: RNA
<213> ORGANISM: Mus musculus

<400> SEQUENCE: 1106
cacuuaacau cgaucgugau agaugaagac a                                31

<210> SEQ ID NO 1107
<211> LENGTH: 31
<212> TYPE: RNA
<213> ORGANISM: Mus musculus

<400> SEQUENCE: 1107
gguauucacc accucucagu ggcaaugcga c                                31

<210> SEQ ID NO 1108
<211> LENGTH: 31
<212> TYPE: RNA
<213> ORGANISM: Mus musculus

<400> SEQUENCE: 1108
ccucacuaaa ccacucaucu acacuuaaca u                                31

<210> SEQ ID NO 1109
<211> LENGTH: 31
<212> TYPE: RNA
<213> ORGANISM: Mus musculus

<400> SEQUENCE: 1109
cucacuaaac cacucaucua cacuuaacau c                                31

<210> SEQ ID NO 1110
<211> LENGTH: 31
<212> TYPE: RNA
<213> ORGANISM: Mus musculus

<400> SEQUENCE: 1110
gccucacuaa accacucauc uacacuuaac a             31

<210> SEQ ID NO 1111
<211> LENGTH: 31
<212> TYPE: RNA
<213> ORGANISM: Mus musculus

<400> SEQUENCE: 1111
ucacuaaacc acucaucuac acuuaacauc g             31

<210> SEQ ID NO 1112
<211> LENGTH: 31
<212> TYPE: RNA
<213> ORGANISM: Mus musculus

<400> SEQUENCE: 1112
cacuaaacca cucaucuaca cuuaacaucg a             31

<210> SEQ ID NO 1113
<211> LENGTH: 31
<212> TYPE: RNA
<213> ORGANISM: Mus musculus

<400> SEQUENCE: 1113
cuaaaccacu caucuacacu uaacaucgau c             31

<210> SEQ ID NO 1114
<211> LENGTH: 31
<212> TYPE: RNA
<213> ORGANISM: Mus musculus

<400> SEQUENCE: 1114
acuaaaccac ucaucuacac uuaacaucga u             31

<210> SEQ ID NO 1115
<211> LENGTH: 31
<212> TYPE: RNA
<213> ORGANISM: Mus musculus

<400> SEQUENCE: 1115
ggccucacua aaccacucau cuacacuuaa c             31

<210> SEQ ID NO 1116
<211> LENGTH: 31
<212> TYPE: RNA
<213> ORGANISM: Mus musculus

<400> SEQUENCE: 1116
aggccucacu aaaccacuca ucuacacuua a             31

<210> SEQ ID NO 1117
<211> LENGTH: 31
<212> TYPE: RNA
<213> ORGANISM: Mus musculus

<400> SEQUENCE: 1117
uaaaccacuc aucuacacuu aacaucgauc g             31

<210> SEQ ID NO 1118
<211> LENGTH: 31
<212> TYPE: RNA
<213> ORGANISM: Mus musculus

```
<400> SEQUENCE: 1118
uaccuuaaua ugcagagugg gagagguaag g                                31

<210> SEQ ID NO 1119
<211> LENGTH: 31
<212> TYPE: RNA
<213> ORGANISM: Mus musculus

<400> SEQUENCE: 1119 gcagagiguggg agagguaagg ccucacuaaa c                              31

<210> SEQ ID NO 1120
<211> LENGTH: 31
<212> TYPE: RNA
<213> ORGANISM: Mus musculus

<400> SEQUENCE: 1120
cagaguggga gagguaaggc cucacuaaac c                                31

<210> SEQ ID NO 1121
<211> LENGTH: 31
<212> TYPE: RNA
<213> ORGANISM: Mus musculus

<400> SEQUENCE: 1121
gagugggaga gguaaggccu cacuaaacca c                                31

<210> SEQ ID NO 1122
<211> LENGTH: 31
<212> TYPE: RNA
<213> ORGANISM: Mus musculus

<400> SEQUENCE: 1122
ggcuugggau cuuuugcgau cugcucgagc a                                31

<210> SEQ ID NO 1123
<211> LENGTH: 31
<212> TYPE: RNA
<213> ORGANISM: Mus musculus

<400> SEQUENCE: 1123
gcuugggauc uuuugcgauc ugcucgagca g                                31

<210> SEQ ID NO 1124
<211> LENGTH: 31
<212> TYPE: RNA
<213> ORGANISM: Mus musculus

<400> SEQUENCE: 1124
agagugggag agguaaggcc ucacuaaacc a                                31

<210> SEQ ID NO 1125
<211> LENGTH: 31
<212> TYPE: RNA
<213> ORGANISM: Mus musculus

<400> SEQUENCE: 1125
cuuuugcgau cugcucgagc agauuuggcu g                                31

<210> SEQ ID NO 1126
<211> LENGTH: 31
<212> TYPE: RNA
<213> ORGANISM: Mus musculus
```

<400> SEQUENCE: 1126
ggggugagga ucuaccuuaa uaugcagagu g                              31

<210> SEQ ID NO 1127
<211> LENGTH: 31
<212> TYPE: RNA
<213> ORGANISM: Mus musculus

<400> SEQUENCE: 1127
gggugaggau cuaccuuaau augcagagug g                              31

<210> SEQ ID NO 1128
<211> LENGTH: 31
<212> TYPE: RNA
<213> ORGANISM: Mus musculus

<400> SEQUENCE: 1128
ggugaggauc uaccuuaaua ugcagagugg g                              31

<210> SEQ ID NO 1129
<211> LENGTH: 31
<212> TYPE: RNA
<213> ORGANISM: Mus musculus

<400> SEQUENCE: 1129
ggaucuaccu uaauaugcag agugggagag g                              31

<210> SEQ ID NO 1130
<211> LENGTH: 31
<212> TYPE: RNA
<213> ORGANISM: Mus musculus

<400> SEQUENCE: 1130
accuuaauau gcagaguggg agagguaagg c                              31

<210> SEQ ID NO 1131
<211> LENGTH: 31
<212> TYPE: RNA
<213> ORGANISM: Mus musculus

<400> SEQUENCE: 1131
cuuaauaugc agagugggag agguaaggcc u                              31

<210> SEQ ID NO 1132
<211> LENGTH: 31
<212> TYPE: RNA
<213> ORGANISM: Mus musculus

<400> SEQUENCE: 1132
uuaauaugca gagugggaga gguaaggccu c                              31

<210> SEQ ID NO 1133
<211> LENGTH: 31
<212> TYPE: RNA
<213> ORGANISM: Mus musculus

<400> SEQUENCE: 1133
uaauaugcag agugggagag guaaggccuc a                              31

<210> SEQ ID NO 1134
<211> LENGTH: 31
<212> TYPE: RNA

```
<213> ORGANISM: Mus musculus

<400> SEQUENCE: 1134
ucuuuugcga ucugcucgag cagauuuggc u                           31

<210> SEQ ID NO 1135
<211> LENGTH: 31
<212> TYPE: RNA
<213> ORGANISM: Mus musculus

<400> SEQUENCE: 1135
cuguccgugg ugcugaaguu uauucggauu u                           31

<210> SEQ ID NO 1136
<211> LENGTH: 31
<212> TYPE: RNA
<213> ORGANISM: Mus musculus

<400> SEQUENCE: 1136 gaaagggugug aggaucuacc uuaauaugca g                          31

<210> SEQ ID NO 1137
<211> LENGTH: 31
<212> TYPE: RNA
<213> ORGANISM: Mus musculus

<400> SEQUENCE: 1137
aaggggugag gaucuaccuu aauaugcaga g                           31

<210> SEQ ID NO 1138
<211> LENGTH: 31
<212> TYPE: RNA
<213> ORGANISM: Mus musculus

<400> SEQUENCE: 1138
aggggugagg aucuaccuua auaugcagag u                           31

<210> SEQ ID NO 1139
<211> LENGTH: 31
<212> TYPE: RNA
<213> ORGANISM: Mus musculus

<400> SEQUENCE: 1139
gugaggaucu accuuaauau gcagaguggg a                           31

<210> SEQ ID NO 1140
<211> LENGTH: 31
<212> TYPE: RNA
<213> ORGANISM: Mus musculus

<400> SEQUENCE: 1140
ugaggaucua ccuuaauaug cagaguggga g                           31

<210> SEQ ID NO 1141
<211> LENGTH: 31
<212> TYPE: RNA
<213> ORGANISM: Mus musculus

<400> SEQUENCE: 1141
gaggaucuac cuuaauaugc agagugggag a                           31

<210> SEQ ID NO 1142
<211> LENGTH: 31
```

```
<212> TYPE: RNA
<213> ORGANISM: Mus musculus

<400> SEQUENCE: 1142
aggaucuacc uuaauaugca gagugggaga g                               31

<210> SEQ ID NO 1143
<211> LENGTH: 31
<212> TYPE: RNA
<213> ORGANISM: Mus musculus

<400> SEQUENCE: 1143
gaucuaccuu aauaugcaga gugggagagg u                               31

<210> SEQ ID NO 1144
<211> LENGTH: 31
<212> TYPE: RNA
<213> ORGANISM: Mus musculus

<400> SEQUENCE: 1144
cuaccuuaau augcagagug ggagagguaa g                               31

<210> SEQ ID NO 1145
<211> LENGTH: 31
<212> TYPE: RNA
<213> ORGANISM: Mus musculus

<400> SEQUENCE: 1145
uguccguggu gcugaaguuu auucggauuu a                               31

<210> SEQ ID NO 1146
<211> LENGTH: 31
<212> TYPE: RNA
<213> ORGANISM: Mus musculus

<400> SEQUENCE: 1146
guccguggug cugaaguuua uucggauuua u                               31

<210> SEQ ID NO 1147
<211> LENGTH: 31
<212> TYPE: RNA
<213> ORGANISM: Mus musculus

<400> SEQUENCE: 1147
ucugaaaggg gugaggaucu accuuaauau g                               31

<210> SEQ ID NO 1148
<211> LENGTH: 31
<212> TYPE: RNA
<213> ORGANISM: Mus musculus

<400> SEQUENCE: 1148
ugaaaggggu gaggaucuac cuuaauaugc a                               31

<210> SEQ ID NO 1149
<211> LENGTH: 31
<212> TYPE: RNA
<213> ORGANISM: Mus musculus

<400> SEQUENCE: 1149
aaagggguga ggaucuaccu uaauaugcag a                               31

<210> SEQ ID NO 1150
```

```
<211> LENGTH: 31
<212> TYPE: RNA
<213> ORGANISM: Mus musculus

<400> SEQUENCE: 1150
aucuaccuua auaugcagag ugggagaggu a                              31

<210> SEQ ID NO 1151
<211> LENGTH: 31
<212> TYPE: RNA
<213> ORGANISM: Mus musculus

<400> SEQUENCE: 1151
ucuaccuuaa uaugcagagu gggagaggua a                              31

<210> SEQ ID NO 1152
<211> LENGTH: 31
<212> TYPE: RNA
<213> ORGANISM: Mus musculus

<400> SEQUENCE: 1152 uccgugugc ugaaguuuau ucggauuuau u                               31

<210> SEQ ID NO 1153
<211> LENGTH: 31
<212> TYPE: RNA
<213> ORGANISM: Mus musculus

<400> SEQUENCE: 1153
uuucugaaag gggugaggau cuaccuuaau a                              31

<210> SEQ ID NO 1154
<211> LENGTH: 31
<212> TYPE: RNA
<213> ORGANISM: Mus musculus

<400> SEQUENCE: 1154
uucugaaagg ggugaggauc uaccuuaaua u                              31

<210> SEQ ID NO 1155
<211> LENGTH: 31
<212> TYPE: RNA
<213> ORGANISM: Mus musculus

<400> SEQUENCE: 1155
caagcugugu gacacaccgc aagggcuugg g                              31

<210> SEQ ID NO 1156
<211> LENGTH: 31
<212> TYPE: RNA
<213> ORGANISM: Mus musculus

<400> SEQUENCE: 1156
gacaggaagc ugcagcucca ggaggguauu c                              31

<210> SEQ ID NO 1157
<211> LENGTH: 31
<212> TYPE: RNA
<213> ORGANISM: Mus musculus

<400> SEQUENCE: 1157
caggaagcug cagcuccagg aggguauuca c                              31
```

```
<210> SEQ ID NO 1158
<211> LENGTH: 31
<212> TYPE: RNA
<213> ORGANISM: Mus musculus

<400> SEQUENCE: 1158
aggaagcugc agcuccagga ggguauucac c                              31

<210> SEQ ID NO 1159
<211> LENGTH: 31
<212> TYPE: RNA
<213> ORGANISM: Mus musculus

<400> SEQUENCE: 1159
ggaagcugca gcuccaggag gguauucacc a                              31

<210> SEQ ID NO 1160
<211> LENGTH: 31
<212> TYPE: RNA
<213> ORGANISM: Mus musculus

<400> SEQUENCE: 1160
gaagcugcag cuccaggagg guauucacca c                              31

<210> SEQ ID NO 1161
<211> LENGTH: 31
<212> TYPE: RNA
<213> ORGANISM: Mus musculus

<400> SEQUENCE: 1161
aagcugcagc uccaggaggg uauucaccac c                              31

<210> SEQ ID NO 1162
<211> LENGTH: 31
<212> TYPE: RNA
<213> ORGANISM: Mus musculus

<400> SEQUENCE: 1162
aagcugugug acacaccgca agggcuuggg a                              31

<210> SEQ ID NO 1163
<211> LENGTH: 31
<212> TYPE: RNA
<213> ORGANISM: Mus musculus

<400> SEQUENCE: 1163
gugggagagg uaaggccuca cuaaaccacu c                              31

<210> SEQ ID NO 1164
<211> LENGTH: 31
<212> TYPE: RNA
<213> ORGANISM: Mus musculus

<400> SEQUENCE: 1164
agacaggaag cugcagcucc aggaggguau u                              31

<210> SEQ ID NO 1165
<211> LENGTH: 31
<212> TYPE: RNA
<213> ORGANISM: Mus musculus

<400> SEQUENCE: 1165
acaggaagcu gcagcuccag gaggguauuc a                              31
```

<210> SEQ ID NO 1166
<211> LENGTH: 31
<212> TYPE: RNA
<213> ORGANISM: Mus musculus

<400> SEQUENCE: 1166
ccuuaauaug cagaguggga gagguaaggc c                                    31

<210> SEQ ID NO 1167
<211> LENGTH: 31
<212> TYPE: RNA
<213> ORGANISM: Mus musculus

<400> SEQUENCE: 1167
aauaugcaga gugggagagg uaaggccuca c                                    31

<210> SEQ ID NO 1168
<211> LENGTH: 31
<212> TYPE: RNA
<213> ORGANISM: Mus musculus

<400> SEQUENCE: 1168
auaugcagag ugggagaggu aaggccucac u                                    31

<210> SEQ ID NO 1169
<211> LENGTH: 31
<212> TYPE: RNA
<213> ORGANISM: Mus musculus

<400> SEQUENCE: 1169
ugcagagugg gagagguaag gccucacuaa a                                    31

<210> SEQ ID NO 1170
<211> LENGTH: 31
<212> TYPE: RNA
<213> ORGANISM: Mus musculus

<400> SEQUENCE: 1170
agugggagag guaaggccuc acuaaaccac u                                    31

<210> SEQ ID NO 1171
<211> LENGTH: 31
<212> TYPE: RNA
<213> ORGANISM: Mus musculus

<400> SEQUENCE: 1171
ugggagaggu aaggccucac uaaaccacuc a                                    31

<210> SEQ ID NO 1172
<211> LENGTH: 31
<212> TYPE: RNA
<213> ORGANISM: Mus musculus

<400> SEQUENCE: 1172
gggagaggua aggccucacu aaaccacuca u                                    31

<210> SEQ ID NO 1173
<211> LENGTH: 31
<212> TYPE: RNA
<213> ORGANISM: Mus musculus

<400> SEQUENCE: 1173
cuugggaucu uuugcgaucu gcucgagcag a                                    31

<210> SEQ ID NO 1174
<211> LENGTH: 31
<212> TYPE: RNA
<213> ORGANISM: Mus musculus

<400> SEQUENCE: 1174
uugggaucuu uugcgaucug cucgagcaga u                                        31

<210> SEQ ID NO 1175
<211> LENGTH: 31
<212> TYPE: RNA
<213> ORGANISM: Mus musculus

<400> SEQUENCE: 1175
ugggaucuuu ugcgaucugc ucgagcagau u                                        31

<210> SEQ ID NO 1176
<211> LENGTH: 31
<212> TYPE: RNA
<213> ORGANISM: Mus musculus

<400> SEQUENCE: 1176
ggaucuuuug cgaucugcuc gagcagauuu g                                        31

<210> SEQ ID NO 1177
<211> LENGTH: 31
<212> TYPE: RNA
<213> ORGANISM: Mus musculus

<400> SEQUENCE: 1177
gaucuuuugc gaucugcucg agcagauuug g                                        31

<210> SEQ ID NO 1178
<211> LENGTH: 31
<212> TYPE: RNA
<213> ORGANISM: Mus musculus

<400> SEQUENCE: 1178
aucuuuugcg aucugcucga gcagauuugg c                                        31

<210> SEQ ID NO 1179
<211> LENGTH: 31
<212> TYPE: RNA
<213> ORGANISM: Mus musculus

<400> SEQUENCE: 1179
uuuuuccaac ugcuuucuga aaggggugag g                                        31

<210> SEQ ID NO 1180
<211> LENGTH: 31
<212> TYPE: RNA
<213> ORGANISM: Mus musculus

<400> SEQUENCE: 1180
uuuuccaacu gcuuucugaa aggggugagg a                                        31

<210> SEQ ID NO 1181
<211> LENGTH: 31
<212> TYPE: RNA
<213> ORGANISM: Mus musculus

<400> SEQUENCE: 1181
gcuuucugaa aggggugagg aucuaccuua a                                         31

<210> SEQ ID NO 1182
<211> LENGTH: 31
<212> TYPE: RNA
<213> ORGANISM: Mus musculus

<400> SEQUENCE: 1182
cugaaagggg ugaggaucua ccuuaauaug c                                        31

<210> SEQ ID NO 1183
<211> LENGTH: 31
<212> TYPE: RNA
<213> ORGANISM: Mus musculus

<400> SEQUENCE: 1183
uuuuuuccaa cugcuuucug aaagggguga g                                        31

<210> SEQ ID NO 1184
<211> LENGTH: 31
<212> TYPE: RNA
<213> ORGANISM: Mus musculus

<400> SEQUENCE: 1184
cuuucugaaa ggggugagga ucuaccuuaa u                                        31

<210> SEQ ID NO 1185
<211> LENGTH: 31
<212> TYPE: RNA
<213> ORGANISM: Mus musculus

<400> SEQUENCE: 1185
uuuuuuccca acugcuuucu gaaagggug a                                         31

<210> SEQ ID NO 1186
<211> LENGTH: 31
<212> TYPE: RNA
<213> ORGANISM: Mus musculus

<400> SEQUENCE: 1186
gcugcagcuc caggagggua uucaccaccu c                                        31

<210> SEQ ID NO 1187
<211> LENGTH: 31
<212> TYPE: RNA
<213> ORGANISM: Mus musculus

<400> SEQUENCE: 1187
gcugugugac acaccgcaag ggcuugggau c                                        31

<210> SEQ ID NO 1188
<211> LENGTH: 31
<212> TYPE: RNA
<213> ORGANISM: Mus musculus

<400> SEQUENCE: 1188
agcugcagcu ccaggagggu auucaccacc u                                        31

<210> SEQ ID NO 1189
<211> LENGTH: 31
<212> TYPE: RNA
<213> ORGANISM: Mus musculus

<400> SEQUENCE: 1189

-continued cugcagcucc aggaggguau ucaccaccuc u    31

<210> SEQ ID NO 1190
<211> LENGTH: 31
<212> TYPE: RNA
<213> ORGANISM: Mus musculus

<400> SEQUENCE: 1190
ugcagcucca ggaggguauu caccaccucu c    31

<210> SEQ ID NO 1191
<211> LENGTH: 31
<212> TYPE: RNA
<213> ORGANISM: Mus musculus

<400> SEQUENCE: 1191
gcagcuccag gaggguauuc accaccucuc a    31

<210> SEQ ID NO 1192
<211> LENGTH: 31
<212> TYPE: RNA
<213> ORGANISM: Mus musculus

<400> SEQUENCE: 1192
cagcuccagg aggguauuca ccaccucuca g    31

<210> SEQ ID NO 1193
<211> LENGTH: 31
<212> TYPE: RNA
<213> ORGANISM: Mus musculus

<400> SEQUENCE: 1193
gcuccaggag gguauucacc accucucagu g    31

<210> SEQ ID NO 1194
<211> LENGTH: 31
<212> TYPE: RNA
<213> ORGANISM: Mus musculus

<400> SEQUENCE: 1194
cuccaggagg guauucacca ccucucagug g    31

<210> SEQ ID NO 1195
<211> LENGTH: 31
<212> TYPE: RNA
<213> ORGANISM: Mus musculus

<400> SEQUENCE: 1195
uccaggaggg uauucaccac cucucagugg c    31

<210> SEQ ID NO 1196
<211> LENGTH: 31
<212> TYPE: RNA
<213> ORGANISM: Mus musculus

<400> SEQUENCE: 1196
ccaggagggu auucaccacc ucucaguggc a    31

<210> SEQ ID NO 1197
<211> LENGTH: 31
<212> TYPE: RNA
<213> ORGANISM: Mus musculus

```
<400> SEQUENCE: 1197
agcuguguga cacaccgcaa gggcuuggga u                                31

<210> SEQ ID NO 1198
<211> LENGTH: 31
<212> TYPE: RNA
<213> ORGANISM: Mus musculus

<400> SEQUENCE: 1198
cugugugaca caccgcaagg gcuugggauc u                                31

<210> SEQ ID NO 1199
<211> LENGTH: 31
<212> TYPE: RNA
<213> ORGANISM: Mus musculus

<400> SEQUENCE: 1199
caggagggua uucaccaccu cucaguggca a                                31

<210> SEQ ID NO 1200
<211> LENGTH: 31
<212> TYPE: RNA
<213> ORGANISM: Mus musculus

<400> SEQUENCE: 1200
ugugugacac accgcaaggg cuugggaucu u                                31

<210> SEQ ID NO 1201
<211> LENGTH: 31
<212> TYPE: RNA
<213> ORGANISM: Mus musculus

<400> SEQUENCE: 1201
gugugacaca ccgcaagggc uugggaucuu u                                31

<210> SEQ ID NO 1202
<211> LENGTH: 31
<212> TYPE: RNA
<213> ORGANISM: Mus musculus

<400> SEQUENCE: 1202
agcuccagga ggguauucac caccucucag u                                31

<210> SEQ ID NO 1203
<211> LENGTH: 31
<212> TYPE: RNA
<213> ORGANISM: Mus musculus

<400> SEQUENCE: 1203
ggaggguauu caccaccucu caguggcaau g                                31

<210> SEQ ID NO 1204
<211> LENGTH: 31
<212> TYPE: RNA
<213> ORGANISM: Mus musculus

<400> SEQUENCE: 1204
gaggguauuc accaccucuc aguggcaaug c                                31

<210> SEQ ID NO 1205
<211> LENGTH: 31
<212> TYPE: RNA
<213> ORGANISM: Mus musculus
```

-continued

<400> SEQUENCE: 1205
aggguauuca ccaccucuca guggcaaugc g    31

<210> SEQ ID NO 1206
<211> LENGTH: 31
<212> TYPE: RNA
<213> ORGANISM: Mus musculus

<400> SEQUENCE: 1206
ggguauucac caccucucag uggcaaugcg a    31

<210> SEQ ID NO 1207
<211> LENGTH: 31
<212> TYPE: RNA
<213> ORGANISM: Mus musculus

<400> SEQUENCE: 1207
aggaggguau ucaccaccuc ucaguggcaa u    31

<210> SEQ ID NO 1208
<211> LENGTH: 31
<212> TYPE: RNA
<213> ORGANISM: Mus musculus

<400> SEQUENCE: 1208
guggugcuga aguuuauucg gauuuauuuu u    31

<210> SEQ ID NO 1209
<211> LENGTH: 31
<212> TYPE: RNA
<213> ORGANISM: Mus musculus

<400> SEQUENCE: 1209
uggugcugaa guuuauucgg auuuauuuuu u    31

<210> SEQ ID NO 1210
<211> LENGTH: 31
<212> TYPE: RNA
<213> ORGANISM: Mus musculus

<400> SEQUENCE: 1210
gggcuuggga ucuuuugcga ucugcucgag c    31

<210> SEQ ID NO 1211
<211> LENGTH: 31
<212> TYPE: RNA
<213> ORGANISM: Mus musculus

<400> SEQUENCE: 1211
cguggugcug aaguuuauuc ggauuuauuu u    31

<210> SEQ ID NO 1212
<211> LENGTH: 31
<212> TYPE: RNA
<213> ORGANISM: Mus musculus

<400> SEQUENCE: 1212
auucggauuu auuuuuuccc aacugcuuuc u    31

<210> SEQ ID NO 1213
<211> LENGTH: 31
<212> TYPE: RNA

```
<213> ORGANISM: Mus musculus

<400> SEQUENCE: 1213
ccgcaagggc uugggaucuu uugcgaucug c                                31

<210> SEQ ID NO 1214
<211> LENGTH: 31
<212> TYPE: RNA
<213> ORGANISM: Mus musculus

<400> SEQUENCE: 1214
cgcaagggcu ugggaucuuu ugcgaucugc u                                31

<210> SEQ ID NO 1215
<211> LENGTH: 31
<212> TYPE: RNA
<213> ORGANISM: Mus musculus

<400> SEQUENCE: 1215
gcaagggcuu gggaucuuuu gcgaucugcu c                                31

<210> SEQ ID NO 1216
<211> LENGTH: 31
<212> TYPE: RNA
<213> ORGANISM: Mus musculus

<400> SEQUENCE: 1216
caagggcuug ggaucuuuug cgaucugcuc g                                31

<210> SEQ ID NO 1217
<211> LENGTH: 31
<212> TYPE: RNA
<213> ORGANISM: Mus musculus

<400> SEQUENCE: 1217
agggcuuggg aucuuuugcg aucugcucga g                                31

<210> SEQ ID NO 1218
<211> LENGTH: 31
<212> TYPE: RNA
<213> ORGANISM: Mus musculus

<400> SEQUENCE: 1218
ccguggugcu gaaguuuauu cggauuuauu u                                31

<210> SEQ ID NO 1219
<211> LENGTH: 31
<212> TYPE: RNA
<213> ORGANISM: Mus musculus

<400> SEQUENCE: 1219
uucggauuua uuuuuuucca acugcuuucu g                                31

<210> SEQ ID NO 1220
<211> LENGTH: 31
<212> TYPE: RNA
<213> ORGANISM: Mus musculus

<400> SEQUENCE: 1220
ucggauuuau uuuuuccaa cugcuuucug a                                 31

<210> SEQ ID NO 1221
<211> LENGTH: 31
```

```
<212> TYPE: RNA
<213> ORGANISM: Mus musculus

<400> SEQUENCE: 1221
cggauuuauu uuuuccaac ugcuuucuga a                              31

<210> SEQ ID NO 1222
<211> LENGTH: 31
<212> TYPE: RNA
<213> ORGANISM: Mus musculus

<400> SEQUENCE: 1222
ggauuuauuu uuuccaacu gcuuucugaa a                              31

<210> SEQ ID NO 1223
<211> LENGTH: 31
<212> TYPE: RNA
<213> ORGANISM: Mus musculus

<400> SEQUENCE: 1223
gauuuauuuu uuccaacug cuuucugaaa g                              31

<210> SEQ ID NO 1224
<211> LENGTH: 31
<212> TYPE: RNA
<213> ORGANISM: Mus musculus

<400> SEQUENCE: 1224
auuuauuuuu uccaacugc uuucugaaag g                              31

<210> SEQ ID NO 1225
<211> LENGTH: 31
<212> TYPE: RNA
<213> ORGANISM: Mus musculus

<400> SEQUENCE: 1225
caccgcaagg gcuugggauc uuuugcgauc u                             31

<210> SEQ ID NO 1226
<211> LENGTH: 31
<212> TYPE: RNA
<213> ORGANISM: Mus musculus

<400> SEQUENCE: 1226
accgcaaggg cuugggaucu uuugcgaucu g                             31

<210> SEQ ID NO 1227
<211> LENGTH: 31
<212> TYPE: RNA
<213> ORGANISM: Mus musculus

<400> SEQUENCE: 1227
aagggcuugg gaucuuuugc gaucugcucg a                             31

<210> SEQ ID NO 1228
<211> LENGTH: 31
<212> TYPE: RNA
<213> ORGANISM: Mus musculus

<400> SEQUENCE: 1228
gggaucuuuu gcgaucugcu cgagcagauu u                             31

<210> SEQ ID NO 1229
```

```
<211> LENGTH: 31
<212> TYPE: RNA
<213> ORGANISM: Mus musculus

<400> SEQUENCE: 1229
gggaucuuuu gcgaucugcu cgagcagauu u                              31

<210> SEQ ID NO 1230
<211> LENGTH: 31
<212> TYPE: RNA
<213> ORGANISM: Mus musculus

<400> SEQUENCE: 1230
uuauuuuuuu ccaacugcuu ucugaaaggg g                              31

<210> SEQ ID NO 1231
<211> LENGTH: 31
<212> TYPE: RNA
<213> ORGANISM: Mus musculus

<400> SEQUENCE: 1231 uauuuuuuc caacugcuuu cugaaagggg u                               31

<210> SEQ ID NO 1232
<211> LENGTH: 31
<212> TYPE: RNA
<213> ORGANISM: Mus musculus

<400> SEQUENCE: 1232
uuuauuuuuu uccaacugcu uucugaaagg g                              31

<210> SEQ ID NO 1233
<211> LENGTH: 31
<212> TYPE: RNA
<213> ORGANISM: Mus musculus

<400> SEQUENCE: 1233
gacacaccgc aagggcuugg gaucuuugc g                               31

<210> SEQ ID NO 1234
<211> LENGTH: 31
<212> TYPE: RNA
<213> ORGANISM: Mus musculus

<400> SEQUENCE: 1234
gugacacacc gcaagggcuu gggaucuuuu g                              31

<210> SEQ ID NO 1235
<211> LENGTH: 31
<212> TYPE: RNA
<213> ORGANISM: Mus musculus

<400> SEQUENCE: 1235
ugacacaccg caagggcuug ggaucuuuug c                              31

<210> SEQ ID NO 1236
<211> LENGTH: 31
<212> TYPE: RNA
<213> ORGANISM: Mus musculus

<400> SEQUENCE: 1236
cacaccgcaa gggcuuggga ucuuuugcga u                              31
```

```
<210> SEQ ID NO 1237
<211> LENGTH: 31
<212> TYPE: RNA
<213> ORGANISM: Mus musculus

<400> SEQUENCE: 1237
acaccgcaag ggcuugggau cuuuugcgau c                              31

<210> SEQ ID NO 1238
<211> LENGTH: 31
<212> TYPE: RNA
<213> ORGANISM: Mus musculus

<400> SEQUENCE: 1238
ugugacacac cgcaagggcu ugggaucuuu u                              31

<210> SEQ ID NO 1239
<211> LENGTH: 31
<212> TYPE: RNA
<213> ORGANISM: Mus musculus

<400> SEQUENCE: 1239
acacaccgca agggcuuggg aucuuuugcg a                              31

<210> SEQ ID NO 1240
<211> LENGTH: 31
<212> TYPE: RNA
<213> ORGANISM: Mus musculus

<400> SEQUENCE: 1240
ggugcugaag uuuauucgga uuuauuuuuu u                              31

<210> SEQ ID NO 1241
<211> LENGTH: 31
<212> TYPE: RNA
<213> ORGANISM: Mus musculus

<400> SEQUENCE: 1241
gugcugaagu uuauucggau uuauuuuuuu c                              31

<210> SEQ ID NO 1242
<211> LENGTH: 31
<212> TYPE: RNA
<213> ORGANISM: Mus musculus

<400> SEQUENCE: 1242
uauucggauu uauuuuuuuc caacugcuuu c                              31

<210> SEQ ID NO 1243
<211> LENGTH: 31
<212> TYPE: RNA
<213> ORGANISM: Mus musculus

<400> SEQUENCE: 1243
uuuauucgga uuuauuuuuu uccaacugcu u                              31

<210> SEQ ID NO 1244
<211> LENGTH: 31
<212> TYPE: RNA
<213> ORGANISM: Mus musculus

<400> SEQUENCE: 1244
uuauucggau uuauuuuuuu ccaacugcuu u                              31
```

<210> SEQ ID NO 1245
<211> LENGTH: 31
<212> TYPE: RNA
<213> ORGANISM: Mus musculus

<400> SEQUENCE: 1245
ugcugaaguu uauucggauu uauuuuuuc c                          31

<210> SEQ ID NO 1246
<211> LENGTH: 31
<212> TYPE: RNA
<213> ORGANISM: Mus musculus

<400> SEQUENCE: 1246
gcugaaguuu auucggauuu auuuuuucc a                          31

<210> SEQ ID NO 1247
<211> LENGTH: 31
<212> TYPE: RNA
<213> ORGANISM: Mus musculus

<400> SEQUENCE: 1247
aguuuauucg gauuuauuuu uuccaacug c                          31

<210> SEQ ID NO 1248
<211> LENGTH: 31
<212> TYPE: RNA
<213> ORGANISM: Mus musculus

<400> SEQUENCE: 1248
guuuauucgg auuuauuuuu uccaacugc u                          31

<210> SEQ ID NO 1249
<211> LENGTH: 31
<212> TYPE: RNA
<213> ORGANISM: Mus musculus

<400> SEQUENCE: 1249
cugaaguuua uucggauuua uuuuuucca a                          31

<210> SEQ ID NO 1250
<211> LENGTH: 31
<212> TYPE: RNA
<213> ORGANISM: Mus musculus

<400> SEQUENCE: 1250
ugaaguuuau ucggauuuau uuuuuccaa c                          31

<210> SEQ ID NO 1251
<211> LENGTH: 31
<212> TYPE: RNA
<213> ORGANISM: Mus musculus

<400> SEQUENCE: 1251
gaaguuuauu cggauuuauu uuuuccaac u                          31

<210> SEQ ID NO 1252
<211> LENGTH: 31
<212> TYPE: RNA
<213> ORGANISM: Mus musculus

```
<400> SEQUENCE: 1252
aaguuuauuc ggauuuauuu uuuuccaacu g                          31
```

CONDITIONAL-SIRNAS AND USES THEREOF IN TREATING CARDIAC HYPERTROPHY

PRIORITY CLAIM

This application is a U.S. National Phase Application of International Application No. PCT/US2018/046379, filed Aug. 10, 2018, which claims priority to U.S. Provisional Patent Application No. 62/543,882, filed Aug. 10, 2017, the subject matter of which is hereby incorporated by reference in its entirety, as if fully set forth herein.

STATEMENT REGARDING FEDERALLY SPONSORED RESEARCH

This invention was made with government support under Grant Number 1332411, awarded by National Science Foundation through the Emerging Frontiers in Research and Innovation, Origami Design for Integration of Self-assembling Systems for Engineering Innovation (EFRI-ODISSEI), and Grant Number A1029329, awarded by National Institutes of Health (NIH). The government has certain rights to the invention.

SEQUENCE LISTING

This disclosure includes a sequence listing, which is submitted in ASCII format via EFS-Web, and is hereby incorporated by reference in its entirety. The ASCII copy, created Nov. 29, 2021, is named SubstituteSequenceListing.txt and is 252 kilobytes in size.

BACKGROUND

RNA interference (RNAi) is a sequence-specific mRNA degradation pathway mediated by siRNA duplexes, key for cellular immunity and developmental regulation. Researchers have utilized synthetic RNAi triggers for therapeutics by inhibiting a specific gene product found to be essential in disease driving pathways but non-essential for normal functioning.

Consider however that some genes essential in disease progression may have vital functions in normal cells and are dangerous to target. Meanwhile other upregulated genes are not essential for disease progression, but serve as effective indicators. Therefore, there is a need in the art to develop effective therapies to exploit this differential expression in various indications. The conditionally active siRNA complexes described below are candidates for investigation of treatments for those indications, such as cardiac hypertrophy.

Heart Failure (HF) is a chronic cardiac condition, affecting millions of people worldwide, and considered a major contributor to healthcare expenditure in the US. Compensatory cardiac hypertrophy is one of the initial hallmarks of pathological ventricular remodeling, which is characterized by an upregulation of a variety of genes and miRNA that mediate and regulate myocardial hypertrophy, and ultimately HF. Even though important advances have been done in the treatment of HF, no cardiac specific therapies with lack of adverse effects have been developed to date. Therefore, there is a need in the art to develop an effective therapy for HF.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-C: A) General construct design of cond-siRNA with green sensor strand designed reverse comp. to signal gene mRNA, red core strand with nick either 11 or 12 bp from toehold end on sensor side designed comp. to sensor and guide, and yellow guide strand designed reverse comp. to target gene mRNA. B) Model of cond-siRNA. C) Molecular simulation of cond-siRNA.

FIGS. 12A-B show schematic depicting in vivo and in vitro screening approaches.

FIGS. 13A-B: A) NuPack generated secondary structure of selected NPPB 31 bp sensor strand. Minimal secondary structure with approximately 40-50% probability of folding onto itself. B) NPPB sensor strand bound to 5' and 3' core overhangs 99% of the time.

FIGS. 14A-B: A) NuPack generated secondary structure of selected MYH7 31 bp sensor strand. Minimal secondary structure with approximately 30% probability folding onto itself. B) NPPB sensor strand bound to 5' and 3' core overhangs 97% of the time.

FIGS. 15A-B: A) NuPack generated secondary structure of HDAC2 25 bp guide strand. Significant secondary structure indicated by the equilibrium probabilities of binding. B) NuPack generated secondary structure of HDAC2 guide bound to core strand with the 5' and 3' overhangs that bind to the appropriate sensor strand. Although guide strand has significant and strong secondary structure, when placed with core strand, guide binds to core 100%.

FIG. 16 shows test constructs detecting murine ANP mRNA and targeting murine Calcineurin according to certain embodiments.

FIG. 17 shows test constructs detecting murine and human mir-23a-3p and targeting murine Calcineurin according to certain embodiments.

FIG. 21: Differential miRNA expression in NRVM under hypoxia.

FIG. 39 is a table including candidate sensor strands for the 3' UTR of the human myh7 gene. Column abbreviations are as follows: BS is Bad Segments; 3LN is 3-Letteredness; NBP is Number Bad Points; P is Position.

FIG. 40 is a table including candidate sensor strands for the 3' UTR of the rat myh7 gene. Column abbreviations are as follows: BS is Bad Segments; 3LN is 3-Letteredness; NBP is Number Bad Points; P is Position.

FIG. 41 is a table including candidate sensor strands for the 3' UTR of the human nppa gene. Column abbreviations are as follows: BS is Bad Segments; 3LN is 3-Letteredness; NBP is Number Bad Points; P is Position.

FIG. 42 is a table including candidate sensor strands for the 3' UTR of the rat nppa gene. Column abbreviations are as follows: BS is Bad Segments; 3LN is 3-Letteredness; NBP is Number Bad Points; P is Position.

FIG. 43 is a table including candidate sensor strands for the 3' UTR of the human nppb gene. Column abbreviations are as follows: BS is Bad Segments; 3LN is 3-Letteredness; NBP is Number Bad Points; P is Position.

FIG. 44 is a table including candidate sensor strands for the 3' UTR of the rat nppb gene. Column abbreviations are as follows: BS is Bad Segments; 3LN is 3-Letteredness; NBP is Number Bad Points; P is Position.

FIG. 48 illustrates NCBI check for calcineurin and HDAC2 guide strand sequences.

FIGS. 50A-50D show that NuPack analyses were performed on core (FIG. 50A), guide (FIG. 50B), Sensor with two small overhangs of core: 97% (FIG. 50C), and calcineurin guide with core: 100% (FIG. 50D).

FIGS. 54A-54B illustrate the check of guide vs. NCBI human transcripts and sequence alignment, respectively.

FIG. 56 shows the BNP sensor sequence (SEQ ID NO: 4) together with core and guide sequences.

FIGS. 57A and 57B show Nupack analyses of BNP sensor (SEQ ID NO: 4) with overhangs, and guide with core, respectively.

FIG. 60 shows the BNP sensor sequence (SEQ ID NO: 5) together with core and guide sequences.

FIGS. 61A and 61B show Nupack analyses of BNP sensor (SEQ ID NO: 5) with overhangs, and guide with core, respectively.

FIG. 64 shows the BNP sensor sequence (SEQ ID NO: 6) together with core and guide sequences.

FIG. 68 shows the MYH7 sensor sequence (SEQ ID NO: 7) together with core and guide sequences.

FIGS. 69A and 69B show Nupack analyses of MYH7 sensor (SEQ ID NO: 7) with overhangs, and guide with core, respectively.

FIG. 71 shows the MFE structure of NPPA HDAC2 construct #1.

FIG. 72 shows the MFE structure of NPPA HDAC2 construct #3.

DETAILED DESCRIPTION

Overview of Conditional-siRNA

Described herein are conditional siRNA complexes (also referred to herein as Cond-siRNA, a conditional RNA-sensor, or an RNA-sensor) that include a therapeutic component (e.g., siRNA molecule) associated with a molecular sensor via a core molecule. The conditional siRNA complexes are inactive under normal conditions, but are activated upon interaction between the molecular sensor and a biomarker. Such molecules are synthetic riboswitch molecules that allow an input gene or RNA molecule to "switch on" an RNAi pathway against a target output gene.

Figure 1:
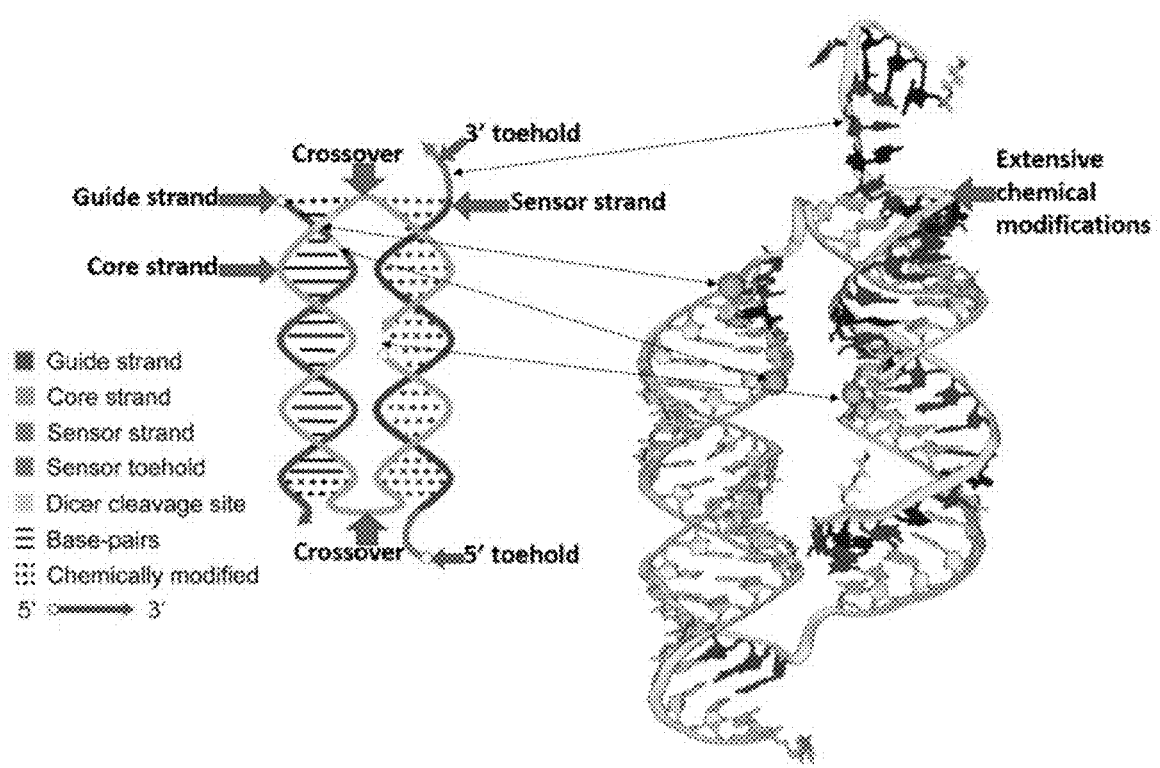
FIG. 1 shows a comparison of secondary and tertiary structure (from full atomistic MD simulations) of a Cond-siRNA construct according to one embodiment. Black arrows show corresponding features between the 2D and 3D representations.
Figure 2:
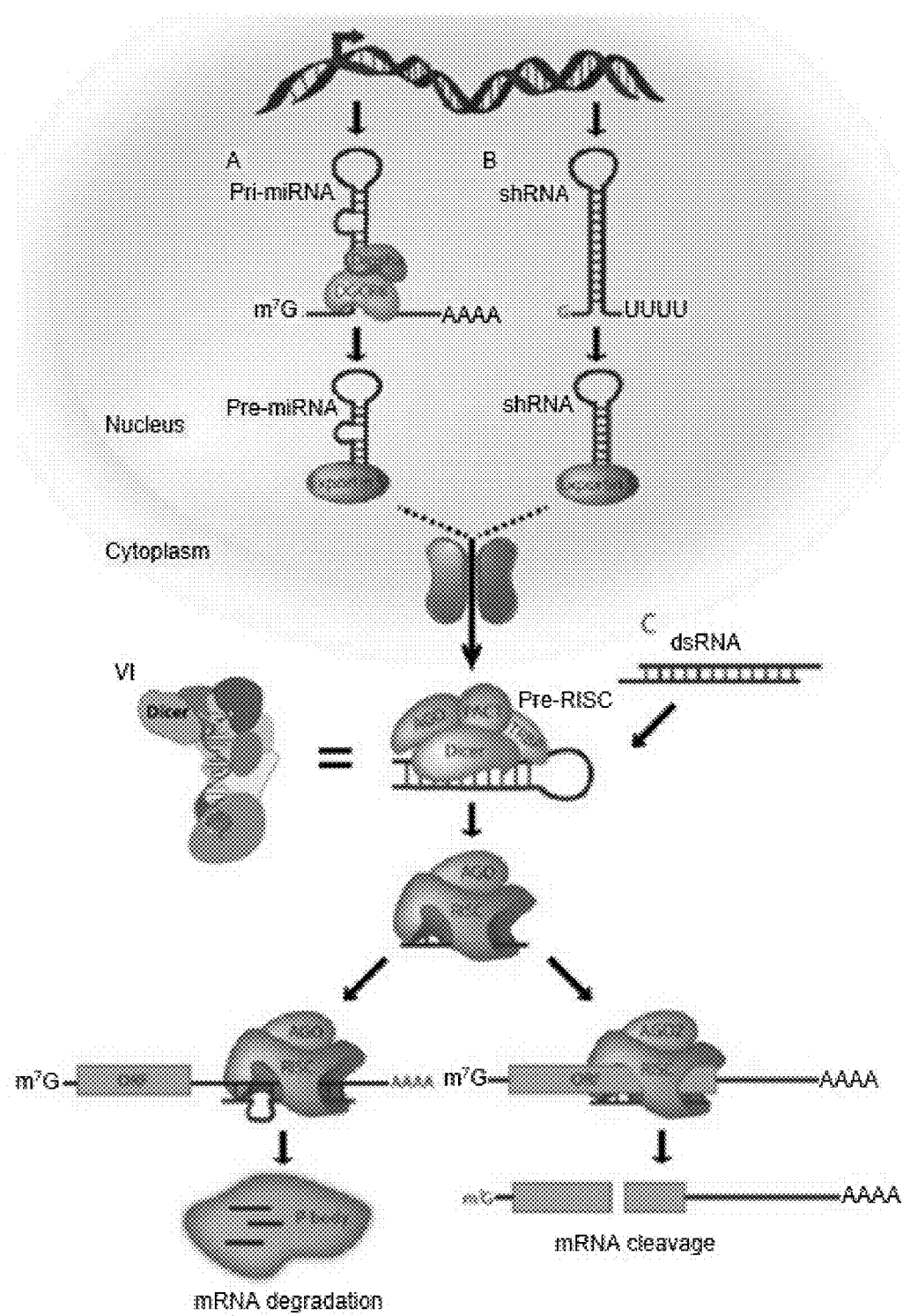
FIG. 2 is a diagram showing the RNAi pathway.
Figure 36:
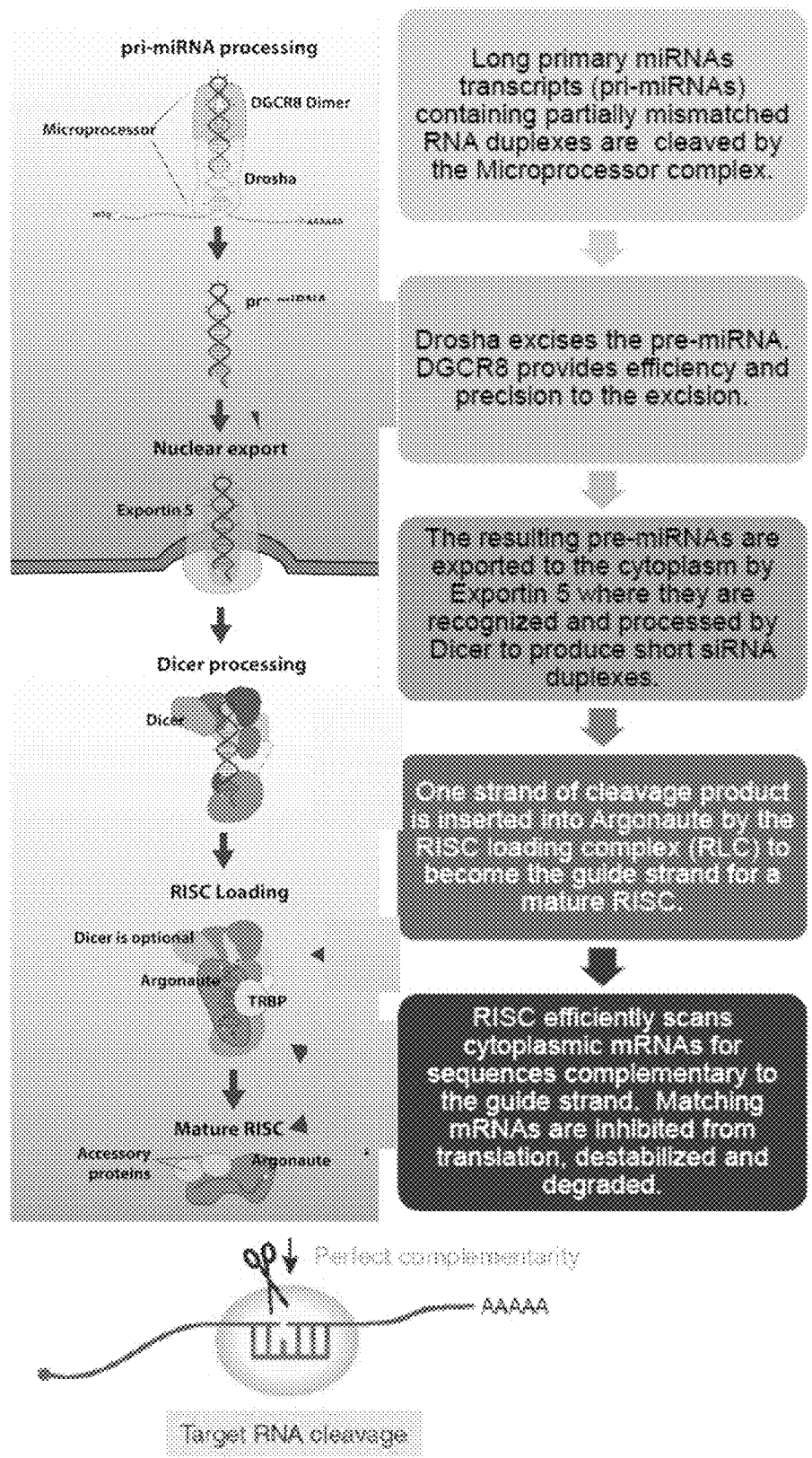
FIG. 36 is a flowchart accompanied by a corresponding schematic showing the RNA interference pathway starting with pri-miRNA processing in the nucleus.
Figure 45:
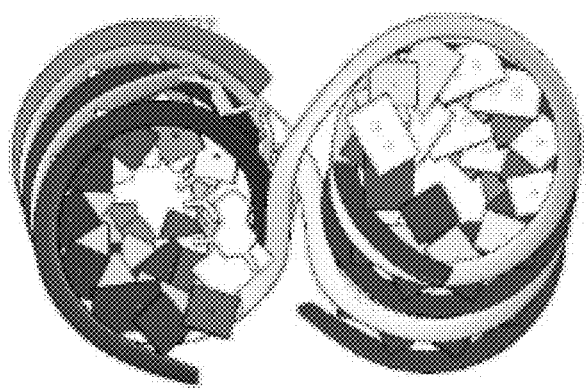
FIG. 45 shows a top view of a 3D schematic of a Cond-siRNA construct according to one embodiment.

An RNA-sensor molecule or complex includes sensor strand, a guide strand, and a core strand that bind to each other to form a multi-strand molecular complex having a dual duplex structure shown in FIGS. 1, 45. In certain embodiments, those three strands (core, sensor and guide) form two parallel oligonucleotide duplexes connected in a double crossover configuration. [14] (See FIG. 1). In some aspects, the length of each of the oligonucleotide duplexes is sufficient to operate within the RNA interference (RNAi) pathway (See FIGS. 2, 36). For example, the duplexes may be between about 15 and 30 base pairs in length. In some embodiments, the duplexes are between 15 and 20 base pairs in length, between 20 and 25 base pairs in length, between 25 and 30 base pairs in length. In other embodiments, the duplexes are about 15, 16, 17, 18, 19, 20, 21, 22, 23, 24, 25, 25, 26, 27, 28, 29, 30, or more than 30 base pairs in length.

The double crossover configuration as shown in FIG. 1 represents the inactive or "OFF" state of the RNA-sensor complex wherein the sensor duplex inhibits RNAi loading of the siRNA duplex, serving as a "lock" on RNAi activity. In the OFF state, the guide strand binds a first portion (or "passenger" segment) of the core strand to form an siRNA duplex that serves as a pro-RNA molecule. The pro-RNA molecule operates in the RNAi pathway of a target cell to alter expression of a target gene or target RNA molecule associated with a pathological condition (i.e., the "therapeutic target molecule"). The second duplex is formed by the sensor strand binding to a second portion (or "protection" segment) of the core strand to form the sensor duplex. In some embodiments, the core strand has a third portion (or "protection" segment) that binds the sensor strand. In certain such embodiments, the core strand includes the passenger strand (P) that is joined to first and second protection segments (A, B) at each end by a linker (L1, L2) in the following configuration:

5' B-L2-P-L1-A 3'

The sequence of the core strand is determined by the sequences of the sensor and guide strands, and may be fully or complementary to the sensor strand, the guide strand, or both. Any suitable linker can be used in accordance with the embodiments described herein, including, but not limited to, an internal C3 spacer, a C6 linker, a tri-ethylene glycol linker.

The RNA-sensor complex is activated to the "ON" state upon interaction with a biomarker in the cell expressing a phenotype associated with the pathological condition targeted by the guide strand of the siRNA duplex. This activation is primarily due to the design of the sensor strand, which serves as the activation signal for RNAi activity. When this is the case, the RNA-sensor complex is said to detect the biomarker.

Figure 3:
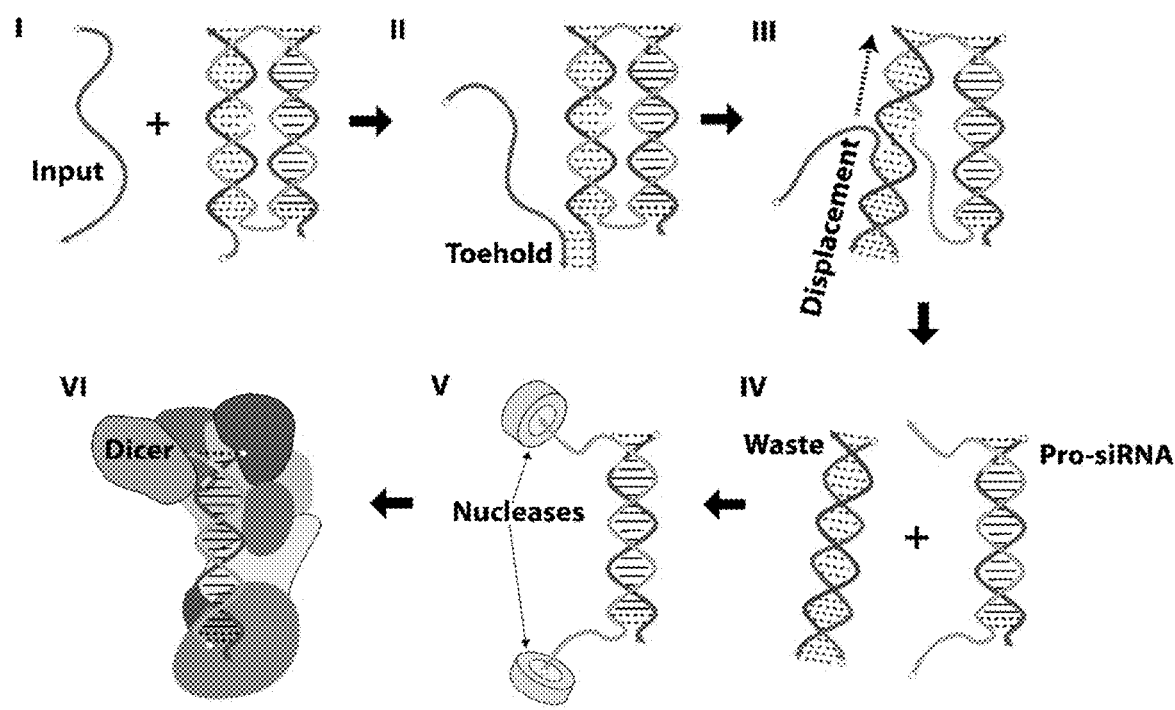
FIG. 3 shows toehold mediated strand displacement process of conditional siRNA. In step I, c-siRNA meets RNA transcript with correct activation sequence (Input). In step II, an Input RNA binds to the toehold. Step III shows toehold mediated strand displacement. Step IV shows the sensor strand and input forming a waste duplex that separates from the pro-siRNA. In step V, XRN1, exosome and other cytosolic RNAses rapidly degrade unprotected overhangs, turning pro-siRNA into efficient Dicer substrate. In step VI, siRNA is processed by Dicer for incorporation into RISC. The basic biophysical process of toehold mediated strand displacement includes a fast 1 D random walk: uS to mS for each of N^2 steps. This results in sequence specificity from both toehold and duplexes. Thermodynamically stable chemical modifications are confined to sensor strand to avoid kinetic traps.

The sensor strand includes a nucleotide sequence designed to bind the biomarker associated with the pathological condition (i.e., "pathological biomarker"). Binding to the biomarker is initiated by the binding of at least one toehold segment (single stranded) to an input RNA strand that encodes at least a portion of the pathological biomarker, as shown in FIG. 3. Upon displacement of the sensor strand, the sensor and input strands from a waste duplex that separates from the pro-siRNA molecule, allowing the pro-siRNA to be processed by the target cell's RNAi system. The structure and binding dynamics of the conditional-siRNAs described herein is explained further in U.S. Pat. No. 9,725, 715, the content of which is incorporated herein by reference in its entirety.

The sequence of the sensor strand can be fully or partially complementary to an RNA sequence present in the pathological biomarker. In certain embodiments, the sensor strand is 100% complementary to the RNA sequence present in the pathological biomarker. Other embodiments may include a sensor strand that is largely complementary to the RNA sequence present in the pathological biomarker, for example, the sensor strand may be greater than 70% complementary, greater than 75% complementary, greater than 80% complementary, greater than 85% complementary, greater than 90% complementary, greater than 95% complementary, greater than 96% complementary, greater than 97% complementary, greater than 98% complementary, or greater than 99% complementary to the RNA sequence present in the pathological biomarker.

In some embodiments, the pathological biomarker is an RNA sequence that forms or encodes a molecule that is associated with the pathologic condition. In some aspects, the pathological biomarker is an RNA sequence that is present in the target cell under pathological conditions, but is substantially absent under normal conditions. Alternatively, the pathological biomarker is an RNA sequence that is upregulated in the target cell under pathological conditions as compared to normal conditions.

The guide strand includes a Dicer cleavage site near the 3' end. The sequence between the Dicer cleavage site and the 3' terminus of the guide strand is either fully or partially complementary to a nucleotide sequence found in the therapeutic target molecule (e.g., target gene, target mRNA or target miRNA). When this is the case, the Cond-siRNA is said to target the gene or RNA molecule. In certain embodiments, the guide strand is 100% complementary to the nucleotide sequence found in the therapeutic target molecule. Other embodiments may include a guide strand that is largely complementary to the nucleotide sequence found in the therapeutic target molecule, for example, the guide strand may be greater than 70% complementary, greater than 75% complementary, greater than 80% complementary, greater than 85% complementary, greater than 90% complementary, greater than 95% complementary, greater than 96% complementary, greater than 97% complementary, greater than 98% complementary, or greater than 99% complementary to the nucleotide sequence found in the therapeutic target molecule.

A challenge of using oligonucleotides in vivo lies in preventing nuclease degradation of RNA nucleotides. Several chemical modifications in the sensor strand can be used to overcome this challenge. For example, Locked Nucleic Acids (LNAs) include a modification of RNA nucleotides with an extra bridge between the 2' O and 4' C increases thermal stability of RNA duplexes and allows for resistance to nucleases. 2' O-Methyl modifications confer stability, increase binding affinity to RNA nucleotides and prevent degradation by nucleases. And, phosphorothioate: modification by replacing one of the non-bridging oxygens in the phosphate linkage between bases with a sulfur that reduces nucleolytic degradation; however also lowers binding affinity.

Thus, in certain embodiments, the RNA-sensor complex includes one or more modifications to the nucleotide sequence of the sensor strand, the core strand, and/or the guide strand. Exemplary modifications that may be used include, but are not limited to, locked nucleic acids (LNA), peptide nucleic acids (PNA), 2'-O-methyl modifications, morpholino modifications, phosphorothioate modifications, terminal modifications, and other linker or backbone modifications or connections. Additional chemical modifications may be chosen according to methods described in U.S. Pat. No. 9,725,715B2, the disclosure of which is hereby fully incorporated herein.

Figure 4A:
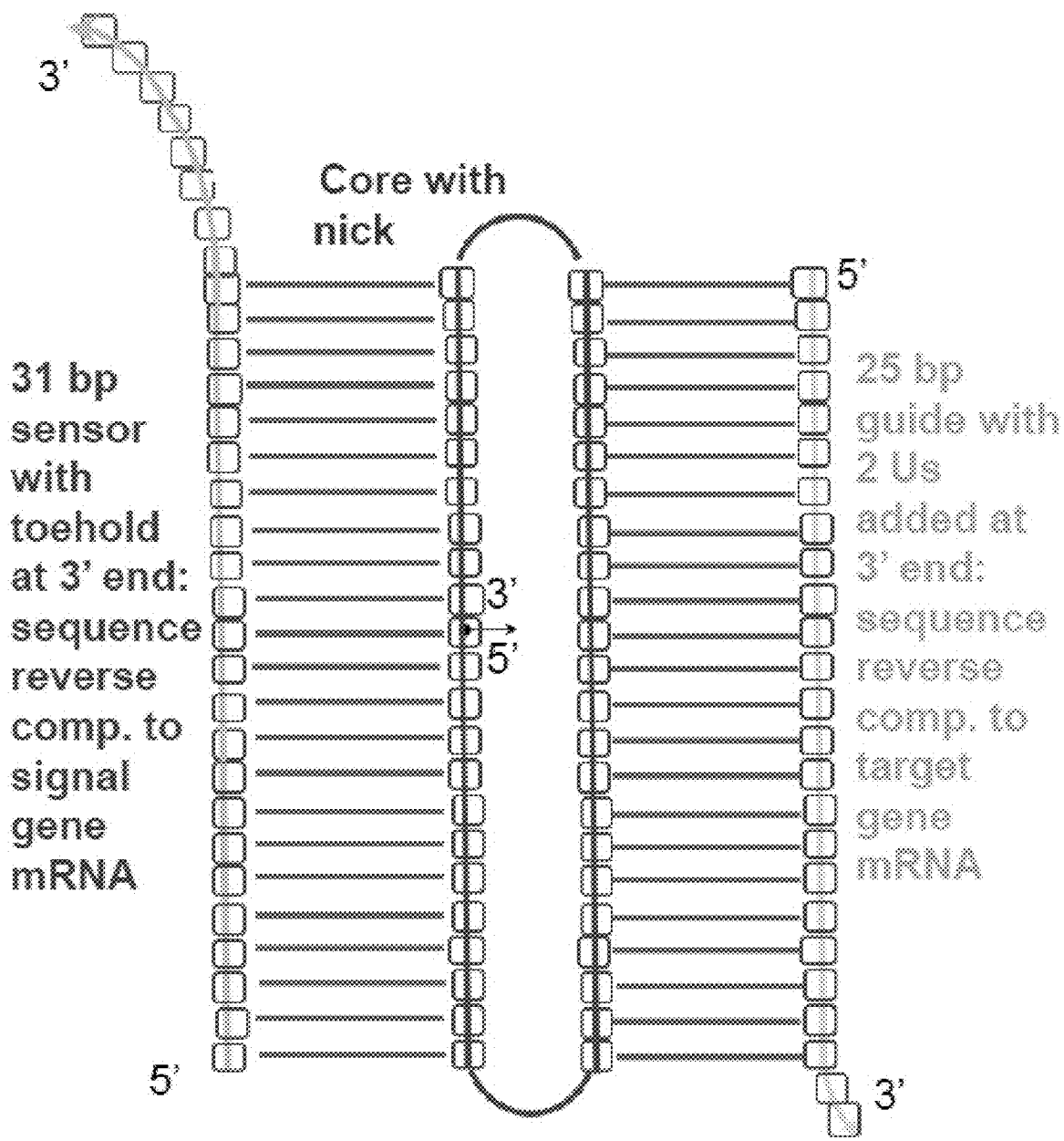

The approach of designing a cond-siRNA sensor complex for use in treating a disease or other pathological condition using the cond-siRNA sensor complexes is advantageous in that it allows the complex to become biologically active only in diseased cells AND remain OFF in healthy cells. In addition, the approach allows for increased disease cell specificity and prevents toxicity from delivery to unintended off-targets. Further, the approach combines disease specificity from one gene with treatment efficacy from a second gene to create therapeutics that are precisely tailored to specific gene expression patterns. Still further, the approach is advantageous due to steric hindrance of the two RNA duplexes positioned in a parallel configuration (FIG. 4). The sensor strand inhibits RNAi loading of siRNA and will only displace when activated in disease cells.

Overview of Methods for Designing a Conditional siRNA Complex

An siRNA complex is designed based on biomarkers and therapeutic target molecules that are specific to each cell type, pathological condition, and/or indication. According to certain embodiments, methods for designing and testing each conditional siRNA complex includes several steps, as described below.

Figure 5:
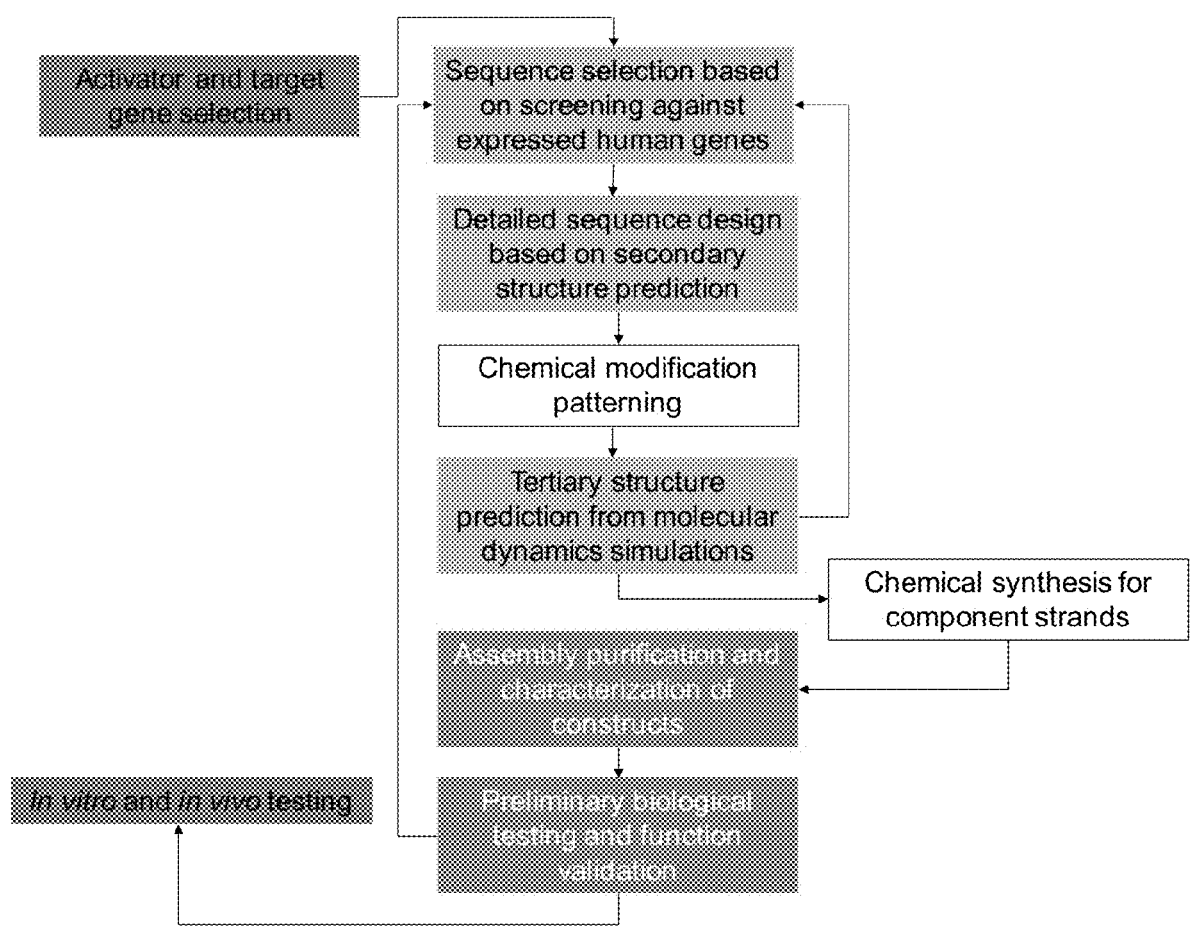
FIG. 5 shows an overview of the design process for Cond-siRNAs according to one embodiment.

FIG. 5 shows an overview of the design process. In certain embodiments methods for designing a conditional siRNA complex (the "design method") includes a step of determining a biomarker that will serve as an input for activation and a therapeutic target for RNAi inhibition. This step may include a determining one or more factors that are differentially expressed (i.e., upregulated or present in a diseased cell as compared to a normal cell) using methods known in the art.

The design method further includes a step of generating a list of candidate target segments of the biomarker (i.e., target mRNA sequence or target miRNA sequence) that can serve as a biomarker segment for binding the sensor strand, and then designing sensor strands for each biomarker.

The design method further includes a step of estimating the thermodynamic stability of the resulting sensor strand-biomarker duplexes (the sensor duplex) generated by the target segments and sensor strands by using secondary structure prediction tools used in the art [15].

The design method further includes a step of checking for the uniqueness of the binding site for the most stable sensor duplexes against the known transcriptome of the animal to which the conditional siRNA complex will be tested against.

The design method further includes a step of generating a list of guide strand sequences by using a protocol that may include, but is not limited to, standard siRNA design tools, literature references, or heuristic rules.

The design method further includes a step of creating a Dicer substrate from the chosen guide strand sequences.

The design method further includes a step of generating sequences for the core strand that connect the sensor strands to the guide strands.

The design method further includes a step of checking that the sensor: guide pairing does not create unwanted interactions.

The design method further includes a step of selecting a pattern of suitable chemical modifications as described herein, and optionally simulating the constructs using molecular simulation methods used in the art [16] to simulate the constructs (optional).

The design method may also include a method of synthesizing or purchasing the sensor, core, and guide strands from commercial vendors such as Qiagen, Dharmacon, or IDT, the constructs of which are then assembled, characterized, and purified using gel electrophoresis.

The design method further includes a step of conducting preliminary biological testing and validation of the construct function, and then optionally test in in vitro and in vivo models of pathological conditions, including, but not limited to, MI induced maladaptive hypertrophy as described below.

Additional embodiments related to designing the guide, the sensor and the core strands are explained below.

Method for Designing Sensor Strands for mRNA Biomarker

According to certain embodiments, methods for designing and testing sensor strands that target an mRNA biomarker includes an algorithm that includes several steps, as described below.

In certain embodiments, a method for designing a sensor strand for an mRNA biomarker (the "mRNA sensor design method") includes a step of identifying the 3' UTR for each messenger RNA biomarker.

The mRNA sensor design method further includes a step of generating all possible consecutive 31 base sequences for each 3' UTR identified above.

The mRNA sensor design method further includes a step of obtaining the prospective sensor strand sequence for each sequence segment from the previous step by identifying the reverse complement (full or partial) of each sequence The mRNA sensor design method further includes a step of checking each sensor strand sequence for the following undesirable features: (i) three or more consecutive Gs, and (ii) four or more consecutive A or U bases.

The mRNA sensor design method further includes a step of checking each sensor strand sequence for the following desirable features: (i) higher than 50% G/C bases—this correlates with thermodynamic stability, (ii) "three letteredness," (iii) The first base at the 5' end of the sensor strand is a C or a G; and (iv) the 9th base from the 3' end of the sensor strand is a C or a G. According to the embodiments described herein, "three letteredness" is defined as the proportion of the sequence comprising of the three most numerous bases (e.g., the extent to which sequence is mostly made of A, U, C; or C, G, A; or A, U, G). A higher three letteredness score correlates with lower internal secondary structure. Exemplar ranking tables can be seen in FIGS. 39-44, which correspond to the genes or nucleotide sequences in Appendices C-H, submitted herewith.

Figure 6:
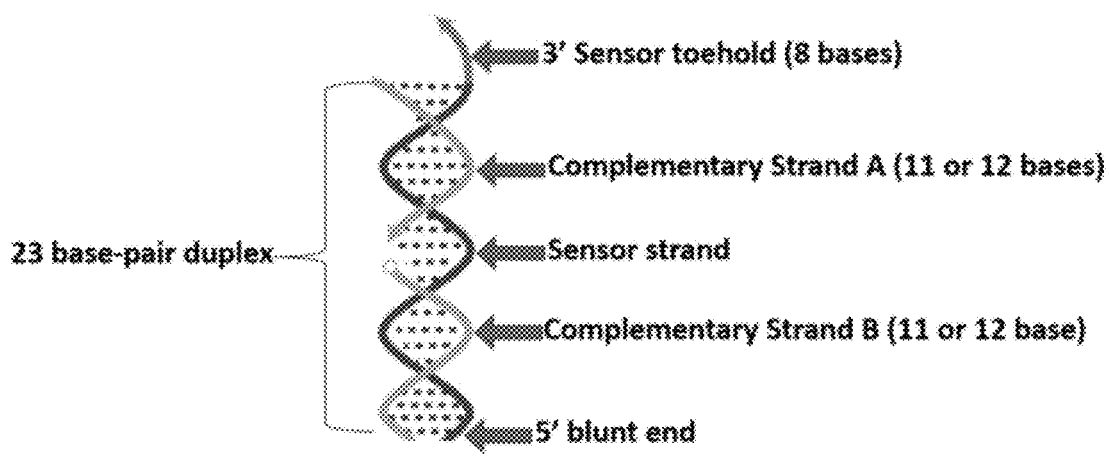
FIG. 6 shows a hypothetical sensor duplex for mRNA used to check for thermodynamic stability of the sensor according to one embodiment.

The mRNA sensor design method further includes a step of ranking all possible sensor strands. Strands with the least number of features from 4 and the highest scores from 5 are ranked highest The mRNA sensor design method further includes a step of generating hypothetical sensor duplexes using the pattern shown in FIG. 6, starting from the highest ranked strands.

Figure 7:
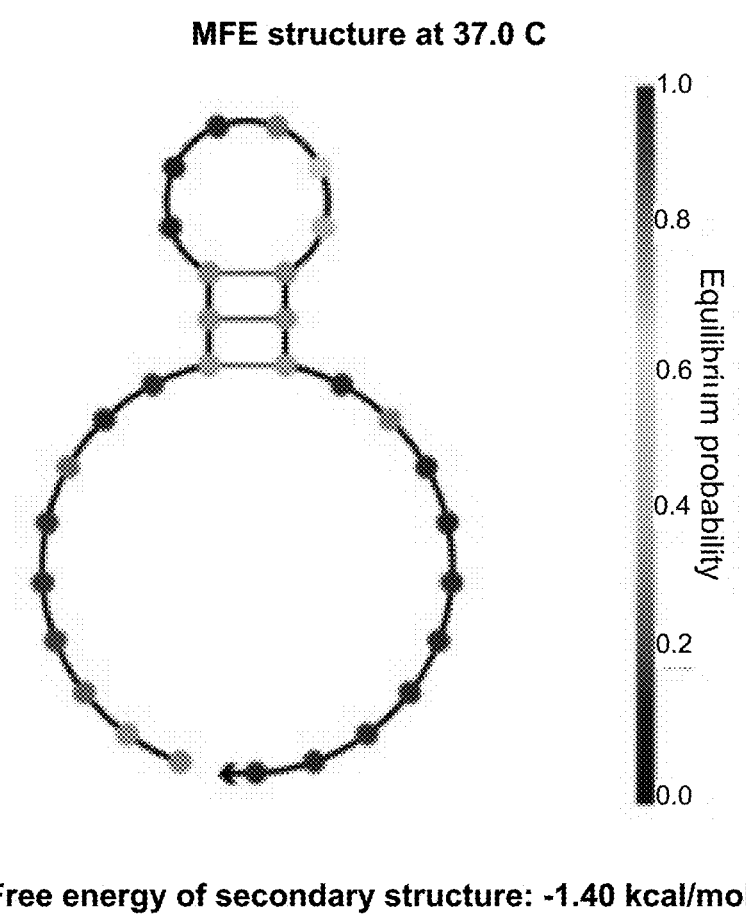
FIG. 7 shows a structure calculation showing sensor strand with low internal secondary structure according to one embodiment.
Figure 8:
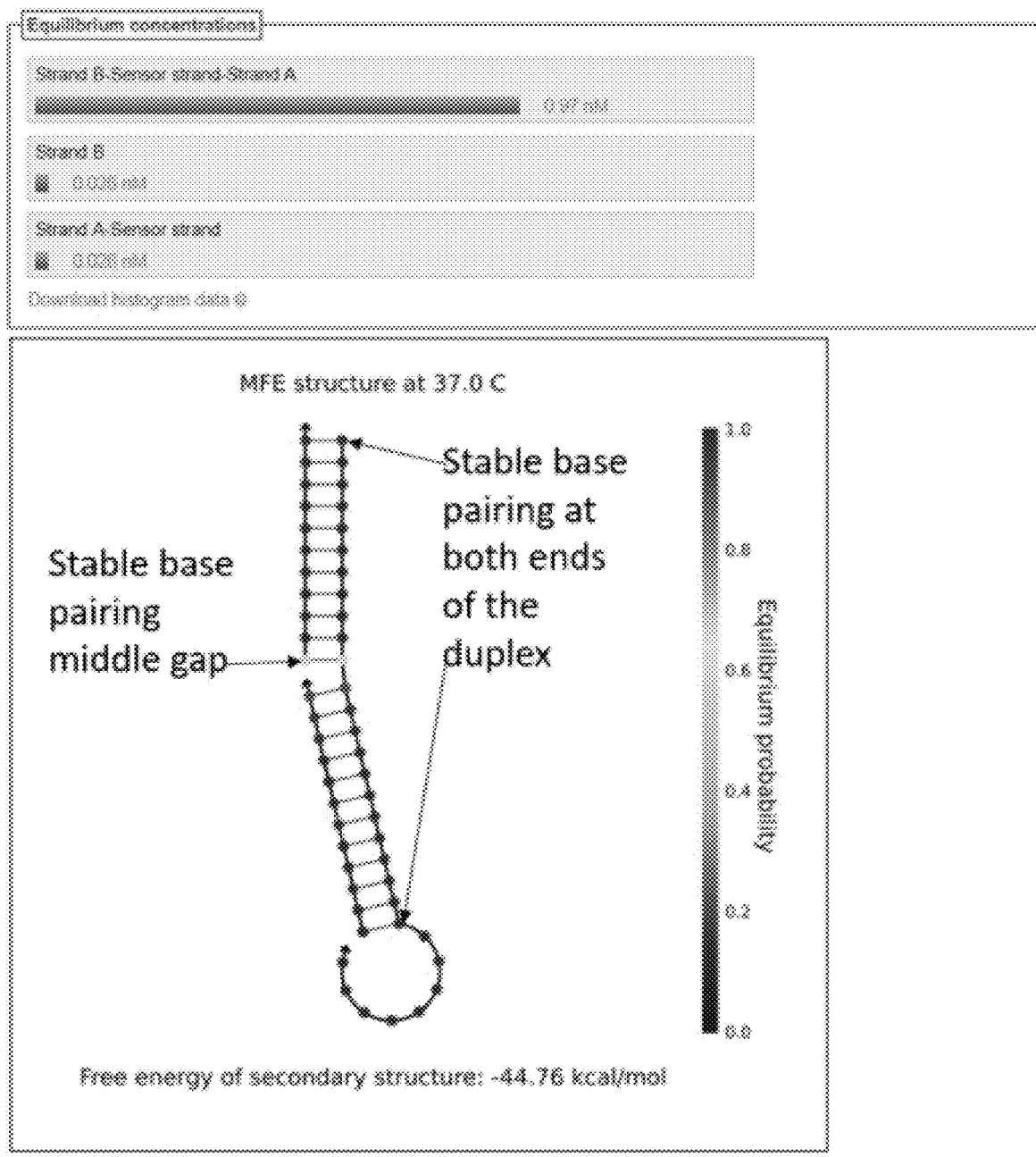
FIG. 8 shows a histogram showing a 97% predicted formation of the hypothetical sensor duplex and correct secondary structure according to one embodiment.

The RNA sensor design method further includes a step of using Nupack or similar secondary structure prediction codes to calculate the following, starting from the highest ranked strands: (i) the internal secondary structure of the sensor strand (lower amounts of internal secondary structure are desirable (FIG. 7), (ii) the thermodynamic stability of the hypothetical duplex from 7. Ideally, at 1 nM strand concentration, Nupack should predict that >90% or >95% of component strands should form the hypothetical sensor duplex (FIG. 8); and (iii) if sensor duplex is not stable, can adjust 1 to 5 bases at the 5' terminus of the sensor sequence to increase stability at the cost of reducing complementarity to the corresponding binding site on the putative biomarker.

The RNA sensor design method further includes a step of screening the sensor strand for thermodynamically stable duplexes using NCBI BLAST according to the following parameters: (i) use the "somewhat similar" search option, (ii) for sensor sequences, the 8 bases at the 3' terminus (constituting the 3' toehold) should have no more than 5 bases complementary to known transcripts in the target animal (eg, human or mouse) other than the intended biomarker, and (iii) if the first two criteria not met, broaden sequences considered in 1 to the coding region or the entirety of the mRNA.

Method for Designing Sensors for miRNA Biomarker

According to certain embodiments, methods for designing and testing sensor strands that target an miRNA biomarker includes an algorithm that includes several steps, as described below.

In certain embodiments, a method for designing a sensor strand for an miRNA biomarker (the "miRNA sensor design method") includes a step of identifying a guide sequence for each miRNA biomarker, to which the sensor strand is designed to bind (typically approximately 21 bases according to one aspect)

The miRNA sensor design method further includes a step of obtaining the reverse complement (full or partial) of the miRNA guide sequence.

The miRNA sensor design method further includes a step of adding 8 more bases to the 5' end of the sequence from the prior step.

Figure 9:
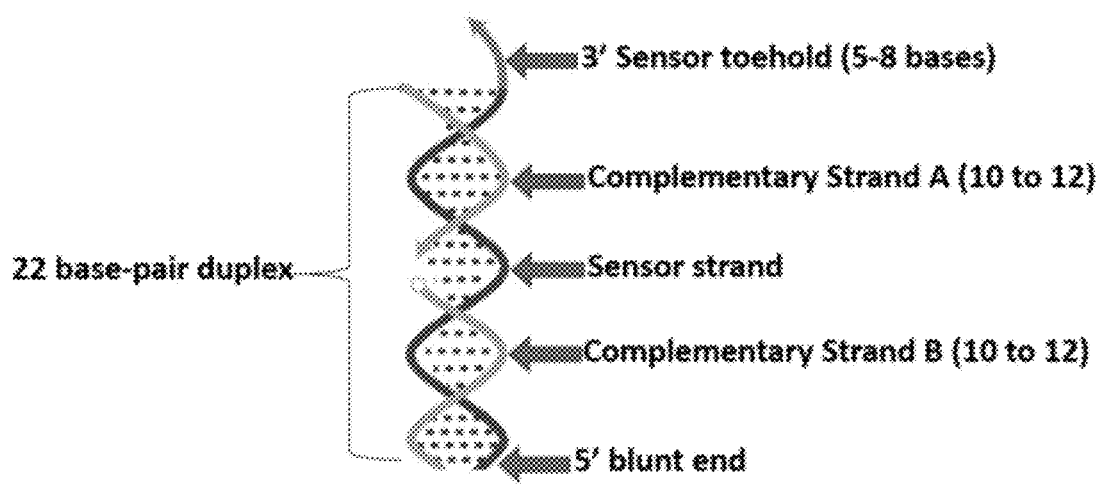
FIG. 9 shows a hypothetical sensor duplex for miRNA used to check for thermodynamic stability of the sensor according to one embodiment.

The miRNA sensor design method further includes a step of generating hypothetical sensor duplexes using the pattern shown in FIG. 9, starting from the sequence developed in the prior step.

The miRNA sensor design method further includes a step of using Nupack or similar secondary structure prediction codes to calculate the following: (i) the thermodynamic stability of the hypothetical duplex from the prior step. Ideally, at 1 nM strand concentration, Nupack should predict that >90% or >95% of component strands should form the hypothetical sensor duplex. (ii) if sensor duplex is not stable or the secondary structure is incorrect, determine whether the 8 terminal bases at the 5' end of the sensor strand, or the length of strand A or strand B can be altered or modified to optimize thermodynamic stability.

The miRNA sensor design method further includes a step of screening the sensor strand for thermodynamically stable duplexes in NCBI BLAST according to the following parameters: (i) use the "somewhat similar" search option, (ii) for sensor sequences, the 8 bases added at the 5' end of the sensor should not increase complementarity to transcripts other than the intended miRNA. If they do, adjust the sequence and start over from 4.

Methods for Designing a Guide Strand Sequence Against a Therapeutic Target Molecule According to certain embodiments, methods for designing a guide strand sequence against a therapeutic target gene or RNA molecule (e.g., mRNA or miRNA) includes several steps, as described below.

In certain embodiments, a method for designing a guide strand sequence against a therapeutic target (the "guide strand design method") includes a step of obtaining one or more prospective guide strand sequences using at least one of the following methods: (i) find a published guide strand sequence for the intended target; (ii) find a known miRNA target site on the target gene, or (iii) use a published algorithm or design tool known in the art [17, 18].

Figure 10:
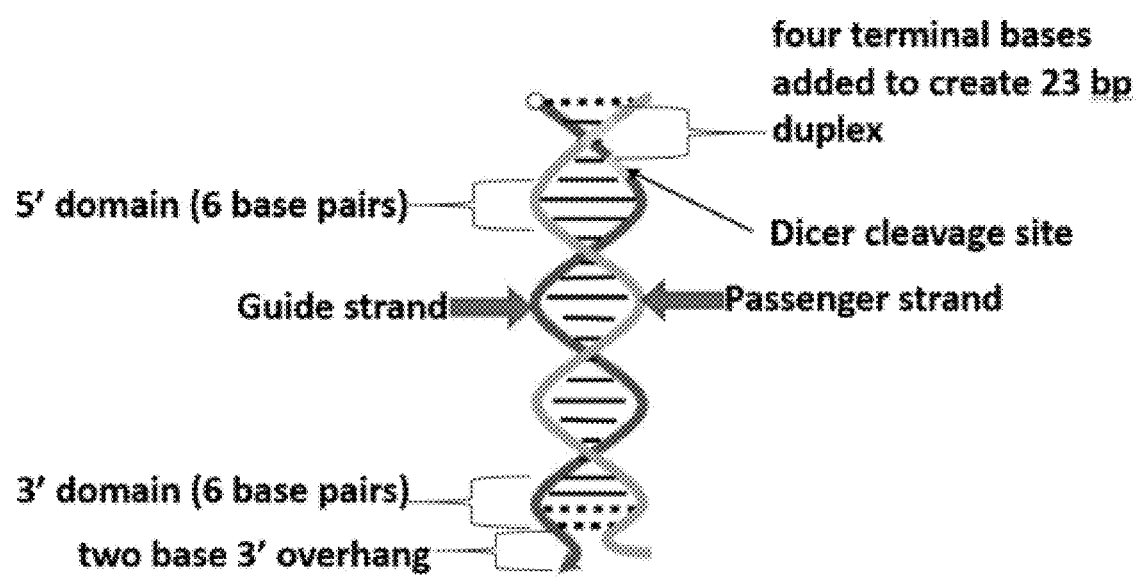
FIG. 10 shows a structure of the RNAi targeting duplex according to one embodiment.

The guide strand design method further includes a step of checking the guide sequence to make sure that the 6 bases at the 5' domain (FIG. 10) is more AU rich than the 6 bases in the 3' domain (FIG. 10). This will improve probability for correct strand loading [19]. Ideally, the 3' domain should be CG rich, and terminate in a CG base-pair.

The guide strand design method further includes a step of adding four terminal bases to the 5' end of the guide strand to complete the duplex. Those should be CG rich to improve thermodynamic stability.

The guide strand design method further includes a step of constructing the hypothetical RNAi targeting duplex as shown in FIG. 10.

The guide strand design method further includes a step of checking that the guide strand has weak internal secondary structure and minimal tendency to bind to itself (no more than 10% at 1 nM strand concentration) using Nupack or similar standard secondary structure calculation tool. Adjust bases added in 3 as necessary.

Methods for Designing a Core Strand Sequence and Checking Compatibility of Pairing Sensor to Guide According to certain embodiments, methods for designing a core strand sequence and checking compatibility of pairing sensor to guide includes several steps, as described below.

In certain embodiments, a method for designing a guide strand sequence against a therapeutic target (the "core strand design method") includes a step of choosing a suitable combination of sensor and guide strands, methods for designing those strands are discussed above and in the working examples, according to the embodiments described herein.

The core strand design method further includes a step of constructing the core strand by constructing a strand of the form 5'-B-C3-P-C3 A-3' where A and B are the sequence of complementary strand B from the hypothetical sensor duplex (FIG. 6 or 9), P is the sequence of the passenger strand from the hypothetical RNAi duplex (FIG. 10) and C3 are C3 linkers.

The core strand design method further includes a step of using Nupack or similar standard secondary structure calculation tool to check that the guide strand and core strand base-pairing has the following properties: (i) >95% of strands are base-paired in the correct duplex at 1 nM strand concentration, (ii) the guide strand duplex has the correct conformation, with a ~23 base-pair duplex, a two base 3' guide strand overhang, and 10-12 base 5' and 3' core overhangs with minimal secondary structures, and (iii) If above criteria not met, choose new sensor or guide pairing.

Conditional siRNA Complexes for Treating Cardiac Hypertrophy

Disclosed herein is a therapeutic strategy that targets molecular pathways involved in cardiac hypertrophy (that often results after a myocardial infarction), with minimal off-target effects. A myocardial infarction (MI) is a heart attack. MIs can occur when a blood clot blocks a coronary artery, interrupting blood flow to the heart—a condition known as cardiac ischemia.

Figure 35A:
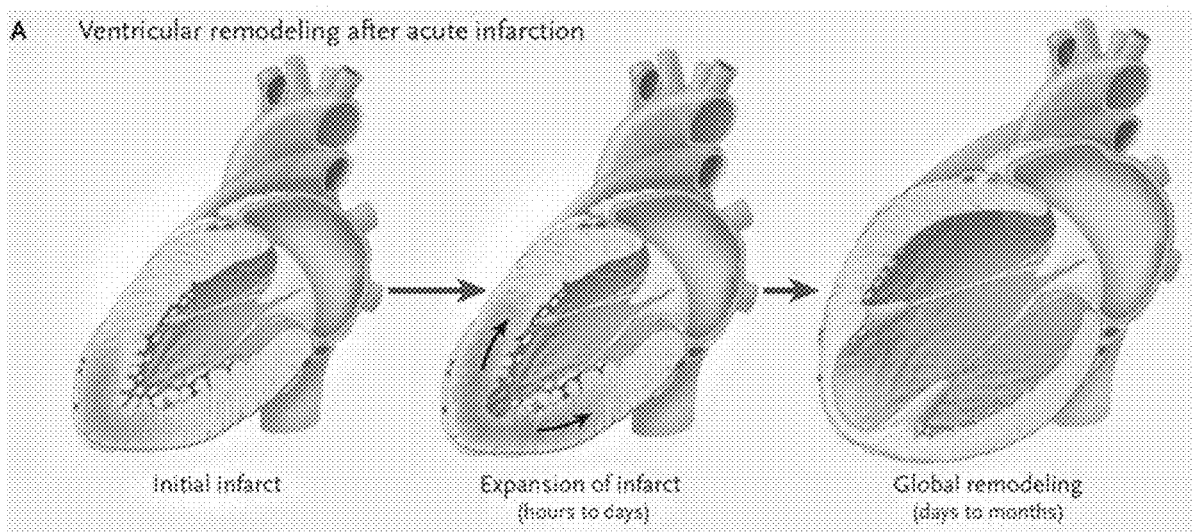
FIG. 35A shows Post-MI cardiac remodeling and left ventricular enlargement.
Figure 35B:
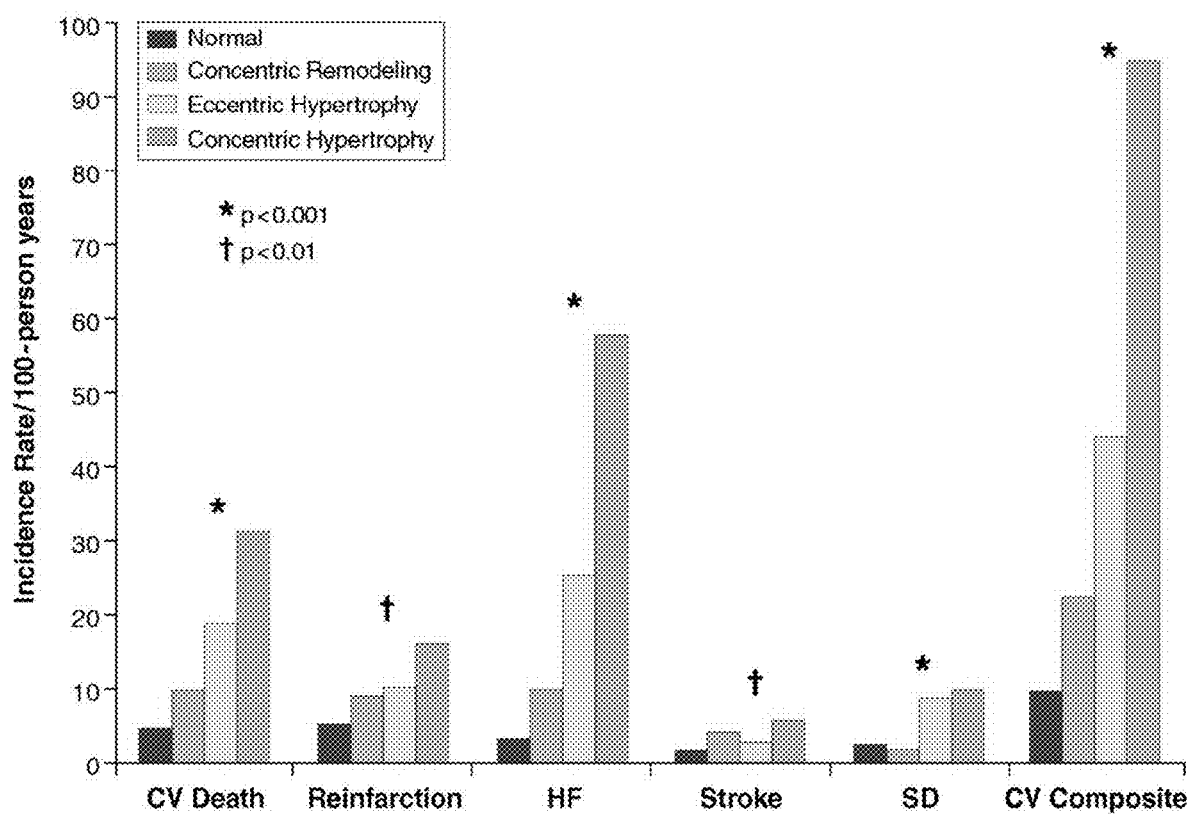
FIG. 35B is a bar graph showing experimental results where patients with any of the patterns of LV remodeling post-MI had a greater risk of the composite of cardiovascular (CV) death, MI, heart failure (HF), stroke, or resuscitated cardiac arrest.
Figure 37:
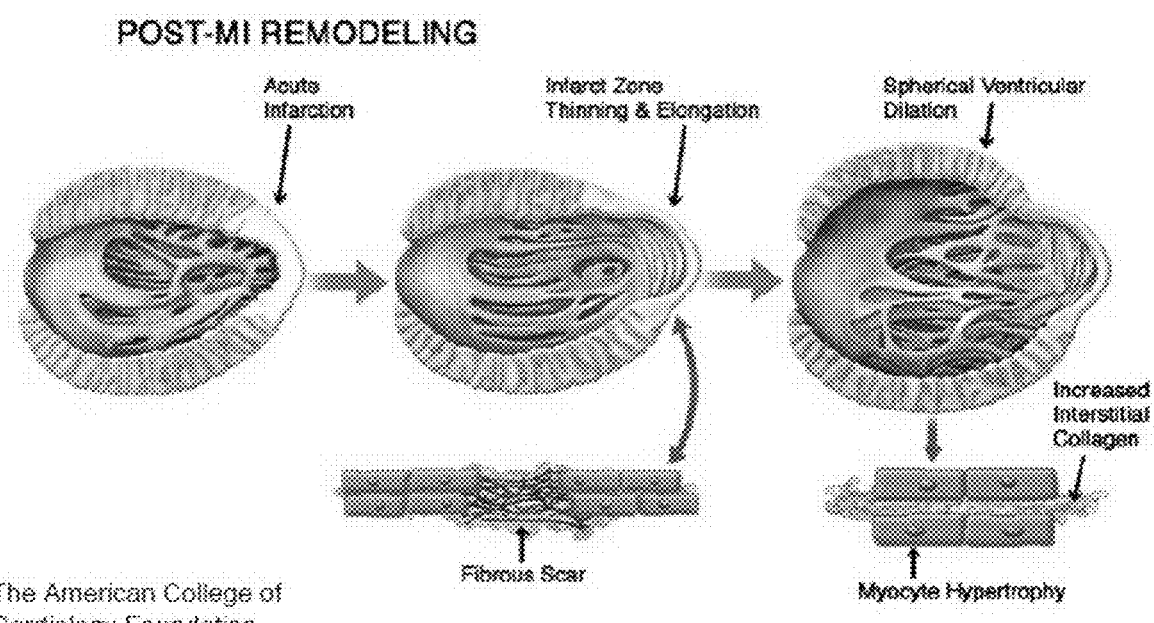
FIG. 37 is a schematic showing post-MI remodeling.
Figure 38:
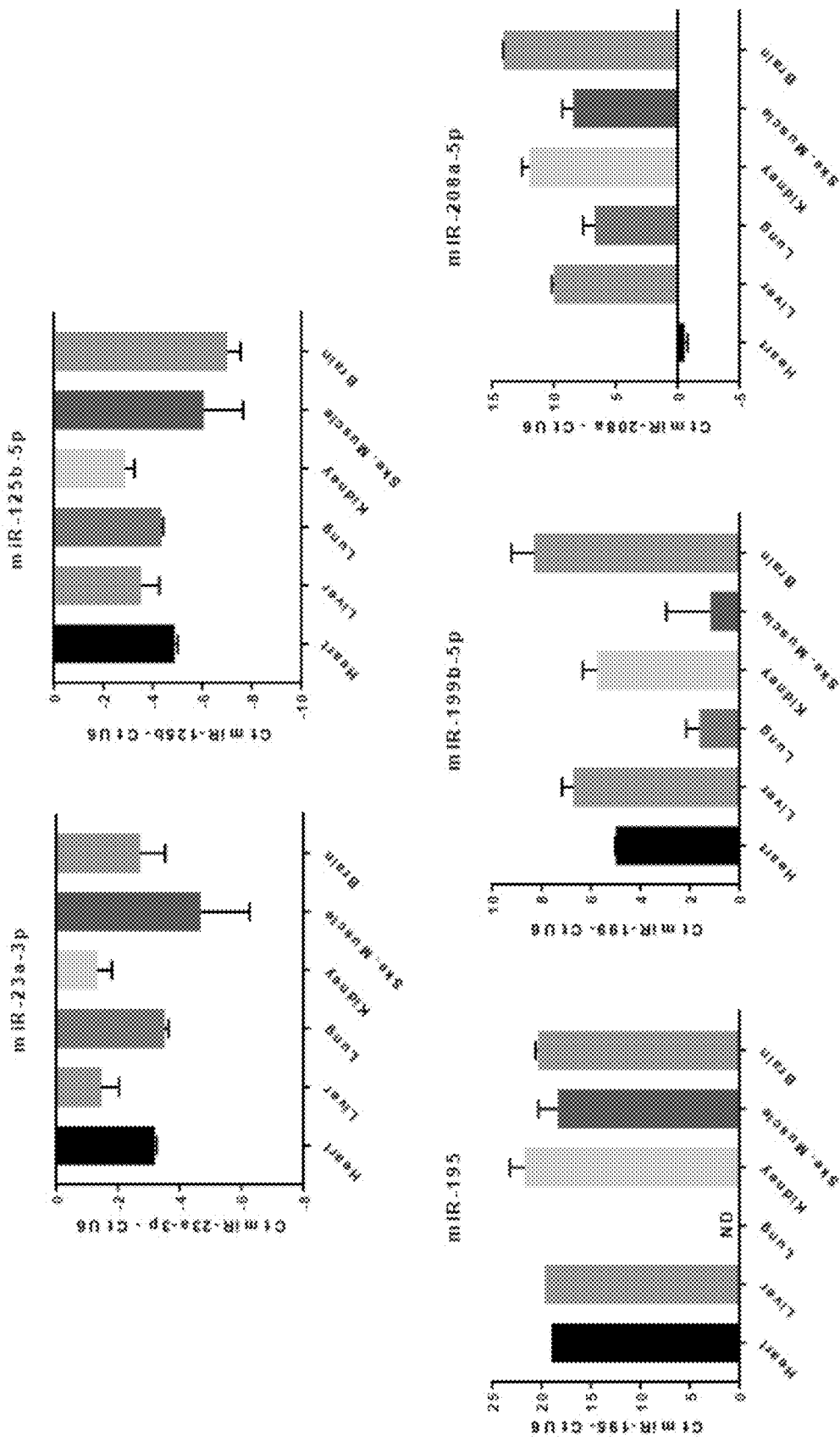
FIG. 38 is a series of bar graphs depicting experimental results of differential miRNA expression in tissues of wild-type mice in homeostasis.

Heart muscles downstream of the blockage lose oxygen, leading to injury and death of the muscle cells. Post-MI, the hypoxia and tissue damage induces left ventricular remodeling (FIGS. 35A, 37). Cardiac reperfusion results in inflammation and oxidative damage. The injuries to cardiomyocytes during MI can cause a cascade of biological signaling events that leads cardiomyocytes to increase in volume and undergo proliferation in a specific way that compromises the functioning of the heart. This hypertrophic response is driven by a complex interplay of factors including a maladaptive regeneration gene program. During maladaptive regeneration, the heart undergoes changes that induce detrimental conditions to the patient (FIG. 35B). The affected ventricle increases its volume, but the walls of the ventricle become thinner, and the ability of the heart to pump blood decreases over time. This can lead to a variety of serious problems, including heart failure, a second heart attack, or sudden death. Thus, this process is called maladaptive hypertrophy (as opposed to adaptive hypertrophy, which strengthens the heart in reaction to stimuli such as exercise).

Maladaptive cardiac hypertrophy can be ameliorated by drugs that inhibit calcineurin and histone deacetylase 2 (HDAC2), for example. However, these drugs can cause serious side effects in non-cardiac tissues. Therefore, it's necessary to have a method to restrict drug activity to the heart.

The specificity and versatility of the conditional small interfering RNAs (cond-siRNA) described herein offers a new class of therapeutics for a variety of diseases and cancers by hijacking the RNA interference (RNAi) pathway. Although current treatment options for post-MI cardiac hypertrophy alleviate the severity of the condition, it is necessary to target the internal maladaptive gene program that drives the hypertrophic responses. In particular, cond-siRNAs (FIG. 4) are sequenced with a signal and target strand that due to steric hindrance, will only activate when the appropriate cardiac hypertrophy signal is present-thus only targeting disease cells through toehold-mediated strand displacement.

The Cond-siRNAs described herein can achieve this by using cardiac RNA biomarkers of MI as activation signals to switch ON RNAi silencing against calcineurin or HDAC2. Using this approach, RNAi silencing of the target genes are restricted to cardiomyocytes that express MI associated RNA biomarkers. This means that RNAi activity will NOT occur in other organs and tissues where inhibition of the targets can cause serious side effects. In one aspect, disclosed herein is a strand-displacement operated, programmable conditional-siRNA complex that can be activated by specific mRNA and miRNA transcripts expressed in the hypertrophied myocardium, to target unrelated pro-hypertrophic pathways by RNAi knockdown.

To design an effective Cond-siRNA for treating Cardiac Hypertrophy, in vivo and/or in vitro screening approaches for measuring relevant gene expression may be used in accordance with the embodiments described herein.

Figure 11:
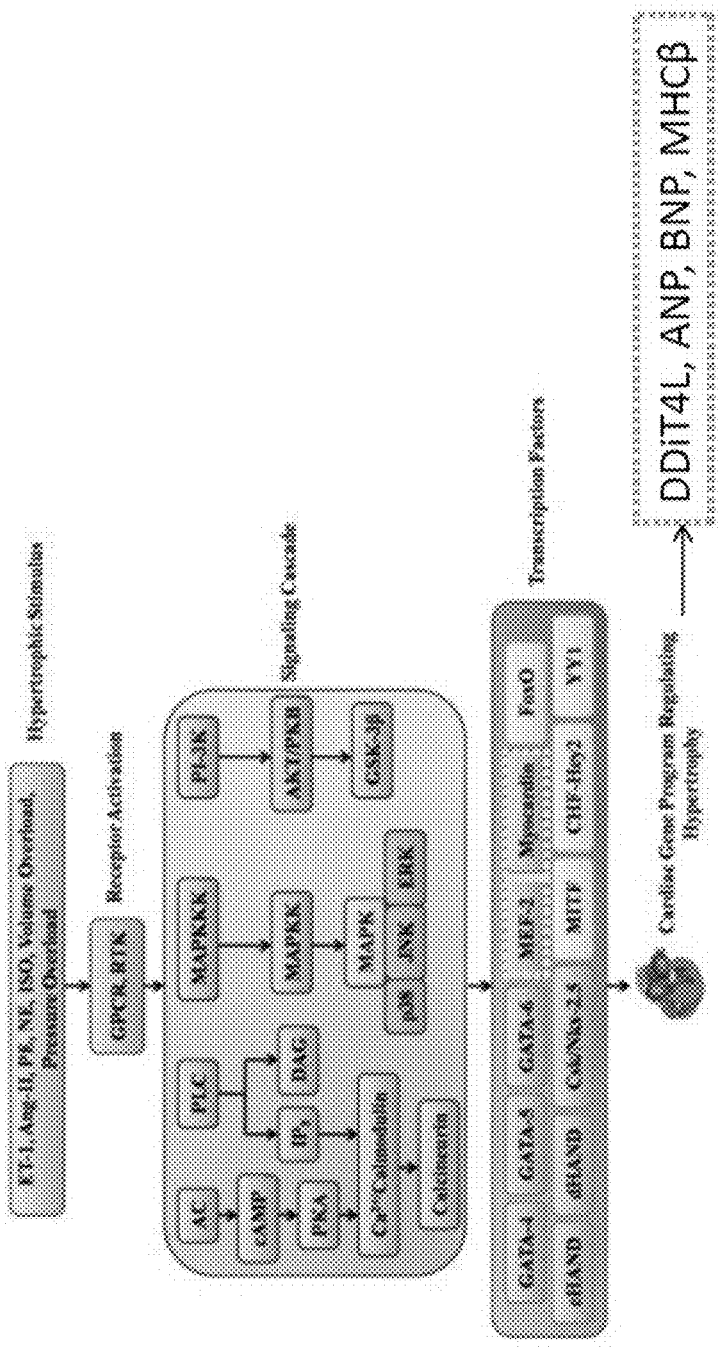
FIG. 11 is a schematic diagram of a signaling pathway involved in cardiac gene program regulating hypertrophy.

Certain genes are upregulated under pathological cardiac hypertrophic conditions, which may be candidate pathological biomarkers to guide a Cond-siRNA molecule to a population of target cells, and which can be used to displace the sensor strand of the Cond-siRNA. For example, certain signaling cascades are activated under hypertrophic stimulating conditions (see FIG. 11). For example, genes and miRNAs that are upregulated in pathological cardiac hypertrophy were screened for differential gene expression in wild type (wt) mice as well as under various hypertrophic conditions to determine which genes are suitable candidates for use as a target for designing a sensor strand. See working examples below In vitro screening approaches may include the use of a cardiomyocyte cell line (e.g., neonatal rat ventricular myocytes (NRVM), human cardiac myocytes (HCM)) cultured under hypoxic conditions or treated with phenylephrine. FIG. 12A. In vivo approaches may also be used including, but not limited to, rat models for ischemic heart failure (HF) (e.g., ischemia/reperfusion model), or rat models for non-ischemic HF (e.g., thoracic aortic constriction (TAC) model). See FIG. 12B.

Selection of RNA pathological biomarkers (input signals) for activation of Cond-siRNAs an important process for designing the cond-siRNA complexes described herein. The purpose of using pathological RNA biomarkers specific to the condition of cardiac hypertrophy for conditional RNAi activation is to ensure that RNAi activity is only active in cardiac tissues. Ideally, these biomarkers should be highly overexpressed in cardiac tissues affected by MI and not expressed in other tissues of the body. By comparing data gathered from in vitro and in vivo experiments on NRVM cell cultures and mice models with known organism wide expression patterns for the tested mRNAs and miRNAs (see working examples below), it was determined that at least three mRNAs and three miRNAs fit the criteria, including mRNAs that encode atrial naturetic peptide (ANP), B-type natriuretic peptide (BNP), and myosin heavy chain β (MHCP), and miRNAs that encode mir-23a-3p, mir-125-5p, and mir-199b-5p.

Thus therapeutic biomarkers that may be used to activate the conditional siRNA complexes in accordance with the embodiments described herein include, but are not limited to, mRNA biomarkers for MI affected cardiomyocytes, such as those described below.

In certain embodiments, a Cond-siRNA for treating cardiac hypertrophy includes a sensor strand designed to target a biomarker that is present and/or upregulated in heart cells (e.g., cardiac myocytes). Such biomarkers may include, but are not limited to, atrial naturetic peptide (ANP), B-type natriuretic peptide (BNP), myosin heavy chain β (MHCP), mir-23a-3p, mir-125-5p, and mir-199b-5p. In some aspects, the sensor strand detects an mRNA or an miRNA sequence that encodes the biomarker. And, in certain aspects, the sensor strand detects an mRNA sequence that encodes the biomarker by binding to the 3' UTR of the mRNA. Additional information regarding exemplary biomarkers is discussed below.

ANP (nppa) signal sensor strands. nppa (Natruiretic Peptide A) encodes for ANP protein that is overexpressed in hypertrophic conditions, thus is suitable as a biomarker for hypertrophy.

BNP (nppb) signal sensor strands. nppb (Natruiretic Peptide B) encodes for BNP protein that functions as a cardiac hormone and regulates natruiresis, diuresis, vasorelaxation and cardiovascular homeostasis. Low levels of BNP naturally found in the bloodstream in healthy individuals; high levels from cardiac ventricles. High concentrations of BNP in bloodstream indicates heart failure, and is a biomarker for hypertrophy. Thus, significant upregulation of BNP in induced cardiac hypertrophic conditions is indicative of effective sensor strand gene selection.

In some embodiments, a NPPB RH SSS v2.0 sensor was designed, wherein 31 bp sequence windows checked by hand through screening in entire 3' UTR of *Homo sapiens* mRNA based on A-U richness, hairpins, poly G tracts, and 8 bp toehold region. Three areas were found; NCBI Blast check for matches with other mRNAs and % yield of binding narrowed down options to chosen sensor (see NPPB sensor structures, FIG. 13).

MHC3 (myh7) signal sensor strands. MYH7 (myosin heavy chain 7) encodes for the p-heavy chain subunit of cardiac myosin. Varying amounts of the encoded protein correlate with cardiac muscle fiber contractile velocity. myh7 is predominantly expressed in the ventricle and type I muscle fibers. Gene mutations are associated with hypertrophic cardiomyopathy, and mybh7 is upregulated in pathological cardiac hypertrophy. A significant upregulation of myh7 is seen in induced cardiac hypertrophic conditions, indicating that myh7 is another potential sensor strand gene selection.

In some embodiments, a myh7 RH SSS v2.0 sensor was designed, wherein 31 bp sequence windows checked by hand through screening of entire *Homo sapiens* mRNA. Because 3' UTR of mRNA is short with numerous poly G tracts, screening went into the coding region; however those contained secondary structure. Only 1 area found and chosen; checked NCBI Blast for matches with other mRNAs (see, e.g., myh7 sensor structures, FIG. 14).

In some embodiments, the sensor strand is fully complementary to any of the biomarkers discussed above (i.e., 100% complementary). In some embodiments the sensor strand is partially complementary to any of the biomarkers discussed above. For example, the sensor strand may be at least 70% complementary to the biomarker, at least 70% complementary to the biomarker, at least 75% complementary to the biomarker, at least 80% complementary to the biomarker, at least 85% complementary to the biomarker, at least 90% complementary to the biomarker, at least 95% complementary to the biomarker, at least 96% complementary to the biomarker, at least 97% complementary to the biomarker, at least 98% complementary to the biomarker, or at least 99% complementary to the biomarker.

Further, the complementarity of the sensor strand to the biomarker may be matched to any 19-40 base segment of any variant of the mRNA sequence that encodes ANP (nppa), BNP (nppb), or MHCβ (myh7).

In other embodiments, the sensor strand includes one of the sequences in Table 1 below:

| SEQ ID NO | STRAND | BIO-MARKER | SEQUENCE |
|---|---|---|---|
| 1 | SENSOR | MIR-23A-3P | 5' CGAAGAACGGAAAUCCCUGGCAAUGTGAT 3' |
| 2 | SENSOR | MIR-23A-3P | 5' CGAAGAACGGAAAUCCCTGGCAATGTGAU 3' |
| 3 | SENSOR | MIR-23A-3P | 5' GGAGAAGAACGGAAAUCCCUGGCAAUGUGAU 3' |
| 4 | SENSOR | BNP | 5' AUCAGAAGCAGGUGUCUGCAGCCAGGACUUC 3' (used with HDAC2 - 2) + $\overline{2\ U}$ |
| 5 | SENSOR | BNP | 5' CUUGUGGAAUCAGAAGCAGGUGUCUGCAGCC 3' |
| 6 | SENSOR | BNP | 5' CAAAGGCGGCCACAGGGUUGAGGAAAAAGCC 3' |
| 7 | SENSOR | MHCβ/myh7 | 5' AUCUUGAUCUGCUCAGCCCUGGAGGUGCCAG 3' |
| 8 | SENSOR | ANP | 5' CAACAAGAUGACACAAAUGCAGCAGAGACCC 3' |
| 9 | SENSOR | ANP | 5' AUGACACAAAUGCAGCAGAGACCCCAGGGGA 3' |
| 10 | SENSOR | ANP | 5' CTUCACCACCUCUCAGTGGCAAUGCGACCAA 3' |

In certain embodiments, a Cond-siRNA for treating cardiac hypertrophy includes a guide strand designed to target a therapeutic RNAi target that is present and/or upregulated in heart cells (e.g., cardiac myocytes) and known to the field to ameliorate post-MI maladaptive hypertrophy, but whose systemic inhibition or expression may lead to unwanted side effects. In certain embodiments, therapeutic targets that may be used to design guide strands of Cond-siRNAs include, but are not limited to, Calcineurin [7-10] (or a subunit thereof, e.g., PPP3Ca, PPP3CB, PPP3CC, PPP3R1, PPP3R2), and HDAC2 [11, 12] or HDAC2 [11, 12]. In some aspects, the guide strand binds to an mRNA or an miRNA sequence that encodes the therapeutic target.

HDAC2 guide strands. HDAC2 (Histone deacetylase 2) functions as a central regulator in transcriptional regulation, cell cycle progression and developmental pathways by modifying chromatin structure. HDAC2 inhibition represses the maladaptive regeneration program through a pathway involving GSK3β, inhibiting the hypertrophic response. HDAC2 serves as a key cardiac hypertrophic regulator and a potential therapeutic target.

In some embodiments, an HDAC2 RH TGS v2.1 guide strand was designed, wherein a 23 base-pair sequence was taken from the HDAC2 *Homo sapiens* mRNA based on past research utilizing HDAC2-targeted siRNAs. Two U base pairs added to the 3' end. Four base pairs at 5' end purposefully changed to mismatch the mRNA in order to prevent potential improper Dicer cleavage and RISC complex loading incorporation. An NCBI Blast check was also done to check for matches with other mRNAs. See HDAC2 guide strand structures, FIG. 15

Calcineurin guide strands. Calcineurin is a major promoter of cardiac hypertrophy, and inhibition of Calcineurin has been found to reduce hypertrophy. And, since it's always present in ischemic cells, calcineurin is a good therapeutic target for the present invention.

In some aspects, the RNAi targeting segment of the guide strand (i.e., bases 1-21 from the 3' terminus) is fully complementary to any of the therapeutic targets discussed above (i.e., 100% complementary). In some aspects, the RNAi targeting segment of the guide strand (i.e., bases 1-21 from the 3' terminus) is partially complementary to any of the therapeutic targets discussed above. For example, the sensor strand may be at least 70% complementary to the biomarker, at least 70% complementary to the biomarker, at least 75% complementary to the biomarker, at least 80% complementary to the biomarker, at least 85% complementary to the biomarker, at least 90% complementary to the biomarker, at least 95% complementary to the biomarker, at least 96% complementary to the biomarker, at least 97% complementary to the biomarker, at least 98% complementary to the biomarker, or at least 99% complementary to any of the therapeutic targets discussed above. In other embodiments, bases 14-20 from the 3' terminus (the putative seed region of the guide strand) has at least 90% complementarity to the 3' UTR of an mRNA sequence that encodes at least a portion of a subunit of calcineurin (e.g., PPP3Ca, PPP3CB, PPP3CC, PPP3R1, PPP3R2) or HDAC2.

In certain embodiments, Cond-siRNAs that inhibit maladaptive hypertrophy are Cond-siRNAs that detect any biomarker from list A and target any member of list B in Table 2 below

TABLE 2

| List A-cardiomyocytes biomarkers | List B-anti-maladaptive hypertrophy targets |
| --- | --- |
| ANP (nppa) | Calcineurin |
| BNP (nppb) | HDAC2 |
| MHCβ (myh7) | |
| mir-23a-3p | |
| mir-125-5p | |
| mir-199b-5p | |

Thus, according to some embodiments, the Cond-siRNA described herein may have a sensor strand that is mostly or completely complementary to a sequence of the RNA transcripts corresponding to biomarkers listed in A, and a guide strand that targets a member of list B in the manner described above.

In other embodiments, the sensor strand includes one of the sequences in Table 3 below:

| SEQ ID NO | STRAND | THERAPEUTIC TARGET | SEQUENCE |
| --- | --- | --- | --- |
| 11 | GUIDE | CALCINEURIN | 5' CGAGUGUUGUUUGGCUUUUCCUGUU 3' (green: change from C to G) |
| 12 | GUIDE | CALCINEURIN | 5' CGAGUGUUGUUUGGCUUUUCCUGUU 3' |
| 13 | GUIDE | HDAC2 | 5' GCACUUAGAUUGAAACAACCCAGUU 3' |
| 14 | GUIDE | HDAC2 | 5' UGUUAUCUGGUGU UAUUGACCGU 3' |
| 15 | GUIDE | HDAC2 | 5' CGAGAUCUGGUGU UAUUGACCGU 3' (4 bp of 5' guide purposefully mismatched?) (used with BNP Sensor) |
| 16 | GUIDE | HDAC2 | 5' GCUCUUAGAUUGAAACAACCCAGUU3' |

In other embodiments, a Cond-siRNA for treating cardiac hypertrophy includes a core strand designed to connect the sensor to the guide strand according a method described above. IN certain aspects the core strand includes one of the sequences in Table 4 below:

| SEQ ID NO | STRAND | THERAPEUTIC TARGET | SEQUENCE |
| --- | --- | --- | --- |
| 17 | CORE | CALCINEURIN | 5' CGUUCUUCUC C-linker-CAGGAAAAGCCAAACAACACUCG-linker-GCCAGGGAUUUC 3' |
| 18 | CORE | CALCINEURIN | 5' GUCAUCUUGUUG-linker-CAGGAAAAGCCAAACAACACUCG-linker-GCUGCAUUUGU 3' |
| 19 | CORE | CALCINEURIN | 5' AGGUGGUGAAG-linker-CAGGAAAAGCCAAACAACACUCG-linker-AUUGCCACUGAG 3' |
| 20 | CORE | HDAC2 | 5' CGUUC UUCUC C CUGGGUUGUUUCAAUCUAAGUGC GCCAG GGAUU UC 3' |
| 21 | CORE | HDAC2 | 5' CCUGCUUCUGAU-linker-ACGGUCAAUAACACCAGAUCUCG-linker-GGCUGCAGACA 3' (used with BNP Sensor) |
| 22 | CORE | HDAC2 | 5' GAUUCCACAAG-linker-ACGGUCAAUAACACCAGAUCUCG- linker-ACACCUGCUUCU 3' |
| 23 | CORE | HDAC2 | 5' GGCCGCCUUUG-linker-ACGGUCAAUAACACCAGAUCUCG-linker-CCUCAACCCUGU 3' |

-continued

| SEQ ID NO | STRAND | THERAPEUTIC TARGET | SEQUENCE |
|---|---|---|---|
| 24 | CORE | HDAC2 | 5' GCAGAUCAAGAU-linker-ACGGUCAAUAACACCAGAUCUCG-linker-UCCAGGGCUGA 3' |
| 25 | CORE | HDAC2 | 5' GUCAUCUUGUUGCUGGGUUGUUUCAAUCUAAGAGCGCUGCAUUUGU 3' |
| 26 | CORE | HDAC2 | 5' CAUUUGUGUCAUUGUUAGAUUGAAACAACCCAGGGUCUCUGCUG 3' |

In some embodiments, the core strands above include O3 spacer linkers, where indicated, but any suitable linker may be used.

In certain embodiments, a Cond-siRNA for treating cardiac hypertrophy is a construct that includes a guide strand, core strand, and sensor strand as indicated in Table 5 below (also see FIGS. 16-17):

|  | SENSOR | CORE | GUIDE |
|---|---|---|---|
| CONSTRUCT 1 | BNP (SEQ ID NO: 4) | HDAC2 (SEQ ID NO 21) | HDAC2 (SEQ ID NO 15) |
| CONSTRUCT 2 | BNP (SEQ ID NO: 5) | HDAC2 (SEQ ID NO 22) | HDAC2 (SEQ ID NO 15) |
| CONSTRUCT 3 | BNP (SEQ ID NO 6) | HDAC2 (SEQ ID NO 23) | HDAC2 (SEQ ID NO 15) |
| CONSTRUCT 4 | MHCp/myh7 (SEQ ID NO 7) | HDAC2 (SEQ ID NO 24) | HDAC2 (SEQ ID NO 15) |
| CONSTRUCT 5 | ANP (SEQ ID NO 8) | HDAC2 (SEQ ID NO 25) | HDAC2 (SEQ ID NO 16) |
| CONSTRUCT 6 | ANP (SEQ ID NO 9) | HDAC2 (SEQ ID NO 26) | HDAC2 (SEQ ID NO 16) |
| CONSTRUCT 7 | ANP (SEQ ID NO 8) | Calcineurin (SEQ ID NO 18) | Calcineurin (SEQ ID NO 11) |
| CONSTRUCT 8 | ANP (SEQ ID NO 10) | Calcineurin (SEQ ID NO 19) | Calcineurin (SEQ ID NO 12) |
| CONSTRUCT 9 | MIR-23A-3P (SEQ ID NO: 1) | Calcineurin (SEQ ID NO 19) | Calcineurin (SEQ ID NO 12) |
| CONSTRUCT 10 | MIR-23A-3P (SEQ ID NO. 2) | Calcineurin (SEQ ID NO 19) | Calcineurin (SEQ ID NO 12)) |

In other embodiments, the conditional siRNA complex may comprise any combination of one sensor strand, one guide strand, and one core strand selected from Tables 1, 3, and 4, respectively. Additional embodiments of the conditional siRNA complex showing the full complex may be found in Appendix A, which is attached hereto.

Further, as described in the examples below, several mRNA and miRNA transcripts were screened under different pro-hypertrophic conditions both in vivo and in vitro, to assist with designing cond-siRNA complex strands.

Methods of Treatment

The cond-siRNA complexes described above may be used in methods to treat cardiac hypertrophy. Thus, in some embodiments, a method for treating cardiac hypertrophy is disclosed herein, wherein the method includes a step of administering to a subject a therapeutically effective amount of one or more of the cardiac hypertrophy-related cond-siRNAs described above. As disclosed herein, the subject may be any human or other animal suffering from post-MI cardiac hypertrophy, or any other type of cardiac hypertrophy.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The methods for treating cardiac hypertrophy include administering a therapeutically effective amount of a therapeutic composition. An "effective amount," "therapeutically effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21st Edition, Univ. of Sciences in Philadelphia (USIP), Lippincott Williams & Wilkins, Philadelphia, PA, 2005.

In some embodiments, one or more cond-siRNAs may be used alone or as part of a pharmaceutical composition for treating cardiac hypertrophy. Thus, in some embodiments, a pharmaceutical composition comprising any one or more of the cardiac hypertrophy-related Cond-siRNAs described above is disclosed. The therapeutic compositions may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

Figure 18:
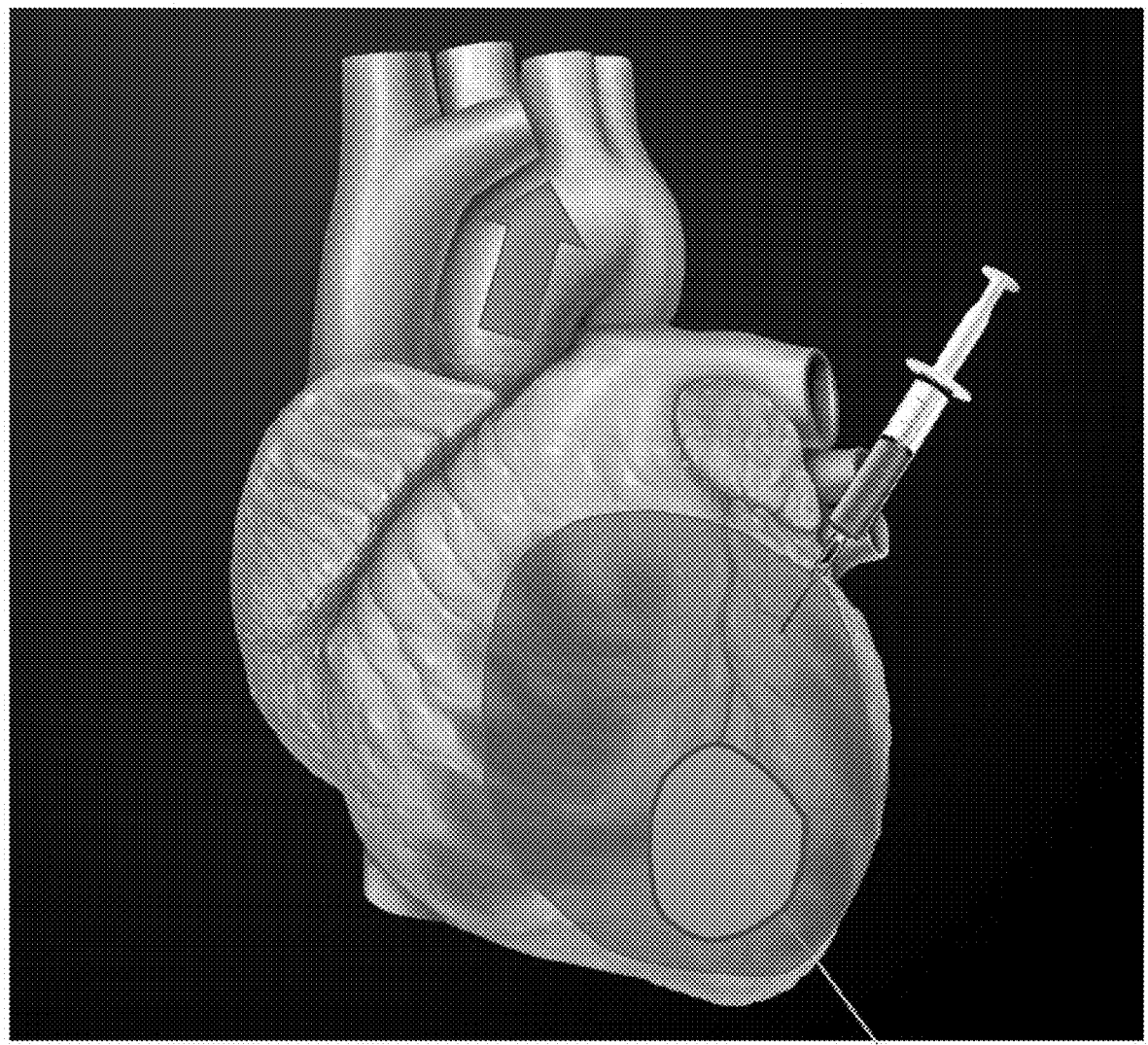
FIG. 18 is a schematic depicting a site of injury that can be targeted for treatment according to methods of the present invention.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In one embodiment the cardiac hypertrophy-related cond-siRNAs or therapeutic compositions thereof is administered by intracardial injection (FIG. 18) to ensure local delivery to the heart tissue.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein. All appendices A-E submitted herewith constitute part of the complete disclosure.

EXAMPLES

Example 1: Prohypertrophic Gene and miRNA Expression Screening for Selection of Sensor Candidates for Treatment of Cardiac Hypertrophy Genes and miRNA that are upregulated under pathological cardiac hypertrophic conditions were screened for differential expression in mice and in NRVM under various conditions to determine which molecules are suitable candidates for use as a biomarker target for designing a sensor strand.

Figure 19:
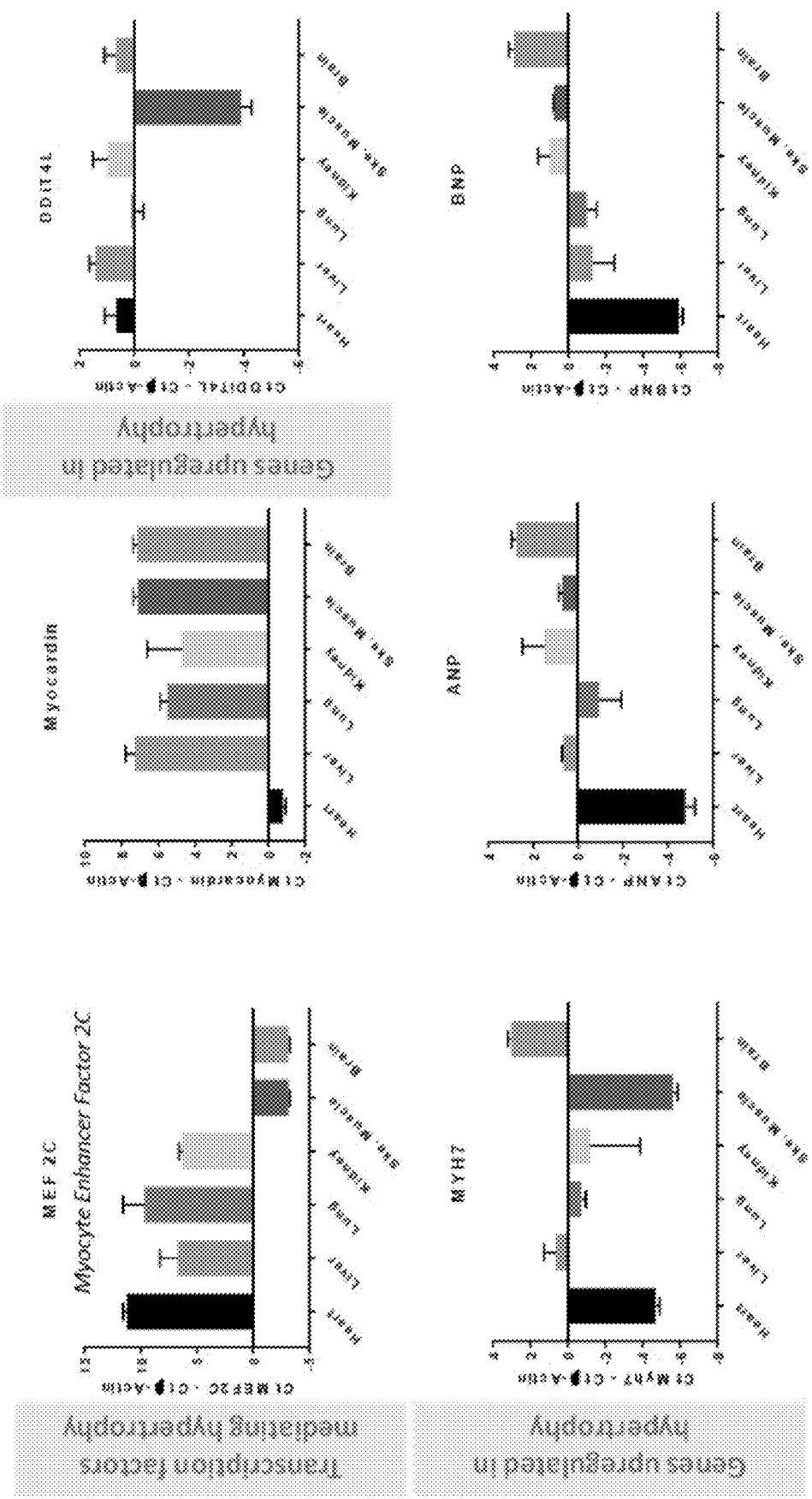
FIG. 19 is a series of bar graphs depicting experimental results of differential gene expression in tissues of wild-type mice in homeostasis.

Differential gene expression in tissues of wild type mice in homeostasis. Suitable pathological biomarker candidates should be differentially expressed in the heart as compared to other tissues to minimize off target effects. Several genes that are upregulated in pathological cardiac hypertrophy (DDiT4L, MYH7, ANP, BNP), as well as transcription factors that control their expression (MEF2C, Myocardin), were measured in normal heart, liver, lung, kidney, skeletal muscle, and brains of wt mice. FIG. 19. Several miRNA were also measured, as shown in 38

Differential gene and miRNA expression in NRVM under hypoxic conditions. Suitable pathological biomarker candidates (ANP, BNP, MYH7, MEF2C, Myocardin, DDiT4L, and miRNAs) were screened in NRVM for differential expression under hypoxic conditions as shown in FIGS. 20-21.

This experiment mimics oxygen deprivation (hypoxia) during myocardial infarction (MI). NRVM cells were prepared cultured on standard petri dish substrates using techniques known to those who are skilled in the art [1,2]. Cultured NRVM cells are then exposed to hypoxic conditions (0.2% $O_2$ atmosphere) for 24 hours at 37 C. This was followed by incubation for 12 hours under normal oxygen conditions (95% ambient air/5% $CO_2$).

Following incubation, NRVM cells were harvested and total RNA was extracted using protocols and kits standard in the art [3]. The messenger RNAs ANP, BNP, Myh7, MEF2C, Myocardin, DDiT4L, and the microRNAs mir-23a-3p, mir-125b-5p, mir-199b-5p, mir-208 and mir-195 were quantified by quantitative RT-PCR using standard methods appropriate for mRNAs4 and miRNAs [5].

Figure 20:
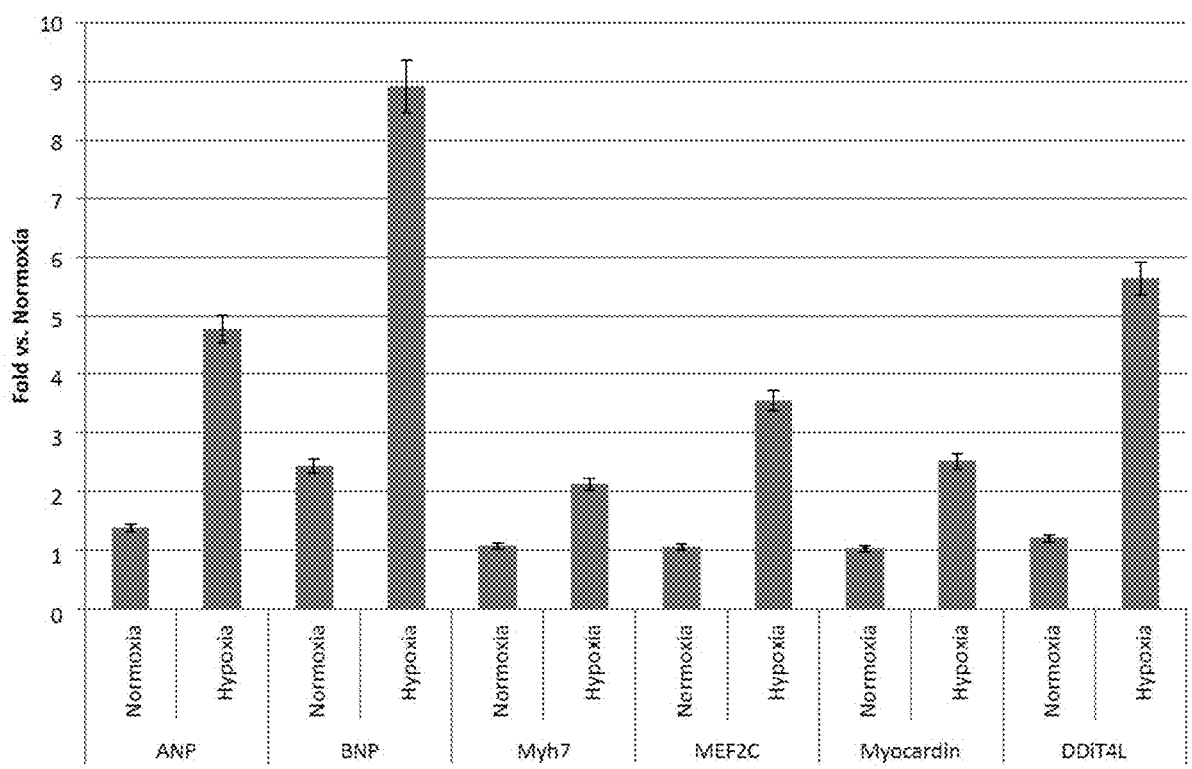
FIG. 20: Gene expression in NRVM under hypoxia.

Results are presented in FIGS. 20-21 as fold change in copy numbers of mRNA or miRNA present in NRVM cells exposed to hypoxia compared to those incubated for 36 hours under normal oxygen conditions.

The results of this experiment show that ANP, BNP, DDiT4L, mir-23a-3p, and mir-199b-5p, were over expressed by more than 4× under hypoxic conditions.

Differential gene and miRNA expression in NRVM after phenylephrine treatment. Expression of miRNAs, and of ANP, BNP, MYH7, MEF2C, Myocardin, DDiT4L was measured in phenylephrine (PE) treated as compared to untreated NRVM.

Phenylephrine stimulation is a standard method for studying hypertrophy in cardiomyocytes [6,7]. In this experiment, NRVM cells were prepared by standard protocols. Phenylephrine was then added to the culture media to 50 µM concentration for 24 hours. After 24 hours, cells were harvested for RNA isolation and analysis as described above.

Figure 22:
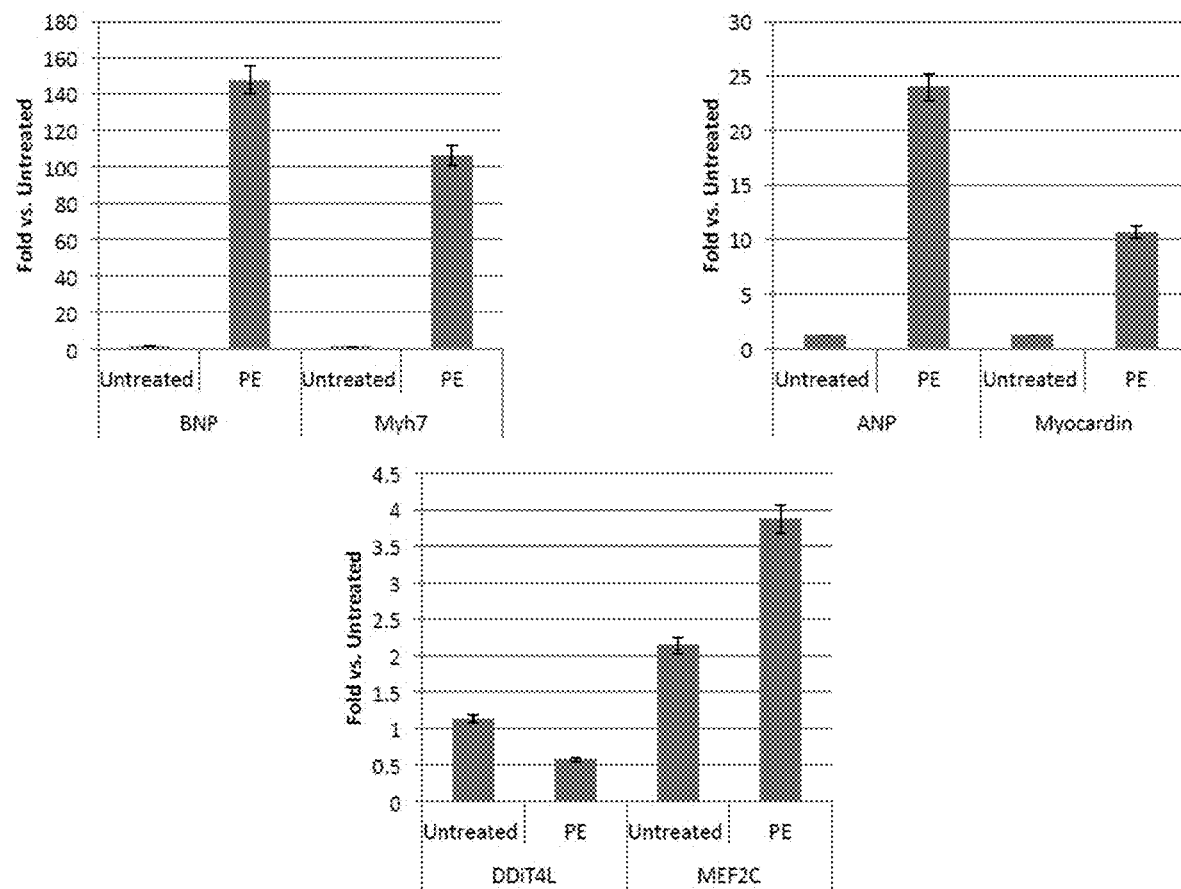
FIG. 22: Gene expression in NRVM after PE treatment.
Figure 23:
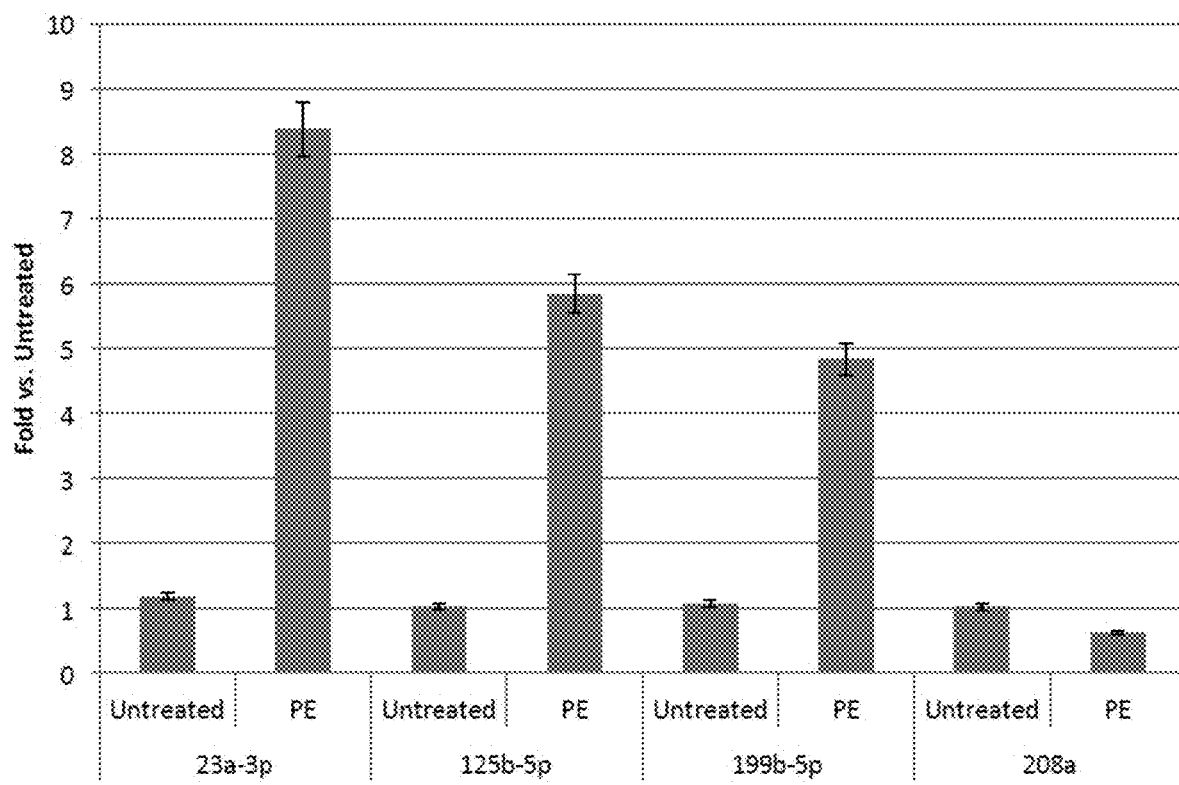
FIG. 23: Differential miRNA expression in NRVM after treatment with PE.

The results of the experiment show that ANP, BNP, Myh7, myocardin mRNA were overexpressed by more than 10× after PE stimulation (FIG. 22), and that miRNAs, mir-23a-3p, mir-125b-5p, and mir-199b-5p were overexpressed by more than 4× after PE stimulation (FIG. 23).

Differential gene expression in mouse models of heart failure. Expression of ANP, BNP, MYH7, MEF2C, Myocardin, DDiT4L was measured in heart tissue of mice with non-ischemic heart failure in a thoracic aortic constriction (TAC) model and of mice with ischemic heart failure in an ischemia/reperfusion (I/R) model as compared to sham-treated mice.

In experiments related to the ischemia/reperfusion (I/R) model, mice underwent procedures to simulate ischemic (deprivation of blood flow) heart failure. At day zero, mice were subject to ischemic heart failure via surgical clamping of a coronary artery for 20 min, followed by reperfusion. After 28 days, the experimental mice were sacrificed. Heart tissue was harvested and RNA was isolated using standard protocols as described above. mRNA and miRNAs were quantified using RT-PCR as described above. The mRNA and miRNA in the treated mice were compared with those found in control mice who were subjected to a sham procedure that did not involve clamping of the coronary artery to induce ischemia/reperfusion.

Figure 24:
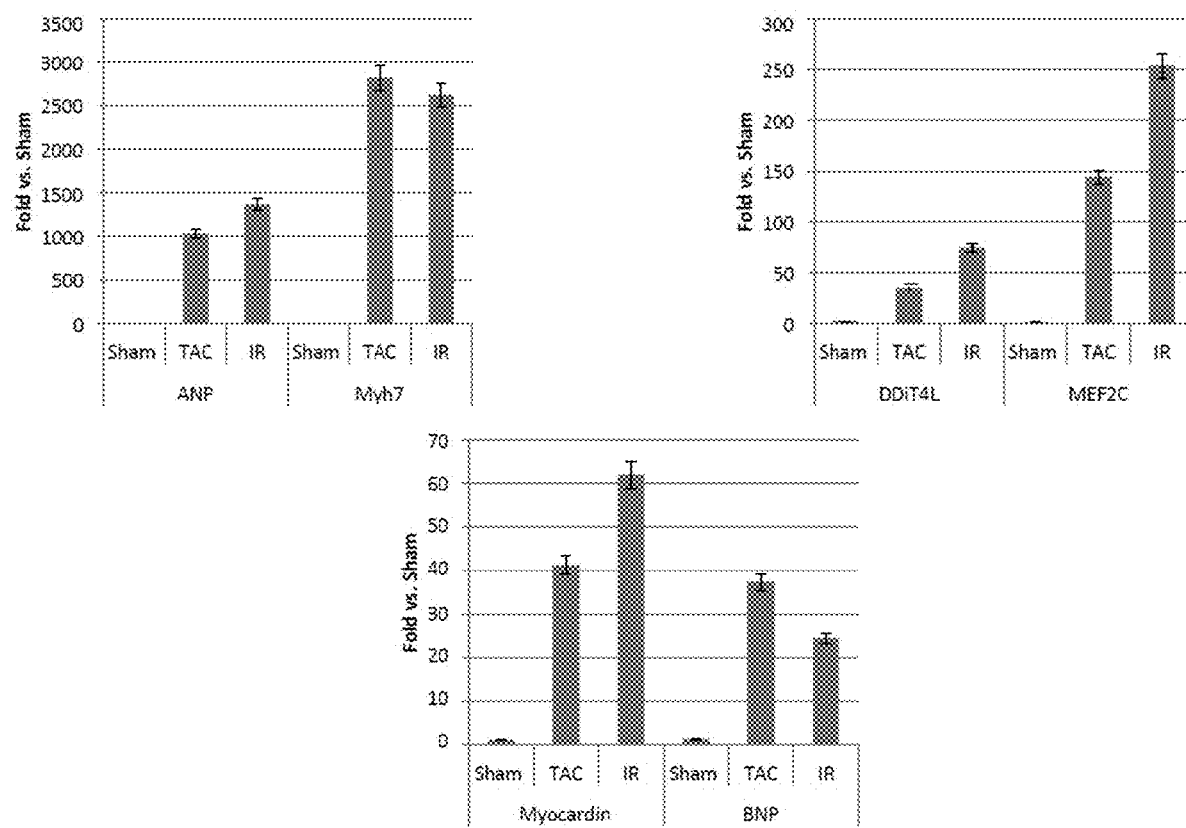
FIG. 24: Gene expression in mice with non-ischemic (TAC) and ischemic (I/R) HF.
Figure 25:
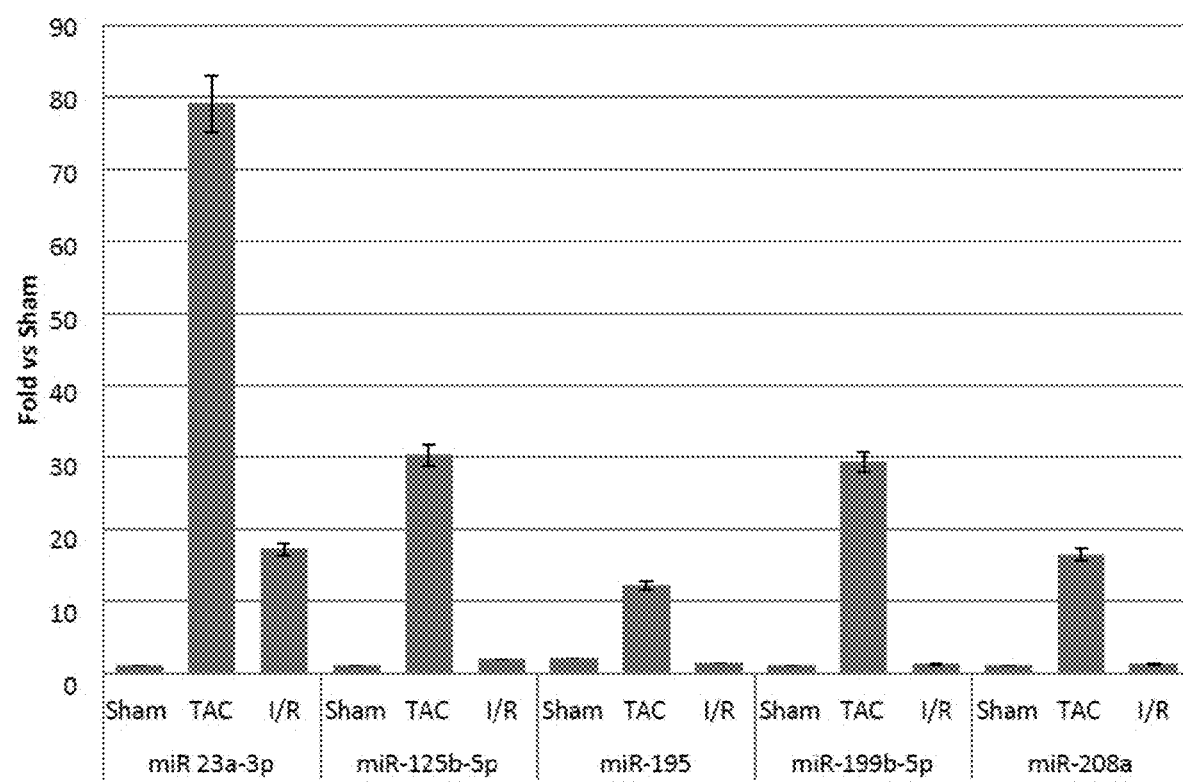
FIG. 25: miRNA expression in mice with non-ischemic (TAC) and ischemic (I/R) HF.

The results show that all mRNAs tested were overexpressed by more than 10× in mice with ischemic HF (FIG. 24). ANP and myh7 were overexpressed by more than 1000× (FIG. 24). And for miRNAs, only mir-23a-3p was significantly overexpressed, by ~15× (FIG. 25).

In experiments related to the non-ischemic HF model (TAC), mice underwent thoracic aortic constriction (TAC) procedures to induce non-ischemic heart failure. Briefly the upper thorax of mice constricted to reduce blood flow through the aorta for 28 days. This induced non-ischemic heart failure. After 28 days, the animals were sacrificed and heart tissue was harvested. RNA was isolated using standard protocols as described above. mRNA and miRNAs were quantified using RT-PCR as described above. The mRNA and miRNA in the treated mice were compared with those found in control mice who were subjected to a sham procedure that did not involve aortic constriction.

The results show that all mRNAs tested were overexpressed by more than 20× in the constricted mice (FIG. 24). ANP and myh7 were overexpressed by more than 1000× (FIG. 24). For miRNAs, all tested miRNAs were overexpressed by more than 10×. (FIG. 25). And, mir-23a-3p was overexpressed by ~80× (FIG. 25).

Example 2: Design of ANP:Calcineurin Cond-siRNA

The 5' UTR and coding sequences of messenger RNAs are frequently occupied by mRNA binding proteins or transiting ribosomes. In mammals, miRNAs commonly bind at 3' UTR sites to regulate mRNAs. Thus, binding sites in the 3' UTR may be more accessible than sites in the 5' UTR and the coding sequence of region of mRNAs.

When designing sensors to detect mRNAs, it is desirable to start with sites in the 3' UTR. If such sites cannot be found or there are other reasons (such as the need to detect a particular important sequence in the coding region or the 5' UTR), then sensors can be designed to those sites.

ANP 3'UTR sequencing results. Murine models were used to test the ability of ANP:Calcineurin Cond-siRNAs to inhibit phenylephrine induced cardiomyocytes hypertrophy. Thus, an ANP sensor was designed to target rat ANP.

To design the ANP sensor, the 3' UTR of ANP mRNA found in neonatal rat ventricular cardiomyocytes cells was sequenced by extracting RNA using standard procedures, amplifying the 3' UTR via RT-PCR, and submitting the amplified DNA for sequencing by the Massachusetts General Hospital's DNA sequencing core.

The sequenced DNA is as follows (N indicates indetermined base)

ANP 3'UTR sequencing results from CCIB DNA Core (MGH)
293387-293389_D10_1_074_nppa_3_UTR_Ane.seq
this is the forward sequence:

(SEQ ID NO: 27)
TCAGCCANNNNNNNNNNGAGCAGATCGCAAAAGATCCCAAGGCCTTGCG

GTGTGTCACACAGCTTGGTCGCATTGCCACTGAGAGGTGGTGAATACCC

TCCTGGAGCTGCAGCTTCCTGTCTTCATCTATCACGATCGATGTTAAGTG

-continued
TAGATGAGTGGTTTAGTGAGGCCTTACCTCTCCCACTCTGCATATTAAGG

TAGATCCTCACCCNNNNANNANNNNCNNNNNNNNNNNNNNNNNNNNNN

NNNNNNNN

Using NCBI BLAST, it was determined that the central sequence (SEQ ID NO: 28)
GAGCAGATCGCAAAAGATCCCAAGGCCTTGCGGTGTGTCACACAGCTTGG

TCGCATTGCCACTGAGAGGTGGTGAATACCCTCCTGGAGCTGCAGCTTCC

TGTCTTCATCTATCACGATCGATGTTAAGTGTAGATGAGTGGTTTAGTGA

GGCCTTACCTCTCCCACTCTGCATATTAAGGTAGATCCTCACCC

Is 99% homologous to Rattus norvegicus nppa mRNA 3' UTR and 92% homologous to Mus musculus nppa mRNA 3' UTR.

Generation of Sensor Candidates:

To generate candidate sensor strands, the reverse complement of the above sequence was determined.

(SEQ ID NO: 29)
NNNNNNNNNNNNNNNNNNNNNNNNNNNNNNNNNGNNNNTNNTNNNNGGGTGAG

GATCTACCTTAATATGCAGAGTGGGAGAGGTAAGGCCTCACTAAACCACT

CATCTACACTTAACATCGATCGTGATAGATGAAGACAGGAAGCTGCAGCT

CCAGGAGGGTATTCACCACCTCTCAGTGGCAATGCGACCAAGCTGTGTGA

CACACCGCAAGG<u>C</u>CTTGGGATCTTTTGCGATCTGCTCNNNNNNNNNNTGGC

TGA

Then, a Python script was used to generate all possible consecutive 31 nt segments (8 nt for toehold, plus 23 nt for duplex region) of the central bold sequence (rat nppa 3 prime utr sensor.xlsx). These are the initial possible sensor sequences for this region (T needs to be converted to U). The python script is attached herewith as Appendix B.

The Python code that was generated performed following analyses for each sensor sequence: (i) add one demerit point for each occurrence of three or more consecutive Gs (eg: GGG, GGGG, GGGGG); (ii) add one demerit point for each occurrence of four or more consecutive A/Ts (eg: ATAT, AAAA, TTTT, TTAT, etc), (iii) calculate the percent of the sequence composed of G or Cs; and (iv) calculate the percent of the sequence accounted for by the most numerous three bases (e.g., out of A, G, C, T, if A, G and T are the most numerous in the sequence, what percent of bases are A, G or T).

Then the list of possible sensors were ranked by the following criteria, in order of importance: (i) least number of demerit points, preferably 0' (ii) highest 3 letteredness; and (iii) highest GC content (see, e.g., FIGS. 41-42)

The sequences on the ranked list were screened one by one for two qualities: (i) the hypothetical sensor duplex has high stability and correctness according to standard RNA secondary structure prediction codes; and (ii) the sensor strand has few significant matches to RNA transcripts other than nppa mRNA in rats and mice that extends from the toehold region (8 bases at 3') into more than 50% of the duplex region (bases 9 to 31 from the 3').

The following sensor sequence was identified as favorable:

(SEQ ID NO: 30)
<u>A</u>TTCACCACCTCTCAGTGGCAATGCGACCAA

Figure 26:
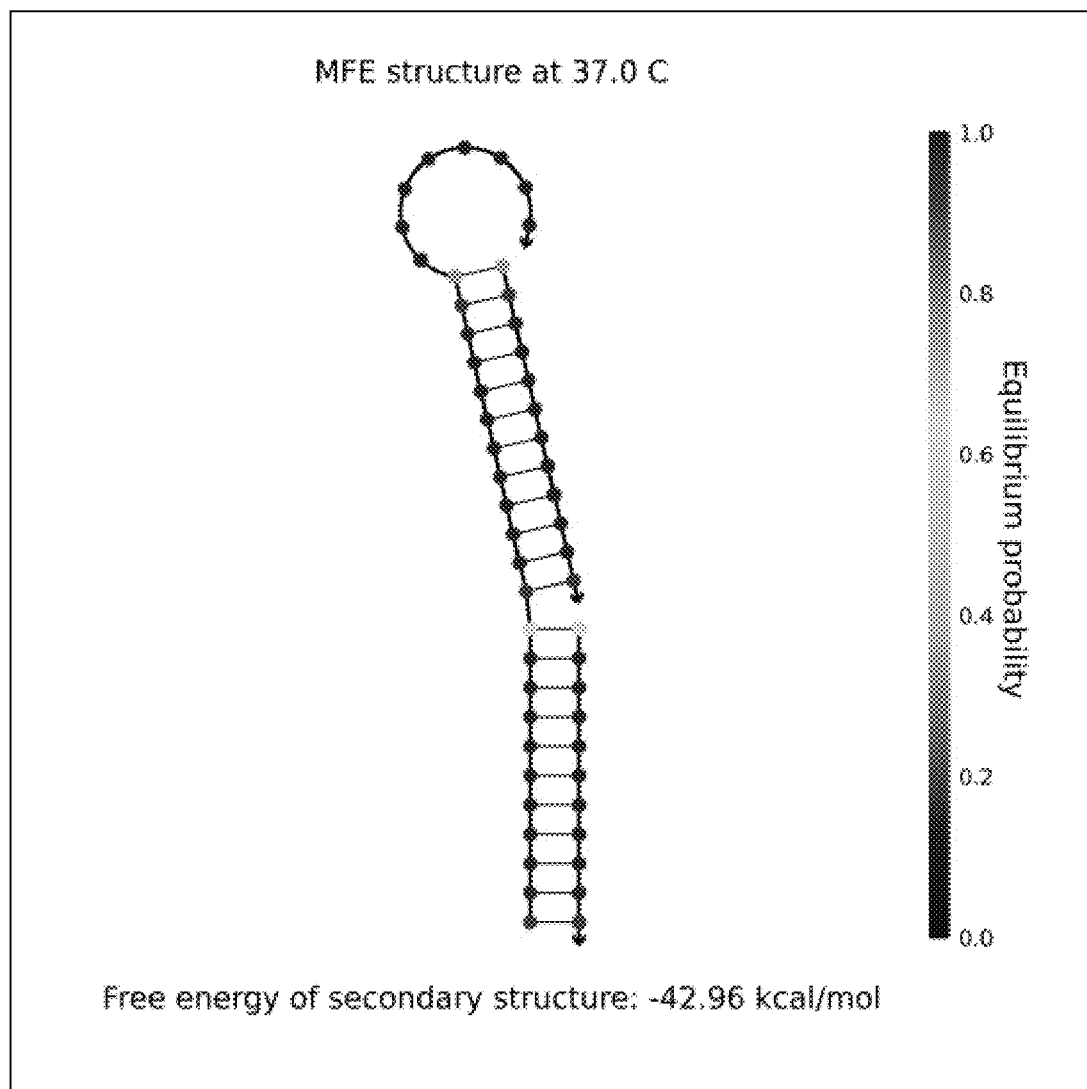
FIG. 26 shows an equilibrium probability for an MFE structure.

To further improve the thermodynamic stability of the sensor, the first base was changed at the 5' from an A to a C. This gives the following sensor sequence:

Sensor (mutated base underlined):
(SEQ ID NO: 31)
<u>C</u>UUCACCACCUCUCAGUGGCAAUGCGACCAA On nupack, the hypothetical sensor duplex constructed from this sequence showed 8 thermodynamic stability, with an equilibrium concentration of 0.97 nM. Also see FIG. 26.

NCBI BLAST of the sensor sequence using "somewhat similar" settings showed no significant sequence matches other than to mouse and rat ANP (nppa) mRNA.

Calcineurin is a heterodimer composed of one of three catalytic isozymes (PPP3CA, PPP3CB, PPP3CC) and one of two regulatory subunits (PPP3R1 and PPP3R2). To target Calcineurin, a guide sequence against the PPP3CA subunit of Calcineurin was identified that targets a widely conserved target site present in human, rat, and mice: UGUUGU UUGGCUU UUCCUG UU (SEQ ID NO:32)

The segment CGAG was then added to the 5' end to create a 23 nt guide strand, and then generated the core strand according to the previous stated rules. Those sequences are shown below:

Guide:
(SEQ ID NO: 11)
CG AG UGUUGU UUGGC UU UUCCUG UU

Figure 27:
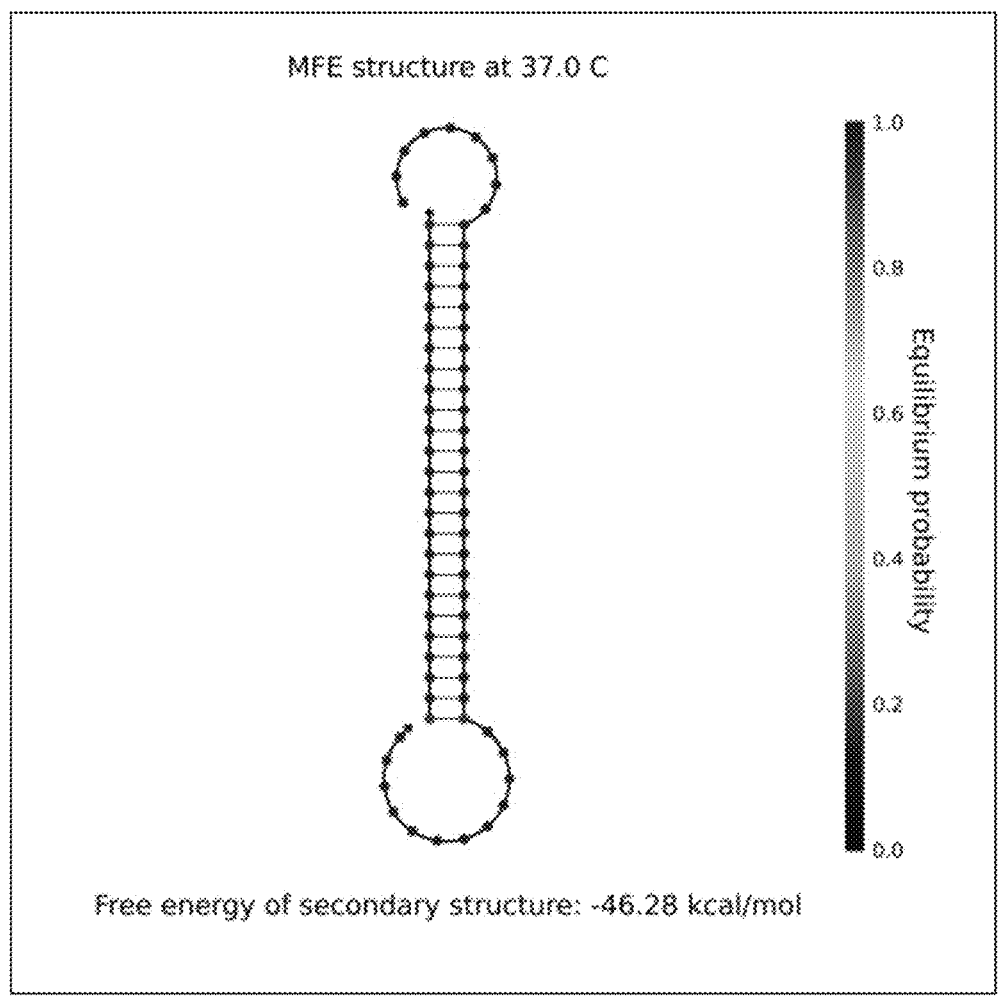
FIG. 27 shows an equilibrium probability for an MFE structure.

Sensor (mutated base underlined):
(SEQ ID NO: 33)
CUUCACCACCU CUCAGUGGCAAU GCGACCAA Core:
(SEQ ID NO: 19)
AGGUGGUGAAG-linker-CAGGAAAAGCCAAACAACACUCG-linker-
AUUGCCACUGAG The guide strand plus the core strand showed good thermodynamic stability as predicted by Nupack (FIG. 27)

Then, chemical modifications were added according to schemes previously disclosed in U.S. Pat. No. 9,725,715, the subject matter of which is incorporated by reference herein. The final sequences are shown below:

Sensor:
(SEQ ID NO: 34)
/5Sp9/mC*+T*mU*mC*+A*mC*mC*+A*mC*+C*mU*mC*mU*+C*mA

*mG*+T*mG*+G*mC*mA*+A*mU*mG*mC*+G*mA*mC*mC*+A*mA*/

3AmMO/

Guide:
(SEQ ID NO: 35)
/5AmMC6/+C*+G rArG rUrGrUrUrGrU rUrUrGrGrC rUrU rUrUrCrCrUrG rUrU Core:
(SEQ ID NO: 36)
mArGmGrUrGrGrUrGrArArG/iSpC3/mC*+A*mGrGrArArArArGr CrCrArArArCrArArCrArCrUrC*mG/iSpC3/rArUrUrGrCrCrAr CrUrGrAmG The nucleotides and modifications are indicated as follows: (1)+A, +T, +C, +G are LNA; (2) mA, mU, mC, mG are 2'-O-methyl; (3) rA, rU, rC, rG are RNA; (4) * denotes phosphorothioate backbone connection; (5) /5Sp9/ is a triethylene glycol linker; (6) /iSpC3/ is an internal C3 spacer; (7) /5AmMC6/ is a 5' primary amine modification on a C6 linker; (8) /3AmMO/ is a 3' primary amine modification.

Example 3: Design of mir-23a-3p:Calcineurin Cond-siRNA

An mir-23a-3p sensor was designed as follows. The mir-23a entry for miRbase is found at the following URL: http://www.mirbase.org/cgi-bin/mirna entry.pl?acc=M10000079
The sequence of mir-23a-3P sequence, 5'-3' is:

>hsa-miR-23a-3p MIMAT0000078
(SEQ ID NO: 37)
AUCACAUUGCCAGGGAUUUCC

The reverse complement of mir-23a-3p is GGAAAUCC-CUGGCAAUGUGAU (SEQ ID NO:38)

The Cond-siRNA sensor to sense a microRNA input is that the microRNA guide strand is usually only 21 nt long, whereas the Cond-siRNA sensor's duplex region is usually 23 nucleotides long and the toehold is usually 5 to 8 nucleotides long. This means that a microRNA guide strand is not long enough to completely displace the sensor strand from the core strand.

This issue was solved by configuring the sensor strand so that the guide strand will displace the sensor from base-pairing with the 3' overhang of the core strand and the last few bases at the 5' terminus of 5' overhang of the core strand.

This way, the 3' overhang of the core strand becomes unprotected and is degraded. The 5' terminus of the 5' overhang also becomes unprotected and subject to degradation, leading to eventual degradation of the entire 5' overhang. This then allows the sensor strand to completely dissociate from the RNAi region.

Thus, assuming a 21 nt miRNA guide strand, some of the possible geometries for the sensor strand, starting from the 3' end, are shown in Table 6 below:

| Scheme | Toehold length | Length bound to 3' core strand overhang | Length bound to 5' core strand overhang |
|---|---|---|---|
| A | 6 | 11 | 12 |
| B | 7 | 11 | 12 |
| C | 7 | 10 | 13 |
| D | 6 | 10 | 13 |
| E | 6 | 10 | 12 |
| F | 7 | 11 | 11 |

In Table 6, scheme A gives a 23 bp sensor duplex and allows the miRNA to displace up to 4 terminal bases of the 5' core strand segment, scheme B, 23 bp sensor, 3 terminal bases displaced, scheme C, 23 bp sensor, 4 terminal bases displaced, scheme D, 23 bp sensor, 5 terminal bases displaced, scheme E, 22 bp sensor, 5 terminal bases displaced, and scheme F, 22 bp sensor, 3 terminal bases displaced Calcineurin Sensor Design:

Scheme F from Table 6 was used to design the following calcineurin sensor:

```
                                        (SEQ ID NO: 39)
5' CGAAGAACGGAAAUCCCUGGCAAUGUGAU 3'
```

A sequence: CGAAGAAC (SEQ ID NO:40) is added to the 5' of the sensor. This sequence is designed to improve thermodynamic stability of the sensor duplex, minimize secondary structure in the sensor strand, and minimize overlap with non-mir23a-3p transcripts.

According to NCBI BLAST, the sensor has no significant unintended matches to human RNA transcripts, and there are only a few significant unintended matches to mouse RNA transcripts.

The same Calcineurin PPP3CA siRNA guide identified for the ANP: Calcineurin construct above was used and the core strand sequence was generated using the algorithms described herein.

```
Core:
                                        (SEQ ID NO: 41)
UCCGUUCUUCG-linker-CAGGAAAAGCCAAACAACACUCG-linker-

UGCCAGGGAUU
```

Figure 28:
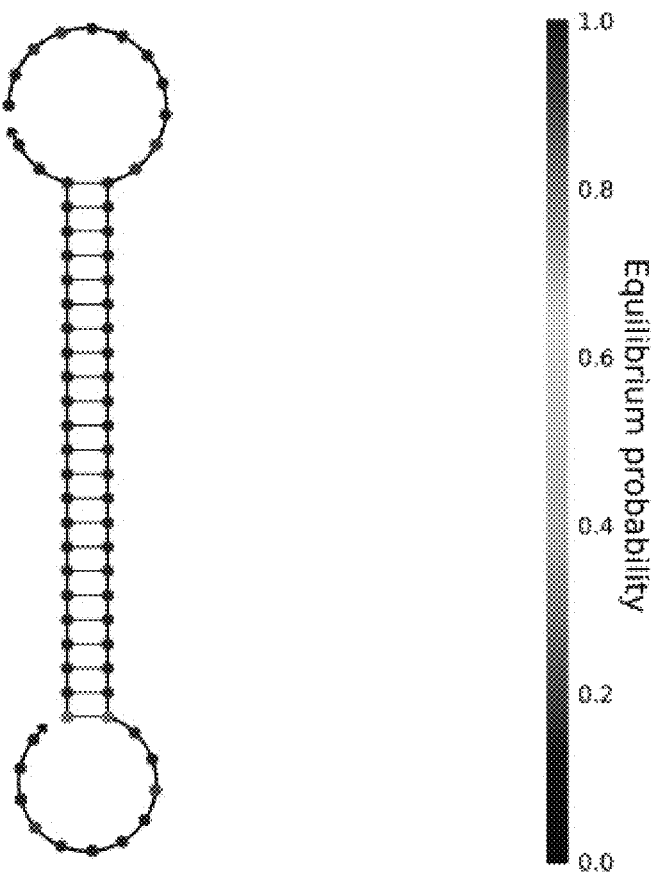
FIG. 28 shows an equilibrium probability for an MFE structure.
Figure 29:
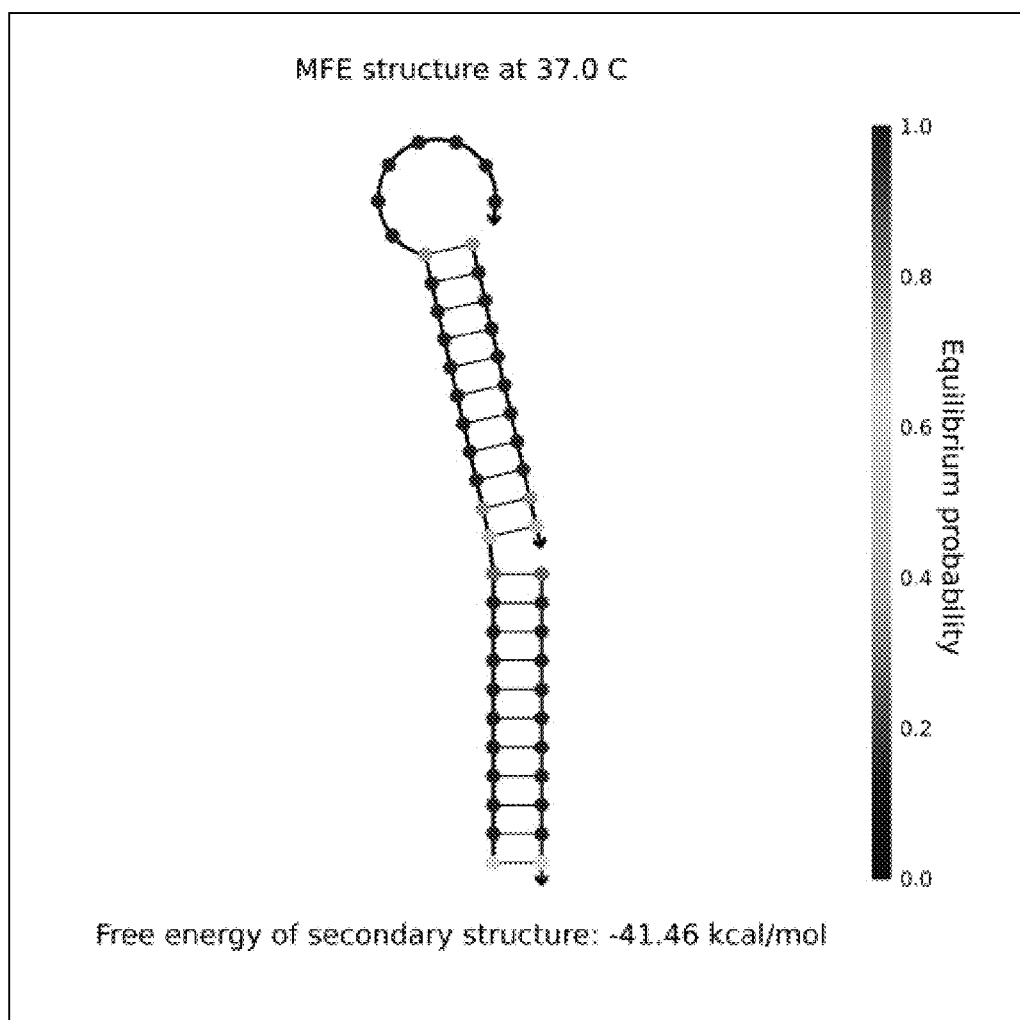
FIG. 29 shows an equilibrium probability for an MFE structure.

The guide strand plus the core strand showed good thermodynamic stability as predicted by Nupack (FIG. 28), as did the hypothetical sensor duplex (FIG. 29).

Thus, the final fully modified sequences are as follows:

```
Calcineurin guide:
                                        (SEQ ID NO: 42)
C6Amine+C*+GrArG rUrGrUrUrGrU rUrUrGrGrC rUrU rUrUrCrCrUrG rUrU Mir-23a-3p sensor using a 22 bp sensor duplex
with LNA pattern:
                                        (SEQ ID NO: 43)
/5Sp9/mC*+G*mA*+A*mG*mA+A*mC *+G*mG*mA*+A*mA*mU* mC*mC*+C*mU*mG*+G*mC*mA*+A*mU*mG*+T*mG*+A*+T*/

3AmMO/

Core strand:
                                        (SEQ ID NO: 44)
mUrCrCrGrUrUrCrUrUrCrG/iSpC3/mC*+A*mGrGrArArArArGr CrCrArArArCrArArCrArCrUrC*mG/iSpC3/rUrGrCrCrArGrGr G mA rU mU
```

The nucleotides and modifications are indicated as follows: (1) +A, +T, +C, +G are LNA; (2) mA, mU, mC, mG are 2'-O-methyl; (3) rA, rU, rC, rG are RNA; (3) * denotes phosphorothioate backbone connection; (4) /5Sp9/ is a triethylene glycol linker; (5) /iSpC3/ is an internal C3 spacer; (6) /5AmMC6/ is a 5' primary amine modification on a C6 linker; (7) /3AmMO/ is a 3' primary amine modification.

Example 4: Synthesis and Testing of Cond-siRNA Constructs

To demonstrate use of Cond-siRNAs to inhibit hypertrophy of cardiomyocytes, Cond-siRNAs were designed and synthesized to detect murine ANP or mir-23a-3p and inhibit calcineurin. The constructs are shown in FIGS. 16 and 17.

All strands were purchased from a commercial oligonucleotide vendor (Exiqon Inc, now a part of Qiagen).

Assembly and purification. Sensor, core, and guide strands were mixed at 1.0:1.1:1.0 ratios at 50 nM to 1 uM strand concentrations and underwent thermal annealing in 1×PBS buffer (80 C for 30 seconds followed by constant temperature incubation at 50 C to 60 C for ~1 hour followed by cooling to room temperature).

Where purification was desired, constructs were annealed at 500 nM, loaded at 20 uL per well in 10% non-denaturing PAGE. Run in 1×TBE buffer at 120V for 90 min. The correct bands were excised. The Cond-siRNA constructs were then extracted via the crush and soak method using standard RNA isolation kits.

Figure 30:
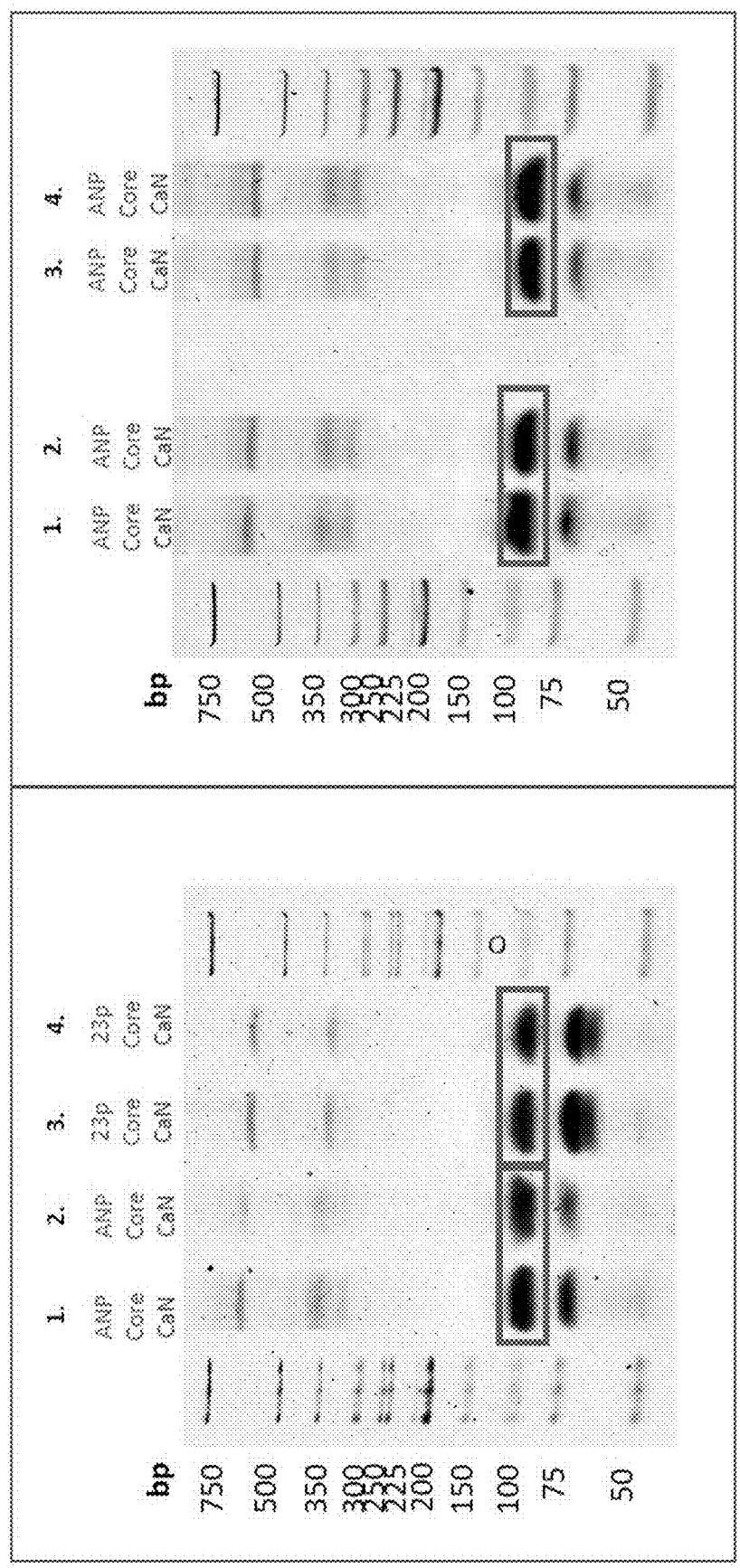
FIG. 30 shows (ANP:calcineurin) and (mir-23a-3p:calcineurin) Cond-siRNAs on 10% non-denaturing PAGE gel in TBE. The correct assemblies are indicated in the green boxes.

FIG. 30 shows an example gel where Cond-siRNAs were assembled and purified.

Figure 31:
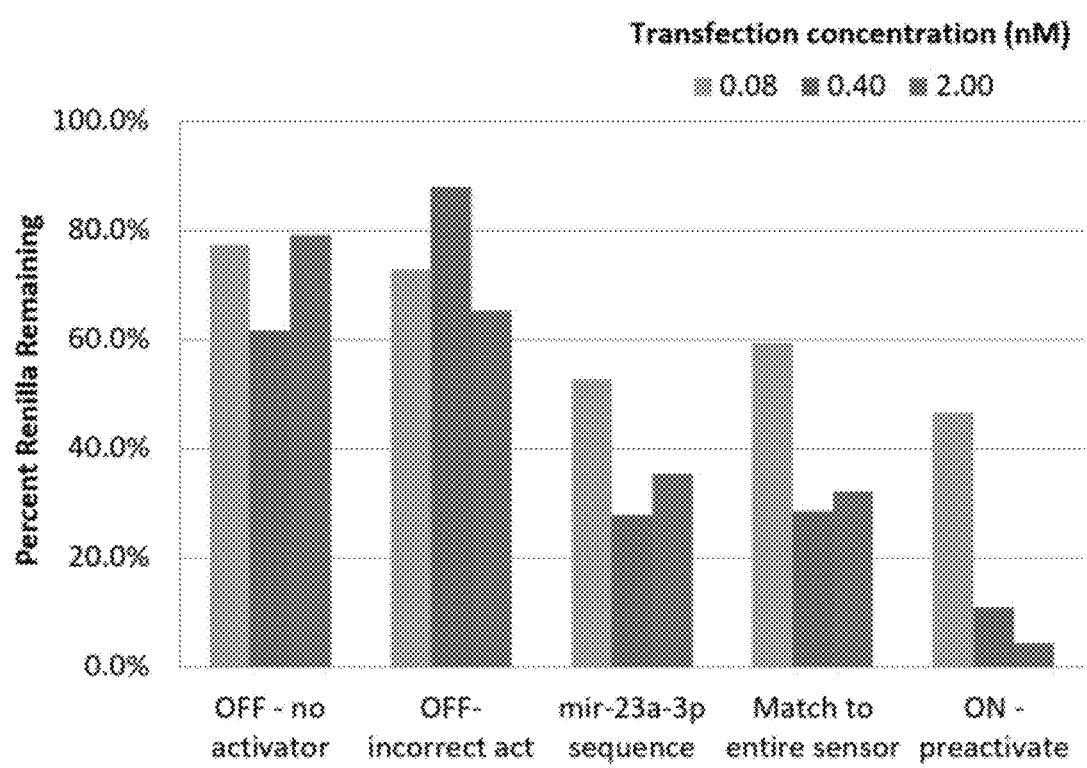
FIG. 31 shows results of a dual luciferase assay of mir-23a-3p calcineurin Cond-siRNA according to certain embodiments.

Dual luciferase assays of mir-23a-3p:calcineurin Cond-siRNA (FIG. 31). For this assay, the Cond-siRNA described above was assessed for its ability of to keep RNAi activity OFF in the absence of the correct biomarker and switching RNAi ON in the presence of RNA transcripts bearing the mir-23a-3p sequence. For this test, unpurified mir-23a-3p:calcineurin Cond-siRNAs was co-transfected at the indicated concentrations into human Hek 293 cells, along activator and dual luciferase plasmids.

The activator plasmids expressed either a null transcript, a transcript with an incorrect activator, the 21 base mir-23a-3p sequence, or a longer sequence that was complementary to the entire sensor strand.

The dual luciferase plasmid encoded Firefly luciferase as the control and a Renilla luciferase with the calcineurin target site in its 3' UTR as the target of RNAi.

The results show that this Cond-siRNA had significantly increased RNAi activity against the calcineurin target when either the mir-23a-3p sequence or the fully matching sequence was expressed. FIG. 31. Thus, this construct should be able to activation RNAi activity against calcineurin in the presence of mir-23a-3p.

in vitro experiment for purified ANP:calcineurin Cond-siRNA in NRVM cells under PE stimulation. For this experiment, it was tested whether the murine ANP calcineurin Cond-siRNA could detect overexpression of ANP upon phenylephrine (PE) stimulation, and activate RNAi knockdown against calcineurin.

The biological effects of ANP:calcineurin against murine biomarkers and targets is tested because there are no suitable human models to test against. The biological effect of this murine oriented Cond-siRNA should be representative of biological effects that Cond-siRNA configured for humans would have.

For this experiment, NRVM cells were incubated using standard protocols under normal conditions (95% air, 5% CO2, 37 C). The purified ANP: calcineurin Cond-siRNA was transfected at 20 nM concentration into NRVM cells using RNAiMax. The transfected cells were incubated for 24 hours. PE was then added to the media to 50 μM final concentration. After a further 48 hours, cells were harvested and stained or processed for RNA isolation.

Figure 32:
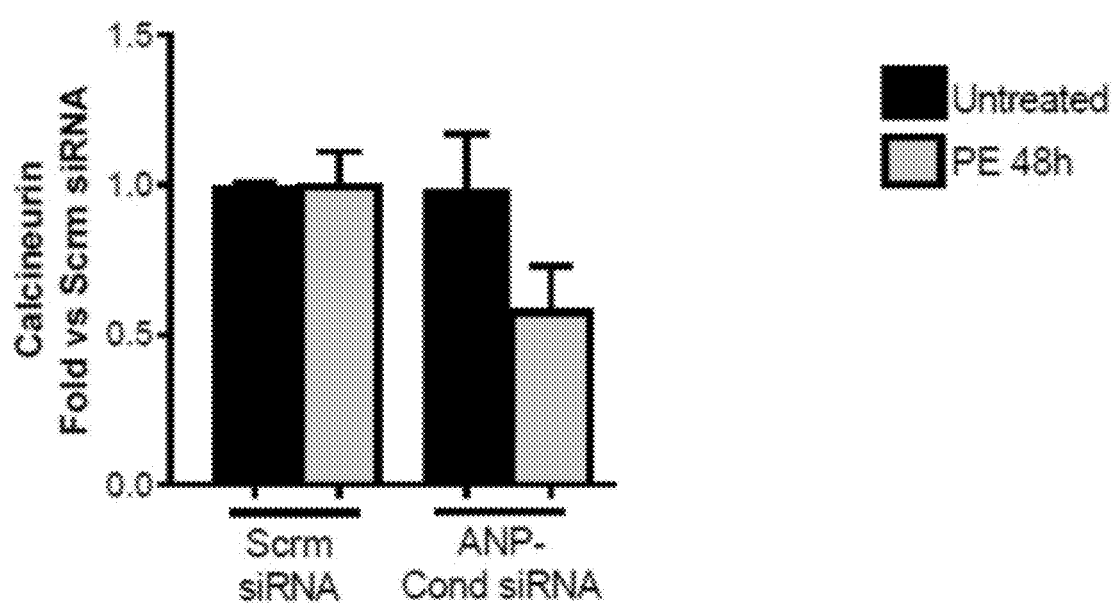
FIG. 32 is a bar graph showing RNAi activity against Calcineurin in NRVM cells under PE stimulation according to one embodiment.

The results for RT-PCR quantitation of calcineurin mRNA are shown in FIG. 32. For each cohort (untreated and PE treated cells), the level of calcineurin mRNA observed in cells transfected with scrambled siRNA (negative control) was normalized to 1.0. In the untreated cohort, cells transfected with ANP:Calcineurin Cond-siRNA had no detectable knockdown of calcineurin. This means that, as intended, the Cond-siRNA has very little RNAi activity in normal cells.

In cells treated with PE, the Cond-siRNA activated RNAi, and reduced calcineurin mRNA levels by ~ 50% compared with levels seen in cells transfected with the scrambled siRNA control. This shows that the ANP:calcineurin Cond-siRNA can detect overexpression of ANP mRNA, and respond with RNAi inhibition of calcineurin as intended.

Figure 33:
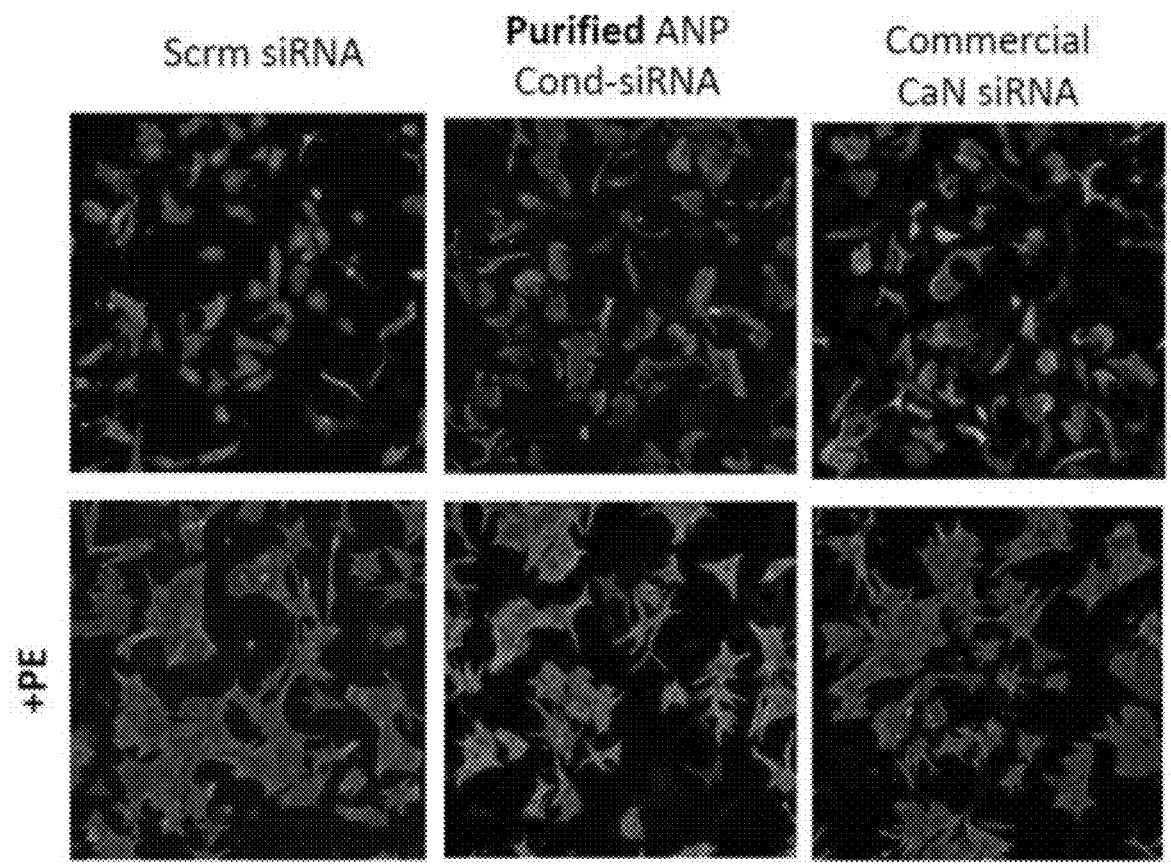
FIG. 33 shows images of NRVM cells with and without PE stimulation when treated with scrambled siRNA (negative control), (ANP:calcineurin) Cond-siRNA, and commercial calcineurin siRNA (positive control) according to one embodiment.

The results of imaging of the treated and untreated cells by fluorescence microscopy are shown in FIG. 33. The results show that cells treated with purified ANP:calcineurin Cond-siRNAs underwent less hypertrophy than cells treated with scrambled siRNA. Furthermore, the effects of treatment with Cond-siRNAs was similar to treatment with the positive control (commercial, non-conditional calcineurin siRNA).

Figure 34:
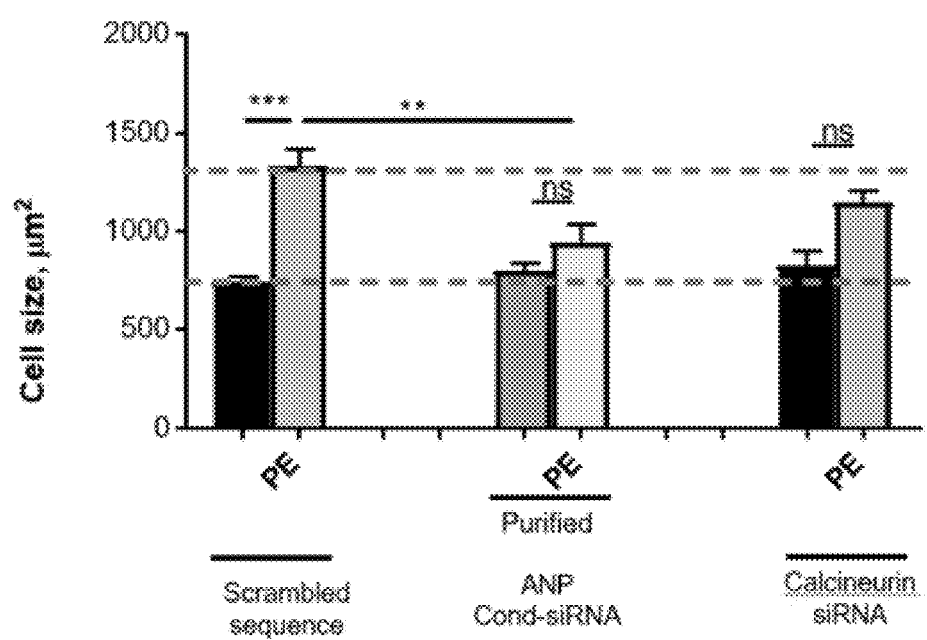
FIG. 34 shows results of cell size quantitation according to one embodiment.

The results of cell size quantitation using fluorescence microscopy are shown in FIG. 34. The results show that PE stimulation resulting in the increase in the average cell size from ~750 µm2 to ~1300 µm2 in cells treated with the negative control scrambled siRNA. However, in cells treated with the Cond-siRNA, average cell size increased from ~750 µm2 to ~900 µm2, and was not statistically significant. This result is similar to the non-conditional, commercial calcineurin siRNA.

The above results show that the ANP:Calcineurin Cond-siRNA has low background RNAi activity, can detect and respond to PE stimulation of NRVM cells, and has significant biological effects on reducing hypertrophy of NRVM cells.

Example 5: Exemplary Guide and Sensor Strand Sequences

Below are examples of automatically generating core strand sequences from guide and sensor strand sequences. These have 23 bp sensor duplexes with 8 base toeholds Example 5a, randomly chosen human/rat PPP3CA mRNA guide paired with randomly chosen human NPPA sensor

```
Cond-siRNA Guide:
                                        (SEQ ID NO: 45)
CCAC UUUACCAGCAUCUCAGUCAUU Cond-siRNA Sensor:
                                        (SEQ ID NO: 46)
GGAGAGGCGAGGAAGUCACCAUCAAACCACU Core is:
                                        (SEQ ID NO: 47)
CUCGCCUCUCC UGACUGAGAUGCUGGUAAAGUGGGAUGGUGACUUC
```

Example 5b, human/rat PPP3CA mRNA guide above paired with randomly chosen human NPPB sensor

```
Cond-siRNA Guide:
                                        (SEQ ID NO: 45)
CCAC UUUACCAGCAUCUCAGUCAUU Cond-siRNA Sensor:
                                        (SEQ ID NO: 48)
GGAAUCAGAAGCAGGUGUCUGCAGCCAGGAC Core is:
                                        (SEQ ID NO: 49)
CUUCUGAUUCC UGACUGAGAUGCUGGUAAAGUGGUGCAGACACCUG
```

Example 5c, human/rat PPP3CA mRNA guide above paired with randomly chosen human Myh7 sensor

```
Cond-siRNA Guide:
                                        (SEQ ID NO: 45)
CCAC UUUACCAGCAUCUCAGUCAUU Cond-siRNA Sensor:
                                        (SEQ ID NO: 50)
CCAAGGAGCUGUUACACAGGCUCCAGCAUGG Core is:
                                        (SEQ ID NO: 51)
CAGCUCCUUGG UGACUGAGAUGCUGGUAAAGUGGGAGCCUGUGUAA
```

Example 5d, randomly chosen human/rat HDAC2 mRNA guide paired with human NPPA sensor from example 1

```
Cond-siRNA Guide:
                                        (SEQ ID NO: 52)
CCAC UUCAUCACAAGCUAUCCGCUU Cond-siRNA Sensor:
                                        (SEQ ID NO: 46)
GGAGAGGCGAGGAAGUCACCAUCAAACCACU Core is:
                                        (SEQ ID NO: 53)
CUCGCCUCUCC GCGGAUAGCUUGUGAUGAAGUGGGAUGGUGACUUC
```

Example 5e, randomly chosen human/rat HDAC2 mRNA guide above paired with human NPPB sensor from example 2

```
Cond-siRNA Guide:
                                        (SEQ ID NO: 52)
CCAC UUCAUCACAAGCUAUCCGCUU Cond-siRNA Sensor:
                                        (SEQ ID NO: 48)
GGAAUCAGAAGCAGGUGUCUGCAGCCAGGAC Core is:
                                        (SEQ ID NO: 54)
CUUCUGAUUCC GCGGAUAGCUUGUGAUGAAGUGGUGCAGACACCUG
```

Example 5f, randomly chosen human/rat HDAC2 mRNA guide above paired with human Myh7 sensor from example 3

```
Cond-siRNA Guide:
                                        (SEQ ID NO: 52)
CCAC UUCAUCACAAGCUAUCCGCUU Cond-siRNA Sensor:
                                        (SEQ ID NO: 50)
CCAAGGAGCUGUUACACAGGCUCCAGCAUGG Core is:
                                        (SEQ ID NO: 55)
CAGCUCCUUGG GCGGAUAGCUUGUGAUGAAGUGG
GAGCCUGUGUAA
```

In the next examples, we reuse the guide from examples 1-6, but choose miRNA sensors. The sensors are configured as 22 bp duplexes with 7 base overhangs and symmetric 11 base core strand overhangs Example 5g, randomly chosen human/rat PPP3CA mRNA guide paired with mir-23a-3p sensor

```
Cond-siRNA Guide:
                                        (SEQ ID NO: 45)
CCAC UUUACCAGCAUCUCAGUCAUU Cond-siRNA Sensor:
                                        (SEQ ID NO: 39)
CGAAGAAC GGAAAUCCCUGGCAAUGUGAU Core is:
                                        (SEQ ID NO: 56)
UCCGUUCUUCG UGACUGAGAUGCUGGUAAAGUGG

UGCCAGGGAUU
```

Example 5h, human/rat PPP3CA mRNA guide above paired with mir-125b-5p sensor

```
Cond-siRNA Guide:
                                        (SEQ ID NO: 45)
CCAC UUUACCAGCAUCUCAGUCAUU Cond-siRNA Sensor:
                                        (SEQ ID NO: 57)
CGACAGU UCACAAGUUAGGGUCUCAGGGA Core is:
                                        (SEQ ID NO: 58)
GUGAACUGUCG UGACUGAGAUGCUGGUAAAGUGG

GACCCUAACUU
```

Example 5i, human/rat PPP3CA mRNA guide above paired with mir-195b-5p sensor

```
Cond-siRNA Guide:
                                        (SEQ ID NO: 45)
CCAC UUUACCAGCAUCUCAGUCAUU Cond-siRNA Sensor:
                                        (SEQ ID NO: 59)
CCUGAA GAACAGAUAGUCUAAACACUGGG Core is:
                                        (SEQ ID NO: 60)
UGUUCUUCAGG UGACUGAGAUGCUGGUAAAGUGG

UUUAGACUAUC
```

Example 5j, randomly chosen human/rat HDAC2 mRNA guide paired with mir-23a-3p sensor

```
Cond-siRNA Guide:
                                        (SEQ ID NO: 52)
CCAC UUCAUCACAAGCUAUCCGCUU Cond-siRNA Sensor:
                                        (SEQ ID NO: 39)
CGAAGAAC GGAAAUCCCUGGCAAUGUGAU Core is:
                                        (SEQ ID NO: 61)
AACAGCUCCUUGG GCGGAUAGCUUGUGAUGAAGUGG

GGAGCCUGUGU
```

Example 5k, randomly chosen human/rat HDAC2 mRNA guide above paired with mir-125b-5p sensor

```
Cond-siRNA Guide:
                                        (SEQ ID NO: 52)
CCAC UUCAUCACAAGCUAUCCGCUU Cond-siRNA Sensor:
                                        (SEQ ID NO: 57)
CGACAGU UCACAAGUUAGGGUCUCAGGGA Core is:
                                        (SEQ ID NO: 62)
UCCGUUCUUCG GCGGAUAGCUUGUGAUGAAGUGG

UGCCAGGGAUU
```

Example 5l, randomly chosen human/rat HDAC2 mRNA guide above paired with mir-195b-5p sensor

```
Cond-siRNA Guide:
                                        (SEQ ID NO: 52)
CCAC UUCAUCACAAGCUAUCCGCUU Cond-siRNA Sensor:
                                        (SEQ ID NO: 59)
CCUGAA GAACAGAUAGUCUAAACACUGGG Core is:
                                        (SEQ ID NO: 63)
UGUUCUUCAGG GCGGAUAGCUUGUGAUGAAGUGG

UUUAGACUAUC
```

Example 6: Exemplar siRNAs Designed by a Commercial siRNA Automated Design Website From: http://dharmacon.horizondiscovery.com/design-center/

For each category below, the design tool was tasked with designing siRNAs targeting the protein coding region of both the human and the rat mRNA. The top three candidates are shown. Cond-siRNA guides are made by adding 4 G/C rich bases to the 5' of the antisense strand.

Candidate siRNA guide strands sequences (antisense) and corresponding target sites (sense) targeting both Human (NM_000944) and Rat (NM_017041) PPP3CA mRNA

```
Sense:
                                        (SEQ ID NO: 64)
5' G.A.A.C.A.A.G.A.U.C.C.G.A.G.C.A.A.U.A.U.U 3'

Antisense:
                                        (SEQ ID NO: 65)
5' U.A.U.U.G.C.U.C.G.G.A.U.C.U.U.G.U.U.C.U.U 3'

Cond-siRNA Guide:
                                        (SEQ ID NO: 66)
5' CGACU.A.U.U.G.C.U.C.G.G.A.U.C.U.U.G.U.U.C.U.U 3'

Sense:
                                        (SEQ ID NO: 67)
5' U.G.A.C.U.G.A.G.A.U.G.C.U.G.G.U.A.A.A.U.U 3'

Antisense:
                                        (SEQ ID NO: 68)
5' U.U.U.A.C.C.A.G.C.A.U.C.U.C.A.G.U.C.A.U.U 3'
```

-continued

Cond-siRNA Guide:
(SEQ ID NO: 69)
5' CGACU.U.U.A.C.C.A.G.C.A.U.C.U.C.A.G.U.C.A.U.U 3'

Sense:
(SEQ ID NO: 70)
5' G.G.U.C.A.G.A.A.G.A.A.G.A.U.G.G.A.U.U.U.U 3'

Antisense:
(SEQ ID NO: 71)
5' A.A.U.C.C.A.U.C.U.U.C.U.U.C.U.G.A.C.C.U.U 3'

Cond-siRNA Guide:
(SEQ ID NO: 72)
5' CCACA.A.U.C.C.A.U.C.U.U.C.U.U.C.U.G.A.C.C.U.U 3'

Candidate siRNA guide strands sequences (antisense) and corresponding target sites (sense) targeting both Human (NM_001142353) and Rat (NM_017042) PPP3CB mRNA Sense:
(SEQ ID NO: 73)
5' G.C.U.A.U.A.G.A.A.U.G.U.A.C.A.G.A.A.A.U.U 3'

Antisense:
(SEQ ID NO: 74)
5' U.U.U.C.U.G.U.A.C.A.U.U.C.U.A.U.A.G.C.U.U 3'

Cond-siRNA Guide:
(SEQ ID NO: 75)
5' CGACU.U.U.C.U.G.U.A.C.A.U.U.C.U.A.U.A.G.C.U.U Sense:
(SEQ ID NO: 76)
5' C.C.U.U.U.A.A.G.C.A.G.G.A.A.U.G.U.A.A.U.U 3'

Antisense:
(SEQ ID NO: 77)
5' U.U.A.C.A.U.U.C.C.U.G.C.U.U.A.A.A.G.G.U.U 3'

Cond-siRNA Guide:
(SEQ ID NO: 78)
5' GGACU.U.A.C.A.U.U.C.C.U.G.C.U.U.A.A.A.G.G.U.U Sense:
(SEQ ID NO: 79)
5' G.C.A.A.U.U.G.G.C.A.A.G.A.U.G.G.C.A.A.U.U 3'

Antisense:
(SEQ ID NO: 80)
5' U.U.G.C.C.A.U.C.U.U.G.C.C.A.A.U.U.G.C.U.U 3'

Cond-siRNA Guide:
(SEQ ID NO: 81)
5' CCACU.U.G.C.C.A.U.C.U.U.G.C.C.A.A.U.U.G.C.U.U Candidate siRNA guide strands sequences (antisense) and corresponding target sites (sense) targeting both Human (NM_001243974) and Rat (NM_134367) PPP3CB mRNA Sense:
(SEQ ID NO: 82)
5' G.U.A.U.A.G.A.G.U.G.U.G.U.G.C.U.G.U.A.U.U 3'

Antisense:
(SEQ ID NO: 83)
5' U.A.C.A.G.C.A.C.A.C.A.C.U.C.U.A.U.A.C.U.U 3'

Cond-siRNA Guide:
(SEQ ID NO: 84)
5' CCACU.A.C.A.G.C.A.C.A.C.A.C.U.C.U.A.U.A.C.U.U 3'

Sense:
(SEQ ID NO: 85)
5' A.G.U.A.U.U.U.G.A.G.A.A.U.G.G.G.A.A.A.U.U 3'

Antisense:
(SEQ ID NO: 86)
5' U.U.U.C.C.C.A.U.U.C.U.C.A.A.A.U.A.C.U.U.U 3'

Cond-siRNA Guide:
(SEQ ID NO: 87)
5' CCACU.U.U.C.C.C.A.U.U.C.U.C.A.A.A.U.A.C.U.U.U 3'

Sense:
(SEQ ID NO: 88)
5' C.U.A.U.G.U.G.G.A.C.A.G.A.G.G.C.U.A.U.U.U 3'

Antisense:
(SEQ ID NO: 89)
5' A.U.A.G.C.C.U.C.U.G.U.C.C.A.C.A.U.A.G.U.U 3'

Cond-siRNA Guide:
(SEQ ID NO: 90)
5' CCACA.U.A.G.C.C.U.C.U.G.U.C.C.A.C.A.U.A.G.U.U 3'

Candidate siRNA guide strands sequences (antisense) and corresponding target sites (sense) targeting both Human (NM_001527) and Rat (NM_053447) HDAC2 mRNA Sense:
(SEQ ID NO: 91)
5' G.C.G.G.A.U.A.G.C.U.U.G.U.G.A.U.G.A.A.U.U 3'

Antisense:
(SEQ ID NO: 92)
5' U.U.C.A.U.C.A.C.A.A.G.C.U.A.U.C.C.G.C.U.U 3'

Cond-siRNA Guide:
(SEQ ID NO: 52)
5' CCACU.U.C.A.U.C.A.C.A.A.G.C.U.A.U.C.C.G.C.U.U 3'

Sense:
(SEQ ID NO: 93)
5' G.G.A.U.A.U.U.G.G.U.G.C.U.G.G.A.A.A.A.U.U 3'

Antisense:
(SEQ ID NO: 94)
5' U.U.U.U.C.C.A.G.C.A.C.C.A.A.U.A.U.C.C.U.U 3'

Cond-siRNA Guide:
(SEQ ID NO: 95)
5' CCACU.U.U.U.C.C.A.G.C.A.C.C.A.A.U.A.U.C.C.U.U 3'

Sense:
(SEQ ID NO: 96)
5' A.A.G.C.A.G.A.U.G.C.A.G.A.G.A.U.U.U.A.U.U 3'

Antisense:
(SEQ ID NO: 97)
5' U.A.A.A.U.C.U.C.U.G.C.A.U.C.U.G.C.U.U.U.U 3'

Cond-siRNA Guide:
(SEQ ID NO: 98)
5' CCACU.A.A.A.U.C.U.C.U.G.C.A.U.C.U.G.C.U.U.U.U 3'

Example 7: Example Designs for miRNA Sensor Strands

Example designs for miRNA sensor strands are shown below.

miRNAs have highly conserved sequences across mammalian species. Therefore, we can design a single miRNA sensor for all test animals, including humans.

For each sequence, we first take the reverse complement of the guide sequence, then add 8 bases to create a 29 nt sensor.

```
>hsa-miR-23a-3p MIMAT0000078
                              (SEQ ID NO: 37)
AUCACAUUGCCAGGGAUUUCC > reverse complement
                              (SEQ ID NO: 38)
GGAAAUCCCUGGCAAUGUGAU > Sensor, add 8 bases to make 29 mer
                              (SEQ ID NO: 39)
CGAAGAAC GGAAAUCCCUGGCAAUGUGAU
```

Nupack shows minimum secondary structure and no self-self base-pairing accept

```
>hsa-miR-125b-5p MIMAT0000423
                              (SEQ ID NO: 99)
UCCCUGAGACCCUAACUUGUGA > reverse complement
                              (SEQ ID NO: 100)
UCACAAGUUAGGGUCUCAGGGA > Sensor, add 7 bases to make 29 mer,
                              (SEQ ID NO: 57)
CGACAGU UCACAAGUUAGGGUCUCAGGGA
```

Use secondary structure prediction codes make sure that the secondary structure is relatively open. If not, change the added bases and try again

```
>hsa-miR-199b-5p MIMAT0000263
                              (SEQ ID NO: 101)
CCCAGUGUUUAGACUAUCUGUUC > reverse complement
                              (SEQ ID NO: 102)
GAACAGAUAGUCUAAACACUGGG > Sensor, add 6 bases to make 29 mer,
                              (SEQ ID NO: 59)
CCUGAA GAACAGAUAGUCUAAACACUGGG
```

Acceptably Low Secondary Structure

Example 8: miRNAs

Additional miRNAs are shown below:

```
>rno-miR-23a-3p MIMAT0000792
                              (SEQ ID NO: 37)
AUCACAUUGCCAGGGAUUUCC >hsa-miR-23a-3p MIMAT0000078
                              (SEQ ID NO: 37)
AUCACAUUGCCAGGGAUUUCC >rno-miR-23a-3p MIMAT0000792
                              (SEQ ID NO: 37)
AUCACAUUGCCAGGGAUUUCC >mmu-miR-125b-5p MIMAT0000136
                              (SEQ ID NO: 99)
UCCCUGAGACCCUAACUUGUGA >hsa-miR-125b-5p MIMAT0000423
                              (SEQ ID NO: 99)
UCCCUGAGACCCUAACUUGUGA >rno-miR-125b-5p MIMAT0000830
                              (SEQ ID NO: 99)
UCCCUGAGACCCUAACUUGUGA >hsa-miR-199b-5p MIMAT0000263
                              (SEQ ID NO: 101)
CCCAGUGUUUAGACUAUCUGUUC >mmu-miR-199b-5p MIMAT0000672
                              (SEQ ID NO: 103)
CCCAGUGUUUAGACUACCUGUUC
```

Figure 46:
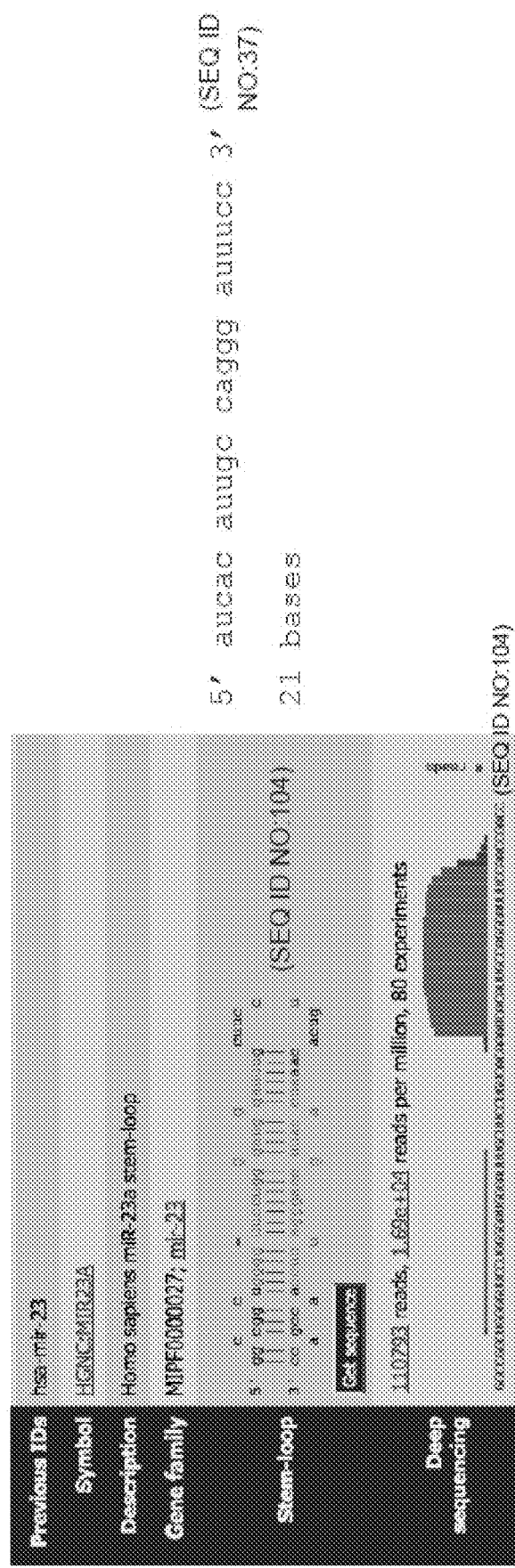
FIG. 46 shows the design of sensor miR-23-a-3p gene sequence.
Figure 47:
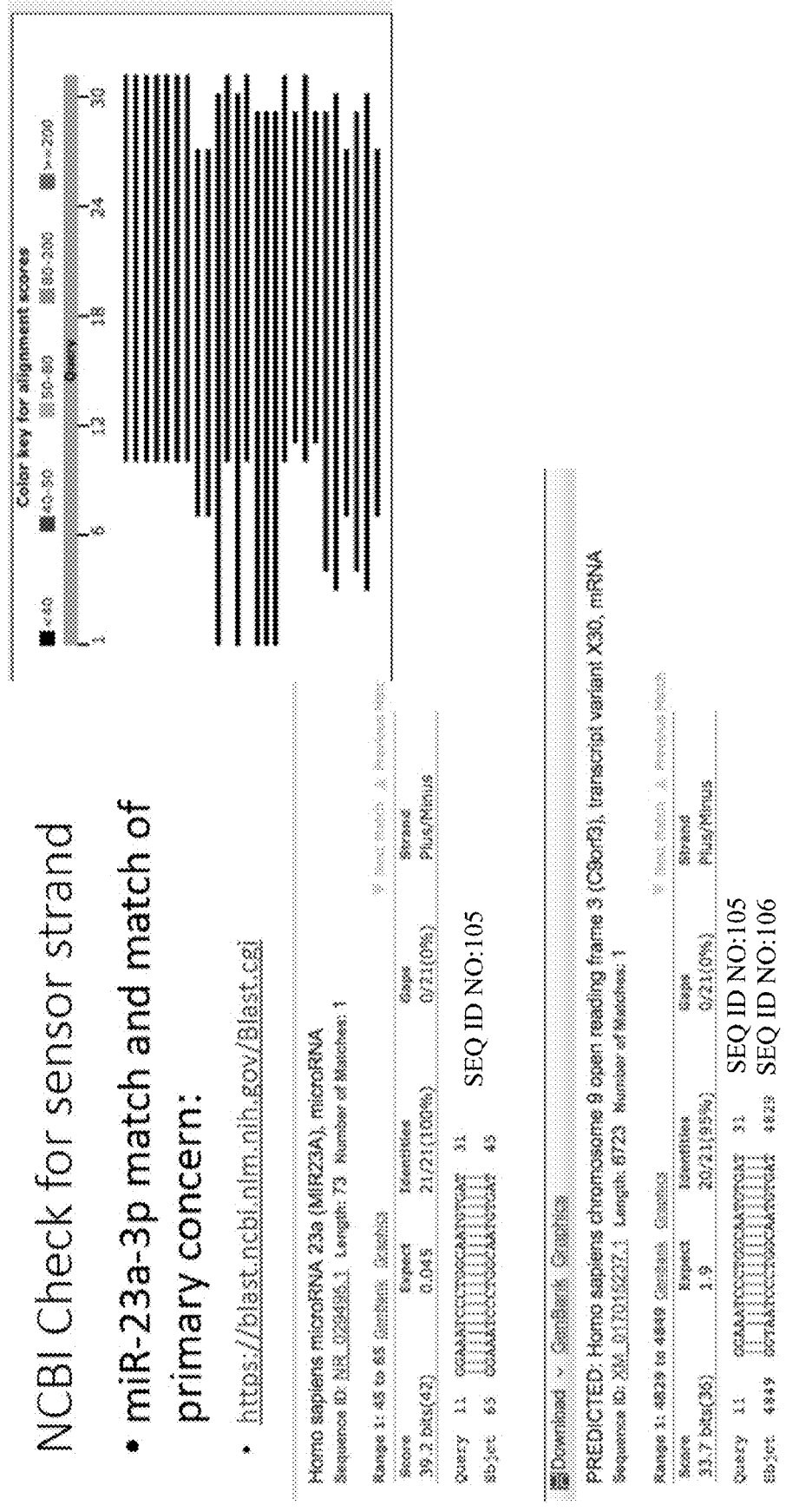
FIG. 47 illustrates NCBI check for sensor strand.
Figure 49:
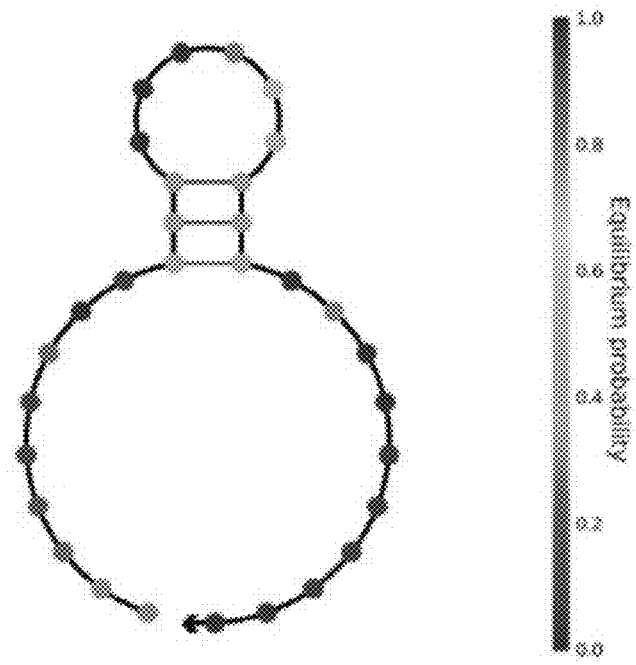
FIG. 49 shows the secondary structure and MFE structure at 37° C. of the full miR-23a-3p sensor strand with toehold for calcineurin.

Example 9: Design Review for Sensor Strand miR-23a-3p with Calcineurin and HDAC2 Targets FIG. 46 illustrates the design of sensor miR-23a-3p. FIG. 47 illustrates that the sequence of the sensor strand was checked against NCBI by blast. FIG. 48 illustrates that calcineurin and HDAC2 guide strand sequences are checked against NCBI by blast as well. FIG. 49 illustrates the secondary structure and MFE structure at 37° C. of the full miR-23a-3p sensor strand with toehold for calcineurin or HDAC2. The sensor has the following sequence, with toe hold shown in bold and underlined:

```
                              (SEQ ID NO: 3)
5' GGAGA AGAAC G (nick) GAAA UCCCU GGCAA UGUGAU 3'
(31 bp).
```

The Nupack analysis was performed on the sensor strand. The exiqon code with LNA modifications is shown as follows:

```
                              (SEQ ID NO: 109)
5' G + GA + GA + AG + AA + C G G + AA + A TC +
CCT + GGC + AA + TGT + G + A + T 3'.
```

Calcineurin is a protein phosphatase and is composed of two subunits: PPP3CA (catalytic) and PPP3R1 (regulatory). Thermo Fisher has an siRNA for this protein (PPP3CA) beginning at base pair 1549 (www.thermofisher.com/order/genome-database/browse/sirna/keyword/s72075). The guide and core strand sequences are as follows:

Guide (calcineurin target of 19 bp), starting from 1549: 5' CGAG UGUUG UUUGG CUUUU CCUG UU 3' (SEQ ID NO: 11, mutation from C to G is shown in bold and underlined);

```
Core strand:
                              (SEQ ID NO: 17)
5' CGUUC UUCUC C CAGGA AAAGC CAAAC AACAC UCG GCCAG
GGAUU UC 3'.
```

Figure 50B:
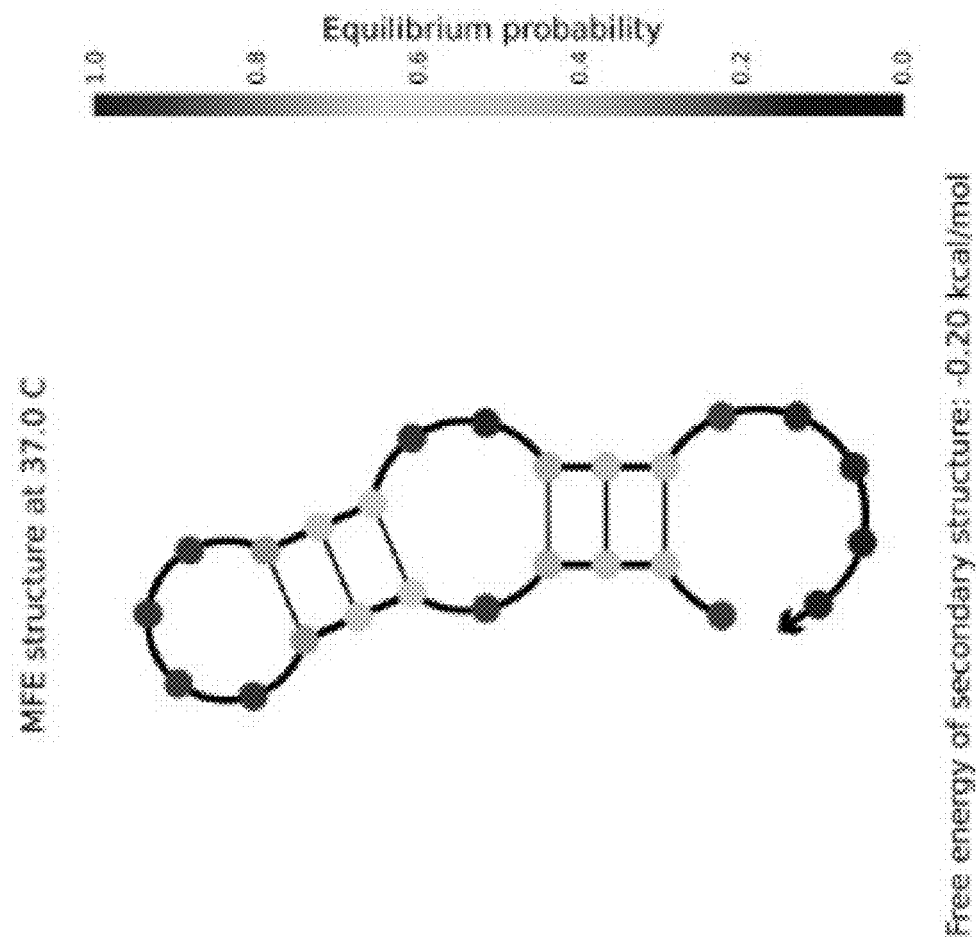
Figure 50C:
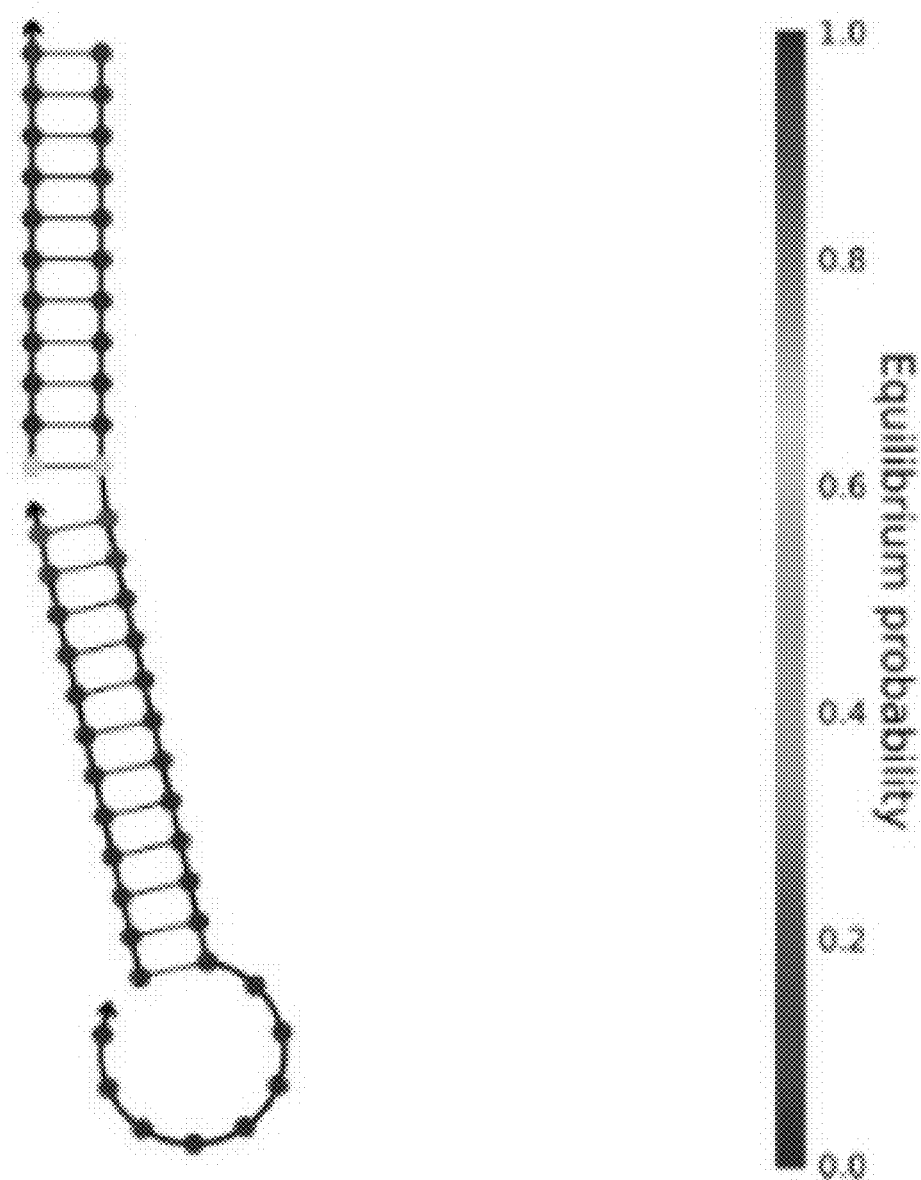

FIG. 50 shows that NuPack analyses of miR-23a-3p sensor strand for calcineurin were performed on core (FIG.

Figure 50D:
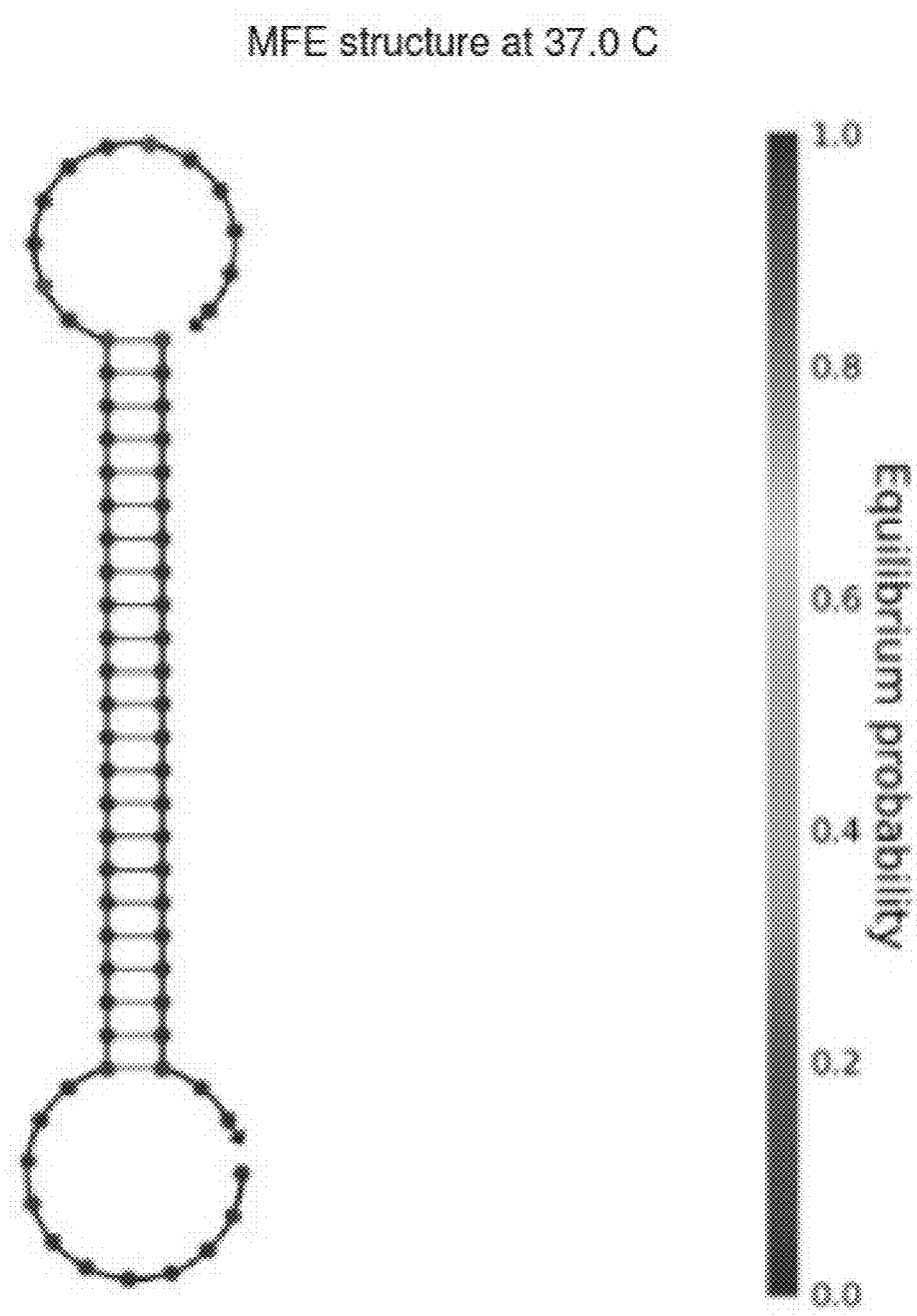

50A), guide (FIG. 50B), Sensor with two small overhangs of core: 97% (FIG. 50C), and calcineurin guide with core: 100% (FIG. 50D).

Figure 51:
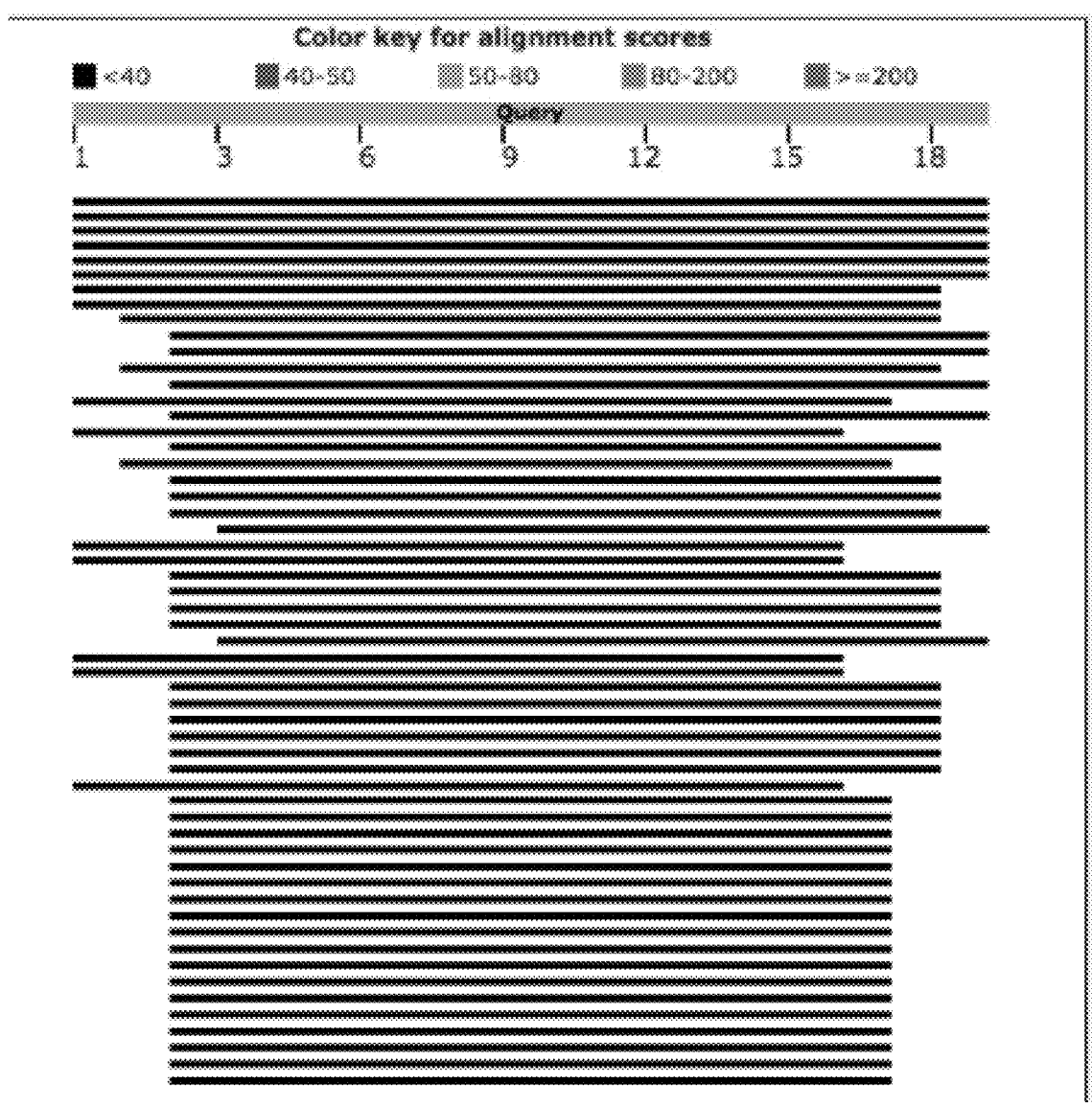
FIG. 51 shows NCBI check for calcineurin guide strand vs. human constructs.

FIG. 51 shows NCBI check for calcineurin guide strand vs. human constructs. The matches of primary concern include: *Homo sapiens* poly(ADP-ribose) polymerase family member 14 (PARP14), transcript variant X2, mRNA (20/21 plus/minus match); *Homo sapiens* uncharacterized LOC105374732 (LOC105374732), ncRNA (15 bp plus/minus match); *Homo sapiens* zinc finger FYVE-type containing 16 (ZFYVE16), transcript variant X19, mRNA (15 bp plus/minus match); and *Homo sapiens* GC-rich promoter binding protein 1 (GPBP1), transcript variant X11, misc_RNA (15 bp plus/minus match).

The guide of HDAC2 was from S100434959 (www.qiagen.com/us/shop/rnai/flexitube-sirna/?catno=S100434952#orderinginformation), having the following sequence: 5' GC ACUUA GAUUG AAACA ACCCA GUU 3' (25 bp) (SEQ ID NO: 13). The core with HDAC2 target has the following sequence, with short overhangs shown in bold and underlined: 5' CGUUC UUCUC C CUGGGUU-GUUUCAAUCUAAGUGC GCCAG GGAUU UC 3' (SEQ ID NO: 20).

Figure 52A:
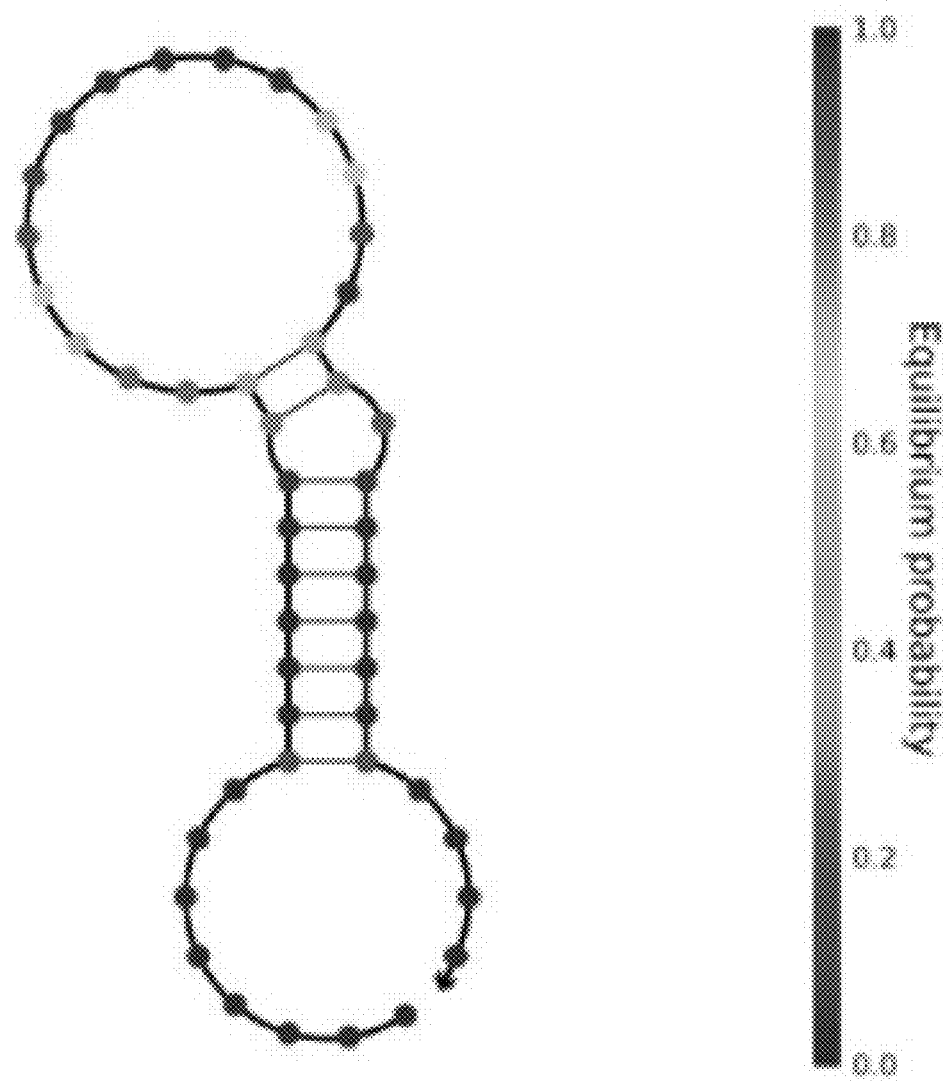
FIGS. 52A-52D show that NuPack analyses of miR-23a-3p sensor strand for HDAC2 were performed on core (FIG. 52A), guide (FIG. 52B), HDAC2 guide with core: 100% (FIG. 52C), and sensor with core overhangs: 97% (FIG. 52D).
Figure 52B:
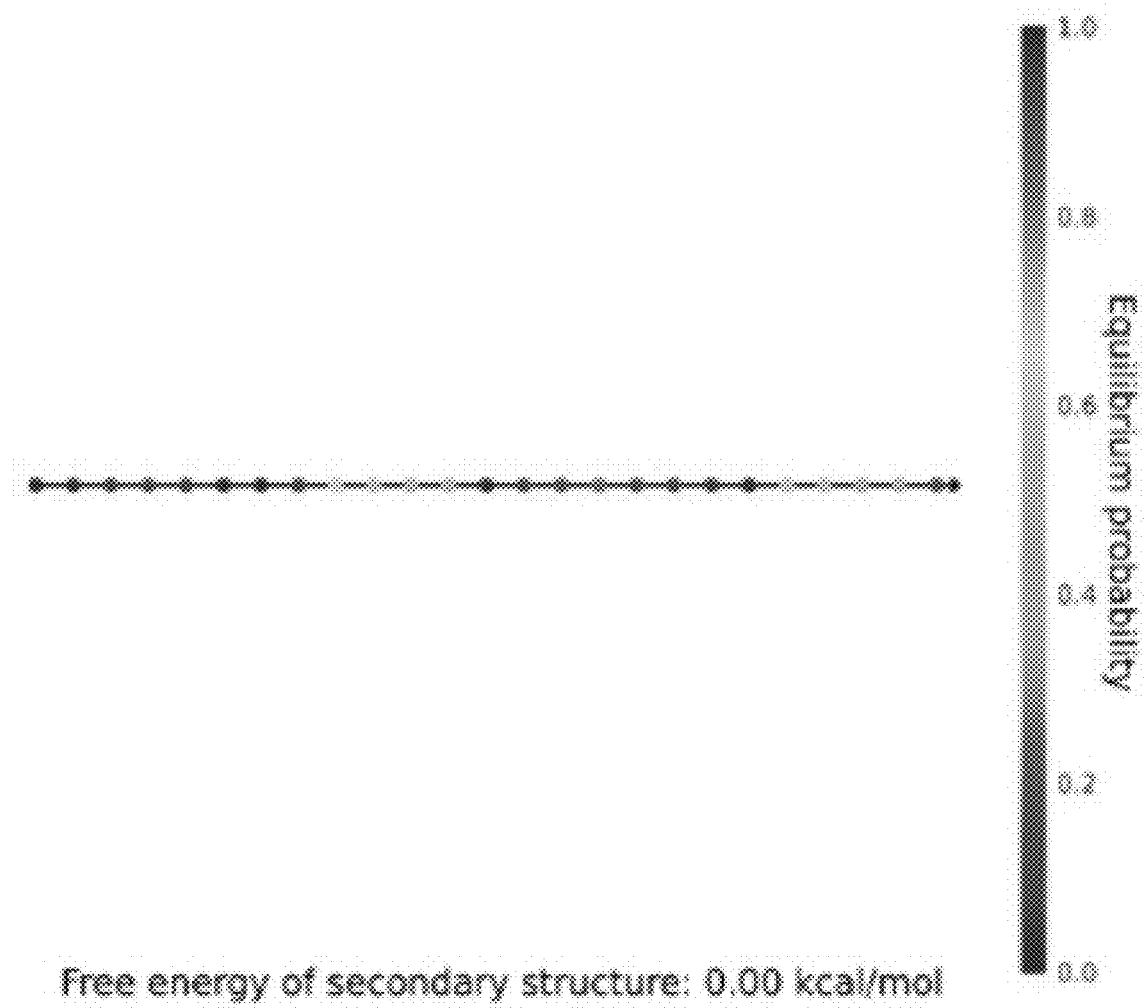
Figure 52C:
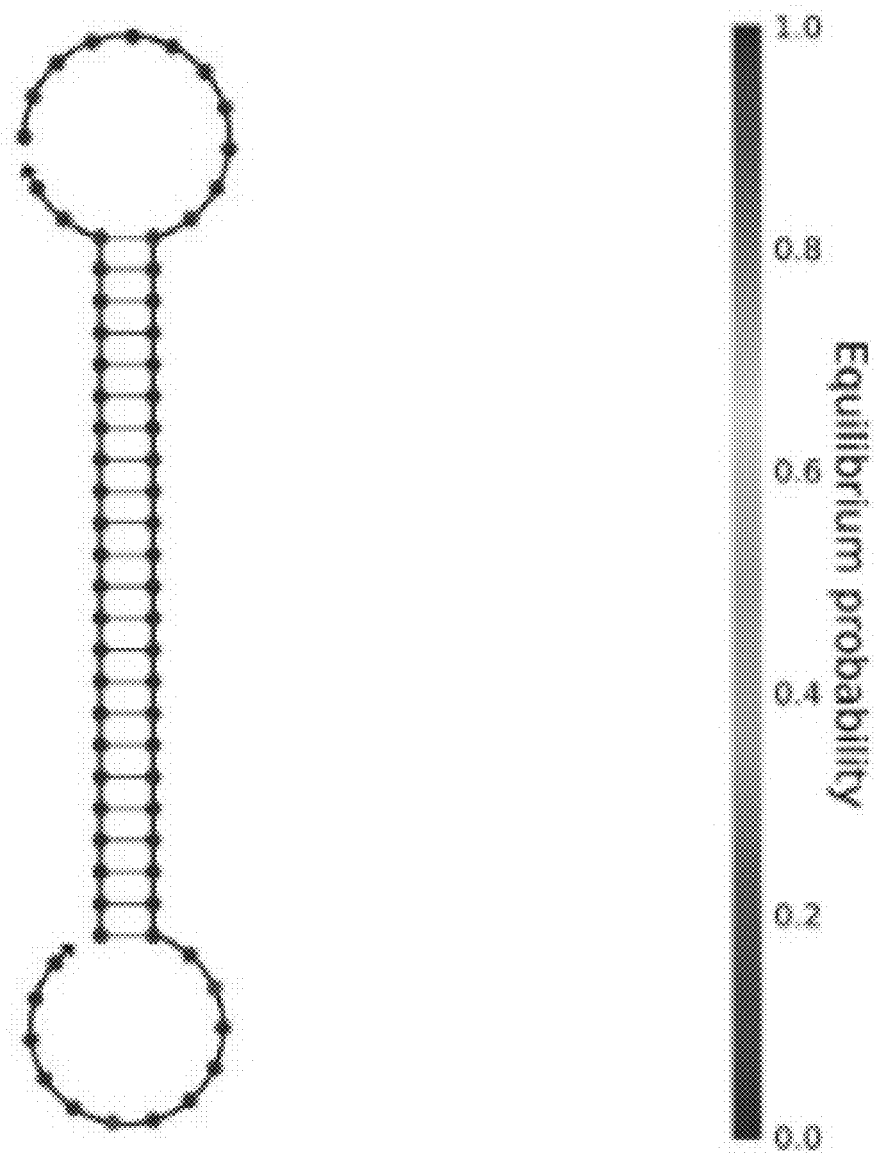
Figure 52D:
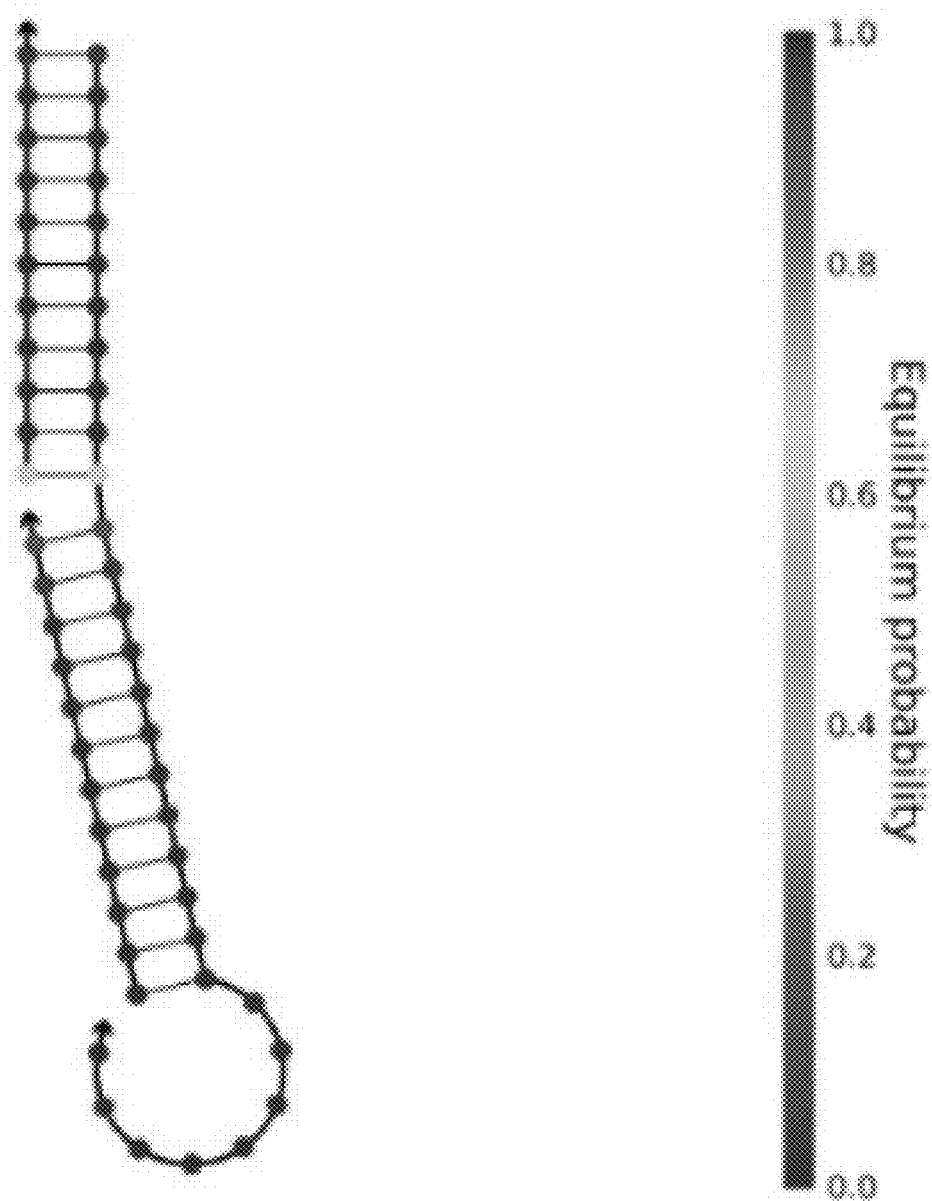

FIG. 52 shows that NuPack analyses of miR-23a-3p sensor strand for HDAC2 were performed on core (FIG. 52A), guide (FIG. 52B), HDAC2 guide with core: 100% (FIG. 52C), and sensor with core overhangs: 97% (FIG. 52D).

Figure 53:
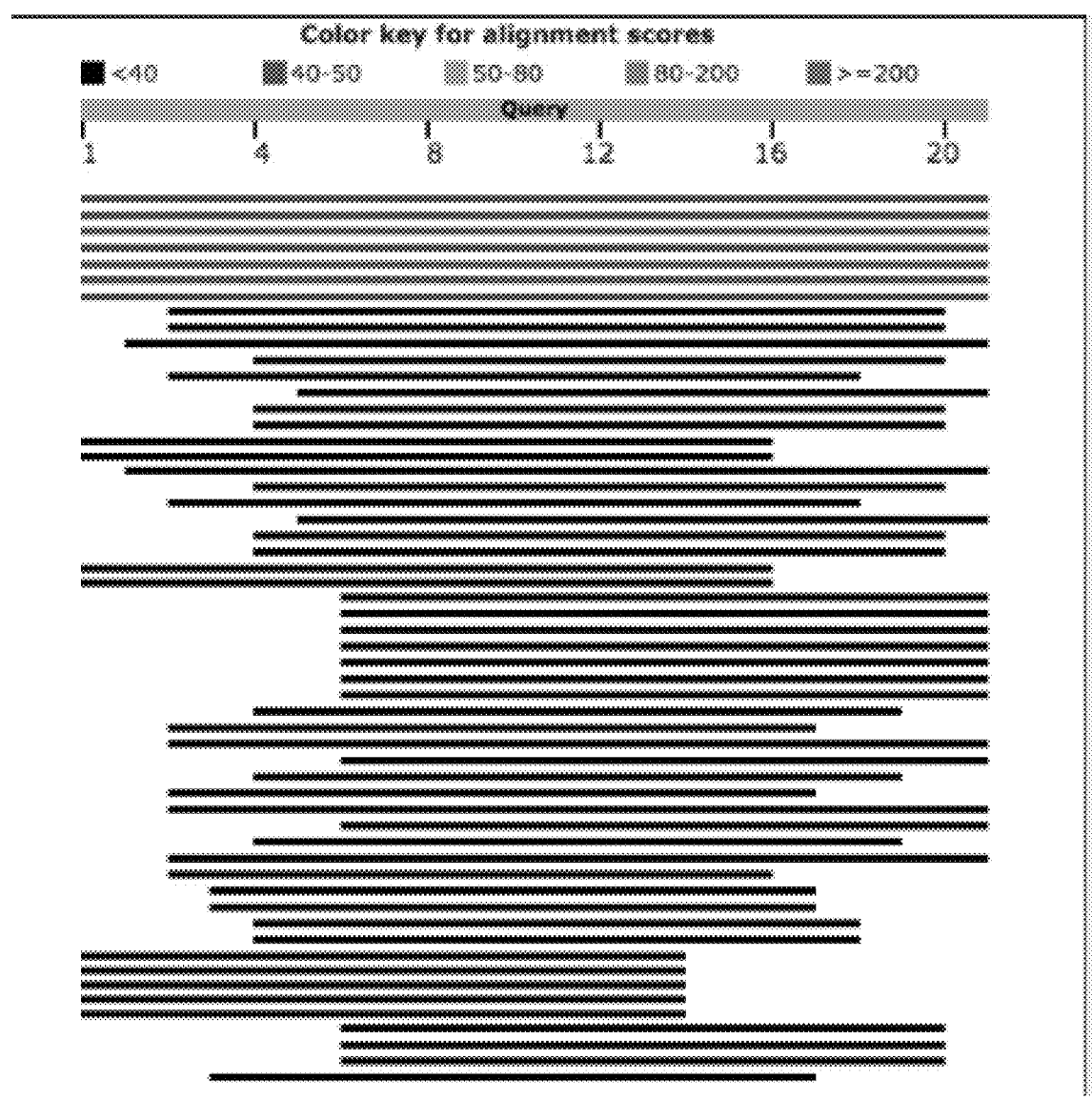
FIG. 53 shows NCBI check for HDAC2 guide strand vs. human transcripts.

FIG. 53 shows NCBI check for HDAC2 guide strand vs. human transcripts. The matches of primary concern include: *Homo sapiens* solute carrier family 35 member F5 (SLC35F5), transcript variant X6, mRNA (15 bp plus/minus match); and PREDICTED: *Homo sapiens* aquaporin 12B (AQP12B), transcript variant X16, misc_RNA (14 bp plus/minus match).

Example 10: Design Review for HDAC2 Targeted Conditional siRNA Constructs with Signals of BNP and MYH7

HDAC2 target guide sequence was designed as follows. HDAC2 siRNA was disclosed in published literature: www.nature.com/cddis/journal/v8/n3/extref/cddis201749x1.docx. The sequence was checked against the HDAC2 mRNA sequence from NCBI: www.ncbi.nlm.nih.gov/nuccore/NM_001527.3. A given DNA sequence was made into an RNA sequence, and then taken the reverse complement for the guide strand, starting at bp 518 on HDAC2 mRNA:

(SEQ ID NO: 111)
5' ACG GTCAATAAGA CCAGATAACA 3';

(SEQ ID NO: 112)
5' ACG GUCAAUAACA CCAGAUAACA 3';

Guide target HDAC2: 5' UGU UAUCUGGUGU UAUUGACCGU 3' (SEQ ID NO: 14); and then 4 bp of 5' guide were purposefully mismatched: 5' CGAG AUCUG-GUGU UAUUGACCGU 3' (SEQ ID NO: 15).

Figure 54B:
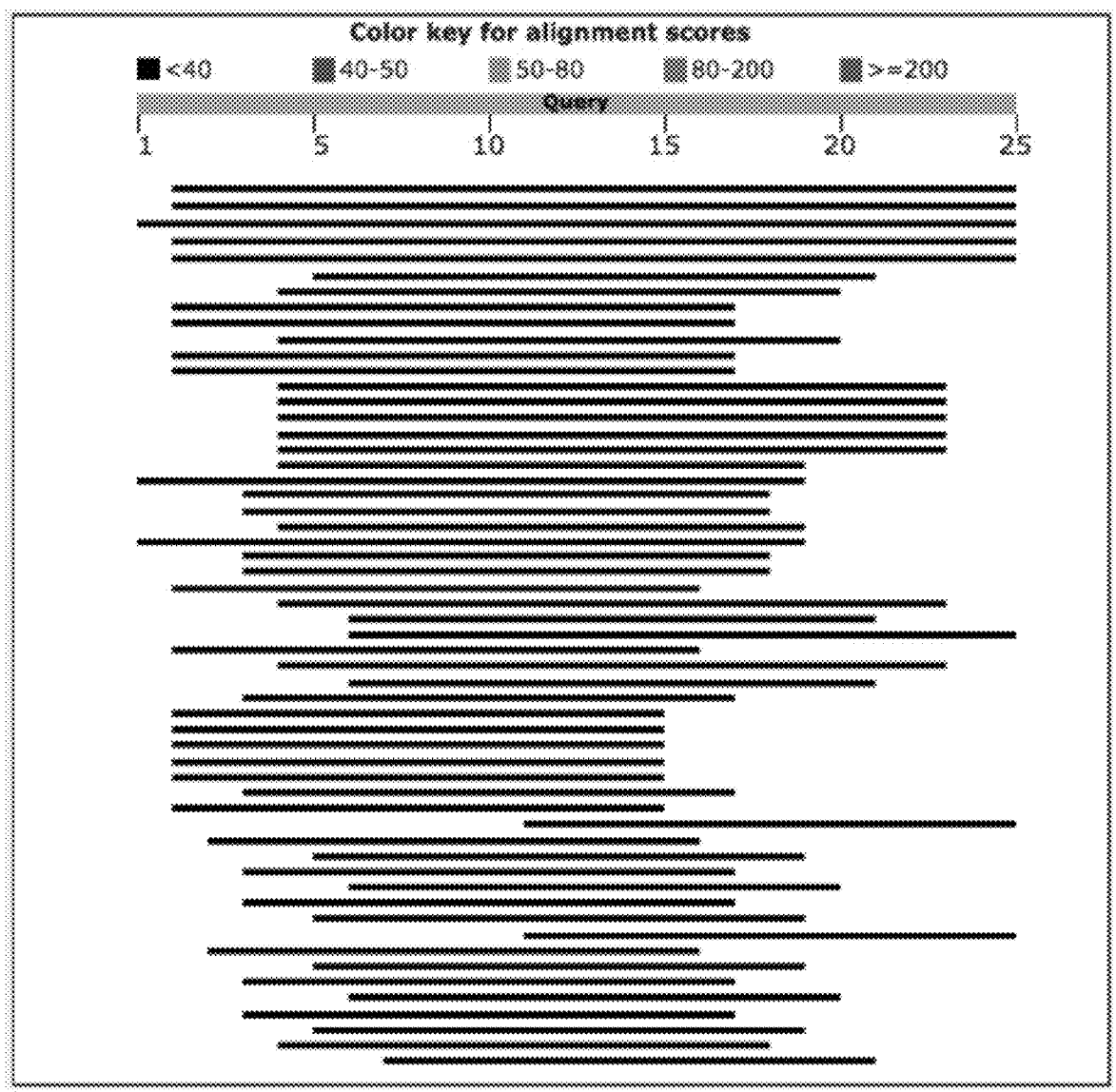

FIG. 54 illustrates the check of guide vs. NCBI human transcripts and sequence alignment.

Three BNP candidates were selected. The first BNP candidate had an mRNA sequence source from www.ncbi.nlm.nih.gov/nuccore/83700236. The sequence starting from 3' UTR of BNP mRNA is as follows, with the 31 bp sequence used for reference for sensor strand shown in bold and underlined:

(SEQ ID NO: 121)
GAGGAAGUCCUGGCUGCAGACACUGCUUCUGAUUCCACAAGGGGCUUUUU

CCUCAACCCUGUGCCGCCUUUGAAGUGACUCAUUUUUUUAAUGUAUUUAU

GAUUUAUUUGAUUGUUUUAUAUAAGAUGGUUUCUUACCUUUGAGCACAAA

AUUUCCACGGGAAAUAAAGUCAACAUUAU AAGCUUUAAAAAAAAAAA.

The BNP sensor was designed by taking the reverse complement of the bold and underlined portion of SEQ ID NO: 121. The sequence is as follows, with the 8 bp toehold shown in bold and underlined:

(SEQ ID NO: 4)
AUCAGAAGCAGGUGUCUGCAGCCAGGACUUC.

Figure 55:
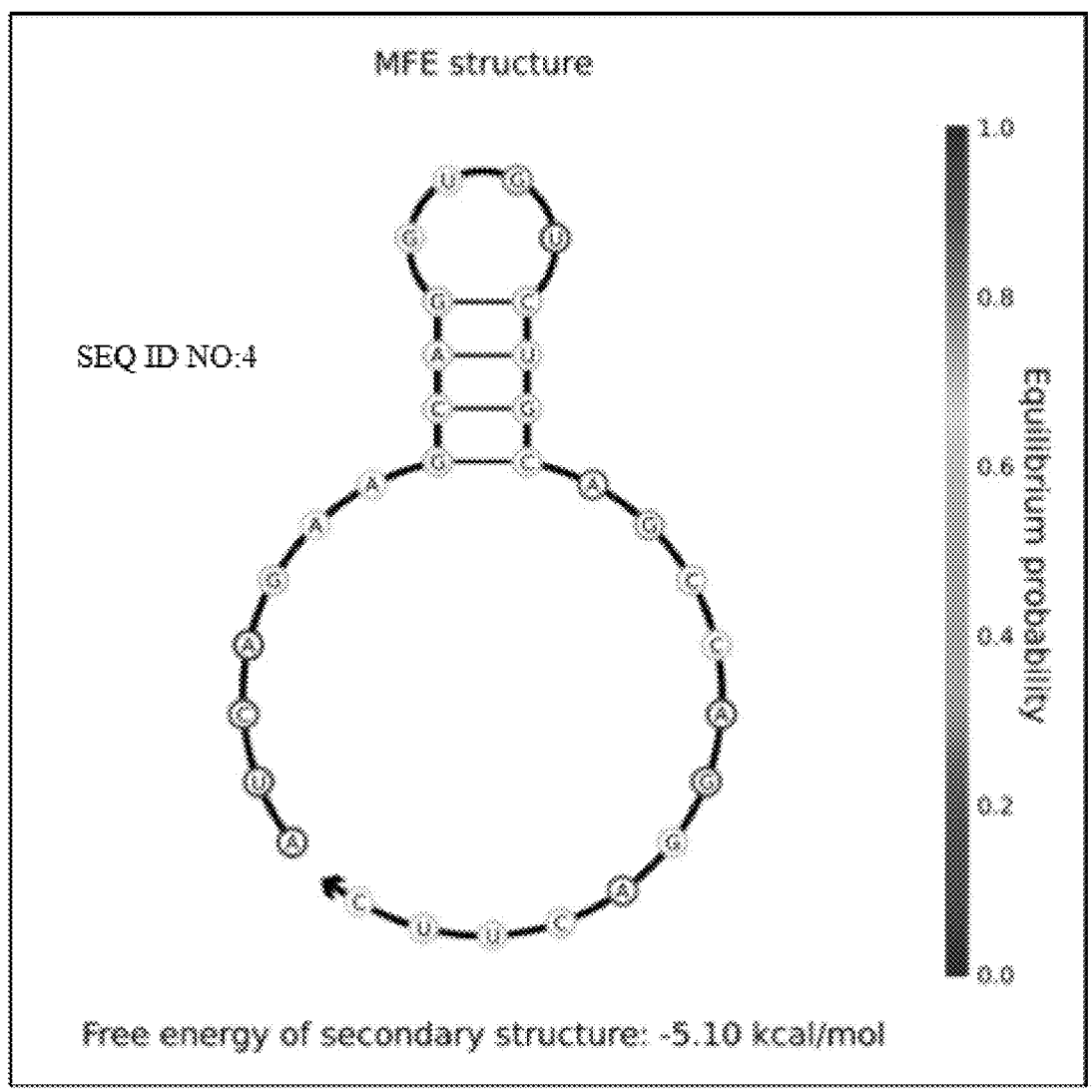
FIG. 55 shows the MFE structure of SEQ ID NO: 4.

The Nupack assessment was performed (www.nupack.org/partition/histogram_detail/1166536?token=PcTqQEaZRt&strand_id=0) and the MFE structure of SEQ ID NO: 4 is shown in FIG. 55.

Figure 58:
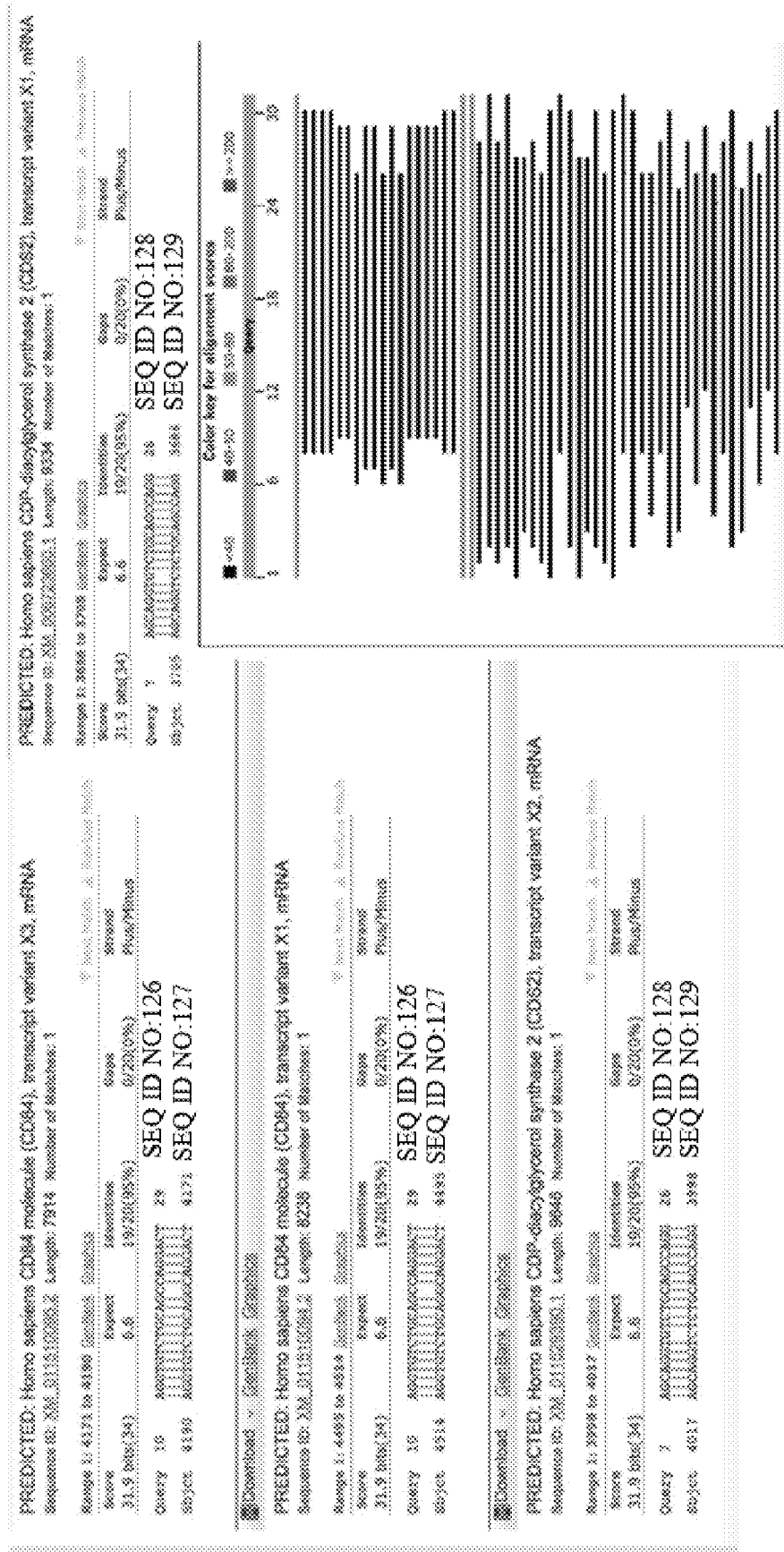
FIG. 58 shows NCBI check of BNP sensor first candidate vs. human transcripts.

FIG. 56 shows the BNP sensor sequence (SEQ ID NO: 4) together with core and guide sequences. FIGS. 57A and 57B show Nupack analyses of BNP sensor (SEQ ID NO: 4) with overhangs, and guide with core, respectively. The revised guide strand with the first 4 bp of 5' end with CGAG to provide mismatching in case of incorrect Dicer cleavage and RISC complex loading. The modified guide has 2 U overhang: 5' CGAG AUCUGGUGUU AUUGACCGUUU 3' (SEQ ID NO: 4). The modified core has the following sequence: CCUGCUUCUGAUACGGUCAAUAACACC-AGAUCUCGGGCUGCAGACA (SEQ ID NO: 122). FIG. 58 shows NCBI check of BNP sensor vs. human transcripts.

The design of the second BNP candidate was similar to the first except that the 31 bp sequence used for reference for sensor strand was a different portion from SEQ ID NO: 121 shown in bold and underlined:

(SEQ ID NO: 121)
GAGGAAGUCCUGGCUGCAGACACUGCUUCUGAUUCCACAAGGGCUUUUU

CCUCAACCCUGUGCCGCCUUUGAAGUGACUCAUUUUUUUAAUGUAUUUAU

GAUUUAUUUGAUUGUUUUAUAUAAGAUGGUUUCUUACCUUUGAGCACAAA

AUUUCCACGGGAAAUAAAGUCAACAUUAU AAGCUUUAAAAAAAAAAA.

The sequence of the second BNP sensor is as follows, with the 8 bp toehold shown in bold and underlined:

(SEQ ID NO: 5)
CUUGUGGAAUCAGAAGCAGGUGUCUGCAGCC.

Figure 59:
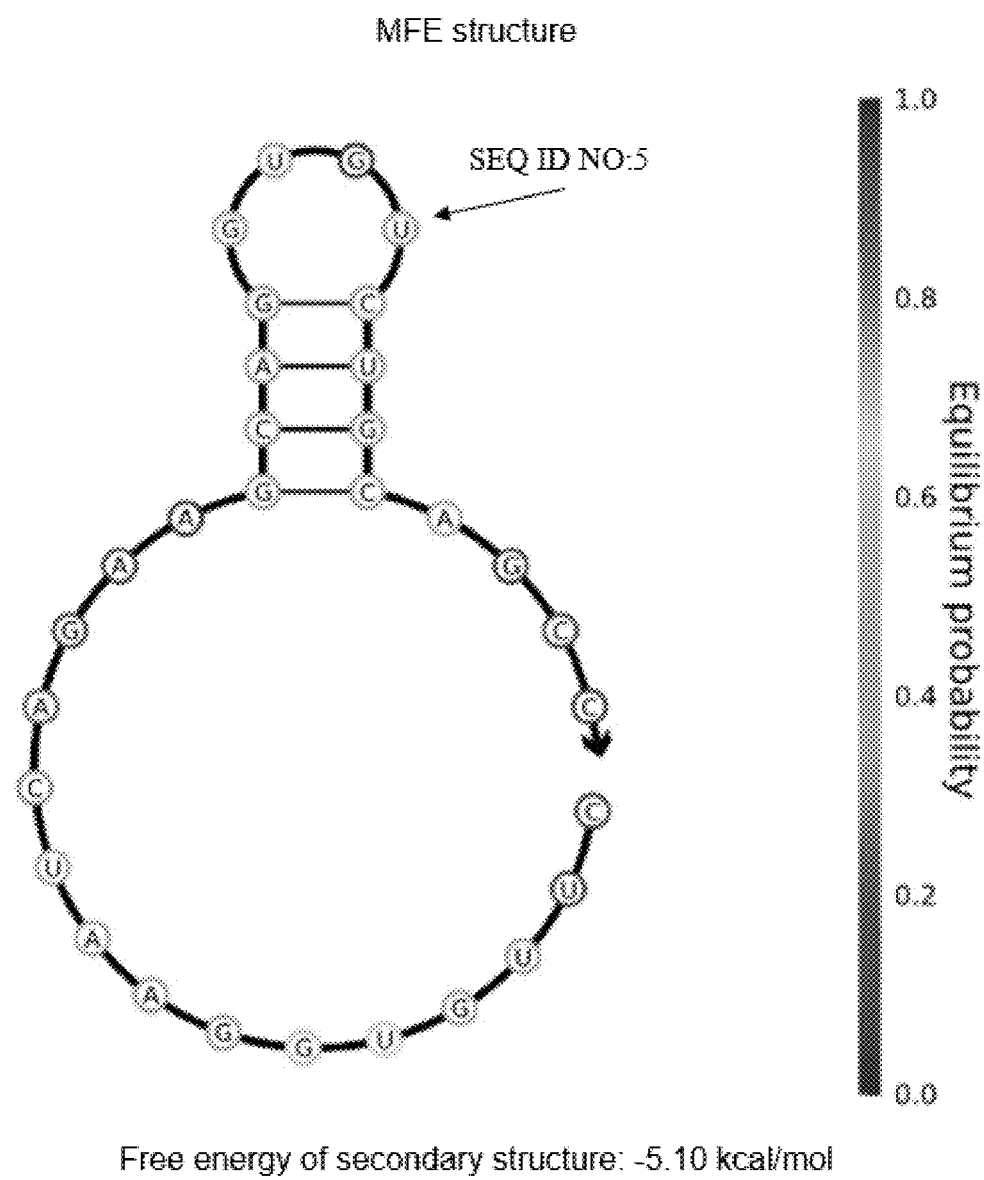
FIG. 59 shows the MFE structure of SEQ ID NO: 5.
Figure 61B:
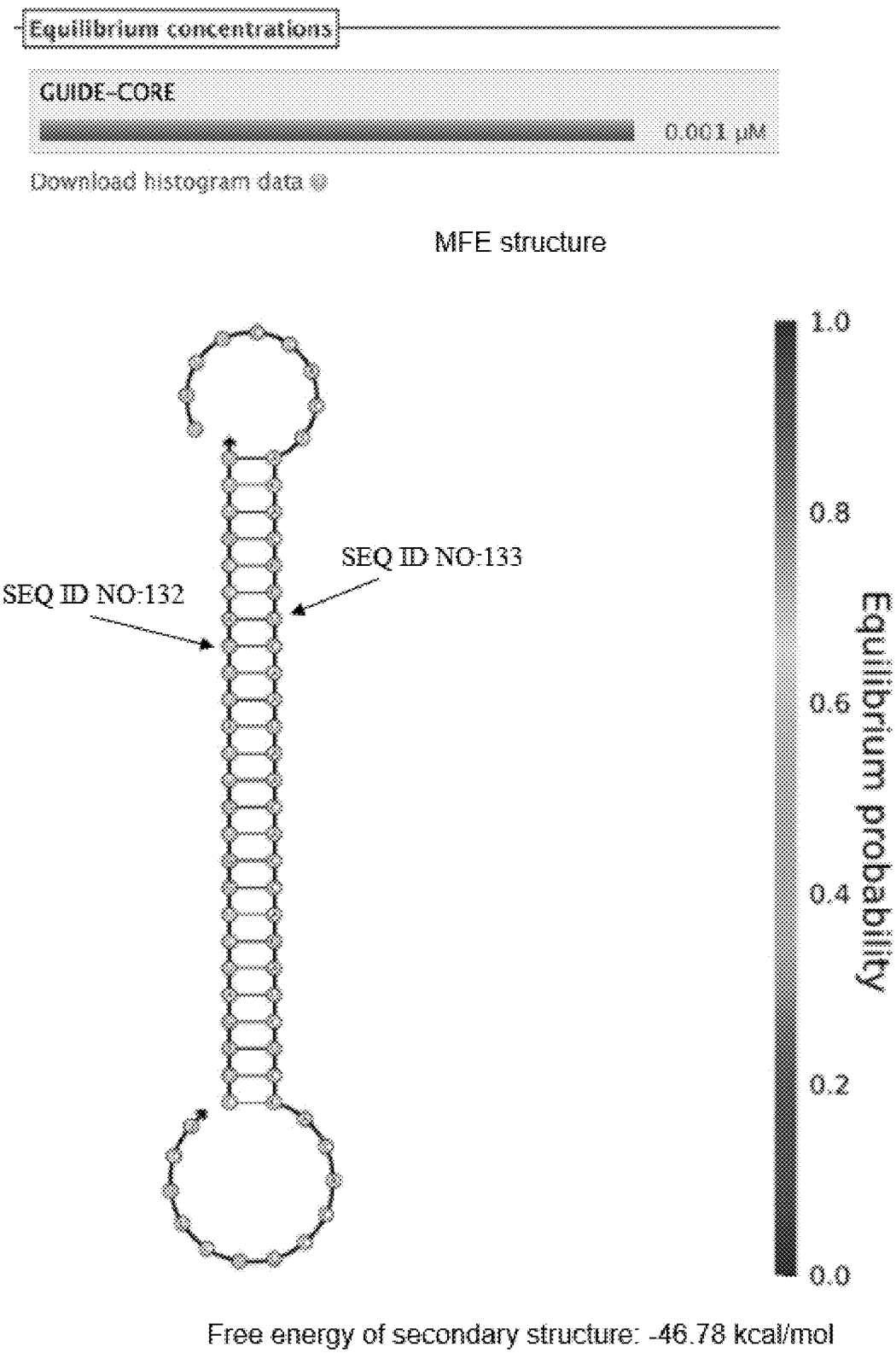
Figure 62:
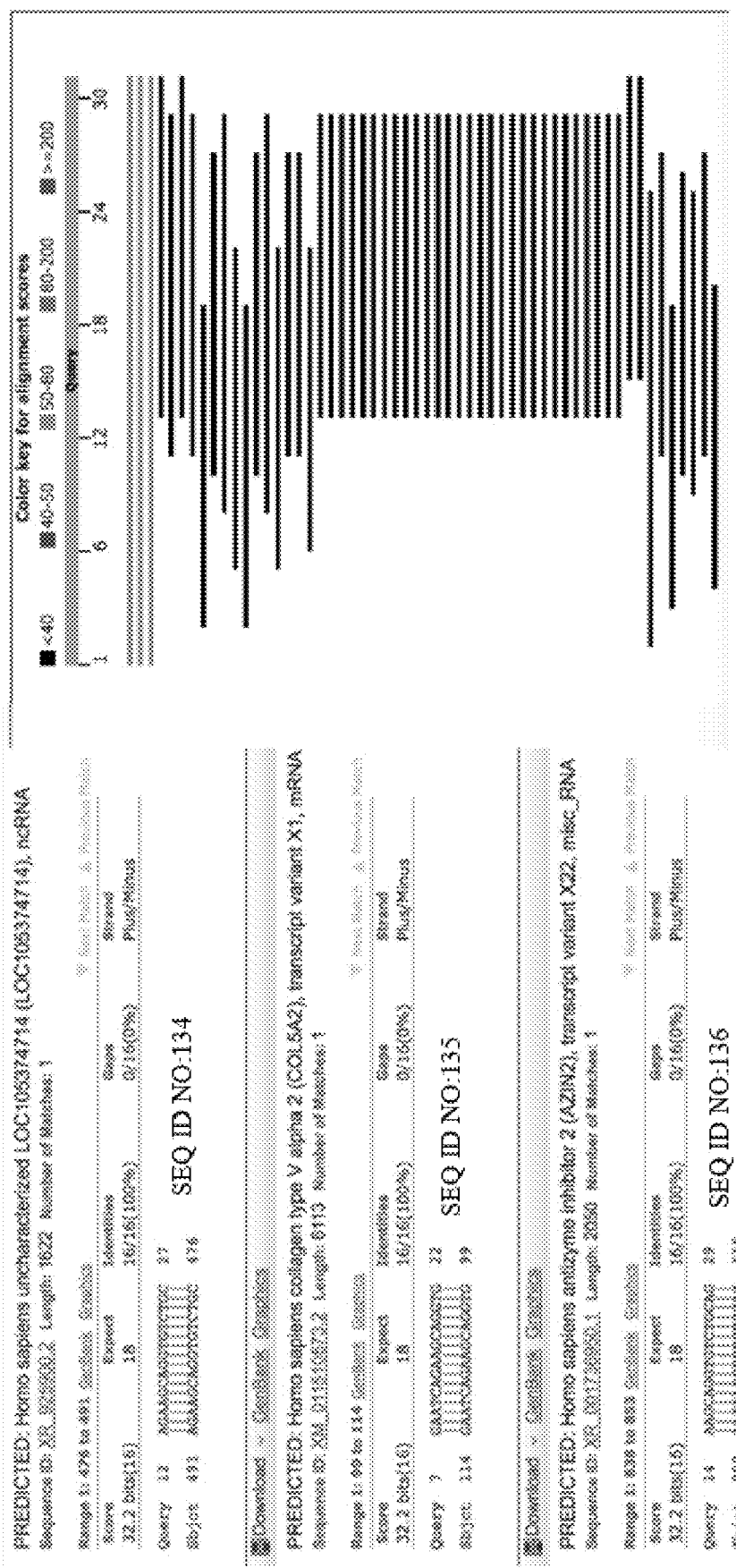
FIG. 62 shows NCBI check of BNP sensor second candidate vs. human transcripts.

The Nupack assessment was performed (www.nupack.org/partition/histogram_detail/1166628?token=wqLsVGJXbN&strand_id=0) and the MFE structure of SEQ ID NO: 5 is shown in FIG. 59. FIG. 60 shows the BNP sensor sequence (SEQ ID NO: 5) together with core and guide sequences. FIGS. 61A and 61B show Nupack analyses of BNP sensor (SEQ ID NO: 5) with overhangs, and guide with core, respectively. FIG. 62 shows NCBI check of BNP sensor second candidate vs. human transcripts.

Likewise, the design of the third BNP candidate was similar to the first and second except that the 31 bp sequenceused for reference for sensor strand was a different portion from SEQ ID NO: 121 shown in bold and underlined:

(SEQ ID NO: 121)
GAGGAAGUCCUGGCUGCAGACACUGCUUCUGAUUCCACAAGGGGCUUUUU

CCUCAACCCUGUGGCCGCCUUUGAAGUGACUCAUUUUUUUAAUGUAUUUA

UGAUUUAUUUGAUUGUUUUAUAUAAGAUGGUUUCUUACCUUUGAGCACAA

AAUUUCCACGGGAAAUAAAGUCAACAUUAU AAGCUUUAAAAAAAAAA.

The sequence of the third BNP sensor is as follows, with the 8 bp toehold shown in bold and underlined:

(SEQ ID NO: 6)
CAAAGGCGGCCACAGGGUUGAGGAAAAAGCC.

Figure 63:
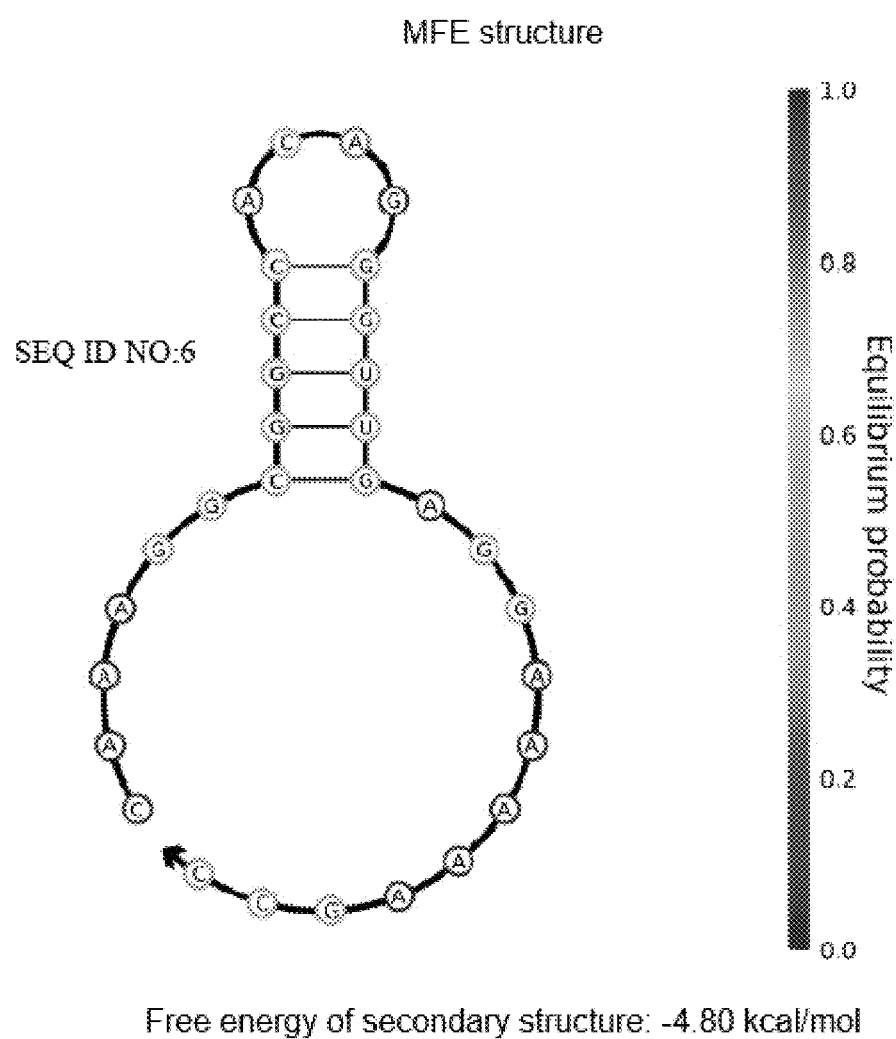
FIG. 63 shows the MFE structure of SEQ ID NO: 6.
Figure 65:
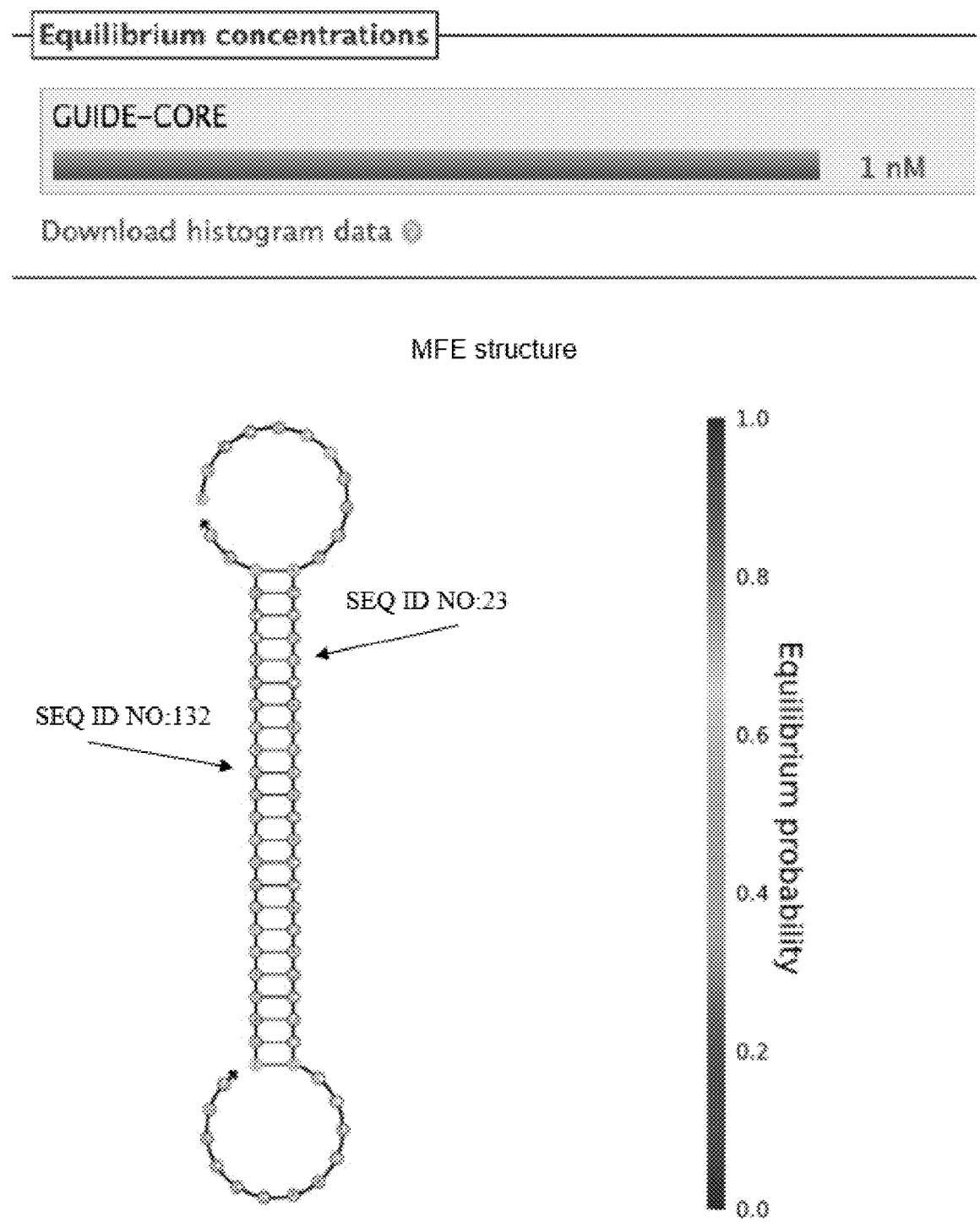
FIG. 65 shows Nupack analysis of guide with core for the third BNP candidate.
Figure 66:
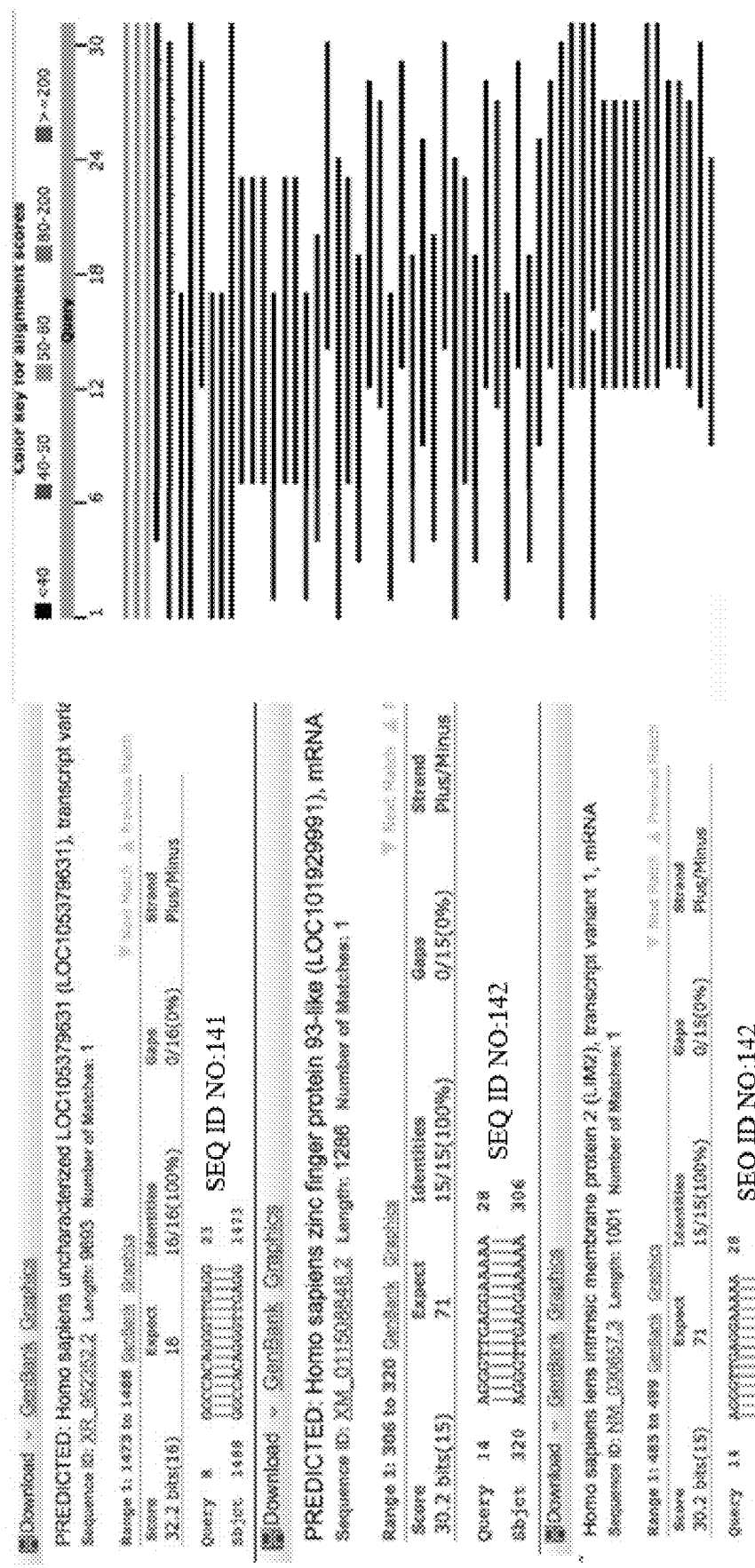
FIG. 66 shows NCBI check of BNP sensor third candidate vs. human transcripts.

The Nupack assessment was performed (www.nupack.org/partition/histogram_detail/1166638?token=wZSopNPdBt&strand_id=0) and the MFE structure of SEQ ID NO: 6 is shown in FIG. 63. FIG. 64 shows the BNP sensor sequence (SEQ ID NO: 6) together with core and guide sequences. FIG. 65 shows Nupack analysis of guide with core for the third BNP candidate. FIG. 66 shows NCBI check of BNP sensor third candidate vs. human transcripts.

Myosin heavy chain 7 (MYH7) encodes for a heavy chain subunit of cardiac myosin-contractile velocity of cardiac muscle. Myosin has 2 heavy chains, 2 alkali light chains, and 2 regulatory light chains. It is expressed in normal human ventricles as well as type 1 (slow twitch) muscle fibers. Mutations in this gene result in hypertrophic cardiomyopathy, myosin storage myopathy, and numerous other cardiac diseases. See www.genecards.org/cgi-bin/carddisp.pl?gene=MYH7.

The MYH7 candidate had an mRNA sequence source from www.ncbi.nlm.nih.gov/nuccore/NM_000257.3. The sequence starting from 3' UTR of MYH7 mRNA is as follows, with the 31 bp sequence used for reference for sensor strand shown in bold and underlined:

(SEQ ID NO: 143)
UUUUUUUUUU UUUUUCUCGG CUUCAAGGAA AAUUGCUUUA

UUCUGCUUCC UCCCAAGGAG CUGUUACACA GGCUCCAGCA

UGGGGCUUUG CUGGCACCUC CAGGGCUGAG CAGAUCAAGA

UGUGGCAAAG.

The MYH7 sensor was designed by taking the reverse complement of the bold and underlined portion of SEQ ID NO: 143. The sequence is as follows, with the 8 bp toehold shown in bold and underlined:

(SEQ ID NO: 7)
AUCUUGAUCUGCUCAGCCCUGGAGGUGCCAG.

Figure 67:
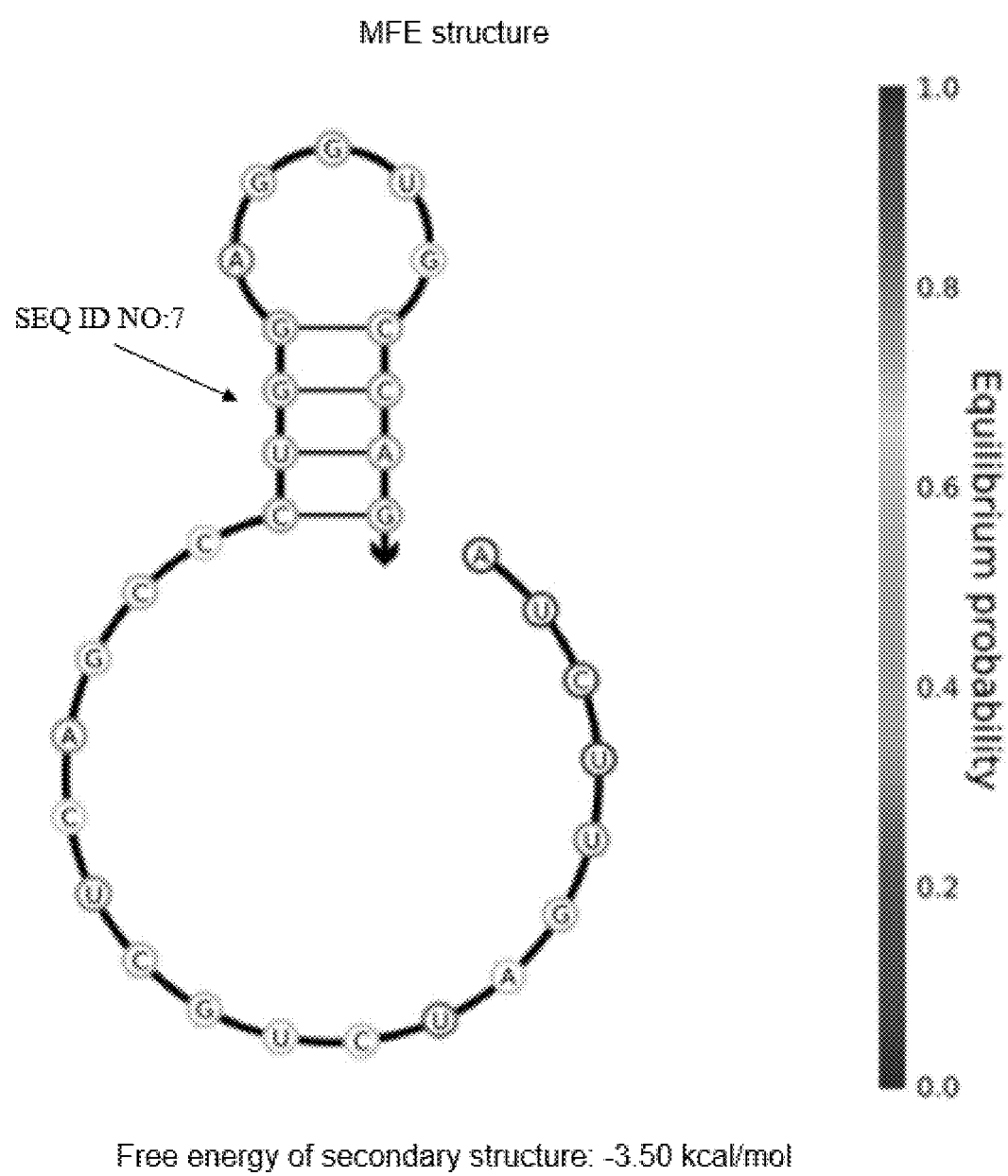
FIG. 67 shows the MFE structure of SEQ ID NO: 7.

The Nupack assessment was performed (www.nupack.org/partition/histogram_detail/1167009?token=OyDl4ywh0J&strand_id=0) and the MFE structure of SEQ ID NO: 7 is shown in FIG. 67.

Figure 69A:
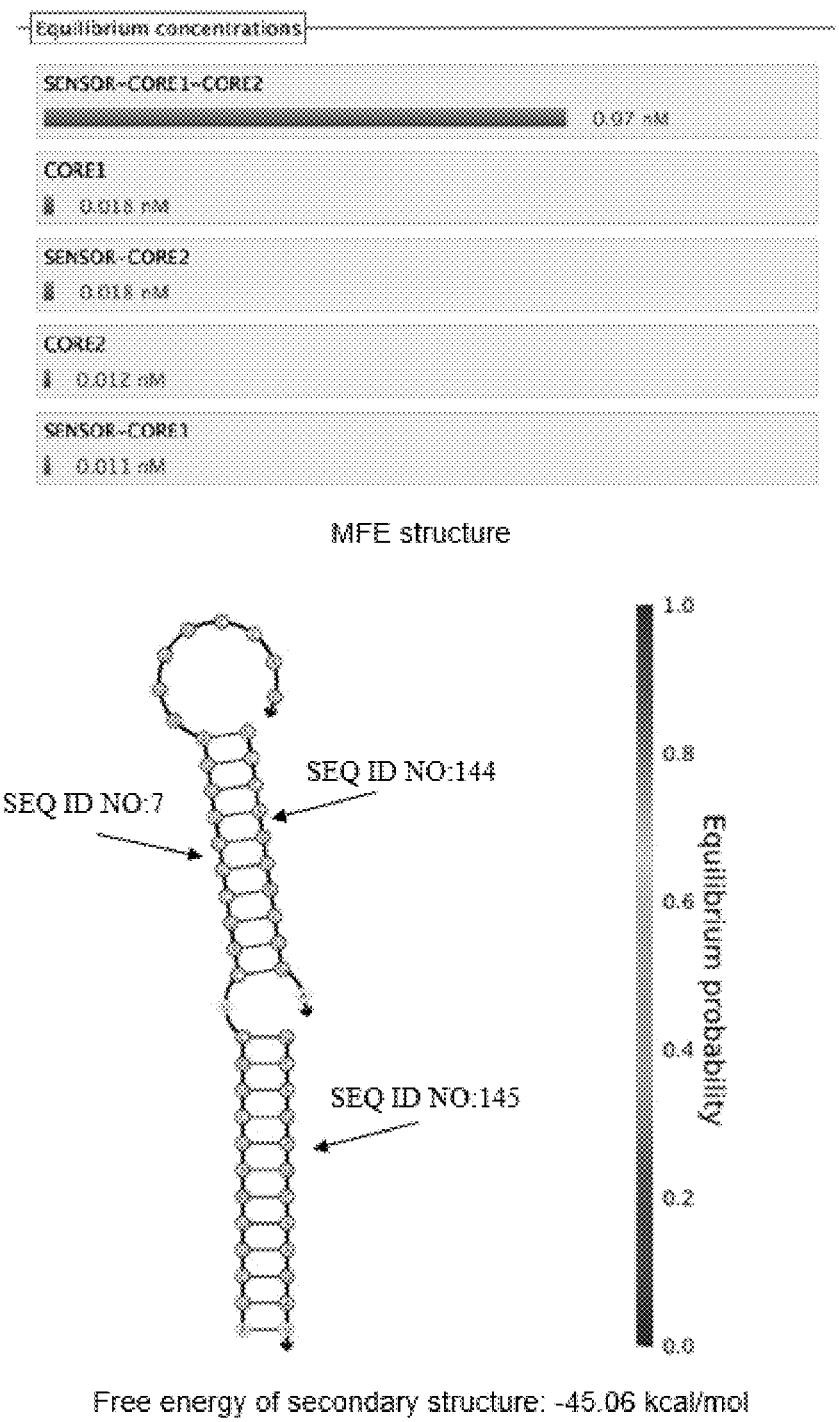
Figure 70:
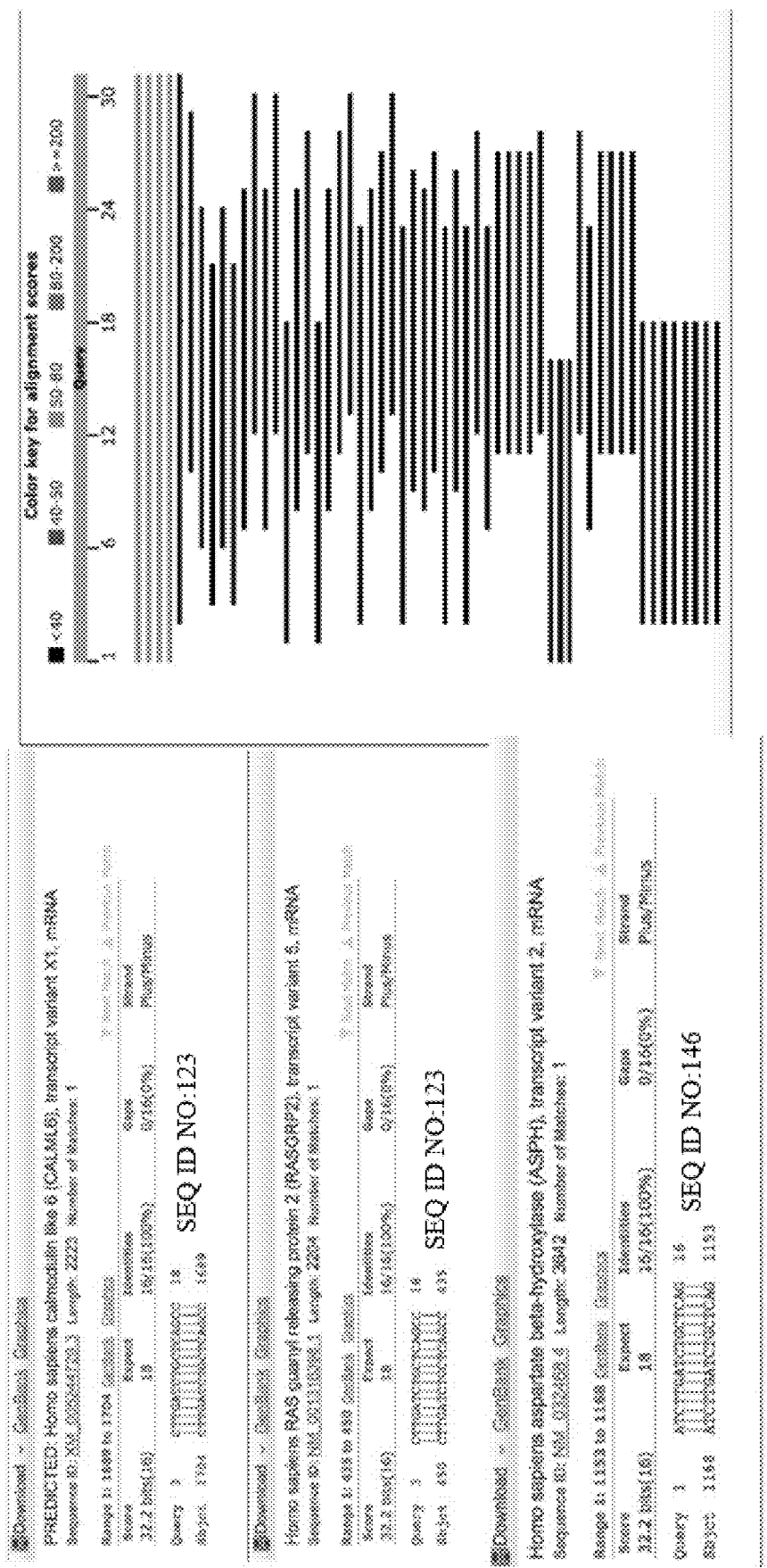
FIG. 70 shows NCBI check of MYH7 sensor vs. human transcripts.

FIG. 68 shows the MYH7 sensor sequence (SEQ ID NO: 7) together with core and guide sequences. FIGS. 69A and 69B show Nupack analyses of MYH7 sensor (SEQ ID NO: 7) with overhangs, and guide with core, respectively. FIG. 70 shows NCBI check of MYH7 sensor vs. human transcripts.

Example 11: Design Review of Conditional siRNAs in Cardiac Ischemia

NPPA (aka: ANP, ANF, ANH, or CDD), if overexpressed in heart cells, inhibits, maladaptive cardiac hypertrophy. High levels of NPPB (aka: BNP) serve as a biomarker for heart failure in ischemic patients. Overexpression or mutation of MYH7 (aka: CMD1S, C1, MYHCB, SPMD, or SPMM) can cause cells to die prematurely and increase cardiac fibrosis. This design uses NPPA, NPPB or MYH7 as sensor, and HDAC2 and calcineurin as targets. Inhibition of HDAC2 or calcineurin causes reduced cardiac hypertrophy.

Examples of NPPA HDAC2 designs are illustrated as follows. Construct #1 (best, MPE structure shown in FIG. 71) (www.nupack.org/partition/histogram_detail/1157307?temperature=37.0&token=gYZWv2FATz&permutation_id=2&complex_id=23) was designed with the following sequences:

```
Core: 5' GUCAUCUUGUUGCUGGGUUGUUUCAAUCUAAGAGCGCUGCAUUUGU
3' (SEQ ID NO: 25);

Sensor: 5' CAACAAGAUGACACAAAUGCAGCAGAGACCC 3' (SEQ ID NO: 8)

Modified sensor (SEQ ID NO: 147):
CA + ACA + AG + ATG + AC + ACA + AA + TGC + AGC + AG + AGA + C + C + C
s1-s1: 28 S1: 24 DNA ™: 87 RNA ™: 92;
and Guide: 5' GCUCUUAGAUUGAAACAACCCAGUU 3' (SEQ ID NO: 16)
```

Construct #3 (MPE structure shown in FIG. 72) (www.nupack.org/partition/show/1169058?time_refresh=1.0&token=OXLbgX6bBo) was designed with the following sequences:

```
Core: 5' CAUUUGUGUCAUUGUUAGAUUGAAACAACCCAGGGUCUCUGCUG 3'
(SEQ ID NO: 26);

Sensor: 5' AUGACACAAAUGCAGCAGAGACCCCAGGGGA 3' (SEQ ID NO: 9)
```

```
Modified sensor (SEQ ID NO: 148):
A + TG + AC + ACA + AA + TGC + AGC + A + G + A + G + ACCCC + AG + GGG + A
sl-sl: 40 sl: 33 DNA ™: 95 RNA ™: 100
and Guide: 5' GCUCUUAGAUUGAAACAACCCAGUU 3' (SEQ ID NO: 16).
```

Figure 73:
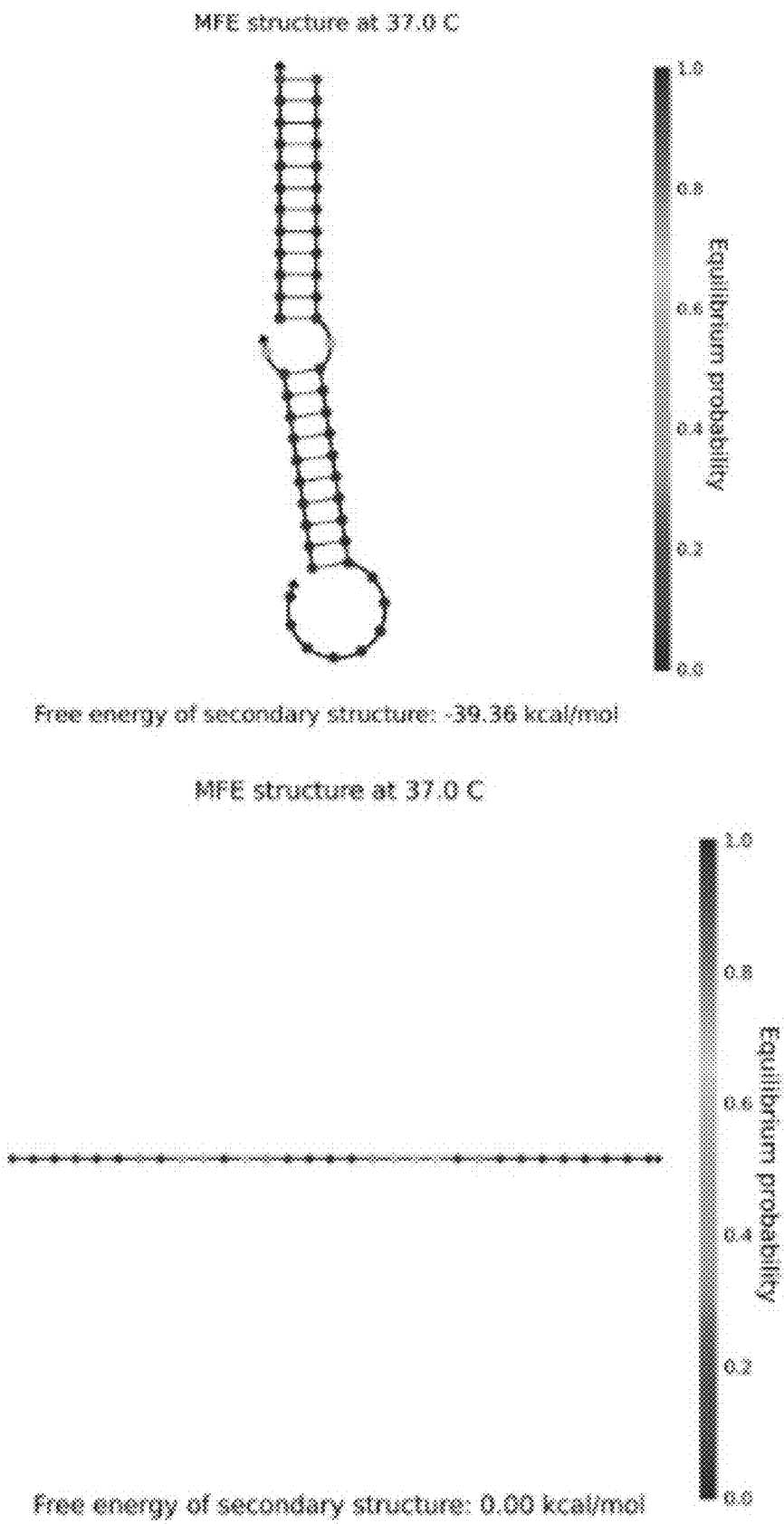
FIG. 73 shows the MFE structure of NPPA calcineurin construct #1.

An example of NPPA calcineurin design is illustrated as follows. Construct #1 (best, MPE structure shown in FIG. 73) (www. www.nupack.org/partition/show/1169063?time_refresh=1.0&to ken=RnEIROmvsz) was designed with the following sequences:

```
Core: 5' GUCAUCUUGUUGCAGGAAAAGCCAAACAACACUCGGCUGCAUUUGU

3' (SEQ ID NO: 149);

Sensor: 5' CAACAAGAUGACACAAAUGCAGCAGAGACCC 3' (SEQ ID NO: 8)

Modified sensor (SEQ ID NO: 147):
Modified sensor: CA + ACA + AG + ATG + AC + ACA + AA + TGC +
AGC + AG + AGA + C + C + C
sl-sl: 28 sl: 24 DNA ™: 87 RNA ™: 92
and Guide: 5' CGAGUGUUGUUUGGCUUUUCCUGUU 3' (SEQ ID NO: 12).
```

REFERENCES

1 Au-Graham, E. L., Au-Balla, C., Au-Franchino, H., Au-Melman, Y., Au-del Monte, F. & Au-Das, S. Isolation, Culture, and Functional Characterization of Adult Mouse Cardiomyoctyes. JoVE, e50289, doi:doi:10.3791/50289 (2013).

2 Paradis, A. N., Gay, M. S., Wilson, C. G. & Zhang, L. Newborn Hypoxia/Anoxia Inhibits Cardiomyocyte Proliferation and Decreases Cardiomyocyte Endowment in the Developing Heart: Role of Endothelin-1. PLOS ONE 10, e0116600, doi:10.1371/journal.pone.0116600 (2015).

3 Xiao, J., Liu, H., Cretoiu, D., Toader, D. O., Suciu, N., Shi, J., Shen, S., Bei, Y., Sluijter, J. P. G., Das, S., Kong, X. & Li, X. miR-31a-5p promotes postnatal cardiomyocyte proliferation by targeting RhoBTB1. Experimental &Amp; Molecular Medicine 49, e386, doi:10.1038/emm.2017.150 (2017).

4 Nolan, T., Hands, R. E. & Bustin, S. A. Quantification of mRNA using real-time RT-PCR. Nature Protocols 1, 1559, doi:10.1038/nprot.2006.236 (2006).

5 Fiedler, S. D., Carletti, M. Z. & Christenson, L. K. in RT-PCR Protocols: Second Edition (ed Nicola King) 49-64 (Humana Press, 2010).

6 Hartmann, H. A., Mazzocca, N. J., Kleiman, R. B. & Houser, S. R. Effects of phenylephrine on calcium current and contractility of feline ventricular myocytes. American Journal of Physiology-Heart and Circulatory Physiology 255, H1173-H1180, doi:10.1152/ajpheart.1988. 255.5. H1173 (1988).

7 Katanosaka, Y., Iwata, Y., Kobayashi, Y., Shibasaki, F., Wakabayashi, S. & Shigekawa, M. Calcineurin Inhibits Na+/Ca2+ Exchange in Phenylephrine-treated Hypertrophic Cardiomyocytes. Journal of Biological Chemistry 280, 5764-5772, doi:10.1074/jbc.M410240200 (2005).

8 Sussman, M. A., Lim, H. W., Gude, N., Taigen, T., Olson, E. N., Robbins, J., Colbert, M. C., Gualberto, A., Wieczorek, D. F. & Molkentin, J. D. Prevention of Cardiac Hypertrophy in Mice by Calcineurin Inhibition. Science 281, 1690-1693, doi:10.1126/science.281.5383.1690 (1998).

9 Tham, Y. K., Bernardo, B. C., Ooi, J. Y. Y., Weeks, K. L. & McMullen, J. R. Pathophysiology of cardiac hypertrophy and heart failure: signaling pathways and novel therapeutic targets. Archives of Toxicology 89, 1401-1438, doi:10.1007/s00204-015-1477-x (2015).

10 Molkentin, J. D., Lu, J.-R., Antos, C. L., Markham, B., Richardson, J., Robbins, J., Grant, S. R. & Olson, E. N. A Calcineurin-Dependent Transcriptional Pathway for Cardiac Hypertrophy. Cell 93, 215-228, doi:https://doi.org/10.1016/S0092-8674(00)81573-1 (1998).

11 Cao, D. J., Wang, Z. V., Battiprolu, P. K., Jiang, N., Morales, C. R., Kong, Y., Rothermel, B. A., Gillette, T. G. & Hill, J. A. Histone deacetylase (HDAC) inhibitors attenuate cardiac hypertrophy by suppressing autophagy. Proceedings of the National Academy of Sciences 108, 4123-4128, doi:10.1073/pnas.1015081108 (2011).

12 Trivedi, C. M., Luo, Y., Yin, Z., Zhang, M., Zhu, W., Wang, T., Floss, T., Goettlicher, M., Noppinger, P. R., Wurst, W., Ferrari, V. A., Abrams, C. S., Gruber, P. J. & Epstein, J. A. Hdac2 regulates the cardiac hypertrophic response by modulating Gsk3p activity. Nature Medicine 13, 324, doi:10.1038/nm1552 https://www.nature.com/articles/nm1552#supplementary-information (2007).

13 Liu, X., Xiao, J., Zhu, H., Wei, X., Platt, C., Damilano, F., Xiao, C., Bezzerides, V., Boström, P., Che, L., Zhang, C., Spiegelman, Bruce M. & Rosenzweig, A. miR-222 Is Necessary for Exercise-Induced Cardiac Growth and Protects against Pathological Cardiac Remodeling. Cell Metabolism 21, 584-595, doi:https://doi.org/10.1016/j.cmet.2015.02.014 (2015).

14 Han, S.-P., Goddard III, W. A., Scherer, L. & Rossi, J. J. Signal activatable constructs and related components compositions methods and systems. U.S. Pat. No. 9,725,715B2 (2015).

15 Zadeh, J. N., Steenberg, C. D., Bois, J. S., Wolfe, B. R., Pierce, M. B., Khan, A. R., Dirks, R. M. & Pierce, N. A. NUPACK: Analysis and design of nucleic acid systems. Journal of Computational Chemistry 32, 170-173, doi:10.1002/jcc.21596 (2011).

16 Jaramillo-Botero, A., Nielsen, R., Abrol, R., Su, J., Pascal, T., Mueller, J. & Goddard, W. Vol. 307 Topics in Current Chemistry (eds Barbara Kirchner & Jadran Vrabec) 1-42 (Springer Berlin/Heidelberg, 2012).
17 Naito, Y. & Ui-Tei, K. in siRNA Design: Methods and Protocols (ed Debra J. Taxman) 57-68 (Humana Press, 2013).
18 Boudreau, R. L., Spengler, R. M. & Davidson, B. L. Rational Design of Therapeutic siRNAs: Minimizing Off-targeting Potential to Improve the Safety of RNAi Therapy for Huntington's Disease. Mol Ther, doi:http://www.nature.com/mt/journal/vaop/ncurrent/suppinfo/mt2011185s1.html (2011).
19 Sano, M., Sierant, M., Miyagishi, M., Nakanishi, M., Takagi, Y. & Sutou, S. Effect of asymmetric terminal structures of short RNA duplexes on the RNA interference activity and strand selection. Nucleic Acids Research 36, 5812-5821, doi:10.1093/nar/gkn584 (2008).
20 Konstam M A, Kramer D G, Patel A R, Maron M S, Udelson J E. Left ventricular remodeling in heart failure: current concepts in clinical significance and assessment. JACC Cardiovasc Imaging. 2011; 4(1): 98-108. doi: 10.1016/j.jcmg.2010.10.008.
21 Rij R P V. Virus meets RNAi. Symposium on Antiviral Applications of RNA Interference. EMBO Reports. 2008; 9(8):725-729. doi:10.1038/embor.2008.133.
22 J. N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. J Comput Chem. 32:170-173, 2011.
23 Jessup M, Brozena S. Heart Failure. New England Journal of Medicine. 2003; 348:2007-2018. doi: 10.1056/NEJMra021498.

APPENDIX B

```
import re
def check_sequence(seq, n, filename, exclude = ['CCC', 'GGG', '[A, U, T]{4}']):
 '"This will check through a sequence and see if it meets a set of requirements"'
 nseq = len(seq)
 assert nseq >= n
 excludereg = [ ]
 for i in exclude:
    exclude_reg.append(re.compile(i))
 # make everything upper case
 seq = seq.upper( )
 lines = [ ]
 for i in range(nseq-n+1):
  bad=0
  excluded = [ ]
    seg = seq[i:i+n]
  gcau = (seg.count('G'), seg.count('C'), seg.count('A'), seg.count('U')+seg.count('T'))
  assert (gcau[0]+gcau[1]+ gcau[2] + gcau[3]) == n
  gc_percent = float((gcau[0]+gcau[1]))/n
  for pat in exclude reg:
     x = pat.findall(seg)
     bad += len(x)
     excluded, append(x)
     threeletter = 1-float(min(gcau))/n
     lines.append((seg, excluded, gc_percent, threeletter, bad, i))
  f = open(filename, 'w')
  f.write('Sequence \t Bad Segments\t GCness\t 3-letteredness\t Number bad points\t position\n')
   for i in lines:
     for j in i:
     fwrite(repr(j)+'\f')
    f.write('\n')
 f.close()
 return lines
def reverse_complement_RNA(input):
  output ="
  input=input.upper()
  for i in range(len(input)):
   x = input[i]
   if x== 'A':
   output += U
   elif x == 'a'
   output += 'u'
   elif x == U or x=T':
   output += 'A'
   elif x == 'u':
   output += 'a'
   elif x == 'G':
   output += 'C'
   elif x == 'g':
   output += 'c'
   elif x == 'C':
   output += 'G'
   elif x == 'c':
   output += 'g'
   return output[::-1]
# generate 31 nt sensor candidates for human myh7 3' utr
hmyh7 =
'gctttgccacatcttgatctgctcagccctggaggtgccagcaa
```

```
agccccatgctggagcctgtgtaacagctccttgggaggaagca gaataaagcaattttccttgaagccgag'  (SEQ ID NO: 150)

chmyh7 = reverse_complement_RNA(hmyh7)
print(chmyh7)
print('\n')
check_sequence(chmyh7, 31, 'myh7 human.tsv')
# generate 31 nt sensor candidates for human nppa 3' utr
hnppa ='"agata acagccaggg aggacaagca gggctgggcc tagggacaga ctgcaagagg ctcctgtccc ctggggtctc tgctgcattt gtgtcatctt gttgccatgg agttgtgatc atcccatcta agctgcagct tcctgtcaac acttctcaca tcttatgcta actgtagata aagtggtttg atggtgactt cctcgcctct cccaccccat gcattaaatt ttaaggtaga acctcacctg ttactgaaag tggtttgaaa gtgaataaac ttcagcacca tggacagaag ac"'  (SEQ ID NO: 151)

chnppa = reverse_complement_RNA(hnppa)
print(chnppa)
printin')
check_sequence(chnppa, 31, 'nppa human.tsv')
# generate 31 nt sensor candidates for human nppb 3' utr
hnppb = '"gag gaagtcctgg ctgcagacac ctgcttctga ttccacaagg ggcttttttcc tcaaccctgt ggccgccttt gaagtgactc attttttttaa tgtatttatg tatttatttg attgttttat ataagatggt ttcttacctt tgagcacaaa atttccacgg tgaaataaag tcaacattat aagcttf"'  (SEQ ID NO: 152)

chnppb = reversecomplementRNA(hnppb)
print(chnppb)
print('\n')
check_sequence(chnppb, 31, 'nppb human.tsv')
# generate 31 nt sensor candidates for rat myh7 3' utr
rmyh7 = '"atct tgtgctaccc aaccctaagg atgcctgtga agccctgaga cctggagcct ttgaaacagc accttaggca gaaacacaat aaagcaattt tccttcaagc c"'  (SEQ ID NO: 153)

crmyh7 = reverse_complement_RNA(rmyh7)
print(crmyh7)
print('\n')
check_sequence(crmyh7, 31, 'myh7 rat.tsv')
# generate 31 nt sensor candidates for rat nppa 3' utr
rnppa = '"cagcc
aaatctgctc gagcagatcg caaaagatcc caagcccttg cggtgtgtca cacagcttgg tcgcattgcc actgagaggt ggtgaatacc ctcctggagc tgcagcttcc tgtcttcatc tatcacgatc gatgttaagt gtagatgagt ggtttagtga ggccttacct ctcccactct gcatattaag gtagatcctc accccttttca gaaagcagtt ggaaaaaaat aaatccgaat aaacttcagc accacggaca gacgctgagg cctg"'  (SEQ ID NO: 154)

crnppa = reversecomplementRNA(rnppa)
print(crnppa)
print('\n')
check_sequence(crnppa, 31, 'nppa rat.tsv')
# generate 31 nt sensor candidates for rat nppa 3' utr
rnppb = '"gaagacc tcctggctgc agactccggc ttctgactct gcctgcggct cttctttccc cagctctggg accacctctc aagtgatcct gtttatttat ttgtttattt atttattttt atgttgctga ttttctacaa gactgtttct tatcttccag cacaaacttg ccacagtgta ataaacatag cctatttctt gcttttgg"'  (SEQ ID NO: 155)

crnppb = reversecomplementRNA(rnppb)
print(crnppb)
print('\n')
check_sequence(crnppb, 31, 'nppb rat.tsv')
```

APPENDIX C

```
Homo sapiens myosin heavy chain 7 (MYH7), mRNA
NCBI Reference Sequence: NM_000257.3
FASTA Graphics
Go to:
LOCUS           NM_0002576069 bp mRNA linear PRI 17-JUN-2018
DEFINITION      Homo sapiens myosin heavy chain 7 (MYH7), mRNA.
ACCESSION       NM_000257 XM_005267696
VERSION         NM_000257.3
KEYWORDS        RefSeq.
SOURCE          Homo sapiens (human)

ORGANISM        Homo sapiens
                Eukaryota; Metazoa; Chordata; Craniata; Vertebrata; Euteleostomi;
                Mammalia; Eutheria; Euarchontoglires; Primates; Haplorrhini;
                Catarrhini; Hominidae; Homo.

REFERENCE       1 (bases 1 to 6069)
AUTHORS         Feng X, He T, Wang JG and Zhao P.
TITLE           Asn391Thr Mutation of beta-Myosin Heavy Chain in a Hypertrophic
                 Cardiomyopathy Family
JOURNAL         Int Heart J 59 (3), 596-600 (2018)
PUBMED          29743414
REMARK          GeneRIF: Asn391Thr mutation of MYH7 is a malignant mutation for
                hypertrophic cardiomyopathy and that mutation carriers should get
                effective treatment to prevent sudden death.

REFERENCE       2 (bases 1 to 6069)
AUTHORS         Viswanathan SK, Sanders HK, McNamara JW, Jagadeesan A, Jahangir A,
                Tajik AJ and Sadayappan S.
TITLE           Hypertrophic cardiomyopathy clinical phenotype is independent of
                gene mutation and mutation dosage
JOURNAL         PLoS ONE 12 (11), e0 187948 (2017)
PUBMED          29121657
REMARK          GeneRIF: Data provide evidence that MYH7 mutations contributed to
                24.4% MYBPC3 mutations of hypertrophic cardiomyopathy (HCM) cases,
                that MYBPC3 constitute the preeminent cause of HCM and that both
                mutations are phenotypically indistinguishable.
                Publication Status: Online-Only REFERENCE       3 (bases 1 to 6069)
AUTHORS         Wang B, Guo R, Zuo L, Shao H, Liu Y, Wang Y, Ju Y, Sun C, Wang L,
                Zhang Y and Liu L.
TITLE           [Analysis of genotype and phenotype correlation of MYH7-V878A
                mutation among ethnic Han Chinese pedigrees affected with
                hypertrophic cardiomyopathy]
JOURNAL         Zhonghua Yi Xue Yi Chuan Xue Za Zhi 34 (4), 514-518 (2017)
PUBMED          28777849
REMARK          GeneRIF: MYH7-V878A is a hot spot among ethnic Han Chinese with a
                high penetrance.

REFERENCE       4 (bases 1 to 6069)
AUTHORS         OldforsA.
TITLE           Hereditary myosin myopathies
JOURNAL         Neuromuscul. Disord. 17 (5), 355-367 (2007)
PUBMED          17434305
REMARK          Review article REFERENCE       5 (bases 1 to 6069)
AUTHORS         Cirino, A.L. and Ho, C.
TITLE           Hypertrophic Cardiomyopathy Overview
JOURNAL         (in) Adam MP, Ardinger HH, Pagon RA, Wallace SE, Bean LJH, Stephens
                K and Amemiya A (Eds.);
                GENEREVIEW S((R));
                (1993)
PUBMED          20301725

REFERENCE       6 (bases 1 to 6069)
AUTHORS         Lamont, P. and Laing, N.G.
TITLE           Laing Distal Myopathy
JOURNAL         (in) Adam MP, Ardinger HH, Pagon RA, Wallace SE, Bean LJH, Stephens
                K and Amemiya A (Eds.);
                GENEREVIEW S((R));
                (1993)
PUBMED          20301606

REFERENCE       7 (bases 1 to 6069)
AUTHORS         Hershberger, R.E. and Morales, A.
TITLE           Dilated Cardiomyopathy Overview
JOURNAL         (in) Adam MP, Ardinger HH, Pagon RA, Wallace SE, Bean LJH, Stephens
```

```
                    K and Amemiya A (Eds.);
                    GENEREVIEW S((R));
                    (1993)
PUBMED              20301486

REFERENCE           8 (bases 1 to 6069)
AUTHORS             DeChene, E.T., Kang, P.B. and Beggs, A.H.
TITLE               Congenital Fiber-Type Disproportion
JOURNAL             (in) Adam MP, Ardinger HH, Pagon RA, Wallace SE, Bean LJH, Stephens
                    K and Amemiya A (Eds.);
                    GENEREVIEW S((R));
                    (1993)
PUBMED              20301436

REFERENCE           9 (bases 1 to 6069)
AUTHORS             Warlick CA, Ramachandra S, Mishra S and Donis-Keller H.
TITLE               Dinucleotide repeat polymorphism at the human cardiac beta-myosin
                    heavy chain gene (HMSYHCO1) locus
JOURNAL             Hum. Mol. Genet. 1 (2), 136 (1992)
PUBMED              1301151

REFERENCE           10 (bases 1 to 6069)
AUTHORS             Fougerousse F, Dufour C, Roudaut C and Beckmann JS.
TITLE               Dinucleotide repeat polymorphism at the human gene for cardiac
                    beta-myosin heavy chain (MYH6)
JOURNAL             Hum. Mol. Genet. 1 (1), 64 (1992)
PUBMED              1301139
                    COMMENT REVIEWED REFSEQ: This record has been curated by NCBI staff The
                    reference sequence was derived from BF834726.1, EU747717.1,
                    M58018.1 andBC112173.L
                    On or before Jun. 20, 2014 this sequence version replaced
                    XM_005267696.1, NM_000257.2.

Summary: Muscle myosin is a hexameric protein containing 2 heavy
                    chain subunits, 2 alkali light chain subunits, and 2 regulatory
                    light chain subunits. This gene encodes the beta (or slow) heavy
                    chain subunit of cardiac myosin. It is expressed predominantly in
                    normal human ventricle. It is also expressed in skeletal muscle
                    tissues rich in slow-twitch type I muscle fibers. Changes in the
                    relative abundance of this protein and the alpha (or fast) heavy
                    subunit of cardiac myosin correlate with the contractile velocity
                    of cardiac muscle. Its expression is also altered during thyroid
                    hormone depletion and hemodynamic overloading. Mutations in this
                    gene are associated with familial hypertrophic cardiomyopathy,
                    myosin storage myopathy, dilated cardiomyopathy, and Laing
                    early-onset distal myopathy, [provided by RefSeq, Jul 2008].

Publication Note: This RefSeq record includes a subset of the
                    publications that are available for this gene. Please see the Gene
                    record to access additional publications.

##Evidence-Data-START ##
                    Transcript exon combination :: EU747717.1, M58018.1 [ECO:0000332]
                    RNAseq introns:: mixed/partial sample support
                    SAMEA1965299, SAMEA1968540
                    [ECO:0000350]
                    ##Evidence-Data-END##
                    COMPLETENESS: complete on the 3' end.
```

| PRIMARY COMP | REFSEQ_SPAN | PRIMARY IDENTIFIER PRIMARY SPAN |
|---|---|---|
| 1-25 | BF834726.1 | 60-84 |
| 26-320 | EU747717.1 | 1-295 |
| 321-1831 | M58018.1 | 276-1786 |
| 1832-3501 | BC112173.1 | 1756-3425 |
| 3502-6053 | M58018.1 | 3457-6008 |
| 6054-6069 | EU747717.1 | 6029-6044 |

| FEATURES | Location/Qualifiers |
|---|---|
| source | 1 . . . 6069<br>/organism="Homo sapiens"<br>/mol_type="mRNA"<br>/db_xref="taxon:9606"<br>/chromosome="14"<br>/map="14q11.2" |

```
gene              1...6069
                  /gene="MYH7"
                  /gene_synonym="CMD1S; CMH1; MPD1; MYHCB; SPMD; SPMM"
                  /note="myosin heavy chain 7"
                  /db_xref="GeneID:4625"

exon              1...67
                  /gene="MYH7"
                  /gene_synonym="CMD1S; CMH1; MPD1; MYHCB; SPMD; SPMM"
                  /inference="alignment: Splign:2.1.0"

exon              68...123
                  /gene="MYH7"
                  /gene_synonym="CMD1S; CMH1; MPD1; MYHCB; SPMD; SPMM"
                  /inference="alignment: Splign:2.1.0"

misc_feature      102...104
                  /gene="MYH7"
                  /gene_synonym="CMD1S; CMH1; MPD1; MYHCB; SPMD; SPMM"
                  /note="upstream in-frame stop codon"

exon              124...332
                  /gene="MYH7"
                  /gene_synonym="CMD1S; CMH1; MPD1; MYHCB; SPMD; SPMM"
                  /inference="alignment: Splign:2.1.0"

CDS               132...5939
                  /gene="MYH7"
                  /gene_synonym="CMD 1S; CMH1; MPDI; MYHCB, SPMD; SPMM"
                  /note="myosin, heavy polypeptide 7, cardiac muscle, beta;
                  myhc-slow; myopathy, distal 1; cardiac muscle myosin heavy
                  chain 7 beta; rhabdomyosarcoma antigen MU-RMS-40.7A;
                  myHC-beta; myosin heavy chain slow isoform; myosin heavy
                  chain, cardiac muscle beta isoform; myosin 7; myosin,
                  heavy chain 7, cardiac muscle, beta; myosin heavy chain
                  beta-subunit"
                  /codon_start=1
                  /product="myosin-7"
                  /protein_id="NP_000248.2"
                  /db_xref="CCDS:CCDS9601.1"
                  /db_xref="GeneID:4625"
                  /db_xref="HGNC:HGNC:7577"
                  /db_xref="MIM: 160760"
                  /gene_synonym="CMD 1S; CMH1; MPDI; MYHCB, SPMD; SPMM"
                  /note="myosin, heavy polypeptide 7, cardiac muscle, beta;
                  myhc-slow; myopathy, distal 1; cardiac muscle myosin heavy
                  chain 7 beta; rhabdomyosarcoma antigen MU-RMS-40.7A;
                  myHC-beta; myosin heavy chain slow isoform; myosin heavy
                  chain, cardiac muscle beta isoform; myosin 7; myosin,
                  heavy chain 7, cardiac muscle, beta; myosin heavy chain
                  beta-subunit"
                  /codon_start=1
                  /product="myosin-7"
                  /protein_id="NP_000248.2"
                  /db_xref="CCDS:CCDS9601.1"
                  /db_xref="GeneID:4625"
                  /db_xref="HGNC:HGNC:7577"
                  /db xref="MIM: 160760"
```

/translation=
"MGDSEMAVFGAAAPYLRKSEKERLEAQTRPFDLKKDVFVPDDKQ
EFVKAKIVSREGGKVTAETEYGKTVTVKEDQVMQQNPPKFDKIEDMAMLTF
LHEPAVLYNLKDRYGSWMIYTYSGLFCVTVNPYKWLPVYTPEVVAAYRGK
KRSEAPPHIFSISDNAYQYMLTDRENQSILITGESGAGKTVNTKRVIQYF
AVIAAIGDRSKKDQSPGKGTLEDQIIQANPALEAFGNAKTVRNDNSSRFG
KFIRIHFGATGKLASADIETYLLEKSRVIFQLKAERDYHIFYQILSNKKP
ELLDMLLITNNPYDYAFISQGETTVASIDDAEELMATDNAFDVLGFTSEE
KNSMYKLTGAIMHFGNMKFKLKQREEQAEPDGTEEADKSAYLMGLNSADL
LKGLCHPRVKVGNEYVTKGQNVQQVIYATGALAKAVYERMFNWMVTRINA
TLETKQPRQYFIGVLDIAGFEIFDFNSFEQLCINFTNEKLQQFFNHHMFV
LEQEEYKKEGIEWTFIDFGMDLQACIDLIEKPMGIMSILEEECMFPKATD
MTFKAKLFDNHLGKSANFQKPRNIKGKPEAHFSLIHYAGIVDYNIIGWLQ
KNKDPLNETVVGLYQKSSLKLLSTLFANYAGADAPIEKGKGKAKKGSSFQ
TVSALHRENLNKLMTNLRSTHPHFVRCIIPNETKSPGVMDNPLVMHQLRC
NGVLEGIRICRKGFPNRILYGDFRQRYRILNPAAIPEGQFIDSRKGAEKL
LSSLDIDHNQYKFGHTKVFFKAGLLGLLEEMRDERLSRIITRIQAQSRGV
LARMEYKKLLERRDSLLVIQWNIRAFMGVKNWPWMKLYFKIKPLLKSAER
EKEMASMKEEFTRLKEALEKSEARRKELEEKMVSLLQEKNDLQLQVQAEQ
DNLADAEERCDQLIKNKIQLEAKVKEMNERLEDEEEMNAELTAKKRKLED

```
ECSELKRDIDDLELTLAKVEKEKHATENKVKNLTEEMAGLDEIIAKLTKE
KKALQEAHQQALDDLQAEEDKVNTLTKAKVKLEQQVDDLEGSLEQEKKVR
MDLERAKRKLEGDLKLTQESIMDLENDKQQLDERLKKKDFELNALNARIE
DEQALGSQLQKKLKELQARIEELEEELEAERTARAKVEKLRSDLSRELEE
ISERLEEAGGATSVQIEMNKKREAEFQKMRRDLEEATLQHEATAAALRKK
HADSVAELGEQIDNLQRVKQKLEKEKSEFKLELDDVTSNMEQIIKAKANL
EKMCRTLEDQMNEHRSKAEETQRSVNDLTSQRAKLQTENGELSRQLDEKE
ALISQLTRGKLTYTQQLEDLKRQLEEEVKAKNALAHALQSARHDCDLLRE
QYEEETEAKAELQRVLSKANSEVAQWRTKYETDAIQRTEELEEAKKKLAQ
RLQEAEEAVEAVNAKCSSLEKTKHRLQNEIEDLMVDVERSNAAAAALDKK
QRNFDKILAEWKQKYEESQSELESSQKEARSLSTELFKLKNAYEESLEHL
ETFKRENKNLQEEISDLTEQLGSSGKTIHELEKVRKQLEAEKMELQSALE
EAEASLEHEEGKILRAQLEFNQIKAEIERKLAEKDEEMEQAKRNHLRVVD
SLQTSLDAETRSRNEALRVKKKMEGDLNEMEIQLSHANRMAAEAQKQVKS
LQSLLKDTQIQLDDAVRANDDLKENIAIVERRNNLLQAELEELRAVVEQT
ERSRKLAEQELIETSERVQLLHSQNTSLINQKKKMDADLSQLQTEVEEAV
QECRNAEEKAKKAITDAAMMAEELKKEQDTSAHLERMKKNMEQTIKDLQH
RLDEAEQIALKGGKKQLQKLEARVRELENELEAEQKRNAESVKGMRKSER
RIKELTYQTEEDRKNLLRLQDLVDKLQLKVKAYKRQAEEAEEQANTNLSK
FRKVQHELDEAEERADIAESQVNKLRAKSRDIGTK
GLNEE" (SEQ ID NO: 156)
```

| | | |
|---|---|---|
| misc_feature | 516 . . . 518 | /gene="MYH7"<br>/gene_synonym="CMD1S; CMH1; MPD1; MYHCB; SPMD; SPMM"<br>/experiment="experimental evidence, no additional details recorded"<br>/note="N6, N6, N6-trimethyllysine. {ECO:0000255}; propagated from UniProtKB/Swiss-Prot (P12883.5); methylation site" |
| misc_feature | 1263 . . . 1265 | /gene="MYH7"<br>/gene_synonym="CMD1S; CMH1; MPD1; MYHCB; SPMD; SPMM"<br>/experiment-'experimental evidence, no additional details recorded"<br>/note="Phosphothreonine. {ECO:0000250 UniProtKB:P02563}; propagated from UniProtKB/Swiss-Prot (P12883.5); phosphorylation site" |
| misc_feature | 2094 . . . 2162 | /gene="MYH7"<br>/gene_synonym="CMD1S; CMH1; MPD1; MYHCB; SPMD; SPMM"<br>/experiment="experimental evidence, no additional details recorded"<br>/note="propagated from UniProtKB/Swiss-Prot (P12883.5); Region: Actin-binding" |
| misc_feature | 2400 . . . 2444 | /gene="MYH7"<br>/gene_synonym="CMD1S; CMH1; MPD1; MYHCB; SPMD; SPMM"<br>/experiment-'experimental evidence, no additional details recorded"<br>/note="propagated from UniProtKB/Swiss-Prot (P12883.5); Region: Actin-binding" |
| misc_feature | 3540 . . . 3542 | /gene="MYH7"<br>/gene_synonym="CMD1S; CMH1; MPD1; MYHCB; SPMD; SPMM"<br>/experiment-'experimental evidence, no additional details recorded"<br>/note="Phosphoserine. {ECO:0000250 UniProtKB:P02563}; propagated from UniProtKB/Swiss-Prot (P12883.5); phosphorylation site" |
| misc_feature | 3936 . . . 3938 | /gene="MYH7"<br>/gene_synonym="CMD1S; CMH1; MPD1; MYHCB; SPMD; SPMM"<br>/experiment="experimental evidence, no additional details recorded"<br>/note="Phosphoserine. {ECO:0000250 UniProtKB:Q02566}; propagated from UniProtKB/Swiss-Prot (P12883.5); phosphorylation site" |
| misc_feature | 3975 . . . 3977 | /gene="MYH7"<br>/gene_synonym="CMD1S; CMH1; MPD1; MYHCB; SPMD; SPMM"<br>/experiment="experimental evidence, no additional details recorded"<br>/note="Phosphothreonine. {ECO:0000250 UniProtKB:P02563}; |

| | | |
|---|---|---|
| | | propagated from UniProtKB/Swiss-Prot (P12883.5); phosphorylation site" |
| misc_feature | 4053 . . . 4055 | /gene="MYH7"<br>/gene_synonym="CMD1S; CMH1; MPD1; MYHCB; SPMD; SPMM"<br>/experiment-'experimental evidence, no additional details recorded"<br>/note="Phosphotyrosine. {ECO:0000250 UniProtKB:P02563}; propagated from UniProtKB/Swiss-Prot (P12883.5); phosphorylation site" |
| misc_feature | 4056 . . . 4058 | /gene="MYH7"<br>/gene_synonym="CMD1S; CMH1; MPD1; MYHCB; SPMD; SPMM"<br>/experiment-'experimental evidence, no additional details recorded"<br>/note="Phosphothreonine. {ECO:0000250 UniProtKB:P02563}; propagated from UniProtKB/Swiss-Prot (P12883.5); phosphorylation site" |
| misc_feature | 4659 . . . 4661 | /gene="MYH7"<br>/gene_synonym="CMD1S; CMH1; MPD1; MYHCB; SPMD; SPMM"<br>/experiment-'experimental evidence, no additional details recorded"<br>/note="Phosphoserine. {ECO:0000250 UniProtKB:P02564}; propagated from UniProtKB/Swiss-Prot (P12883.5); phosphorylation site" |
| misc_feature | 4668 . . . 4670 | /gene="MYH7"<br>/gene_synonym="CMD1S; CMH1; MPD1; MYHCB; SPMD; SPMM"<br>/experiment-'experimental evidence, no additional details recorded"<br>/note="Phosphothreonine. {ECO:0000250 UniProtKB:P02563}; propagated from UniProtKB/Swiss-Prot (P12883.5); phosphorylation site" |
| exon | 333 . . . 476 | /gene="MYH7"<br>/gene_synonym="CMD1S; CMH1; MPD1; MYHCB; SPMD; SPMM"<br>/inference="alignment: Splign:2.1.0" |
| STS | 431 . . . 602 | /gene="MYH7"<br>/gene_synonym="CMD1S; CMH1; MPD1; MYHCB; SPMD; SPMM"<br>/standard_name="MYH7"<br>/db_xref="UniSTS:264117" |
| exon | 477 . . . 633 | /gene="MYH7"<br>/gene_synonym="CMD1S; CMH1; MPD1; MYHCB; SPMD; SPMM"<br>/inference="alignment: Splign:2.1.0" |
| exon | 634 . . . 661 | /gene="MYH7"<br>/gene_synonym="CMD1S; CMH1; MPD1; MYHCB; SPMD; SPMM"<br>/inference="alignment: Splign:2.1.0" |
| exon | 662 . . . 770 | /gene="MYH7"<br>/gene_synonym="CMD1S; CMH1; MPD1; MYHCB; SPMD; SPMM"<br>/inference="alignment: Splign:2.1.0" |
| exon | 771 . . . 863 | /gene="MYH7"<br>/gene_synonym="CMD1S; CMH1; MPD1; MYHCB; SPMD; SPMM"<br>/inference="alignment: Splign:2.1.0" |
| exon | 864 . . . 927 | /gene="MYH7"<br>/gene_synonym="CMD1S; CMH1; MPD1; MYHCB; SPMD; SPMM"<br>/inference="alignment: Splign:2.1.0" |
| exon | 928 . . . 1026 | /gene="MYH7"<br>/gene_synonym="CMD1S; CMH1; MPD1; MYHCB; SPMD; SPMM"<br>/inference="alignment: Splign:2.1.0" |

| | | |
|---|---|---|
| exon | 1027...1130 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 1131...1269 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 1270...1388 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 1389...1538 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 1539...1709 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 1710...2019 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 2020...2087 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 2088...2175 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 2176...2293 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 2294...2417 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 2418...2554 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 2555...2810 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 2811...3053 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 3054...3230 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 3231...3376 | |
| | /gene="MYH7" | |
| | /gene_synonym="CMD1S; CMH1; MPD1; MYHCB; SPMD; SPMM" | |
| | /inference="alignment: Splign:2.1.0" | |
| exon | 3377...3467 | |
| | /gene="MYH7" | |
| | /gene_synonym="CMD1S; CMH1; MPD1; MYHCB; SPMD; SPMM" | |

|  |  |
|---|---|
|  | /inference="alignment: Splign:2.1.0" |
| exon | 3468 . . . 3857<br>/gene="MYH7"<br>/gene_synonym="CMD1S; CMH1; MPD1; MYHCB; SPMD; SPMM"<br>/inference="alignment: Splign:2.1.0" |
| exon | 3858 . . . 3984<br>/gene="MYH7"<br>/gene_synonym="CMD1S; CMH1; MPD1; MYHCB; SPMD; SPMM"<br>/inference="alignment: Splign:2.1.0" |
| STS | 3985 . . . 4103<br>/gene="MYH7"<br>/gene_synonym="CMD1S; CMH1; MPD1; MYHCB; SPMD; SPMM"<br>/inference="alignment: Splign:2.1.0" |
| exon | 4064 . . . 4184<br>/gene="MYH7"<br>/gene_synonym="CMD1S; CMH1; MPD1; MYHCB; SPMD; SPMM"<br>/standard_name="RH93331"<br>/db_xref="UniSTS:87562" |
| exon | 4104 . . . 4300<br>/gene="MYH7"<br>/gene_synonym="CMD1S; CMH1; MPD1; MYHCB; SPMD; SPMM"<br>/inference="alignment: Splign:2.1.0" |
| exon | 4301 . . . 4484<br>/gene="MYH7"<br>/gene_synonym="CMD1S; CMH1; MPD1; MYHCB; SPMD; SPMM"<br>/inference="alignment: Splign:2.1.0" |
| exon | 4485 . . . 4650<br>/gene="MYH7"<br>/gene_synonym="CMD1S; CMH1; MPD1; MYHCB; SPMD; SPMM"<br>/inference="alignment: Splign:2.1.0" |
| exon | 4651 . . . 4775<br>/gene="MYH7"<br>/gene_synonym="CMD1S; CMH1; MPD1; MYHCB; SPMD; SPMM"<br>/inference="alignment: Splign:2.1.0" |
| exon | 4776 . . . 5084<br>/gene="MYH7"<br>/gene_synonym="CMD1S; CMH1; MPD1; MYHCB; SPMD; SPMM"<br>/inference="alignment: Splign:2.1.0" |
| exon | 5085 . . . 5288<br>/gene="MYH7"<br>/gene_synonym="CMD1S; CMH1; MPD1; MYHCB; SPMD; SPMM"<br>/inference="alignment: Splign:2.1.0" |
| exon | 5289 . . . 5414<br>/gene="MYH7"<br>/gene_synonym="CMD1S; CMH1; MPD1; MYHCB; SPMD; SPMM"<br>/inference="alignment: Splign:2.1.0" |
| exon | 5415 . . . 5690<br>/gene="MYH7"<br>/gene_synonym="CMD1S; CMH1; MPD1; MYHCB; SPMD; SPMM"<br>/inference="alignment: Splign:2.1.0" |
| STS | 5636 . . . 5719<br>/gene="MYH7"<br>/gene_synonym="CMD1S; CMH1; MPD1; MYHCB; SPMD; SPMM"<br>/standard_name="MARC_5445-5446:996690391:1"<br>/db_xref="UniSTS:269515" |
| exon | 5691 . . . 5786<br>/gene="MYH7"<br>/gene_synonym="CMD1S; CMH1; MPD1; MYHCB; SPMD; SPMM"<br>/inference="alignment: Splign:2.1.0" |
| exon5 | 787 . . . 5921<br>/gene="MYH7"<br>/gene_synonym="CMD1S; CMH1; MPD1; MYHCB; SPMD; SPMM"<br>/inference="alignment: Splign:2.1.0" |

```
STS             5814 . . . 6036
                /gene="MYH7"
                /gene_synonym="CMD1S; CMH1; MPD1; MYHCB; SPMD; SPMM"
                /standard_name="MARC_1 924-1925 99 1931692:3"
                /db_xref="UniSTS:230890"

STS             5814 . . . 5971
                /gene="MYH7"
                /gene_synonym="CMD1S; CMH1; MPD1; MYHCB; SPMD; SPMM"
                /standard_name="RH66825"
                /db_xref="UniSTS:5241"

exon            5922 . . . 6055
                /gene="MYH7"
                /gene_synonym="CMD1S; CMH1; MPD1; MYHCB; SPMD; SPMM"
                /inference="alignment: Splign:2.1.0"

STS             5948 . . . 6047
                /gene="MYH7"
                /gene_synonym="CMD1S; CMH1; MPD1; MYHCB; SPMD; SPMM"
                /standard_name="STS-N91549"
                /db_xref="Uni STS: 64175"

ORIGIN
    1 cagccctga gaccaggtct ggctccacag ctctgtcctg ctctgtgtct ttccctgctg
   61 ctctcaggtc ccctgcaggc cttggcccct ttcctcatct gtagacacac ttgagtagcc
  121 caggcacagc catgggagat tcggagatgg cagtctttgg ggctgccgcc ccctacctgc
  181 gcaagtcaga aaggagcgg ctagaagcgc agaccaggcc ttttgacctc aagaaggatg
  241 tcttcgtgcc tgatgacaaa caggagtttg tcaaggccaa gatcgtgtct cgagagggtg
  301 gcaaagtcac tgccgagacc gagtatggca gacagtgac cgtgaaggag gaccaggtga
  361 tgcagcagaa cccacccaag ttcgacaaaa tcgaggacat ggccatgctg accttcctgc
  421 atgagcccgc ggtgctctac aacctcaagg atcgctacgg ctcctggatg atctacacct
  481 actcgggcct cttctgtgtc accgtcaacc cttacaagtg gctgccggtg tacactcctg
  541 aggtggttgc tgcctaccgg ggcaagaaga ggagcgaggc cccgccccac atcttctcca
  601 tctccgacaa cgcctatcag tacatgctga cagacagaga aaaccagtcc atcctgatca
  661 ccggagaatc cggagcaggg aagacagtca acaccaagag ggtcatccag tactttgctg
  721 ttattgcagc cattggggac gcagcaaga aggaccagag cccgggcaag ggcaccctgg
  781 aggaccagat catccaggcc aaccctgctc tggaggcctt tggcaatgcc aagaccgtcc
  841 ggaacgacaa ctcctcccgc ttcgggaaat tcattcgaat tcattttggg gcaacaggaa
  901 agttggcatc tgcagacata gagacctatc ttctggaaaa atccagagtt atttccagc
  961 tgaaagcaga gagagattat cacattttct accaaatcct gtctaacaaa aagcctgagc
 1021 tgctggacat gctgctgatc accaacaacc cctacgatta tgcattcatc tcccaaggag
 1081 agaccaccgt ggcctccatt gatgacgctg aggagctgat ggccactgat aacgctttg
 1141 atgtgctggg cttcacttca gaggagaaaa actccatgta agctgaca ggcgccatca
 1201 tgcactttgg aaacatgaag ttcaagctga gcagcgggaa ggagcaggcg gagccagacg
 1261 gcactgaaga ggctgacaag tctgcctacc tcatgggct gaactcagcc gacctgctca
 1321 aggggctgtg ccaccctcgg gtgaaagtgg gcaatgagta cgtcaccagg gggcagaatg
 1381 tccagcaggt gatatatgcc actggggcac tggccaaggc agtgtatgag aggatgttca
 1441 actggatggt gacgcgcatc aatgccaccc tggagaccaa gcagcacgc cagtacttca
 1501 taggagtcct ggacatcgct ggcttcgaga tcttcgattt caacagcttt gagcagctct
 1561 gcatcaactt caccaacgag aagctgcagc agttcttcaa caccacatg tttgtgctgg
 1621 agcaggagga gtacaagaag gagggcatcg agtggacatt cattgacttt ggcatggacc
 1681 tgcaggcctg cattgacctc atcgagaagc ccatgggcat catgtccatc ctggaagagg
 1741 agtgcatgtt cccccaaggcc accgacatga ccttcaaggc caagctgttt gacaaccacc
 1801 tgggcaaatc cgccaacttc cagaagccac gcaatatcaa ggggaagcct gaagcccact
 1861 tctccctgat ccactatgcc ggcatcgtgg actacaacat cattggctgg ctgcagaaga
 1921 acaaggatcc tctcaatgag actgtcgtgg gcttgtatca gaagtcttcc ctcaagctgc
 1981 tcagcaccct gtttgccaac tatgctgggg ctgatgcgcc tattgagaag ggcaaaggca
 2041 aggccaagaa aggctcgtcc tttcagactg tgtcagctct gcacagggaa aatctgaaca
 2101 agctgatgac caacttgcgc tccacccatc cccactttgt acgttgtatc atccctaatg
 2161 agacaaagtc tccaggggtg atggacaacc cctggtcat gcaccagctg cgctgcaatg
 2221 gtgtgctgga gggcatccgc atctgcagga aggcttccc caaccgcatc ctctacgggg
 2281 acttccgca gaggtatcgc atcctgaacc cagcggccat cctgagggac agttcattg
 2341 atagcaggaa gggggcagag aagctgctca gctccctgga cattgatcac aaccagtaca
 2401 agtttggcca caccaaggtg ttcttcaagg ccgggctgct ggggctgctg gaggaaatga
 2461 gggacgagag gctgagccgc atcatcacgc gtatccaggc ccagtcccga ggtgtgctcg
 2521 ccagaatgga gtacaaaaag ctgctggaac gtagagactc cctgctggta atccagtgga
 2581 acattcgggc cttcatgggg gtcaagaatt ggccctggat gaagctctac ttcaagatca
 2641 agccgctgct gaagagtgca gaaagagaga aggagatgcc ctccatgaag gaggagttca
 2701 cacgcctcaa agaggcgcta gagaagtccg aggctcgccg caaggagctg gaggaagaa
 2761 tggtgtccct gctgcaggag aagaatgacc tgcagctcca agtgcaggcg gaacaagaca
 2821 acctggcaga tgctgaggag cgctgtgatc agctgatcaa aaacaagatt cagctggagg
 2881 ccaaggtgaa ggagatgaac gagaggctgg aggatgagga ggagatgaat gctgagctca
 2941 ctgccaagaa gcgcaagctg gaagatgagt gctcagagct catgaagga atcgatgatc
 3001 tggagctgac actggccaaa gtggagaagg agaaacacgc aacagagaac aaggtgaaaa
 3061 acctgacaga ggagatggct gggctggatg agatcattgc caagctgacc aaggagaaga
 3121 aagctctgca gagggcccac caacaggctc tggatgacct tcaggccgag gaggacaagg
 3181 tcaacaccct gactaaggcc aaagtcaagc tggagcagca agtggatgat ctggaaggat
 3241 ccctggagca agagaagaag gtgcgcatgg acctggagcg agcgaagcgg aagctggagg
```

-continued

```
3301 gcgacctgaa gctgacccag gagagcatca tggacctgga gaatgacaag cagcagctgg
3361 atgagcggct gaaaaaaaaa gactttgagc tgaatgctct caacgcaagg attgaggatg
3421 aacaggccct cggcagccag ctgcagaaga agctcaagga gcttcaggca cgcatcgagg
3481 agctggagga ggagctggag gccgagcgca ccgccagggc taaggtggag aagctgcgct
3541 cagacctgtc tcgggagctg gaggagatca gcgagcggct ggaagaggcc ggcggggcca
3601 cgtccgtgca gatcgagatg aacaagaagc gcgaggccga gttccagaag atgcggcggg
3661 acctggagga ggccacgctg cagcacgagg ccactgccgc ggccctgcgc aagaagcacg
3721 ccgacagcgt ggccgagctg ggcgagcaga tcgacaacct gcagcgggtg aagcagaagc
3781 tggagaagga gaagacgag ttcaagctgg agctggatga cgtcacctcc aacatggagc
3841 agatcatcaa ggccaaggct aacctggaga agatgtgccg gaccttggaa gaccagatga
3901 atgagcaccg gagcaaggcg gaggagaccc agcgttctgt caacgacctc accagccagc
3961 gggccaagtt gcaaaccgag aatggtgagc tgtcccggca gctggatgag aaggaggcac
4021 tgatctccca gctgacccga ggcaagctca cctacaccca gcagctggag gacctcaaga
4081 ggcagctgga ggaggaggtt aaggcgaaga acgccctggc ccacgcactg cagtcggccc
4141 ggcatgactg cgacctgctg cgggagcagt acgaggagga gacggaggcc aaggccgagc
4201 tgcagcgcgt cctttccaag gccaactcgg aggtggccca gtggaggacc aagtatgaga
4261 cggacgccat tcagcggact gaggagctcg aggaggccaa gaagaagctg gcccagcggc
4321 tgcaggaagc tgaggaggcc gtggaggctg ttaatgccaa gtgctcctcg ctggagaaga
4381 ccaagcaccg gctacagaat gagatcgagg acttgatggt ggacgtagag cgctccaatg
4441 ctgctgctgc agccctggac aagaagcaga ggaacttcga caagatcctg gccgagtgga
4501 agcagaagta tgaggagtcg cagtcggagc tggagtcctc gcagaaggag gctcgctccc
4561 tcagcacaga gctcttcaaa ctcaagaacg cctatgagga gtccctggaa catctggaga
4621 ccttcaagcg ggagaacaaa aacctgcagg aggagatctc cgacttgact gagcagttgg
4681 gttccagcgg aaagactatc catgagctgg agaaggtccg aaagcagctg gaggccgaga
4741 agatggagct gcagtcagcc ctggaggagg ccgaggcctc cctggagcac gaggagggca
4801 agatcctccg ggcccagctg gagttcaacc agatcaaggc agagatcgag cggaagctgg
4861 cagagaagga cgaggagatg aacaggcca agcgcaacca cctgcgggtg gtggactcgc
4921 tgcagacctc cctggacgca gagacacgca gccgcaacga ggccctgagg gtgaagaaga
4981 agatggaagg agacctcaat gagatggaga tccagtcag ccacgccaac cgcatggccg
5041 ccgaggccca gaagcaagtc aaggcctcc agagcttgtt gaaggacacc cagattcagc
5101 tggacgatgc agtccgtgcc aacgacgacc tgaaggagaa catcgccatc gtggagcggc
5161 gcaacaacct gctgcaggct gagctggagg agttgcgtgc cgtggtggag cagacagagc
5221 ggtcccggaa gctggcggag caggagctga ttgagactag tgagcgggtg cagctgctgc
5281 attcccagaa caccagcctc atcaaccaga agaagaagat ggatgctgac ctgtcccagc
5341 tccagactga agtgggaggag gcagtgcagg agtgcaagga tgctgaggag aaggccaaga
5401 aggccatcac ggatgccgcc atgatggcag aggagctgaa gaaggagcag gacaccagcg
5461 cccacctgga gcgcatgaag aagaacatgg aacagaccat taaggacctg cagcaccggc
5521 tggacgaagc cgagcagatc gccctcaagg gcggcaagaa gcagctgcag aagctggaag
5581 cgcgggtgcg ggagctggaa aatgagctgg aggccgagca gaagcgcaac gcagagtcgg
5641 tgaagggcat gaggaagagc gagcggcgca tcaaggagct cacctaccag acggaggagg
5701 acaggaaaaa cctgctgcgg ctgcaggacc tggtagacaa gctgcagcta aaggtcaagg
5761 cctacaagcg ccaggccgag gaggcggagg agcaagccaa caccaacctg tccaagttcc
5821 gcaaggtgca gcacgagctg gatgaggcag aggagcggga ggacatccgc gagtcccagg
5881 tcaacaagct gcgggccaag agccgtgaca ttggcacgaa gggcttgaat gaggagtagc
5941 tttgccacat cttgatctgc tcagccctgg aggtgccagc aaagccccat gctggagcct
6001 gtgtaacagc tccttgggag gaagcagaat aaagcaattt tccttgaagc cgagaaaaaa
6061 aaaaaaaaa (SEQ ID NO: 157)
//
```

APPENDIX D

*Homo sapiens* natriuretic peptide A (NPPA), mRNA
NCBI Reference Sequence: NM_006172.3
FASTA Graphics
Go to:
LOCUS NM_006172 858 bp mRNA linear PRI 29-JUL.-2018
DEFINITION *Homo sapiens* natriuretic peptide A (NPPA), mRNA.
ACCESSION NM_006172
VERSION NM_006172.3
KEYWORDS RefSeq.
SOURCE *Homo sapiens* (human)
ORGANISM *Homo sapiens*
Eukaryota; Metazoa; Chordata; Craniata; Vertebrata; Euteleostomi;
Mammalia; Eutheria; Euarchontoglires; Primates; Haplorrhini;
Catarrhini; Hominidae; Homo.

REFERENCE 1 (bases 1 to 858)
AUTHORS Cannone V., Scott C. G., Decker P. A., Larson N. B., Palmas W, Taylor K. D.,
Wang T. J., Gupta D. K., Bielinski S. J. and Burnett J. C. Jr.
TITLE A favorable cardiometabolic profile is associated with the G allele
of the genetic variant rs5068 in African Americans: The
Multi-Ethnic Study of Atherosclerosis (MESA)
JOURNAL PLoS ONE 12 (12), e0189858 (2017)
PUBMED 29253899
REMARK GeneRIF: the G allele of the genetic variant rs5068 in African
Americans is associated with lower prevalence of metabolic syndrome and lower triglycerides values
Publication Status: Online-Only REFERENCE 2 (bases 1 to 858)
AUTHORS Salo, P. P., Havulinna, A. S., Tukiainen, T., Raitakari, O.,
Lehtimaki, T., Kahonen, M., Kettunen, J., Mannikko, M., Eriksson, J. G.,
Jula, A., Blankenberg, S., Zeller, T., Salomaa, V., Kristiansson, K. and
Perola, M.
TITLE Genome-Wide Association Study Implicates Atrial Natriuretic Peptide
Rather Than B-Type Natriuretic Peptide in the Regulation of Blood
Pressure in the General Population
JOURNAL Circ Cardiovasc Genet 10 (6) (2017)
PUBMED 29237677
REMARK GeneRIF: Data indicate the blood pressure-lowering effect of atrial
natriuretic peptide (ANP) in the general population.

REFERENCE 3 (bases 1 to 858)
AUTHORS Wakula P., Neumann B., Kienemund J., Thon-Gutschi E., Stojakovic T.,
Manninger M., Scherr D., Schamagl H., Kapi M., Pieske B. and Heinzel
F. R.
TITLE CHA2DS2-VASc score and blood biomarkers to identify patients with
atrial high-rate episodes and paroxysmal atrial fibrillation
JOURNAL Europace 19 (4), 544-551 (2017)
PUBMED 28431065
REMARK GeneRIF: TIMP-4, NT-proANP, NT-proBNP were strongest associated
with PAF and AHRE. The discriminatory performance of CHADS2-VASc
for PAF was increased by addition of selected biomarkers.

REFERENCE 4 (bases 1 to 858)
AUTHORS Bartus K., Podolec J., Lee R. J., Kapelak B., Sadowski J., Bartus M., Oles
K., Ceranowicz P., Trabka R. and Litwinowicz R.
TITLE Atrial natriuretic peptide and brain natriuretic peptide changes
after epicardial percutaneous left atrial appendage suture ligation
using LARIAT device
JOURNAL J. Physiol. Pharmacol. 68 (1), 117-123 (2017)
PUBMED 28456775
REMARK GeneRIF: In summary, there were no significant differences in ANP
and BNP levels after percutaneous epicardial left atrial appendage
suture ligation using LARIAT device 3 months after procedure.

REFERENCE 5 (bases 1 to 858)
AUTHORS Suga S., Nakao K., Hosoda K., Mukoyama M., Ogawa Y., Shirakami G., Arai
H., Saito Y., Kambayashi Y., Inouye K. et al.
TITLE Receptor selectivity of natriuretic peptide family, atrial
natriuretic peptide, brain natriuretic peptide, and C-type
natriuretic peptide
JOURNAL Endocrinology 130 (1), 229-239 (1992)
PUBMED 1309330

REFERENCE 6 (bases 1 to 858)
AUTHORS Bennett B. D., Bennett G. L., Vitangcol R. V., Jewett J. R., Burnier J., Henzel
W. and Lowe D. G.
TITLE Extracellular domain-IgG fusion proteins for three human
natriuretic peptide receptors. Hormone pharmacology and application
to solid phase screening of synthetic peptide antisera
JOURNAL J. Biol. Chern. 266 (34), 23060-23067 (1991)
PUBMED 1660465

REFERENCE 7 (bases 1 to 858)
AUTHORS Koller K. J, Lowe D. G., Bennett G. L., Minamino N., Kangawa K., Matsuo H. and
Goeddel D. V.
TITLE Selective activation of the B natriuretic peptide receptor by
C-type natriuretic peptide (CNP)
JOURNAL Science 252 (5002), 120-123 (1991)
PUBMED 1672777

REFERENCE 8 (bases 1 to 858)
AUTHORS Yang-Feng, T. L., Floyd-Smith, G., Nemer, M., Drouin, J. and Francke, U.
TITLE The pronatriodilatin gene is located on the distal short arm of
human chromosome 1 and on mouse chromosome 4
JOURNAL Am. J. Hum. Genet. 37 (6), 1117-1128 (1985)
PUBMED 2934979

REFERENCE 9 (bases 1 to 858)
AUTHORS Zivin, R. A., Condra, J. H., Dixon, R. A., Seidah, N. G., Chretien, M.,
Nemer, M., Chamberland, M. and Drouin, J.
TITLE Molecular cloning and characterization of DNA sequences encoding
rat and human atrial natriuretic factors
JOURNAL Proc. Natl. Acad. Sci. U.S.A. 81 (20), 6325-6329 (1984)

```
PUBMED      6238331

REFERENCE   10 (bases 1 to 858)
AUTHORS     Oikawa, S., Imai, M., Ueno, A., Tanaka, S., Noguchi, T., Nakazato, H.,
            Kangawa, K., Fukuda, A. and Matsuo, H.
TITLE       Cloning and sequence analysis of cDNA encoding a precursor for
            human atrial natriuretic polypeptide
JOURNAL     Nature 309 (5970), 724-726 (1984)
PUBMED      6203042

COMMENT     REVIEWED REFSEQ: This record has been curated by NCBI staff The
            reference sequence was derived from BC005893.1 and AA779538.1.
            This sequence is a reference standard in the RefSeqGene project.
            On Jun. 13, 2009 this sequence version replaced NM_006172.2.

Summary: The protein encoded by this gene belongs to the
            natriuretic peptide family. Natriuretic peptides are implicated in
            the control of extracellular fluid volume and electrolyte
            homeostasis. This protein is synthesized as a large precursor
            (containing a signal peptide), which is processed to release a
            peptide from the N-terminus with similarity to vasoactive peptide,
            cardiodilatin, and another peptide from the C-terminus with
            natriuretic-diuretic activity. Mutations in this gene have been
            associated with atrial fibrillation familial type 6. This gene is
            located adjacent to another member of the natriuretic family of
            peptides on chromosome 1. [provided by RefSeq, October 2015].

Publication Note: This RefSeq record includes a subset of the
            publications that are available for this gene. Please see the Gene
            record to access additional publications.

##Evidence-Data-START ##
            Transcript exon combination :: BC005893.1, ERR279837.2678.1
            [ECO: 0000332]
            RNAseq introns :: single sample supports all introns
            SAMEA2154361, SAMEA2155550
            [ECO: 0000348]
            ##Evidence-Data-END##
            COMPLETENESS: complete on the 3'end.
```

| PRIMARY COMP | REFSEQ_SPAN | PRIMARY_IDENTIFIER | PRIMARY_SPAN |
|---|---|---|---|
| 1-552 | BC005893.1 | 1-552 | |
| 553-858 | AA779538.1 | 1-306 c | |

| FEATURES | Location/Qualifiers |
|---|---|
| source | 1 . . . 858<br>/organism = "Homo sapiens"<br>/mol_type = "mRNA"<br>/db_xref = "taxon: 9606"<br>/chromosome = "1"<br>/map = "1p36.22" |
| gene | 1 . . . 858<br>/gene = "NPPA"<br>/gene_synonym = "ANF; ANP; ATFB6; ATRST2; CDD; CDD-ANF; CDP; PND"<br>/note = "natriuretic peptide A"<br>/db_xref = "GeneID: 4878"<br><br>/db_xref = "HGNC :HGNC: 7939"<br>/db_xref = "MIM: 108780" |
| exon | 1 . . . 222<br>/gene = "NPPA"<br>/gene_synonym = "ANF; ANP; ATFB6; ATRST2; CDD; CDD-ANF; CDP; PND"<br>/inference = "alignment: Splign: 2.1.0" |
| CDS | 100 . . . 555<br>/gene = "NPPA"<br>/gene_synonym = "ANF; ANP; ATFB6; ATRST2; CDD; CDD-ANF; CDP; PND"<br>/note = "cardiodilatin-related peptide; cardionatrin; atriopeptin; prepronatriodilatin; natriuretic peptide precursor A variant 1"<br>/codon_start = 1 |

```
                /product = "natriuretic peptides A preproprotein"
                /protein_id = "NP_006163.1"
                /db_xref = "CCDS: CCDS139.1"
                /db_xref = "GeneID: 4878"
                /db_xref = "HGNC: HGNC: 7939"
                /db_xref = "MIM: 108780"

/translation = "MSSFSTTTVSFLLLLAFQLLGQTRANPMYNAVSNADLMDFKNLL
DHLEEKMPLEDEVVPPQVLSEPNEEAGAALSPLPEVPPWTGEVSPAQRDGGALGRGP
W
DSSDRSALLKSKLRALLTAPRSLRRSSCFGGRMDRIGAQSGLGCNSFRY"
(SEQ ID NO: 158)

sig_peptide     100 . . . 174
                /gene = "NPPA"
                /gene_synonym = "ANF; ANP; ATFB6; ATRST2; CDD; CDD-ANF; CDP;
                PND"
                /inference = "COORDINATES: ab initio prediction:SignalP: 4.0"

misc_feature    466 . . . 471
                /gene = "NPPA"
                /gene_synonym = "ANF; ANP; ATFB6; ATRST2; CDD; CDD-ANF; CDP;
                PND"
                /experiment= "experimental evidence, no additional details
                recorded"
                /note = "Cleavage, by CORIN. {ECO: 0000269|PubMed: 10880574};
                propagated from UniProtKB/Swiss-Prot (P01160.1); cleavage
                site"

mat_peptide     469 . . . 552
                /gene = "NPPA"
                /gene_synonym = "ANF; ANP; ATFB6; ATRST2; CDD; CDD-ANF; CDP;
                PND"
                /product = "Atrial natriuretic factor.
                {ECO: 0000269|PubMed: 10880574, ECO: 0000269|PubMed:6230082}"
                /experiment = "experimental evidence, no additional details
                recorded"
                /note = "propagated from UniProtKB/Swiss-Prot (P01160.1)"

misc_feature    487 . . . 492
                /gene = "NPPA"
                /gene_synonym = "ANF; ANP; ATFB6; ATRST2; CDD; CDD-ANF; CDP;
                PND"
                /experiment = "experimental evidence, no additional details
                recorded"
                /note = "Cleavage, by MME. {ECO: 0000269|PubMed: 2972276};
                propagated from UniProtKB/Swiss-Prot (P01160.1); cleavage
                site"

exon            223 . . . 549
                /gene = "NPPA"
                /gene_synonym = "ANF; ANP; ATFB6; ATRST2; CDD; CDD-ANF; CDP;
                PND"
                /inference = "alignment: Splign: 2.1.0"

STS             354 . . . 604
                /gene = "NPPA"
                /gene_synonym = "ANF; ANP; ATFB6; ATRST2; CDD; CDD-ANF; CDP;
                PND"
                /standard_name = "GDB: 226664"
                /db_xref = "UniSTS: 156242"

STS             367 . . . 548
                /gene = "NPPA"
                /gene_synonym = "ANF; ANP; ATFB6; ATRST2; CDD; CDD-ANF; CDP;
                PND"
                /standard_name = "NPPA"
                /db_xref = "UniSTS: 253991"

exon            550 . . . 855
                /gene = "NPPA"
                /gene_synonym = "ANF; ANP; ATFB6; ATRST2; CDD; CDD-ANF; CDP;
                PND"
                /inference = "alignment: Splign: 2.1.0"

STS             588 . . . 847
                /gene = "NPPA"
                /gene_synonym = "ANF; ANP; ATFB6; ATRST2; CDD; CDD-ANF; CDP;
                PND"
```

|  |  |
|---|---|
| | /standard_name = "RH80468"<br>/db_xref = "UniSTS: 87961" |
| STS | 595 . . . 762<br>/gene = "NPPA"<br>/gene_synonym = "ANF; ANP; ATFB6; ATRST2; CDD; CDD-ANF; CDP; PND"<br>/standard_name = "SHGC-7423_8"<br>/db_xref = "UniSTS: 43068" |
| regulatory | 824 . . . 829<br>/regulatory_class = "polyA_signal_sequence"<br>/gene = "NPPA"<br>/gene_synonym = "ANF; ANP; ATFB6; ATRST2; CDD; CDD-ANF; CDP; PND" |
| polyA_site | 855<br>/gene = "NPPA"<br>/gene_synonym = "ANF; ANP; ATFB6; ATRST2; CDD; CDD-ANF; CDP; PND" |

```
ORIGIN
  1 gagacaggga cagacgtagg ccaagagagg ggaaccagag aggaaccaga ggggagagac
 61 agagcagcaa gcagtggatt gctccttgac dacgccagca tgagctcctt ctccaccacc
121 accgtgagct tcctcctttt actggcattc cagctcctag gtcagaccag agctaatccc
181 atgtacaatg ccgtgtccaa cgcagacctg atggatttca agaatttgct ggaccatttg
241 gaagaaaaga tgcctttaga agatgaggtc gtgccccac aagtgctcag tgagccgaat
301 gaagaagcgg gggctgctct cagccccctc cctgaggtgc ctccctggac cggggaagtc
361 agcccagccc agagagatgg aggtgccctc gggcggggcc cctgggactc tctgatcga
421 tctgccctcc taaaaagcaa gctgagggcg ctgctcactg cccctcggag cctgcggaga
481 tccagctgct tcggggggcag gatggacagg attggagccc agagcggact gggctgtaac
541 agcttccggt actgaagata acagccaggg aggacaagca gggctgggcc tagggacaga
601 ctgcaagagg ctcctgtccc ctggggtctc tgctgcattt gtgtcatctt gttgccatgg
661 agttgtgatc atcccatcta agctgcagct tcctgtcaac acttctcaca tcttatgcta
721 actgtagata aagtggtttg atggtgactt cctcgcctct cccaccccat gcattaaatt
781 ttaaggtaga acctcacctg ttactgaaag tggtttgaaa gtgaataaac ttcagcacca
841 tggacagaag acaaaaaa (SEQ ID NO: 159)
```

APPENDIX E

*Homo sapiens* natriuretic peptide B (NPPB), mRNA
NCBI Reference Sequence: NM_002521.2
FASTA Graphics
Go to:
LOCUS       NM_002521              708 bp mRNA linear PRI 22-JUL.-2018
DEFINITION  *Homo sapiens* natriuretic peptide B (NPPB), mRNA.
ACCESSION   NM_002521
VERSION     NM_002521.2
KEYWORDS    RefSeq.
SOURCE      *Homo sapiens* (human)
  ORGANISM  *Homo sapiens*
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.

REFERENCE   1  (bases 1 to 708)
AUTHORS     Hex C., Smeets M., Penders J., Van Hoof V., Verbakel J., Buntinx F. and
Vaes B.
TITLE       Accuracy, user-friendliness and usefulness of the Cobas h232
point-of-care test for NT-proBNP in primary care
JOURNAL     J. Clin. Pathol. 71 (6), 539-545 (2018)
PUBMED      29263170
REMARK      GeneRIF: Report usefulness of point-of-care test for NT-proBNP in
primary care for the diagnosis of heart failure.

REFERENCE   2  (bases 1 to 708)
AUTHORS     Drozdz T., Kwinta P., Kordon Z., Sztefko K., Rudzinski A., Zachwieja K.,
Miklaszewska M., Czarnecka D. and Drozdz D.
TITLE       [B-type natriuretic peptide as a marker of cardiac dysfunction in
children with chronic kidney disease]
JOURNAL     Pol. Merkur. Lekarski 44 (262), 171-176 (2018)
PUBMED      29775443
REMARK      GeneRIF: In children with chronic kidney disease, BNP is an
indicator of heart failure correlating with renal function
parameters and left ventricular mass index.

```
REFERENCE 3  (bases 1 to 708)
AUTHORS   Fernandez-Susavila H, Rodriguez-Yanez M., Dopico-Lopez A., Arias S.,
          Santamaria M., Avila-Gomez P., Doval-Garcia J. M., Sobrino T.,
          Iglesias-Rey R., Castillo J. and Campos F.
TITLE     Heads and Tails of Natriuretic Peptides: Neuroprotective Role of
          Brain Natriuretic Peptide
JOURNAL   J Am Heart Assoc 6 (12), e007329 (2017)
PUBMED    29203579
REMARK    GeneRIF: Suggest potential role for BNP as a protective endogenous
          factor against cerebral ischemia.
          Publication Status: Online-Only REFERENCE 4  (bases 1 to 708)
AUTHORS   Legaz-Arrese A., Carranza-Garcia L. E., Navarro-Orocio R., Valadez-Lira
          A., Mayolas-Pi C., Munguia-Izquierdo D., Reverter-Masia J. and George
          K.
TITLE     Cardiac Biomarker Release after Endurance Exercise in Male and
          Female Adults and Adolescents
JOURNAL   J. Pediatr. 191, 96-102 (2017)
PUBMED    29173327
REMARK    GeneRIF: An exercise-associated increase in hs-cTnT and NT-proBNP
          occurred in response to a 60-minute maximal swimming test that was
          independent of pubertal status/adolescent vs adults. The present
          data also suggests that baseline and postexercise hs-cTnT values
          are higher in male compared with female, with no sex differences in
          NT-proBNP values.

REFERENCE 5  (bases 1 to 708)
AUTHORS   Krause A., Liepke C., Meyer M., Adermann K., Forssmann W. G. and Maronde
          E.
TITLE     Human natriuretic peptides exhibit antimicrobial activity
JOURNAL   Eur. J. Med. Res. 6 (5), 215-218 (2001)
PUBMED    11410403
REMARK    GeneRIF: Brain-type natriuretic peptide (hBNP-32) is an
          antimicrobial peptide active against Gram-positive and
          Gram-negative bacteria and yeast.

REFERENCE 6  (bases 1 to 708)
AUTHORS   Arden K. C., Viars C. S., Weiss S., Argentin S. and Nemer M.
TITLE     Localization of the human B-type natriuretic peptide precursor
          (NPPB) gene to chromosome 1p36
JOURNAL   Genomics 26 (2), 385-389 (1995)
PUBMED    7601467

REFERENCE 7  (bases 1 to 708)
AUTHORS   Suga S., Nakao K., Hosoda K., Mukoyama M., Ogawa Y., Shirakami G., Arai
          H., Saito Y., Kambayashi Y., Inouye K. et al.
TITLE     Receptor selectivity of natriuretic peptide family, atrial
          natriuretic peptide, brain natriuretic peptide, and C-type
          natriuretic peptide
JOURNAL   Endocrinology 130 (1), 229-239 (1992)
PUBMED    1309330

REFERENCE 8  (bases 1 to 708)
AUTHORS   Bennett B. D., Bennett G. L., Vitangcol R. V., Jewett J. R., Burnier J., Henzel
          W. and Lowe D. G..
TITLE     Extracellular domain-IgG fusion proteins for three human
          natriuretic peptide receptors. Hormone pharmacology and application
          to solid phase screening of synthetic peptide antisera
JOURNAL   J. Biol. Chern. 266 (34), 23060-23067 (1991)
PUBMED    1660465

REFERENCE 9  (bases 1 to 708)
AUTHORS   Koller K. J., Lowe D. G., Bennett G. L., Minamino N., Kangawa K., Matsuo H. and
          Goeddel D. V..
TITLE     Selective activation of the B natriuretic peptide receptor by
          C-type natriuretic peptide (CNP)
JOURNAL   Science 252 (5002), 120-123 (1991)
PUBMED    1672777

REFERENCE 10 (bases 1 to 708)
AUTHORS   Sudoh T., Maekawa K., Kojima M., Minamino N., Kangawa K. and Matsuo H.
TITLE     Cloning and sequence analysis of cDNA encoding a precursor for
          human brain natriuretic peptide
JOURNAL   Biochem. Biophys. Res. Commun. 159 (3), 1427-1434 (1989)
PUBMED    2522777

COMMENT   REVIEWED REFSEQ: This record has been curated by NCBI staff. The
          reference sequence was derived from AJ708502.1, M25296.1 and
          BC025785.1.
```

-continued

On Dec. 16, 2005 this sequence version replaced NM_002521.1.

Summary: This gene is a member of the natriuretic peptide family and encodes a secreted protein which functions as a cardiac hormone. The protein undergoes two cleavage events, one within the cell and a second after secretion into the blood. The protein's biological actions include natriuresis, diuresis, vasorelaxation, inhibition of renin and aldosterone secretion, and a key role in cardiovascular homeostasis. A high concentration of this protein in the bloodstream is indicative of heart failure. The protein also acts as an antimicrobial peptide with antibacterial and antifungal activity. Mutations in this gene have been associated with postmenopausal osteoporosis, [provided by RefSeq, November 2014].

Publication Note: This RefSeq record includes a subset of the publications that are available for this gene. Please see the Gene record to access additional publications.

Evidence-Data-START##
Transcript exon combination :: BC025785.1, ERR279856.3578.1
[ECO: 0000332]
RNAseq introns :: single sample supports all introns
SAMEA2148093, SAMEA2151741
[ECO: 0000348]
Evidence-Data-END##
RefSeq-Attributes-START##
Protein has antimicrobial activity :: PMID: 11410403
RefSeq-Attributes-END##
COMPLETENESS: complete on the 3'end.

| PRIMARY COMP | REFSEQ_SPAN | PRIMARY_IDENTIFIER | PRIMARY_SPAN |
|---|---|---|---|
| 1-4 | AJ708502.1 | | 19-22 |
| 5-695 | M25296.1 | | 2-692 |
| 696-708 | BC025785.1 | | 683-695 |

| FEATURES | Location/Qualifiers |
|---|---|
| source | 1 . . . 708<br>/organism = "*Homo sapiens*"<br>/mol_type = "mRNA"<br>/db_xref = "taxon: 9606"<br>/chromosome = "1"<br>/map = "1p36.22" |
| gene | 1 . . . 708<br>/gene = "NPPB"<br>/gene_synonym = "BNP"<br>/note = "natriuretic peptide B"<br>/db_xref = "GeneID: 4879"<br>/db_xref = "HGNC: HGNC: 7940"<br>/db_xref = "MIM: 600295" |
| exon | 1 . . . 234<br>/gene = "NPPB"<br>/gene_synonym = "BNP"<br>/inference = "alignment: Splign: 2.1.0" |
| CDS | 103 . . . 507<br>/gene = "NPPB"<br>/gene_sy nony m = "BNP"<br>/note = "natriuretic peptide precursor B; brain type natriuretic peptide; natriuretic peptides B; natriuretic protein; gamma-brain natriuretic peptide"<br>/codon_start = 1<br>/product = "natriuretic peptides B preproprotein"<br>/protein_id = "NP_002512.1"<br>/db_xref = "CCDS: CCDS140.1"<br>/db_xref = "GeneID: 4879"<br>/db_xref = "HGNC HGNC: 7940"<br>/db_xref = "MIM: 600295" |

/translation = "MDPQTAPSRALLLLLFLHLAFLGGRSHPLGSPGSASDLETSGLQ
EQRNHLQGKLSELQVEQTSLEPLQESPRPTGVWKSREVATEGIRGHRKMVLYTLRAP
R
SPKMVQGSGCFGRKMDRISSSSGLGCKVLRRH"(SEQ ID NO: 160)

sig_peptide 103 . . . 180

```
            /gene = "NPPB"
            /gene_synonym = "BNP"
            /inference = "COORDINATES: ab initio prediction: SignalP: 4.0"

proprotein  181 . . . 504
            /gene = "NPPB"
            /gene_synonym = "BNP"
            /product = "natriuretic peptides B proprotein"
            /note = "proBNP; gamma-brain natriuretic peptide"

mat_peptide 409 . . . 504
            /gene = "NPPB"
            /gene_synonym = "BNP"
            /product = "natriuretic peptides B"
            /experiment = "DESCRIPTION: antimicrobial
            peptide[PMID: 11410403]"
            /note = "brain natriuretic peptide 32"

exon        235 . . . 490
            /gene = "NPPB"
            /gene_synonym = "BNP"
            /inference = "alignment: Splign: 2.1.0"

exon        491 . . . 698
            /gene = "NPPB"
            /gene_synonym = "BNP"
            /inference = "alignment: Splign: 2.1.0"

regulatory  674 . . . 679
            /regulatory_class = "poly A_signal_sequence"
            /gene = "NPPB"
            /gene_synonym = "BNP"

polyA_site  698
            /gene = "NPPB"
            /gene_synonym = "BNP"

ORIGIN
        1   ccccgcaggc tgagggcagg tgggaagcaa acccggacgc atcgcagcag cagcagcagc
       61   agcagaagca gcagcagcag cctccgcagt ccctccagag acatggatcc ccagacagca
      121   ccttcccggg cgctcctgct cctgctcttc ttgcatctgg ctttcctggg aggtcgttcc
      181   cacccgctgg gcagccccgg ttcagcctcg gacttggaaa cgtccgggtt acaggagcag
      241   cgcaaccatt tgcagggcaa actgtcggag ctgcaggtgg agcagacatc cctggagccc
      301   ctccaggaga gcccccgtcc cacaggtgtc tggaagtccc gggaggtagc caccgagggc
      361   atccgtgggc accgcaaaat ggtcctctac accctgcggg caccacgaag ccccaagatg
      421   gtgcaagggt ctggctgctt tgggaggaag atggaccgga tcagctcctc cagtggcctg
      481   ggctgcaaag tgctgagggc gcattaagag gaagtcctgg ctgcagacac ctgcttctga
      541   ttccacaagg ggcttttttcc tcaaccctgt ggccgccttt gaagtgactc attttttttaa
      601   tgtatttatg tatttatttg attgttttat ataagatggt ttcttacctt tgagcacaaa
      661   atttccacgg tgaaataaag tcaacattat aagctttaaa aaaaaaaa    (SEQ ID NO: 161)
    //
```

45

APPENDIX F

*Rattus norvegicus* myosin heavy chain 7 (Myh7), mRNA
NCBI Reference Sequence: NM_017240.2
FASTA Graphics
Go to:
LOCUS NM_0172405923 bp mRNA linear ROD 31-MAY.-2018
DEFINITION *Rattus norvegicus* myosin heavy chain 7 (Myh7), mRNA.
ACCESSION NM_017240
VERSION NM_017240.2
KEYWORDS RefSeq.
SOURCE *Rattus norvegicus* (Norway rat)
ORGANISM *Rattus norvegicus*
Eukaryota; Metazoa; Chordata; Craniata; Vertebrata; Euteleostomi;
Mammalia; Eutheria; Euarchontoglires; Glires; Rodentia; Myomorpha;
Muroidea; Muridae; Murinae; Rattus.

REFERENCE 1 (bases 1 to 5923)
AUTHORS Tomita-Mitchell A., Stamm K. D., Mahnke D. K., Kim M. S., Hidestrand P. M.,
Liang H. L., Goetsch M. A., Hidestrand M., Simpson P., Pelech A. N., Tweddell
J. S., Benson D. W., Lough J. W. and Mitchell M.E.
TITLE Impact of MYH6 variants in hypoplastic left heart syndrome
JOURNAL Physiol. Genomics 48 (12), 912-921 (2016)
PUBMED 27789736

```
REFERENCE   2  (bases 1 to 5923)
  AUTHORS   Chandra V., Gollapudi S. K. and Chandra M.
  TITLE     Rat cardiac troponin T mutation (F72L)-mediated impact on thin
            filament cooperativity is divergently modulated by alpha- and
            beta-myosin heavy chain isoforms
  JOURNAL   Am. J. Physiol. Heart Circ. Physiol. 309 (8), H1260-H1270 (2015)
  PUBMED    26342069
  REMARK    GeneRIF: TnT mutation F72L leads to contractile changes that are
            linked to dilated cardiomyopathy in the presence of MYH6 and
            hypertrophic cardiomyopathy in the presence of MYH7.

REFERENCE   3  (bases 1 to 5923)
  AUTHORS   Kralova E., Doka G., Pivackova L., Srankova J., Kuracinova K., Janega P.,
            Babal P., Klimas J. and Krenek P.
  TITLE     l-Arginine Attenuates Cardiac Dysfunction, But Further
            Down-Regulates alpha-Myosin Heavy Chain Expression in
            Isoproterenol-Induced Cardiomyopathy
  JOURNAL   Basic Clin. Pharmacol. Toxicol. 117 (4), 251-260 (2015)
  PUBMED    25865156

REFERENCE   4  (bases 1 to 5923)
  AUTHORS   Taylor K. C., Buvoli M., Korkmaz E. N., Buvoli A., Zheng Y., Heinze N. T., Cui
            Q., Leinwand L. A. and Rayment I.
  TITLE     Skip residues modulate the structural properties of the myosin rod
            and guide thick filament assembly
  JOURNAL   Proc. Natl. Acad. Sci. U.S.A. 112 (29), E3806-E3815 (2015)
  PUBMED    26150528

REFERENCE   5  (bases 1 to 5923)
  AUTHORS   Zhang P., Shan T., Liang X., Deng C. and Kuang S.
  TITLE     Mammalian target of rapamycin is essential for cardiomyocyte
            survival and heart development in mice
  JOURNAL   Biochem. Biophys. Res. Commun. 452 (1), 53-59 (2014)
  PUBMED    25139234

REFERENCE   6  (bases 1 to 5923)
  AUTHORS   O'Neill L., Holbrook N. J., Fargnoli J. and Lakatta E. G.
  TITLE     Progressive changes from young adult age to senescence in mRNA for
            rat cardiac myosin heavy chain genes
  JOURNAL   Cardioscience 2 (1), 1-5 (1991)
  PUBMED    1888877

REFERENCE   7  (bases 1 to 5923)
  AUTHORS   Schuyler G. T. and Yarbrough L. R.
  TITLE     Changes in myosin and creatine kinase mRNA levels with cardiac
            hypertrophy and hypothyroidism
  JOURNAL   Basic Res. Cardiol. 85 (5), 481-494 (1990)
  PUBMED    1703406

REFERENCE   8  (bases 1 to 5923)
  AUTHORS   McNally E. M., Kraft R., Bravo-Zehnder M., Taylor D. A. and Leinwand L. A.
  TITLE     Full-length rat alpha and beta cardiac myosin heavy chain
            sequences. Comparisons suggest a molecular basis for functional
            differences
  JOURNAL   J. Mol. Biol. 210 (3), 665-671 (1989)
  PUBMED    2614840

REFERENCE   9  (bases 1 to 5923)
  AUTHORS   Kraft R., Bravo-Zehnder M., Taylor D. A. and Leinwand L. A.
  TITLE     Complete nucleotide sequence of full length cDNA for rat beta
            cardiac myosin heavy chain
  JOURNAL   Nucleic Acids Res. 17 (18), 7529-7530 (1989)
  PUBMED    2798112

REFERENCE   10 (bases 1 to 5923)
  AUTHORS   Izumo, S., Lompre, A. M., Matsuoka, R., Koren, G., Schwartz, K.,
            Nadal-Ginard, B. and Mahdavi, V.
  TITLE     Myosin heavy chain messenger RNA and protein isoform transitions
            during cardiac hypertrophy. Interaction between hemodynamic and
            thyroid hormone-induced signals
  JOURNAL   J. Clin. Invest. 79 (3), 970-977 (1987)
  PUBMED    2950137

COMMENT     PROVISIONAL REFSEQ: This record has not yet been subject to final
            NCBI review. The reference sequence was derived from X15939.1.
            On Feb. 21, 2013 this sequence version replaced NM_017240.1.

Summary: heavy chain of myosin; involved in muscle contraction
```

-continued

[RGD, February 2006].

Publication Note: This RefSeq record includes a subset of the publications that are available for this gene. Please see the Gene record to access additional publications.

Evidence-Data-START##
Transcript exon combination :: X15939.1 [ECO: 0000332]
RNAseq introns :: mixed/partial sample support
SAMD00052296, SAMD00052297
[ECO: 0000350]
Evidence-Data-END##

| | PRIMARY COMP | REFSEQ_SPAN | PRIMARY_IDENTIFIER | PRIMARY_ SPAN |
|---|---|---|---|---|
| | 1-5923 | X15939.1 | | 3-5925 |
| FEATURES | Location/Qualifiers | | | |
| source | 1 . . . 5923<br>/organism = "Rattus norvegicus"<br>/mol_type = "mRNA"<br>/db_xref = "taxon: 10116"<br>/chromosome = "15"<br>/map = "15p13" | | | |
| gene | 1 . . . 5923<br>/gene = "Myh7"<br>/gene_synonym = "Bmyo; myHC-beta; myHC-slow; Myhcb"<br>/note = "myosin heavy chain 7"<br>/db_xref = "GeneID: 29557"<br>/db_xref = "RGD: 62030" | | | |
| exon | 1 . . . 209<br>/gene = "Myh7"<br>/gene_synonym = "Bmyo; myHC-beta; myHC-slow; Myhcb"<br>/inference = "alignment: Splign: 2.0.8" | | | |
| CDS | 9 . . . 5816<br>/gene = "Myh7"<br>/gene_synonym = "Bmyo; myHC-beta; myHC-slow; Myhcb"<br>/note = "myosin heavy chain, cardiac muscle, fetal; beta myosin heavy chain; myosin heavy chain slow isoform; myosin heavy chain, cardiac muscle beta isoform; myosin, heavy polypeptide 7, cardiac muscle, beta; myosin heavy chain, polypeptide 7; myosin heavy chain polypeptide 7 cardiac muscle fetal; myosin, heavy chain 7, cardiac muscle, beta"<br>/codon_start = 1<br>/product = "myosin-7"<br>/protein_id = "NP_058936.1"<br>/db_xref = "GeneID: 29557"<br>/db_xref = "RGD: 62030" | | | |

/translation = "MADREMAAFGAGAPFLRKSEKERLEAQTRPFDLKKDVFVPDDKE
EFVKAKIVSREGGKVTAETENGKTVTVKEDQVMQQNPPKFDKIEDMAMLTFLHEPA
VL
YNLKERYASWMIYTYSGLFCVTVNPYKWLPVYNAQVVAAYRGKKRSEAPPHIFSIS
DN
AYQYMLTDRENQSILITGESGAGKTVNTKRVIQYFAVIAAIGDRSKKDQTPGKGTLE
D
QIIQANPALEAFGNAKTVRNDNSSRFGKFIRIHFGATGKLASADIETYLLEKSRVIFQ
LKAERDYHIFYQILSNKKPELLDMLLITNNPYDYAFFSQGETTVASIDDSEEHMATDS
AFDVLGFTPEEKNSIYKLTGAIMHFGNMKFKQKQREEQAEPDGTEEADKSAYLMGL
NS
ADLLKGLCHPRVKVGNEYVTKGQNVQQVAYAIGALAKSVYEKMFNWMVTRINAT
LETK
QPRQYFIGVLDIAGFEIFDFNSFEQLCINFTNEKLQQFFNHHMFVLEQEEYKKEGIEW
TFIDFGMDLQACIDLIEKPMGIMSILEEECMFPKATDMTFKAKLYDNHLGKSNNFQK
P
RNIKGKQEAHFSLIHYAGTVDYNILGWLQKNKDPLNETVVGLYQKSSLKLLSNLFAN
Y
AGADAPVDKGKGKAKKGSSFQTVSALHRENLNKLMTNLRSTHPHFVRCIIPNETKSP
G
VMDNPLVMHQLRCNGVLEGIRICRKGFPNRILYGDFRQRYRILNPAAIPEGQFIDSRK
GAEKLLGSLDIDHNQYKFGHTKVFFKAGLLGLLEEMRDERLSRIITRIQAQSRGVLSR
MEFKKLLERRDSLLIIQWNIRAFMGVKNWPWMKLYFKIKPLLKSAETEKEMANMKE
EF -continued

```
GRVKDALEKSEARRKELEEKMVSLLQEKNDLQLQVQAEQDNLADAEERCDQLIKN
KIQ
LEAKVKEMTERLEDEEEMNAELTAKKRKLEDECSELKRDIDDLELTLAKVEKEKHA
TE
NKVKNLTEEMAGLDEIIVKLTKEKKALQEAHQQALDDLQAEEDKVNTLTKAKVKLE
QQ
VDDLEGSLDQDKKVRMDLERAKRKLEGDLKLTQESIMDLENDKQQLDERLKKKDF
ELN
ALNARIEDEQALGSQLQKKLKELQARIEELEEELEAERTARAKVEKLRSDLSRELEEI
SERLEEAGGATSVQIEMNKKREAEFQKMRRDLEEATLQHEATAAALRKKHADSVAE
LG
EQIDNLQRVKQKLEKEKSEFKLELDDVTSNMEQIIKAKANLEKMCRTLEDQMNEHR
SK
AEETQRSVNDLTRQRAKLQTENGELSRQLDEKEALISQLTRGKLTYQQLEDLKRQL
E
EEVKAKNALAHALQSARHDCDLLREQYEEETEAKAELQRVLSKANSEVAQWRTKY
ETD
AIQRTEELEEAKKKLAQRLQDAEEAVEAVNAKCSSLEKTKHRLQNEIEDLMVDVER
SN
AAAAALDKKQRNFDKILVEWKQKYEESQSELESSQKEARSLSTELFKLKNAYEESLE
H
LETFKRENKNLQEEISDLTEQLGSTGKSIHELEKIRKQLEAEKLELQSALEEAEASLE
HEEGKILRAQLEFNQIKAEIERKLAEKDEEMEQAKRNHLRVVDSLQTSLDAETRSRN
E
ALRVKKKMEGDLNEMEIQLSHANRMAAEAQKQVKSLQSLLKDTQIQLDDAVRAND
DLK
ENIAIVERRNNLLQAELEELRAVVEQTERSRKLAEQELIETSERVQLLHSQNTSLINQ
KKKMDADLSQLQTEVEEAVQECRNAEEKAKKAITDAAMMAEELKKEQDTSAHLER
MKN
NMEQTIKDLQHRLDEAEQIALKGGKKQLQKLEARVRELENELEAEQKRNAESVKGM
RK
SERRIKELTYQTEEDRKNLLRLQDLVDKLQLKVKAYKRQAEEAEEQANTNLSKFRK
VQ
HELDEAEERADIAESQVNKLRAKSRDIGAKGLNEE" (SEQ ID NO: 162)

misc_feature  393 . . . 395
              /gene = "Myh7"
              /gene_synonym = "Bmyo; myHC-beta; myHC-slow; Myhcb"
              /experiment = "experimental evidence, no additional details
              recorded"
              /note = "N6,N6,N6-trimethyllysine. {ECO: 0000255}; propagated
              from UniProtKB/Swiss-Prot (P02564.2); methylation site"

misc_feature  1140 . . . 1142
              /gene = "Myh7"
              /gene_synonym = "Bmyo; myHC-beta; myHC-slow; Myhcb"
              /experiment = "experimental evidence, no additional details
              recorded"
              /note = "Phosphothreonine. {ECO: 0000250|UniProtKB: P02563};
              propagated from UniProtKB/Swiss-Prot (P02564.2);
              phosphorylation site"

misc_feature  1971 . . . 203 9
              /gene = "Myh7"
              /gene_synonym = "Bmyo; myHC-beta; myHC-slow; Myhcb"
              /experiment = "experimental evidence, no additional details
              recorded"
              /note = "propagated from UniProtKB/Swiss-Prot (P02564.2);
              Region: Actin-binding"

misc_feature  2277 . . . 2321
              /gene = "Myh7"
              /gene_synonym = "Bmyo; myHC-beta; myHC-slow; Myhcb"
              /experiment = "experimental evidence, no additional details
              recorded"
              /note = "propagated from UniProtKB/Swiss-Prot (P02564.2);
              Region: Actin-binding"

misc_feature  3417 . . . 3419
              /gene = "Myh7"
              /gene_synonym = "Bmyo; myHC-beta; myHC-slow; Myhcb"
              /experiment = "experimental evidence, no additional details
              recorded"
              /note = "Phosphoserine. {ECO: 0000250|UniProtKB: P02563};
              propagated from UniProtKB/Swiss-Prot (P02564.2);
              phosphorylation site"

misc_feature  3813 . . . 3815
              /gene = "Myh7"
```

```
                /gene_synonym = "Bmyo; myHC-beta; myHC-slow; Myhcb"
                /experiment = "experimental evidence, no additional details
                recorded"
                /note = "Phosphoserine. {ECO: 0000250|UniProtKB: Q02566};
                propagated from UniProtKB/Swiss-Prot (P02564.2);
                phosphorylation site"
misc_feature    3852 . . . 3854
                /gene = "Myh7"
                /gene_synonym = "Bmyo; myHC-beta; myHC-slow; Myhcb"
                /experiment = "experimental evidence, no additional details
                recorded"
                /note = "Phosphothreonine. {ECO: 0000250|UniProtKB: P02563};
                propagated from UniProtKB/Swiss-Prot (P02564.2);
                phosphorylation site"
misc_feature    3930 . . . 3932
                /gene = "Myh7"
                /gene_synonym = "Bmyo; myHC-beta; myHC-slow; Myhcb"
                /experiment = "experimental evidence, no additional details
                recorded"
                /note = "Phosphotyrosine. {ECO: 0000250|UniProtKB: P02563};
                propagated from UniProtKB/Swiss-Prot (P02564.2);
                phosphorylation site"
misc_feature    3993 . . . 3935
                /gene = "Myh7"
                /gene_synonym = "Bmyo; myHC-beta; myHC-slow; Myhcb"
                /experiment = "experimental evidence, no additional details
                recorded"
                /note = "Phosphothreonine. {ECO: 0000250|UniProtKB: P02563};
                propagated from UniProtKB/Swiss-Prot (P02564.2);
                phosphorylation site"
misc_feature    4536 . . . 4538
                /gene = "Myh7"
                /gene_synonym = "Bmyo; myHC-beta; myHC-slow; Myhcb"
                /experiment = "experimental evidence, no additional details
                recorded"
                /note = "Phosphoserine. {ECO: 0000244|PubMed: 22673903};
                propagated from UniProtKB/Swiss-Prot (P02564.2);
                phosphorylation site"
misc_feature    4545 . . . 4547
                /gene = "Myh7"
                /gene_synonym = "Bmyo; myHC-beta; myHC-slow; Myhcb"
                /experiment = "experimental evidence, no additional details
                recorded"
                /note = "Phosphothreonine. {ECO: 0000250|UniProtKB: P02563};
                propagated from UniProtKB/Swiss-Prot (P02564.2);
                phosphorylation site"
exon            210 . . . 353
                /gene = "Myh7"
                /gene_synonym = "Bmyo; myHC-beta; myHC-slow; Myhcb"
                /inference = "alignment: Splign: 2.0.8"
exon            354 . . . 510
                /gene = "Myh7"
                /gene_synonym = "Bmyo; myHC-beta; myHC-slow; Myhcb"
                /inference = "alignment: Splign: 2.0.8"
exon            511 . . . 538
                /gene = "Myh7"
                /gene_synonym = "Bmyo; myHC-beta; myHC-slow; Myhcb"
                /inference = "alignment: Splign: 2.0.8"
exon            539 . . . 647
                /gene = "Myh7"
                /gene_synonym = "Bmyo; myHC-beta; myHC-slow; Myhcb"
                /inference = "alignment: Splign: 2.0.8"
exon            648 . . . 740
                /gene = "Myh7"
                /gene_synonym = "Bmyo; myHC-beta; myHC-slow; Myhcb"
                /inference = "alignment: Splign: 2.0.8"
exon            741 . . . 804
                /gene = "Myh7"
```

```
        /gene_synonym = "Bmyo; myHC-beta; myHC-slow; Myhcb"
        /inference = "alignment: Splign: 2.0.8"
exon    805 . . . 903
        /gene = "Myh7"
        /gene_synonym = "Bmyo; myHC-beta; myHC-slow; Myhcb"
        /inference = "alignment: Splign: 2.0.8"

exon    904 . . . 1007
        /gene = "Myh7"
        /gene_synonym = "Bmyo; myHC-beta; myHC-slow; Myhcb"
        /inference = "alignment: Splign: 2.0.8"

exon    1008 . . . 1146
        /gene = "Myh7"
        /gene_synonym = "Bmyo; myHC-beta; myHC-slow; Myhcb"
        /inference = "alignment: Splign: 2.0.8"

exon    1147 . . . 1265
        /gene = "Myh7"
        /gene_synonym = "Bmyo; myHC-beta; myHC-slow; Myhcb"
        /inference = "alignment: Splign: 2.0.8"

exon    1266 . . . 1415
        /gene = "Myh7"
        /gene_synonym = "Bmyo; myHC-beta; myHC-slow; Myhcb"
        /inference = "alignment: Splign: 2.0.8"

exon    1416 . . . 1586
        /gene = "Myh7"
        /gene_synonym = "Bmyo; myHC-beta; myHC-slow; Myhcb"
        /inference = "alignment: Splign: 2.0.8"

exon    1587 . . . 1896
        /gene = "Myh7"
        /gene_synonym = "Bmyo; myHC-beta; myHC-slow; Myhcb"
        /inference = "alignment: Splign: 2.0.8"

exon    1897 . . . 1964
        /gene = "Myh7"
        /gene_synonym = "Bmyo; myHC-beta; myHC-slow; Myhcb"
        /inference = "alignment: Splign: 2.0.8"

exon    1965 . . . 2052
        /gene = "Myh7"
        /gene_synonym = "Bmyo; myHC-beta; myHC-slow; Myhcb"
        /inference = "alignment: Splign: 2.0.8"

exon    2053 . . . 2170
        /gene = "Myh7"
        /gene_synonym = "Bmyo; myHC-beta; myHC-slow; Myhcb"
        /inference = "alignment: Splign: 2.0.8"

exon    2171 . . . 2294
        /gene = "Myh7"
        /gene_synonym = "Bmyo; myHC-beta; myHC-slow; Myhcb"
        /inference = "alignment: Splign: 2.0.8"

exon    2295 . . . 2431
        /gene = "Myh7"
        /gene_synonym = "Bmyo; myHC-beta; myHC-slow; Myhcb"
        /inference = "alignment: Splign: 2.0.8"

exon    2432 . . . 2687
        /gene = "Myh7"
        /gene_synonym = "Bmyo; myHC-beta; myHC-slow; Myhcb"
        /inference = "alignment: Splign: 2.0.8"

exon    2688 . . . 2930
        /gene = "Myh7"
        /gene_synonym = "Bmyo; myHC-beta; myHC-slow; Myhcb"
        /inference = "alignment: Splign: 2.0.8"

exon    2931 . . . 3107
        /gene = "Myh7"
        /gene_synonym = "Bmyo; myHC-beta; myHC-slow; Myhcb"
        /inference = "alignment: Splign: 2.0.8"

exon    3108 . . . 3253
```

```
               /gene = "Myh7"
               /gene_synonym = "Bmyo; myHC-beta; myHC-slow; Myhcb"
               /inference = "alignment: Splign: 2.0.8"
exon           3254 . . . 3344
               /gene = "Myh7"
               /gene_synonym = "Bmyo; myHC-beta; myHC-slow; Myhcb"
               /inference = "alignment: Splign: 2.0.8"
exon           3345.3734
               /gene = "Myh7"
               /gene_synonym = "Bmyo; myHC-beta; myHC-slow; Myhcb"
               /inference = "alignment: Splign: 2.0.8"
exon           3735 . . . 3861
               /gene = "Myh7"
               /gene_synonym = "Bmyo; myHC-beta; myHC-slow; Myhcb"
               /inference = "alignment: Splign: 2.0.8"
exon           3862 . . . 3980
               /gene = "Myh7"
               /gene_synonym = "Bmyo; myHC-beta; myHC-slow; Myhcb"
               /inference = "alignment: Splign: 2.0.8"
exon           3981 . . . 4177
               /gene = "Myh7"
               /gene_synonym = "Bmyo; myHC-beta; myHC-slow; Myhcb"
               /inference = "alignment: Splign: 2.0.8"
exon           4178 . . . 4361
               /gene = "Myh7"
               /gene_synonym = "Bmyo; myHC-beta; myHC-slow; Myhcb"
               /inference = "alignment: Splign: 2.0.8"
exon           4362 . . . 4527
               /gene = "Myh7"
               /gene_synonym = "Bmyo; myHC-beta; myHC-slow; Myhcb"
               /inference = "alignment: Splign: 2.0.8"
exon           4528 . . . 4652
               /gene = "Myh7"
               /gene_synonym = "Bmyo; myHC-beta; myHC-slow; Myhcb"
               /inference = "alignment: Splign: 2.0.8"
exon           4653 . . . 4961
               /gene = "Myh7"
               /gene_synonym = "Bmyo; myHC-beta; myHC-slow; Myhcb"
               /inference = "alignment: Splign: 2.0.8"
exon           4962 . . . 5165
               /gene = "Myh7"
               /gene_synonym = "Bmyo; myHC-beta; myHC-slow; Myhcb"
               /inference = "alignment: Splign: 2.0.8"
STS            5116 . . . 5288
               /gene = "Myh7"
               /gene_synonym = "Bmyo; myHC-beta; myHC-slow; Myhcb"
               /standard_name = "Myh7"
               /db_xref = "UniSTS: 530876"
exon           5166 . . . 5291
               /gene = "Myh7"
               /gene_synonym = "Bmyo; myHC-beta; myHC-slow; Myhcb"
               /inference = "alignment: Splign: 2.0.8"
exon           5292 . . . 5567
               /gene = "Myh7"
               /gene_synonym = "Bmyo; myHC-beta; myHC-slow; Myhcb"
               /inference = "alignment: Splign: 2.0.8"
STS            5388 . . . 5807
               /gene = "Myh7"
               /gene_synonym = "Bmyo; myHC-beta; myHC-slow; Myhcb"
               /standard_name = "Myh7"
               /db_xref = "UniSTS: 463417"
STS            5513 . . . 5596
               /gene = "Myh7"
               /gene_synonym = "Bmyo; myHC-beta; myHC-slow; Myhcb"
```

```
                    /standard_name = "MARC_5445-5446: 996690391: 1"
                    /db_xref = "UniSTS: 269515"
    exon            5568 . . . 5663
                    /gene = "Myh7"
                    /gene_synonym = "Bmyo; myHC-beta; myHC-slow; Myhcb"
                    /inference = "alignment: Splign: 2.0.8"
    exon            5664 . . . 5798
                    /gene = "Myh7"
                    /gene_synonym = "Bmyo; myHC-beta; myHC-slow; Myhcb"
                    /inference = "alignment: Splign: 2.0.8"
    exon            5799 . . . 5923
                    /gene = "Myh7"
                    /gene_synonym = "Bmyo; myHC-beta; myHC-slow; Myhcb"
                    /inference = "alignment: Splign: 2.0.8"
ORIGIN
       1    gctcagtcat ggcggatcga gagatggctg catttggggc cggagccccc ttcctgcgaa
      61    aatctgagaa ggagcggctg gaggcgcaga ccaggccctt tgacctcaag aaagatgttt
     121    ttgtgcctga tgacaaagaa gagtttgtca aggccaagat cgtgtctcga gagggtggca
     181    aagtcaccgc tgagacagag aatggcaaga cggtgactgt gaaggaggac caggtgatgc
     241    agcagaaccc tcccaagttc gacaagatcg aggacatggc catgctgacc ttcctgcacg
     301    agccggctgt gctctacaat ctcaaggaga ggtacgcttc ctggatgatc tacacctact
     361    caggcctctt ctgtgtcacc gtcaacccct ataagtggct gccagtgtac aatgcgcaag
     421    tggtagctgc ctaccgggga aagaagagga gcgaggctcc accccacatc ttctccatct
     481    ctgacaacgc ctatcagtac atgctgacga tcgggagaa ccagtccatc ctcatcaccg
     541    gagaatccgg agctggtaag accgtcaaca ccaagagggt catccaatat tttgctgtta
     601    ttgctgccat tgggaccgc agcaagaagg accagactcc aggcaagggc accttggaag
     661    atcaaatcat ccaagccaac cccgctctgg aggcctttgg caatgccaag acagttcgga
     721    atgataactc ctcccgattt gggaaattca ttcgaatcca ttttggggca acaggaaagt
     781    tggcatctgc agatatagag acctaccttc tggaaaaatc cagagttatt ttccagctga
     841    aagcagaaag agattatcac attttctacc aaatcctgtc taataaaaag cctgagcttc
     901    tagacatgct gctgatcacc aacaacccct acgattatgc gttcttctcc cagggagaa
     961    cgactgtggc ctcaatagat gactctgaag agcacatggc caccgatagc gcctttgatg
    1021    tgctgggctt cactccagaa gagaagaact ccatttacaa gctgacaggc gccatcatgc
    1081    actttggaaa catgaagttc aaacagaagc agagggagga gcaggcagag ccagacggca
    1141    cggaagaagc tgacaagtca gcctacctca tgggactgaa ctcggctgac ctgctcaagg
    1201    ggttgtgcca ccctcgagtc aaagtgggca acgagtatgt caccaaaggg cagaatgtcc
    1261    agcaggtggc atatgccatc ggggcactgg ccaagtcagt gtacgagaag atgttcaact
    1321    ggatggtgac acgcatcaac gcaaccctga gaccaagca gccacgccag tacttcatag
    1381    gtgtcctgga catcgccggc tttgagatct tgattcaa cagctttgag aacctggaag
    1441    tcaacttcac caatgagaag ctgcagcagt tcttcaacca ccacatgttc gtgctggagc
    1501    aggaggagta caagaaggaa ggcatcgagt ggacgtttat tgacttcggc atggacctgc
    1561    aggcctgcat cgacctcatc gagaagccca tgggcatcat gtccatcctg gaggaggagt
    1621    gcatgttccc caaggccacg gacatgacct tcaaggccaa gctgtacgac aaccacctgg
    1681    gcaagtccaa caacttccag aagcctcgca atatcaaggg aaagcaggaa gccccacttct
    1741    ctctgatcca ctatgctggg accgtggact acaatatcct gggctggcta cagaagaaca
    1801    aggaccctct caatgagacg gtggtggggc tgtaccagaa gtcctccctc aagctcctaa
    1861    gtaatctgtt tgccaactat gctggagctg atgcacctgt agacaagggc aaaggcaaag
    1921    caaagaaagg ctcatccttt cagaccgtgt ccgcactgca cagggaaaat ctgaacaaac
    1981    ttatgacaaa cctgcgctcc acgcacccct actttgtacg ctgcatcatc cccaatgaga
    2041    cgaagtctcc aggggtgatg gacaaccccc tggtcatgca ccagctgcga tgcaacggag
    2101    tgctggaggg tatccgcatc tgtaggaagg gcttccccaa ccgcattctt tatggggact
    2161    tccggcagag gtatcgaatc ctgaacccag cagccatccc tgagggccaa ttcattgata
    2221    gccggaaagg ggctgagaag ctgctgggct ccctggacat tgaccacaac cagtacaagt
    2281    ttggccacac caaggtgttc ttcaaggcgg gctgctgggg gctgctggag gagatgcgag
    2341    atgagaggct gagccgcatc atcaccagaa tccaggcccc agtcccgagg gtactttcca
    2401    gaatggagtt taagaagctg ctggagcgca gagactccct gctgattatc cagtggaaca
    2461    tccgcgcctt catgggggtc aagaattggc cgtggatgaa gctctacttc aagatcaagc
    2521    cgctgctgaa gagcgcagag acagagaagg agatgccaa catgaaggag gagttcggc
    2581    gagtcaaaga tgcactagag aagtctgagg ctcgccgcaa ggagctggag gagaagatgg
    2641    tgtccctgct gcaggagaag aatgacctgc agctccaagt gcagggcgaa caagcaacc
    2701    tggcagatgc cgaggagcgc tgcgaccagc tgatcaagaa caagatccag ctggaggcca
    2761    aggtgaagga gatgaccgag aggctggagg acgaggagga tgaacgccag aacacccgg
    2821    ccaagaagcg caaactggaa gacgagtgct cagagctcaa gagagatatc gatgacctgg
    2881    agctgaccct ggccaaggtg gagaaggaaa agcacgcaac agagaacaag gtgaaaaacc
    2941    tgacagagga gatggctggg ctggacgaga tcattgtcaa gctgaccaag gagaagaaag
    3001    ctctacaaga ggcccaccag caagcctag atgaccttca ggctgaggag acaaggtca
    3061    acactctgac caaggccaag gtcaagctgg agcagcaagt ggatgatctg gagggatccc
    3121    tggatcagga caagaaggtg cgcatggacc tggagcgagc aaagcggaag ctggaggtg
    3181    acctgaagct gacccaggag agcatcatga cctggagaa cgacaagcag cagttggatg
    3241    agcgactcaa aaagaaggac tttgagttaa atgcactcaa cgccaggatt gaggatgagc
    3301    aggccctggg cagccagctg cagaagaagc tcaaagagct tcaggcacgc atcgaggagc
    3361    tggaggagga gctggaggct gagcgcacag cccgggccaa ggtggagaag ctgcgctcag
    3421    acctgtcccg ggagctggag gagatcagtg agaggctaga ggaagccggt gggccacat
    3481    ctgtgcagat agagatgaac aagaagcgcg aggccgagtt ccagaagatg cggcgggacc
    3541    tagaggaggc cacgctgcag catgaggcca cagctgcggc cctgcgcaag aaacacgcgg
```

-continued

```
3601    acagcgtggc cgagctgggc gagcagatag acaatctaca gcgggtgaag cagaagctgg
3661    agaaagagaa gagcgagttc aagctggagc tggatgacgt tacctccaac atggagcaga
3721    tcatcaaggc caaggctaac ctggagaaga tgtgccggac cctggaggac cagatgaatg
3781    aacaccggag caaggctgag gagacacagc gttctgtcaa tgacctcacc cgccagcggg
3841    ccaagctgca gacagagaat ggggagctgt ccagacagct ggatgagaag gaggctctta
3901    tctctcagct gacccgaggc aagctcacgt atacccagca gctggaggac ctcaagaggc
3961    agctggagga ggaggtcaag gccaagaatg ccctggccca cgcactgcag tcagcccggc
4021    atgattgcga cctgctgcgg gaacagtacg aggaggaaac agaagccaag gctgagctgc
4081    agcgtgtcct gtccaaggcc aactcagagg tggcccagtg gaggaccaag tatgagacgg
4141    acgccataca gaggacggag gagctggagg aagccaagaa gaagctggct cagaggcttc
4201    aggatgctga ggaggcagtg gaggccgtca acgccaagtg ctcctcgctg gagaagacca
4261    agcacaggct gcagaacgag atcgaggacc tgatggtgga tgtggagcgc tccaatgcgg
4321    ccgccgcagc cctggacaag aagcagagga cttcgacaa gatcctggtt gagtggaagc
4381    agaagtatga ggagtcccag tcagagctgg agtcttccca gaaggaggcg cgctccctga
4441    gcacagagct cttcaagctg aagaatgcct atgaggagtc tctggagcac ctggagacct
4501    tcaagcggga gaacaagaac ctccaggagg agatctcaga cctgactgaa cagctgggct
4561    caactgggaa gagcatccac gagctggaga agatccgaaa gcaactggag gctgagaagc
4621    tggagctgca gtcagccctg gaagaggctg aggcctccct ggagcatgag gagggcaaga
4681    tcctccgagc ccagctggag ttcaaccaga tcaaggcaga gatcgaaagg aagctggcag
4741    agaaggacga ggagatggag caggccaagc gcaaccacct gcgggtggtg gactccctgc
4801    agacctccct ggatgccgag acgcgcagcc gcaacgaggc cctgcgggtg aagaagaaga
4861    tggagggcga cctcaacgag atggagatcc agctcagtca tgccaaccgc atggctgctg
4921    aggcccagaa acaagtgaag agcctccaga gtttgctgaa ggacactcaa atccagctgg
4981    atgacgcagt ccgtgccaat gacgacctga aggagaacat cgccatcgtg gagcggcgca
5041    acaacctgct gcaggcggag ctggaggagc tgcgggccgt ggtggagcag acggagcggt
5101    ctcggaagct ggcagagcag gagctgatcg agaccagtga gcgggtgcag ctgctgcact
5161    cccagaacac cagcctcatc aaccagaaga agaagatgga tgcagacctc tcccagctcc
5221    agacagaggt ggaggaggcg gtgcaggagt gtaggaacgc agaggagaag gccaagaagg
5281    ccatcacaga tgccgccatg atggccgagg agctgaagaa ggagcaggac accagcgccc
5341    acctggagcg catgaagaat aacatggagc agaccctgag caccggctgg
5401    acgaggcaga gcagatcgcc ctcaagggtg gcaagaagca gctgcagaag ctggaggccc
5461    gggtccggga gctggagaat gagctggagg ctgagcagaa gcgcaatgcg gagtcggtga
5521    agggcatgag gaagagcgag cggcgcatca aggagctcac ctaccagaca gaggaagaca
5581    ggaagaacct actgcgactg caggacctgg tggacaagct gcagttaaag gtgaaggcct
5641    acaagcgcca ggctgaggag gcggaggaac aggccaacac caacctgtcc aagttccgca
5701    aggtgcagca cgagctggat gaggcagagg agagggcgga cattgccgag tcccaggtca
5761    acaagctgcg ggccaagagc cgtgacattg gcgccaaggg cctgaatgaa gagtagatct
5821    tgtgctaccc aaccctaagg atgcctgtga agccctgaga cctggagcct ttgaaacagc
5881    accttaggca gaaacacaat aaagcaattt tccttcaagc caa (SEQ ID NO: 163)
//
```

APPENDIX G

*Rattus norvegicus* natriuretic peptide A (Nppa), mRNA
NCBI Reference Sequence: NM_012612.2

FASTA Graphics
Go to:
LOCUS          NM_012612831 bp mRNA linear ROD 10-JUN-2018

DEFINITION     *Rattus norvegicus* natriuretic peptide A (Nppa), mRNA.

ACCESSION      NM_012612

VERSION        NM_012612.2

KEYWORDS       RefSeq.

SOURCE         *Rattus norvegicus* (Norway rat)

ORGANISM       *Rattus norvegicus*
               Eukaryota; Metazoa; Chordata; Craniata; Vertebrata; Euteleostomi;
               Mammalia; Eutheria; Euarchontoglires; Glires; Rodentia; Myomorpha;
               Muroidea; Muridae; Murinae; Rattus.

REFERENCE      1 (bases 1 to 831)
               AUTHORS Barallobre-Barreiro J, Gupta SK, Zoccarato A, Kitazume-Taneike R,
               Fava M, Yin X, Werner T, Hirt MN, Zampetaki A, Viviano A, Chong M,
               Bern M, Kourliouros A, Domenech N, Willeit P, Shah AM, Jahangiri M,
               Schaefer L, Fischer JW, Iozzo RV, Viner R, Thum T, Heineke J,
               Ki chi er A, Otsu K and Mayr M.

TITLE          Glycoproteomics Reveals Decorin Peptides With Anti-Myostatin
               Activity in Human Atrial Fibrillation JOURNAL        Circulation 134 (11), 817-832 (2016)

| | | |
|---|---|---|
| PUBMED | | 27559042 |
| REFERENCE | | 2 (bases 1 to 831) |
| AUTHORS | | Yuan K, Park BM, Choi YT, Kim JH, Cho KW and Kim SH. |
| TITLE | | Effects of endothelin family on ANP secretion |
| JOURNAL | | Peptides 82, 12-19 (2016) |
| PUBMED | | 27208702 |
| REMARK | | GeneRIF: we suggest that the order of secretagogue effect of ET family on ANP secretion was ET-1>/ = ET-2>>ET-3>s6C and ET-1-induced atrial natriuretic peptide secretion negatively regulates the pressor effect of ET-1. |
| REFERENCE | | 3 (bases 1 to 831) |
| AUTHORS | | Lee CH, Ha GW, Kim JH and Kim SH. |
| TITLE | | Modulation in Natriuretic Peptides System in Experimental Colitis in Rats |
| JOURNAL | | Dig. Dis. Sci. 61 (4), 1060-1068 (2016) |
| PUBMED | | 26660905 |
| REMARK | | GeneRIF: augmentation of inhibitory effect on basal motility by ANP in experimental colitis may be due an increased expression of colonic natriuretic peptide receptor-A mRNA |
| REFERENCE | | 4 (bases 1 to 831) |
| AUTHORS | | Bugrova, M.L. |
| TITLE | | [ATRIAL AND BRAIN NATRIURETIC PEPTIDES OF CARDIAC MUSCLE CELLS IN POSTREPERFUSION PERIOD IN RATS] |
| JOURNAL | | Tsitologiia 58 (2), 129-134 (2016) |
| PUBMED | | 27228659 |
| REMARK | | GeneRIF: This is due to the fact that ANP is the main hormone of the natriuretic peptide system involved in the regulation of blood pressure in normal conditions, while BNP is the principal regulator of pressure in cardiovascular pathology |
| REFERENCE | | 5 (bases 1 to 831) |
| AUTHORS | | Pang A, Hu Y, Zhou P, Long G, Tian X, Men L, Shen Y, Liu Y and Cui Y. |
| TITLE | | Corin is down-regulated and exerts cardioprotective action via activating pro-atrial natriuretic peptide pathway in diabetic cardiomyopathy |
| JOURNAL | | Cardiovasc Diabetol 14, 134 (2015) |
| PUBMED | | 26446774 |
| REMARK | | GeneRIF: ANP mRNA and protein are decreased in diabetic cardiomyopathy.<br>Publication Status: Online-Only |
| REFERENCE | | 6 (bases 1 to 831) |
| AUTHORS | | Bennett BD, Bennett GL, Vitangcol RV, Jewett JR, Burnier J, Henzel W and Lowe DG. |
| TITLE | | Extracellular domain-IgG fusion proteins for three human natriuretic peptide receptors. Hormone pharmacology and application to solid phase screening of synthetic peptide antisera |
| JOURNAL | | J. Biol. Chern. 266 (34), 23060-23067 (1991) |
| PUBMED | | 1660465 |
| REFERENCE | | 7 (bases 1 to 831) |

| | | |
|---|---|---|
| AUTHORS | Levin ER and Frank HJ. | |
| TITLE | Natriuretic peptides inhibit rat astroglial proliferation: mediation by C receptor | |
| JOURNAL | Am. J. Physiol. 261 (2 Pt 2), R453-R457 (1991) | |
| PUBMED | 1652217 | |
| REFERENCE | 8 (bases 1 to 831) | |
| AUTHORS | Koller KJ, Lowe DG, Bennett GL, Minamino N, Kangawa K, Matsuo H and Goeddel DV. | |
| TITLE | Selective activation of the B natriuretic peptide receptor by C-type natriuretic peptide (CNP) | |
| JOURNAL | Science 252 (5002), 120-123 (1991) | |
| PUBMED | 1672777 | |
| REFERENCE | 9 (bases 1 to 831) | |
| AUTHORS | Mukoyama,M., Nakao,K., Saito,Y., Ogawa,Y., Hosoda,K., Suga,S., Shirakami,G., Jougasaki,M. and Imura,H. | |
| TITLE | Increased human brain natriuretic peptide in congestive heart failure | |
| JOURNAL | N. Engl. J. Med. 323 (11), 757-758 (1990) | |
| PUBMED | 2143809 | |
| REFERENCE | 10 (bases 1 to 831) | |
| AUTHORS | Jin H, Yang RH, Chen YF, Jackson RM and Oparil S. | |
| TITLE | Atrial natriuretic peptide attenuates the development of pulmonary hypertension in rats adapted to chronic hypoxia | |
| JOURNAL | J. Clin. Invest. 85 (1), 115-120 (1990) | |
| PUBMED | 2136863 | |
| COMMENT VALIDATED REFSEQ: | This record has undergone validation or preliminary review. The reference sequence was derived from CB724799.1, X00665.1 and AI602287.1.<br>On Oct 17, 2007 this sequence version replaced NM_012612.1.<br>Summary: peptide involved in the control of fluid volume and vascular function [RGD, Feb 2006].<br>Publication Note: This RefSeq record includes a subset of the publications that are available for this gene. Please see the Gene record to access additional publications.<br>##Evidence-Data-START##<br>Transcript exon combination:: EV765126.1, BC158590.1 [ECO:0000332]<br>RNAseq introns:: single sample supports all introns SAMD00052296, SAMD00052297<br>[ECO:0000348]<br>##Evidence-Data-END## | |

| PRIMARY COMP | REFSEQ_SPAN | PRIMARY IDENTIFIER PRIMARY SPAN |
|---|---|---|
| 1-8 | CB724799.1 | 128-135 |
| 9-576 | X00665.1 | 1-568 |
| 577-831 | AI602287.1 | 1-255 c |

| FEATURES | Location/Qualifiers |
|---|---|
| source | 1..831<br>/organism = "Rattus norvegicus"<br>/mol_type = "mRNA"<br>/strain = "Sprague-Dawley"<br>/db_xref = "taxon: 10116"<br>/chromosome = " 5"<br>/map = "5q36" |

```
gene              1..831
                  /gene = "Nppa"
                  /gene_synonym = "ANF; ANP; Pnd; RATANF"
                  /note = "natriuretic peptide A"
                  /db_xref = "GeneID:24602"
                  /db_xref = "RGD:3193"

exon              1..196
                  /gene = "Nppa"
                  /gene_synonym = "ANF; ANP; Pnd; RATANF"
                  /inference = "alignment: Splign: 2.0.8"

unsure            9..14
                  /gene = "Nppa"
                  /gene_synonym = "ANF; ANP; Pnd; RATANF"
                  /note = "pot. cloning artefact"

STS               73..481
                  /gene = "Nppa"
                  /gene_synonym = "ANF; ANP; Pnd; RATANF"
                  /standard_name = "PMC 123178P1"
                  /db_xref = "UniSTS:270444"

CDS               77..535
                  /gene = "Nppa"
                  /gene_synonym = "ANF; ANP; Pnd; RATANF"
                  /note = "Natriuretic peptide precursor A (pronatriodilatin,
                  also Anf, Pnd); atrial natriuretic factor; natriuretic
                  peptides A; prepronatriodilatin; atrial natriuretic
                  peptide; natriuretic peptide precursor type A"
                  /codon_start = 1
                  /product = "natriuretic peptides A precursor"
                  /protein_id = "NP_036744.1"
                  /db_xref = "GeneID:24602"
                  /db_xref = "RGD:3193"

/translation = "MGSFSITKGFFLFLAFWLPGHIGANPVYSAVSNTDLMDFKNLLD
HLEEKMPVEDEVMPPQALSEQTDEAGAALSSLSEVPPWTGEVNPSQRDGGALGRGP
WD
PSDRSALLKSKLRALLAGPRSLRRSSCFGGRIDRIGAQSGLGCNSFRYRR"
(SEQ ID NO: 164)

sig_peptide       77..148
                  /gene = "Nppa"
                  /gene_synonym = "ANF; ANP; Pnd; RATANF"
                  /inference = "COORDINATES: ab initio prediction:SignalP:4.0"

misc_feature      440..445
                  /gene = "Nppa"
                  /gene_synonym = "ANF; ANP; Pnd; RATANF"
                  /experiment = "experimental evidence, no additional details
                  recorded"
                  /note = "Cleavage, by CORIN. {ECO:0000250UniProtKB:P01160};
                  propagated from UniProtKB/Swiss-Prot (P01161.1); cleavage
                  site"

miscfeature       461..466
                  /gene = "Nppa"
                  /gene_synonym = "ANF; ANP; Pnd; RATANF"
                  /experiment = "experimental evidence, no additional details
                  recorded"
                  /note = "Cleavage, by MME. {ECO:0000269|PubMed:2966343};
                  propagated from UniProtKB/Swiss-Prot (P01161.1); cleavage
                  site"

STS               131..520
                  /gene = "Nppa"
                  /gene_synonym = "ANF; ANP; Pnd; RATANF"
                  /standard_name = "PMC3 16718P1"
                  /db_xref = "UniSTS:273041"

prim_transcript   149.. 532
                  /gene = "Nppa"
                  /gene_synonym = "ANF; ANP; Pnd; RATANF"
                  /note = "AFN"

exon              197..523
                  /gene = "Nppa"
```

```
                          /gene_synonym = "ANF; ANP; Pnd; RATANF"
                          /inference = "alignment: Splign: 2.0.8"
     STS             197..413
                          /gene = "Nppa"
                          /gene_synonym = "ANF; ANP; Pnd; RATANF"
                          /standard_name = "NoName"
                          /db_xref = "UniSTS:547523"

STS             257..522
                          /gene = "Nppa"
                          /gene_synonym = "ANF; ANP; Pnd; RATANF"
                          /standard_name = "PMC15566P1"
                          /db_xref = "UniSTS:271346"

misc_feature    449..454
                          /gene = "Nppa"
                          /gene_synonym = "ANF; ANP; Pnd; RATANF"
                          /note = "pot. proteolytic processing site"

STS             469..621
                          /gene = "Nppa"
                          /gene_synonym = "ANF; ANP; Pnd; RATANF"
                          /standard_name = "B1280386"
                          /db_xref = "UniSTS:249035"

STS             518..724
                          /gene = "Nppa"
                          /gene_synonym = "ANF; ANP; Pnd; RATANF"
                          /standard_name = "RH127740"
                          /db_xref = "UniSTS:211050"

exon            524..814
                          /gene = "Nppa"
                          /gene_synonym = "ANF; ANP; Pnd; RATANF"
                          /inference = "alignment: Splign: 2.0.8"

misc_feature    527..532
                          /gene = "Nppa"
                          /gene_synonym = "ANF; ANP; Pnd; RATANF"
                          /note = "pot. proteolytic processing site"

ORIGIN
   1    cggacaaagg ctgagagaga aaccagagag tgagccgaga cagcaaacat cagatcgtgc
  61    cccgacccac gccagcatgg gctccttctc catcaccaag ggcttcttcc tcttcctggc
 121    cttttggctc ccaggccata ttggagcaaa tcccgtatac agtgcggtgt ccaacacaga
 181    tctgatggat ttcaagaacc tgctagacca cctggaggag aagatgccgg tagaagatga
 241    ggtcatgcct ccgcaggccc tgagcgagca gaccgatgaa gcggggggcgg cacttagctc
 301    cctctctgag gtgcctccct ggactgggga agtcaacccg tctcagagag atggaggtgc
 361    tctcgggcgc ggcccctggg accctccga tagatctgcc ctcttgaaaa gcaaactgag
 421    ggctctgctc gctggccctc ggagcctgcg aaggtcaagc tgcttcgggg gtaggattga
 481    caggattgga gcccagagcg gactaggctg caacagcttc cggtaccgaa gataacagcc
 541    aaatctgctc gagcagatcg caaaagatcc caagcccttg cggtgtgtca cacagcttgg
 601    tcgcattgcc actgagaggt ggtgaatacc ctcctggagc tgcagcttcc tgtcttcatc
 661    tatcacgatc gatgttaagt gtagatgagt ggtttagtga ggccttacct ctcccactct
 721    gcatattaag gtagatcctc accccttttca gaaagcagtt ggaaaaaaat aaatccgaat
 781    aaacttcagc accacggaca gacgctgagg cctgaaaaaa aaaaaaaaaa a (SEQ ID NO: 165)
//
```

APPENDIX H

*Rattus norvegicus* natriuretic peptide B (Nppb), mRNA
NCBI Reference Sequence: NM_031545.1

FASTA Graphics
Go to:
LOCUS          NM_031545      628 bp    mRNA    linear   ROD 21-JUL-2018

DEFINITION     *Rattus norvegicus* natriuretic peptide B (Nppb), mRNA.

ACCESSION      NM_031545

VERSION        NM_031545.1

KEYWORDS       RefSeq.

| | |
|---|---|
| SOURCE | *Rattus norvegicus* (Norway rat) |
| ORGANISM | *Rattus norvegicus*<br>Eukaryota; Metazoa; Chordata; Craniata; Vertebrata; Euteleostomi;<br>Mammalia; Eutheria; Euarchontoglires; Glires; Rodentia; Myomorpha;<br>Muroidea; Muridae; Murinae; Rattus. |
| REFERENCE | 1 (bases 1 to 628) |
| AUTHORS | Saklani R, Gupta SK, Mohanty IR, Kumar B, Srivastava S and Mathur R. |
| TITLE | Cardioprotective effects of rutin via alteration in TNF-alpha, CRP, and BNP levels coupled with antioxidant effect in STZ-induced diabetic rats |
| JOURNAL | Mol. Cell. Biochem. 420 (1-2), 65-72 (2016) |
| PUBMED | 27443845 |
| REMARK | GeneRIF: Cardioprotective effects of rutin via alteration in TNF-alpha, CRP, and BNP levels coupled with antioxidant effect in STZ-induced diabetic rats. |
| REFERENCE | 2 (bases 1 to 628) |
| AUTHORS | Holditch SJ, Schreiber CA, Burnett JC and Ikeda Y. |
| TITLE | Arterial Remodeling in B-Type Natriuretic Peptide Knock-Out Females |
| JOURNAL | Sci Rep 6, 25623 (2016) |
| PUBMED | 27162120 |
| REMARK | GeneRIF: Data show that approximately 60% of natriuretic peptide precursor type B (Nppb)-/- females developed mesenteric polyarteritis-nodosa (PAN)-like vasculitis in their life span, some as early as 4 months of age.<br>Publication Status: Online-Only |
| REFERENCE | 3 (bases 1 to 628) |
| AUTHORS | Terse PS, Joshi PS, Bordelon NR, Brys AM, Patton KM, Arndt TP and Sutula TP. |
| TITLE | 2-Deoxy-d-Glucose (2-DG)-Induced Cardiac Toxicity in Rat: NT-proBNP and BNP as Potential Early Cardiac Safety Biomarkers |
| JOURNAL | Int. J. Toxicol. 35 (3), 284-293 (2016) |
| PUBMED | 26838190 |
| REMARK | GeneRIF: NT-proBNP and BNP are potential early biomarkers for 2-DG-induced cardiac toxicity that can be useful to monitor 2-DG therapy in clinical trials. |
| REFERENCE | 4 (bases 1 to 628) |
| AUTHORS | Bugrova,ML. |
| TITLE | [ATRIAL AND BRAIN NATRIURETIC PEPTIDES OF CARDIAC MUSCLE CELLS IN POSTREPERFUSION PERIOD IN RATS] |
| JOURNAL | Tsitologiia 58 (2), 129-134 (2016) |
| PUBMED | 27228659 |
| REMARK | GeneRIF: This is due to the fact that ANP is the main hormone of the natriuretic peptide system involved in the regulation of blood pressure in normal conditions, while BNP is the principal regulator of pressure in cardiovascular pathology |
| REFERENCE | 5 (bases 1 to 628) |
| AUTHORS | Dogan H, Sarikaya S, Neijmann ST, Uysal E, Yucel N, Ozucelik DN, Okuturlar Y, Solak S, Sever N and Ayan C. |
| TITLE | N-terminal pro-B-type natriuretic peptide as a marker of blunt cardiac contusion in trauma |

| | |
|---|---|
| JOURNAL | Int J Clin Exp Pathol 8 (6), 6786-6792 (2015) |
| PUBMED | 26261563 |
| REMARK | GeneRIF: Serum NT-proBNP levels significantly increased after 5 hours of the blunt chest trauma.<br>Publication Status: Online-Only |
| REFERENCE | 6 (bases 1 to 628)<br>AUTHORS Bennett BD, Bennett GL, Vitangcol RV, Jewett JR, Burnier J, Henzel W and Lowe DG. |
| TITLE | Extracellular domain-IgG fusion proteins for three human natriuretic peptide receptors. Hormone pharmacology and application to solid phase screening of synthetic peptide antisera |
| JOURNAL | J. Biol. Chern. 266 (34), 23060-23067 (1991) |
| PUBMED | 1660465 |
| REFERENCE | 7 (bases 1 to 628) |
| AUTHORS | Dagnino L, Drouin J and Nemer M. |
| TITLE | Differential expression of natriuretic peptide genes in cardiac and extracardiac tissues |
| JOURNAL | Mol. Endocrinol. 5 (9), 1292-1300 (1991) |
| PUBMED | 1837590 |
| REFERENCE | 8 (bases 1 to 628) |
| AUTHORS | Levin ER and Frank HJ. |
| TITLE | Natriuretic peptides inhibit rat astroglial proliferation: mediation by C receptor |
| JOURNAL | Am. J. Physiol. 261 (2 Pt 2), R453-R457 (1991) |
| PUBMED | 1652217 |
| REFERENCE | 9 (bases 1 to 628) |
| AUTHORS | Hoffman A, Grossman E and Keiser HR. |
| TITLE | Increased plasma levels and blunted effects of brain natriuretic peptide in rats with congestive heart failure |
| JOURNAL | Am. J. Hypertens. 4 (7 Pt 1), 597-601 (1991) |
| PUBMED | 1831369 |
| REFERENCE | 10 (bases 1 to 628) |
| AUTHORS | Koller KJ, Lowe DG, Bennett GL, Minamino N, Kangawa K, Matsuo H and Goeddel DV. |
| TITLE | Selective activation of the B natriuretic peptide receptor by C-type natriuretic peptide (CNP) |
| JOURNAL | Science 252 (5002), 120-123 (1991) |
| PUBMED | 1672777 |
| COMMENT PROVISIONAL REFSEQ: | This record has not yet been subject to final NCBI review. The reference sequence was derived from M25297.1.<br>Summary: hormone produced primarily by the atrium and ventricle of the heart [RGD, Feb 2006].<br>Publication Note: This RefSeq record includes a subset of the publications that are available for this gene. Please see the Gene record to access additional publications.<br>##Evidence-Data-START##<br>Transcript exon combination:: M25297.1, FQ228997.1 [ECO:0000332]<br>RNAseq introns:: single sample supports all introns SAMEA2689596, SAMEA2689600<br>[ECO:0000348]<br>##Evidence-Data-END## |

```
FEATURES             Location/Qualifiers
source               1..628
                     /organism = "Rattus norvegicus"
                     /mol_type = "mRNA"
                     /db_xref = "taxon: 10116"
                     /chromosome = "5"
                     /map = "5q36"

gene                 1..628
                     /gene = "Nppb"
                     /gene_synonym = "Bnf; BNP"
                     /note = "natriuretic peptide B"
                     /db_xref = "GeneID:25105"
                     /db_xref = "RGD:3194"

exon                 1..183
                     /gene = "Nppb"
                     /gene_synonym = "Bnf; BNP"
                     /inference = "alignment: Splign: 2.0.8"

CDS                  58..423
                     /gene = "Nppb"
                     /gene_synonym = "Bnf; BNP"
                     /note = "natriuretic peptides B; brain natriuretic peptide;
                     natriuretic peptide precursor B; iso-ANP; gamma-brain
                     natriuretic peptide; Brain natriuretic factor; natriuretic
                     peptide precursor type B"
                     /codon_start = 1
                     /product = "natriuretic peptides B precursor"
                     /protein _id = "NP_1 13733.1"
                     /db_xref = "GeneID:25105"
                     /db_xref = "RGD:3194"

/translation = "MDLQKVLPQMILLLLFLNLSPLGGHSHPLGSPSQSPEQSTMQKL
LELIREKSEEMAQRQLSKDQGPTKELLKRVLRSQDSAFRIQERLRNSKMAHSSSCFG
Q
KIDRIGAVSRLGCDGLRLF" (SEQ ID NO: 166)

sig_peptide          58..135
                     /gene = "Nppb"
                     /gene_synonym = "Bnf; BNP"
                     /inference = "COORDINATES: ab initio prediction:SignalP:4.0"

mat_peptide          136..420
                     /gene = "Nppb"
                     /gene_synonym = "Bnf; BNP"
                     /product = "natriuretic peptides B"
                     /note = "putative"

misc_feature         328..333
                     /gene = "Nppb"
                     /gene_synonym = "Bnf; BNP"
                     /experiment = "experimental evidence, no additional details
                     recorded"
                     /note = "Cleavage, by FAP. {ECO:0000250|UniProtKB:P16860};
                     propagated from UniProtKB/Swiss-Prot (P13205.3); cleavage
                     site"

exon                 184..406
                     /gene = "Nppb"
                     /gene_synonym = "Bnf; BNP"
                     /inference = "alignment: Splign: 2.0.8"

STS                  280..464
                     /gene = "Nppb"
                     /gene_synonym = "Bnf; BNP"
                     /standard_name = "RH130424"
                     /db_xref = "UniSTS:213708"

exon                 407..628
                     /gene = "Nppb"
                     /gene_synonym = "Bnf; BNP"
                     /inference = "alignment: Splign: 2.0.8"

polyA_site           628
                     /gene = "Nppb"
                     /gene_synonym = "Bnf; BNP"
ORIGIN
```

-continued

```
  1     gcgagacaag agagagcagg acaccatcgc agctgcctgg cccatcactt ctgcagcatg
 61     gatctccaga aggtgctgcc ccagatgatt ctgctcctgc ttttccttaa tctgtcgccg
121     ctgggaggtc actcccatcc cctgggaagt cctagccagt ctccagaaca atccacgatg
181     cagaagctgc tggagctgat aagagaaaag tcagaggaaa tggctcagag acagctctca
241     aaggaccaag gccctacaaa agaacttcta aaaagagtcc ttaggtctca agacagcgcc
301     ttccggatcc aggagagact tcgaaattcc aagatggcac atagttcaag ctgctttggg
361     cagaagatag accggatcgg cgcagtcagt cgcttgggct gtgacgggct gaggttgttt
421     taggaagacc tcctggctgc agactccggc ttctgactct gcctgcggct cttctttccc
481     cagctctggg accacctctc aagtgatcct gtttatttat ttgtttattt atttattttt
541     atgttgctga ttttctacaa gactgtttct tatcttccag cacaaacttg ccacagtgta
601     ataaacatag cctatttctt gcttttgg (SEQ ID NO: 167)
//
```

What is claimed is:

1. A conditional RNA-sensor complex comprising:
a sensor strand comprising at least one toehold segment, wherein the toehold segment capable of binding a pathological biomarker present in or overexpressed in a target cell, wherein the pathological biomarker comprises a molecule that encodes ANP, BNP, MHCβ, mir-23a-3p, mir-125-6p, or mir-199b-5p; and
a double stranded pro-RNA molecule comprising
a guide strand comprising an RNA molecule capable of binding a therapeutic target molecule in the target cell, wherein the therapeutic target molecule is an RNA molecule that encodes calcineurin or histone deacetylase 2 (HDAC2); and
a core strand comprising
a first portion comprising a passenger strand that is fully or partially complimentary to and binds the guide strand,
a second portion comprising a first protection segment that is fully or partially complimentary to and binds the sensor strand, and
a first linker that joins a first end of the passenger strand to the first protection segment.

2. The conditional RNA-sensor complex of claim 1, wherein the core strand further comprises a third portion comprising a second protection segment that is fully or partially complimentary to and binds the sensor strand, and a second linker that joins a second end of the passenger strand to the second protection segment.

3. The conditional RNA-sensor complex of claim 1, wherein the toehold segment is an aptamer.

4. The conditional RNA-sensor complex of claim 1, wherein the sensor strand is displaced from the double stranded pro-RNA molecule when the pathological biomarker binds the toehold segment and the resulting double stranded pro-RNA molecule is a substrate for Dicer.

5. The conditional RNA-sensor complex of claim 1, wherein the target cell is a cardiac myocyte.

6. The conditional RNA-sensor complex of claim 1, wherein the molecule that encodes ANP, BNP, or MHCβ is an mRNA molecule and the molecule that encodes mir-23a-3p, mir-125-6p, or mir-199b-5p is an miRNA molecule.

7. The conditional RNA-sensor complex of claim 6, wherein the molecule that encodes ANP comprises a sequence selected from SEQ ID Nos: 8-10, the molecule that encodes BNP comprises a sequence selected from SEQ ID Nos: 4-6, the molecule that encodes MHCβ comprises a sequence of SEQ ID NO: 7, and the molecule that encodes mir-23a-3p comprises a sequence selected from SEQ ID Nos: 1-3.

8. The conditional RNA-sensor complex of claim 7, wherein the sensor strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

9. The conditional RNA-sensor complex of claim 5, wherein the double stranded pro-RNA molecule is an RNA interference (RNAi) molecule.

10. The conditional RNA-sensor complex of claim 9, wherein the guide strand comprises a sequence selected from SEQ ID NOS: 11-16.

11. The conditional RNA-sensor complex of claim 2, wherein the first linker, the second linker, or both the first and second linkers is a C3 spacer.

12. The conditional RNA-sensor complex of claim 9, wherein the guide strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

13. The conditional RNA-sensor complex of claim 2, wherein the core strand comprises
a passenger strand;
a first linker that joins a 3' end of the passenger strand to the first protection segment; and
a second linker that joins a 5' end of the passenger strand to the second protection segment.

14. The conditional RNA-sensor complex of claim 13, wherein the core strand comprises a sequence selected from SEQ ID NOS: 17-26.

15. The conditional RNA-sensor complex of claim 13, wherein the core strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

16. The conditional RNA-sensor complex of claim 1, wherein:
(a) the sensor strand comprises a sequence having at least 95% homology to SEQ ID NO:4, the core strand comprises a sequence having at least 95% homology to SEQ ID NO:21, SEQ ID NO: 49, and SEQ ID NO: 50, and the guide strand comprises a sequence having at least 95% homology to SEQ ID NO:15;
(b) the sensor strand comprises a sequence having at least 95% homology to SEQ ID NO:5, the core strand comprises a sequence having at least 95% homology to SEQ ID NO:22, SEQ ID NO: 49, and SEQ ID NO: 51, and the guide strand comprises a sequence having at least 95% homology to SEQ ID NO:15;
(c) the sensor strand comprises a sequence having at least 95% homology to SEQ ID NO:6, the core strand comprises a sequence having at least 95% homology to SEQ ID NO:23, SEQ ID NO: 49, and SEQ ID NO: 52, and the guide strand comprises a sequence having at least 95% homology to SEQ ID NO:15;
(d) the sensor strand comprises a sequence having at least 95% homology to SEQ ID NO:7, the core strand comprises a sequence having at least 95% homology to SEQ ID NO:24, SEQ ID NO: 49, and SEQ ID NO: 53, and the guide strand comprises a sequence having at least 95% homology to SEQ ID NO:15;
(e) the sensor strand comprises a sequence having at least 95% homology to SEQ ID NO:8, the core strand comprises a sequence having at least 95% homology to SEQ ID NO:25, and the guide strand comprises a sequence having at least 95% homology to SEQ ID NO:16;
(f) the sensor strand comprises a sequence having at least 95% homology to SEQ ID NO:8, the core strand comprises a sequence having at least 95% homology to SEQ ID NO:18, SEQ ID NO: 45, and SEQ ID NO: 47, and the guide strand comprises a sequence having at least 95% homology to SEQ ID NO:11;
(g) the sensor strand comprises a sequence having at least 95% homology to SEQ ID NO:10, the core strand comprises a sequence having at least 95% homology to SEQ ID NO:19, SEQ ID NO: 45, and SEQ ID NO: 48, and the guide strand comprises a sequence having at least 95% homology to SEQ ID NO:12;
(h) the sensor strand comprises a sequence having at least 95% homology to SEQ ID NO:1, the core strand comprises a sequence having at least 95% homology to SEQ ID NO: 41, SEQ ID NO: 45, and SEQ ID NO: 56, and the guide strand comprises a sequence having at least 95% homology to SEQ ID NO:12;
(i) the sensor strand comprises a sequence having at least 95% homology to SEQ ID NO:2, the core strand comprises a sequence having at least 95% homology to SEQ ID NO: 41, SEQ ID NO: 45, and SEQ ID NO: 56, and the guide strand comprises a sequence having at least 95% homology to SEQ ID NO: 12; or
(j) the sensor strand comprises a sequence having at least 95% homology to SEQ ID NO:39, the core strand comprises a sequence having at least 95% homology to SEQ ID NO: 41, SEQ ID NO: 45, and SEQ ID NO: 56, and the guide strand comprises a sequence having at least 95% homology to SEQ ID NO:12.

17. The conditional RNA-sensor complex of claim 16, wherein the sensor strand, the guide strand and/or the core strand further comprises one or more chemical modifications to the RNA sequence, wherein the one or more chemical modifications are selected from a locked nucleic acid (LNA) modification, a peptide nucleic acid (PNA) modification, a 2'-O-methyl modification, morpholino modification, a phosphorothioate modification, a terminal modification, or a linker modification.

18. A pharmaceutical composition comprising:
a conditional RNA-sensor complex of claim 1; and
a pharmaceutically acceptable carrier or excipient.

19. A method of treating a pathological condition comprising administering a therapeutically effective amount of a conditional RNA-sensor complex of claim 1 to a subject suffering from the pathological condition, wherein the pathological condition is myocardial infarction (MI), or cardiac hypertrophy.

20. The method of claim 19, wherein administering a therapeutically effective amount comprises an intramyocardial injection of the conditional RNA-sensor complex or the pharmaceutical composition after detection of MI.

21. The conditional RNA-sensor complex of claim 1, wherein the passenger strand bound to the guide strand forms a duplex between 15 and 30 base pairs in length.

* * * * *